(12) United States Patent
Chamberlain et al.

(10) Patent No.: US 7,981,903 B2
(45) Date of Patent: Jul. 19, 2011

(54) 2-[2-{PHENYLAMINO}-1H-PYRROLO[2,3-D]PYRIMIDIN-4-YL)AMINO] BENZAMIDE DERIVATIVES AS IGF-1R INHIBITORS FOR THE TREATMENT OF CANCER

(75) Inventors: Stanley Dawes Chamberlain, Chapel Hill, NC (US); Felix Deanda, Jr., Durham, NC (US); Roseanne Gerding, Durham, NC (US); Masaichi Hasegawa, Tsukuba (JP); Kevin Kuntz, Durham, NC (US); Huangshu Lei, Durham, NC (US); Yasushi Miyazaki, Tsukuba (JP); Naohiko Nishigaki, Tsukuba (JP); Samarjit Patnaik, Durham, NC (US); Aniko Redman, Durham, NC (US); John Brad Shotwell, Durham, NC (US); Kirk Stevens, Durham, NC (US); Joseph Wilson, Durham, NC (US); Bin Yang, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 12/671,960

(22) PCT Filed: Aug. 6, 2008

(86) PCT No.: PCT/US2008/072267
§ 371 (c)(1),
(2), (4) Date: Feb. 3, 2010

(87) PCT Pub. No.: WO2009/020990
PCT Pub. Date: Feb. 12, 2009

(65) Prior Publication Data
US 2010/0204196 A1 Aug. 12, 2010

Related U.S. Application Data

(60) Provisional application No. 60/954,649, filed on Aug. 8, 2007, provisional application No. 61/030,082, filed on Feb. 20, 2008.

(51) Int. Cl.
*A01N 43/90* (2006.01)
*A61K 31/519* (2006.01)
*C07D 487/00* (2006.01)
(52) U.S. Cl. .................... 514/265.1; 544/280
(58) Field of Classification Search .................. None
See application file for complete search history.

(56) References Cited

FOREIGN PATENT DOCUMENTS
WO 2005016894 A 2/2005
WO 2006017443 A 2/2006

*Primary Examiner* — James O Wilson
*Assistant Examiner* — Jeffrey H Murray
(74) *Attorney, Agent, or Firm* — J. Scott Young

(57) ABSTRACT

Novel pyrrolopyrimidines as shown in formula (I):

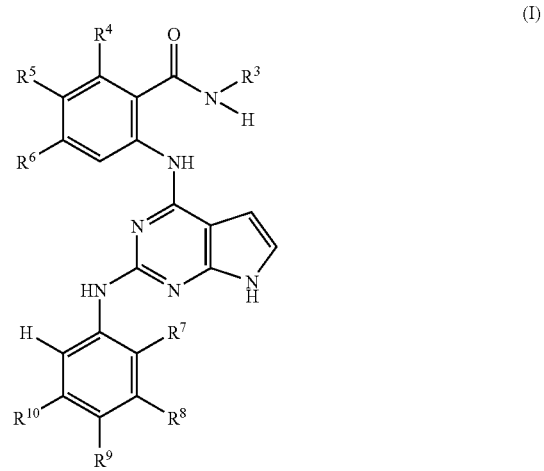

and pharmaceutically acceptable derivatives thereof. The compounds are useful in the inhibition of IGF-1R.

17 Claims, 1 Drawing Sheet

2-[2-{PHENYLAMINO}-1H-PYRROLO[2,3-D]PYRIMIDIN-4-YL)AMINO] BENZAMIDE DERIVATIVES AS IGF-1R INHIBITORS FOR THE TREATMENT OF CANCER

CROSS-REFERENCE TO RELATED APPLICATIONS

This application is filed pursuant to 35 USC 371 as a United States National Phase Application of International Patent Application Ser. No. PCT/US2008/072267 filed on Aug. 6, 2008, which claims priority from 60/954,649 filed on Aug. 8, 2007 and 61/030,082 filed on Feb. 20, 2008 in the United States.

FIELD OF THE INVENTION

The present invention relates to pyrrolopyrimidine derivatives, compositions and medicaments containing the same, as well as processes for the preparation and use of such compounds, compositions and medicaments. Such pyrrolopyrimidine derivatives are useful in the treatment of diseases associated with inappropriate IGF-1R and IR activity.

BACKGROUND OF THE INVENTION

Receptor tyrosine kinases (RTKs) have been implicated in cellular signaling pathways that control various cellular functions, including cell division, growth, metabolism, differentiation, and survival, through reversible phosphorylation of the hydroxyl groups of tyrosine residues in proteins. Extracellular signals are transduced via activation of the cell surface receptors, with amplification and propagation using a complex choreography of cascades of protein phosphorylation, and protein dephosphorylation events to avoid uncontrolled signaling. These signaling pathways are highly regulated, often by complex and intermeshed kinase pathways where each kinase may itself be regulated by one or more other kinases and protein phosphatases. The biological importance of these finely tuned systems is such that a variety of cell proliferative disorders have been linked to defects in one or more of the various cell signaling pathways mediated by tyrosine or serine/threonine kinases.

Receptor tyrosine kinases (RTKs) catalyse phosphorylation of certain tyrosyl amino acid residues in various proteins, including themselves, which govern cell growth, proliferation and differentiation. Insulin-like growth factor-1 receptor (IGF-1R) is a transmembrane tyrosine kinase ubiquitous among fetal and post-natal cell types.

The IGF signaling axis is made up of multiple ligands (IGF-1, IGF-2 and Insulin), at least six high affinity ligand binding proteins and proteases, multiple receptors (IGF-1R & IGF-2R, IR and IRR), and many other down stream signaling proteins (Pollak, M N et al., Nature Reviews Cancer (2004) 4(7):505-518). The structure and function of the IGF-1R has been reviewed by Adams et al., Cell. Mol. Life Sci. (2000) 57:1050-1093 and Benito, M et al., Int J Biochem Cell Biol (1996) 28(5):499-510. The receptor is activated by the ligands IGF-1 and IGF-2, which are mitogenic proteins that signal through the IGF-1R and IR in an endocrine, paracrine or autocrine manner. Activation of the IGF-1 receptor elicits cellular responses which include cellular proliferation and protection of cells from apoptosis. (Id.) Overexpression of IGF-1R leads to malignant transformation of cultured cells, while downregulation can reverse the transformed phenotype of tumor cells and potentially render them susceptible to apoptosis. (Id.)

There are two splice variants of the IR gene, the IR-B isoform which regulates glucose uptake and is expressed in liver, muscle and adipose tissue, and the exon 11 variant human insulin receptor isoform A (IR-A) binds IGF-2 with high affinity and promotes proliferation and protection from apoptosis (Sciacca L. Oncogene (2002) 21(54):8240-8250). IR-A is predominantly expressed in fetal tissue and malignancies and at this receptor, IGF-2 is more potent than insulin in stimulating cancer cell migration. (Sciacca, Oncogene (2002) supra). Insulin receptor-related receptor (IRR) has 79% homology with the kinase domain of IR and is expressed only in a few limited cell types (Dandekar, A A et al., Endocrinology (1998) 139(8):3578-3584).

IGF-1R is a hetero-tetrameric, transmembrane, cell surface receptor. (Benito, Int J Biochem Cell Biol (1996)) An IGF-1 binding domain is part of the extracellular alpha-chain of IGF-1R, whereas the intracellular beta-chain contains the tyrosine kinase domain. Three tyrosine residues represent autophosphorylation sites, specifically Tyr1131, Tyr1135, and Tyr1136, within the activation loop of the IGF-1R beta catalytic domain (Li, W et al., J. Biol. Chem. (2006) 281(33):23785-23791). Phosphorylation of all three is required for full receptor activation, and preceeds phosphorylation of juxtamembrane tyrosines and carboxy terminus serines. The insulin receptor has three similar autophosphorylation sites on the activation loop and juxtamembrane region. Activation and autophoshorylation results in the recruitment of multiple docking proteins and the generation of intracellular signaling (Benito, Int J Biochem Cell Biol (1996)). Once activated, IGF-1R and IR can phosphorylate or interact directly with a number of intracellular protein substrates, including IRS-1, IRS-2, grb2, grb10, grb14, Shc, SOC, 14.3.3, FAK, or indirectly with other proteins like PI3K and MAPK (Benito, M et al. Int J Biochem Cell Biol (1996) 28(5):499-510) (Brown, G C et al., Biochem. J (1992) 284:1-13; Bruning, J C et al., Mol. Cell (1998) 2(5):559-569). Focal adhesion kinase (FAK) is of particular interest because of its role as a regulator of cell survival, proliferation, migration and invasion. FAK is activated by growth factor receptors such as IGF-1R, by binding through its N-terminal domain and autophosphorylation at $TyR^397$. Activated or over expressed FAK is common in a wide variety of cancers, and may play a role in human carcinogenesis (van Nimwegen, M J et al., Biochem. Pharmacol. (2007) 73(5):597-609).

In addition to its role in cancers, the insulin-like growth factor receptor plays important and diverse roles in growth and development (Benito, M et al. Int J Biochem Cell Biol (1996) 28(5):499-510). It IGF-1R has been implicated in several metabolic, and immunological diseases (Walenkamp, M J et al., Horm. Res. (2006) 66(5):221-230; Kurmasheva, R. T et al., Biochim. Biophys. Acta—Rev on Cancer (2006) 1766(1):1-22; Bateman, J M et al., Cell. Mol. Life Sci. (2006) 63(15):1701-1705, LeRoith, D, et al., Can. Lett. (2003) 195:127-137 and Samani A, et al., Endocrine Reviews 28(1):20-47.)

The role of the IGF/IGF-1R signaling system in cancer has been thoroughly examined over the last 15 years. In particular, the implication of IGF-1R in human cancer stems from its roles in stimulating mitogenesis, mobility and metastasis and in protecting against apoptosis. (Kurmasheva, Biochim. Biophys. Acta (2006).) Interest has grown with the understanding that in addition to its antiapoptotic and mitogenic roles, IGF/IGF-1R signaling seems to be necessary for the establishment and continuation of a transformed phenotype. It has been well established that constitutive activation or over expression, often results in non-adherent cell growth, even under serum depleted conditions in vitro, and is associated with the formation of tumors in nude mice. (Kaleko M et al, Mol Cell Biol. (1990) 10(2): 464-473). Perhaps even more importantly, it has been firmly established that cells, in which the gene encoding for IGF-1R has been deactivated, are totally resistant to transformation by agents which are normally capable of immortalizing normal cells, such as over expression of PDGFR or EGFR, the T antigen of the SV40 virus, the E5 protein of bovine papilloma virus, and activated ras. (DeAngelis T et al., Cell. Physiol. (1995) 164( ):214-221; Coppola D et al., Mol. Cell. Biol. (1994) 14(7):4588-4595; Morrione A J, Virol. 1995 695300-5303; Sell C et al., Mol. Cell. Biol. (1994) 14(6):3604-3612; Sell C et al., Proc. Natl. Acad. Sci. USA (1993) 90(23):11217-11221). Thus, IGF-1R has been identified as the major survival factor that protects from oncogene induced cell death (Harrington et al., EMBO J. (1994) 13( ):3286-3295). IGF-1R is expressed in a large number and variety of tumors and the IGFs amplify the tumor growth through their interaction with the receptor. Evidence supporting the role of IGF-1R in carcinogenesis can be found in studies using monoclonal antibodies directed towards the receptor which inhibit the proliferation of numerous cell lines in culture and in vivo (Arteaga C et al., Cancer Res. (1989) 49(22):6237-6241; Li et al., Biochem. Biophys. Res. Com. (1993) 196(1):92-98; Scotlandi K et al., Cancer Res. (1998) 58(18):4127-4131). Dominant negative IGF-1R is capable of inhibiting tumor proliferation (Jiang et al., Oncogene (1999) 18(44):6071-6077).

The IGF signaling axis is implicated in various tumor types including: breast cancer (Surmacz, J. Mammary Gland Bio. Neoplasia (2000) 5(1):95-105, LeRoith, Can. Lett. (2003) and Artega, Cancer Res. (1989)), bone and bone marrow cancers including Ewing's sarcoma, osteosarcoma, giant cell tumor of bone (Scotlandi, Cancer Res. (1998) lung cancer, including non-small cell and small cell lung carcinomas and mesotheliomas (Jiang, Y et al., Oncogene (1999) 18:6071-6077 and LeRoith, Can. Lett. (2003), prostate cancer (Djavan et al., World J Urol. (2001) 19(4):225-233; O'Brien et al., Urology (2001) 58(1):1-7 and LeRoith, Can. Lett. (2003)), colorectal cancer (Guo et al., Gastroenterology, 1992, 102, 1101-1108; Durai, R et al., Int. J Colorectal Dis. (2005) 20(3):203-220 and LeRoith, Can. Lett. (2003)), renal cancer (Kellerer M. et al., Int. J. Cancer (1995) 62(5):501-507), pancreatic cancer (Bergmann, U et al., Cancer Res. (1995) 55(10):2007-2011), hematopoietic cancers, including lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, multiple myeloma, megakaryoblastic leukemia, acute megakaryocytic leukemia, promyelocytic leukemia, erythroleukemia, malignant lymphoma, Hodgkins lymphoma, non-Hodgkins lymphoma, lymphoblastic T cell lymphoma, Burkitt's lymphoma, follicular lymphoma, myelodysplastic syndromes, (Zumkeller W et al., Leuk. Lymph (2002) 43(3):487-491; and Qi, Ann Hematol. (2006) 85:95-101.), neuroblastomas (Zumkeller, W et al., Horm. Metab. Res. 1999, 31, 138-141), gliomas, meningiomas, medulloblastomas, astrocytomas, and glioblastoma (Zumkeller, Wet al., Mol. Pathol. (2001) 54(4):227-229, Del Valle L, et al., Clin. Cancer Res. (2002) 8:1822-1830 and Trojan et al., Proc. Natl. Acad. Sci. U.S.A. (1992) 89:4874-4878.), thyroid cancer (Vella V et al., J. Clin. Endocrinol. Metab. (2002) 87:245-254; Vella V et al., Mol. Pathol. (2001) 54(3):121-124), and hepatocarcinoma (Alexia, C et al., Biochem. Pharmacol. (2004) 68(1):1003-1015). ovarian cancer, testicular cancer, vulval cancer, cervical cancer, endometrial cancer, bladder cancer, esophageal cancer, gastric cancer, nasopharangeal cancer, buccal cancer, cancer of the mouth, GIST (gastrointestinal stromal tumor), skin cancer including melanoma, and soft-tissue sarcoma.

Thus, in virtually all types of human cancers there is a strong association between dysregulation of IGF signaling and carcinogenesis (Bohula E A et al., Anticancer Drugs (2003) 14(9):669-682). Inhibition of IGF-1R expression or function has been shown to block tumor growth and metastasis and also enhance sensitivity to other anti-neoplastic therapies, including cytotoxic drugs and radiation. (Bohula, Anticancer Drugs (2003).

SUMMARY OF THE INVENTION

We have now found a group of novel pyrrolopyrimidines that are inhibitors of IGF-1R.

The present invention provides a compound of formula (I):

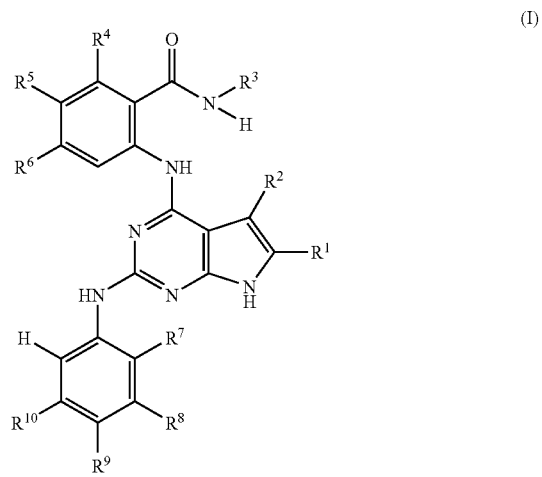

(I)

a pharmaceutically acceptable salt or solvate thereof wherein:
$R^1$ is selected from H and alkyl$_{C1-C3}$;
$R^2$ is selected from H, alkyl$_{C1-C3}$, and halo;
$R^3$ is selected from H, OH, alkyl$_{C1-C6}$, -alkylene$_{C1-C6}$-OH, -alkylene$_{C1-C6}$-phenyl (optionally substituted with a halo), and -alkylene$_{C1-C6}$-C(O)NH$_2$;
$R^4$ is selected from H, halo, alkyl$_{C1-C6}$, and —O-alkyl$_{C1-C6}$; or,
$R^3$ and $R^4$, together with the atoms to which they are bound, form a five or six membered lactam;
$R^5$ and $R^6$ are each independently selected from H, halo, alkyl$_{C1-C6}$, and —O-alkyl$_{C1-C6}$, or
$R^5$ and $R^6$ together with the aryl to which they are attached form a napthalene;
$R^7$ is selected from alkyl$_{C1-C6}$, —O-alkyl$_{C1-C6}$, halo, —N—R$^{19}$R$^{19}$, and —O-alkylene$_{C1-C6}$-halo$_{1-3}$;
$R^8$ is selected from H, halo, and alkyl$_{C1-C6}$;
one of $R^9$ and $R^{10}$ is selected from -alkylene$_{C1-C6}$-SO$_2$-alkyl$_{C1-C6}$,
—NR$^{19}$-alkylene$_{C0C0-C6}$-C(O)-alkylene$_{C0-C6}$-NR$^{22}$R$^{23}$, —O-alkylene$_{C0-C6}$(optionally substituted with —OH)—NR$^{22}$R$^{23}$,

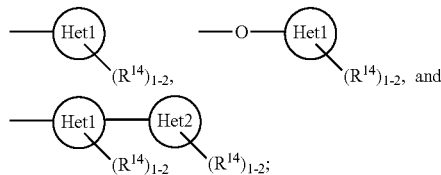

and the other of R$^9$ and R$^{10}$ is selected from H, alkyl$_{C1-C6}$, —O-alkyl$_{C1-C6}$, and halo;

wherein Het1 and Het2 are each independently a five or six membered heterocyclic ring having an N atom and optionally one or two additional heteroatoms selected from N and O, and each R$^{14}$ is independently selected from H, OH, halo, alkyl$_{C1-C6}$, —O-alkyl$_{C1-C6}$, -cyclopropyl, —C(O)-alkyl$_{C1-C8}$, SO$_2$-alkyl$_{C1-C6}$, —(CH$_2$)$_{1-4}$-halo, and —(CH$_2$)$_{1-4}$-SO$_2$-alkyl$_{C1-C6}$;

or

R$^9$ and R$^{10}$, together with the atoms to which they are attached form a five, six, or seven-membered heterocyclic ring containing one or two N atom and the remainder C atoms, wherein at least one N atom is substituted with R$^{15}$, and the C atoms of the heterocyclic ring are optionally substituted with one or more groups selected from R$^{16}$ and (R$^{19}$)$_{1-2}$;

wherein R$^{15}$ is selected from H, -alkyl$_{C1-C4}$, -alkylene$_{C1-C4}$-halo, —C(O)-alkylene$_{C0-C6}$-NR$^{22}$R$^{23}$, —C(O)-alkyl$_{C1-C6}$, -alkylene$_{C1-C4}$-NR$^{22}$R$^{23}$, -alkylene$_{C1-C4}$-C(O)—NR$^{22}$R$^{23}$, —C(O)-alkylene$_{C1-C4}$-O-alkyl$_{C1-C6}$, —C(O)-pyrrolidine, and —C(O)-pyrrolidine-alkyl$_{C1-C6}$;

R$^{16}$ is selected from H and =O; and, each R$^{19}$ is independently selected from H and alkyl$_{C1-C6}$;

R$^{22}$ is selected from H, alkyl$_{C1-C6}$, —O-alkyl$_{C1-C6}$, -alkylene$_{C1-C6}$-O-alkyl$_{C1-C6}$, —(CH$_2$)$_{2-4}$-halo, and —(CH$_2$)$_{2-4}$—SO$_2$-alkyl$_{C1-C6}$; and, R$^{23}$ is selected from H, alkyl$_{C1-C6}$, —(CH$_2$)$_{2-4}$halo, and —(CH$_2$)$_{2-4}$—SO$_2$-alkyl$_{C1-C6}$; or R$^{22}$ and R$^{23}$ combine to form a four, five, or six membered, heterocyclic ring containing the N atom to which they are attached and optionally an additional heteroatom selected from N and O, wherein the ring is optionally substituted with —OH or -alkyl$_{C1-C6}$.

According to another embodiment, a compound of formula I is provided as described in any one of the examples. According to another embodiment, a pharmaceutically acceptable derivative of the compound of formula I described in any one of the examples is provided.

According to another embodiment, the invention provides a pharmaceutical composition comprising compound of Formula I, or pharmaceutically acceptable derivative thereof together with one or more pharmaceutically acceptable carrier, diluent, or excipient.

According to another embodiment, the invention provides a method of treatment of a condition mediated by inappropriate activity of at least one IGF-1R family receptor in a mammal in need thereof, with a compound of Formula I, or pharmaceutically acceptable derivative thereof.

According to another embodiment, the invention provides a method for treating a susceptible neoplasm in a mammal in need thereof, comprising: administering to the mammal, a therapeutically effective amount of a compound of formula (I) or a pharmaceutically acceptable derivative thereof.

According to another embodiment, the invention provides a method for treating a condition selected from breast cancer, sarcomas, lung cancer (including non-small cell lung carcinoma), prostate cancer, colorectal cancer, renal cancer, pancreatic cancer, hematologic cancers (including multiple myeloma), neuroblastomas, gliomas, head and neck cancer, thyroid cancer, hepatocarcinoma, ovarian cancer, vulval cancer, cervical cancer, endometrial cancer, testicular cancer, bladder cancer, esophageal cancer, gastric cancer, nasopharangeal cancer, buccal cancer, cancer of the mouth, gastrointestinal stromal tumor and skin cancer (including melanoma) in a mammal in need thereof, comprising: administering to the mammal, a therapeutically effective amount of a compound of formula (I) or a pharmaceutically acceptable derivative thereof.

According to another embodiment, the invention provides a method for treating a condition selected from breast cancer, sarcoma, lung cancer, non-small cell lung carcinoma, prostate cancer, colorectal cancer, pancreatic cancer, hematologic cancers, multiple myeloma, head and neck cancer or ovarian cancer in a mammal in need thereof, comprising: administering to the mammal, a therapeutically effective amount of a compound of formula (I) or a pharmaceutically acceptable derivative thereof.

According to another embodiment, the invention provides a compound of Formula I, or a pharmaceutically acceptable derivative thereof for use in the treatment of a condition mediated by inappropriate activity of at least one IGF-1R family receptor.

According to another embodiment, the invention provides a compound of Formula I, or a pharmaceutically acceptable derivative thereof for use in the treatment of a susceptible neoplasm in a mammal in need thereof.

According to another embodiment, the invention provides a compound of Formula I, or a pharmaceutically acceptable derivative thereof for use in the treatment of a condition selected from breast cancer, sarcomas, lung cancer (including non-small cell lung carcinoma), prostate cancer, colorectal cancer, renal cancer, pancreatic cancer, hematologic cancers (including multiple myeloma), neuroblastomas, gliomas, head and neck cancer, thyroid cancer, hepatocarcinoma, ovarian cancer, vulval cancer, cervical cancer, endometrial cancer, testicular cancer, bladder cancer, esophageal cancer, gastric cancer, nasopharangeal cancer, buccal cancer, cancer of the mouth, gastrointestinal stromal tumor and skin cancer (including melanoma) in a mammal in need thereof.

According to another embodiment, the invention provides a compound of Formula I, or a pharmaceutically acceptable derivative thereof for use in the treatment of a condition selected from breast cancer, sarcoma, lung cancer, non-small cell lung carcinoma, prostate cancer, colorectal cancer, pancreatic cancer, hematologic cancers, multiple myeloma, head and neck cancer or ovarian cancer in a mammal in need thereof.

According to another embodiment, the invention provides the use of a compound of formula I, or pharmaceutically acceptable derivative thereof in the manufacture of a medicament for use in the treatment of a condition mediated by inappropriate activity of at least one IGF-1R family receptor.

According to another embodiment, the invention provides the use of a compound of formula I, or pharmaceutically acceptable derivative thereof in the manufacture of a medicament for use in the treatment of a susceptible neoplasm in a mammal in need thereof.

According to another embodiment, the invention provides the use of a compound of formula I, or pharmaceutically acceptable derivative thereof in the manufacture of a medicament for use in the treatment of a condition selected from breast cancer, sarcomas, lung cancer (including non-small cell lung carcinoma), prostate cancer, colorectal cancer, renal cancer, pancreatic cancer, hematologic cancers (including multiple myeloma), neuroblastomas, gliomas, head and neck cancer, thyroid cancer, hepatocarcinoma, ovarian cancer, vulval cancer, cervical cancer, endometrial cancer, testicular cancer, bladder cancer, esophageal cancer, gastric cancer, nasopharangeal cancer, buccal cancer, cancer of the mouth, gastrointestinal stromal tumor and skin cancer (including melanoma) in a mammal in need thereof.

According to another embodiment, the invention provides the use of a compound of formula I, or pharmaceutically acceptable derivative thereof in the manufacture of a medicament for use in the treatment of a condition selected from breast cancer, sarcoma, lung cancer, non-small cell lung carcinoma, prostate cancer, colorectal cancer, pancreatic cancer, hematologic cancers, multiple myeloma, head and neck cancer or ovarian cancer in a mammal in need thereof.

According to another embodiment, the invention provides for a process for preparing a compound of formula I, comprising the steps of reacting a compound of formula (III),

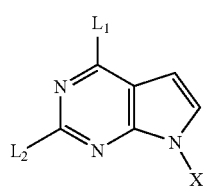

(III)

with a compound of formula (II),

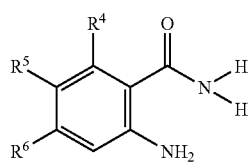

(II)

in the presence of a tertiary amine to form intermediate (V)

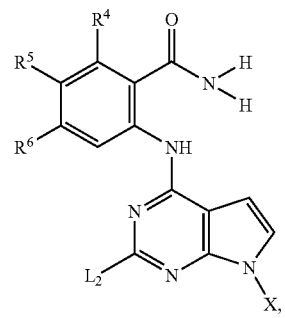

(V)

wherein $L_1$ and $L_2$ are leaving groups, X is a protecting group, and $R^4$, $R^5$, and $R^6$ are as described above;

then reacting intermediate (V) with a compound of formula (IV)

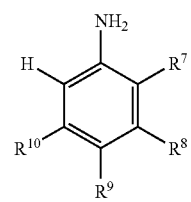

(IV)

in the presence of an acid, a catalyst, and a polar protic solvent having low nucleophilicity, under heat, wherein $R^7$, $R^8$, $R^9$, and $R^{10}$ are as described above;

then reacting the product of the preceding step with an amine-containing heteroatom nucleophile in solvent; and then removing the protecting group X with a base in solvent.

DETAILED DESCRIPTION OF THE INVENTION

Figure 1:
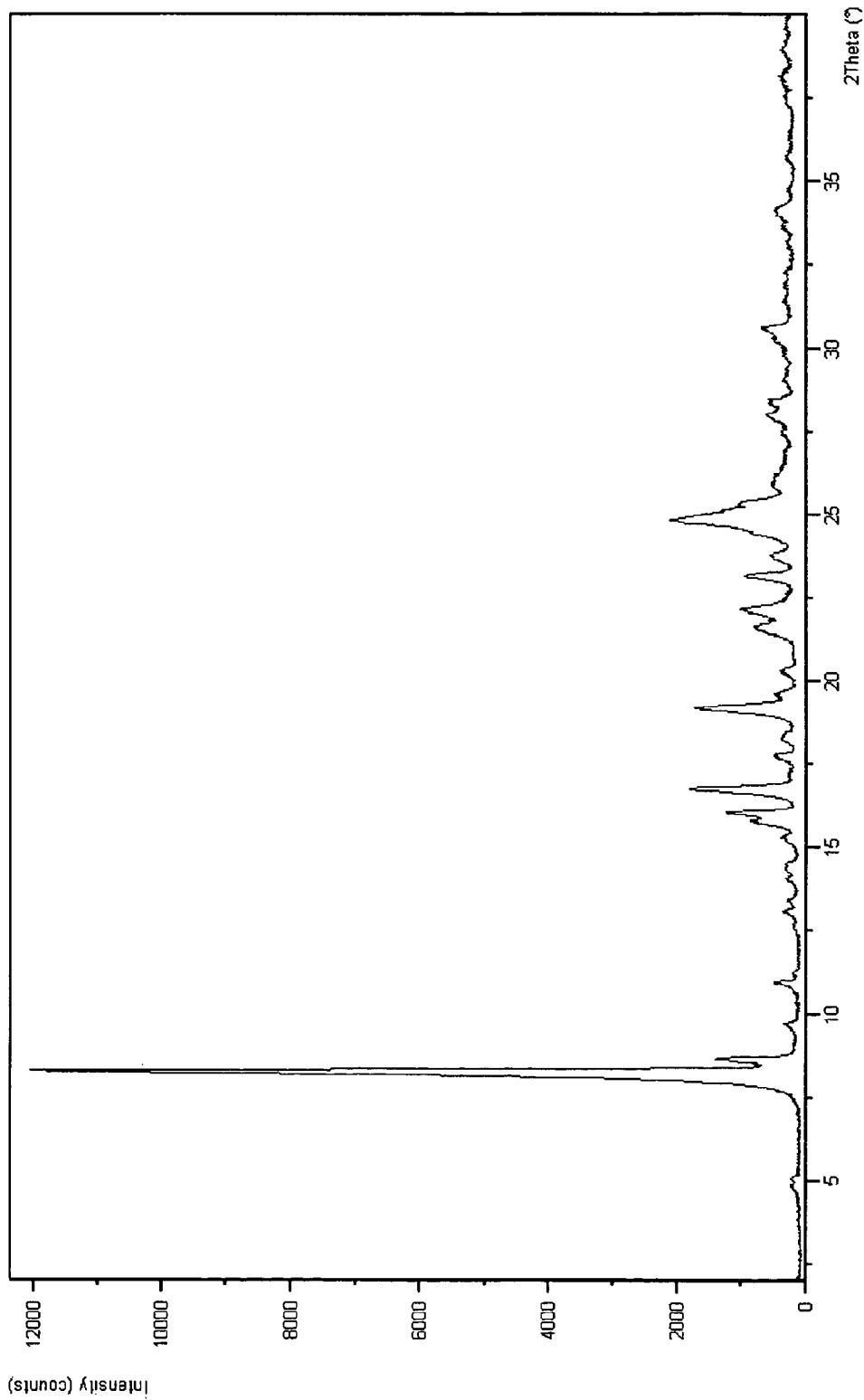
FIG. 1 depicts the powder X-ray diffraction pattern of 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluoro-N-methylbenzamide monohydrate.

As used herein, the terms "alkyl" (and "alkylene") refer to straight or branched hydrocarbon chains containing from 1 to 6 carbon atoms, unless a different number of atoms is specified. Examples of "alkyl" as used herein include, but are not limited to, methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. "Alkyl" also includes substituted alkyl. The alkyl (and alkylene) groups may be optionally substituted one or more times with a halogen or hydroxyl. Thus, the term "alkyl" may include for example, trifluoromethyl and trifluoroethyl, among other halogenated alkyls, and hydroxymethyl and other hydroxylated alkyls when specified.

As used herein, the term "alkenyl" (and "alkylene") refers to straight or branched hydrocarbon chains containing from 2 to 6 carbon atoms, unless a different number of atoms is specified, and at least one and up to three carbon-carbon double bonds. Examples of "alkenyl" as used herein include, but are not limited to ethenyl and propenyl. Examples of "alkenylene" as used herein include, but are not limited to, ethenylene, propenylene and butenylene. "Alkenyl" (and "alkenylene") also may include substituted alkenyl. The alkenyl groups may optionally be substituted one or more times with a halogen or hydroxyl, as specified.

As used herein, the term "alkynyl" refers to straight or branched hydrocarbon chains containing from 2 to 6 carbon atoms, unless a different number of atoms is specified, and at least one and up to three carbon-carbon triple bonds. Examples of "alkynyl" as used herein include, but are not limited to ethynyl and propynyl. "Alkynyl" may also include substituted alkynyl. The alkynyl groups may optionally be substituted one or more times with a halogen or hydroxyl, as specified.

As used herein, the term "cycloalkyl" refers to a saturated monocyclic carbocyclic ring having from 3 to 6 carbon atoms, unless a different number of atoms is specified. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may optionally be substituted on any available carbon with one or more substituents selected from the group consisting of alkoxy, halo, and haloalkyl, e.g., perfluoroalkyl.

The term "halo" or "halogen" refers to fluoro, chloro, bromo and iodo. According to a preferred embodiment, halo is fluoro or chloro.

As used herein, the term "alkoxy" refers to the group —O-alkyl, where alkyl is as defined above. Examples of "alkoxy" as used herein include, but are not limited to, methoxy, ethoxy, n-propoxy, isopropoxy, n-butoxy, and t-butoxy. "Alkoxy" also includes substituted alkoxy. The alkoxy groups may be optionally substituted one or more times with a halogen.

The term "aryl" refers to monocyclic carbocyclic groups and fused bicyclic carbocyclic groups having from 6 to 10 carbon atoms, unless a different number of atoms is specified, and having at least one aromatic ring. Examples of particular aryl groups include but are not limited to phenyl and naphthyl. One particular aryl group according to the invention is phenyl.

The term "heterocycle", "heterocyclic ring", or "heterocyclyl" refers to a mono- or poly-cyclic ring system containing optionally one or more degrees of unsaturation and also containing one or more heteroatoms. Heteroatoms may include N, O, and/or S. Preferred heteroatoms are N and O, particularly N. The heterocycle is three to ten-membered and is either saturated or has one or more degrees of unsaturation. Heterocycles may be optionally fused to one or more of another heterocyclic ring, heteroaryl ring, aryl ring, or cycloalkyl ring. Examples of heterocyclic groups include, e.g. indole, indoline, isoquinoline.

The term "pharmaceutically acceptable derivative" refers to salts and solvates of the selected compound.

The term "solvate" as used herein refers to a complex of variable stoichiometry formed by a solute (a compound of formula (I)) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As stated above, the main embodiment of the present invention provides a compound of formula (I):

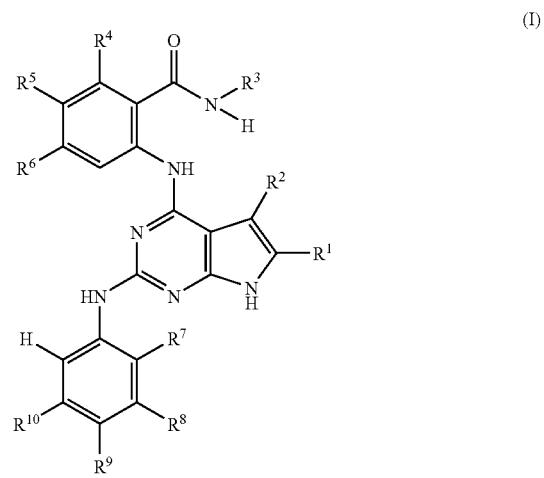

or a pharmaceutically acceptable salt or solvate thereof wherein:

$R^1$ is selected from H and $alkyl_{C1-C3}$;

$R^2$ is selected from H, $alkyl_{C1-C3}$, and halo;

$R^3$ is selected from H, OH, $alkyl_{C1-C6}$, $-alkylene_{C1-C6}$-OH, $-alkylene_{C1-C6}$-phenyl (optionally substituted with a halo), and $-alkylene_{C1-C6}$-C(O)NH$_2$;

$R^4$ is selected from H, halo, $alkyl_{C1-C6}$, and $-O-alkyl_{C1-C6}$; or, $R^3$ and $R^4$, together with the atoms to which they are bound, form a five or six membered lactam;

$R^5$ and $R^6$ are each independently selected from H, halo, $alkyl_{C1-C6}$, and $-O-alkyl_{C1-C6}$, or $R^5$ and $R^6$ together with the aryl to which they are attached form a napthalene;

$R^7$ is selected from $alkyl_{C1-C6}$, $-O-alkyl_{C1-C6}$, halo, $-N-R^{19}R^{19}$, and $-O-alkylene_{C1-C6}-halo_{1-3}$;

$R^8$ is selected from H, halo, and $alkyl_{C1-C6}$;

one of $R^9$ and $R^{10}$ is selected from $-alkylene_{C1-C6}$-SO$_2$-$alkyl_{C1-C6}$, $-NR^{19}$-$alkylene_{C0-C6}$-C(O)-$alkylene_{C0-C6}$-NR$^{22}$R$^{23}$, $-O-alkylene_{C0-C6}$(optionally substituted with $-OH$)$-NR^{22}R^{23}$,

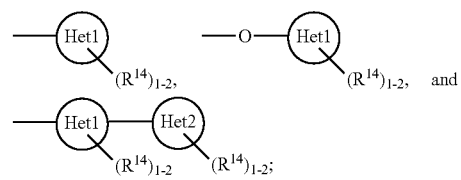

and the other of $R^9$ and $R^{10}$ is selected from H, $alkyl_{C1-C6}$, $-O-alkyl_{C1-C6}$, and halo;

wherein Het1 and Het2 are each independently a five or six membered heterocyclic ring having an N atom and optionally one or two additional heteroatoms selected from N and O, and each $R^{14}$ is independently selected from H, OH, halo, alkyl$_{C1-C6}$, —O-alkyl$_{C1-C6}$, -cyclopropyl, —C(O)-alkyl$_{C1-C6}$, SO$_2$-alkyl$_{C1-C6}$, —(CH$_2$)$_{1-4}$-halo, and —(CH$_2$)$_{1-4}$—SO$_2$-alkyl$_{C1-C6}$, or $R^9$ and $R^{10}$, together with the atoms to which they are attached form a five, six, or seven-membered heterocyclic ring containing one or two N atom and the remainder C atoms, wherein at least one N atom is substituted with $R^{15}$, and the C atoms of the heterocyclic ring are optionally substituted with one or more groups selected from $R^{16}$ and $(R^{19})_{1-2}$;

wherein $R^{15}$ is selected from H, -alkyl$_{C1-C4}$, -alkylene$_{C1-C4}$-halo, —C(O)-alkylene$_{C0-C6}$-NR$^{22}$R$^{23}$, —C(O)-alkyl$_{C1-C6}$, -alkylene$_{C1-C4}$-NR$^{22}$R$^{23}$, -alkylene$_{C1-C4}$-C(O)—NR$^{22}$R$^{23}$, —C(O)-alkylene$_{C1-C4}$-O-alkyl$_{C1-C6}$, —C(O)-pyrrolidine, and —C(O)-pyrrolidine-alkyl$_{C1-C6}$;

$R^{16}$ is selected from H and =O; and, each $R^{19}$ is independently selected from H and alkyl$_{C1-C6}$;

$R^{22}$ is selected from H, alkyl$_{C1-C6}$, —O-alkyl$_{C1-C6}$, -alkylene$_{C1-C6}$-O-alkyl$_{C1-C6}$, —(CH$_2$)$_{2-4}$-halo, and —(CH$_2$)$_{2-4}$—SO$_2$-alkyl$_{C1-C6}$; and, $R^{23}$ is selected from H, alkyl$_{C1-C6}$, —(CH$_2$)$_{2-4}$-halo, and —(CH$_2$)$_{2-4}$—SO$_2$-alkyl$_{C1-C6}$; or $R^{22}$ and $R^{23}$ combine to form a four, five, or six membered, heterocyclic ring containing the N atom to which they are attached and optionally an additional heteroatom selected from N and O, wherein the ring is optionally substituted with —OH or -alkyl$_{C1-C6}$.

According to an alternative embodiment of the invention, $R^7$ is —O-alkyl$_{C1-C6}$ and the remaining substituents are as described above in the main embodiment.

According to another embodiment, $R^7$ is —O-alkyl$_{C1-C6}$, $R^{10}$ is H, and the remaining substituents are as described above in the main embodiment.

According to another embodiment, $R^7$ is —O-alkyl$_{C1-C6}$; $R^{10}$ is H; $R^4$, $R^5$, and $R^6$ are independently selected from H and halo; and the remaining substituents are as described above in the main embodiment.

According to another embodiment, $R^7$ is —O-alkyl$_{C1-C6}$; $R^{10}$ is H; $R^4$, $R^5$, $R^6$ are independently selected from H and halo; $R^3$ is H; and the remaining substituents are as described above in the main embodiment.

According to another embodiment, $R^7$ is —O-alkyl$_{C1-C6}$, $R^9$ is H, and the remaining substituents are as described above in the main embodiment.

According to another embodiment, $R^7$ is —O-alkyl$_{C1-C6}$; $R^9$ is H; $R^4$, $R^5$, and $R^6$ are independently selected from H and halo; and the remaining substituents are as described above in the main embodiment.

According to another embodiment, $R^7$ is —O-alkyl$_{C1-C6}$; $R^9$ is H; $R^4$, $R^5$, $R^6$ are independently selected from H and halo; $R^3$ is H; and the remaining substituents are as described above in the main embodiment.

According to another embodiment, the substituents are as described in the above embodiments, respectively, wherein $R^7$ is —O-methyl.

According to another embodiment, each of $R^4$, $R^5$, and $R^6$ are H, and the remaining substituents are as described above in the main embodiment.

According to another embodiment, one of $R^4$, $R^5$, and $R^6$ is halo; the remaining two of $R^4$, $R^5$, and $R^6$ are H, and the remaining substituents are as described above in the main embodiment. According to a variation of this embodiment, halo is F.

According to another embodiment, two of $R^4$, $R^5$, and $R^6$ are halo; the remaining one of $R^4$, $R^5$, and $R^6$ is H, and the remaining substituents are as described above in the main embodiment. According to a variation of this embodiment, both halo are F.

According to another embodiment, $R^5$ and $R^6$ together with the adjoining phenyl, form a naphthalene, and the remaining substituents are as described above in the main embodiment.

According to another embodiment, $R^3$ is H; and the remaining substituents are as described above in the main embodiment.

According to another embodiment, $R^3$ is selected from OH, alkyl$_{C1-C6}$, -alkylene$_{C1-C6}$-OH, -alkylene$_{C1-C6}$-phenyl (optionally substituted with halo), and -alkylene$_{C1-C6}$-C(O)NH$_2$; and the remaining substituents are as described above in the main embodiment.

According to another embodiment, $R^9$ is H and $R^{10}$ is selected from -alkylene$_{C1-C6}$-SO$_2$-alkyl$_{C1-C6}$, —N-alkyl$_{C0-C6}$-C(O)-alkylene$_{C0-C6}$-NR$^{22}$R$^{23}$, —O-alkylene$_{C0-C6}$(optionally substituted with OH)—NR$^{22}$R$^{23}$,

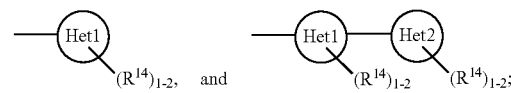

and the remaining substituents are as described above in the main embodiment.

According to another embodiment, $R^9$ is H and $R^{10}$ is selected from

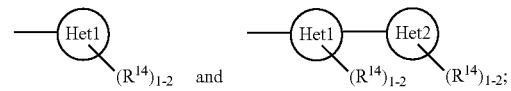

and the remaining substituents are as described above in the main embodiment.

According to another embodiment, $R^9$ is H and $R^{10}$ is selected from

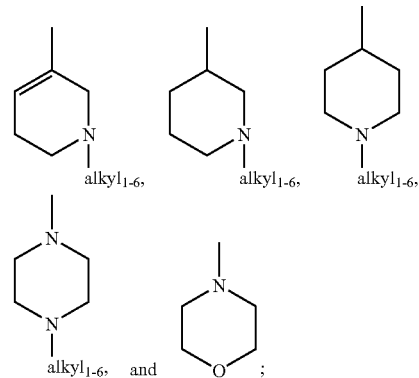

and the remaining substituents are as described above in the main embodiment. According to a variation of this embodiment, alkyl$_{C1-C6}$ is n-propyl or i-propyl.

According to another embodiment, $R^{10}$ is H and $R^9$ is selected from -alkylene$_{C1-C6}$-SO$_2$-alkyl$_{C1-C6}$, —N- alkyl$_{C0-C6}$-C(O)-alkylene$_{C0-C6}$-NR$^{22}$R$^{23}$, —O-alkylene$_{C0-C6}$(optionally substituted with OH)—NR$^{22}$R$^{23}$,

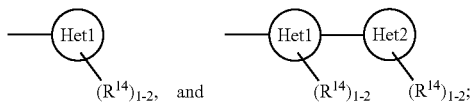

and the remaining substituents are as described above in the main embodiment.

According to another embodiment. R$^{10}$ is H and R$^9$ is selected from

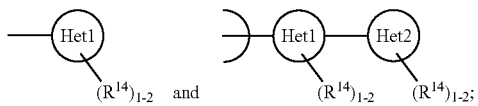

and the remaining substituents are as described above in the main embodiment.

According to another embodiment, R$^{10}$ is H and R$^9$ is selected from

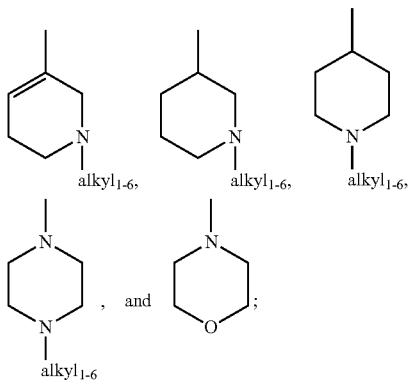

and the remaining substituents are as described above in the main embodiment. According to a variation of this embodiment, alkyl$_{C1-C6}$ is n-propyl or i-propyl.

According to another embodiment, the compound is of formula (Ia)

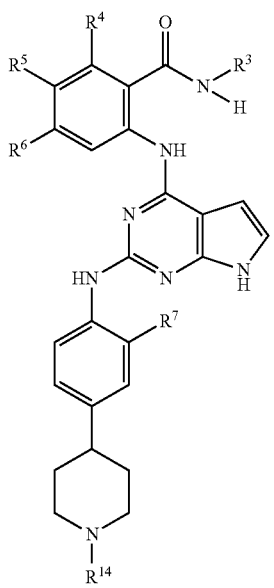

wherein the substituents are as described above in the main embodiment.

According to another embodiment, the compound is of formula (Ia), R$^{14}$ is -alkyl$_{C1-C6}$, and the remaining substituents are as described above in the main embodiment.

According to another embodiment, the compound is of formula (Ia), R$^7$ is -alkyl$_{C1-C6}$, R$^4$ is fluoro, R$^5$ is H, and R$^6$ is fluoro, and the remaining substituents are as described above in the main embodiment.

According to another embodiment, the compound is of formula (Ib)

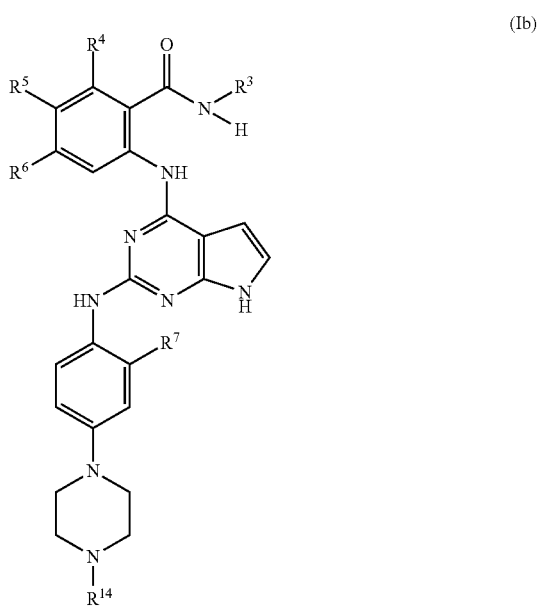

wherein the substituents are as described above in the main embodiment.

According to another embodiment, the compound is of formula (Ib), R$^{14}$ is -alkyl$_{C1-C6}$, and the remaining substituents are as described above in the main embodiment.

According to another embodiment, the compound is of formula (Ib), R$^7$ is -alkyl$_{C1-C6}$, R$^4$ is fluoro, R$^5$ is H, and R$^6$ is H, and the remaining substituents are as described above in the main embodiment.

According to another embodiment of the invention, R$^9$ and R$^{10}$, together with the atoms to which they are attached form a five, six, or seven-membered heterocyclic ring containing one or two N atom and the remainder C atoms, wherein at least one N atom is substituted with R$^{15}$, and the C atoms of the heterocyclic ring are optionally substituted with one or more groups selected from R$^{16}$ and (R$^{19}$)$_{1-2}$, and the remaining substituents are as described above in the main embodiment.

According to another embodiment, R$^9$ and R$^{10}$, together with the atoms to which they are attached form a five, six, or seven-membered heterocyclic ring containing one or two N atom and the remainder C atoms, wherein at least one N atom is substituted with R$^{15}$, and the C atoms of the heterocyclic ring are optionally substituted with one or more groups selected from R$^{16}$ and (R$^{19}$)$_{1-2}$, R$^7$ is —O-alkyl$_{C1-C6}$, and the remaining substituents are as described above in the main embodiment.

According to another embodiment, R$^9$ and R$^{10}$, together with the atoms to which they are attached form a five, six, or seven-membered heterocyclic ring containing one or two N atom and the remainder C atoms, wherein at least one N atom is substituted with R$^{15}$, and the C atoms of the heterocyclic ring are optionally substituted with one or more groups selected from $R^{16}$ and $(R^{19})_{1-2}$, $R^7$ is —O-alkyl$_{C1-C6}$, $R^{15}$ is —C(O)-alkylene$_{C0-C6}$-NR$^{22}$R$^{23}$, and the remaining substituents are as described above in the main embodiment.

According to another embodiment, $R^9$ and $R^{10}$, together with the atoms to which they are attached form a five, six, or seven-membered heterocyclic ring containing one or two N atom and the remainder C atoms, wherein at least one N atom is substituted with $R^{15}$, and the C atoms of the heterocyclic ring are optionally substituted with one or more groups selected from $R^{16}$ and $(R^{19})_{1-2}$, $R^7$ is —O-alkyl$_{C1-C6}$, each of $R^4$, $R^5$, and $R^6$ is independently selected from H and halo, and the remaining substituents are as described above in the main embodiment.

According to an alternative embodiment of the invention, $R^9$ and $R^{10}$, together with the atoms to which they are attached form a five or six-membered heterocyclic ring selected from

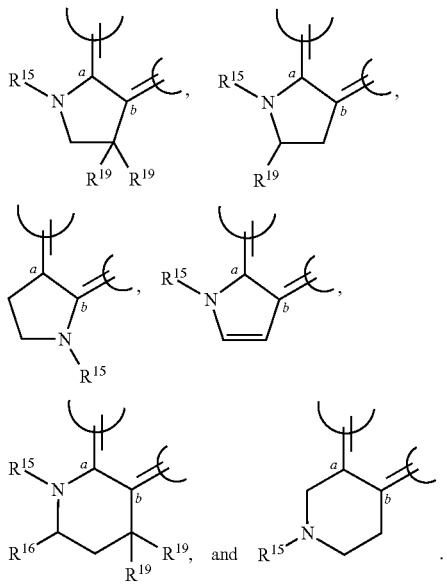

According to another embodiment, $R^9$ and $R^{10}$, together with the atoms to which they are attached form a five or six-membered heterocyclic ring selected from

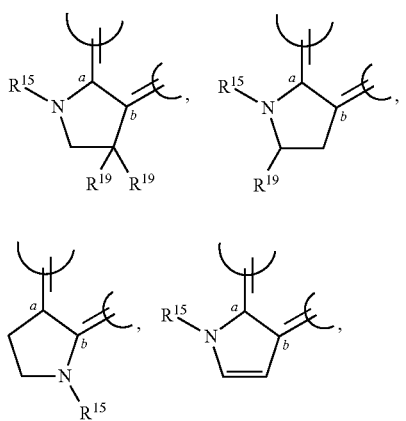

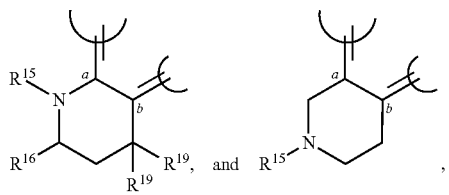

$R^7$ is —O-alkyl$_{C1-C6}$, and the remaining substituents are as described above in the main embodiment.

According to another embodiment, $R^9$ and $R^{10}$, together with the atoms to which they are attached form a five or six-membered heterocyclic ring selected from

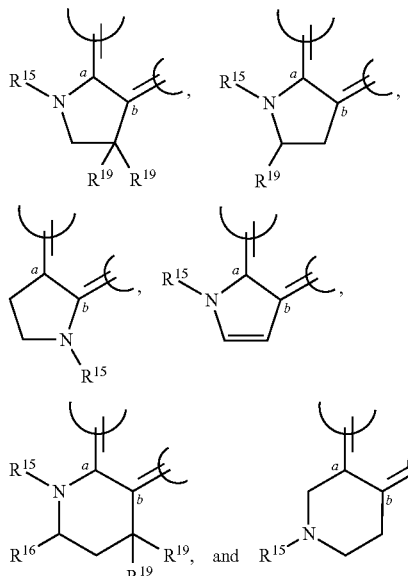

$R^7$ is —O-alkyl$_{C1-C6}$, $R^{15}$ is —C(O)-alkylene$_{C0-C6}$-NR$^{22}$R$^{23}$, and the remaining substituents are as described above in the main embodiment.

According to another embodiment, $R^9$ and $R^{10}$, together with the atoms to which they are attached form a five or six-membered heterocyclic ring selected from

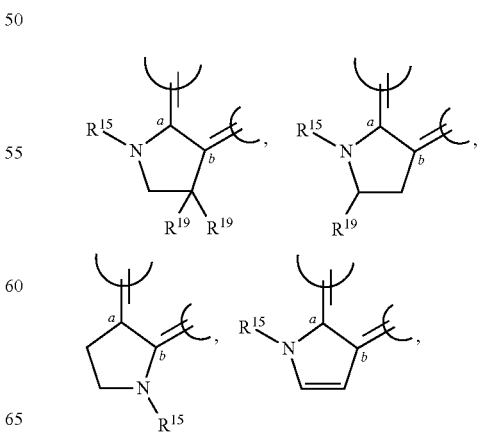

-continued

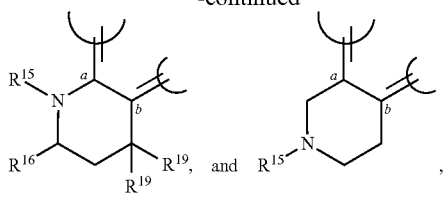

$R^7$ is —O-alkyl$_{C1-C6}$, each of $R^4$, $R^5$, and $R^6$ is independently selected from H and halo, and the remaining substituents are as described above in the main embodiment.

According to another embodiment, the compound is of formula (Ic)

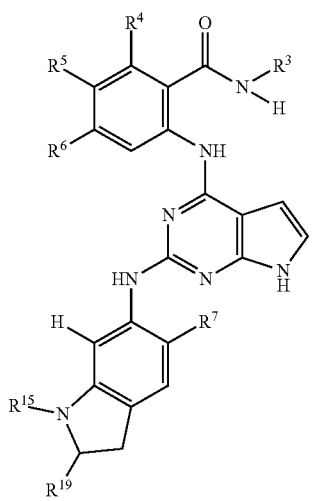

(Ic)

wherein the substituents are as described above in the main embodiment.

According to another embodiment, the compound is of formula (Ic), $R^7$ is —O-alkyl$_{C1-C6}$, and the remaining substituents are as described above in the main embodiment.

According to another embodiment, the compound is of formula (Ic), $R^7$ is —O-alkyl$_{C1-C6}$, $R^{15}$ is —C(O)-alkylene$_{C0-C6}$-NR$^{22}$R$^{23}$, and the remaining substituents are as described above in the main embodiment.

According to another embodiment, the compound is of formula (Ic), $R^7$ is —O-alkyl$_{C1-C6}$, each of $R^4$, $R^5$, and $R^6$ is independently selected from H and halo, and the remaining substituents are as described above in the main embodiment.

According to another embodiment, the compound is of formula (Ic), $R^7$ is —O-methyl, $R^4$ is flouro, each of $R^5$ and $R^6$ is H, and the remaining substituents are as described above in the main embodiment.

According to another embodiment, the compound is of formula (Ic), $R^7$ is —O-methyl, $R^4$ is flouro, each of $R^5$ and $R^6$ is H, $R^3$ is methyl, and $R^{15}$ is —C(O)—CH$_2$—N(CH$_3$)(CH$_3$).

According to another embodiment, the compound is of formula (Ic), $R^7$ is —O-methyl, $R^4$ is flouro, each of $R^5$ and $R^6$ is H, $R^3$ is methyl, $R^{15}$ is —C(O)—CH$_2$—N(CH$_3$)(CH$_3$), and $R^{19}$ is H.

According to another embodiment, the compound is of formula (Id)

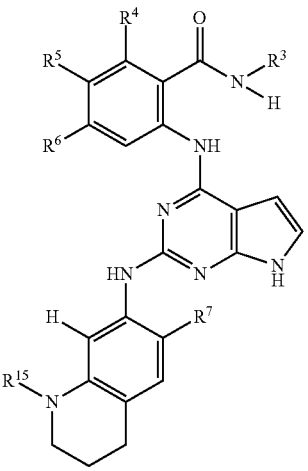

(Id)

wherein the substituents are as described above in the main embodiment.

According to another embodiment, the compound is of formula (Id), $R^7$ is —O-alkyl$_{C1-C6}$, and the remaining substituents are as described above in the main embodiment.

According to another embodiment, the compound is of formula (Id), $R^7$ is —O-alkyl$_{C1-C6}$, $R^{15}$ is —C(O)-alkylene$_{C0-C6}$-NR$^{22}$R$^{23}$, and the remaining substituents are as described above in the main embodiment.

According to another embodiment, the compound is of formula (Id), $R^7$ is —O-alkyl$_{C1-C6}$, each of $R^4$, $R^5$, and $R^6$ is independently selected from H and halo, and the remaining substituents are as described above in the main embodiment.

According to another embodiment, the compound is of formula (Id), $R^7$ is —O-methyl, $R^4$ is flouro, each of $R^5$ and $R^6$ is H, and the remaining substituents are as described above in the main embodiment.

According to another embodiment, the compound is of formula (Ie)

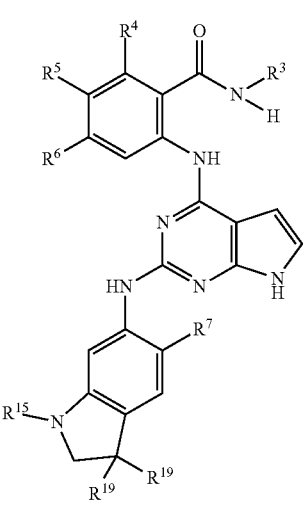

(Ie)

wherein the substituents are as described above in the main embodiment.

According to another embodiment, the compound is of formula (Ie), $R^7$ is —O-alkyl$_{C1-C6}$, and the remaining substituents are as described above in the main embodiment.

According to another embodiment, the compound is of formula (Ie), $R^7$ is —O-alkyl$_{C1-C6}$, $R^{15}$ is —C(O)-alkylene$_{C0-C6}$-NR$^{22}$R$^{23}$, and the remaining substituents are as described above in the main embodiment.

According to another embodiment, the compound is of formula (Ie), $R^7$ is —O-alkyl$_{C1-C6}$, each of $R^4$, $R^5$, and $R^6$ is independently selected from H and halo, and the remaining substituents are as described above in the main embodiment.

According to another embodiment, the compound is of formula (Ie), $R^7$ is —O-methyl, $R^4$ is flouro, each of $R^5$ and $R^6$ is H, and the remaining substituents are as described above in the main embodiment.

According to another embodiment, the compound is of a formula selected from the following formulas:

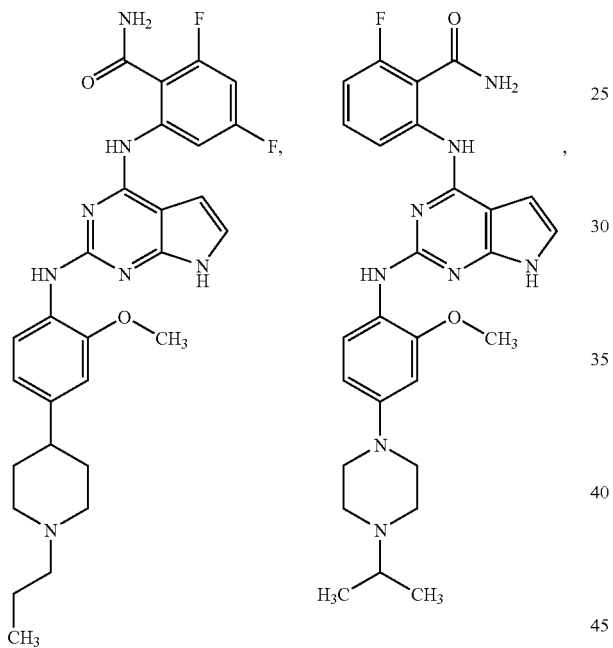

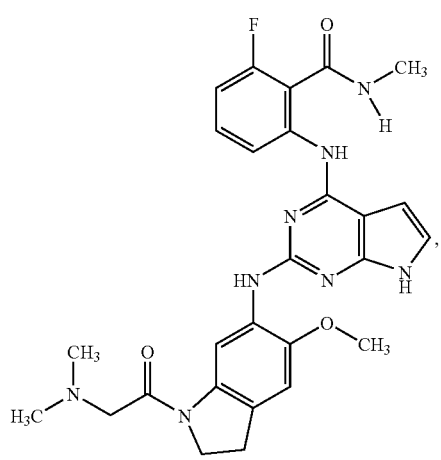

According to another embodiment, $R^3$ and $R^4$, together with the atoms to which they are bound, form a five or six membered lactam, and the remaining substituents are as described above in the main embodiment.

According to another embodiment, $R^5$ and $R^6$ together with the aryl to which they are attached form a napthalene, and the remaining substituents are as described above in the main embodiment.

According to another embodiment, the compound is in a solvated form.

According to another embodiment, the compound is in a hydrated form.

According to another embodiment, the compound is in a monohydrate form.

It is to be understood that the present invention includes all combinations and subsets of the particular groups defined herein, including the substituents as defined in the Summary defined hereinabove, as illustrated in the various examples throughout the specification, and as recited in the attached claims.

According to one embodiment of the invention, the invention is selected from the compounds consisting of:

2-[(2-{[2-methyl-4-(1-propyl-1,2,5,6-tetrahydro-3-pyridinyl)phenyl]amino}-1H-pyrrolo[2,3-d]pyrimidin-4-yl)amino]benzamide;

2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide;

2-[(2-{[2-(methyloxy)-4-(1-propyl-3-piperidinyl)phenyl]amino}-1H-pyrrolo[2,3-d]pyrimidin-4-yl)amino]benzamide;

2-[(2-{[2-(methyloxy)-4-(1-methyl-1,2,5,6-tetrahydro-3-pyridinyl)phenyl]amino}-1H-pyrolo[2,3-d]pyrimidin-4-yl)amino]benzamide;

2-[(2-{[2-(methyloxy)-4-(1-methyl-3-piperidinyl)phenyl]amino}-1H-pyrrolo[2,3-d]pyrimidin-4-yl)amino]benzamide;

2-[(2-{[4-[1-(1-methylethyl)-1,2,5,6-tetrahydro-3-pyridinyl]-2-(methyloxy)phenyl]amino}-1H-pyrrolo[2,3-d]pyrimidin-4-yl)amino]benzamide;

2-[(2-{[4-[4-(1-methylethyl)-1-piperazinyl]-2-(methyloxy)phenyl]amino}-1H-pyrrolo[2,3-d]pyrimidin-4-yl)amino]benzamide;

2-[(2-{[2-(methyloxy)-4-(4-propyl-1-piperazinyl)phenyl]amino}-1H-pyrrolo[2,3-d]pyrimidin-4-yl)amino]benzamide;

2-[(2-{[2-(methyloxy)-5-(4-methyl-1-piperazinyl)phenyl]amino}-1H-pyrrolo[2,3-d]pyrimidin-4-yl)amino]benzamide;

2-[(2-{[5-[4-(1-methylethyl)-1-piperazinyl]-2-(methyloxy)phenyl]amino}-1H-pyrrolo[2,3-d]pyrimidin-4-yl)amino]benzamide;

2-[(2-{[2-methyl-4-(4-morpholinyl)phenyl]amino}-1H-pyrrolo[2,3-d]pyrimidin-4-yl)amino]benzamide;

2-[(2-{[2-(methyloxy)-4-(4-morpholinyl)phenyl]amino}-1H-pyrrolo[2,3-d]pyrimidin-4-yl)amino]benzamide;

2-{[2-({5-[(N,N-dimethylglycyl)amino]-2-methylphenyl}amino)-1H-pyrrolo[2,3-d]pyrimidin-4-yl]amino}benzamide;

2-{[2-({2-methyl-5-[(1-pyrrolidinylacetyl)amino]phenyl}amino)-1H-pyrrolo[2,3-d]pyrimidin-4-yl]amino}benzamide;

2-[(2-{[5-[(N,N-dimethylglycyl)amino]-2-(methyloxy)phenyl]amino}-1H-pyrrolo[2,3-d]pyrimidin-4-yl)amino]benzamide;

2-{[2-({5-[(N,N-dimethylglycyl)amino]-2-[(trifluoromethyl)oxy]phenyl}amino)-1H-pyrrolo[2,3-d]pyrimidin-4-yl]amino}benzamide;

2-{[2-({5-[(N,N-dimethylglycyl)amino]-2-fluorophenyl}amino)-1H-pyrrolo[2,3-d]pyrimidin-4-yl]amino}benzamide;

2-{[2-({2-chloro-5-[(N,N-dimethylglycyl)amino]phenyl}amino)-1H-pyrrolo[2,3-d]pyrimidin-4-yl]amino}benzamide;

2-{[2-({2-(methyloxy)-4-[(methylsulfonyl)methyl]phenyl}amino)-1H-pyrrolo[2,3-d]pyrimidin-4-yl]amino}benzamide;

2-{[2-({2-(methyloxy)-5-[(methylsulfonyl)methyl]phenyl}amino)-1H-pyrrolo[2,3-d]pyrimidin-4-yl]amino}benzamide;

N-methyl-2-[(2-{[2-(methyloxy)-4-(1-methyl-1,2,5,6-tetrahydro-3-pyridinyl)phenyl]amino}-1H-pyrrolo[2,3-d]pyrimidin-4-yl)amino]benzamide;

N-methyl-2-[(2-{[2-(methyloxy)-4-(1-methyl-3-piperidinyl)phenyl]amino}-1H-pyrrolo[2,3-d]pyrimidin-4-yl)amino]benzamide;

N-methyl-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide;

N-methyl-2-[(2-{[2-(methyloxy)-4-(1-propyl-3-piperidinyl)phenyl]amino}-1H-pyrrolo[2,3-d]pyrimidin-4-yl)amino]benzamide;

N-methyl-2-[(2-{[4-[4-(1-methylethyl)-1-piperazinyl]-2-(methyloxy)phenyl]amino}-1H-pyrrolo[2,3-d]pyrimidin-4-yl)amino]benzamide;

2-{[2-({5-[(N,N-dimethylglycyl)amino]-2-methylphenyl}amino)-1H-pyrrolo[2,3-d]pyrimidin-4-yl]amino}-N-(2-hydroxyethyl)benzamide;

2-{[2-({5-[(N,N-dimethylglycyl)amino]-2-methylphenyl}amino)-1H-pyrrolo[2,3-d]pyrimidin-4-yl]amino}-N-[(4-fluorophenyl)methyl]benzamide;

2-{[2-({5-[(N,N-dimethylglycyl)amino]-2-methylphenyl}amino)-1H-pyrrolo[2,3-d]pyrimidin-4-yl]amino}-N-hydroxybenzamide;

3-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]-2-naphthalenecarboxamide;

3-{[2-({5-[(N,N-dimethylglycyl)amino]-2-methylphenyl}amino)-1H-pyrrolo[2,3-d]pyrimidin-4-yl]amino}-2-naphthalenecarboxamide;

2-methyl-6-[(2-{[4-[4-(1-methylethyl)-1-piperazinyl]-2-(methyloxy)phenyl]amino}-1H-pyrrolo[2,3-d]pyrimidin-4yl)amino]benzamide;

5-methyl-2-[(2-{[2-methyl-4-(1-propyl-1,2,5,6-tetrahydro-3-pyridinyl)phenyl]amino}-1H-pyrrolo[2,3-d]pyrimidin-4-yl)amino]benzamide;

5-methyl-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide;

2-{[2-({5-[(N,N-dimethylglycyl)amino]-2-methylphenyl}amino)-1H-pyrrolo[2,3-d]pyrimidin-4-yl]amino}-5-methylbenzamide;

4-methyl-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide;

2-(methyloxy)-6-[(2-{[2-(methyloxy)-4-(1-propyl-3-piperidinyl)phenyl]amino}-1H-pyrrolo[2,3-d]pyrimidin-4-yl)amino]benzamide;

5-(methyloxy)-2-[(2-{[2-methyl-4-(1-propyl-1,2,5,6-tetrahydro-3-pyridinyl)phenyl]amino}-1H-pyrrolo[2,3-d]pyrimidin-4-yl)amino]benzamide;

5-(methyloxy)-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide;

2-[(2-{[4-[(3S)-3-methyl-4-morpholinyl]-2-(methyloxy)phenyl]amino}-1H-pyrrolo[2,3-d]pyrimidin-4-yl)amino]-4-(methyloxy)benzamide;

2-fluoro-6-[(2-{[2-methyl-4-(1-propyl-1,2,5,6-tetrahydro-3-pyridinyl)phenyl]amino}-1H-pyrrolo[2,3-d]pyrimidin-4-yl)amino]benzamide;

2-fluoro-6-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide;

2-fluoro-6-[(2-{[2-(methyloxy)-4-(1-propyl-4-piperidinyl)phenyl]amino}-1H-pyrrolo[2,3-d]pyrimidin-4-yl)amino]benzamide;

2-fluoro-6-[(2-{[4-{4-[(3S)-3-fluoro-1-pyrrolidinyl]-1-piperidinyl}-2-(methyloxy)phenyl]amino}-1H-pyrrolo[2,3-d]pyrimidin-4-yl)amino]benzamide;

2-fluoro-6-[(2-{[4-{4-[(3R)-3-fluoro-1-pyrrolidinyl]-1-piperidinyl}-2-(methyloxy)phenyl]amino}-1H-pyrrolo[2,3-d]pyrimidin-4-yl)amino]benzamide;

2-[(2-{[4-(1,4'-bipiperidin-1-yl)-2-(methyloxy)phenyl]amino}-1H-pyrrolo[2,3-d]pyrimidin-4-yl)amino]-6-fluorobenzamide;

2-fluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide;

2-fluoro-6-[(2-{[4-[4-(1-methylethyl)-1-piperazinyl]-2,5-bis(methyloxy)phenyl]amino}-1H-pyrrolo[2,3-d]pyrimidin-4-yl)amino]benzamide;

2-fluoro-6-[(2-{[5-fluoro-4-[4-(1-methylethyl)-1-piperazinyl]-2-(methyloxy)phenyl]amino}-1H-pyrrolo[2,3-d]pyrimidin-4-yl)amino]benzamide;

2-fluoro-6-[(2-{4-[(3S)-3-methyl-4-morpholinyl]-2-(methyloxy)phenyl}amino)-1H-pyrrolo[2,3-d]pyrimidin-4-yl)amino]benzamide;

2-fluoro-6-[(2-{[3-methyl-4-[4-(1-methylethyl)-1-piperazinyl]-2-(methyloxy)phenyl]amino}-pyrrolo[2,3-d]pyrimidin-4-yl)amino]benzamide;

2-fluoro-6-[(2-{[3-fluoro-4-[4-(1-methylethyl)-1-piperazinyl]-2-(methyloxy)phenyl]amino}-1H-pyrrolo[2,3-d]pyrimidin-4-yl)amino]benzamide;

2-fluoro-6-({2-[(5-methyl-2-(methyloxy)-4-{4-[2-(methylsulfonyl)ethyl]-1-piperazinyl}phenyl)amino]-1H-pyrrolo[2,3-d]pyrimidin-4-yl}amino)benzamide;

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluorobenzamide;

5-fluoro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide;

5-fluoro-2-[(2-{[2-(methyloxy)-4-(1-methyl-1,2,5,6-tetrahydro-3-pyridinyl)phenyl]amino}-1H-pyrrolo[2,3-d]pyrimidin-4-yl)amino]benzamide;

5-fluoro-2-[(2-{[2-(methyloxy)-4-(1-methyl-3-piperidinyl)phenyl]amino}-1H-pyrrolo[2,3-d]pyrimidin-4-yl)amino]benzamide;

5-fluoro-2-[(2-{[2-(methyloxy)-5-(1-propyl-1,2,5,6-tetrahydro-3-pyridinyl)phenyl]amino}-1H-pyrrolo[2,3-d]pyrimidin-4-yl)amino]benzamide;

5-fluoro-2-[(2-{[4-[1-(1-methylethyl)-4-piperidinyl]-2-(methyloxy)phenyl]amino}-1H-pyrrolo[2,3-d]pyrimidin-4-yl)amino]benzamide;

5-fluoro-2-{[2-({2-(methyloxy)-4-[4-(4-morpholinyl)-1-pipeddinyl]phenyl}amino)-1H-pyrrolo[2,3-d]pyrimidin-4-yl]amino}benzamide;

5-fluoro-2-[(2-{[4-[4-(1-methylethyl)-1-piperazinyl]-2-(methyloxy)phenyl]amino}-1H-pyrrolo[2,3-d]pyrimidin-4-yl)amino]benzamide;

5-fluoro-2-[(2-{[4-[(3S)-3-methyl-4-morpholinyl]-2-(methyloxy)phenyl]amino}-1H-pyrrolo[2,3-d]pyrimidin-4-yl)amino]benzamide;

2-{[2-({5-[(N,N-dimethylglycyl)amino]-2-methylphenyl}amino)-1H-pyrrolo[2,3-d]pyrimidin-4-yl]amino}-5-fluorobenzamide;

2-{[2-({5-[(N,N-dimethylglycyl)amino]-2-[(trifluoromethyl)oxy]phenyl}amino)-1H-pyrrolo[2,3-d]pyrimidin-4-yl]amino}-5-fluorobenzamide;

2-[(2-{[5-{[3-(dimethylamino)propyl]oxy}-2-(methyloxy)phenyl]amino}-1H-pyrrolo[2,3-d]pyrimidin-4-yl)amino]-5-fluorobenzamide;

5-fluoro-N-methyl-2-[(2-{[4-[4-(1-methylethyl)-1-piperazinyl]-2-(methyloxy)phenyl]amino}-1H-pyrrolo[2,3-d]pyrimidin-4-yl)amino]benzamide;

5-fluoro-N-(2-hydroxyethyl)-2-[(2-{[4-[4-(1-methylethyl)-1-piperazinyl]-2-(methyloxy)phenyl]amino}-1H-pyrrolo[2,3-d]pyrimidin-4-yl)amino]benzamide;

N-(2-amino-2-oxoethyl)-4-fluoro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide;

5-bromo-2-[(2-{[4-[4-(1-methylethyl)-1-piperazinyl]-2-(methyloxy)phenyl]amino}-1H-pyrrolo[2,3-d]pyrimidin-4-yl)amino]benzamide;

2-{[2-({2-ethyl-4-[4-(1-methylethyl)-1-piperazinyl]phenyl}amino)-1H-pyrrolo[2,3-d]pyrimidin-4-yl]amino}-4-fluorobenzamide;

4-fluoro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide;

4-fluoro-2-[(2-{[2-(methyloxy)-4-(1-propyl-3-piperidinyl)phenyl]amino}-1H-pyrrolo[2,3-d]pyrimidin-4-yl)amino]benzamide;

4-fluoro-2-[(2-{[4-[1-(1-methylethyl)-1,2,3,6-tetrahydro-4-pyridinyl]-2-(methyloxy)phenyl]amino}-1H-pyrrolo[2,3-d]pyrimidin-4-yl)amino]benzamide;

4-fluoro-2-[(2-{[2-(methyloxy)-4-(1-propyl-4-piperidinyl)phenyl]amino}-1H-pyrrolo[2,3-d]pyrimidin-4-yl)amino]benzamide;

4-fluoro-2-[(2-{[4-[(3S)-3-hydroxy-1-piperidinyl]-2-(methyloxy)phenyl]amino}-1H-pyrrolo[2,3-d]pyrimidin-4-yl)amino]benzamide;

4-fluoro-2-[(2-{[4-{4-[(3R)-3-fluoro-1-pyrrolidinyl]-1-piperidinyl}-2-(methyloxy)phenyl]amino}-1H-pyrrolo[2,3-d]pyrimidin-4-yl)amino]benzamide;

4-fluoro-2-[(2-{[4-{4-[(3S)-3-fluoro-1-pyrrolidinyl]-1-piperidinyl}-2-(methyloxy)phenyl]amino}-1H-pyrrolo[2,3-d]pyrimidin-4-yl)amino]benzamide;

2-[(2-{[4-(3,3-difluoro-1,4'-bipiperidin-1'-yl)-2-(methyloxy)phenyl]amino}-1H-pyrrolo[2,3-d]pyrimidin-4-yl)amino]-4-fluorobenzamide;

4-fluoro-2-{[2-({2-(methyloxy)-4-[4-(4-morpholinyl)-1-pipendinyl]phenyl}amino)-1H-pyrrolo[2,3-d]pyrimidin-4-yl]amino}benzamide;

4-fluoro-2-[(2-{[4-[4-(1-methylethyl)-1-piperazinyl]-2-(methyloxy)phenyl]amino}-1H-pyrrolo[2,3-d]pyrimidin-4-yl)amino]benzamide;

4-fluoro-2-{[2-({2-(methyloxy)-4-[4-(2-methylpropyl)-1-piperazinyl]phenyl}amino)-1H-pyrrolo[2,3-d]pyrimidin-4-yl]amino}benzamide;

2-[(2-{[4-[4-(cyclopropylmethyl)-1-piperazinyl]-2-(methyloxy)phenyl]amino}-1H-pyrrolo[2,3-d]pyrimidin-4-yl)amino]-4-fluorobenzamide;

4-fluoro-2-[(2-{[4-[4-(1-methylethyl)-1-piperazinyl]-2,5-bis(methyloxy)phenyl]amino}-1H-pyrrolo[2,3-d]pyrimidin-4-yl)amino]benzamide;

4-fluoro-2-[(2-{[2-(methyloxy)-4-(4-morpholinyl)phenyl]amino}-1H-pyrrolo[2,3-d]pyrimidin-4-yl)amino]benzamide;

4-fluoro-2-[(2-{[4-[(3S)-3-methyl-4-morpholinyl]-2-(methyloxy)phenyl]amino}-1H-pyrrolo[2,3-d]pyrimidin-4-yl)amino]benzamide;

2-{[2-({5-[(N,N-dimethylglycyl)amino]-2-methylphenyl}amino)-1H-pyrrolo[2,3-d]pyrimidin-4-yl]amino}-4-fluorobenzamide;

2-[(2-{[5-{[(2S)-3-(dimethylamino)-2-hydroxypropyl]oxy}-2-(methyloxy)phenyl]amino}-1H-pyrrolo[2,3-d]pyrimidin-4-yl)amino]-4-fluorobenzamide;

4-fluoro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]-N-[(1S)-1-methylpropyl]benzamide;

4-fluoro-2-[(2-{[4-[4-(1-methylethyl)-1-piperazinyl]-2-(methyloxy)phenyl]amino}-1H-pyrrolo[2,3-d]pyrimidin-4-yl)amino]-6-(methyloxy)benzamide;

2,4-difluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide;

2,4-difluoro-6-[(2-{[4-[(3S)-3-methyl-4-morpholinyl]-2-(methyloxy)phenyl]amino}-1H-pyrrolo[2,3-d]pyrimidin-4-yl)amino]benzamide;

2,4-difluoro-6-[(2-{[5-methyl-4-[4-(1-methylethyl)-1-piperazinyl]-2-(methyloxy)phenyl]amino}-1H-pyrrolo[2,3-d]pyrimidin-4-yl)amino]benzamide;

2,4-difluoro-6-[(2-{[2-(methyloxy)-4-(1-propyl-4-piperidinyl)phenyl]amino}-1H-pyrrolo[2,3-d]pyrimidin-4-yl)amino]benzamide;

4-chloro-2-fluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide;

2,3-difluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide;

4,5-difluoro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide;

4,5-difluoro-2-[(2-{[4-[1-(1-methylethyl)-1,2,5,6-tetrahydro-3-pyridinyl]-2-(methyloxy)phenyl]amino}-1H-pyrrolo[2,3-d]pyrimidin-4-yl)amino]benzamide;

4,5-difluoro-2-[(2-{[4-[1-(1-methylethyl)-4-piperidinyl]-2-(methyloxy)phenyl]amino}-1H-pyrrolo[2,3-d]pyrimidin-4-yl)amino]benzamide;

4,5-difluoro-2-[(2-{[2-(methyloxy)-4-(1-propyl-4-piperidinyl)phenyl]amino}-1H-pyrrolo[2,3-d]pyrimidin-4-yl)amino]benzamide;

4,5-difluoro-2-[(2-{[4-(4-hydroxy-1-piperidinyl)-2-(methyloxy)phenyl]amino}-1H-pyrrolo[2,3-d]pyrimidin-4-yl)amino]benzamide;

2-[(2-{[4-(1,4'-bipiperidin-1'-yl)-2-(methyloxy)phenyl]amino}-1H-pyrrolo[2,3-d]pyrimidin-4-yl)amino]-4,5-difluorobenzamide;

4,5-difluoro-2-{[2-({2-(methyloxy)-4-[4-(4-morpholinyl)-1-piperidinyl]phenyl}amino)-1H-pyrrolo[2,3-d]pyrimidin-4-yl]amino}benzamide;

4,5-difluoro-2-[(2-{[4-[4-(1-methylethyl)-1-piperazinyl]-2-(methyloxy)phenyl]amino}-1H-pyrrolo[2,3-c]pyrimidin-4-yl)amino]benzamide;

2-[(2-{[4-(4-acetyl-1-piperazinyl)-2-(methyloxy)phenyl]amino}-1H-pyrrolo[2,3-d]pyrimidin-4-yl)amino]-4,5-difluorobenzamide;

4,5-difluoro-2-[(2-{[2-(methyloxy)-4-(4-morpholinyl)phenyl]amino}-1H-pyrrolo[2,3-d]pyrimidin-4-yl)amino]benzamide;

4,5-difluoro-2-[(2-{[4-[(3S)-3-methyl-4-morpholinyl]-2-(methyloxy)phenyl]amino}-1H-pyrrolo[2,3-d]pyrimidin-4-yl)amino]benzamide;

2-{[2-({5-[(N,N-dimethylglycyl)amino]-2-methylphenyl}amino)-1H-pyrrolo[2,3-d]pyrimidin-4-yl]amino}-4,5-difluorobenzamide;

4,5-difluoro-2-[(2-{[5-{[(2S)-2-hydroxy-3-(1-pyrrolidinyl)propyl]oxy}-2-(methyloxy)phenyl]amino}-1H-pyrrolo[2,3-d]pyrimidin-4-yl)amino]benzamide;

5-chloro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide;

5-chloro-2-{[2-({5-[(N,N-dimethylglycyl)amino]-2-methylphenyl}amino)-1H-pyrrolo[2,3-d]pyrimidin-4-yl]amino}benzamide;

4-chloro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide;

4-chloro-2-{[2-({5-[(N,N-dimethylglycyl)amino]-2-methylphenyl}amino)-1H-pyrrolo[2,3-d]pyrimidin-4-yl]amino}benzamide;

2-fluoro-6-({2-[(2-(methyloxy)-4-{1'-[2-(methylsulfonyl)ethyl]-4,4'-bipiperidin-1-yl}phenyl)amino]-1H-pyrrolo[2,3-d]pyrimidin-4-yl}amino)benzamide;

2-fluoro-6-({2-[(2-(methyloxy)-4-{4-[4-(methylsulfonyl)-1-piperazinyl]-1-piperidinyl}phenyl)amino]-1H-pyrrolo[2,3-d]pyrimidin-4-yl}amino)benzamide;

2-fluoro-6-[(2-{[4-{4-[4-(2-fluoroethyl)-1-piperazinyl]-1-piperidinyl}-2-(methyloxy)phenyl]amino}-1H-pyrrolo[2,3-d]pyrimidin-4-yl)amino]benzamide;

2-fluoro-6-[(2-{[2-(methyloxy)-4-(4-{4-[2-(methylsulfonyl)ethyl]-1-piperazinyl}-1-piperidinyl)phenyl]amino}-1H-pyrrolo[2,3-d]pyrimidin-4-yl)amino]benzamide;

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluoro-N-methylbenzamide;

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-4,6-difluoro-N-methylbenzamide; and 2-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-6-fluoro-N-methylbenzamide.

Specific examples of compounds of the present invention include those recited in the Examples which follow, and pharmaceutically acceptable salts or solvates thereof.

It will be appreciated by those skilled in the art that the compounds of the present invention may be utilized in the form of a pharmaceutically acceptable salt or solvate. The pharmaceutically acceptable salts of the compounds of formula (I) include conventional salts formed from pharmaceutically acceptable (i.e., non-toxic) inorganic or organic acids or bases as well as quaternary ammonium salts. Representative salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, such as oxalic, which are not themselves pharmaceutically acceptable, may be useful in the preparation of salts useful as intermediates in obtaining compounds of this invention and these form a further aspect of the invention.

Processes for preparing pharmaceutically acceptable salts and solvates of compounds such as the compounds of formula (I) are conventional in the art. See, e.g., Burger's Medicinal Chemistry And Drug Discovery 5th Edition, Vol 1: Principles And Practice.

As will be apparent to those skilled in the art, in the processes described below for the preparation of compounds of formula (I) certain intermediates may be in the form of pharmaceutically acceptable salts or solvates of the compound. Those terms as applied to any intermediate employed in the process of preparing compounds of formula (I) have the same meanings as noted above with respect to compounds of formula (I). Processes for preparing pharmaceutically acceptable salts and solvates of intermediates are known in the art and are analogous to the process for preparing pharmaceutically acceptable salts and solvates of compounds such as the compounds of formula (I).

The compounds of this invention may be in crystalline or non-crystalline form, and, if crystalline, may optionally be hydrated or solvated. This invention includes within its scope stoichiometric hydrates as well as compounds containing variable amounts of water.

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. It is understood that compounds of formula (I) may exist in tautomeric forms other than that shown in the formula and these are also included within the scope of the present invention.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

The compounds of the present invention are inhibitors of one or more IGFR family receptors. By "IGFR inhibitor" is meant a compound which exhibits a $pIC_{50}$ of greater than 5.5 against at least one IGFR family receptor in the IGFR inhibition enzyme assay described below (TR-FRET) and/or an $IC_{50}$ of below about 1.0 µM potency against IGFR cellular autophosphorylation and/or in cell proliferation of a cell line that is dependent upon IGF signaling (e.g. Colo205, NCI-H929) in at least one of the cellular assay described below. In a more particular embodiment "IGFR inhibitor" refers to a compound which exhibits a $pIC_{50}$ of greater than 7.6 against at least one IGFR family receptor in the IGFR inhibition enzyme assay described below. In an alternative particular embodiment "IGFR inhibitor" refers to a compound which exhibits an $IC_{50}$ of below about 250 nM potency against IGFR cellular autophosphorylation and/or in cell proliferation of a cell line that is dependent upon IGF signaling (e.g. Colo205, NCl-H929) in at least one of the cellular assay described below.

The present invention is not limited to compounds of formula (I) which are selective for IGFR family receptor kinases; rather, the present invention expressly contemplates compounds of formula (I) which may also possess activity against receptors in addition to the IGFR family receptors. For instance, the compounds of formula (I) are selective for insulin receptor (IR) family kinases. Several compounds of the present invention also possess activity against, for instance, one or more of the Jnk1, Jnk2, and Jnk3, insulin related receptor (IRR), and anaplastic lymphoma kinase (ALK).

With regard to Anaplastic lymphoma kinase, ALK is a receptor tyrosine kinase believed to be involved in the pathogenesis of various cancers, and is named for its involvement in anaplastic large cell lymphoma (ALCL), a sub-type of non-Hodgkins lymphoma (Chiarle et al. (2008) Nature 8, 11-23).

Dysregulated activation of ALK in cancers is believed to occur primarily by fusion of the C-terminal intracellular domain containing the catalytic activity with one of several proteins having an oligomerization domain that drives the dimerization of the receptor (Duyster et al (2001) Oncogene 20, 5623-5637). Dimerization of the ALK fusion proteins results in autophosphorylation and activation of downstream signal transduction cascades, ultimately leading to uncontrolled cell proliferation. Full-length ALK expression with or without gene amplification has been observed in neuroblastomas, rhabdomyosarcomas, and breast cancer in the absence of gene fusion (Chiarle et al. (2008)).

ALK fusions are found in some cases of inflammatory myofibroblastic tumors and rare cases of diffuse large B-cell lymphomas (DLBCL). In these cases, fusion of the ALK gene may play a role in tumorigenesis (Chiarle et al. (2008)). NPM-ALK has been found to be a transforming oncogene in in vitro models [Bai et al. (1998) Mol. Cell Biol. 18, 6951-6961) and in transgenic mice (Chiarle et al. (2003) Blood 101, 1919-1927), where expression of NPM-ALK in bone marrow precursor cells results in B-and T-cell lymphomas. More recently, fusions of ALK have been observed in lung cancers (Soda et al. (2007) Nature 448, 561-567; Rikova et al. (2007) Cell, 131, 1190-1203; Inamura et al. (2008) J. Thoracic Oncol. 3, 13-17; Koivenen et al, (2008) AACR Annual Meeting, San Diego, Calif., Abstract No. 2373).

Previously, a potent selective inhibitor of ALK, NVP-TAE68 (5-chloro-2,4-diaminophenylpyrimidine), has been shown to be active against ALCL cells in vitro and in tumor xenograft models (Galkin et al (2007) Proc. Natl. Acad. Sci. U.S.A. 104, 270-275). The compound inhibited ALK autophosphorylation, resulting in cell cycle arrest and apoptosis. PF2341066, a dual inhibitor of the Met tyrosine kinase and ALK has also been shown to inhibit the growth of ALCL cells in experimental systems in vitro and in vivo (Christensen et al. (2007) Mol. Cancer Ther. 6, 3314-3322). A series of fused pyrrolocarbazole-derived molecules (Wan et al. (2006) Blood, 107, 1617-1623), pyrazoloisoquinolines ((Li and Morris (2007)), and 5-aryl-pyridine-carboximides (Li et al (2006) J. Med. Chem. 49, 1006-1015) have also been reported to inhibit ALK activity and the proliferation of ALCL cells in vitro.

The present invention further provides compounds of formula (I) for use in medical therapy in a mammal, e.g. a human. In particular, the present invention provides compounds of formula (I) for use in the treatment of a condition mediated by at least one IGFR family receptor in a mammal, and, advantageously, conditions mediated by inappropriate activity of one or more IGFR family receptor in a mammal.

The inappropriate IGFR family receptor activity referred to herein is any IGFR receptor activity that deviates from the normal IGFR family receptor activity expected in a particular mammalian subject. Inappropriate IGFR family receptor activity may take the form of, for instance, an abnormal increase in activity, or an aberration in the timing and/or control of IGFR family receptor activity. Such inappropriate activity may result then, for example, from overexpression or mutation of the protein kinase or ligand leading to inappropriate or uncontrolled activation of the receptor. Furthermore, it is also understood that unwanted IGFR family receptor activity may reside in an abnormal source, such as a malignancy. That is, the level of IGFR family activity does not have to be abnormal to be considered inappropriate, rather the activity derives from an abnormal source.

The compounds of formula (I) and salts and solvates thereof, are believed to have anticancer and antitumor activity as a result of inhibition of one or more IGFR family receptor and its effect on selected cell lines whose growth is dependent on IGFR family activity.

The present invention provides compounds of formula (I) for use in the treatment of a susceptible neoplasm. "Susceptible neoplasm" as used herein refers to neoplasms which are susceptible to treatment with a IGFR inhibitor. Neoplasms which have been associated with inappropriate activity of one or more IGFR family receptors and are therefor susceptible to treatment with a IGFR inhibitor are known in the art, and include both primary and metastatic tumors and cancers. For example, susceptible neoplasms within the scope of the present invention include but are not limited to breast cancer, sarcomas, lung cancer (including non-small cell lung carcinoma), prostate cancer, colorectal cancer, renal cancer, pancreatic cancer, hematologic cancers (including multiple myeloma), neuroblastomas, gliomas, head and neck cancer, thyroid cancer, hepatocarcinoma, ovarian cancer, vulval cancer, cervical cancer, endometrial cancer, testicular cancer, bladder cancer, esophageal cancer, gastric cancer, nasopharangeal cancer, buccal cancer, cancer of the mouth, gastrointestinal stromal tumor, and skin cancer (including melanoma). More particularly, susceptible neoplasms may be selected from breast cancer, sarcoma, lung cancer, non-small cell lung carcinoma, prostate cancer, colorectal cancer, pancreatic cancer, hematologic cancers, multiple myeloma, head and neck cancer, and ovarian cancer.

The present invention provides methods for the treatment of several conditions in a mammal in need thereof, all of which comprise the step of administering a therapeutically effective amount of a compound of formula (I). The mammal in need of treatment with a compound of the present invention is advantageously a human.

As used herein, the term "treatment" refers to alleviating the specified condition, eliminating or reducing the symptoms of the condition, slowing or eliminating the progression of the condition and preventing or delaying the reoccurrance of the condition in a previously afflicted subject.

As used herein, the term "therapeutically effective amount" means an amount of a compound of formula (I) which is sufficient, in the subject to which it is administered, to elicit the biological or medical response of a cell culture, tissue, system, mammal (including human) that is being sought, for instance, by a researcher or clinician. The term also includes within its scope amounts effective to enhance normal physiological function. For example, a therapeutically effective amount of a compound of formula (I) for the treatment of a condition mediated by at least one IGFR family receptor is an amount sufficient to treat the condition in the subject. Similarly, a therapeutically effective amount of a compound of formula (I) for the treatment of a susceptible neoplasm is an amount sufficient to treat the susceptible neoplasm in the subject. In one embodiment of the present invention, a therapeutically effective amount of a compound of formula (I) is an amount sufficient to regulate, modulate, bind or inhibit at least one IGFR family receptor.

The precise therapeutically effective amount of the compounds of formula (I) will depend on a number of factors including, but not limited to, the age and weight of the subject being treated, the precise condition requiring treatment and its severity, the nature of the formulation, and the route of administration, and will ultimately be at the discretion of the attendant physician or veterinarian. Typically, the compound of formula (I) will be given for treatment in the range of 0.1 to 200 mg/kg body weight of recipient (mammal) per day and more usually in the range of 1 to 100 mg/kg body weight per day. Acceptable daily dosages, may be from about 0.1 to about 2000 mg/day, and preferably from about 0.1 to about 100 mg/day. Thus, for a 70 kg adult human being treated for a condition mediated by at least one IGFR family receptor, the actual amount per day would usually be from 5 to 700 mg and this amount may be given in a single dose per day or more usually in a number (such as two, three, four, five or six) of sub-doses per day or, alternatively, on an alternative dosing schedule such as weekly or monthly, such that the total daily dose is the same. A therapeutically effective amount of a salt or solvate, may be determined as a proportion of the therapeutically effective amount of the compound of formula (I) per se. It is envisaged that similar dosages would be appropriate for treatment of the other conditions referred to above.

The present invention also provides the use of a compound of formula (I) for the preparation of a medicament for the treatment of condition mediated by at least one IGFR family receptor in a mammal (e.g., a human) in need thereof. The present invention further provides the use of a compound of formula (I) for the preparation of a medicament for the treatment of a susceptible neoplasm in a mammal.

While it is possible that, for use in therapy, a therapeutically effective amount of a compound of formula (I) may be administered as the raw chemical, it is typically presented as the active ingredient of a pharmaceutical composition or formulation. Accordingly, the invention further provides a pharmaceutical composition comprising a compound of the formula (I). The pharmaceutical composition may further comprise one or more pharmaceutically acceptable carriers, diluents, and/or excipients. The carrier(s), diluent(s) and/or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I) with one or more pharmaceutically acceptable carriers, diluents and/or excipients.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) may be administered by inhalation, such as by metered dose pressurised aerosols, metered dose inhalers, dry powder inhalers, nebulizers or insufflators.

According to one embodiment, the compound is provided in the form of a dry powder composition. As such, the composition is suitable for inhaled administration and may be incorporated into a plurality of sealed dose containers (e.g. containing the dry powder composition) mounted in a strip or ribbon inside a suitable inhalation device. The container is rupturable or peel-openable on demand and the dose of the dry powder composition may be administered by inhalation via a device such as the DISKUS™ device, marketed by GlaxoSmithKline. The DISKUS™ inhalation device is, for example, described in GB2242134A.

According to another embodiment, the compounds of formula (I) may be formulated into spray compositions for inhalation which may, for example, be formulated as aqueous solutions or suspensions or as aerosols delivered from pressurised packs, such as a metered dose inhaler (MDI), with the use of a suitable liquefied propellant. Aerosol compositions suitable for inhalation can be either a suspension or a solution and generally contain a compound of formula (I) or a pharmaceutically acceptable salt or solvate thereof and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid, lecithin or an oligolactic acid derivative e.g. as described in WO94/21229 and WO98/34596 and cosolvents e.g. ethanol.

The compounds of formula (I) can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations. Pharmaceutical formulations adapted for parenteral administration include aqueous and non-aqueous sterile injection solutions which may contain anti-oxidants, buffers, bacteriostats and solutes which render the formulation near isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

In the above-described methods of treatment and uses, a compound of the invention may be employed alone, in combination with one or more other compounds of the invention, or in combination with other therapeutic methods or agents. In particular, in methods of treating a condition improved by inhibition of IGF-1R and in methods of treating susceptible neoplasms, the compound of the invention may be used alone or in combination with one or more of a chemotherapeutic, a hormonal and/or antibody agent, surgical therapy, and radiotherapy.

The term "chemotherapeutic" as used herein refers to any chemical agent having a therapeutic effect on the subject to which it is administered. "Chemotherapeutic" agents include but are not limited to anti-neoplastic agents, analgesics and anti-emetics. As used herein, "anti-neoplastic agents" include both cytostatic and cytotoxic agents. Anti-emetics include but are not limited to $5HT_3$ antagonists such as ondansetron, granisetron, and the like; metaclopromide; dexamethasone and neurokinin-1 antagonists.

As an additional aspect, the present invention provides the methods of treatment and uses as described above, which comprise administering a compound of the invention together with at least one chemotherapeutic agent. In one particular embodiment, the chemotherapeutic agent is an anti-neoplastic agent. In another embodiment, the present invention provides a pharmaceutical composition as described above further comprising at least one other chemotherapeutic agent, more particularly, the chemotherapeutic agent is an anti-neoplastic agent.

The compounds of the invention and at least one additional anti-neoplastic therapy may be employed in combination concomitantly or sequentially in any therapeutically appropriate combination. The administration of a compound of the invention with one or more other anti-neoplastic agents may be in combination in accordance with the invention by administration concomitantly in (1) a unitary pharmaceutical composition including both or all compounds or (2) separate pharmaceutical compositions each including one of the compounds. The combination may be administered separately in a sequential manner wherein one anti-neoplastic agent is administered first and the other(s) second or vice versa. Such sequential administration may be close in time or remote in time.

When a compound of the invention is used in combination with a chemotherapeutic agent, the dose of each compound may differ from that when the compound is used alone. Appropriate doses will be readily appreciated by those skilled in the art. The appropriate dose of the compound(s) of the invention and the other therapeutically active agent(s) and the relative timings of administration will be selected in order to achieve the desired combined therapeutic effect, and are within the expertise and discretion of the attendant clinician.

Among the many chemotherapeutic agents, which may be used in combination with a compound of the present invention, are anti-proliferative/anti-neoplastic agents. Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms. Both types of anti-neoplastic agents may be employed in combination with the compounds of the present invention.

Typically, any chemotherapeutic agent that has activity against a susceptible neoplasm being treated may be utilized in combination with the compounds the invention, provided that the particular agent is clinically compatible with therapy employing a compound of the invention. Typical anti-neoplastic agents useful in the present invention include, but are not limited to: alkylating agents, anti-metabolites, antitumor antibiotics, antimitotic agents, topoisomerase I and II inhibitors, hormones and hormonal analogues, matrix metalloprotease inhibitors; signal transduction pathway inhibitors including inhibitors of cell growth or growth factor function, angiogenesis inhibitors, and serine/threonine inhibitors; cyclin dependent kinase inhibitors; antisense therapies and immunotherapeutic agents.

Examples of alkylating agents include but are not limited to: nitrogen mustards such as cyclophosphamides, temozolamide, melphalan, and chlorambucil; oxazaphosphor-ines; alkyl sulfonates such as busulfan; nitrosoureas such as carmustine; triazenes such as dacarbazine; and platinum coordination complexes such as cisplatin, oxapliplatin and carboplatin.

Examples of antimetabolite anti-neoplastic agents include purine and pyrimidine analogues and anti-folate compounds, and more specifically, hydroxyurea, cytosine, arabinoside, raltitrexed, tegafur, fluorouracil (e.g., 5FU), methotrexate, cytarabine, mecaptopurine and thioguanine.

Examples of antitumor antibiotic agents include, but are not limited to, actinomycins such as dactinomycin, mitomycin-C, anthracyclins such as daunorubicin, doxorubicin, idarubicin, epirubicin; daunomycin, adriamycin and bleomycins.

Examples of antimitotic agents include, but are not limited to, diterpenoids, vinca alkaloids, polo-like kinase (PLK) inhibitors and CenpE inhibitors. Examples of diterpenoids include, but are not limited to, taxol, taxotere, paclitaxel and its analog docetaxel. Examples of vinca alkaloids include, but are not limited to, vinblastine, vincristine, vindesine and vinorelbine. PLK inhibitors are discussed further below.

Examples of topoisomerase I inhibitors include camptothecins, such as amsacrine, irinotecan, topotecan, and the various optical forms of 7-(4-methylpiperazino-methylene)-10, 11-ethylenedioxy-20-camptothecin. Examples of topoisomerase II inhibitors include epipodophyllotoxins, such as etoposide and teniposide.

Examples of hormones and hormonal analogues believed to be useful in the treatment of neoplasms include, but are not limited to: antiestrogens, such as tamoxifen, toremifene, raloxifene, fulvestrant, iodoxyfene and droloxifene; anti-androgens; such as flutamide, nilutamide, bicalutamide and cyproterone acetate; adrenocorticosteroids such as prednisone and prednisolone; aminoglutethimide and other aromatase inhibitors such as anastrozole, letrazole, vorazole, and exemestane; progestrins such as megestrol acetate; 5α-reductase inhibitors such as finasteride and dutasteride; and gonadotropin-releasing hormones (GnRH) and analogues thereof, such as Leutinizing Hormone-releasing Hormone (LHRH) agonists and antagagonists such as goserelin luprolide, leuprorelin and buserelin.

An example of a matrix metalloproteinases (MMP) inhibitor is marimastat.

Signal transduction pathway inhibitors useful in the present invention include, but are not limited to, inhibitors of receptor tyrosine kinases, non-receptor tyrosine kinases, SH2/SH3 domain blockers, serine/threonine kinases, phosphatidyl inositol-3-OH kinases, myo-inositol signaling, and Ras oncogenes (e.g. farnesyltransferase, geranyl-geranyl transferase, and CAAX proteases as well as anti-sense oligonucleotides, ribozymes and immunotherapy).

Several protein tyrosine kinases catalyse the phosphorylation of specific tyrosyl residues in various proteins involved in the regulation of cell growth. Such protein tyrosine kinases can be broadly classified as receptor or non-receptor kinases.

Examples of receptor tyrosine kinases, also known as "growth factor receptor inhibitors", in addition to IGF-1R inhibitors, include but are not limited to inhibitors of: epidermal growth factor family receptors (EGFR, ErbB2, and ErbB4); platelet derived growth factor receptors (PDGFRs), vascular endothelial growth factor receptors (VEGFRs), tyrosine kinase with immunoglobulin-like and epidermal growth factor homology domains (TIE-2), macrophage colony stimulating factor (c-fms), c-kit, c-met, fibroblast growth factor receptors (FGFRs), hepatocyte growth factor receptors (HGFRs), Trk receptors (TrkA, TrkB, and TrkC), ephrin (Eph) receptors, the RET protooncogene, and Akt kinases.

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the compounds of the present invention in any of the compositions and methods/uses described herein. Trastuzumab (Herceptin®) is an example of an anti-erbB2 antibody inhibitor of growth factor function. One example of an anti-erbB1 antibody inhibitor of growth factor function is cetuximab (Erbitux™, C225). Examples of small molecule inhibitors of epidermal growth factor receptors include but are not limited to lapatinib (Tykerb™), erlotinib (TARCEVA®), gefitinib (IRESSA®), canetinib or CI1033. Imitanib is one example of a PDGFR inhibitor. Examples of VEGFR inhibitors include pazopanib, ZD6474, AZD2171, PTK787, SU11248 and sunitinib.

Tyrosine kinases that are not growth factor receptor kinases are termed non-receptor tyrosine kinases. Inhibitors of non-receptor tyrosine kinases are sometimes referred to as "anti-metastatic agents" and are useful in the present invention. Targets or potential targets of anti-metastatic agents, include, but are not limited to, c-Src, Lck, Fyn, Yes, Jak, abl kinase (c-Abl and Bcr-Abl), FAK (focal adhesion kinase) and Bruton's tyrosine kinase (BTK). Non-receptor kinases and agents, which inhibit non-receptor tyrosine kinase function, are described in Sinha, S. and Corey, S. J., (1999) J. Hematother. Stem Cell Res. 8:465-80; and Bolen, J. B. and Brugge, J. S., (1997) Annu. Rev. of Immunol. 15:371-404.

SH2/SH3 domain blockers are agents that disrupt SH2 or SH3 domain binding in a variety of enzymes or adaptor proteins including, but not limited to, PI3-K p85 subunit, Src family kinases, adaptor molecules (Shc, Crk, Nck, Grb2) and Ras-GAP. Examples of Src inhibitors include but are not limited to dasatinib and BMS-354825 (J. Med. Chem (2004) 47:6658-6661).

Examples of serine/threonine kinase inhibitors include, but are not limited to polo-like kinase inhibitors (Plk family e.g., Plk1, Plk2, and Plk3),such as 5-{6-[(4-Methylpiperazin-1-yl) methyl]-1H-benzimidazol-1-yl}-3-{(1R)-1-[2-(trifluoromethyl)phenyl]ethoxy}thiophene-2-carboxamide; MAP kinase cascade blockers, which include Ras/Raf kinase inhibitors, mitogen or extracellular regulated kinases (MEKs), and extracellular regulated kinases (ERKs); Aurora kinase inhibitors (including inhibitors of Aurora A and Aurora B); protein kinase C (PKC) family member blockers; inhibitors of kappa-B (IkB) kinase family (IKK-alpha, IKK-beta); PKB/Akt kinase family inhibitors; and inhibitors of TGF-beta receptor kinases. Examples of Plk inhibitors are described in PCT Publication No. WO04/014899 to Glaxo-SmithKline.

Inhibitors of urokinase, also referred to as urokinase-type Plasminogen Activator (uPA), expression may be used in combination with the compounds of the present invention in the compositions and methods described above.

Inhibitors of kinases involved in the IGF signalling axis may also be useful in combination with the compounds of the present invention. Such inhibitors include but are not limited to inhibitors of JNK1/2/3, PI3K, AKT and MEK, and 14.3.3 signalling inhibitors.

Cell cycle signaling inhibitors, including inhibitors of cyclin dependent kinases (CDKs) are also useful in combination with the compounds of the invention in the compositions and methods described above. Examples of cyclin dependent kinases, including CDK2, CDK4, and CDK6 and inhibitors for the same are described in, for instance, Rosania G. R., et al., Exp. Opin. Ther. Patents (2000) 10:215-230.

Receptor kinase angiogenesis inhibitors may also find use in the present invention. Inhibitors of angiogenesis related to VEGFR and TIE-2 are discussed above in regard to signal transduction inhibitors (both are receptor tyrosine kinases). Other inhibitors may be used in combination with the compounds of the present invention. For example, anti-VEGF antibodies, which do not recognize VEGFR (the receptor tyrosine kinase), but bind to the ligand; small molecule inhibitors of integrin (alpha$_v$, beta$_3$) that inhibit angiogenesis; endostatin and angiostatin (non-RTK) may also prove useful in combination with the compounds of the invention. One example of a VEGFR antibody is bevacizumab (Avastin™).

Inhibitors of phosphotidyl inositol-3-OH kinase family members including blockers of PI3-kinase, ATM, DNA-PK, and Ku may also be useful in combination with the present invention.

Also of potential use in combination with the compounds of the invention are myo-inositol signaling inhibitors such as phospholipase C blockers and myoinositol analogues.

Examples of antisense therapies include those directed towards the targets described above such as ISIS 2503 and gene therapy approaches such as those using thymidine kinase or cytosine deaminase.

Agents used in immunotherapeutic regimens may also be useful in combination with the compounds of the invention. Immunotherapeutic regimens include ex-vivo and in-vivo approaches to increasing immunogenicity of patient tumor cells such as transfection with cytokines (IL-2, IL-4, gMCFS and MCFS), approaches to increase T-cell activity, approaches with transfected immune cells and approaches with anti-idiotypic antibodies.

Agents used in proapoptotic regimens (e.g., Bcl-2 antisense oligonucleotides) may also be used in combination with the compounds of the invention. Members of the Bcl-2 family of proteins block apoptosis. Upregulation of Bcl-2 has therefore been linked to chemoresistance. Studies have shown that the epidermal growth factor (EGF) stimulates anti-apoptotic members of the Bcl-2 family (i.e., mcl-1). Therefore, strategies designed to downregulate the expression of Bcl-2 in tumors have demonstrated clinical benefit and are now in Phase II/III trials, namely Genta's G3139 bcl-2 antisense oligonucleotide. Such proapoptotic strategies using the antisense oligonucleotide strategy for Bcl-2 are discussed in Water, J. S., et al., J. Clin. Oncol. (2000) 18:1812-1823; and Kitada, S., et al., Antisense Res. Dev. (1994) 4:71-79.

Compounds of formula (I) may be prepared using the processes described below. In all of the schemes described below, it is understood that protecting groups may be employed where necessary in accordance with general principles known to those of skill in the art, for example, see T. W. Green and P. G. M. Wuts (1991) Protecting Groups in Organic Synthesis, John Wiley & Sons. These groups may be removed at a convenient stage of the compound synthesis using methods known to those of skill in the art. The selection of processes as well as the reaction conditions and order of their execution shall be consistent with the preparation of compounds of formula (I).

The invention also provides a process for preparing the compound of formula (I) and pharmaceutically acceptable derivatives thereof. Specifically, compounds of formula (I) are prepared by reacting the three main components of the compounds, referred to herein as the head, core, and tail of the compounds.

SYNTHESIS AND SCHEMES

Each compound of formula (I) may be conveniently prepared by separately preparing three constituents of the compound and subsequently combining those constituents to form the compound (I). For convenience, the three constituents are referred to herein as the head (II), the core (III), and the tail (IV). For convenience, the head, core, and tail nomenclature is used throughout to refer to each constituent when referred to individually, and also to refer to the corresponding moiety when described in the context of head/core, tail/core, and/or head/core/tail combinations.

The head component of the invented compounds is an o-amino carboxamide represented by formula (II):

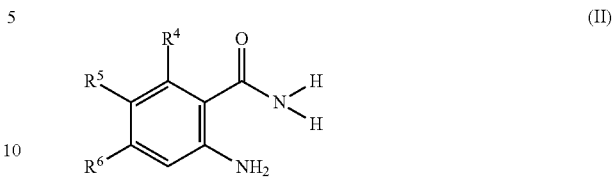

wherein substituents $R^4$, $R^5$, and $R^6$ are as defined above.

The core component of the invented compounds is pyrrolopyrimidine represented by formula (III):

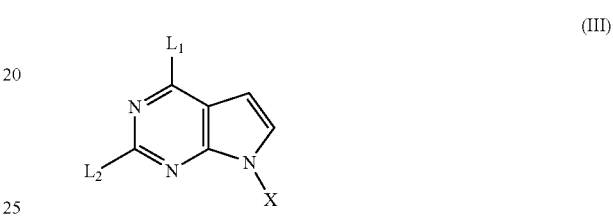

wherein each of substituents $L_1$ and $L_2$ represent a leaving group, e.g. a halogen, preferably chlorine, or OTF, and X represents a protecting group, e.g. sulfonamide or alcholated alkyl, e.g. allyl, benzyl, or SEM.

The tail component of the invented compounds is a substituted aniline represented by formula (IV):

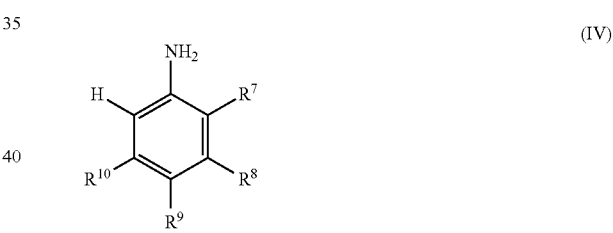

wherein substituents $R^7$, $R^8$, $R^9$, and $R^{10}$ are as defined above.

The head (II), core (III), and tail (IV) of the compounds may be combined, for instance, with the synthetic route shown in Scheme 1:

Scheme 1

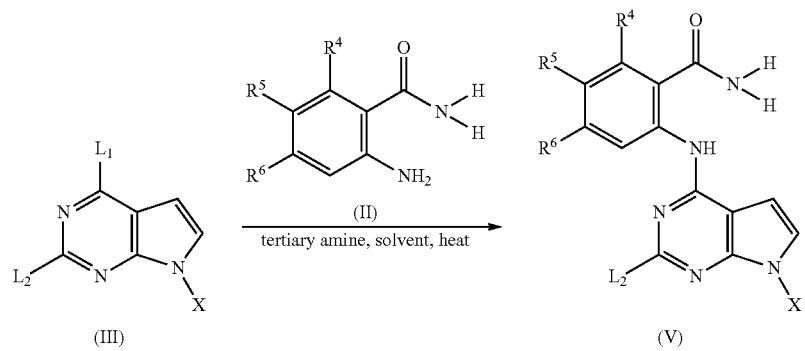

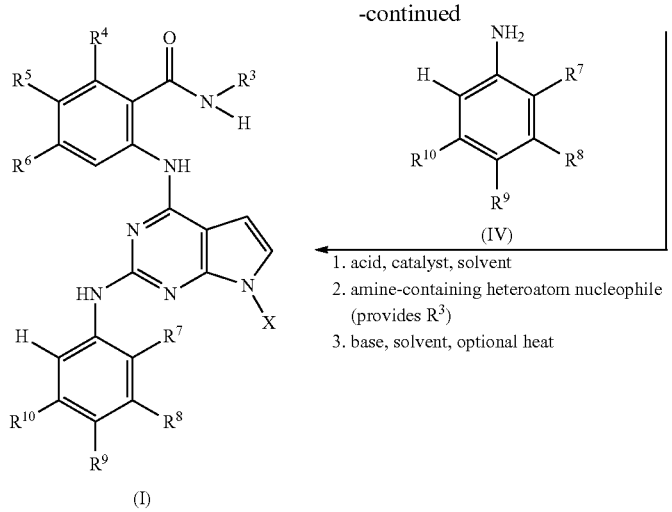

As shown, a core of formula (III), for instance where $L_1$ and $L_2$ are Cl and X is sulfonamide (CiventiChem, Research Triangle Park, N.C.), is reacted with a head of formula (II) in the presence of a tertiary amine, e.g. DIPEA, and a polar protic solvent, preferably a hindered alcoholic solvent, e.g. iPrOH, at heat, e.g. 102° C. The result is the compound of formula (V).

Compound of formula (V) is reacted with a tail of formula (IV) under a series of three sequential reaction conditions. First, an acid, e.g. HCl (2 eq.), is used with a catalyst, e.g. an iodine salt such as KI or TBAI, and a polar protic solvent having low nucleophilicity, e.g. TFE, at heat, e.g. 85° C. Second, an amine-containing heteroatom nucleophile, e.g. $NH_4OH$ or $R^3NH_2$, is added in solvent, e.g. THF or THF/$H_2O$. Third, a base, e.g. NaOMe, in solvent, e.g. MeOH/THF, is used to remove the protecting group X, resulting in the compound of formula (I).

Removal of the protecting group, e.g. sulfonamide, is preferably accomplished with the base with a mixture of polar protic solvent and ethereal solvent, e.g. MeOH/THF. Alternatively, when substituents $R^4$ and $R^6$ are both halogen, e.g. F, removal of the protecting group is preferably accomplished with a base, e.g. NaOH, in solvent, e.g. THF, under heat, e.g. 120° C. by microwave.

Compound (I) is converted from compound (V) by displacement of leaving group $L_2$ with the functionalized aniline (IV) according to Scheme 2.

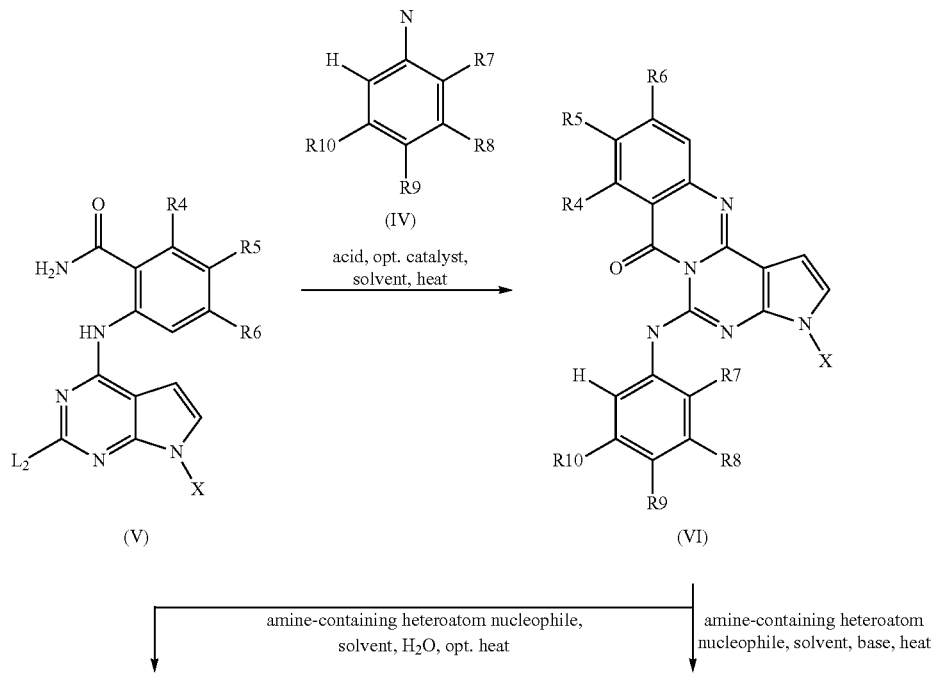

-continued

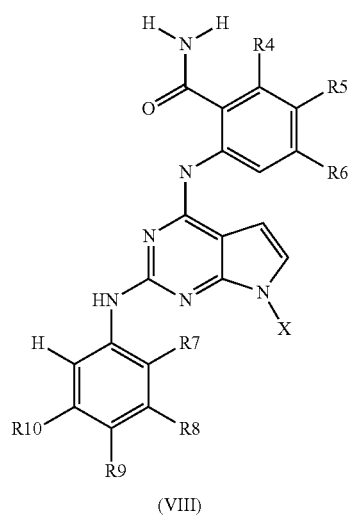

(VIII)

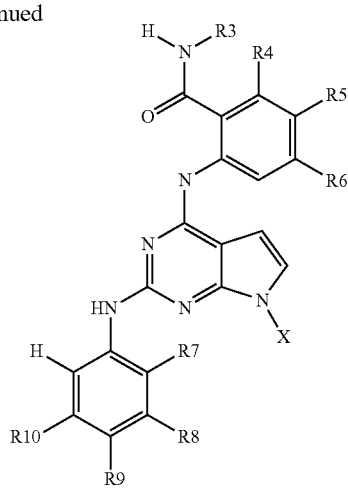

(VII)

A more particular description of the tail addition is shown in Scheme 2. Displacement of the $L_2$ group by the functionalized aniline can be carried out using the carboxamide group as a means of internal activation. Treatment of the functionalized pyrrolopyrimidine with an aniline (IV), acid, e.g. HCl, optional iodide source catalyst, e.g. KI and solvent, e.g. TFE, at heat, e.g. 80° C. for a length of typically 1 or 2 days affords the isolable tetracyclic species (VI). Reaction of the tetracyclic species (VI) to an amine-containing heteroatom nucleophile, e.g. $NH_4OH$ or $R^3NH_2$, added in solvent, e.g. THF or $THF/H_2O$, affords ring opened, rearomatized products (VII) and (VIII). The alkyl group of the nucleophile is retained in the compounds (VII) and (VIII).

Scheme 3

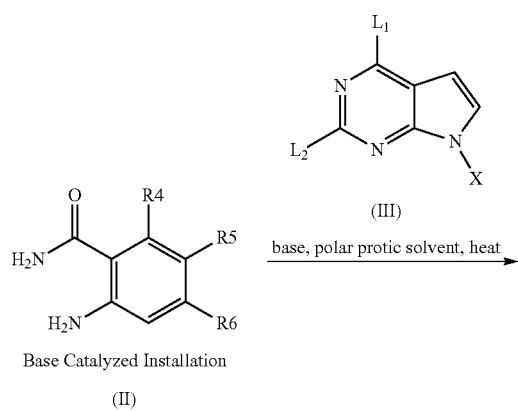

Base Catalyzed Installation (II)

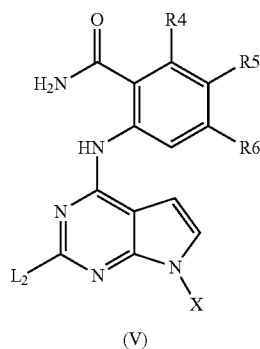

(V)

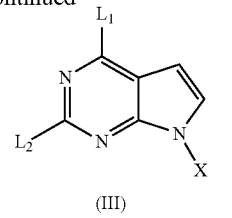

(III)

base, polar protic solvent, heat

Acid Catalyzed Installation, preferred for R4 = halogen (II)

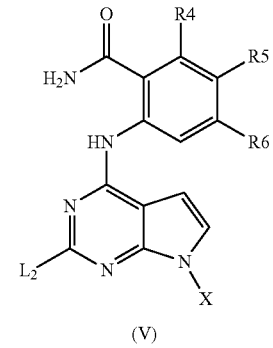

(V)

Referring to Scheme 3, the head (II) may be installed on the core (III) at the 4-$L_1$ position by displacement of the 4-$L_1$ group using either an acid or a base. Displacement under basic conditions with base, e.g. $iPr_2EtN$, and polar protic solvent, e.g. iPrOH, at heat, e.g. 85° C. (2-5 days), is preferable for most classes of compounds (except for compounds II where the $R^4$ position is halogenated). Displacement using an acid is preferred for headgroups (II) having a halogen at position $R^4$. In these cases 4-$L_1$ displacement can be efficiently carried out using an acid, e.g. trifluoroacetic acid, in a polar protic solvent, e.g. trifluoroethanol, at heat, e.g. 80° C.

A variety of aniline tails (IV) having substituents $R^7$, $R^8$, $R^9$, and $R^{10}$ as defined herein, may be prepared in accordance with schemes 4-9.

Scheme 4
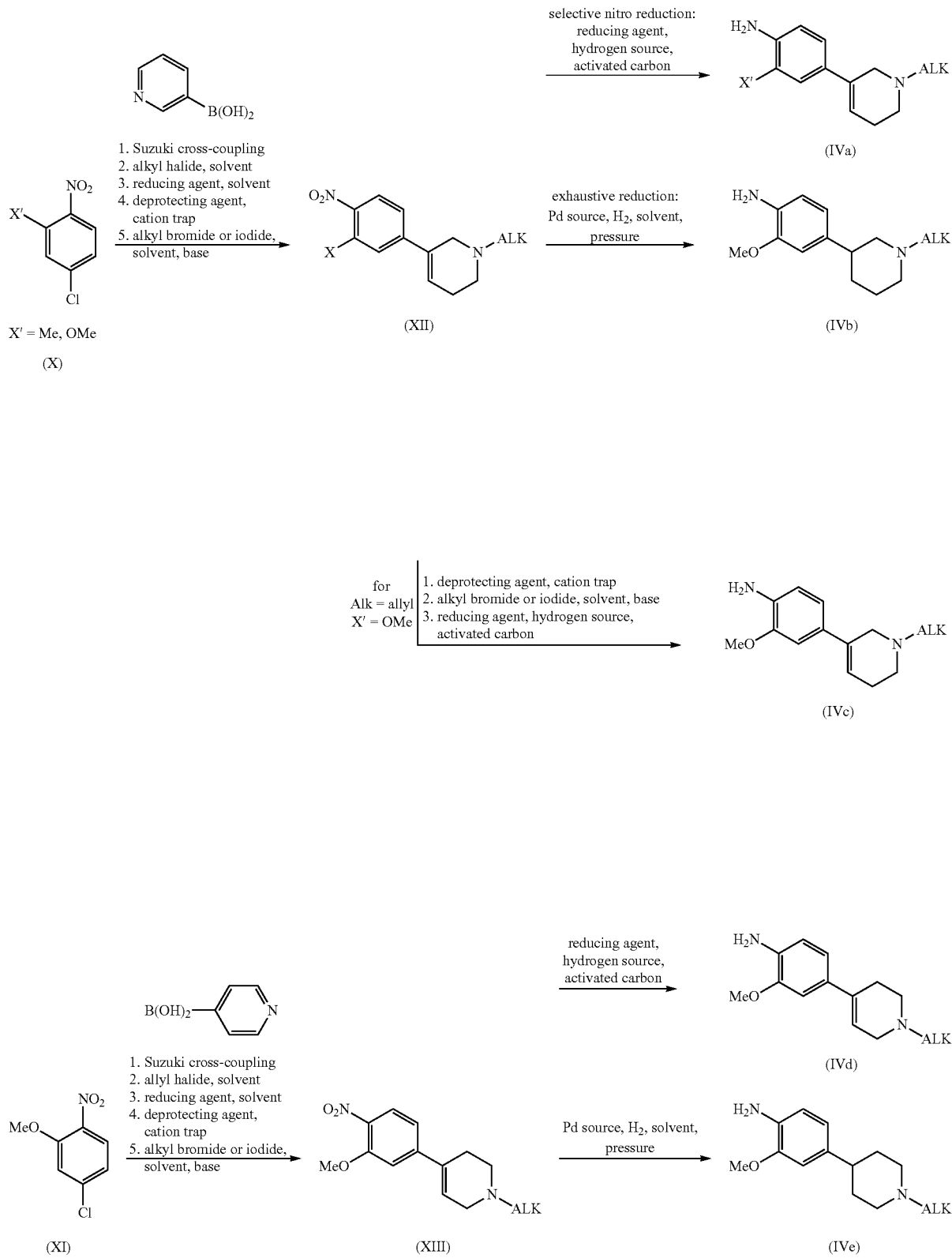

As shown in Scheme 4, 4-piperidinyl aniline tails can be prepared from commercially available starting materials, such as 2-methyl-4-chloro-nitrobenzene and 2-methoxy-4-chloro-nitrobenzene (both from Aldrich). Suzuki cross-coupling (*Palladium Reagents and Catalysts*, Jiro Tsuji, 2004, John Wiley and Sons, Ltd.) using a palladium source and base with either 3- or 4-pyridinyl boronic acid gives the corresponding 4-pyridyl nitrobenzenes in high yield. The pyridine is alkylated with any of a variety of primary alkyl halides, e.g. alkyl iodide or allyl bromide, in solvent, e.g. pinacolone. Reduction of the resulting pyridinium with, for example, a reducing agent and solvent, e.g. NaBH$_4$/THF, gives the corresponding 3- or 4-tetrahydropyridine analogs (XII and XIII, respectively). If an allyl halide is used (see sequence 1-5 for compound XI), then an alkyl substitution may be incorporated by removal of the allyl with a deprotecting agent, e.g. a palladium source such as Pd(PPh$_3$)$_4$, optionally in presence of a cation trapping agent, e.g. dimethylbarbituric acid, to provide N-dealkylated tetrahydropyridines. The N-dealkylated tetrahydropyridines may be subsequently alkylated with alkyl iodides or bromides in polar solvent and base. Compounds XII and XIII may be selectively reduced with a reducing agent and hydrogen source, e.g. with Fe(III) and hydrazine (hereinafter referred to as "selective nitro reduction"), to provide 4-piperidinyl aniline tails IVa and IVd, respectively. Alternatively, compounds XII and XIII may be exhaustively reduced with a palladium source and hydrogen source in solvent, e.g. with Pd/C, H$_2$, EtOH under pressure, such as 60 psi (hereinafter referred to as "exhaustive reduction") to provide 4-piperidinyl anline tails IVb and IVe, respectively. For compounds XII where the alkyl substituent is an allyl group, the allyl may be replaced by a substitute alkyl group, including branched alkyls (see discussion with respect to sequence 1-5 for compound XI above). The resultant compound is then subjected to selective nitro reduction to provide compounds IVc with a branching alkyl group on the piperidyl nitrogen.

Scheme 5

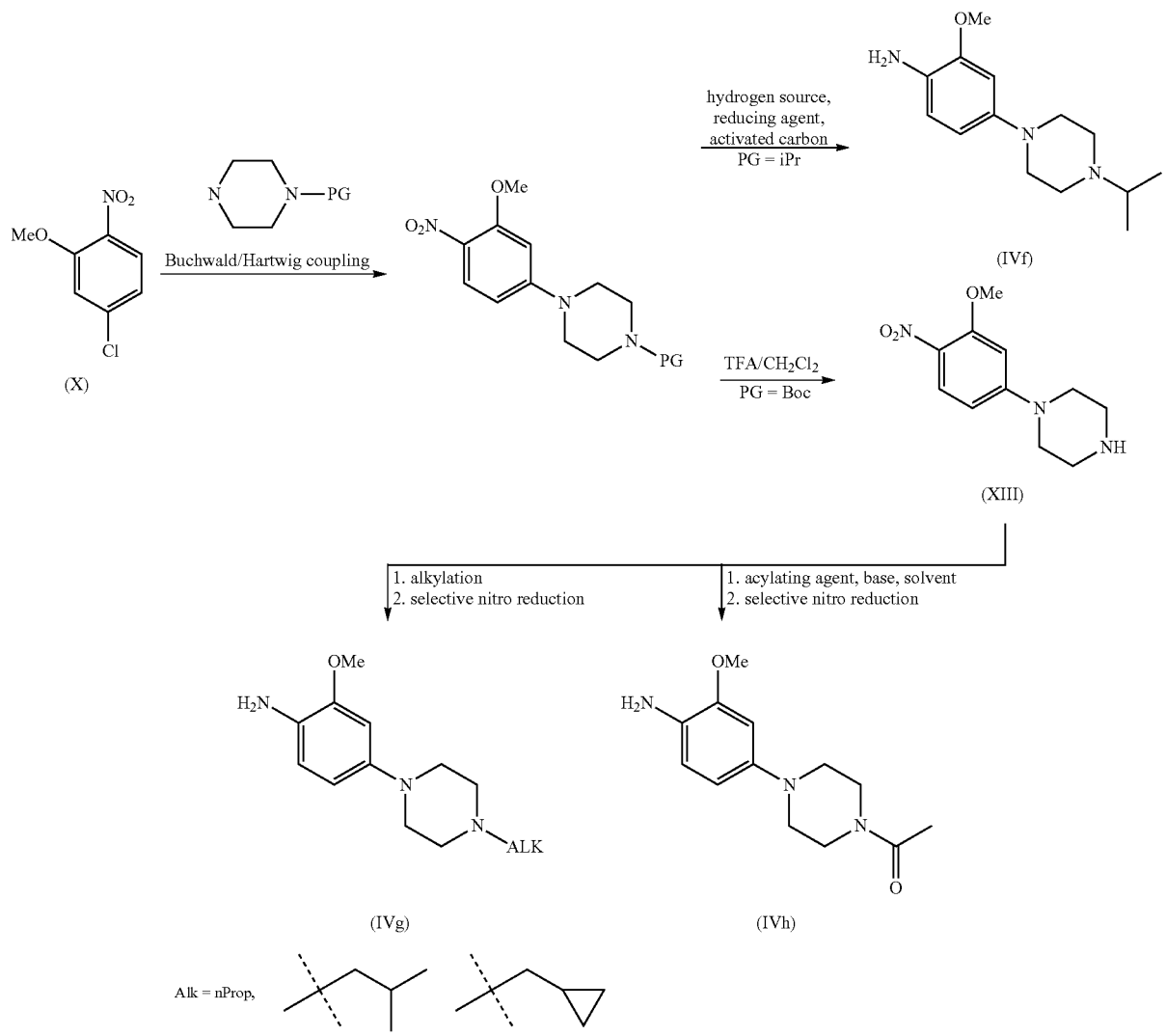

As shown in Scheme 5, 4-piperazine 2-methoxy nitrobenzene tails can be generated via Buchwald/Hartwig coupling with, for instance, Pd$_2$(dba)$_3$, xantphos, dioxane, and CsCO$_3$, (see Yin, Jingjun & Buchwald, Stephen. J. Am. Chem. Soc. 2002, 124, 6043-6048) of a functionalized piperazine, e.g. PG=Me, iPr, Boc, etc., with an aromatic halide. The tail may be selectively nitro reduced to provide a directly functionalized aniline IVf where the protecting group (PG) remains as a substituent of the tail.

Alternatively, the protecting group (PG) may be removed from the piperazine with an acid and solvent, e.g. TFA/ $CH_2Cl_2$, to form compound XIII. Compound XIII may be alkylated and then exhaustively nitro reduced to form aniline tail IVg. Alternatively, compound XIII may be acylated with an acylating agent, e.g. $Ac_2O$, base, e.g. $Et_3N$, and solvent, e.g. $CH_2Cl_2$, and then exhaustively nitro reduced to form aniline tail IVh.

an intermediate which is deprotected with an acid, e.g. TFA/ $CH_2Cl_2$, reacted with an electrophile, e.g. MeI, iPrI, $ClSO_2Me$, under basic conditions, e.g. $K_2CO_3$ or DIPEA, and subsequently hydrogenated to form compound IVbb.

2-methoxy-4-alkoxy anilines can be prepared by reaction of aromatic (IVba) with an alcohol, e.g. HO—R″ where R″ is as shown, under basic conditions, e.g. $K_2CO_3$/DMSO, followed by hydrogenation, e.g. $H_2$ and Pd/C, to provide compounds IVbc and IVbd.

Scheme 5a

Scheme 5a: Homopiperazine and o-linked tails

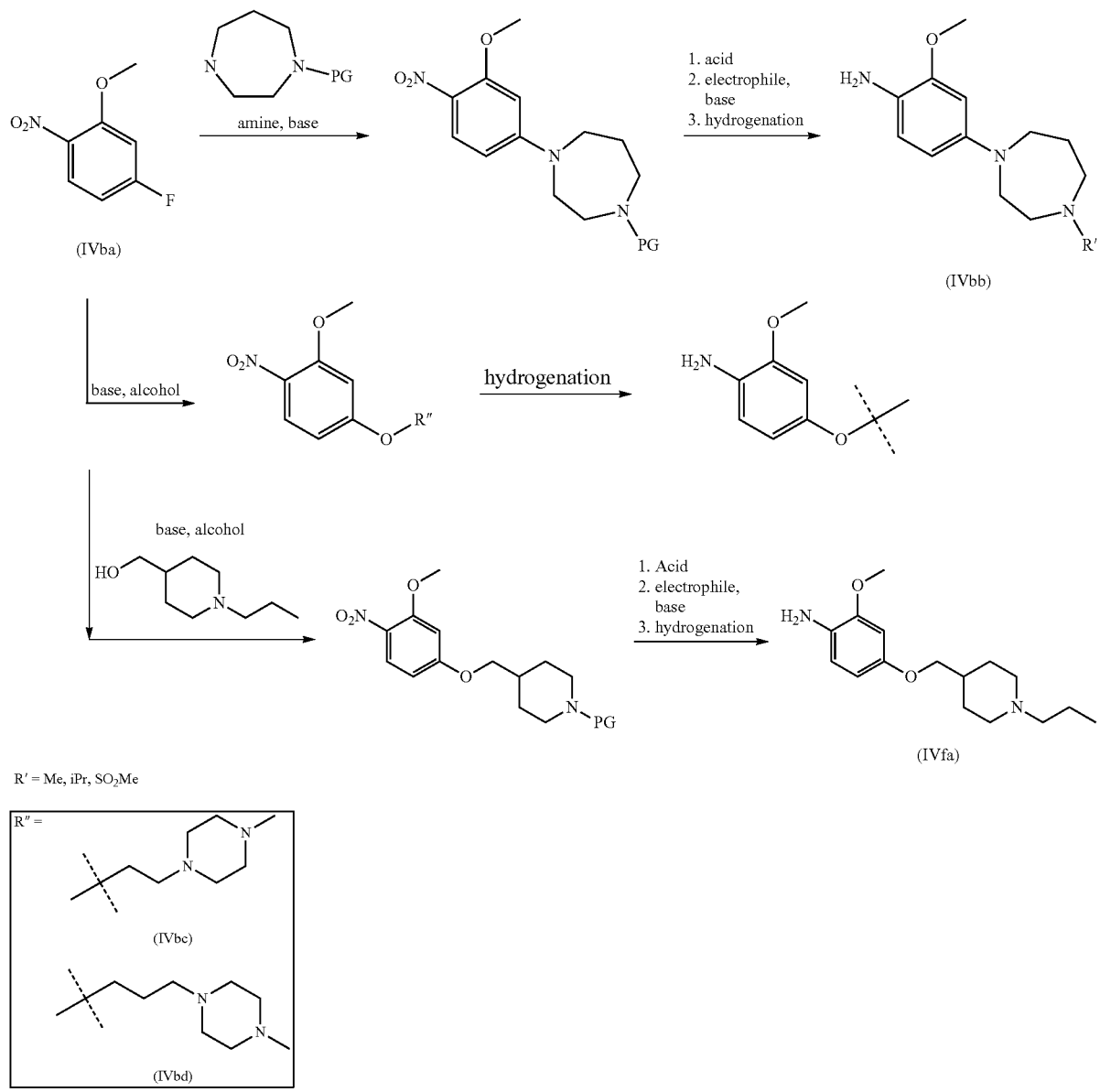

R′ = Me, iPr, $SO_2Me$

As shown in scheme 5a, 4-homopiperazine 2-methoxy nitrobenzene tails can be generated by coupling an aromatic halide (IVba) with a functionalized homopiperazine, e.g. PG=Boc, under basic conditions, e.g. $K_2CO_3$/DMSO, to form Similarly, reaction of (IVba) with (1-propyl-4-piperidinyl) methanol, followed by subsequent deprotection with acid, e.g. TFA, alkylation, e.g. propyl iodide, and nitro-reduction gave aniline (IVfa).

Scheme 6
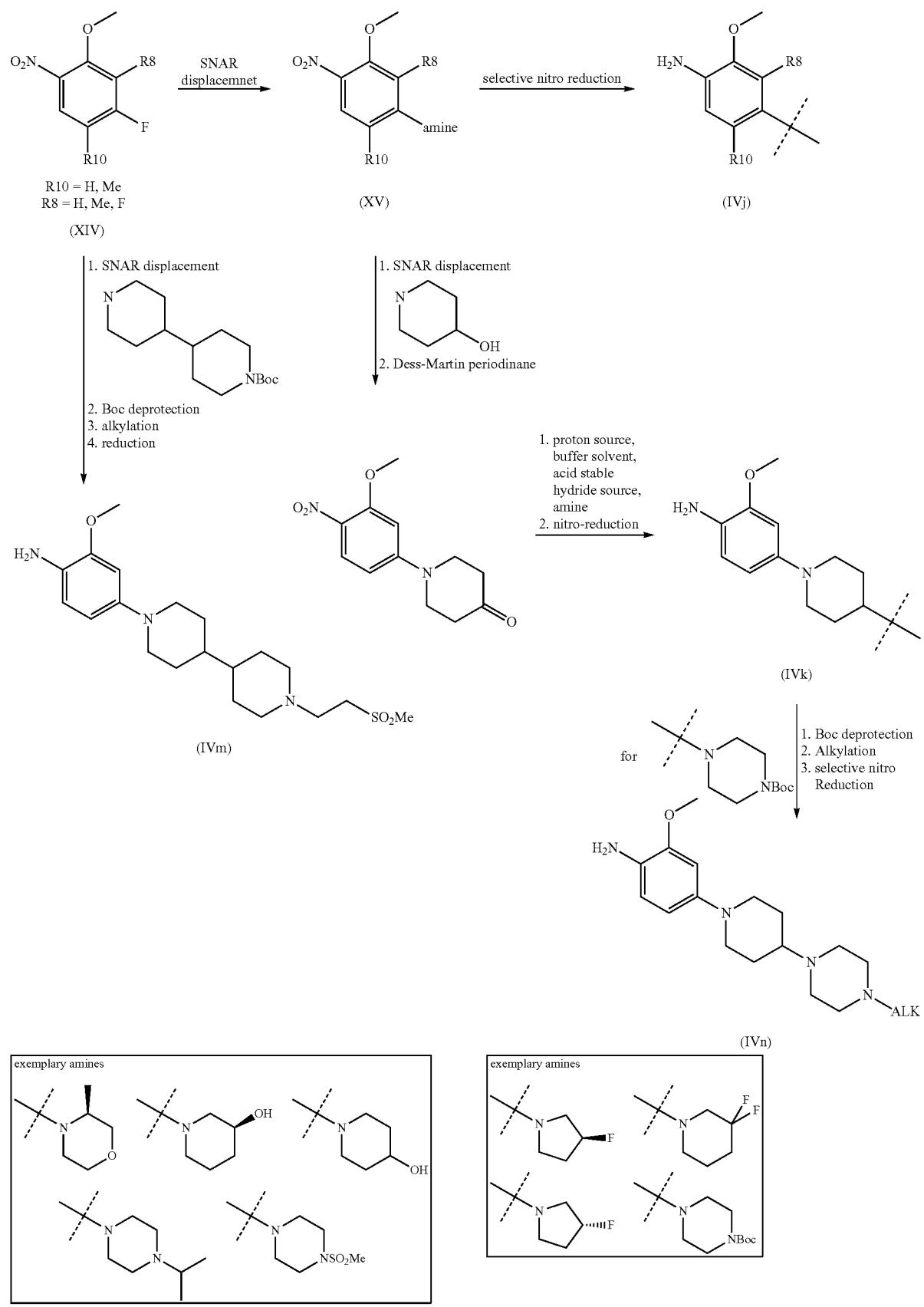

As shown in scheme 6, 4-piperidinyl 2-methoxy nitrobenzenes can be prepared via direct displacement of 4-fluoro nitrobenzenes (XIV) (commercially available, ex. $R^8$=F, $R^{10}$=H from Aldrich; or literature compounds, ex. $R^8$=$R^{10}$=H as shown in Bolton, et al., Nucleophilic displacement in polyhaloaromatic compounds, Journal of the Chemical Society, Perkin Transactions 2: Physical Organic Chemistry (1972-1999) (1978),(2), 141-4; or $R^8$=H, $R^{10}$=Me as shown in Van Zandt, et al., Design and synthesis of highly potent and selective (2-arylcarbamoyl-phenoxy)-acetic acid inhibitors of aldose reductase for treatment of chronic diabetic complications, Bioorganic & Medicinal Chemistry (2004), 12(21), 5661-5675). The 4-piperidinyl 2-methoxy nitrobenzene may be subject to SNAR displacement (reaction with an amine nucleophile, base, e.g. $K_2CO_3$, and polar solvent, e.g. DMSO) to provide aminated intermediate XV and subsequent selective nitro reduction to obtain aniline tails IVj. Alternatively, displacement with 4-piperdinol and oxidation with the Dess-Martin Periodinane (see Tohma, Hirofumi & Kita, Yasuyuki. Adv. Synth. Catal. 2004, 346, 111-124) gives the corresponding functionalized piperidinone, which can be subjected to reductive amination with a proton source, e.g. AcOH, buffer, e.g. $Et_3N$, solvent, e.g. $ClCH_2CH_2Cl$, acid stable hydride source, e.g. $Na(OAc)_3BH$, and primary or secondary amine to give bicyclic 4-piperidinyl 2-methoxy anilines IVk, after nitro-reduction, where the amine provides the substituent of the piperidine ring. Where the amine is a Boc protected piperazine, the piperazine of compound IVk may be alkylated by the steps of Boc deprotection, alkylation, and selective nitro reduction, as described above, to produce aniline tail IVn.

Alternatively, 4-fluoro nitrobenzenes (XIV) may be used to prepare the compounds of (IVm) via SNAR displacement using a Boc protected, followed by Boc deprotection, followed by alkylation with alkylating agent, e.g. ethylene methyl sulfone, a base, e.g. $Et_3N$, solvent, e.g. $CH_2Cl_2$, followed by selective nitro reduction.

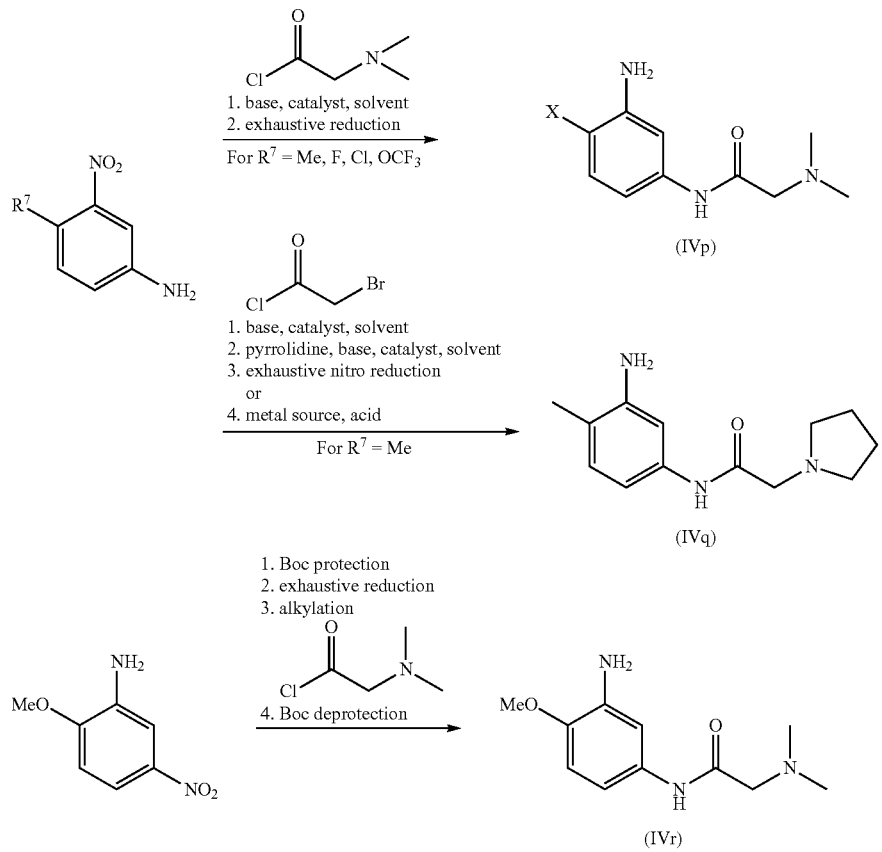

Scheme 7

As shown in Scheme 7, commercially available 3-amino nitrobenzenes (for example $R^7$=Me from Alpha Aesar, Ward Hill, Mass., $R^7$=F from 3B Medical Systems, Libertyville, Ill., $R^7$=Aldrich, $R^7$=$OCF_3$ from Matrix Scientific, Columbia, S.C.) can be acylated with an acylating agent, e.g. N,N-dimethylglycyl chloride in the presence of a base, e.g. $Et_3N$, catalyst, e.g. DMAP, and solvent, e.g. $CH_2CL_2$. Subsequent exhaustive reduction of the nitro gives the corresponding functionalized 3-aminoacyl anilines IVp. If a-bromo-acetyl chloride is used rather than N,N-dimethylglycyl chloride, trapping of the intermediate α-bromo-acyl amine with an appropriate nucleophile (pyrrolidine in the example above) with base, e.g. $K_2CO_3$, catalyst KI, and solvent, e.g. MeCN, and subsequent exhaustive reduction affords further functionalized 3-aminoacyl amines IVq. Alternatively, the compound may be subject to electron transfer reduction after trapping with a metal, e.g. $SnCL_2$, and acid, e.g. AcOH.

Alternatively, 2-methoxy-5-acyl anilines IVr may be made directly from commercially available 2-methoxy-5-nitro aniline, Aldrich. The NH$_2$ of the aniline is first protected with a protecting agent, e.g. Boc$_2$O, solvent, e.g. THF, and base, e.g. Et$_3$N, then exhaustively reduced, then acylated with N,N-dimethylglycyl chloride (see acylation of IVp), and then deprotected with acid, e.g. TFA, and solvent, e.g. CH$_2$CL$_2$.

anilines IVt were generated from Buchwald/Hartwig coupling (see scheme 5) with 5-bromo-2-methoxy nitrobenzene, then selective nitro reduction.

Alternatively, 5-alkoxy 2-methoxy anilines (IVu) may be prepared by direct alkylation of 3-nitro, 4-methoxy phenol

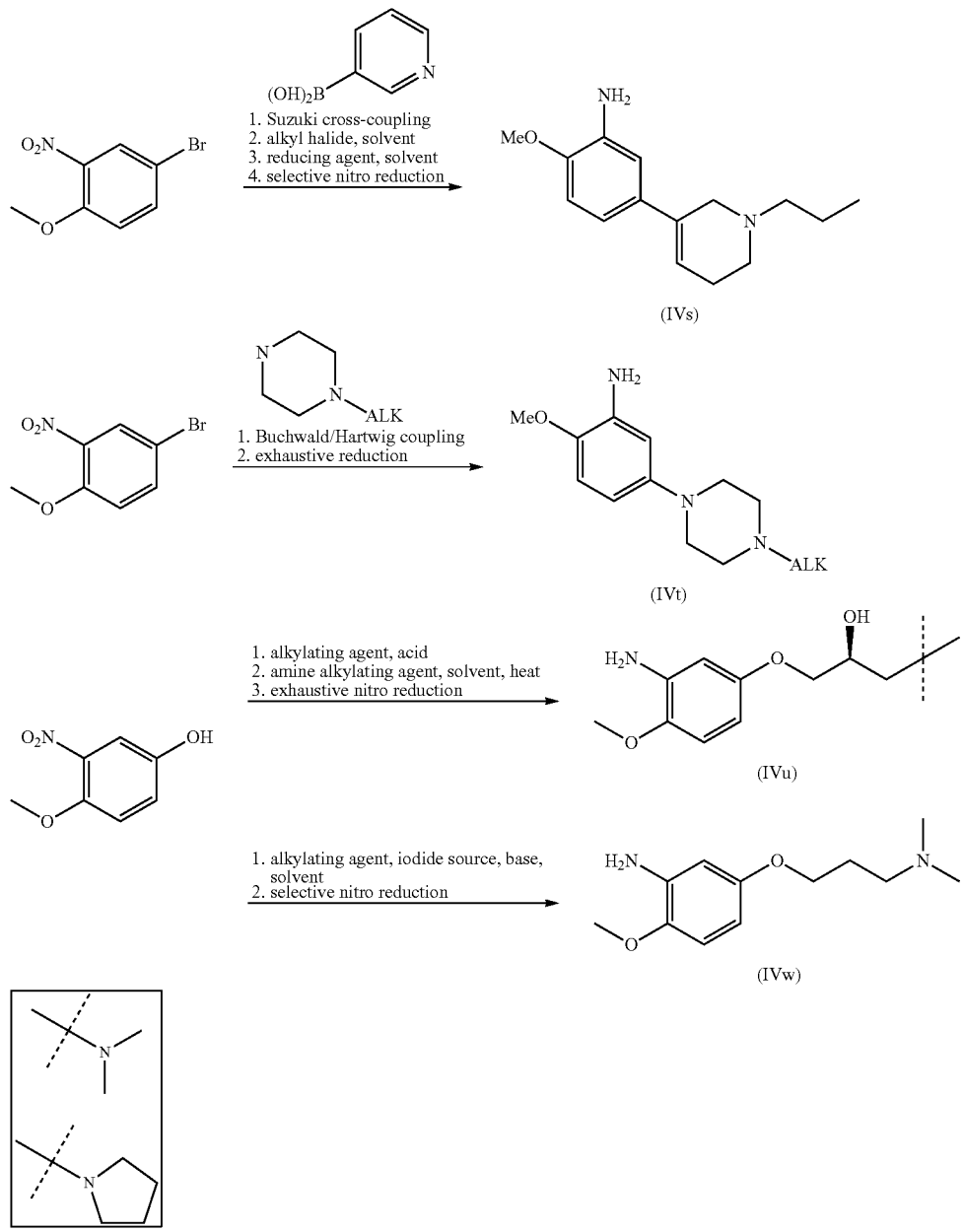

As shown in scheme 8, 5-piperidinyl 2-methoxy anilines IVs were generated from Suzuki cross-coupling reactions (see scheme 4) with 5-bromo-2-methoxy nitrobenzene (3B Medical Systems, Libertyville, Ill.), then alkylation with an alkyl halide, e.g. I-propane, with solvent, e.g. pinacolone, then reduction with reducing agent, e.g. Na(CN)BH3, and acid, e.g. HCl with solvent, e.g. MeOH, then selective nitro reduction or electron transfer reduction (see scheme 7, electron transfer reduction of IVq). 5-Piperazinyl 2-methoxy (CiventiChem, Research Triangle Park, N.C.) with an alkylating agent, e.g. (S)-(+)-Glycigyl-3-nitrobenzenesulfonate, and Lewis acid, e.g. LiCl, followed by alkylation with an amine alkylating agent, and solvent, e.g. isopropanol, at heat, e.g. microwave at 140° C. The product is subjected to selective nitro reduction to provide aniline tail IVu. Alternatively, the 3-nitro, 4-methoxy phenol may be alkylated with an alkylating agent, e.g. dimethylaminopropylchloride HCl, iodide source, e.g. TBAI, base, e.g. K$_2$CO$_3$, and solvent, e.g. MeCN, followed by selective nitro reduction to provide aniline tail IVw.
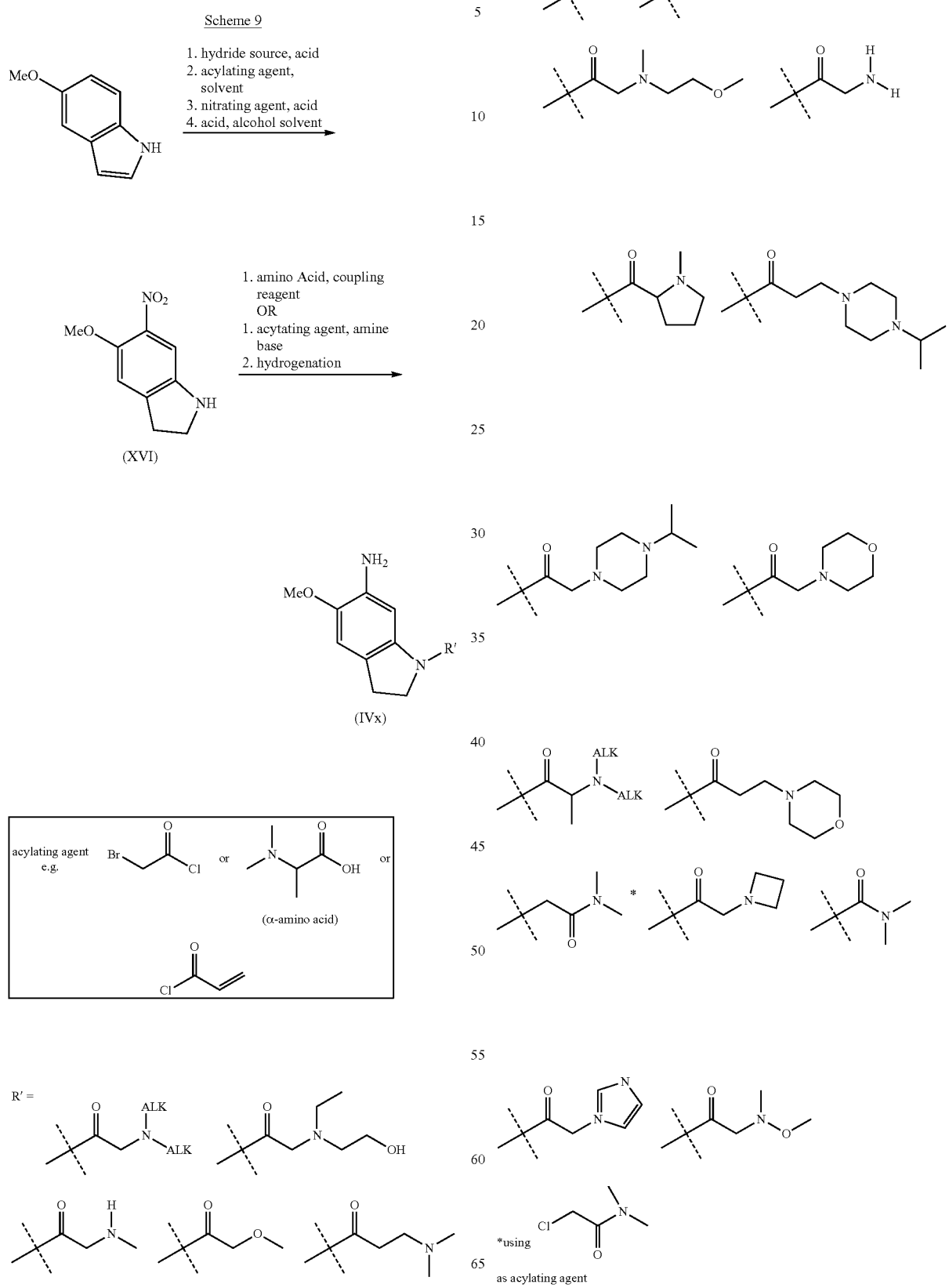

As shown in scheme 9, bicyclic indane tails may be prepared using 5-methoxy indole (Aldrich) as a starting material. The 5-methoxy indole is first reduced using a hydride source, e.g. Na(CN)BH$_3$, and acid, e.g. AcOH, then protected with an acylating agent, e.g. Ac$_2$O, in solvent, e.g. AcOH, optionally with a base. The protection provides for subsequent selective nitration with nitrating agent, e.g. HNO$_3$, and acid, e.g. Ac$_2$O, followed by deprotection with acid, e.g. HCl in solvent, e.g. MeOH to provide intermediate XVI.

Intermediate XVI is subjected to subsequent acylation with an acylating agent, e.g. α-bromoacetyl chloride, acryloyl chloride, or an amino acid, with coupling reagents, e.g. HATU, DMAP, and base, e.g. PS-DIPEA, and solvent, e.g. THF. The acylating agent may be reacted with an appropriate amine base, e.g. Me$_2$NH (with solvent, e.g. THF), and the product then reduced (see reduction of IVa, scheme 4) to provide anilino indoline tails IVx.

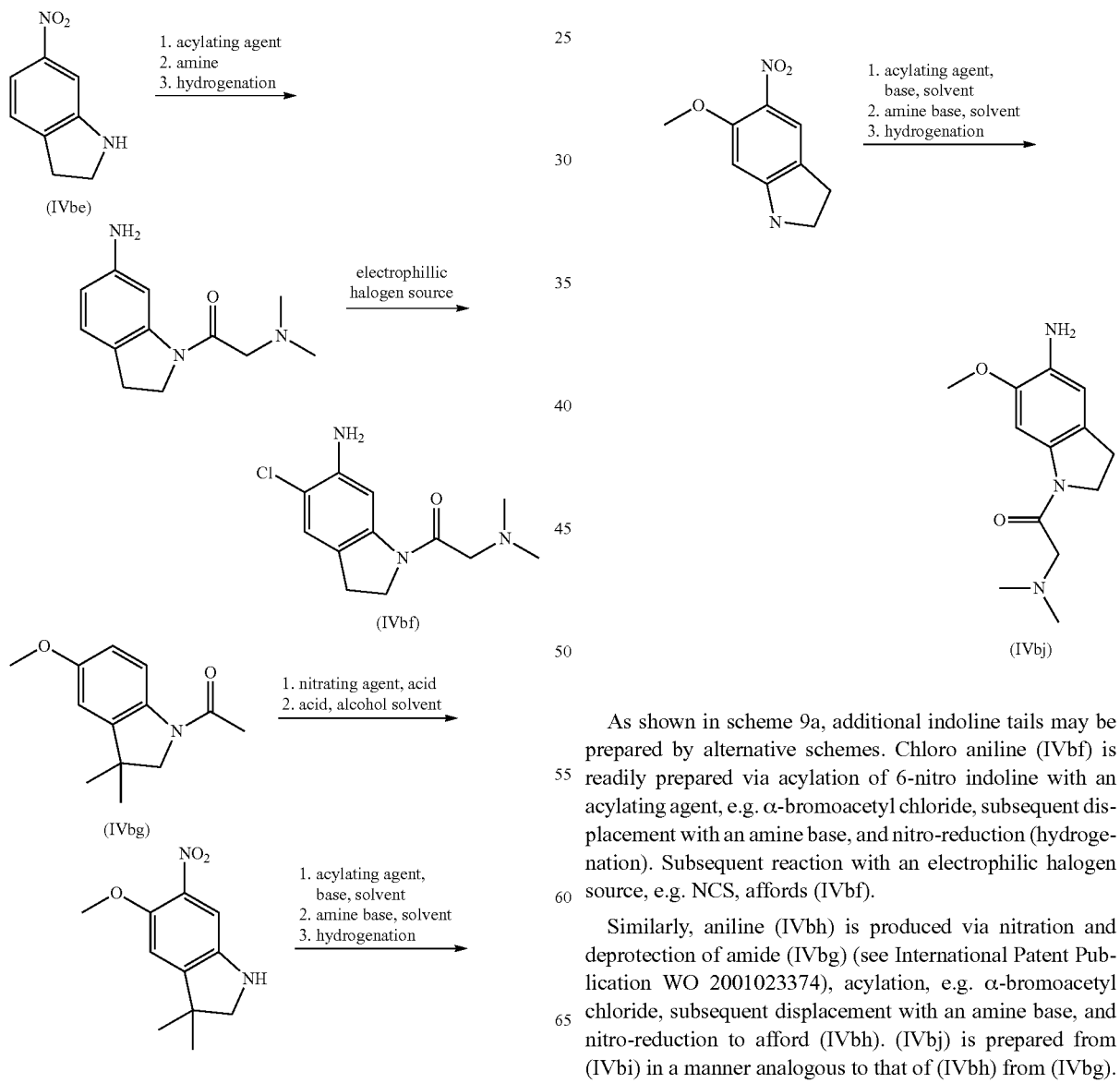

As shown in scheme 9a, additional indoline tails may be prepared by alternative schemes. Chloro aniline (IVbf) is readily prepared via acylation of 6-nitro indoline with an acylating agent, e.g. α-bromoacetyl chloride, subsequent displacement with an amine base, and nitro-reduction (hydrogenation). Subsequent reaction with an electrophilic halogen source, e.g. NCS, affords (IVbf).

Similarly, aniline (IVbh) is produced via nitration and deprotection of amide (IVbg) (see International Patent Publication WO 2001023374), acylation, e.g. α-bromoacetyl chloride, subsequent displacement with an amine base, and nitro-reduction to afford (IVbh). (IVbj) is prepared from (IVbi) in a manner analogous to that of (IVbh) from (IVbg).

Scheme 9b

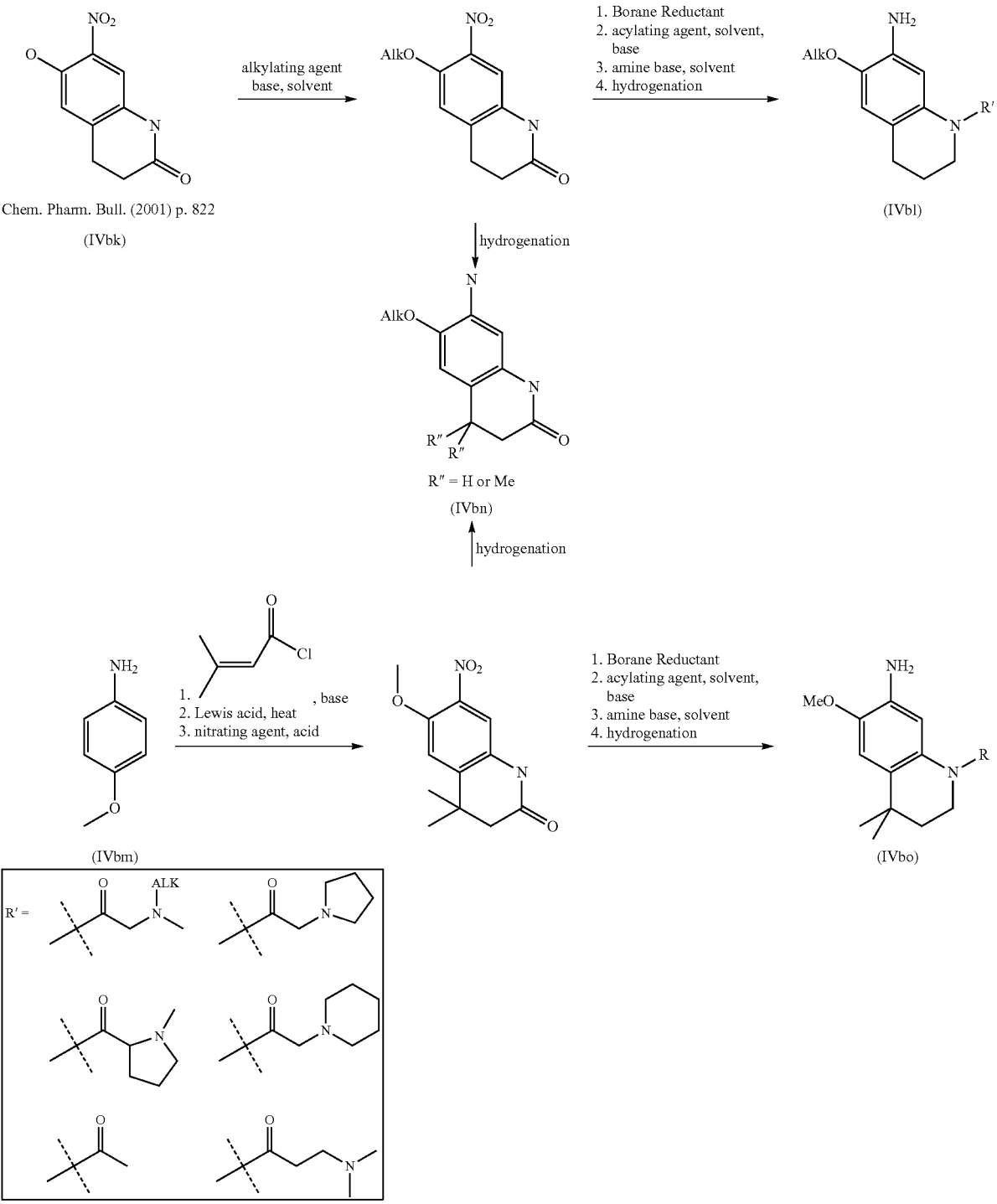

As shown in scheme 9b, tetrahydroquinoline tails may be prepared as follows.

Intermediate (IVbk), prepared according to Chem. Pharm. Bull. (2001) p. 822, may be alkylated with an alkylating agent and base, e.g. MeI and $K_2CO_3$, then amide reduced, e.g. borane, treated with an acylating agent, e.g. α-chloro acetyl choride, an amine base, e.g. dimethyl amine, and nitro-reduced to provide (IVbl).

Intermediate (IVbm), readily available 4-anisidine, may be acylated with 3,3-diemthylacryloyl chloride and base, e.g.

$K_2CO_3$, heated with a Lewis acid, e.g. $AlCl_3$, and solvent, e.g. methylene chloride, followed by nitration with an oxidative reagent, e.g. $NaNO_2$, in acid, e.g. TFA. Subsequent amide reduction, e.g. borane, followed by treatment with an acylating agent, e.g. α-bromoacetyl choride, displacement with an amine base, e.g. dimethyl amine, and nitro reduction provides (IVbo).

Nitroreduction of amide intermediates shown in scheme 9b affords intermediate (IVbn).

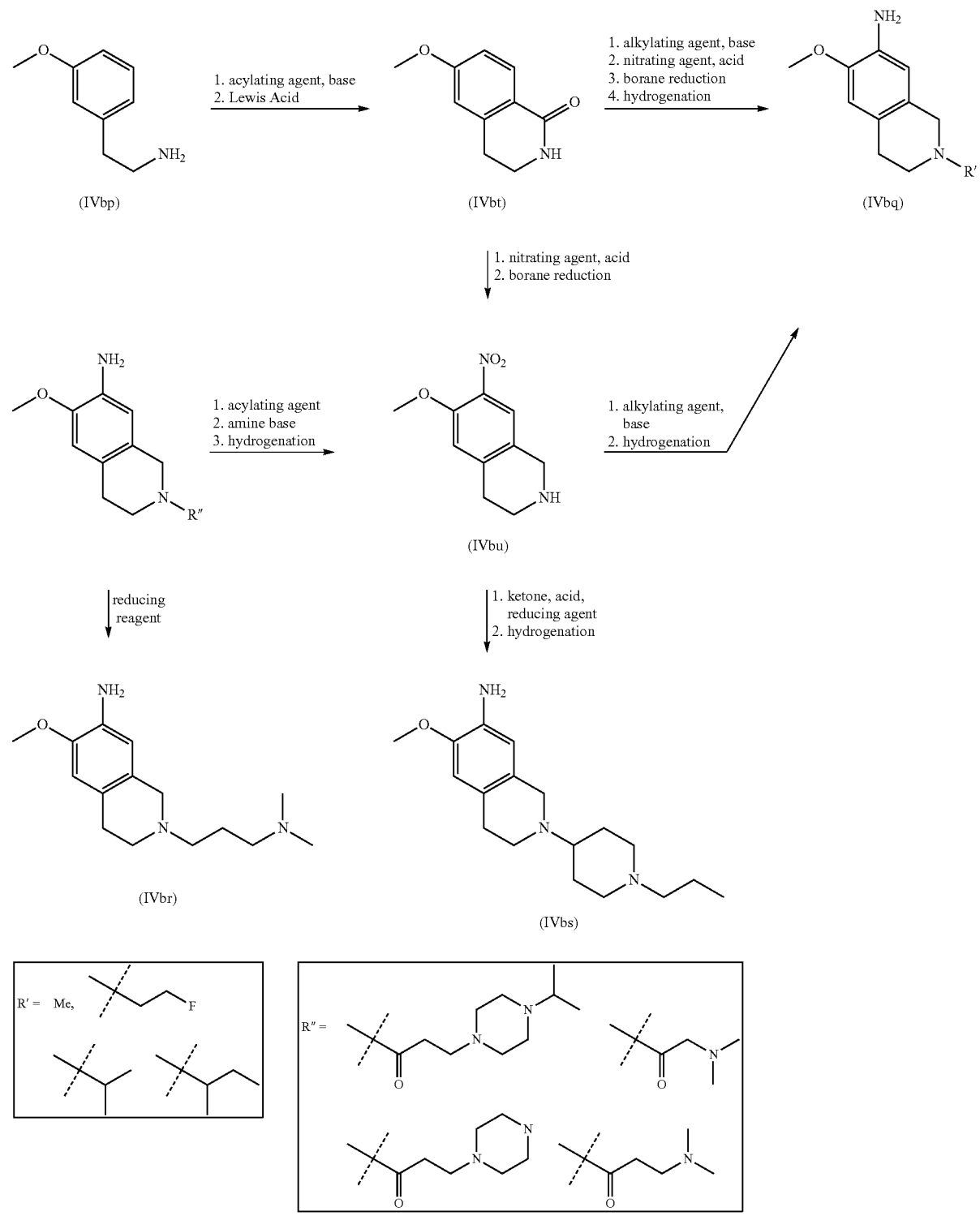

As shown in scheme 9c, tetrahydroisoquinoline tails may be prepared as follows.

Intermediate (IVbp) may be acylated with e.g. ethyl chloroformate, heated with acid, e.g. polyphosphoric acid, to afford intermediate (IVbt). Subsequently, (IVbt) may be alkylated, e.g. MeI, NaH, nitrated, e.g. HNO₃ in acid, amide reduced, e.g. borane, followed by nitro-reduction, e.g. H₂, Pd/C, to afford (IVbq). Alternatively, (IVbq) may be provided from (IVbt) via (IVbu) by nitration and amide reduction prior to alkylation and nitro-reduction.

(IVbs) may be prepared from (IVbu) via reductive amination, e.g. ketone and NaCNBH₃, and nitro-reduction, e.g. H₂, Pd/C.

(IVbr) may be prepared from (IVbu) via acylation, e.g. acryloyl chloride, treatment with an amine base, e.g. dimethyl amine, and heat, followed by nitro-reduction, e.g. H₂, Pd/C, and amide reduction, e.g. LiAlH₄.

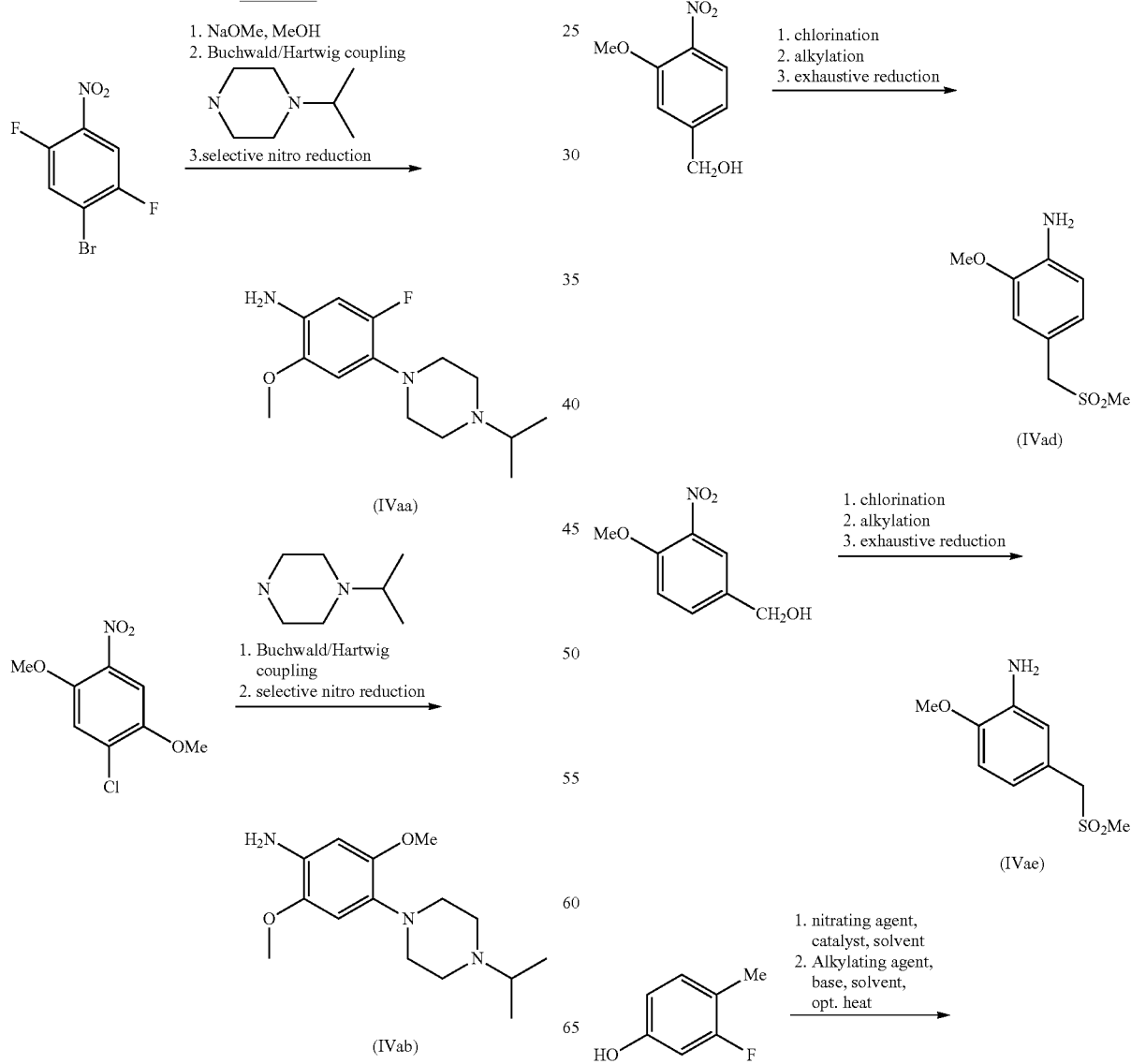

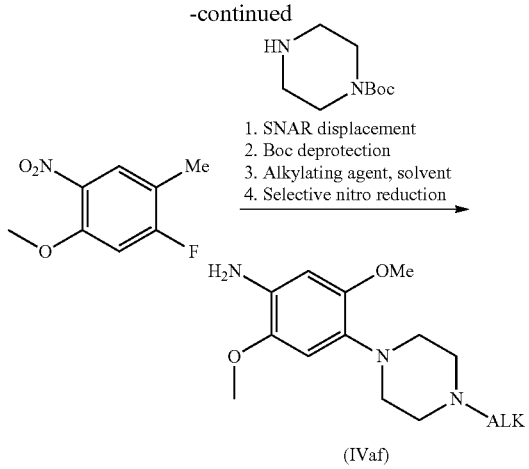

(IVaf)

As shown in scheme 10, a number of 4-piperazinyl anilines can be prepared using standard chemistries and readily available starting materials. For instance, tails IVaa and IVab may be prepared from 2,5-difluoro-4-bromo nitrobenzene and 2,5-dimethoxy-4-chloro-nitrobenzene (Alpha Aesar, Ward Hill, Mass. and ABCR Gmbh & Co., Germany, respectively) by treatment with sodium methoxide (only for compound IVaa) and Buchwald/Hartwig coupling (see scheme 8) with isopropyl piperazine, followed by selective nitro reduction (see reduction of IVa, scheme 4) to afford tails IVaa and IVab. Tail IVac may be prepared from 2-nitro-5-chloro-benzaldehyde (Aldrich) using Buchwald/Hartwig coupling with isopropyl piperazine as with IVaa and IVab, followed by Wittig olefination (see *Reactions and Syntheses in the Organic Chemistry Laboratory*. Tietze, Lutz-Friedjan and Eicher, Theophil. 1989. University Science Books, Mill Valley, Calif.) with a phosphonium salt, e.g. MePPh$_3$Br, and base, e.g. nBuLi, followed by hydrogenation (see hydrogenation of IVb, scheme 4).

Sulfone-containing tails IVad and IVae are readily prepared from 3-methoxy-4-nitro-benzyl alcohol and 3-nitro-4-methoxy benzyl alcohol, respectively (both from Aldrich), via chlorination (with for instance PPh$_3$/NCS) followed by displacement of the derived benzyl chloride with methyl sulfone (with for instance MeSO$_2$Na/EtOH), and nitro-reduction (see reduction of IVb, scheme 4).

The aniline tail (IVaf) was prepared from 2-methyl-5-hydroxy-fluoro-benzene by nitration with a nitrating agent, e.g. HNO$_3$, catalyst, e.g. TBAI, and solvent, e.g. ClCH$_2$CH$_2$Cl, followed by phenolic alkylation with an alkylating agent, e.g. MeI, base, e.g. K$_2$CO$_3$, solvent, e.g. DMF, at heat, e.g. 80° C. The intermediate is subjected to SNAR displacement (see scheme 6) using Boc protected piperizine, followed by Boc deprotection (see scheme 6), followed by alkylation with an alkylating agent, e.g. CH$_2$CHSO$_2$Me, and solvent, e.g. Et$_3$N, followed by selective nitro reduction, to provide IVaf.

Scheme 10b

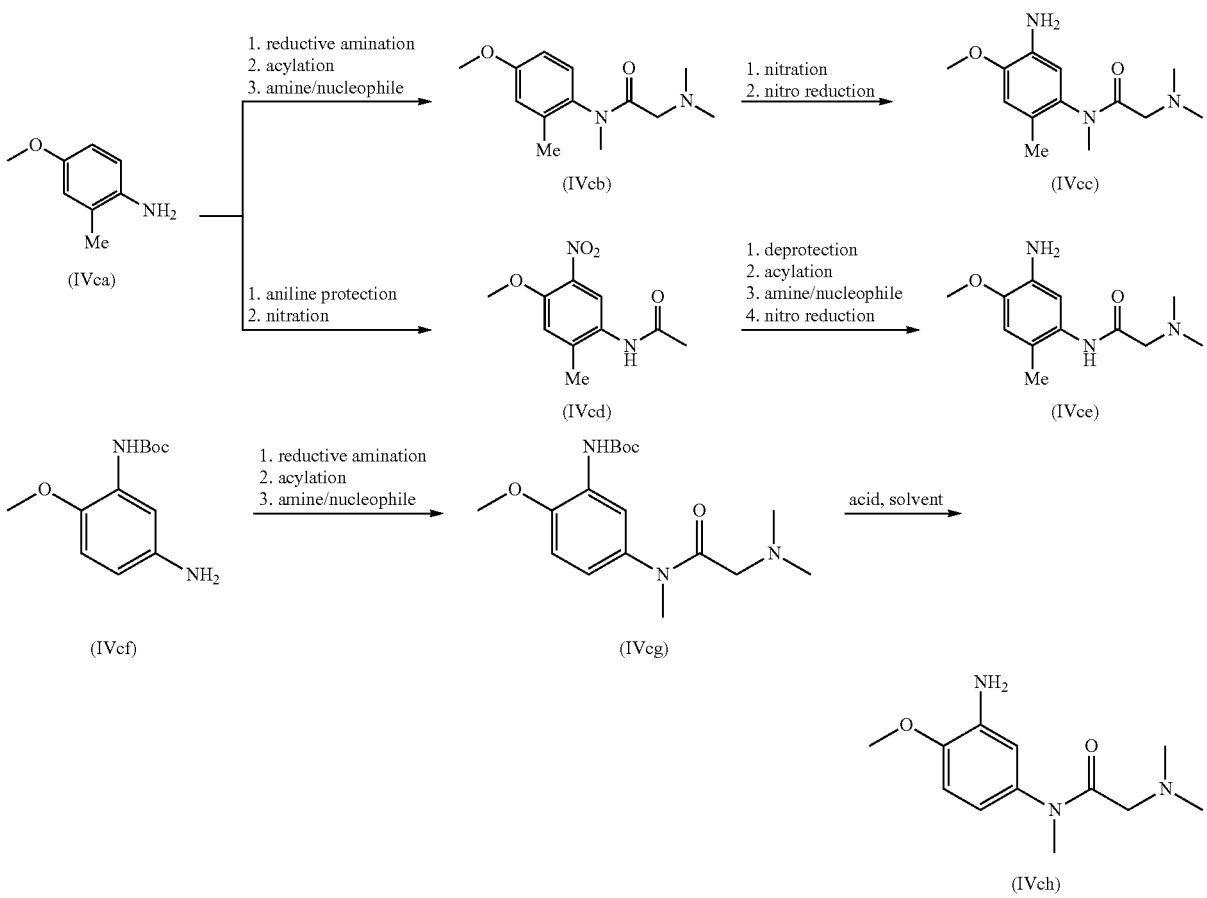

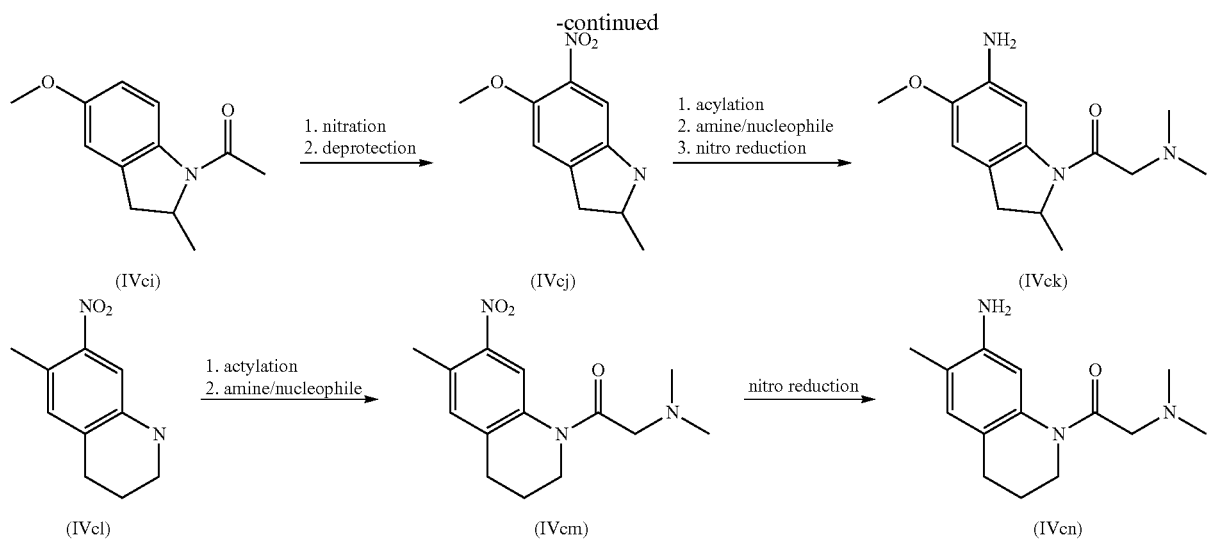

Additional anilines may be prepared as illustrated in Scheme 10b. Aniline (IVca) can be subjected to reductive amination conditions (e.g. formaldehyde, sodium methoxide, sodium borohydride), followed by acylation with an acylating agent and base (e.g. α-bromo-acetyl-chloride and diisopropylethylamine), followed by exposure to an amine or other nucleophile (e.g. diemthyl amine) to afford (IVcb). Nitration of (IVca) with a nitrating agent and acid (e.g. sodium nitrite/ TFA) followed by nitro reduction with a reducing agent (e.g. Pd/C and hydrogen gas) affords aniline (IVcc). Similarly, (IVca) can be protected (e.g. with an acyl group) and subsequently exposed to nitration conditions as described above for (IVcb) to give (IVcd). Subsequent deprotection (e.g. deacylation with acid/alcoholic solvent), reacylation with an acylating agent and base (e.g. a-bromo-acetyl chloride and diisopropylethylamine), treatment with an amine or other nucleophile (for example dimethyl amine) and nitro reduction (e.g. Pd/C and hydrogen gas) affords (IVce). An orthogonally protected diamine (e.g. (IVcf)) can be subjected to reductive amination conditions (e.g. formaldehyde, sodium methoxide, sodium borohydride), followed by acylation with an acylating agent and base (e.g. α-bromo-acetyl-chloride and diisopropylethylamine), followed by exposure to an amine or other nucleophile (e.g. diemthyl amine) to afford (IVcg). Removal of the BOC protecting group with acid (i.e. HCl or TFA) affords (IVch).

Exposure of (IVci) (see Arp, Forrest O.; Fu, Gregory C. Kinetic Resolutions of Indolines by a Nonenzymatic Acylation Catalyst. Journal of the American Chemical Society (2006), 128(44), 14264-14265.) to nitration conditions (e.g. sodium nitrate and TFA) followed by deprotection of the acyl group with acid (e.g. HCl) affords (IVcj). Advancement of (IVcj) and (IVcl) (see: Achvlediani, R.; Natsvlishvili, M.; Baberkina, E.; Khachidze, M.; Abesadze, I.; Suvorov, N. Synthesis of 1H-pyrrolo[3,2-g]- and 1H-pyrrolo[2,3-g] quinoline. Izvestiya Akademii Nauk Gruzii, Seriya Khimicheskaya (1996), 22(1-4), 43-47.) through a reaction sequence similar to that described above (e.g. acylation with α-bromo acetyl chloride, displacement with an amine or other nucleophile, and nitro reduction) affords anilines (IVck) and (IVcn).

Scheme 11

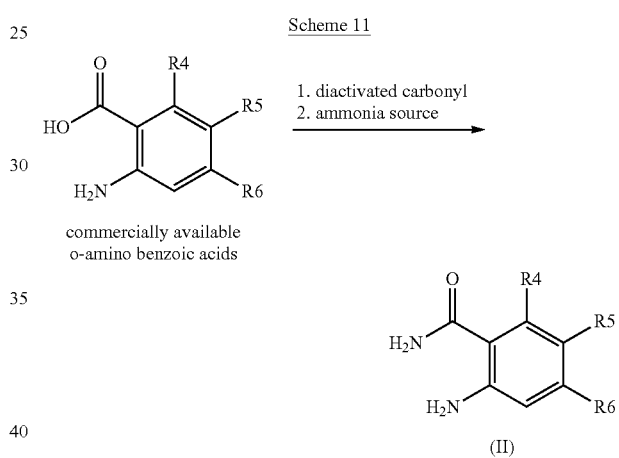

As shown in scheme 11, O-amino carboxamide heads II can be prepared by treatment of the corresponding commercially available o-amino benozic acids with a diactivated carbonyl, e.g. phosgene, and subsequent opening of the in situ generated isatoic anhydride with an ammonia source, e.g. ammonium hydroxide.

Scheme 12

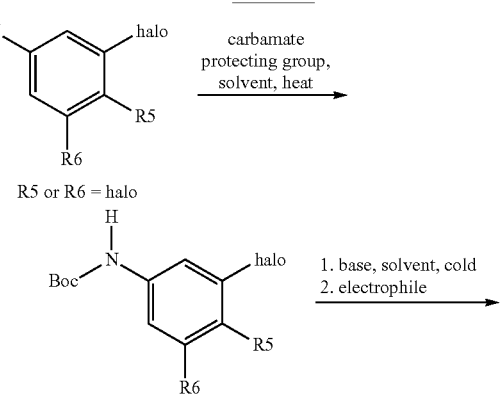

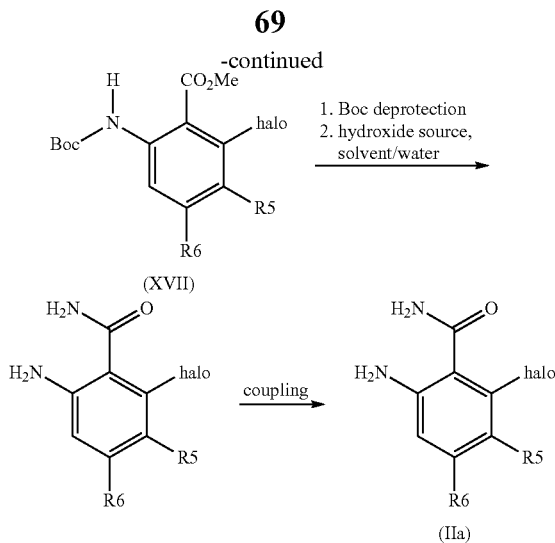

As shown in scheme 12, heads may be prepared from commercially available di-halogenated anilines (for instance 3-choro-5-fluoro-aniline from Apollo Scientific, UK; 3-4-difluoro aniline from ABCR Gmbh & Co., Germany). Note, this scheme is applicable for heads wherein substituent R4 is not H. As shown, the amine group is first protected with a carbamate protecting group, e.g. $Boc_2O$, in solvent, e.g. THF, at heat, e.g. 80° C., and then deprotonating with a strong alkyl lithium base, e.g. tBuLi, in ethereal solvent, e.g. THF, at reduced temperature, e.g. −80° C., with subsequent trapping with an electrophile, e.g. $MeCO_2Cl$ to provide a methyl ester (XVII). The methyl ester XVII is Boc deprotected with with an acid and solvent, e.g. $TFA/CH_2CL_2$, and hydrolyzed with a hydroxide source, e.g. LiOH, in solvent with water, e.g. $THF/H_2O$. Conversion of the amide to the acid (IIa) is carried out using standard coupling procedure, with for instance $NH_3$, EDCl, and dioxane.

EXAMPLES

The following specific examples are included as illustrations and are not to be construed as limiting the scope of the present invention.

As used herein, the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples, schemes, biological writeups, and throughout the specification:

APC (Allophycocyanin)
ATP (adenosine triphosphate)
Ac (acetyl)
atm (atmosphere)
BSA (bovine serum albumin)
CHAPS (3-[3-Cholamidopropyl)Dimethylammonio]-1-Propanesulfonate)
DIPEA(diisopropylethylamine)
DMSO (dimethyl sulfoxide)
DTT (Dithiothreitol)
EDTA (ethylenediaminetetraacetic acid)
Eu (Europium)
G (grams)
GST (Glutathione S-transferase)
h (hours);
HEPES (N-(2-Hydroxyethyl)piperazine-N'-2-ethanesulfonic acid)
hIGF1R or IGF-1R (human Insulin-like growth factor 1 receptor kinase)
hIR (human insulin receptor kinase)
HPLC (high performance/pressureliquid chromatography)
Hz (Hertz);
i-PrOH (isopropanol);
i. v. (intravenous);
L (liters);
M (molar);
MeOH (methanol);
mg (milligrams)
$MgCL_2$, magnesium chloride
MHz (megahertz)
min (minutes)
mL (milliliters)
mM (millimolar)
mmol (millimoles)
mol (moles);
mp (melting point);
NaCl, Sodium chloride
NCBI, National Center for Biotechnology Information
nM, nanomolar
OTF (trifluoromethane sulfonate)
psi (pounds per square inch);
RP (reverse phase);
rt (room temperature);
SEM (2-trimethylsilyl(ethoxymethyl)
TBAI (tetrabutylammonium iodide);
TFA (trifluoroacetic acid);
TFE (trifluoroethanol)
THF (tetrahydrofuran);
TLC (thin layer chromatography);
$T_r$ (retention time);
μL (microliters);
μM, micromolar Unless otherwise noted, reagents and solvents were obtained from commercial suppliers and were used without further purification. Unless otherwise indicated, all reactions were conducted at room temperature and all temperatures are expressed in ° C. (degrees Centigrade).

Throughout the specification, multi-step syntheses are described with respect to various intermediate and exemplary compounds. In general, all but the first step of each multi-step synthesis refer to a product compound of a preceding step. Unless otherwise noted, such reference is understood as reference to the compound in general, though not necessarily to the actual sample of product that was produced in carrying out the preceding step.

Thin-layer chromatography (TLC) was performed on silica gel 60 $F_{254}$ precoated plates. Detection was effected by exposure to UV light (254 nm). Flash and flush column chromatography was performed using Silica Gel 60. Reverse phase preparative and analytical HPLC were performed using C18 columns and acetonitrile:water gradients with 0.05% TFA as a modifier.

Compound purity and characterization were determined by $^1$H-NMR, liquid chromatography-mass spectrometry (LCMS), high resolution mass spectrometry (HRMS), combustion (elemental) analysis, HPLC, and melting point. Compounds of general formula I were typically found to have purities of >90%.

$^1$H NMR spectra were recorded on Varian INOVA-300, Varian INOVA-400, and Bruker AV400 instruments. Chemical shifts are expressed in parts per million (ppm, δ units). Coupling constants are in units of hertz (Hz). Splitting patterns describe apparent multiplicities and are designated as s (singlet), d (doublet), dd (doublet of doublet), t (triplet), q (quartet), m (multiplet), or br (broad).

Low resolution mass spectra were obtained on Micromass ZQ, Micromass ZMD, Micromass QuattroMicro, and Micromass GCT instruments from Micromass Ltd., Altricham, UK, using either Atmospheric Pressure Chemical Ionization (APCI) or ESI Ionization (ESI).

High resolution mass spectral data (HRMS) were recorded with Micromass LCT and Micromass GCT instruments.

Combustion analyses were performed by Atlantic Microlab, Inc. (Norcross, Ga.).

Melting points were recorded in open capillary tubes and are uncorrected.

X-ray diffraction patterns were determined by dusting sample onto a silicon zero background plate of a PANalytical X'Pert Pro diffractometer using the following parameters:

| Radiation Source: | Cu Kα |
| Scan type: | Continous |
| Operating Conditions: | |
| | |
| X-ray tube voltage: | 40 kV |
| X-ray tube current: | 40 mA |
| Scan Conditions: | |
| | |
| Scan range: | 2-40 degrees two-theta |
| Step size: | 0.017 deg 2 · theta./step |
| Time per step: | 10 sec. |
| Sample spinner: | 1 rotation/sec |
| Incident Beam optics: | 0.04 radian soller slits, |
| | 6 mm programmable divergence slit, |
| | 10 mm beam mask, |
| | 0.5 degree anti-scatter slit. |
| Diffracted Beam optics: | 6 mm programmable anti-scatter slit |
| | assembly (X'celerator module), |
| | 0.04 radian soller slits. |
| Detector: | Philips X'Celerator RTMS (Real Time Multi Strip) |
| Data acquisition software: | X'Pert data collector v2.2b, |
| | PANalytical B.V, the Netherlands. |
| Data analysis software: | X'Pert data viewer v1.0c, |
| | PANalytical B.V, the Netherlands |

General Protocol I: Synthesis of o-Amino Carboxamides:

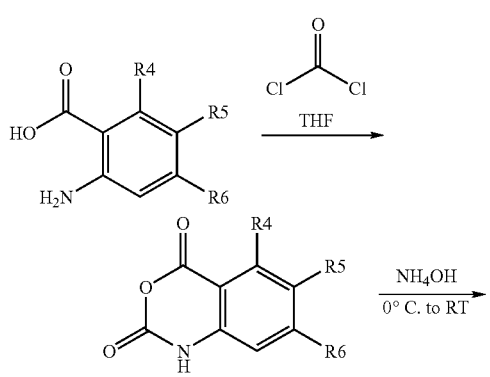

-continued

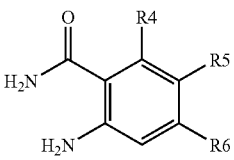

To a solution of the 2-amino benzoic acid in THF was slowly added phosgene as a 20% solution in toluene (1.1 equivalents). The resulting suspension was allowed to stir at room temperature until solids had completely dissolved, and then cooled to 0° C. The flask was fitted with an addition funnel and ammonium hydroxide was cautiously added as a 27% aqueous solution (10 equivalents). After one hour the organic phase was diluted with ethyl acetate, washed twice with aqueous sodium bicarbonate and saturated aqueous sodium chloride, and dried over sodium sulfate. Filtration and removal of the residual solvent gave the desired amides as white solids with sufficient purity for use in subsequent chemical transformations.

Intermediate A1:
3-amino-2-naphthalenecarboxamide

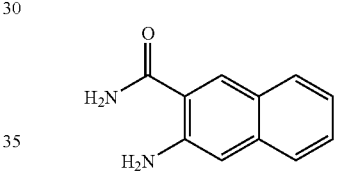

Using General Protocol I and starting with 3-amino-2-naphthalenecarboxylic acid (6.0 g, 32.1 mmol, 3B Medical Systems), 3-amino-2-naphthalenecarboxamide was isolated as a white solid (4.45 g, 74% Yield); 1H NMR (400 MHz, DMSO-$d_6$) δ ppm 6.24 (s, 2 H), 6.92 (s, 1 H), 7.11 (ddd, J=8.00, 6.82, 1.10 Hz, 1 H), 7.32 (ddd, J=8.28, 6.82, 1.19 Hz, 1 H), 7.38 (s, 1 H), 7.48 (d, J=8.42 Hz, 1 H), 7.64 (d, J=8.23 Hz, 1 H), 8.02 (s, 1 H), 8.09 (s, 1 H).

Intermediate A2: 2-amino-6-methylbenzamide

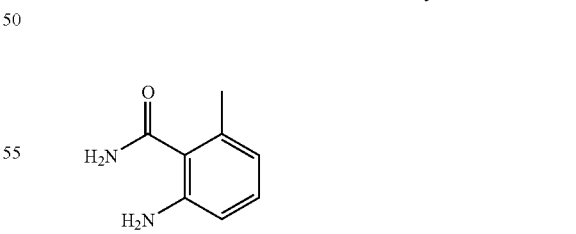

Using General Protocol I and starting with 2-amino-6-methyl benzoic acid (8.0 g, 53 mmol, Acros Organics), 2-amino-6-methyl benzamide was isolated as a yellow solid (1.05 g, 13% yield); 1H NMR (400 MHz, DMSO-$d_6$) δ ppm 2.19 (s, 3 H), 4.88 (s, 2 H), 6.37 (d, J=7.33 Hz, 1 H), 6.49 (d, J=8.06 Hz, 1 H), 6.89 (t, J=7.70 Hz, 1 H), 7.40 (s, 1H), 7.60 (s, 1 H).

Intermediate A3: 2-amino-6-(methyloxy)benzamide

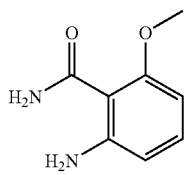

Using General Protocol I and starting with 2-amino-6-(methyloxy)benzoic acid (7.0 g, 42.4 mmol, Peakdale Screening Library), 2-amino-6-(methyloxy)benzamide was isolated as a white solid (3.20 g, 46% Yield); 1H NMR (400 MHz, DMSO-$d_6$) δ ppm 3.72 (s, 3 H), 6.14 (d, J=8.06 Hz, 1 H), 6.27 (dd, J=8.24, 0.92 Hz, 1 H), 6.32 (s, 2 H), 6.97 (t, J=8.15 Hz, 1 H), 7.24 (s, 1 H), 7.50 (s, 1 H).

Intermediate A4: 2-amino-5-(methyloxy)benzamide

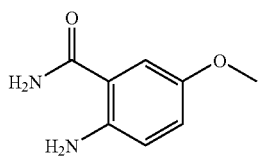

6-methoxy-2H-3,1-benzoxazine-2,4(1H)-dione (3.0 g, 16 mmol, Trans World Chemicals) was treated directly with 27% aqueous ammonium hydroxide. After one hour the organic phase was diluted with ethyl acetate, washed twice with aqueous sodium bicarbonate and saturated aqueous sodium chloride, and dried over sodium sulfate. Filtration and removal of the residual solvent gave 2-amino-5-(methyloxy)benzamide as a white solid (1.42 g, 53% Yield);. 1H NMR (400 MHz, DMSO-$d_6$) δ ppm 3.63 (s, 3 H), 6.07 (s, 2 H), 6.60 (d, J=8.97 Hz, 1 H), 6.79 (dd, J=8.79, 2.93 Hz, 1 H), 7.03 (s, 1 H), 7.06 (d, J=2.93 Hz, 1 H), 7.71 (s, 1 H).

Intermediate A5: 2-amino-4-(methyloxy)benzamide

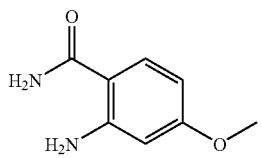

Using the General Protocol I above and starting with 2-amino-4-methoxy benzoic acid (4.55 g, 47.9 mmol, Carbocore), 2-amino-4-(methyloxy)benzamide was isolated as a yellow solid (4.55 g, 57% Yield); 1H NMR (400 MHz, DMSO-$d_6$) δ ppm 3.66 (s, 3H), 6.03 (dd, J=8.80, 2.57 Hz, 1 H), 6.16 (d, J=2.57 Hz, 1 H), 6.71 (s, 2 H), 6.79 (s, 1H), 7.45 (d, J=8.80 Hz, 1 H), 7.52 (s, 1H).

Intermediate A6: 2-amino-4,5-bis(methyloxy)benzamide

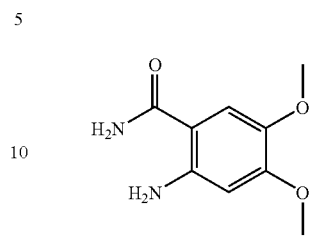

Using General Protocol I and starting with 2-amino-4,5-bis(methyloxy)benzoic acid (7.0 g, 36 mmol, Alfa Aesar), 2-amino-4,5-bis(methyloxy)benzamide was isolated as a white solid (3.75 g, 54% Yield); 1H NMR (400 MHz, DMSO-$d_6$) δ ppm 3.62 (s, 3 H), 3.67 (s, 3 H), 6.24 (s, 1 H), 6.40 (s, 2 H), 6.77 (s, 1 H), 7.07 (s, 1 H), 7.52 (s, 1 H).

Intermediate A7: 2-amino-4-fluorobenzamide

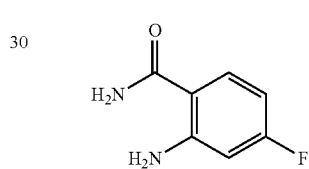

Using General Protocol I and starting with 2-amino-4-fluorobenzoic acid (7.0 g, 45.2 mmol, Aldrich), 2-amino-4-fluorobenzamide was isolated as a white solid (5.86 g, 84% Yield); 1 H NMR (400 MHz, DMSO-$d_6$) δ ppm 6.25 (td, J=8.60, 2.56 Hz, 1 H), 6.41 (dd, J=11.89, 2.56 Hz, 1 H), 6.88 (s, 2 H), 7.06 (s, 1 H), 7.57 (dd, J=8.78, 6.77 Hz, 1H), 7.70 (s, 1 H).

Intermediate A8: 2-amino-4,5-difluorobenzamide

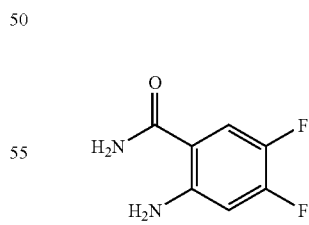

Using General Protocol I and starting with 2-amino-4,5-difluorobenzoic acid (7.0 g, 40.5 mmol, Aldrich), 2-amino-4,5-difluorobenzamide was isolated as a white solid (4.70 g, 67% Yield); 1H NMR (400 MHz, DMSO-$d_6$) δ ppm 6.62 (dd, J=13.36, 7.32 Hz, 1 H), 6.75 (s, 2 H), 7.18 (s, 1 H), 7.62 (dd, J=12.44, 9.15 Hz, 1 H), 7.73 (s, 1 H).

Intermediate A9: 2-amino-4-chlorobenzamide

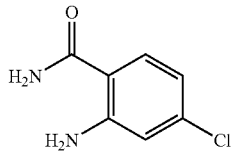

Using General Protocol I and starting with 2-amino-4-chlorobenzoic acid (7.0 g, 40.7 mmol, Alfa Aesar), 2-amino-4-chlorobenzamide was isolated as a white solid (5.10 g, 73% Yield); 1H NMR (400 MHz, DMSO-$d_6$) δ ppm 6.46 (dd, J=8.42, 2.20 Hz, 1 H), 6.72 (d, J=2.01 Hz, 1 H), 6.81 (s, 2 H), 7.13 (s, 1 H), 7.52 (d, J=8.42 Hz, 1 H), 7.76 (s, 1 H).

Intermediate A10: 2-amino-5-bromobenzamide

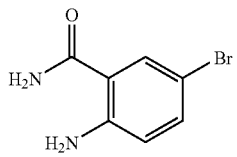

Using General Protocol I and starting with 2-amino-5-bromobenzoic acid (11.0 g, 50.9 mmol, Alfa Aesar), 2-amino-5-bromobenzamide was isolated as a white solid (8.1 g, 74% Yield); 1H NMR (400 MHz, DMSO-$d_6$) δ ppm 6.62 (d, J=8.79 Hz, 1 H), 6.68 (s, 2 H), 7.12 (s, 1 H), 7.21 (dd, J=8.79, 2.38 Hz, 1 H), 7.66 (d, J=2.20 Hz, 1 H), 7.81 (s, 1 H).

Alternate Protocol I: Synthesis of o-amino carboxamides from benzoic acids

Intermediate A11: 2-amino-4,6-difluorobenzamide

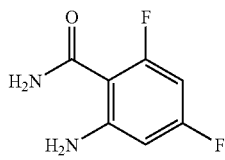

To a solution of 2-amino-4,6-difluoro benzoic acid (4.0 g, 23.12 mmol, Butt Park Ltd.) in tetrahydrofuran (1.0 L) and N,N-dimethylacetamide (150 mL) was added EDCl.HCl (13.44 g, 70 mmol, Aldrich), HOBT (9.5 g, 70 mmol, Aldrich) and ammonia as a 0.5M solution in dioxanes (460 mL, 230 mmol, Aldrich). The resultant slurry was stirred for 24 hours, and then solids removed by filtration through celite. The filtrate was taken to a residue under reduced pressure and partitioned between water and ethyl acetate. The organic layer was dried over sodium sulfate, filtered, taken to a residue under reduced pressure, and purified by chromatography on $SiO_2$ (Ethyl acetate/Hexanes) to afford analytically pure 2-amino-4,6-difluorobenzamide as a white crystalline solid (3.11 g, 78% yield); 1H NMR (400 MHz, DMSO-$d_6$) δ ppm 6.21-6.27 (m, 1 H), 6.27-6.32 (m, 1 H), 6.52 (s, 2 H), 7.48 (s, 1 H), 7.53 (s, 1 H).

Intermediate A12: 6-amino-2,3-difluorobenzamide

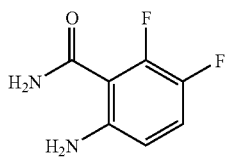

Step A/Intermediate A13: 1,1-dimethylethyl(3,4-difluorophenyl)carbamate

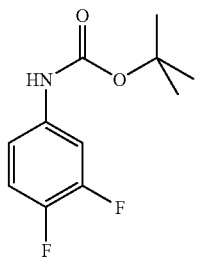

To a solution of 3,4-difluoro aniline (10 g, 77.5 mmol, Aldrich) in tetrahydrofuran (300 mL) was added $Boc_2O$ (20.3 g, 93 mmol, 1.2 equiv, Aldrich). The resulting solution was stirred at 70° C. for 2 days, at which time additional $Boc_2O$ (20.3 g, 93 mmol, 1.2 equiv) was added and the resulting reaction is maintained at 70° C. for an additional 2 days. After 4 days of heating, the tetrahydrofuran was removed under reduced pressure and the product recrystallized from hexanes to afford 1,1-dimethylethyl (3,4-difluorophenyl)carbamate cleanly as a white solid (16.1 g, 70 mmol, 91% yield). 1H NMR (400 MHz, $CDCl_3$) δ ppm 1.48 (s, 9 H), 6.42 (s, 1 H), 6.87 (d, J=8 Hz, 1H), 7.02 (q, J=8.97 Hz, 1 H), 7.40 (s, 1 H).

Step B/Intermediate A14: methyl 6-({[(1,1-dimethylethyl)oxy]carbonyl}amino)-2,3-difluorobenzoate

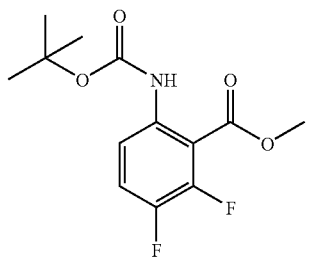

To a solution of 1,1-dimethylethyl(3,4-difluorophenyl)carbamate (8.0 g, 35 mmol) in tetrahydrofuran (250 mL) at −78° C. was slowly added tBuLi as a 1.7M solution in pentane (46 mL, 78.60 mmol, 2.25 equiv., Aldrich). The resulting bright yellow solution was maintained at −78° C. for 3 hours, at which time methylchloroformate (3.24 mL, 42 mmol, 1.20 equiv.) was added dropwise. After 45 minutes, aqueous ammonium chloride (100 mL) was added and the reaction was warmed to room temperature. The organic layer was washed with brine, taken to a residue under reduced pressure, and purified by chromatography on $SiO_2$ (10 to 30% ethyl acetate/hexanes) to afford methyl 6-({[(1,1-dimethylethyl)oxy]carbonyl}amino)-2,3-difluorobenzoate as a pale yellow oil (5.8 g, 20.2 mmol, 58% yield). 1H NMR (400 MHz, $CDCl_3$) δ ppm 1.48 (s, 9 H), 3.94 (s, 3 H), 7.21-7.28 (m, 1 H), 8.08 (ddd, J=9.25, 4.12, 2.20 Hz, 1 H), 9.44 (s, 1 H).

Step C/Intermediate A15:
6-amino-2,3-difluorobenzoic acid

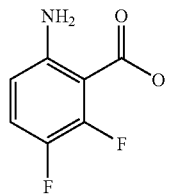

To a solution of methyl 6-({[(1,1-dimethylethyl)oxy]carbonyl}amino)-2,3-difluorobenzoate (5.5 g, 19.2 mmol) in methylene chloride (150 mL) was added trifluoroacetic acid (25 mL, Aldrich). The resulting solution was stirred overnight and then concentrated to an oily residue under reduced pressure. The oil was dissolved in tetrahydrofuran (150 mL) and water (100 mL) and lithium hydroxide (2.3 g, 100 mmol, 5 equiv.) were added. The resulting mixture was rapidly stirred overnight. The next morning the reaction was poured into ethyl acetate and 1.0N HCl was added until the pH is adjusted to 7. The organic layer was washed twice with brine and taken to a residue under reduced pressure to afford 6-amino-2,3-difluorobenzoic acid (3.78 g, 22 mmol) of sufficient purity for use directly in the next transformation. 1H NMR (400 MHz, DMSO-$d_6$) δ ppm 6.51 (ddd, J=9.35, 4.22, 2.20 Hz, 1 H), 7.21-7.31 (m, 1 H), 8.71 (s, 1 H).

Step D/Intermediate A12:
6-amino-2,3-difluorobenzamide

To a solution of 2-amino-5,6-difluoro benzoic acid (3.78 g, 21.8 mmol) in tetrahydrofuran (500 mL) was added EDCl.HCl (8.5 g, 44.0 mmol, 2.0 equiv.), HOBT (5.9 g, 44 mmol, 2.0 equiv.) and ammonia as a 0.5M solution in dioxanes (218 mL, 109 mmol, 5 equiv.). The resultant slurry was stirred for 24 hours, and then solids removed by filtration through celite. The filtrate was taken to a residue under reduced pressure and partitioned between water and ethyl acetate. The organic layer was dried over sodium sulfate, filtered, taken to a residue under reduced pressure, and purified by chromatography on $SiO_2$ (Ethyl acetate/Hexanes) to afford analytically pure 2-amino-5,6-difluorobenzamide as a white crystalline solid (2.73 g, 15.8 mmol, 72% Yield). 1H NMR (400 MHz, DMSO-$d_6$) δ ppm 5.78 (s, 2 H), 6.45 (ddd, J=9.16, 4.03, 1.83 Hz, 1 H), 7.10-7.18 (m, 1 H), 7.69 (d, J=11.00 Hz, 2 H).

Intermediate A16:
2-amino-4-chloro-6-fluorobenzamide

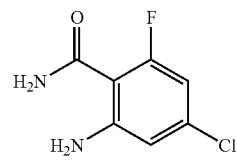

Step A/Intermediate A17: 1,1-dimethylethyl(3-chloro-5-fluorophenyl)carbamate

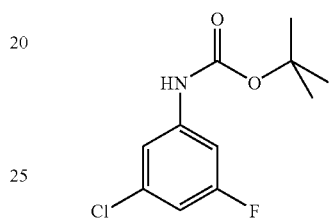

To a solution of 3-chloro-5-fluoro aniline (10 g, 69 mmol, Acros) in tetrahydrofuran was added tert-butyldicarboxylate (23 g, 103 mmol). The reaction was maintained at reflux for six days and the volatiles removed under reduced pressure. The resulting residue was purified via chromatography on $SiO_2$ (0 to 30% Ethyl acetate/Hexanes) but the excess $Boc_2O$ could not be removed. The column fractions containing 1,1-dimethylethyl (3-chloro-5-fluorophenyl)carbamate were concentrated, redissolved in methylene chloride, and stirred with MP-Trisamine resin (35 g, Argonaut Technologies) overnight. Filtration and concentration afforded 1,1-dimethylethyl(3-chloro-5-fluorophenyl)carbamate as a clear oil (9.8 g, 58% yield) of sufficient purity for use in the next transformation. 1H NMR (400 MHz, $CDCl_3$) δ ppm 1.52 (s, 9 H), 6.51 (s, 1 H), 6.75 (dt, J=8.43, 2.02 Hz, 1 H), 7.09-7.17 (m, 2 H).

Step B/Intermediate A18: methyl 4-chloro-2-({[(1,1-dimethylethyl)oxy]carbonyl}amino)-6-fluorobenzoate

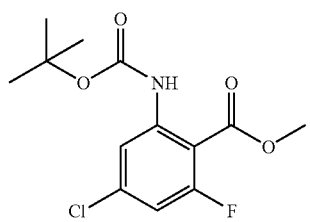

To a solution of 1,1-dimethylethyl(3-chloro-5-fluorophenyl)carbamate (7.34 g, 30 mmol) in tetrahydrofuran (200 mL, Aldrich) at −78° C. was slowly added tBuLi as a 1.7M solution in pentane (46 mL, 78 mmol, 2.6 equiv.). The resulting bright yellow solution was maintained at −78° C. for 3 hours, at which time methylchloroformate (3.02 mL, 39 mmol, Fluka) was added dropwise. After 45 minutes aqueous ammonium chloride (100 mL) was added and the reaction was warmed to room temperature. The organic layer was washed with brine, taken to a residue under reduced pressure, and purified by chromatography on SiO₂ (10 to 30% ethyl acetate/hexanes) to afford methyl 4-chloro-2-({[(1,1-dimethylethyl)oxy]carbonyl}amino)-6-fluorobenzoate as a pale yellow oil (6.4, 70% yield) as a roughly 5:1 mixture with 1,1-dimethylethyl[5-chloro-2-(2,2-dimethylpropanoyl)-3-fluorophenyl]carbamate which was removed in the subsequent step. 1H NMR (400 MHz, CDCl₃) δ ppm 1.52 (s, 9 H), 3.95 (s, 3 H), 6.76 (d, J=2.20 Hz, 1 H), 6.78 (d, J=4 Hz, 1H) 8.31-8.34 (m, 1 H).

Step C/Intermediate A19:
2-amino-4-chloro-6-fluorobenzoic acid

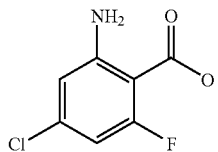

A solution of methyl 4-chloro-2-({[(1,1-dimethylethyl)oxy]carbonyl}amino)-6-fluorobenzoate in methylene chloride (150 mL) and trifluoroacetic acid (25 mL) was stirred for six hours. All solvents were removed under reduced pressure on a rotoevaporator, and the resulting residue was dissolved in THF (150 mL) and water (100 mL) and lithium hydroxide (2.5 g) were added. The biphasic mixture was stirred rapidly for three days, at which time no starting materials remain by TLC. The organic layer was washed with 2.0N sodium hydroxide and then the organic layers are discarded. The aqueous layer was adjusted to pH=2 by careful addition of 1.0N hydrochloric acid and then extracted with ethyl acetate. The combined ethyl acetate washes were dried over sodium sulfate, and volatiles were removed under reduced pressure to afford 2-amino-4-chloro-6-fluorobenzoic acid as a white solid (3.3 g, 69% yield) of sufficient purity for use in the next transformation. 1H NMR (400 MHz, DMSO-d₆) δ ppm 6.38 (dd, J=11.17, 1.47 Hz, 1 H), 6.60 (s, 1 H).

Step D/Intermediate A16:
2-amino-4-chloro-6-fluorobenzamide

To a solution of 2-amino-4-chloro-6-fluorobenzoic acid (3.22 g, 17.04 mmol) in tetrahydrofuran (100 mL) was added EDCI.HCl (6.5 g, 34.1 mmol, Aldrich), HOBT (4.6 g, 34 mmol) and ammonia as a 0.5M solution in dioxanes (170 mL, 85 mmol, Aldrich). The resultant slurry was stirred for 24 hours, and then solids removed by filtration through celite. The filtrate was taken to a residue under reduced pressure and partitioned between water and ethyl acetate. The organic layer was dried over sodium sulfate, filtered, taken to a residue under reduced pressure, and purified by chromatography on SiO₂ (Ethyl acetate/Hexanes) to afford analytically pure 2-amino-4-chloro-6-fluorobenzamide as a white crystalline solid (2.98 g, 92% Yield). 1H NMR (400 MHz, DMSO-d₆) δ ppm 6.40 (s, 2 H), 6.44 (dd, J=10.81, 2.02 Hz, 1 H), 6.57 (s, 1 H), 7.56 (s, 1 H), 7.60 (s, 1 H).

Syntheses of Aniline Intermediates

Intermediate B1: 2-methyl-4-(1-propyl-1,2,5,6-tetrahydro-3-pyridinyl)aniline

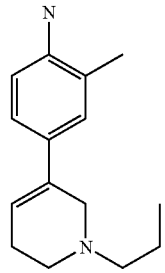

Step A/Intermediate B2:
3-(3-methyl-4-nitrophenyl)pyridine (General Suzuki Coupling Procedure)

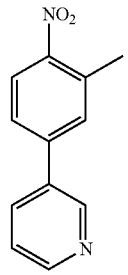

Nitrogen was bubbled through dioxane for 15 minutes (100 mL) prior to the addition of 4-chloro-2-(methyloxy)-1-nitrobenzene (5.0 g, 29.1 mmol, Aldrich). To the solution were added 3-pyridinylboronic acid (4.3 g, 34.9 mmol, Frontier Science), dichloro(triphenylphosphine)palladium (1.0 g, 1.46 mmol, Aldrich) and degassed aqueous Na₂CO₃ (30 mL, 3 N, 87.3 mmol). The reaction mixture was heated at 82° C. for 4 h. Additional water (100 mL) was added to the reaction when it was cooled down to rt, and ethyl acetate was used to extract the crude product. The combined organic phases were dried (Na₂CO₃), concentrated, and purified by silica column chromatography (10-60% Ethyl acetate/hexane) to afford 3-(3-methyl-4-nitrophenyl)pyridine (5.3 g, 85% yield.) 1H NMR (400 MHz, DMSO-d₆) δ ppm 2.58 (s, 3 H), 7.52 (ddd, J=8.0, 4.8, 0.9 Hz, 1 H), 7.80 (dd, J=8.5, 2.1 Hz, 1 H), 7.90 (d, J=1.1 Hz, 1 H), 8.08 (d, J=8.4 Hz, 1 H), 8.16 (ddd, J=8.0, 2.5, 1.6 Hz, 1 H), 8.62 (dd, J=4.8, 1.5 Hz, 1 H), 8.95-8.97 (m, 1 H).

Step B/Intermediate B3:
3-(3-methyl-4-nitrophenyl)-1-propylpyridinium iodide (General Pyridine Alkylation Procedure)

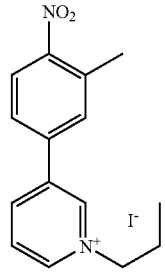

To pinacolone (200 mL, Aldrich) were added 3-(3-methyl-4-nitrophenyl)pyridine (5.3 g, 24.0 mmol) and propyliodide (17.0 g, 100.0 mmol, Fluka). The reaction was stirred at 102° C. for 12 h. Solids were collected and washed with MeOH (2×20 mL) to afford 3-(3-methyl-4-nitrophenyl)-1-propylpyridinium iodide (8.7 g, 90% yield). 1H NMR (400 MHz, DMSO-$d_6$) δ ppm 0.92 (t, J=7.3 Hz, 3 H), 1.97-2.06 (m, 2 H), 2.62 (s, 3 H), 4.62 (t, J=7.3 Hz, 2 H), 7.98 (dd, J=8.5, 1.9 Hz, 1 H), 8.07 (d, J=1.1 Hz, 1H), 8.21 (d, J=8.6 Hz, 1 H), 8.29 (dd, J=8.1, 6.1 Hz, 1 H), 9.00 (d, J=8.4 Hz, 1 H), 9.12 (d, J=6.0 Hz, 1 H), 9.57 (s, 1 H); ESIMS (M+H)$^+$=257.

Step C/Intermediate B4: 5-(3-methyl-4-nitrophenyl)-1-propyl-1,2,3,6-tetrahydropyridine (General Pyridinium Reduction Procedure)

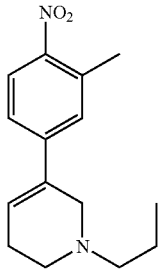

To MeOH (200 mL) was added 3-(3-methyl-4-nitrophenyl)-1-propylpyridinium iodide (9.4 g, 22.7 mmol). The solution was stirred at −10° C. for 10 min followed by the slow portionwise addition of solid NaBH$_4$ (2.8 g, 68.1 mmol, Aldrich) over 5 min. The reaction was kept stirring at −10° C. for 1 h. The mixture was concentrated and diluted with Ethyl acetate (200 mL) before the addition of sat. NaHCO$_3$ aq (150 mL). The organic phase was washed with brine, concentrated, and dried (Na$_2$SO$_4$). Purification via chromatography on SiO$_2$ (0-10% MeOH/DCM) afforded 5-(3-methyl-4-nitrophenyl)-1-propyl-1,2,3,6-tetrahydropyridine (5.0 g, 85% yield). 1H NMR (400 MHz, DMSO-$d_6$) δ ppm 0.87 (t, J=7.3 Hz, 3 H), 1.48-1.57 (m, 2 H), 2.29 (td, J=5.7, 3.2 Hz, 2 H), 2.39-2.43 (m, 2 H), 2.51 (t, J=5.7 Hz, 2 H), 3.26 (d, J=1.8 Hz, 2 H), 3.94 (s, 3 H), 6.43 (ddd, J=3.8, 2.2, 2.0 Hz, 1 H), 7.10 (dd, J=8.5, 1.7 Hz, 1 H), 7.23 (d, J=1.8 Hz, 1 H), 7.83 (d, J=8.4 Hz, 1 H); ESIMS (M+H)$^+$=261.

Step D/Intermediate B1: 2-methyl-4-(1-propyl-1,2,5,6-tetrahydro-3-pyridinyl)aniline, (General Hyrazine-Mediated Reduction Procedure).

To 5-(3-methyl-4-nitrophenyl)-1-propyl-1,2,3,6-tetrahydropyridine (5.0 g, 19.2 mmol) in MeOH (100 mL) was added iron (III) chloride (0.93 g, 5.8 mmol, Aldrich) and activated carbon (1.0 g, Aldrich). The reaction mixture was stirred at 64° C. for 20 min before the dropwise addition of hydrazine hydrate (11.5 mL, 230.8 mmol, Aldrich) over 5 min. The reaction was kept stirring at 64° C. for additional 5 h. Filtration removed the solids and the filtrate was concentrated and purified via chromatography on SiO$_2$ (0-10% 2 M NH$_3$ in MeOH/DCM) to afford 2-methyl-4-(1-propyl-1,2,5,6-tetrahydro-3-pyridinyl)aniline (3.6 g, 82% yield.) 1H NMR (400 MHz, CDCl$_3$) δ ppm 0.94 (t, J=7.4 Hz, 3 H), 1.57-1.67 (m, 2 H), 2.16 (s, 3 H), 2.33 (tt, J=5.9, 2.9 Hz, 2 H), 2.44-2.50 (m, 2 H), 2.59 (t, J=5.8 Hz, 2 H), 3.29 (q, J=2.0 Hz, 2 H), 3.58 (s, 2 H), 5.96 (dq, J=3.9, 2.0 Hz, 1 H), 6.61 (d, J=7.9 Hz, 1 H), 7.02-7.06 (m, 2 H).

Intermediate B5:
2-ethyl-4-[4-(1-methylethyl)-1-piperazinyl]aniline

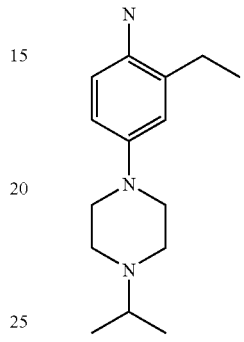

Step A/Intermediate B6: 5-[4-(1-methylethyl)-1-piperazinyl]-2-nitrobenzaldehyde

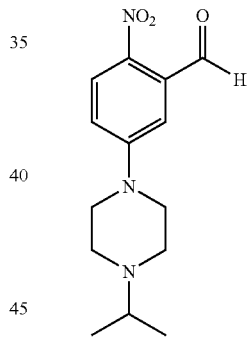

To 5-chloro-2-nitrobenzaldehyde (10.0 g, 54.0 mmol, Aldrich) in dioxane (300 mL) was added 1-(1-methylethyl)piperazine (13.8 g, 108.0 mmol, Aldrich), XANTPHOS (3.1 g, 5.4 mmol, Aldrich), and Cs$_2$CO$_3$ (35.2 g, 108.0 mmol, Aldrich). The mixture was bubbled with N$_2$ for 15 min prior to the addition of Pd$_2$(dba)$_3$ (2.5 g, 2.7 mmol, Aldrich). The reaction was stirred at 100° C. for 5 h. Ethyl acetate (150 mL) was used to dilute the reaction mixture, followed by the addition of water (100 mL). After partitioning, extraction with Ethyl acetate (2×75 mL), drying (Na$_2$SO$_4$), concentration, and silica gel chromatography afforded 5-[4-(1-methylethyl)-1-piperazinyl]-2-nitrobenzaldehyde (1.5 g, 10% yield). 1H NMR (400 MHz, CDCl$_3$) δ ppm 1.08 (d, J=6.6 Hz, 6 H), 2.62-2.69 (m, 4 H), 2.70-2.79 (m, 1 H), 3.46-3.51 (m, 4 H), 6.93 (dd, J=9.2, 2.9 Hz, 1 H), 7.13 (d, J=2.9 Hz, 1 H), 8.09-8.12 (m, 1 H), 10.53 (s, 1 H).

Step B/Intermediate B7: 1-(3-ethenyl-4-nitrophenyl)-4-(1-methylethyl)piperazine

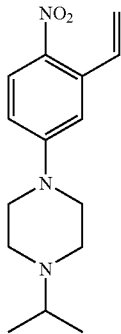

To the THF solution (25 mL) of methyltriphenylphosphonium bromide (3.5 g, 9.8 mmol, Aldrich) at −78° C. was added n-butyl lithium as a 1.7M solution in hexanes (4.2 mL, 2.5 M, Aldrich). The reaction was stirred overnight and then quenched by the addition of potassium sodium tartrate (30 mL of a saturated aqueous solution). After extraction with Ethyl acetate (2×10 mL), drying (Na$_2$CO$_3$), and concentration, the crude product was purified with silica gel column chromatography (0-10% MeOH/DCM). The product was dissolved in hexanes and filtered to remove residual triphenylphosphine oxide. The concentrated filtrate afforded 1-(3-ethenyl-4-nitrophenyl)-4-(1-methylethyl)piperazine (1.4 g, 80% yield.) ESIMS (M+H)$^+$=276.3.

Step C/Intermediate B5: 2-ethyl-4-[4-(1-methylethyl)-1-piperazinyl]aniline (General Hydrogenation Protocol)

A solution of 1-(3-ethenyl-4-nitrophenyl)-4-(1-methylethyl)piperazine (1.4 g, 5.1 mmol) and 10% palladium on carbon (0.5 g) in degassed ethanol was maintained under an atmosphere of hydrogen (60 psi) overnight. The next morning, the reaction was filtered through celite, concentrated, and purified via chromatography on SiO$_2$ to afford 2-ethyl-4-[4-(1-methylethyl)-1-piperazinyl]aniline (0.8 g, 3.2 mmol, 64% Yield). 1H NMR (400 MHz, CDCl$_3$) d ppm 0.92 (t, J=7.3 Hz, 3 H), 1.51-1.60 (m, 2 H), 1.81 (dd, J=7.7, 2.9 Hz, 4 H), 1.98-2.06 (m, 2 H), 2.30-2.37 (m, 2 H), 2.40 (t, J=7.9 Hz, 1 H), 3.06 (d, J=11.7 Hz, 2 H), 3.67 (s, 2 H), 3.82 (s, 3 H), 6.63-6.70 (m, 3 H). 1 H NMR (400 MHz, DMSO-d$_6$) δ ppm 0.96 (d, J=6.6 Hz, 6 H), 1.07 (td, J=7.5, 0.7 Hz, 3H), 2.37 (q, J=7.3 Hz, 2 H), 2.51 (s, 4 H), 2.59-2.67 (m, 1 H), 2.86 (s, 4 H), 4.29 (s, 2 H), 6.48 (s, 1H), 6.51 (d, J=19.0 Hz, 2 H).

Intermediate B8: 2-(methyloxy)-4-(1-propyl-1,2,5,6-tetrahydro-3-pyridinyl)aniline

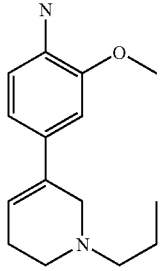

Step A/Intermediate B9: 3-[3-(methyloxy)-4-nitrophenyl]pyridine

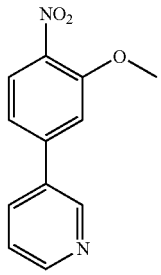

Using the general Suzuki coupling procedure described above for Intermediate B2, 3-[3-(methyloxy)-4-nitrophenyl]pyridine (20 g, 106.4 mmol mmol) was prepared from 4-chloro-2-(methyloxy)-1-nitrobenzene (14.4 g, 117.0 mmol) and 3-pyridinylboronic acid (20 g) in 91% yield. ESIMS (M+H)$^+$=261.

Step B/Intermediate B10: 3-[3-(methyloxy)-4-nitrophenyl]-1-propylpyridinium iodide

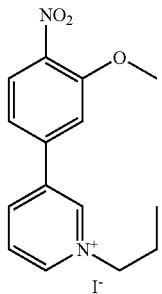

Using the general pyridine alkylation procedure described for Intermediate B3, 3-[3-(methyloxy)-4-nitrophenyl]-1-propylpyridinium iodide (31 g, 77.5 mmol, 89% Yield) was prepared from 3-[3-(methyloxy)-4-nitrophenyl]pyridine (20 g, 87 mmol) and propyl iodide (59 mL, 348 mmol). 1 H NMR (400 MHz, DMSO-d$_6$) δ ppm 0.93 (t, J=7.4 Hz, 3 H), 1.97-2.07 (m, 2 H), 4.05 (s, 3 H), 4.62 (t, J=7.3 Hz, 2 H), 7.61 (dd, J=8.4, 1.8 Hz, 1 H), 7.80 (d, J=1.8 Hz, 1 H), 8.12 (d, J=8.4 Hz, 1 H), 8.30 (dd, J=8.1, 6.1 Hz, 1 H), 9.03 (ddd, J=8.6, 1.5, 1.2 Hz, 1 H), 9.13 (d, J=6.0 Hz, 1 H), 9.55 (s, 1 H).

Step C/Intermediate B11: 5-[3-(methyloxy)-4-nitrophenyl]-1-propyl-1,2,3,6-tetrahydropyridine

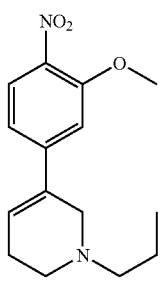

Using the general pyridinium reduction procedure described for Intermediate B4, 5-[3-(methyloxy)-4-nitrophenyl]-1-propyl-1,2,3,6-tetrahydropyridine (19.0 g, 68.8 mmol, 89% Yield) was prepared from 3-[3-(methyloxy)-4-nitrophenyl]-1-propylpyridinium iodide (31 g, 77.5 mmol). 1H NMR (400 MHz, CDCl$_3$) δ ppm 0.93-0.97 (m, 3 H), 1.57-1.66 (m, 2H), 2.38-2.43 (m, 2 H), 2.47-2.52 (m, 2 H), 2.62 (t, J=5.7 Hz, 2H), 3.31 (q, J=2.6 Hz, 2 H), 3.97 (s, 3 H), 6.25 (ddd, J=3.8, 2.2, 2.0 Hz, 1 H), 6.96 (dd, J=8.4, 1.6 Hz, 1 H), 6.99 (d, J=1.6 Hz, 1 H), 7.84 (d, J=8.4 Hz, 1 H); ESIMS (M+H)$^+$=277.

Step D/Intermediate B8: 2-(methyloxy)-4-(1-propyl-1,2,5,6-tetrahydro-3-pyridinyl)aniline Using the general hydrazine reduction procedure described above for Intermediate B1, 2-(methyloxy)-4-(1-propyl-1,2,5,6-tetrahydro-3-pyridinyl)aniline (10 g, 40.7 mmol, 62% Yield) was prepared from 5-[3-(methyloxy)-4-nitrophenyl]-1-propyl-1,2,3,6-tetrahydropyridine (18 g, 65.2 mmol). 1H NMR (400 MHz, CDCl$_3$) δ ppm 0.92-0.96 (m, 3 H), 1.57-1.67 (m, 2 H), 2.31-2.37 (m, 2 H), 2.45-2.50 (m, 2 H), 2.60 (t, J=5.8 Hz, 2 H), 3.30 (q, J=2.6 Hz, 2 H), 3.77 (s, 2 H), 3.85 (s, 3 H), 5.96-5.99 (m, 1H), 6.64 (d, J=8.1 Hz, 1 H), 6.75-6.81 (m, 2 H).

Intermediate B12: 2-(methyloxy)-4-(1-propyl-3-piperidinyl)aniline (General Hydrogenation Protocol)

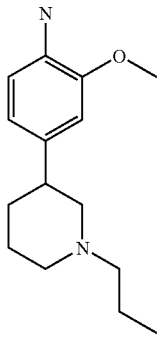

In a pressure vessel was placed 5-[3-(methyloxy)-4-nitrophenyl]-1-propyl-1,2,3,6-tetrahydropyridine (Intermediate B11, 4.1 g, 15.0 mmol) in Ethyl acetate (100 mL). The solution was bubbled with nitrogen for 15 min before the addition of 10% Pd/C (0.5 g). The reaction was stirred at RT for 12 h under 60 psi of H$_2$. After releasing H$_2$ pressure, the mixture was filtered through celite, and the filtrate was concentrated and purified by silica gel chromatography to afford 2-(methyloxy)-4-(1-propyl-3-piperidinyl)aniline (3.5 g, 96% yield). 1H NMR (400 MHz, DMSO-d$_6$) δ ppm 0.82 (t, J=7.3 Hz, 3 H), 1.27-1.45 (m, 3 H), 1.45-1.58 (m, 1 H), 1.61-1.69 (m, 1 H), 1.69-1.77 (m, 1 H), 1.77-1.89 (m, 2 H), 2.16-2.26 (m, 2 H), 2.50-2.58 (m, 1 H), 2.75-2.88 (m, 2 H), 3.72 (s, 3 H), 4.47 (s, 2 H), 6.52 (d, J=0.9 Hz, 2 H), 6.65 (s, 1 H).

Intermediate B13: 2-(methyloxy)-4-(1-methyl-1,2,5,6-tetrahydro-3-pyridinyl)aniline

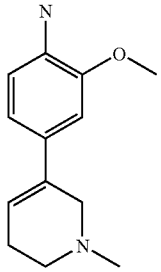

Step A/Intermediate B14: 1-methyl-5-[3-(methyloxy)-4-nitrophenyl]-1,2,3,6-tetrahydropyridine

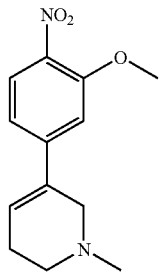

Using the general pyridine alkylation, and pyridinium reduction procedures described for Intermediates B3 and B4, 3-(3-methyl-4-nitrophenyl)pyridine (7.2 g, 31.3 mmol) was converted to 2-(methyloxy)-4-(1-propyl-1,2,5,6-tetrahydro-3-pyridinyl)aniline (5.0 g, 20.2 mmol, 65% Yield, 2 steps) using methyl iodide as the alkylated agent. ESIMS (M+H)$^+$= 249.

Step B/Intermediate B13: 2-(methyloxy)-4-(1-methyl-1,2,5,6-tetrahydro-3-pyridinyl)aniline Using the general hydrazine reduction procedure described for Intermediate B1, 2-(methyloxy)-4-(1-methyl-1,2,5,6-tetrahydro-3-pyridinyl)aniline (1.96 g, 9 mmol, 90% Yield) was prepared from 1-methyl-5-[3-(methyloxy)-4-nitrophenyl]-1,2,3,6-tetrahydropyridine (2.4 g, 10 mmol). 1H NMR (400 MHz, CDCl$_3$) δ ppm 2.35 (td, J=5.9, 3.2 Hz, 2 H), 2.44 (s, 3 H), 2.55 (t, J=5.8 Hz, 2 H), 3.24 (d, J=2.4 Hz, 2 H), 3.78 (s, 2 H), 3.85 (s, 3 H), 5.97 (dt, J=3.8, 1.9 Hz, 1 H), 6.64 (d, J=8.1 Hz, 1 H), 6.75-6.79 (m, 1 H), 6.80 (d, J=1.5 Hz, 1 H).

Intermediate B15: 2-(methyloxy)-4-(1-methyl-3-piperidinyl)aniline

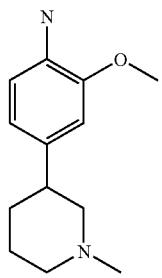

Using the general hydrogenation protocol described for Intermediate B5, 2-(methyloxy)-4-(1-methyl-3-piperidinyl)aniline (2.6 g, 96% yield) was prepared from 1-methyl-5-[3-(methyloxy)-4-nitrophenyl]-1,2,3,6-tetrahydropyridine (3.08 g). 1H NMR (400 MHz, CDCl$_3$) δ ppm 1.32-1.43 (m, 1 H), 1.69-1.81 (m, 2 H), 1.86-1.94 (m, 3H), 2.29 (s, 3 H), 2.72 (tt, J=11.7, 3.5 Hz, 1 H), 2.86-2.96 (m, 2 H), 3.69 (s, 2 H), 3.85 (s, 3 H), 6.65 (s, 3 H).

Intermediate B16: 4-[1-(1-methylethyl)-1,2,5,6-tetrahydro-3-pyridinyl]-2-(methyloxy)aniline

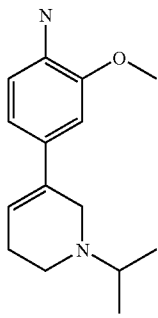

Step A/Intermediate B17: 3-[3-(methyloxy)-4-nitrophenyl]-1-(2-propen-1-yl)pyridinium bromide

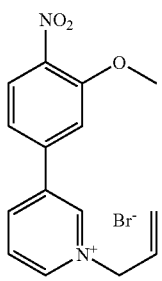

To acetone (300 mL) was added 3-(3-methyl-4-nitrophenyl)pyridine (Intermediate B9, 20.25 g, 88.0 mmol)) and allyl bromide (42.6 g, 352.2 mmol, Aldrich), and the reaction was stirred at 60° C. for 12 h. Filtration removed the liquids and washing with MeOH (2×20 mL) afforded 3-[3-(methyloxy)-4-nitrophenyl]-1-(2-propen-1-yl)pyridinium bromide as a yellow solid (30.8 g, 99% yield).

Step B/Intermediate 18: 5-[3-(methyloxy)-4-nitrophenyl]-1-(2-propen-1-yl)-1,2,3,6-tetrahydropyridine

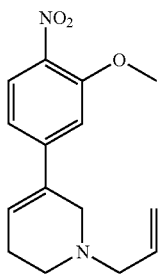

To a solution of 3-[3-(methyloxy)-4-nitrophenyl]-1-(2-propen-1-yl)pyridinium bromide (28.2 g, 80.0 mmol) in MeOH (200 mL) was added NaBH₃CN (21.1 g, 320.0 mmol). The reaction was heated to 65° C. and stirred for 72 h. The cooled solution was concentrated to remove MeOH, and to the residue was added saturated aq. NaHCO₃ (100 mL). After extraction with Ethyl acetate (2×100 mL), concentration, and drying (Na₂SO₄), purification by silica chromatography afforded 5-[3-(methyloxy)-4-nitrophenyl]-1-(2-propen-1-yl)-1,2,3,6-tetrahydropyridine (11.0 g, 50%). ESIMS (M+H)⁺=275.

Step C/Intermediate B19: 5-[3-(methyloxy)-4-nitrophenyl]-1,2,3,6-tetrahydropyridine

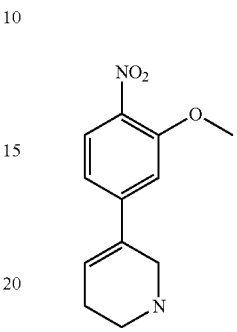

Nitrogen was bubbled through dichloromethane (100 mL) for 10 minutes followed by the addition of N-dimethylbarbituric acid (15.4 g, 98.4 mmol) and Pd(PPh₃)₄ (1.9 g, 1.6 mmol). After the addition of 5-[3-(methyloxy)-4-nitrophenyl]-1-(2-propen-1-yl)-1,2,3,6-tetrahydropyridine, the reaction was heated to 35° C. and stirred for 3 h. To the cooled solution was added saturated aq. Na₂CO₃ (100 mL), and the mixture was allowed to stir at RT for 30 min. After extraction with dichloromethane (2×50 mL), drying (Na₂SO₄), and concentration, chromatography on SiO₂ afforded 5-[3-(methyloxy)-4-nitrophenyl]-1,2,3,6-tetrahydropyridine (5.3 g, 70% yield). 1H NMR (400 MHz, CDCl₃) δ ppm 2.31 (d, J=4.0 Hz, 2 H), 3.02 (t, J=5.7 Hz, 2 H), 3.29 (s, 1H), 3.71 (d, J=1.8 Hz, 2 H), 3.97 (s, 3 H), 6.32 (t, J=4.0 Hz, 1 H), 6.95 (d, J=8.4 Hz, 1H), 6.98 (s, 1 H), 7.85 (d, J=8.4 Hz, 1 H).

Step D/Intermediate B20: 1-(1-methylethyl)-5-[3-(methyloxy)-4-nitrophenyl]-1,2,3,6-tetrahydropyridine

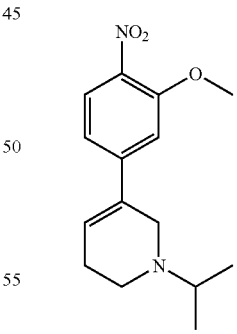

To a pressure vessel containing acetonitrile (40 mL) and potassium carbonate (4.0 g, 29.2 mmol) was added 5-[3-(methyloxy)-4-nitrophenyl]-1,2,3,6-tetrahydropyridine (1.7 g, 7.3 mmol) and 2-iodopropane (1.85 g, 10.9 mmol). The reaction was stirred at 85° C. overnight. After removal of the solvent under reduced pressure the residue was diluted with ethyl acetate (30 mL) and washed with water (40 mL). After partitioning and extraction of the aqueous layer (Ethyl acetate 2×15 mL), the organic layer was dried over sodium sulfate, filtered, concentrated and purified via chromatography on SiO₂ to afford 1-(1-methylethyl)-5-[3-(methyloxy)-4-nitrophenyl]-1,2,3,6-tetrahydropyridine (1.6 g, 80% yield.) ESIMS (M+H)⁺=277.1.

Step E/Intermediate B16: 4-[1-(1-methylethyl)-1,2,5,6-tetrahydro-3-pyridinyl]-2-(methyloxy)aniline In a manner analogous to the general hydrazine reduction described for Intermediate B1, 1-[1-(1-methylethyl)-1,2,5,6-tetrahydro-3-pyridinyl]-2-(methyloxy)aniline (0.90 g, 67% Yield) was prepared from 1-(1-methylethyl)-5-[3-(methyloxy)-4-nitrophenyl]-1,2,3,6-tetrahydropyridine (1.5 g). 1H NMR (400 MHz, DMSO-d₆) δ ppm 1.01 (d, J=6.6 Hz, 6 H), 2.15 (s, 2 H), 2.49 (s, 2 H), 2.74-2.84 (m, 1 H), 3.23 (s, 2 H), 3.73 (s, 3 H), 4.67 (s, 2 H), 5.90 (s, 1 H), 6.52 (d, J=8.1 Hz, 1 H), 6.67 (dd, J=8.1, 1.7 Hz, 1H), 6.78 (d, J=1.6 Hz, 1 H).

Intermediate B21: 2-(methyloxy)-5-(1-propyl-1,2,5,6-tetrahydro-3-pyridinyl)aniline

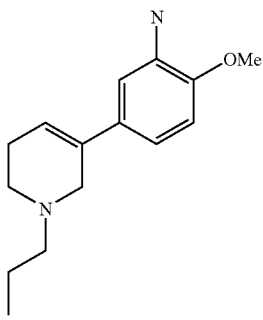

Step A/Intermediate B22: 3-[4-(methyloxy)-3-nitrophenyl]pyridine

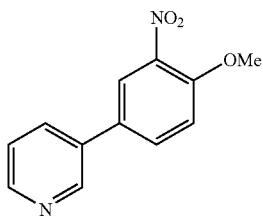

Nitrogen was bubbled through dioxane (100 mL) followed by the addition of 4-bromo-1-(methyloxy)-2-nitrobenzene (5.0 g, 21.55 mmol, Transworld). To the solution were added 3-pyridinylboronic acid (3.16 g, 25.90 mmol, Boron Molecular), dichloro(triphenylphosphine)palladium (0.76 g, 1.08 mmol, Strem) and degassed aqueous Na₂CO₃ (65 mL, 1 M, 65 mmol). The reaction mixture was heated at 80° C. overnight. The reaction mixture was diluted with ethyl acetate (100 ml) and washed with water (100 mL). The organic layer was concentrated under reduced pressure and the crude product was recrystallized from hexanes/ethyl acetate to afford 3-[4-(methyloxy)-3-nitrophenyl]pyridine (1.5 g, 76%). ESIMS (M+H)+=231.

Step B/Intermediate B23: 3-[4-(methyloxy)-3-nitrophenyl]-1-propylpyridinium iodide

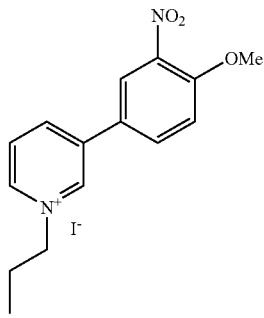

To pinacolone (50 mL, Aldrich) was added 3-[4-(methyloxy)-3-nitrophenyl]pyridine (3.5 g, 15.22 mmol) and propyliodide (10.46 g, 61.52 mmol, Fluke). The reaction was stirred at 95° C. overnight. The solvent was decanted and the remaining solids were dried under reduced pressure overnight to provide 3-[4-(methyloxy)-3-nitrophenyl]-1-propylpyridinium iodide, which was use for the next reaction without further purification.

Step C/Intermediate B24: 5-[4-(methyloxy)-3-nitrophenyl]-1-propyl-1,2,3,6-tetrahydropyridine

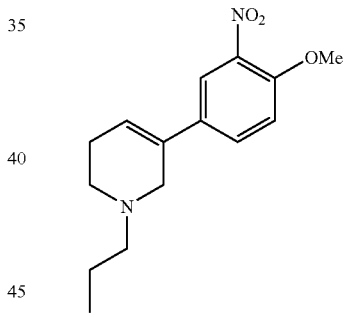

To a solution of 3-[4-(methyloxy)-3-nitrophenyl]-1-propylpyridinium iodide (6.10 g, 15.22 mmol) in methanol (100 mL) was added NaBH₃CN (9.58 g, 152.06 mmol, Aldrich) and the reaction was allowed to stir overnight at rt. The reaction was quenched with water (50 mL), solvent removed under reduced pressure, aqueous layer extracted with dichloromethane (2×50 mL), organic layers combined, taken to a residue under reduced pressure, and purified by column chromatography on SiO₂ to provide 5-[4-(methyloxy)-3-nitrophenyl]-1-propyl-1,2,3,6-tetrahydropyridine (1.89 g, 45% over two steps). ESIMS (M+H)+=277.

Step D/Intermediate B22: 2-(methyloxy)-5-(1-propyl-1,2,5,6-tetrahydro-3-pyridinyl)aniline To 5-[4-(methyloxy)-3-nitrophenyl]-1-propyl-1,2,3,6-tetrahydropyridine (0.25 g, 0.91 mmol) in absolute ethanol (50 mL) was added Sn₂CL₂×2H₂O (1.22 g, 5.41 mmol, Aldrich) and a catalytic HCl (1 mL, 1M solution in dioxanes). After stirring overnight, the reaction was quenched with saturated sodium bicarbonate solution (50 mL), stirred at RT for 1 hr, solids removed by vacuum filtration through a celite pad and rinsed with methanol. The solvent was removed under reduced pressure, aqueous layer extracted with dichloromethane (2×50 mL), combined organic extracts adsorbed to silica gel and purified by silica gel chromatography (dichloromethane to 5% methanol/dichloromethane+0.1% NH$_4$OH) to afford 2-(methyloxy)-5-(1-propyl-1,2,5,6-tetrahydro-3-pyridinyl)aniline (0.145 g, 65%). 1H NMR (400 MHz, CDCl$_3$) δ ppm 0.94 (t, J=7.52 Hz, 3 H) 1.56-1.66 (m, 2 H) 2.28-2.36 (m, 2 H) 2.43-2.48 (m, 2 H) 2.58 (t, J=5.87 Hz, 2 H) 3.23-3.29 (m, 2 H) 3.84 (s, 3 H) 5.94-6.01 (m, 1 H) 6.68-6.76 (m, 3 H). ESIMS (M+H)+=247.

Intermediate B25: 4-[1-(1-methylethyl)-1,2,3,6-tetrahydro-4-pyridinyl]-2-(methyloxy)aniline

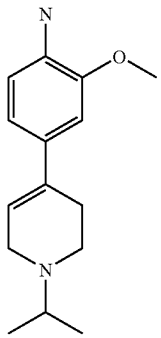

Step A/Intermediate B26:
4-[3-(methyloxy)-4-nitrophenyl]pyridine

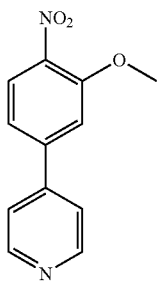

Nitrogen was bubbled through dioxane (800 mL) for 1 h followed by the addition of 4-chloro-2-(methyloxy)-1-nitrobenzene (61 g, 0.33 mol), 3-pyridinylboronic acid (Boron Molecular, 40 g, 0.33 mmol), dichloro(triphenylphosphine) palladium (10 g, 14 mmol), and degassed aqueous 3 N Na$_2$CO$_3$ (325 mL, 975 mmol). The reaction mixture was stirred with a mechanical stirrer and heated at 90° C. for 3 h. The reaction was cooled and most of the dioxane was removed in vacuo. It was diluted with water and then extracted with Ethyl acetate. Combined organic phases were dried (Mg$_2$SO$_4$), filtered and concentrated. The resultant solid was washed with diethyl ether to afford 4-(3-methoxy-4-nitrophenyl)pyridine (50 g, 66% yield). 1H NMR (400 MHz, DMSO-d$_6$) δ ppm 4.05 (s, 3 H), 7.53 (dd, J=8.4, 1.8 Hz, 1 H), 7.69 (d, J=1.8 Hz, 1 H), 7.84 (d, J=6.2 Hz, 2 H), 8.02 (d, J=8.4 Hz, 1 H), 8.72 (d, J=6.2 Hz, 2 H). ESIMS (M+H)+=231.

Step B/Intermediate B27: 4-[3-(methyloxy)-4-nitrophenyl]-1-(2-propen-1-yl)pyridinium bromide

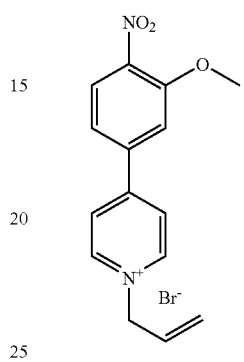

In manner analogous to the pyridine alkylation protocol described for Intermediate B3, 4-[3-(methyloxy)-4-nitrophenyl]-1-(2-propen-1-yl)pyridinium bromide (30 g) was prepared from 4-[3-(methyloxy)-4-nitrophenyl]pyridine (20.0 g) and allyl bromide (42.1 g). ESIMS (M−Br)=271.

Step C/Intermediate B28: 5-[3-(methyloxy)-4-nitrophenyl]-1-(2-propen-1-yl)-1,2,3,6-tetrahydropyridine

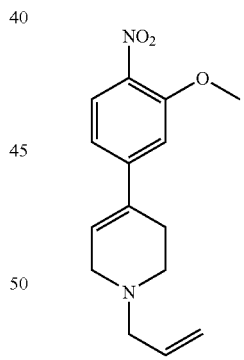

In a manner analgous to the pyridinium reduction described for Intermediate B4, 5-[3-(methyloxy)-4-nitrophenyl]-1-(2-propen-1-yl)-1,2,3,6-tetrahydropyridine was prepared from the reduction of 4-[3-(methyloxy)-4-nitrophenyl]-1-(2-propen-1-yl)pyridinium bromide (30 g) with NaCN (BH$_3$) (21.0 g). 1H NMR (400 MHz, DMSO-d$_6$) δ ppm 2.54 (s, 2 H), 2.70 (d, J=2.2 Hz, 2 H), 3.15 (d, J=5.5 Hz, 2 H), 3.17 (d, J=1.8 Hz, 2 H), 3.94 (s, 3 H), 5.18 (d, J=10.3 Hz, 1 H), 5.26 (d, J=17.2 Hz, 1 H), 5.81-5.91 (m, J=16.9, 10.3, 6.4, 6.4 Hz, 1 H), 6.42 (s, 1 H), 7.16 (s, 1 H), 7.28 (d, J=1.5 Hz, 1 H), 7.85 (d, J=8.4 Hz, 1 H); ESIMS (M+H)+=275.

Step D/Intermediate B29: 4-[3-(methyloxy)-4-nitrophenyl]-1,2,3,6-tetrahydropyridine

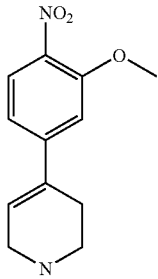

In a manner analogous to the deprotection of Intermediate B29, 4-[3-(methyloxy)-4-nitrophenyl]-1,2,3,6-tetrahydropyridine (1.8 g, 35% Yield) was prepared from 5-[3-(methyloxy)-4-nitrophenyl]-1-(2-propen-1-yl)-1,2,3,6-tetrahydropyridine (6.0 g, 21.9 mmol). 1H NMR (400 MHz, DMSO-$d_6$) δ ppm 2.36 (d, J=1.8 Hz, 2 H), 2.90 (t, J=5.7 Hz, 2 H), 3.30 (s, 1 H), 3.39 (d, J=2.9 Hz, 2 H), 3.94 (s, 3 H), 6.47 (s, 1 H), 7.13 (dd, J=8.4, 1.5 Hz, 1 H), 7.25 (s, 1 H), 7.84 (d, J=8.8 Hz, 1 H); ESI(M+H)$^+$=235.

Step E/Intermediate B30: 1-(1-methylethyl)-4-[3-(methyloxy)-4-nitrophenyl]-1,2,3,6-tetrahydropyridine

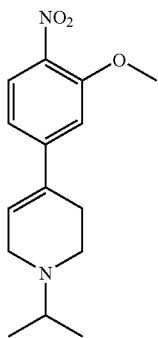

Using an alkylation analgous to that described for Intermediate B20, 1-(1-methylethyl)-4-[3-(methyloxy)-4-nitrophenyl]-1,2,3,6-tetrahydropyridine (2.0 g, 94% yield) was prepared from 4-[3-(methyloxy)-4-nitrophenyl]-1,2,3,6-tetrahydropyridine (1.8 g, 7.70 mmol) and isopropyl iodide (1.96 g, 11.5 mmol). ESIMS (M+H)$^+$=277.3.

Step F/Intermediate B25: 4-[1-(1-methylethyl)-1,2,3,6-tetrahydro-4-pyridinyl]-2-(methyloxy)aniline In a manner analgous to the hydrazine-mediated reduction of Intermediate B1, 4-[1-(1-methylethyl)-1,2,3,6-tetrahydro-4-pyridinyl]-2-(methyloxy)aniline (1.60 g, 90% yield) was prepared from 1-(1-methylethyl)-4-[3-(methyloxy)-4-nitrophenyl]-1,2,3,6-tetrahydropyridine (2.0 g, 7.17 mmol). 1H NMR (400 MHz, CDCl$_3$) δ ppm 1.12 (d, J=6.6 Hz, 6 H), 2.54 (s, 2 H), 2.73 (t, J=5.5 Hz, 2 H), 2.79 (dt, J=12.9, 6.6 Hz, 1 H), 3.24 (d, J=3.3 Hz, 2 H), 3.77 (s, 2 H), 3.85 (s, 3 H), 5.94 (s, 1 H), 6.65 (d, J=8.1 Hz, 1H), 6.80-6.86 (m, 2 H).

Intermediate B31: 4-[1-(1-methylethyl)-4-piperidinyl]-2-(methyloxy)aniline

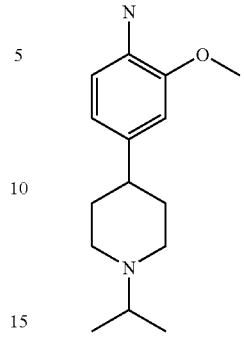

In a manner analogous to the hydrogenation of Intermediate B5, 4-[1-(1-methylethyl)-4-piperidinyl]-2-(methyloxy)aniline (~0.450 g) was prepared from 4-[1-(1-methylethyl)-1,2,3,6-tetrahydro-4-pyridinyl]-2-(methyloxy)aniline (0.500 g, 2.03 mmol). 1H NMR (400 MHz, CDCl$_3$) δ ppm 1.09 (d, J=6.2 Hz, 6 H), 1.73-1.78 (m, J=7.1, 2.7 Hz, 1 H), 1.80-1.86 (m, 3 H), 2.22 (t, J=11.0 Hz, 2 H), 2.38 (d, J=4.0 Hz, 1 H), 2.74 (s, 1 H), 3.00 (d, J=11.0 Hz, 2 H), 3.67 (s, 2 H), 3.82 (s, 3 H), 6.65 (s, 2 H), 6.70 (s, 1 H).

Intermediate B32: 2-(methyloxy)-4-(1-propyl-4-piperidinyl)aniline

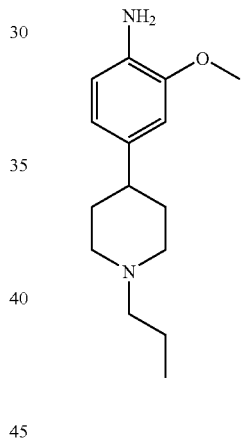

Step A/Intermediate B33: 4-[3-(methyloxy)-4-nitrophenyl]-1-propylpyridinium iodide

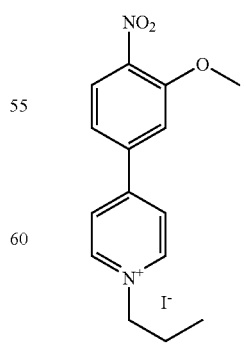

n-Propyliodide (200 mL, 2.05 mol) was added to a solution of 4-(3-methoxy-4-nitrophenyl)pyridine (25.0 g, 109 mmol)

in pinacolone (500 mL). The reaction was fitted with a reflux condenser, stirred, and heated at 100° C. for 12 h. A light brown suspension was observed. An aliquot (~2.0 mL) was taken out from the reaction mixture, concentrated, and analyzed by 1H NMR which revealed the formation of the alkylated product and the absence of starting material. The reaction was cooled; the solids were filtered off and rinsed once with cold (0° C.) acetone to afford 4-(3-methoxy-4-nitrophenyl)-1-propylpyridinium iodide as a light brown residue (29.0 g, 67% yield). 1 H NMR (400 MHz, DMSO-$d_6$) δ ppm 0.92 (t, J=7.3 Hz, 3 H), 1.99 (dt, J=7.3, 7.3 Hz, 2 H), 4.08 (s, 3 H), 4.59 (t, J=7.1 Hz, 2 H), 7.78 (dd, J=1.5, 8.4 Hz, 1H), 7.92 (d, J=1.5 Hz, 1 H), 8.13 (d, J=8.4 Hz, 1 H), 8.65 (d, J=7.0 Hz, 2 H), 9.22 (d, J=6.6 Hz, 2 H).

Step B/Intermediate B34: 4-(3-methoxy-4-nitrophenyl)-1-propyl-1,2,3,6-tetrahydropyridine

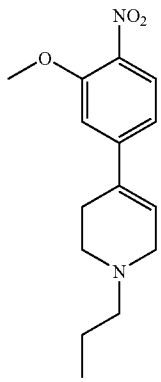

4-(3-methoxy-4-nitrophenyl)-1-propylpyridinium iodide (10 g, 25 mmol) was dissolved in methanol (200 mL). As the mixture was cooled to −10° C. the starting material started to precipitated out of the solution. Sodium borohydride (4.61 g, 11.3 mmol) was added in ~500 mg portions. Effervescence was observed during the addition as dissolution of the solids in the reaction was observed. The reaction was stirred for 2 h at −10° C. when analysis by TLC revealed completion of the reaction. Saturated aqueous ammonium chloride was added and the reaction warmed to room temperature. The mixture was extracted with Ethyl acetate, the organic layers were dried ($Mg_2SO_4$), filtered, and concentrated in vacuo to provide 4-(3-methoxy-4-nitrophenyl)-1-propyl-1,2,3,6-tetrahydropyridine (6.7 g, 97% yield). 1H NMR (400 MHz, DMSO-$d_6$) δ ppm 0.88 (t, J=7.4 Hz, 3 H), 1.50 (dt, J=7.3, 7.3 Hz, 2 H), 2.37 (t, J=7.2 Hz, 2 H), 2.53 (m, 2 H), 2.63 (m, 2 H), 3.11 (br s, 2H), 3.96 (s, 3 H), 6.43 (t, J=3.5 Hz, 1 H), 7.16 (dd, J=8.4, 1.5 Hz, 1 H), 7.29 (d, J=1.3 Hz, 1 H), 7.86 (d, J=8.6 Hz, 1 H). ESIMS (M+H)$^+$=277.

Step C: 2-(methyloxy)-4-(1-propyl-4-piperidinyl)aniline

Palladium on carbon (10% by weight, 2.5 g) was added to a nitrogen-flushed Fischer-Porter vessel. At least a portion of the 4-(3-methoxy-4-nitrophenyl)-1-propyl-1,2,3,6-tetrahydropyridine from Step B was combined with additional 4-(3-methoxy-4-nitrophenyl)-1-propyl-1,2,3,6-tetrahydropyridine prepared by substantially the same method. Then, a solution of the 4-(3-methoxy-4-nitrophenyl)-1-propyl-1,2,3,6-tetrahydropyridine (9.20 g, 33.3 mmol) in Ethyl acetate (150 mL) followed by methanol (50 mL) were added to the vessel. The reaction was purged and then kept under a hydrogen pressure of 60 psi for 2 d. The pressure was released and the reaction was purged with nitrogen. The reaction was filtered through celite and concentrated to afford 2-methoxy-4-(1-propylpiperidin-4-yl)aniline as a white solid (7.0 g, 85% yield). 1H NMR (400 MHz, DMSO-$d_6$) δ ppm 0.86 (t, J=7.5 Hz, 3 H), 1.44 (dt, J=7.4, 7.4 Hz, 2 H), 1.52-1.63 (m, 2 H), 1.63-1.70 (m, 2 H), 1.90 (td, J=11.6, 2.4 Hz, 2 H), 2.20-2.25 (m, 2 H), 2.30 (tt, J=11.9, 4.0 Hz, 1 H), 2.89-2.94 (m, 2 H), 3.74 (s, 3 H), 4.45 (s, 2 H), 6.53 (s, 2 H), 6.65 (s, 1 H). ESIMS (M+H)$^+$=249.

Intermediate B35: (3S)-1-[4-amino-3-(methyloxy)phenyl]-3-piperidinol

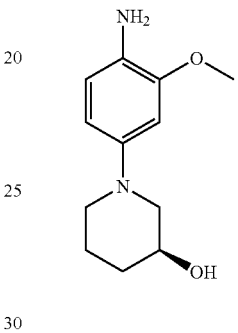

Step A/Intermediate B36: (3S)-1-[3-(methyloxy)-4-nitrophenyl]-3-piperidinol

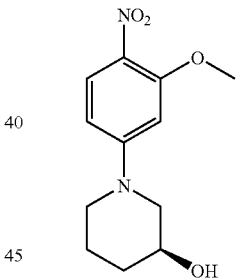

A solution of (3S)-3-piperidinol hydrochloride (3.00 g, 21.7 mmol, Astatech Inc.), 4-fluoro-2-(methyloxy)-1-nitrobenzene (3.38 g, 19.76 mmol) and potassium carbonate (9.00 g, 65.22 mmol) in dimethylsulfoxide (75 mL) was stirred overnight. The next morning, the reaction was diluted with diethyl ether and saturated aqueous sodium chloride. The ether layer was washed with water, and the combined aqueous layers were subsequently washed twice with diethyl ether. The combined organic layers were dried over sodium sulfate, filtered, taken to a residue under reduced pressure, and purified by chromatography on $SiO_2$ (5% MeOH/$CH_2CL_2$) to give (3S)-1-[3-(methyloxy)-4-nitrophenyl]-3-piperidinol as a pale yellow solid (3.90 g, 15.47 mmol, 78% yield). 1H NMR (400 MHz, CDCl$_3$) δ ppm 1.59-1.71 (m, 2 H), 1.79 (s, 1 H), 1.86-1.96 (m, J=12.96, 6.41, 6.27, 3.48 Hz, 1 H), 1.96-2.04 (m, 1 H), 3.13-3.24 (m, 2 H), 3.47 (ddd, J=12.59, 6.36, 3.20 Hz, 1 H), 3.66 (dd, J=12.82, 3.48 Hz, 1 H), 3.86-3.92 (m, J=7.44, 3.94, 3.74, 3.74 Hz, 1 H), 3.93 (s, 3 H), 6.34 (d, J=2.56 Hz, 1 H), 6.43 (dd, J=9.34, 2.38 Hz, 1 H), 7.98 (d, J=9.34 Hz, 1 H).

Step B/Intermediate B35: (3S)-1-[4-amino-3-(methyloxy)phenyl]-3-piperidinol

A solution of (3S)-1-[3-(methyloxy)-4-nitrophenyl]-3-piperidinol (3.90 g, 15.5 mmol), FeCl$_3$ (0.630 g, 3.9 mmol), activated carbon (4.0 g), and hydrazine hydrate (3.9 mL, 124 mmol) was heated in methanol (100 mL) for 3 hours. Once the starting material was judged consumed by thin layer chromatography (10% MeOH/CH$_2$CL$_2$) the mixture was filtered over celite and concentrated to afford (3S)-1-[4-amino-3-(methyloxy)phenyl]-3-piperidinol as a dark purple solid (2.56 g, 11.53 mmol, 74% yield). 1H NMR (400 MHz, CDCl$_3$) δ ppm 1.62-1.72 (m, 2 H), 1.75 (d, J=3.30 Hz, 1H), 1.93 (td, J=8.07, 4.40 Hz, 1 H), 2.44 (s, 2 H), 2.88 (s, 1 H), 2.93 (d, J=9.53 Hz, 1H), 2.99 (dd, J=10.81, 6.05 Hz, 2 H), 3.12 (d, J=10.63 Hz, 1 H), 3.84 (s, 3 H), 3.95 (s, 1 H), 6.44 (d, J=8.07 Hz, 1 H), 6.53 (s, 1 H), 6.64 (d, J=8.07 Hz, 1 H).

Intermediate B37: 1-[4-amino-3-(methyloxy)phenyl]-4-piperidinol

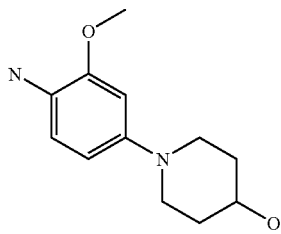

A solution of 4-fluoro-2-(methyloxy)-1-nitrobenzene (3.0 g, 17.5 mmol), 4-hydroxypiperidine (1.77 g, 17.5 mmol) and potassium carbonate (2.9 g, 21 mmol) in DMSO was stirred for 24 h. The reaction was diluted with water and extracted three times with Ethyl acetate. The combined organic solutions were dried over MgSO$_4$ and concentrated. The resulting residue was stirred in ethanol and acetic acid with 10% Pd/C under 30 psi of hydrogen for 16 hr. The reaction was filtered through a pad of celite, rinsed with Ethyl acetate. The filtrate was concentrated and dissolved in methylene chloride. The organic solution was washed with saturated sodium bicarbonate, dried over MgSO$_4$, and concentrated to give 1-[4-amino-3-(methyloxy)phenyl]-4-piperidinol (2.44 g, 63% yield over 2 steps). $^1$H NMR (400 MHz, d$_6$-DMSO) δ 6.49-6.45 (m, 2H), 6.27 (dd, J=8.4 and 2.4 Hz, 1H), 4.60 (d, J=4.0 Hz, 1 H), 4.18 (s, 2H), 3.71 (s, 3H), 3.54-3.48 (m, 1H), 3.25-3.22 (m, 2H), 2.63-2.56 (M, 2H), 1.80-1.76 (m, 2H), 1.51-1.42 (m, 2H).

Intermediate B38: 4-(3,3-difluoro-1,4'-bipiperidin-1'-yl)-2-(methyloxy)aniline

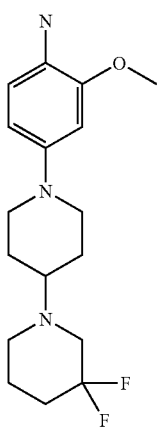

Step A/Intermediate B39: 1-[3-(methyloxy)-4-nitrophenyl]-4-piperidinol

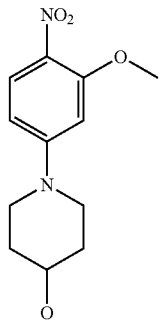

A mixture of 4-fluoro-2-(methyloxy)-1-nitrobenzene (7.52 g, 44 mmol), 4-hydroxypiperidine (4.45 g, 44 mmol) and potassium carbonate in 100 mL DMSO was stirred for 72 h. The reaction was diluted with water and extracted twice with Ethyl acetate. The combined organic layers were washed with brine, dried over MgSO$_4$, and concentrated to give 1-[3-(methyloxy)-4-nitrophenyl]-4-piperidinol (10.9 g, 99% yield). $^1$H NMR (400 MHz, d$_6$-DMSO) δ 7.84 (d, J=9.2 Hz, 1H), 6.54 (d, J=9.6 Hz, 1H), 6.46 (s, 1H), 4.73 (d, J=4.4 Hz, 1H), 3.86 (s, 3H), 3.80-3.69 (m, 3H), 3.18-3.12 (m, 2H), 1.79-1.76 (m, 2H), 1.42-1.34 (m, 2H).

Step B/Intermediate B40—1-[3-(methyloxy)-4-nitrophenyl]-4-piperidinone

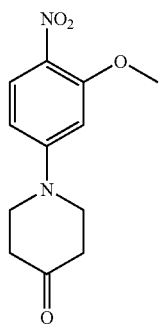

To a solution of (10 g, 40 mmol) in 400 mL DCM was added sodium bicarbonate (16.8 g, 200 mmol), water (0.72 mL, 40 mmol) and 1,1,1-tri(acetyloxy)-1,1-dihydro-1,2-benziodoxol-3-(1H)-one (Dess-Martin periodinane, 20.4 g, 48 mmol, Aldrich). After 1.5 h, the reaction still contained starting material and was not progressing.

The reaction was quenched with equal parts sat'd NaHCO$_3$ and sat'd Na$_2$S$_2$O$_3$. After stirring for 1 hour, the layers were separated. The aqueous phase was extracted with DCM. The combined organics were washed with water and brine, dried over MgSO$_4$, concentrated onto silica gel and purified by flash column chromatography. Fractions containing product were concentrated to give 1.8 g of desired product. Fractions containing starting material were concentrated and resubjected to the above conditions. After workup and purification, a further 6.1 g of product was collected to give 7.9 g (79%) of 1-[3-(methyloxy)-4-nitrophenyl]-4-piperidinone. $^1$H NMR (400 MHz, $d_6$-DMSO) δ 7.89 (d, J=9.2 Hz, 1H), 6.59 (d, J=9.2 Hz, 1H), 6.50 (d, J=1.2 Hz, 1H), 3.90 (s, 3H), 3.82-3.78 (m, 4H), 2.49-2.46 (m, 4 H).

Step C/Intermediate B41: 3,3-difluoro-1'-[3-(methyloxy)-4-nitrophenyl]-1,4'-bipiperidine

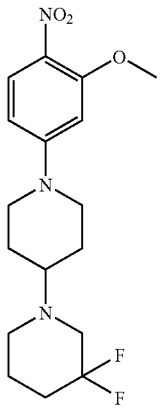

A mixture of 1-[3-(methyloxy)-4-nitrophenyl]-4-piperidinone (600 mg, 2.4 mmol), commercially available 3,3-difluoropiperidine hydrochloride (753 mg, 4.8 mmol), acetic acid (0.20 mL, 3.6 mmol) and triethylamine (0.33 mL, 3.6 mmol) in 1,2-dichloroethane was stirred for 30 minutes. Sodium triacetoxyborohydride (615 mg, 2.9 mmol) was added. When LC/MS indicated the absence of starting material, the reaction was quenched with the addition of sat'd NaHCO₃. The reaction was diluted with dichloromethane and the layers were separated. The aqueous phase was extracted with dichloromethane. The combined organic layers were washed with water, dried over MgSO₄ and concentrated onto silica gel. The crude material was purified by flash column chromatography to give 3,3-difluoro-1'-[3-(methyloxy)-4-nitrophenyl]-1,4'-bipiperidine (584 mg, 68%). ¹H NMR (400 MHz, $d_6$-DMSO) δ 7.84 (d, J=9.6 Hz, 1H), 6.55 (dd, J=9.6 and 2.0 Hz, 1H), 6.46 (d, J=2.0 Hz, 1H), 4.04 (d, J=12.8 Hz, 1H), 3.87 (s, 3H), 2.90 (t, J=12.0 Hz, 2H), 2.72-2.60 (m, 3H), 2.47 (m under DMSO peak, 2H), 1.87-1.74 (m, 4H), 1.61-1.58 (m, 2H), 1.48-1.38 (m, 2H).

Step D/Intermediate B38: 4-(3,3-difluoro-1,4'-bipiperidin-1-yl)-2-(methyloxy)aniline 3,3-difluoro-1'-[3-(methyloxy)-4-nitrophenyl]-1,4'-bipiperidine (580 mg, 1.6 mmol) was added to a solution of nickel (II) chloride hexahydrate (0.190 g, 0.8 mmol) in methanol. Subsequent careful addition of sodium borohydride (0.091 g, 2.4 mmol), addition of methanol, and concentration afforded a purple residue. Purification of the residue via chromatography on silica gel gives 4-(3,3-difluoro-1,4'-bipiperidin-1-yl)-2-(methyloxy)aniline (489 mg, 94% yield). ¹H NMR (400 MHz, $d_6$-DMSO) δ 6.48-6.44 (m, 2H), 6.25 (dd, J=8.4 and 2.4 Hz, 1H), 4.16 (s, 2 H), 3.70 (s, 3H), 3.40 (d, J=12.0 Hz, 2H), 2.70 (t, J=11.6 Hz, 2H), 2.48-2.34 (m under DMSO peak, 5H), 1.88-1.78 (m, 2H), 1.72 (d, J=12.4 Hz, 2H), 1.62-1.47 (m, 4H).

Intermediate B42: 4-{4-[(3R)-3-fluoro-1-pyrrolidinyl]-1-piperidinyl}-2-(methyloxy)aniline

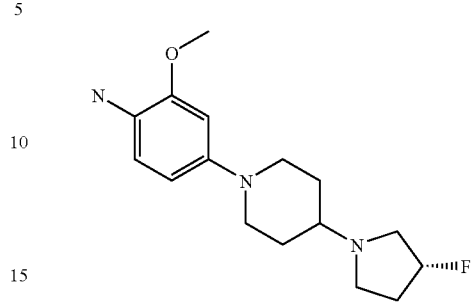

Step A/Intermediate B43: 4-[(3R)-3-fluoro-1-pyrrolidinyl]-1-[3-(methyloxy)-4-nitrophenyl]piperidine

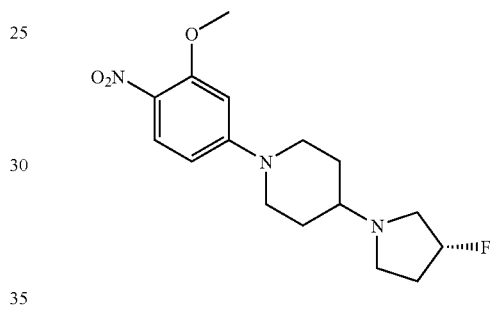

1-[3-(methyloxy)-4-nitrophenyl]-4-piperidinone (1.0 g, 4.0 mmol) and commercially available (R)-(−)-3-fluoropyrrolidine hydrochloride were subjected to a reductive amination analogous to the procedure for 3,3-difluoro-1'-[3-(methyloxy)-4-nitrophenyl]-1,4'-bipiperidine (Intermediate B41) to give 4-[(3R)-3-fluoro-1-pyrrolidinyl]-1-[3-(methyloxy)-4-nitrophenyl]piperidine (1.3 g, 100% yield). ¹H NMR (400 MHz, $d_6$-DMSO) δ 7.84 (d, J=9.6 Hz, 1H), 6.56 (dd, J=9.6 and 2.0 Hz, 1H), 6.47 (d, J=2.0 Hz, 1H), 5.24-5.07 (m, 1H), 3.91-3.87 (m, 5H), 3.05-2.99 (m, 2H), 2.88-2.77 (m, 2H), 2.70-2.58 (m, 1H), 2.38-2.27 (m, 2H), 2.13-2.00 (m,1H), 1.88-1.75 (m, 3H), 1.46-1.36 (m, 2H).

Step B/Intermediate B42: 4-{4-[(3R)-3-fluoro-1-pyrrolidinyl]-1-piperidinyl}-2-(methyloxy)aniline 4-[(3R)-3-fluoro-1-pyrrolidinyl]-1-[3-(methyloxy)-4-nitrophenyl]piperidine (1.33 g, 4.0 mmol) was reduced in a manner analogous to 4-(3,3-difluoro-1,4'-bipiperidin-1'-yl)-2-(methyloxy)aniline (Intermediate B38) above. The filtrate was washed with water, dried over magnesium sulfate and concentrated to give 4-{4-[(3R)-3-fluoro-1-pyrrolidinyl]-1-piperidinyl}-2-(methyloxy)aniline (1.01 g, 86% yield). ¹H NMR (400 MHz, $d_6$-DMSO) δ 6.48-6.45 (m, 2H), 6.26 (dd, J=8.4 and 2.4 Hz, 1H), 5.24-5.07 (m, 1H), 4.16 (s, 2H), 3.70 (s, 3H), 3.33-3.30 (m, 2H), 2.88-2.76 (m, 2H), 2.69-2.56 (m,1H), 2.54-2.46 (m under DMSO peak, 2H), 2.37-2.31 (m, 1H), 2.14-1.99 (m, 2H), 1.90-1.75 (m, 3H), 1.51-1.41 (m, 2H).

Intermediate B44: 4-{4-[(3S)-3-fluoro-1-pyrrolidinyl]-1-piperidinyl}-2-(methyloxy)aniline

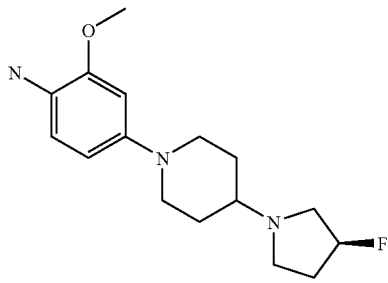

Step A/Intermediate B45: 4-[(3S)-3-fluoro-1-pyrrolidinyl]-1-[3-(methyloxy)-4-nitrophenyl]piperidine

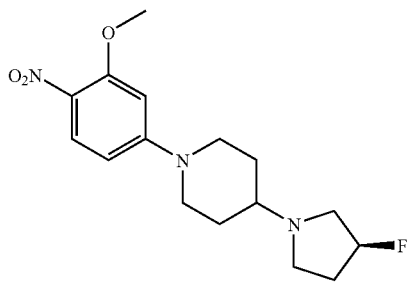

1-[3-(methyloxy)-4-nitrophenyl]-4-piperidinone (1.0 g, 4.0 mmol) and (S)-(+)-3-fluoropyrrolidine hydrochloride were subjected to reductive amination analogous to the procedure for 3,3-difluoro-1'-[3-(methyloxy)-4-nitrophenyl]-1,4'-bipiperidine (Intermediate B41) to give 4-[(3S)-3-fluoro-1-pyrrolidinyl]-1-[3-(methyloxy)-4-nitrophenyl]piperidine in quantitative yield. $^1$H NMR (400 MHz, $d_6$-DMSO) δ 7.84 (d, J=9.6 Hz, 1H), 6.56 (dd, J=9.4 and 2.2 Hz, 1H), 6.47 (d, J=2.0 Hz, 1H), 5.24-5.07 (m, 1H), 3.91-3.87 (m, 5H), 3.05-2.99 (m, 2H), 2.88-2.77 (m, 2H), 2.70-2.58 (m, 1H), 2.38-2.26 (m, 2H), 2.14-1.98 (m,1H), 1.88-1.75 (m, 3H), 1.46-1.36 (m, 2H).

Step B/Intermediate B44: 4-{4-[(3S)-3-fluoro-1-pyrrolidinyl]-1-piperidinyl}-2-(methyloxy)aniline 4-[(3S)-3-fluoro-1-pyrrolidinyl]-1-[3-(methyloxy)-4-nitrophenyl]piperidine (4 mmol) was reduced in a manner analogous to 4-(3,3-difluoro-1,4'-bipiperidin-1'-yl)-2-(methyloxy)aniline (Intermediate B38). The filtrate was washed with water, dried over $MgSO_4$ and concentrated to give 4-{4-[(3S)-3-fluoro-1-pyrrolidinyl]-1-piperidinyl}-2-(methyloxy)aniline (1.02 g, 86% yield). $^1$H NMR (400 MHz, $d_6$-DMSO) δ 6.48-6.45 (m, 2H), 6.26 (dd, J=8.4 and 2.4 Hz, 1H), 5.24-5.07 (m, 1H), 4.16 (s, 2H), 3.70 (s, 3H), 3.33-3.30 (m, 2H), 2.88-2.76 (m, 2H), 2.69-2.56 (m,1H), 2.54-2.46 (m under DMSO peak, 2H), 2.37-2.31 (m, 1H), 2.14-1.99 (m, 2H), 1.90-1.75 (m, 3H), 1.51-1.41 (m, 2H).

Intermediate B46: 4-[4-(1-methylethyl)-1-piperazinyl]-2-(methyloxy)aniline

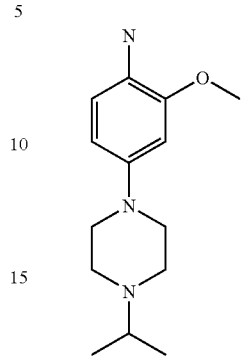

Step A/Intermediate B47: 1-(1-methylethyl)-4-[3-(methyloxy)-4-nitrophenyl]piperazine

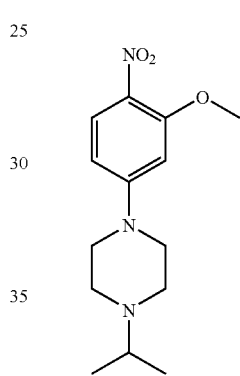

To 4-chloro-2-(methyloxy)-1-nitrobenzene (3.0 g, 16.0 mmol) in dioxane (75 mL) was added 1-(1-methylethyl)piperazine (4.1 g, 32.0 mmol), XANTPHOS (1.4 g, 2.4 mmol), and $Cs_2CO_3$ (10.4 g, 32.0 mmol). The mixture was bubbled with $N_2$ for 15 min prior to the addition of $Pd_2(dba)_3$ (1.5 g, 1.6 mmol). The reaction was stirred at 100° C. for 5 h. Following cooling to room temperature, the reaction mixture was diluted with ethyl acetate (150 mL) and water (100 mL). The organic layer was dried over sodium sulfate, filtered, taken to a residue under reduced pressure, and purified by silica gel chromatography to afford 1-(1-methylethyl)-4-[3-(methyloxy)-4-nitrophenyl]piperazine (4.0 g, 90% yield). ESIMS $(M+H)^+$=280.

Step B/Intermediate B46: 4-[4-(1-methylethyl)-1-piperazinyl]-2-(methyloxy)aniline In a pressure vessel was placed a solution of 1-(1-methylethyl)-4-[3-(methyloxy)-4-nitrophenyl]piperazine (4.0 g, 14.3 mmol) in EtOH (100 mL). The solution was purged with $N_2$ for 15 min before the addition of 10% Pd/C (0.5 g). The reaction was stirred at RT for 5 h under 60 psi $H_2$. After releasing $H_2$ pressure, filtration removed the solid resin, and the filtrate was concentrated and purified with silica gel chromatography (0-5% 2 M $NH_3$ in MeOH/DCM) to furnish 4-[4-(1-methylethyl)-1-piperazinyl]-2-(methyloxy)aniline (3.6 g, 99% yield). 1H NMR (400 MHz, $CDCl_3$) δ ppm 1.09 (d, J=6.6 Hz, 6 H), 2.66-2.75 (m, 5 H), 3.05-3.10 (m, 4 H), 3.47 (s, 3 H), 3.83 (s, 2 H), 6.42 (dd, J=8.2, 2.4 Hz, 1 H), 6.52 (d, J=2.2 Hz, 1 H), 6.64 (d, J=8.4 Hz, 1 H).

Intermediate B48:
2-(methyloxy)-4-(4-propyl-1-piperazinyl)aniline

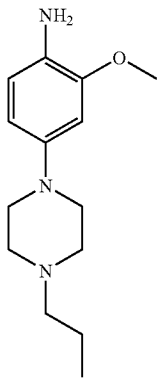

Step A/Intermediate B49: 1,1-dimethylethyl 4-[3-(methyloxy)-4-nitrophenyl]-1-piperazinecarboxylate

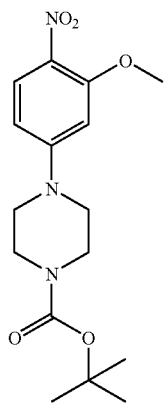

4-chloro-2-(methyloxy)-1-nitrobenzene (10 g, 53.2 mmol, Aldrich), 1,1-dimethylethyl 1-piperazinecarboxylate (20 g, 107.5 mmol), cesium carbonate (35.0 g, 107.5 mmol), Pd$_2$dba$_3$ (5 g, 5.5 mmol), and XANTPHOS (4.62 g, 8.0 mmol) were added to degassed dioxane (100 mL) and heated to 100° C. under a water cooled reflux condenser for 12 hours. The dioxane was removed under reduced pressure and the solids were partitioned between methylene chloride (500 mL) and water (500 mL). The organic layer was dried over sodium sulfate, taken to a residue under reduced pressure, and triturated with a methylene choride/hexanes mixture (15:85) to precipitate out analytically pure 1-dimethylethyl 4-[3-(methyloxy)-4-nitrophenyl]-1-piperazinecarboxylate as a yellow solid (13.2 g, 39.2 mmol, 73% yield). 1H NMR (400 MHz, CDCl$_3$) δ ppm 1.49 (s, 9 H), 3.33-3.42 (m, 4 H), 3.62-3.64 (m, 4 H), 3.96 (s, 3 H), 6.39 (s, 1 H), 6.44 (dd, J=9.16, 2.56 Hz, 1 H), 8.01 (d, J=9.16 Hz, 1 H).

Step B/Intermediate B50:
1-[3-(methyloxy)-4-nitrophenyl]piperazine

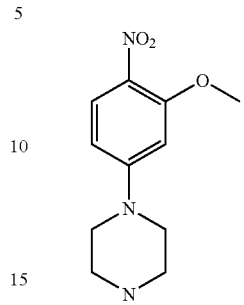

1-dimethylethyl 4-[3-(methyloxy)-4-nitrophenyl]-1-piperazinecarboxylate (2.25 g, 6.67 mmol) was dissolved in methylene chloride (50 mL) and trifluoroacetic acid (10 mL). The resulting solution turns immediately dark and was stirred overnight. The solution was concentrated and partitioned between methylene chloride and 2.0N sodium hydroxide. The organic layer was collected and the aqueous layer was saturated by addition of sodium chloride and subsequently backextracted with additional methylene chloride. The combined organic layers were dried over sodium sulfate, filtered, and taken to a residue under reduced pressure to afford analytically pure 1-[3-(methyloxy)-4-nitrophenyl]piperazine as a yellow solid (1.7 g, 7.2 mmol, quant. yield). 1H NMR (400 MHz, DMSO-d$_6$) δ ppm 2.28-2.37 (m, 1 H), 2.76 (q, J=4.64 Hz, 4 H), 3.29-3.34 (m, 4 H), 3.86 (s, 3 H), 6.46 (d, J=2.38 Hz, 1 H), 6.54 (dd, J=9.43, 2.47 Hz, 1 H), 7.84 (d, J=9.34 Hz, 1 H).

Step C/Intermediate B51:
1-[3-(methyloxy)-4-nitrophenyl]-4-propylpiperazine

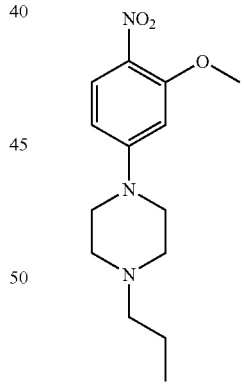

A solution of 1-[3-(methyloxy)-4-nitrophenyl]piperazine (1.78 g, 7.51 mmol), 1-iodopropane (1.92 g, 11.3 mmol), and potassium carbonate (4.15 g, 30.0 mmol) in acetonitrile (50 mL) was heated in a pressure vessel at 80° C. for 24 hours. The reaction was cooled and the acetonitrile was removed under reduced pressure. The solids were dissolved in methylene chloride/water. The organic layer was dried over sodium sulfate and the solvent removed under reduced pressure. The resultant residue was purified by chromatography on SiO$_2$ (10% MeOH/CH$_2$CL$_2$ with 0.2% NH$_3$) to give 1-[3-(methyloxy)-4-nitrophenyl]-4-propylpiperazine as a pale yellow solid (1.5 g, 5.4 mmol, 72% yield). 1H NMR (400

MHz, CDCl₃) δ ppm 0.94 (t, J=7.32 Hz, 3H), 1.51-1.61 (m, 2 H), 2.34-2.42 (m, 2 H), 2.59 (s, 4 H), 3.38-3.45 (m, 4 H), 3.95 (s, 3 H), 6.31 (d, J=2.20 Hz, 1 H), 6.42 (dd, J=9.34, 2.38 Hz, 1 H), 8.00 (d, J=9.52 Hz, 1 H).

Step D/Intermediate 48:
2-(methyloxy)-4-(4-propyl-1-piperazinyl)aniline

A solution of 1-[3-(methyloxy)-4-nitrophenyl]-4-propylpiperazine (Intermediate B50, 1.5 g, 5.4 mmol), FeCl₃ (0.300 g, 1.85 mmol), activated carbon (2.0 g), and hydrazine hydrate (2.1 mL, 65 mmol) was heated in methanol (50 mL) for 3 hours. The mixture was filtered over celite and concentrated to give 2-(methyloxy)-4-(4-propyl-1-piperazinyl) aniline as a white solid (1.03 g, 4.2 mmol, 78% yield). 1H NMR (400 MHz, CDCl₃) δ ppm 0.93 (t, J=7.51 Hz, 3 H), 1.51-1.61 (m, 2 H), 2.37 (d, J=8.06 Hz, 2 H), 2.57-2.66 (m, 4 H), 3.09-3.10 (m, 4 H), 3.53 (s, 2 H), 3.83 (s, 3 H), 6.42 (dd, J=8.24, 2.38 Hz, 1H), 6.52 (d, J=2.20 Hz, 1 H), 6.64 (d, J=8.42 Hz, 1 H).

Intermediate B52: 2-(methyloxy)-4-[4-(2-methylpropyl)-1-piperazinyl]aniline

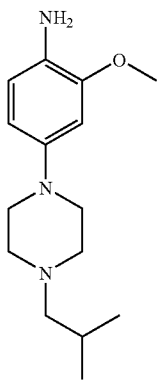

Step A/Intermediate B53: 1-[3-(methyloxy)-4-nitrophenyl]-4-(2-methylpropyl)piperazine

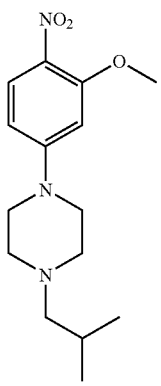

A solution of 1-[3-(methyloxy)-4-nitrophenyl]piperazine (2.09 g, 8.44 mmol), 2-methyl-iodopropane (2.1 g, 11.39 mmol), and potassium carbonate (4.7 g, 34 mmol) in acetonitrile (80 mL) was heated in a pressure vessel at 80° C. for 24 hours. The reaction was cooled and the acetonitrile was removed under reduced pressure. The solids were dissolved in methylene chloride/water. The organic layer was dried over sodium sulfate, filtered, and the solvent removed under reduced pressure. The resultant residue was purified by chromatography on SiO₂ (10% MeOH/CH₂CL₂ with 0.2% NH3) to give 1-[3-(methyloxy)-4-nitrophenyl]-4-(2-methylpropyl) piperazine as a pale yellow solid (1.70 g, 5.8 mmol, 69% yield). 1H NMR (400 MHz, CDCl₃) δ ppm 0.91 (d, J=6.59 Hz, 6 H), 1.80 (ddd, J=13.69, 7.05, 6.91 Hz, 1 H), 2.13 (d, J=6.04 Hz, 2 H), 2.52 (s, 4 H), 3.38 (s, 4 H), 3.93 (s, 3 H), 6.29 (d, J=2.38 Hz, 1 H), 6.40 (dd, J=9.43, 2.47 Hz, 1 H), 7.98 (d, J=9.52 Hz, 1 H).

Step B/Intermediate B52: 2-(methyloxy)-4-[4-(2-methylpropyl)-1-piperazinyl]aniline A solution of 1-[3-(methyloxy)-4-nitrophenyl]-4-(2-methylpropyl)piperazine (1.7 g, 5.82 mmol), FeCl₃ (0.280 g, 1.75 mmol), activated carbon (2.0 g), and hydrazine hydrate (2.23 mL, 70 mmol) was heated in methanol (50 mL) for 3 hours. The mixture was filtered over celite and concentrated to give 2-(methyloxy)-4-[4-(2-methylpropyl)-1-piperazinyl]aniline as a white solid (1.24 g, 4.80 mmol, 83% yield). 1H NMR (400 MHz, CDCl₃) δ ppm 0.94 (d, J=6.22 Hz, 6 H), 1.85 (s, 1 H), 2.20 (s, 2 H), 2.61 H), 3.10 (s, 4 H), 3.54 (s, 2 H), 3.83 (s, 3 H), 6.43 (m, 1 H), 6.52 (d, J=1.83 Hz, 1 H), 6.64 (d, J=8.42 Hz, 1 H).

Intermediate B54: 4-[4-(cyclopropylmethyl)-1-piperazinyl]-2-(methyloxy)aniline

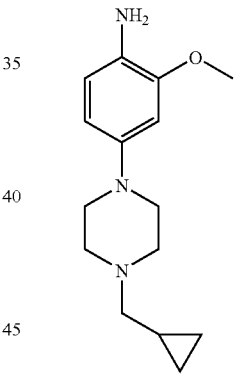

Step A/Intermediate B55: 1-(cyclopropylmethyl)-4-[3-(methyloxy)-4-nitrophenyl]piperazine

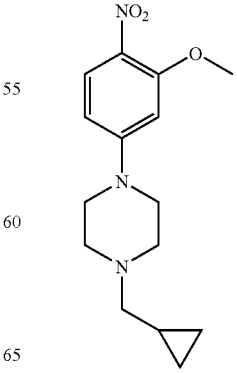

A solution of 1-[3-(methyloxy)-4-nitrophenyl]piperazine (2.00 g, 8.43 mmol), (chloromethyl)cyclopropane (1.15 g, 12.7 mmol mmol), potassium iodide (2.00 g, 12.7 mmol) and potassium carbonate (4.7 g, 34 mmol) in acetonitrile (100 mL) was heated in a pressure vessel at 80° C. for 3 days. The reaction was cooled and the acetonitrile was removed under reduced pressure. The solids were dissolved in methylene chloride/water. The organic layer was dried over sodium sulfate and the solvent removed under reduced pressure. The resultant residue was purified by chromatography on $SiO_2$ (10% MeOH/$CH_2CL_2$ with 0.2% $NH_3$) to give 1-cyclopropylmethyl)-4-[3-(methyloxy)-4-nitrophenyl]piperazine as a pale yellow solid (1.30 g, 4.5 mmol, 53% yield). 1H NMR (400 MHz, $CDCl_3$) δ ppm 0.12-0.22 (m;2 H), 0.54-0.63 (m, 2 H), 0.90 (s, 1 H), 2.33 (d, J=6.23 Hz, 2 H), 2.69 (s, 4 H), 3.99-3.48 (m, 4 H), 3.95 (s, 3 H), 6.32 (d, J=2.56 Hz, 1 H), 6.42 (dd, J=9.16, 2.56 Hz, 8.00 (d, J=9.53 Hz, 1 H).

Step B/Intermediate B54: 4-[4-(cyclopropylmethyl)-1-piperazinyl]-2-(methyloxy)aniline A solution of 1-(cyclopropylmethyl)-4-[3-(methyloxy)-4-nitrophenyl]piperazine (1.05 g, 3.41 mmol), $FeCl_3$ (0.165 g, 1.02 mmol), activated carbon (1.0 g), and hydrazine hydrate (1.3 mL, 41 mmol) was heated in methanol (50 mL) for 3 hours. Once the starting material was judged consumed by thin layer chromatography (10% MeOH/$CH_2CL_2$) the mixture was filtered over celite and concentrated to give 4-[4-(cyclopropylmethyl)-1-piperazinyl]-2-(methyloxy)aniline as a yellow solid (0.800 g, 3.07 mmol, 90% yield). 1H NMR (400 MHz, $CDCl_3$) δ ppm 0.15 (q, J=4.89 Hz, 2 H), 0.52-0.60 (m, 2 H), 0.94 (d, J=6.23 Hz, 1 H), 2.35 (d, J=6.59 Hz, 2 H), 2.74 (s, 4 H), 3.07-3.15 (m, 4 H), 3.53 (s, 2 H), 3.83 (s, 3 H), 6.43 (dd, J=8.43, 2.20 Hz, 1 H), 6.53 (d, J=2.20 Hz, 1 H), 6.65 (d, J=8.06 Hz, 1 H).

Intermediate B56:
4-(4-acetyl-1-piperazinyl)-2-(methyloxy)aniline

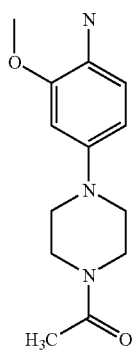

Step A/Intermediate B57:
1-acetyl-4-[3-(methyloxy)-4-nitrophenyl]piperazine

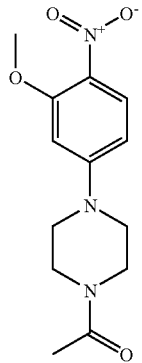

To a solution of 1-[3-(methyloxy)-4-nitrophenyl]piperazine (0.5 g, 2.11 mmol) and triethylamine (1.27 g, 12.63 mmol, Aldrich) in dichloromethane (25 mL) was added acetic anhydride (0.64 g, 6.35 mmol, Aldrich). After stirring 3 hrs at rt, the reaction was washed with water (25 mL), organic layer adsorbed to silica gel and purified by column chromatography (dichloromethane to 10% methanol/dichloromethane) to give 1-acetyl-4-[3-(methyloxy)-4-nitrophenyl]piperazine (0.4 g, 68%). ESIMS (M+H)+=280.

Step B/Intermediate B56:
4-(4-acetyl-1-piperazinyl)-2-(methyloxy)aniline

To a solution of 1-acetyl-4-[3-(methyloxy)-4-nitrophenyl]piperazine (0.4 g, 1.43 mmol) in ethanol: ethyl acetate (5:1) was added 10% Pd/carbon (~0.100 g, Lancaster) and the mixture was rapidly stirred under 50 psi $H_2$ overnight. The catalyst was removed by vacuum filtration through a celite pad, rinsed with methanol, and concentrated by rotary evaporation to give 4-(4-acetyl-1-piperazinyl)-2-(methyloxy)aniline (0.3 g, 84%). ESIMS (M+H)+=250.

Intermediate B58: 4-[4-(1-methylethyl)-1-piperazinyl]-2,5-bis(methyloxy)aniline

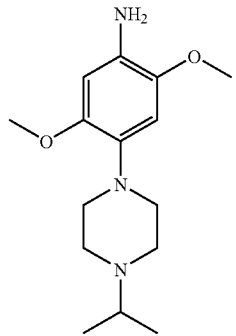

Step A/Intermediate B59: 1-[2,5-bis(methyloxy)-4-nitrophenyl]-4-(1-methylethyl)piperazine

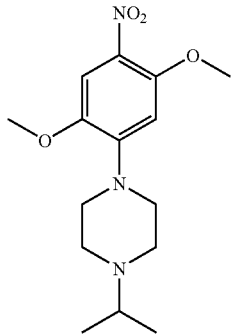

1-chloro-2,5-bis(methyloxy)-4-nitrobenzene (3.25 g, 15 mmol, TCI America), isopropylpiperizine (3.84 g, 30 mmol, Oakwood Products), cesium carbonate (9.8 g, 30 mmol), Pd$_2$dba$_3$ (1.37 g, 1.5 mmol), and XANTPHOS (1.3 g, 2.25 mmol) were added to degassed dioxane (80 mL) and heated to 100° C. under a water cooled reflux condenser for 12 hours. The dioxane was removed under reduced pressure and the solids were partitioned between methylene chloride (500 mL) and water (500 mL). The organic layer was dried over sodium sulfate, taken to a residue under reduced pressure, and purified by chromatography on SiO$_2$ to give 1-[2,5-bis(methyloxy)-4-nitrophenyl]-4-(1-methylethyl)piperazine as a yellow solid (3.5 g, 11.3 mmol, 76% yield). 1H NMR (400 MHz, CDCl$_3$) δ ppm 1.09 (d, J=6.60 Hz, 6 H), 2.69-2.73 (m, 4 H), 2.75 (d, J=6.60 Hz, 1 H), 3.23-3.32 (m, 4 H), 3.88 (s, 3 H), 3.94 (s, 3 H), 6.48 (s, 1 H), 7.55 (s, 1 H).

Step B/Intermediate B58: 4-[4-(1-methylethyl)-1-piperazinyl]-2,5-bis(methyloxy)aniline A solution of 1-[2,5-bis(methyloxy)-4-nitrophenyl]-4-(1-methylethyl)piperazine (3.50 g, 11.3 mmol), FeCl$_3$ (0.550 g, 3.4 mmol), activated carbon (4.0 g), and hydrazine hydrate (3.6 mL, 113 mmol) was heated in methanol (50 mL) for 3 hours. The mixture was filtered over celite and concentrated to give 4-[4-(1-methylethyl)-1-piperazinyl]-2,5-bis(methyloxy)aniline as a grey solid (2.00 g, 7.17 mmol, 63% yield). 1H NMR (400 MHz, CDCl$_3$) δ ppm 1.10 (d, J=6.60 Hz, 6 H), 2.72 (s, 5 H), 3.03 (s, 4H), 3.59 (s, 2 H), 3.78 (s, 3 H), 3.79 (s, 3 H), 6.34 (s, 1 H), 6.57 (s, 1 H).

Intermediate B60: 5-fluoro-4-[4-(1-methylethyl)-1-piperazinyl]-2-(methyloxy)aniline

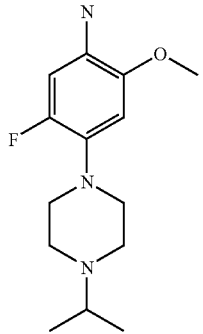

Step A/Intermediate B61: 5-bromo-4-fluoro-2-nitrophenyl methyl ether

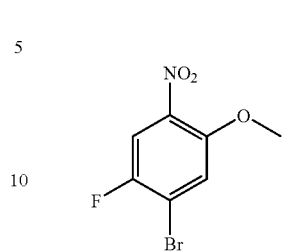

1-Bromo-2,5-difluoro-4-nitrobenzene (15.0 g, 63.0 mmol) was added to a solution of sodium methoxide in methanol (164 mL, 0.5 M, Aldrich). The reaction was heated to 60° C. for 1 h. After cooling to room temperature, the solution was concentrated, and the residue was diluted with water (100 mL) followed by extraction with Ethyl acetate (2×80 mL). The organic phase was dried (Na$_2$SO$_4$) and concentrated to afford 5-bromo-4-fluoro-2-nitrophenyl methyl ether as an orange solid (15.2 g, 95% yield). 1H NMR (400 MHz, DMSO-d$_6$) δ ppm 3.93 (s, 3 H), 7.76 (d, J=5.5 Hz, 1 H), 8.08 (d, J=8.4 Hz, 1 H).

Step B/Intermediate B62: 1-[2-fluoro-5-(methyloxy)-4-nitrophenyl]-4-(1-methylethyl)piperazine

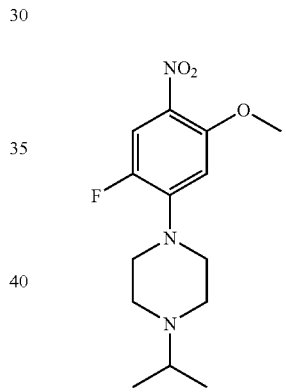

To 5-bromo-4-fluoro-2-nitrophenyl methyl ether (4.0 g, 16.0 mmol) in dioxane (150 mL) was added 1-(1-methylethyl)piperazine (4.1 g, 32.0 mmol), XANTPHOS (0.9 g, 1.6 mmol), and Cs$_2$CO$_3$ (10.4 g, 32.0 mmol). The mixture was bubbled with N$_2$ for 15 min prior to the addition of Pd$_2$(dba)$_3$ (0.7 g, 0.8 mmol). The reaction was stirred at 100° C. for 18 h. Ethyl acetate (100 mL) was used to dilute the reaction mixture, followed by the addition of water (80 mL). After partitioning, extraction with Ethyl acetate (2×75 mL), drying (Na$_2$SO$_4$), filtration and concentration, silica gel chromatography afforded 1-[2-fluoro-5-(methyloxy)-4-nitrophenyl]-4-(1-methylethyl)piperazine as a yellow solid (3.3 g, 70% yield). 1H NMR (400 MHz, DMSO-d$_6$) δ ppm 0.98 (d, J=6.6 Hz, 6 H), 2.54-2.61 (m, 4 H), 2.68 (dt, J=13.2, 6.6 Hz, 1 H), 3.24-3.31 (m, 4 H), 3.91 (s, 3 H), 6.64 (d, J=7.7 Hz, 1 H), 7.82 (d, J=13.6 Hz, 1 H).

Step C/Intermediate B60: 5-fluoro-4-[4-(1-methylethyl)-1-piperazinyl]-2-(methyloxy)aniline To 1-[2-fluoro-5-(methyloxy)-4-nitrophenyl]-4-(1-methylethyl)piperazine (2.0 g, 6.7 mmol) in MeOH (100 mL) was added iron (III) chloride (0.3 g, 2.0 mmol) and actived carbon (2.0 g). The reaction mixture was stirred at 64° C. for 20 min before the dropwise addition of hydrazine hydrate (4.0 mL, 80.7 mmol) over 5 min. The reaction was kept stirring at 64° C. for additional 4 h. Filtration, concentration of the residue, and purification via column chromatography on $SiO_2$ (0-10% 2 M $NH_3$ in MeOH/DCM) afforded 5-fluoro-4-[4-(1-methylethyl)-1-piperazinyl]-2-(methyloxy)aniline as a dark brown solid (1.7 g, 95% yield). 1H NMR (400 MHz, DMSO-$d_6$) δ ppm 0.96 (d, J=6.6 Hz, 6 H), 2.45-2.54 (m, 4 H), 2.62 (dt, J=13.0, 6.6 Hz, 1 H), 2.79-2.86 (m, 4 H), 3.69 (s, 3 H), 4.55 (s, 2 H), 6.38 (d, J=13.6 Hz, 1 H), 6.49 (d, J=8.2 Hz, 1 H).

Intermediate B63:
2-(methyloxy)-5-(4-methyl-1-piperazinyl)aniline

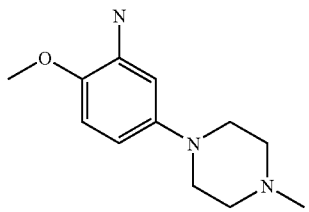

Step A/Intermediate B64:
1-methyl-4-[4-(methyloxy)-3-nitrophenyl]piperazine

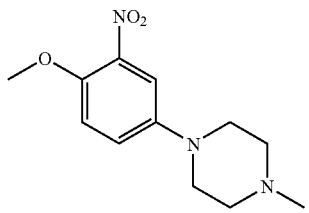

To an $N_2$ degassed solution of 1,4-dioxane (20 mL), was added 4-bromo-1-(methyloxy)-2-nitrobenzene (0.5 g, 2.16 mmol), XANTPHOS (0.37 g, 0.65 mmol, Aldrich), $Pd_2(dba)_3$ (0.39 g, 0.43 mmol, Aldrich), $Cs_2CO_3$ (1.4 g, 4.3 mmol, Aldrich), and 1-methylpiperazine (0.43 g, 4.3 mmol, Aldrich). After heating overnight at 90° C., the reaction was diluted with ethyl acetate (50 mL), washed with water (50 mL), the organic layer adsorbed to silica gel and purified by column chromatography (dichloromethane to 5% methanol/dichloromethane) to afford 1-methyl-4-[4-(methyloxy)-3-nitrophenyl]piperazine (0.4 g, 74%) as a tan solid. ESIMS (M+H)+=252.

Step B/Intermediate B63:
2-(methyloxy)-5-(4-methyl-1-piperazinyl)aniline

A solution of 1-methyl-4-[4-(methyloxy)-3-nitrophenyl]piperazine (0.25 g, 1.0 mmol) in absolute ethanol (100 mL) was hydrogenated with 10% Pd/C at 50 psi overnight. The catalyst was removed by vacuum filtration through a celite pad, rinsed with methanol, filtrate was concentrated under reduced pressure, and the crude aniline was purified by chromatography on $SiO_2$ (dichloromethane to 10% methanol/dichloromethane with 0.1% $NH_4OH$) to afford 2-(methyloxy)-5-(4-methyl-1-piperazinyl)aniline (0.19 g, 85%) as a tan solid. 1H NMR (400 MHz, $CDCl_3$) δ ppm 2.35 (s, 3 H) 2.55-2.64 (m, 4 H) 3.06-3.13 (m, 4 H) 3.78 (s, 3 H) 6.29 (dd, J=8.61, 2.75 Hz, 1 H) 6.38 (d, J=2.75 Hz, 1 H) 6.69 (d, J=8.61 Hz, 1 H). ESIMS (M+H)+=222.

Intermediate B65: 5.[4-(1-methylethyl)-1-piperazinyl]-2-(methyloxy)aniline

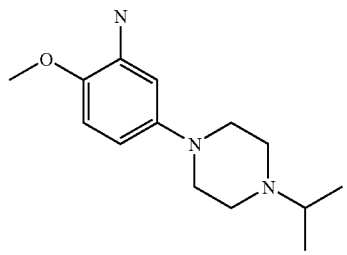

Step A/Intermediate B66: 1-(1-methylethyl)-4-[4-(methyloxy)-3-nitrophenyl]piperazine

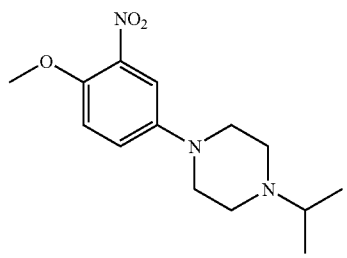

To an $N_2$ degassed solution of 1,4-dioxane (50 mL, Aldrich) was added 4-bromo-1-(methyloxy)-2-nitrobenzene (1.0 g, 4.31 mmol, Aldrich), XANTPHOS (0.74 g, 1.28 mmol, Aldrich), $Pd_2(dba)_3$ (0.79 g, 0.86 mmol, Aldrich), $Cs_2CO_3$ (2.8 g, 8.63 mmol, Aldrich), and 1-isopropylpiperazine (1.10 g, 8.6 mmol, Oakwood Chemicals). After heating overnight at 90° C., the reaction was diluted with ethyl acetate (50 mL), washed with water (50 mL), organic layer adsorbed to silica gel and purified by column chromatography (dichloromethane to 5% methanol/dichloromethane) to afford 1-(1-methylethyl)-4-[4-(methyloxy)-3-nitrophenyl]piperazine (0.66 g, 55%). ESIMS (M+H)+=280.

Step B/Intermediate B65: 5-[4-(1-methylethyl)-1-piperazinyl]-2-(methyloxy)aniline A solution of 1-(1-methylethyl)-4-[4-(methyloxy)-3-nitrophenyl]piperazine (0.6 g, 2.15 mmol) in absolute ethanol (100 mL) was hydrogenated with 10% Pd/C (Lancaster) at 50 psi overnight. The catalyst was removed by vacuum filtration through a celite pad, rinsed with methanol, the filtrate was concentrated under reduced pressure, and the crude aniline was purified by chromatography on $SiO_2$ (dichloromethane to 10% methanol/dichloromethane with 0.1% $NH_4OH$) to provide 5-[4-(1-methylethyl)-1-piperazinyl]-2-(methyloxy)aniline as a white solid (0.42 g, 80%). ESIMS (M+H)+=250.

Intermediate B67: 4-[(3S)-3-methyl-4-morpholinyl]-2-(methyloxy)aniline

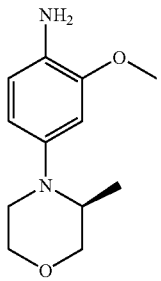

Step A/Intermediate B68: (3S)-3-methyl-4-[3-(methyloxy)-4-nitrophenyl]morpholine

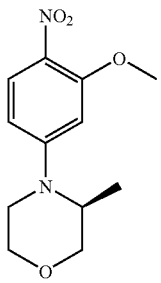

4-chloro-2-(methyloxy)-1-nitrobenzene (6.71 g, 29.7 mmol), (3S)-3-methylmorpholine (Synthetech Inc., 2.0 g, 19.8 mmol), cesium carbonate (13.0 g, 40 mmol), Pd$_2$dba$_3$ (1.83 g, 2.0 mmol), and XANTPHOS (1.73 g, 3.0 mmol) were added to degassed dioxane (200 mL) and heated to 100° C. under a water cooled reflux condenser for 12 hours. The dioxane was removed under reduced pressure and the solids were partitioned between methylene chloride (500 mL) and water (500 mL). The organic layer was dried over sodium sulfate, taken to a residue under reduced pressure, and purified by chromatography on SiO$_2$ to give 4-[(3S)-3-methyl-4-morpholinyl]-2-(methyloxy)aniline as a yellow solid (2.46 g, 8.45 mmol, 43% yield). 1H NMR (400 MHz, CDCl$_3$) δ ppm 1.22 (dd, J=6.41, 4.58 Hz, 3 H), 3.22-3.29 (m, J=12.11, 8.03, 4.03, 4.03 Hz, 1 H), 3.31-3.37 (m, 1 H), 3.59-3.69 (m, 1 H), 3.78 (d, J=2.93 Hz, 2H), 3.92 (d, J=4.21 Hz, 4 H), 4.02 (s, 1 H), 6.25 (s, 1 H), 6.32-6.39 (m, 1 H), 7.98 (dd, J=9.34, 4.21 Hz, 1 H).

Step B/Intermediate B67: 4-[(3S)-3-methyl-4-morpholinyl]-2-(methyloxy)aniline A solution of (3S)-3-methyl-4-[3-(methyloxy)-4-nitrophenyl]morpholine (2.46 g, 9.76 mmol), FeCl$_3$ (0.400 g, 2.44 mmol), activated carbon (2.0 g), and hydrazine hydrate (2.5 mL, 78 mmol) was heated in methanol (150 mL) for 3 hours. Once the starting material was judged consumed by thin layer chromatography (10% MeOH/CH$_2$Cl$_2$) the mixture was filtered over celite and concentrated to give 4-[(3S)-3-methyl-4-morpholinyl]-2-(methyloxy)aniline as a dark purple solid (1.76 g, 7.93 mmol, 81% yield). 1H NMR (400 MHz, CDCl$_3$) δ ppm 0.90 (d, J=6.60 Hz, 3 H), 2.95 (dd, J=6.97, 3.30 Hz, 1 H), 2.98-3.06 (m, 1 H), 3.28 (td, J=6.42, 3.30 Hz, 1 H), 3.50 (dd, J=11.00, 6.60 Hz, 1 H), 3.64 (d, J=13.20 Hz, 2 H), 3.76-3.82 (m, 1 H), 3.83 (s, 3 H), 3.84-3.90 (m, 2 H), 6.50 (dd, J=8.43, 2.20 Hz, 1 H), 6.56 (s, 1 H), 6.66 (d, J=8.43 Hz, 1 H).

Intermediate B69: N$^1$-(3-amino-4-methylphenyl)-N$^2$,N$^2$-dimethylglycinamide

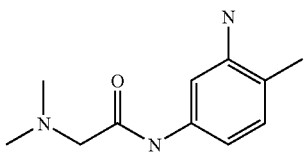

Step A/Intermediate B70: N$^2$,N$^2$-dimethyl-N$^1$-(4-methyl-3-nitrophenyl)glycinamide

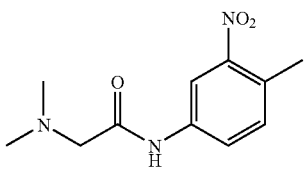

To a solution of 2-methyl-4-amino nitro benzene (5.00 g, 32.3 mmol) in dichloromethane (200 mL) was added triethylamine (12 mL, 97 mmol, 3 equiv.), dimethylaminopyridine (ca 500 mg) and dimethylaminoacetyl chloride hydrochloride (6.50 g, 41.1 mmol, 1.25 equiv.). The resulting clear solution was stirred 24 hours, at which time additional dimethylaminoacetyl chloride hydrochloride (1.50 g, 9.5 mmol, 0.30 equiv.) was added. After an additional 24 hrs. the reaction was poured into saturated aqueous sodium bicarbonate. The organic layer was dried over sodium sulfate, taken to a residue under reduced pressure, and purified by chromatography on SiO$_2$ (0 to 10% methonal/CH$_2$CL$_2$) to give N$^2$,N$^2$-dimethyl-N$^1$-(4-methyl-3-nitrophenyl)glycinamide (7.0 g, 29.5 mmol, 91% yield) as a brown oil. 1H NMR (400 MHz, CDCl$_3$) δ ppm 2.40 (s, 6 H), 2.55 (s, 3 H), 3.11 (s, 2 H), 7.28 (d, J=8.42 Hz, 1H), 7.86 (dd, J=8.32, 2.29 Hz, 1 H), 8.15 (d, J=2.38 Hz, 1 H), 9.33 (s, 1 H),

Step B/Intermediate B69: N$^1$-(3-amino-4-methylphenyl)-N$^2$,N$^2$-dimethylglycinamide N$^2$,N$^2$-dimethyl-N$^1$-(4-methyl-3-nitrophenyl)glycinamide (7.0 g, 19.5 mmol) was dissolved in ethyl acetate and 10% Pd/C (500 mg) was added. The reaction was placed on a Fischer-Porter hydrogenation apparatus and treated with 50 psi of H$_2$ gas overnight. Following purging with N$_2$ the reaction solution was passed through a celite plug to afford analytically pure N$^1$-(3-amino-4-methylphenyl)-N$^2$,N$^2$-dimethylglycinamide (6.0 g, 29.0 mmol, 98% yield) as a pale yellow oil. 1H NMR (400 MHz, DMSO-d$_6$) δ ppm 1.96 (s, 3 H), 2.24 (s, 6 H), 2.97 (s, 2 H), 4.79 (s, 2 H), 6.63 (dd, J=8.05, 2.01 Hz, 1 H), 6.78 (d, J=8.05 Hz, 1 H), 6.96 (d, J=2.01 Hz, 1 H), 9.24 (s, 1 H).

Intermediate B71: N-(3-amino-4-methylphenyl)-2-(1-pyrrolidinyl)acetamide

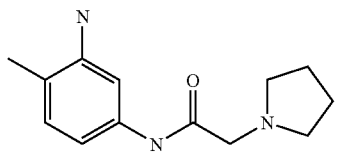

Step A/Intermediate B72: 2-chloro-N-(4-methyl-3-nitrophenyl)acetamide

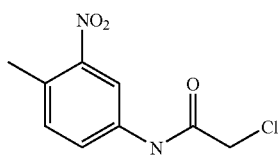

A solution of 4-methyl-3-nitroaniline (1.0 g, 6.58 mmol, Lancaster), triethylamine (2.00 g, 19.7 mmol, Aldrich), and chloroacetyl chloride (0.96 g, 8.55 mmol) in THF (50 mL) was stirred overnight at rt. The reaction was washed with 1M HCl (50 mL), concentrated by rotary evaporation, and placed under high vacuum to give 2-chloro-N-(4-methyl-3-nitrophenyl)acetamide (1.35 g, 90%). ESIMS (M+H)+=229.

Step B/Intermediate B73: N-(4-methyl-3-nitrophenyl)-2-(1-pyrrolidinyl)acetamide

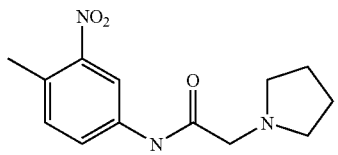

A solution of 2-chloro-N-(4-methyl-3-nitrophenyl)acetamide (1.0 g, 4.39 mmol), potassium carbonate (3.63 g, 26.3 mmol), pyrrolidine (0.93 g, 13.2 mmol, Aldrich), and catalytic KI (~100 mg, Aldrich) in anhydrous THF (50 mL) was heated for 3 hrs at 60° C. The solvent was removed under reduced pressure, residue redissolved in dichloromethane (100 mL), washed with water (100 mL) and purified by column chromatography (dichloromethane to 10% methanol/dichloromethane) to provide N-(4-methyl-3-nitrophenyl)-2-(1-pyrrolidinyl)acetamide (0.86 g, 75%). ESIMS (M+H)+=264.

Step C/Intermediate 71: N-(3-amino-4-methylphenyl)-2-(1-pyrrolidinyl)acetamide A solution of N-(4-methyl-3-nitrophenyl)-2-(1-pyrrolidinyl)acetamide (0.86 g, 3.27 mmol) in absolute ethanol (50 mL) was hydrogenated with 10% Pd/C (~0.200 g, Lancaster) at 50 psi overnight. The catalyst was removed by vacuum filtration through a celite pad, rinsed with methanol, and the filtrate was concentrated under reduced pressure to give N-(3-amino-4-methylphenyl)-2-(1-pyrrolidinyl)acetamide (0.72 g, 95%). 1H NMR (400 MHz, DMSO-$d_6$) δ ppm 1.70 (dt, J=6.55, 3.23 Hz, 4 H) 1.95 (s, 3 H) 2.53 (t, J=5.86 Hz, 4 H) 3.13 (s, 2 H) 4.78 (s, 2 H) 6.62 (dd, J=7.87, 2.01 Hz, 1 H) 6.76 (d, J=8.06 Hz, 1 H) 6.93 (d, J=2.01 Hz, 1 H) 9.23 (s, 1 H). ESIMS (M+H)+=234.

Intermediate B74: $N^1$-[3-amino-4-(methyloxy)phenyl]$N^2$,$N^2$-dimethylglycinamide

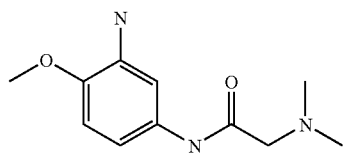

Step A/Intermediate B75: 1,1-dimethylethyl [2-(methyloxy)-5-nitrophenyl]carbamate

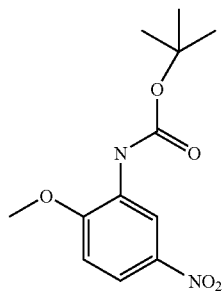

To a solution of 2-(methyloxy)-5-nitroaniline (10 g, 60 mmol, Aldrich) in anhydrous THF (300 mL) was added triethylamine (12.05 g, 120 mmol, Aldrich) and di-tert-butyl dicarbonate (15.6 g, 70 mmol, Aldrich) with catalytic DMAP (~0.100 g). After overnight stirring, the reaction was concentrated under reduced pressure, redissolved in ethyl acetate (300 mL), and washed with 10% citric acid (100 mL). The solvent was then removed by rotary evaporation, and the crude 1,1-dimethylethyl [2-(methyloxy)-5-nitrophenyl]carbamate placed under high vacuum and used without further purification. ESIMS (M+H)+=269.

Step B/Intermediate B76: 1,1-dimethylethyl [5-amino-2-(methyloxy)phenyl]carbamate

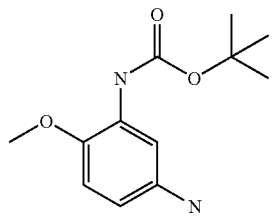

A solution of 1,1-dimethylethyl [2-(methyloxy)-5-nitrophenyl]carbamate (6 g, 22 mmol) in absolute ethanol (150 mL) was hydrogenated with 10% Pd/C (~1.00 g, Lancaster) at 50 psi overnight. The catalyst was removed by vacuum filtra-

Step C/Intermediate B77: 1,1-dimethylethyl [5-[(N,N-dimethylglycyl)amino]-2-(methyloxy)phenyl]carbamate

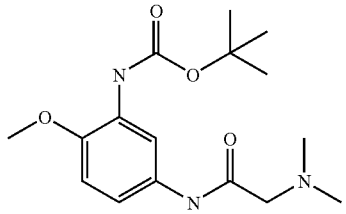

To a solution of 1,1-dimethylethyl [5-amino-2-(methyloxy)phenyl]carbamate (0.5 g, 2.1 mmol) in 1:1 THF/DCE (100 mL) was added triethylamine (1.28 g, 12.6 mmol, Aldrich), 2-dimethylaminoacetyl chloride hydrochloride (0.66 g, 4.20 mmol, Alfa Aesar), and catalytic DMAP. After overnight heating at 65° C., the crude reaction mixture was washed with brine (50 mL), evaporated, and purified by column chromatography (dichloromethane to 5% methanol/dichloromethane) to provide 1,1-dimethylethyl[5-[(N,N-dimethylglycyl)amino]-2-(methyloxy)phenyl]carbamate (0.44 g, 65%) as a brown solid. ESIMS (M+H)+=324.

Step D/Intermediate 74: $N^1$-[3-amino-4-(methyloxy)phenyl]-$N^2,N^2$-dimethylglycinamide A solution of 1,1-dimethylethyl [5-[(N,N-dimethylglycyl)amino]-2-(methyloxy)phenyl]carbamate (0.44 g, 1.36 mmol) and trifluoroacetic acid (1.55 g, 13.6 mmol, Aldrich) in dichloromethane (50 mL) was stirred overnight at room temperature. The crude reaction was diluted with dichloromethane (100 mL), washed with saturated NaHCO$_3$ (100 mL), evaporated under reduced pressure, and dried under high vacuum to provide $N^1$-[3-amino-4-(methyloxy)phenyl]-$N^2,N^2$-dimethylglycinamide (0.29 g, 95%). 1H NMR (400 MHz, DMSO-d$_6$) δ ppm 2.22 (s, 6H) 2.99 (s, 2 H) 3.80 (s, 3 H) 5.29 (s, 2 H) 6.68-6.74 (m, 1 H) 7.03 (d, J=8.61 Hz, 1H) 7.22 (d, J=2.38 Hz, 1 H) 9.49 (s, 1 H). ESIMS (M+H)+=224.

Intermediate 78: $N^1$-[3-amino-4-(trifluoromethoxy)phenyl]-$N^2,N^2$-dimethylglycinamide

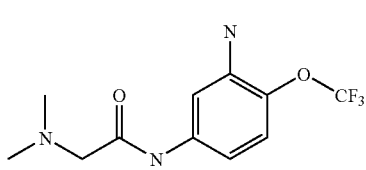

Step A/Intermediate 79: $N^1$-[3-amino-4-(trifluoromethoxy)phenyl]-$N^2,N^2$-dimethylglycinamide

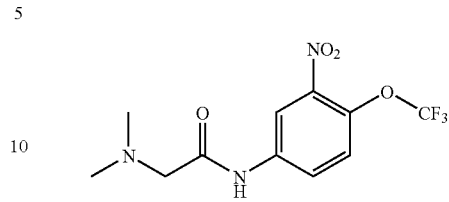

To a solution of 2-trifluoromethoxy-4-amino nitro benzene (5.00 g, 22.5 mmol) in dichloromethane (200 mL) was added triethylamine (12.2 mL, 90 mmol, 4.0 equiv.), dimethylaminopyridine (ca 500 mg) and dimethylaminoacetyl chloride hydrochloride (5.3 g, 33.8 mmol, 1.50 equiv.). The resulting clear solution was stirred 24 hours and was poured into saturated aqueous sodium bicarbonate. The organic layer was dried over sodium sulfate, taken to a residue under reduced pressure, and purified by chromatography on SiO$_2$ (0 to 10% methonal/CH$_2$CL$_2$) to give $N^1$-[3-amino-4-(trifluoromethoxy)phenyl]-$N^2,N^2$-dimethylglycinamide (4.54 g, 14.8 mmol, 66% yield) as a brown oil. 1H NMR (400 MHz, DMSO-d$_6$) δ ppm 2.26 (s, 6 H), 3.11 (s, 2 H), 7.67 (dd, J=8.97, 1.28 Hz, 1 H), 8.08 (dd, J=9.06, 2.65 Hz, 1 H), 8.60 (d, J=2.74 Hz, 1 H), 10.40 (s, 1 H).

Step B/Intermediate B78: $N^1$-[3-amino-4-(trifluoromethoxy)phenyl]-$N^2,N^2$-dimethylglycinamide $N^1$-[3-amino-4-(trifluoromethoxy)phenyl]-$N^2,N^2$-dimethylglycinamide (4.5 g, 14.7 mmol) was dissolved in ethyl acetate and 10% Pd/C (1.2 g) was added. The reaction was placed on a Fischer-Porter hydrogenation apparatus and treated with 50 psi of H$_2$ gas overnight. Following purging with N$_2$ the reaction solution was passed through a celite plug to afford analytically pure $N^1$-[3-amino-4-(trifluoromethoxy)phenyl]-$N^2,N^2$-dimethylglycinamide (3.90 g, 14.1 mmol, 96% yield) as a pale yellow oil. 1H NMR (400 MHz, DMSO-d$_6$) δ ppm 2.22 (s, 6 H), 2.99 (s, 2 H), 5.32 (s, 2 H), 6.70 (dd, J=8.88, 2.47 Hz, 1 H), 6.95 (dd, J=8.70, 1.37 Hz, 1 H), 7.22 (d, J=2.56 Hz, 1 H), 9.51 (s, 1 H).

Intermediate B80: $N^1$-(3-amino-4-fluorophenyl)-$N^2,N^2$-dimethylglycinamide

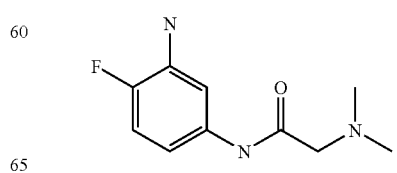

Step A/Intermediate B81: $N^1$-(4-fluoro-3-nitrophenyl)-$N^2$,$N^2$-dimethylglycinamide

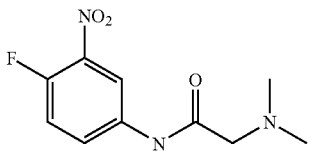

To a solution of 4-fluoro-3-nitroaniline (2.48 g, 15.9 mmol) in 1:1 THF/DCE (200 mL) was added pyridine (7.54 g, 95.4 mmol, Aldrich), 2-dimethylaminoacetyl chloride hydrochloride (0.66 g, 4.20 mmol, Lancaster), and catalytic DMAP (~0.100 g). After heating at 65° C. for 1.5 hrs, the crude reaction mixture was diluted with dichloromethane (300 mL), washed with saturated NaHCO$_3$ (50 mL), evaporated, and purified by column chromatography (dichloromethane to 5% methanol/dichloromethane) to provide $N^1$-(4-fluoro-3-nitrophenyl)-$N^2$,$N^2$-dimethylglycinamide (3.0 g, 78%) as a brown solid. ESIMS (M+H)+=242.

Step B/Intermediate 80: $N^1$-(3-amino-4-fluorophenyl)-$N^2$,$N^2$-dimethylglycinamide A solution of $N^1$-(4-fluoro-3-nitrophenyl)-$N^2$,$N^2$-dimethylglycinamide (3.0 g, 12.4 mmol), 10% Pd/C (~0.500 g, Lancaster) in absolute ethanol (100 mL) was stirred under 50 psi H$_{2(g)}$ overnight. The catalyst was removed by vacuum filtration through a celite pad, rinsed with methanol, and the filtrate was concentrated under reduced pressure to give $N^1$-(3-amino-4-fluorophenyl)-$N^2$,$N^2$-dimethylglycinamide (2.23 g, 85%). 1H NMR (400 MHz, DMSO-d$_6$) δ ppm 2.22 (s, 6 H) 2.97 (s, 2 H) 5.09 (s, 2 H) 6.64 (ddd, J=8.74, 3.98, 2.66 Hz, 1 H) 6.83 (dd, J=11.26, 8.70 Hz, 1 H) 7.15 (dd, J=8.42, 2.56 Hz, 1 H) 9.40 (s, 1 H).

Intermediate B82: $N^1$-(3-amino-4-chlorophenyl)-$N^2$,$N^2$-dimethylglycinamide

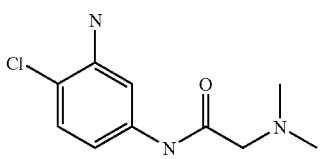

Step A/Intermediate B83: $N^1$-(4-chloro-3-nitrophenyl)-$N^2$,$N^2$-dimethylglycinamide

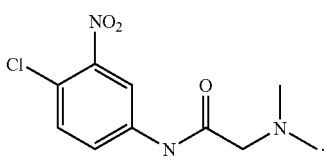

To a solution of 4-chloro-3-nitroaniline (1.0 g, 5.81 mmol) in 1:1 THF/DCE (200 mL) was added triethylamine (3.53 g, 34.9 mmol, Aldrich), 2-dimethylaminoacetyl chloride hydrochloride (1.82 g, 11.6 mmol, Alfa Aesar), and catalytic DMAP (Aldrich). After heating overnight at 65° C., the crude reaction mixture was diluted with dichloromethane (300 mL), washed with saturated NaHCO$_3$ (50 mL), evaporated, and purified by column chromatography (dichloromethane to 5% methanol/dichloromethane) to provide $N^1$-(4-chloro-3-nitrophenyl)-$N^2$,$N^2$-dimethylglycinamide (1.0 g, 67%) as a brown solid. ESIMS (M+H)+=258.

Step B/Intermediate B82: $N^1$-(3-amino-4-chlorophenyl)-$N^2$,$N^2$-dimethylglycinamide A solution of $N^1$-(4-chloro-3-nitrophenyl)-$N^2$,$N^2$-dimethylglycinamide (1.0 g, 3.89 mmol), SnCL$_{2 \times 2}$H$_2$O (5.26 g, 23.3 mmol, Aldrich), and 1M HCl (2 mL, Aldrich) in absolute ethanol (100 mL) was allowed to stir at RT overnight. The reaction was diluted with methanol (100 mL) and quenched with saturated NaHCO$_3$ (200 mL). After stirring 2 hrs at rt, the emulsion was filtered through a celite pad and filtrate evaporated. The residue was then resuspended in dichloromethane (200 mL), washed with water (200 mL), organic layer concentrated by rotary evaporation, and placed under high vacuum to provide $N^1$-(3-amino-4-chlorophenyl)-$N^2$,$N^2$-dimethylglycinamide (0.9 g, 55%) as a brown solid. 1H NMR (400 MHz, DMSO-d$_6$) δ ppm 2.22 (s, 6 H) 2.99 (s, 2 H) 5.29 (s, 2 H) 6.68-6.74 (m, 1 H) 7.03 (d, J=8.61 Hz, 1 H) 7.22 (d, J=2.38 Hz, 1 H) 9.49 (s, 1 H). ESIMS (M+H)+=228.

Intermediate B84: 2-(methyloxy)-4-[(methylsulfonyl)methyl]aniline

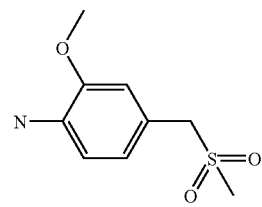

Step A/Intermediate B85: 4-(chloromethyl)-2-(methyloxy)-1-nitrobenzene

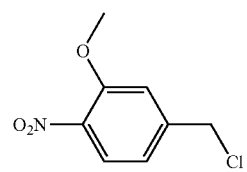

To a solution of 3-methoxy-4-nitrobenzyl alcohol (3.0 g, 16.4 mmol) in 150 mL of dichloromethane was added triphenylphosphine (5.6 g, 21.3 mmol). The reaction was cooled to 0° C. and N-chlorosuccinimide (2.8 g, 21.3 mmol) was added. The reaction was warmed to room temperature and then heated gently to 50° C. for 2 h. The reaction was poured into aqueous sodium carbonate solution and the aqueous layer was extracted with dichloromethane and then ethyl acetate. Combined organics were dried over anhydrous MgSO$_4$, filtered, concentrated onto silica gel and purified by flash chromatography with ethyl acetate/hexanes as the eluent to afford 3-methoxy-4-nitrobenzyl chloride (2.76 g, 84%). ¹H NMR (400 MHz, CDCl₃) δ ppm 7.88 (d, J=8.2 Hz, 1H), 7.44 (d, J=1.6 Hz, 1H), 7.17 (d, J=8.2, 1.7 Hz, 1H), 4.81 (s, 2H), 3.91 (s, 3H).

Step B/Intermediate B84:
2-(methyloxy)-4-[(methylsulfonyl)methyl]aniline

To a solution of 3-methoxy-4-nitrobenzyl chloride (2.76 g, 13.7 mmol) in 20 mL of absolute ethanol was added methanesulphinic acid sodium salt (1.0 g, 27.4 mmol). The reaction was heated to 80° C. for 16 h. The reaction was cooled to room temperature and poured into water and the aqueous layer was extracted with ethyl acetate. Combined organics were dried over anhydrous MgSO₄, filtered, concentrated onto silica gel and purified by flash chromatography with ethyl acetate/hexanes as the eluent. The fractions containing the desired product were concentrated to dryness, then redisolved in absolute ethanol and 10% Palladium on carbon (500 mg) was added and the reaction was placed on the Fischer-Porter hydrogenation apparatus and treated with 50 psi of H₂ gas overnight to afford 2-(methyloxy)-4-[(methylsulfonyl)methyl]aniline (2.46 g, 83%). ¹H NMR (400 MHz, CDCl₃) δ ppm 6.80 (d, J=1.7 Hz, 1H), 6.68 (d, J=8.0, 1.6 Hz, 1H), 6.57 (d, J=8.1, 1H), 4.82 (s, 2H), 4.21 (s, 2H), 3.72 (s, 3H).

Intermediate B86:
2-(methyloxy)-5-[(methylsulfonyl)methyl]aniline

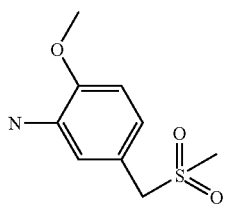

Step A/Intermediate B87:
4-(chloromethyl)-1-(methyloxy)-2-nitrobenzene

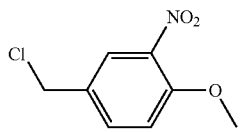

To a solution of 4-methoxy-3-nitrobenzyl alcohol (4.9 g, 24.4 mmol) in 150 mL of dichloromethane was added triphenylphosphine (4.2 g, 31.7 mmol). The reaction was cooled to 0° C. and N-chlorosuccinimide (8.3 g, 31.7 mmol) was added. The reaction was warmed to room temperature and then heated gently to 50° C. for 2 h. The reaction was poured into aqueous sodium carbonate solution and the aqueous layer was extracted with dichloromethane and then ethyl acetate. Combined organics were dried over anhydrous MgSO₄, filtered, concentrated onto silica gel and purified by flash chromatography with ethyl acetate/hexanes as the eluent to give 4-methoxy-3-nitrobenzyl chloride (3.09 g, 63%). ¹H NMR (400 MHz, CDCl₃) δ ppm 7.98 (d, J=2.4 Hz, 1H), 7.73 (d, J=8.8, 2.4 Hz, 1H), 7.37 (d, J=8.8 Hz, 1H), 4.78 (s, 2H), 3.91 (s, 3H).

Step B/Intermediate B86:
2-(methyloxy)-5-[(methylsulfonyl)methyl]aniline

To a solution of 4-methoxy-3-nitrobenzyl chloride (3.09 g, 15.3 mmol) in 75 mL of absolute ethanol was added methanesulphinic acid sodium salt (3.1 g, 30.7 mmol). The reaction was heated to 80° C. for 16 h. The reaction was cooled to room temperature and poured into water and the aqueous layer was extracted with ethyl acetate. Combined organics were dried over anhydrous MgSO₄, filtered, concentrated onto silica gel and purified by flash chromatography with ethyl acetate/hexanes as the eluent. The fractions containing the desired product were concentrated to dryness, then redisolved in absolute ethanol and 10% palladium on carbon (500 mg) was added and the reaction was placed on the Fischer-Porter hydrogenation apparatus and treated with 50 psi of H₂ gas overnight to give 2-(methyloxy)-5-[(methylsulfonyl)methyl]aniline (1.7 g, 52%). ¹H NMR (400 MHz, CDCl₃) δ ppm 6.74 (d, J=8.2 Hz, 1H), 6.62 (d, J=2.2 Hz, 1H), 6.52 (d, J=8.2, 2.2, 1H), 4.76 (s, 2H), 4.19 (s, 2H), 3.72 (s, 3H).

Intermediate B88: (2S)-1-{[3-amino-4-(methyloxy)phenyl]oxy}-3-(1-pyrrolidinyl)-2-propanol

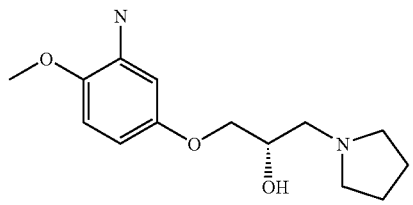

Step A/Intermediate B89: (2S)-2-({[4-(methyloxy)-3-nitrophenyl]oxy}methyl)oxirane

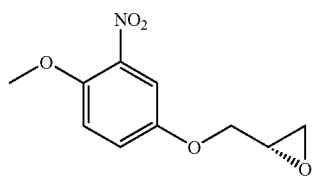

In DMF (10 mL) were added 4-methoxy-3-nitro-phenol(4-hydroxy-2-nitro-anisole) (2.2 g, 12.9 mmol), (S)-(+)-Glycidyl-3-nitrobenzenesulfonate (10.0 g, 39.6 mmol), and cesium fluoride (9.8 g, 64.5 mmol). The reaction was heated to 80° C. overnight and to the cooled solution was added aq. LiCl (500 mL, 5%). After stirring for 10 min, filtration afforded (2S)-2-({[4-(methyloxy)-3-nitrophenyl]oxy}methyl)oxirane as a yellow solid (2.6 g, 90% yield). 1H NMR (400 MHz, CDCl₃) δ ppm 2.76 (dd, J=4.8, 2.6 Hz, 1 H), 2.90-2.94 (m, 1 H), 3.36 (d, J=4.4 Hz, 1 H), 3.88-3.92 (m, 1 H), 3.92 (s, 3 H), 4.28 (dd, J=11.0, 2.6 Hz, 1 H), 7.03 (d, J=9.2 Hz, 1 H), 7.17 (dd, J=9.2, 3.3 Hz, 1 H), 7.43 (d, J=3.3 Hz, 1 H).

Step B/Intermediate B88: (2S)-1-{[3-amino-4-(methyloxy)phenyl]oxy}-3-(1-pyrrolidinyl)-2-propanol In a sealed tube were placed (2S)-2-({[4-(methyloxy)-3-nitrophenyl]oxy}methyl)oxirane (1.0 g, 4.4 mmol), pyrrolidine (3.2 g, 44 mmol), and isopropanol (20 mL). The mixture was heated under microwave to 140° C. for 10 min. Removal of the isopropanol afforded the crude product which was placed in ethanol (100 mL) with 10% palladium on carbon (0.5 g). The reation mixture was kept stirring under $H_2$ at 60 psi overnight. Filtration removed the catalyst and concentration afforded (2S)-1-{[3-amino-4-(methyloxy)phenyl]oxy}-3-(1-pyrrolidinyl)-2-propanol (1.1 g, 95% yield). 1H NMR (400 MHz, DMSO-$d_6$) δ ppm 1.67 (ddd, J=6.4, 3.5, 3.3 Hz, 4H), 2.47-2.50 (m, 1 H), 2.55 (d, J=1.8 Hz, 4 H), 2.64 (dd, J=12.3, 5.7 Hz, 1 H), 3.63-3.71 (m, 4 H), 3.75-3.82 (m, 1 H), 3.83-3.89 (m, 1 H), 4.70 (s, 2 H), 4.88 (s, 1 H), 6.03 (dd, J=8.4, 2.9 Hz, 1 H), 6.24 (d, J=2.9 Hz, 1 H), 6.63 (d, J=8.8 Hz, 1 H).

Intermediate B90: (2S)-1-{[3-amino-4-(methyloxy)phenyl]oxy}-3-(dimethylamino)-2-propanol

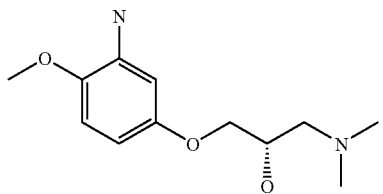

In an analogous procedure to the preparation of (2S)-1-{[3-amino-4-(methyloxy)phenyl]oxy}-3-(1-pyrrolidinyl)-2-propanol (Intermediate B88), (2S)-1-{[3-amino-4-(methyloxy)phenyl]oxy}-3-(dimethylamino)-2-propanol (ca 0.660 g) was prepared from (2S)-2-({[4-(methyloxy)-3-nitrophenyl]oxy}methyl)oxirane (1.7 g) and dimethyl amine. ESIMS $(M+H)^+$=241.2.

Intermediate B91: 5-{[3-(dimethylamino)propyl]oxy}-2-(methyloxy)aniline

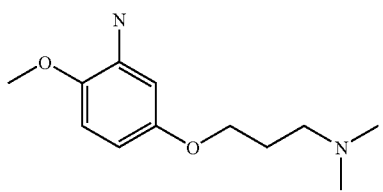

In 2-butanone (200 mL) were added 4-(methyloxy)-3-nitrophenol (6.0 g, 26.7 mmol), 3-dimethylaminopropylchlordiehydrochloride (12.6 g, 80.0 mmol), potassium carbonate (16.6 g, 120.2 mmol), and TBAI (0.5 g). The reaction was kept stirring at 80° C. for 48 h. After concentration the residue was partitioned between ethyl acetate and water and the aqueous layer was washed three times with ethyl acetate. The combined organic layers were dried ($Na_2SO_4$), Mitered, and concentrated. Silica gel column chromatography afforded the purified dimethyl(3-{[4-(methyloxy)-3-nitrophenyl]oxy}propyl)amine, and the product was dissolved in ethanol (100 mL) with the addition of 10% palladium on carbon (0.5 g). The reaction was kept stirring under $H_2$ at 60 psi over the weekend. After releasing the $H_2$ pressure, filtration removed the catalyst and the filtrate was concentrated. The crude product was purified by silica gel column chromatography to afford 5-{[3-(dimethylamino)propyl]oxy}-2-(methyloxy)aniline (5.3 g, 90% yield). 1H NMR (400 MHz, DMSO-$d_6$) δ ppm 1.71-1.81 (m, 2 H), 2.11 (s, 6 H), 2.29 (t, J=7.1 Hz, 2 H), 3.66 (s, 3 H), 3.81 (t, J=6.4 Hz, 2 H), 4.63-4.73 (m, 2 H), 6.02 (dd, J=8.4, 2.9 Hz, 1 H), 6.22 (d, J=2.9 Hz, 1 H), 6.62 (d, J=8.8 Hz, 1 H).

Intermediate B92: 3-fluoro-4-[4-(1-methylethyl)-1-piperazinyl]-2-(methyloxy)aniline

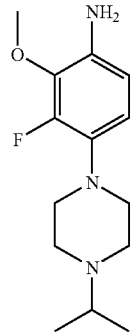

Step A/Intermediate B93: 1,2-difluoro-3-(methyloxy)-4-nitrobenzene

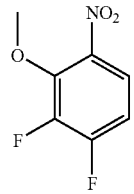

To a solution of 2,3-difluoro-6-nitrophenol (15.01 g, 85.8 mmol) in anhydrous dimethylformamide (120 mL) was cautiously added potassium carbonate (16.6 g, 120 mmol) and methyl iodide (6.63 mL, 107 mmol). The resulting suspension was stirred overnight. The next morning the reaction was poured into water and extracted twice with diethyl ether. The organic layers were washed twice with 5% LiCl, dried over sodium sulfate. The solvents were removed under reduced pressure to afford 1,2-difluoro-3-(methyloxy)-4-nitrobenzene as a yellow oil (14.7 g, 91% yield). 1H NMR (400 MHz, CDCl$_3$) δ ppm 4.13 (s, 3 H), 7.00 (td, J=9.07, 7.15 Hz, 1 H), 7.67 (ddd, J=9.35, 5.32, 2.20 Hz, 1 H).

Step B/Intermediate B94: 1-[2-fluoro-3-(methyloxy)-4-nitrophenyl]-4-(1-methylethyl)piperazine

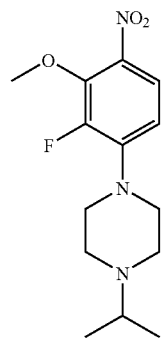

A pressure flask was charged with 1,2-difluoro-3-(methyloxy)-4-nitrobenzene (3.5 g, 18.5 mmol), dimethylsulfoxide (100 mL), isopropyl piperazine (5.41 mL, 22.2 mmol) and potassium carbonate (5.1 g, 37.04 mmol). The resulting slurry was warmed to 70° C. and stirred overnight. The next morning, the orange solution was poured into water and extracted with diethyl ether. The organic layer was dried over sodium sulfate, taken to a residue under reduced pressure, and purified via chromatography on $SiO_2$ (0 to 10% MeOH/$CH_2CL_2$ with 0.2% NH3) to afford 1-[2-fluoro-3-(methyloxy)-4-nitrophenyl]-4-(1-methylethyl)piperazine as a yellow solid (5.7 g, quant. yield). 1H NMR (400 MHz, $CDCl_3$) δ ppm 1.10 (d, J=6.60 Hz, 6 H), 2.71 (s, 4 H), 2.76 (s, 1 H), 3.29 (s, 4 H), 4.03 (s, 3 H), 6.64 (dd, J=9.53, 8.07 Hz, 1 H), 7.70 (dd, J=9.35, 2.02 Hz, 1 H).

Step C/Intermediate B92: 3-fluoro-4-[4-(1-methylethyl)-1-piperazinyl]-2-(methyloxy)aniline To a solution of 1-[2-fluoro-3-(methyloxy)-4-nitrophenyl]-4-(1-methylethyl)piperazine (5.70 g, 19.2 mmol) in methanol (200 mL) was added hydrazine (4.2 mL, 134 mmol), iron (III) chloride (0.78 g, 4.18 mmol) and activated charcoal (6 g). The resulting slurry was warmed to 60° C. and maintained overnight. The next morning the slurry was filtered and concentrated to a residue. The residue was partitioned between ethyl acetate and sat. NaCl(aq). The organic layer was washed twice with saturated brine, dried over sodium sulfate, and taken to a residue under reduced pressure to afford-fluoro-4-[4-(1-methylethyl)-1-piperazinyl]-2-(methyloxy)aniline (3.6 g, 70% yield) of sufficient purity for use directly in the next step. 1H NMR (400 MHz, DMSO-$d_6$) δ ppm 0.97 (d, J=6.60 Hz, 6 H), 2.49-2.55 (m, 4 H), 2.57-2.67 (m, J=6.60, 6.60, 6.60 Hz, 1 H), 2.74-2.82 (m, 4 H), 3.69 (s, 3 H), 4.73 (s, 2 H), 6.36 (dd, J=8.80, 1.83 Hz, 1 H), 6.51 (t, J=8.80 Hz, 1 H).

Intermediate B95: 1-[(dimethylamino)acetyl]-5-(methyloxy)-2,3-dihydro-1 H-indol-6-amine

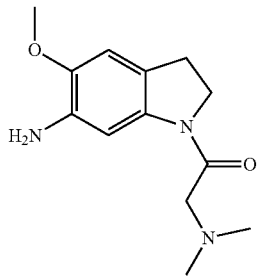

Step A/Intermediate B96:
5-(methyloxy)-2,3-dihydro-1 H-indole

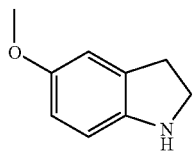

A 4-neck 22 L round bottom flask equipped with a nitrogen inlet, mechanical stirrer and thermowell was charged with commercially available 5-methoxyindole (750 g, 5.1 mol) and acetic acid (3.75 L). The resulting solution was cooled to 10° C. by ice bath. Sodium cyanoborohydride (640 g, 10.2 mol, 2 equiv) was added portionwise to maintain the reaction temperature below 25° C. Upon the completion of addition, the reaction was stirred at room temperature for 3 hours and then water was added slowly (2.2 L). The mixture was basified to pH>12 with 50% NaOH (~5.3 L, slow addition to avoid foaming, the temperature kept below 30° C.). The resulting mixture was extracted with dichloromethane (2×12 L). The combined organic layers were dried over sodium sulfate and evaporated in vacuo to give 5-(methyloxy)-2,3-dihydro-1 H-indole (760 g, >90% purity), which was used for the next step without further purification. $^1$H NMR ($CDCl_3$, 300 MHz) δ 6.76 (s, 1 H), 6.60 (s, 2H), 3.54 (t, 2H), 3.01 (t, 2H).

Step B/Intermediate B97:
1-acetyl-5-(methyloxy)-2,3-dihydro-1H-indole

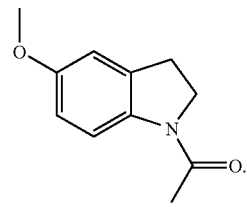

A 4-neck 22L round bottom flask equipped with a reflux condenser, mechanical stirrer and thermowell was charged with 5-methoxyindoline (1520 g, ca. 10.2 mol) produced in accordance with Step A, immediately above and dichloromethane (15 L). To the solution was added 4-dimethylaminopyridine (50 g, 0.446 mol), followed by slow addition of acetic anhydride (1051 mL, 11.22 mol, 1.1 equiv, maintaining gentle reflux of the solvent). The reaction mixture was stirred at room temperature overnight. After completion, the reaction mixture was diluted with dichloromethane (10 L), then washed with water (15 L) and saturated sodium bicarbonate solution (15 L). The organic layer was dried over sodium sulfate and evaporated in vacuo to a crude solid, which was triturated from heptane (4 L) to afford 1-acetyl-5-(methyloxy)-2,3-dihydro-1H-indole (1800 g, 92% yield over two steps). $^1$H-NMR ($CDCl_3$, 300 MHz) δ 8.13 (d, J=6.3 Hz, 1H), 6.74-6.71 (m, 2 H), 4.05 (t, 2 H), 3.78 (s, 3 H), 3.17 (t, 2 H), 2.21 (s, 3 H).

Step C/Intermediate B98: 1-acetyl-5-(methyloxy)-6-nitro-2,3-dihydro-1H-indole

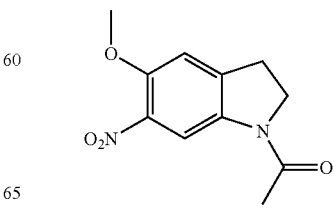

A 4-neck 22 L round bottom flask equipped with mechanical stirrer and thermowell was charged with 1-acetyl-5-(methyloxy)-2,3-dihydro-1H-indole (300 g, 1.56 mol) made in accordance with Step B, immediately above, and acetic anhydride (12 L). The resulting mixture was cooled to 0° C. then nitric acid (70%, .100 mL, 1.56 mol) was added dropwise. The reaction was stirred at room temperature overnight and then cooled to 0° C. The solid formed was collected by vacuum filtration and washed with water (200 mL) and MTBE (200 mL), then dried in a oven to give 1-acetyl-5-(methyloxy)-6-nitro-2,3-dihydro-1H-indole as a yellow solid (239 g, 65% yield). $^1$H-NMR (CDCl$_3$, 300 MHz) δ 8.43 (s, 1H), 7.31 (s, 1H), 4.13 (t, 2H), 3.87 (s, 3H), 3.22 (t, 2H), 2.14 (s, 3H).

Step D/Intermediate B99:
5-(methyloxy)-6-nitro-2,3-dihydro-1H-indole

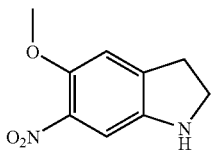

A roundbottom flask equipped with a reflux condenser, mechanical stirrer and thermowell was charged with 1-acetyl-5-(methyloxy)-6-nitro-2,3-dihydro-1H-indole (954 g, 4.04 mol) produced in accordance with Step C, immediately above, and aqueous 6N hydrochloric acid (9.5 L). The resulting suspension was heated to reflux for 4 hrs (became clear solution after 2 hrs). The reaction mixture was allowed to cool to room temperature then sodium hydroxide (50% w/w) was added to adjust the pH to 10. The resulting mixture was extracted with ethyl acetate (3×10L). The combined organic layers were washed with saturated potassium carbonate solution (10 L) and brine (10 L), then dried over sodium sulfate, evaporated in vacuo to afford 5-(methyloxy)-6-nitro-2,3-dihydro-1H-indole (737 g, 94%), which was used for the next step without further purification. $^1$H-NMR (DMSO, 300 MHz) δ 7.11 (s, 1H), 6.87 (s, 1H), 5.59 (brs, 1H), 3.78 (s, 3H), 3.43 (t, 2H), 2.97 (t, 2H).

Step E/Intermediate B100: N,N-dimethyl-2-[5-(methyloxy)-6-nitro-2,3-dihydro-1H-indol-1-1-yl]-2-oxoethanamine

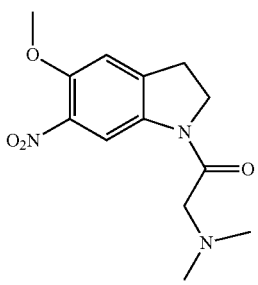

A 4-neck 22 L round bottom flask equipped with a nitrogen inlet, mechanical stirrer and thermowell was charged with chloroacetyl chloride (605 mL, 857.5 g, 7.59 mol, 2 equiv), powdered potassium carbonate (1153.7 g, 8.36 mol, 2.2 equiv) and dichloromethane (10 L). The resulting suspension was cooled by an ice bath and a solution of 5-(methyloxy)-6-nitro-2,3-dihydro-1H-indole (737 g, 3.795 moll in 4 L dichloromethane) produced in accordance with step D, immediately above, was added slowly. The reaction mixture was stirred for 2 hrs and filtered by vacuum filtration. The solid collected (a mixture of product and inorganic salts) was suspended in water (10 L) and refiltered. The solid was washed with water (3×1 L) and dichloromethane (2×1 L), dried in the oven to give 1-(chloroacetyl)-5-(methyloxy)-6-nitro-2,3-dihydro-1H-indole as a yellow solid (750 g). The filtrates from both filtrations were combined and the layers were separated. The organic layer was washed with saturated potassium carbonate solution (2×10 L) and brine (5 L), dried over sodium sulfate and evaporated in vacuo to a crude solid, which was triturated from MTBE (1 L) to afford a second crop of 1-(chloroacetyl)-5-(methyloxy)-6-nitro-2,3-dihydro-1H-indole (260 g). The combined product was 1010 g (98% yield). A 4-neck 22L round bottom flask equipped with a reflux condenser, mechanical stirrer and thermowell was charged with 1-(chloroacetyl)-5-(methyloxy)-6-nitro-2,3-dihydro-1H-indole (500 g, 1.852 mol), as described immediately above, potassium carbonate (767 g, 5.556 mol, 3 equiv), tetrahydrofuran (7.5 L) and water (3.75 L). Then dimethylamine hydrochloride salt (453 g, 5.556 mol, 3 equiv) was added as one portion. The resulting mixture was heated to reflux for 4 hrs and then allowed to cool to room temperature. Two reactions of the same size were combined. The organic solvent (THF) was removed in vacuo and the resulting suspension was filtered by vacuum filtration. The solid collected was triturated from methanol to afford N,N-dimethyl-2-[5-(methyloxy)-6-nitro-2,3-dihydro-1H-indol-1-yl]-2-oxoethanamine as a yellow solid (740 g). The mother liquor from methanol trituration was evaporated in vacuo to afford a crude solid, which was partitioned between ethyl acetate (10 L) and water (10 L). The insoluble solid was removed by filtration through Celite. The layers were separated and the organic layer was washed with brine (5 L), dried over sodium sulfate and evaporated in vacuo to afford a solid, which was triturated from heptane (2 L) to give a second crop of N,N-dimethyl-2-[5-(methyloxy)-6-nitro-2,3-dihydro-1H-indol-1-yl]-2-oxoethanamine (220 g). The combined amount of product was 960 g (93% yield). $^1$H NMR (400 MHz, CDCl$_3$) δ ppm 2.59 (s, 6H), 3.24 (t, J=8.24 Hz, 2H), 3.52 (s, 2 H), 3.89 (s, 3 H), 4.19 (t, J=8.52 Hz, 2 H), 6.89 (s, 1 H), 8.60 (s, 1 H).

Step F/Intermediate B95: 1-[(dimethylamino)acetyl]-5-(methyloxy)-2,3-dihydro-1H-indol-6-amine In a 18 L pressure reactor a solution of N,N-dimethyl-2-[5-(methyloxy)-6-nitro-2,3-dihydro-1H-indol-1-yl]-2-oxoethanamine (499 g, 1.79 mol), produced in accordance with step E, immediately above, in methanol (6 L) and ethyl acetate (6 L) was stirred under 25 psi of hydrogen in the presence of 10% Pd/C (50 g, containing 50% water) until no hydrogen was further consumed. The reaction mixture was filtered over a celite cake and the filtered cake was washed with tetrahydrofuran (20 L). The solvents were combined, dried over sodium sulfate and evaporated in vacuo to give a crude solid, which was triturated from methyl tert-butyl ether (2 L) to give 1-[(dimethylamino)acetyl]-5-(methyloxy)-2,3-dihydro-1H-indol-6-amine (380 g, 85% yield). $^1$H NMR (400 MHz, DMSO-d$_6$) δ ppm 2.23 (s, 6 H), 2.95 (t, J=8.43 Hz, 2 H), 3.11 (s, 2 H), 3.68 (s, 3 H), 4.05 (t, J=8.25 Hz, 2 H), 4.61 (s, 2 H), 6.68 (s, 1 H), 7.53 (s, 1 H).

Intermediate B95: 1-[(dimethylamino)acetyl]-5-(methyloxy)-2,3-dihydro-1H-indol-6-amine (First Alternate Synthesis)

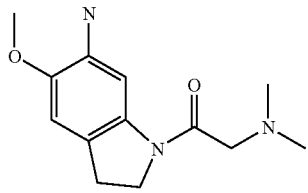

Step A/Intermediate B126 (First Alternate Synthesis): N,N-dimethyl-2-[5-(methyloxy)-2,3-dihydro-1H-indol-1-yl]-2-oxoethanamine

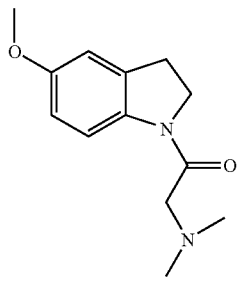

A suspension of 5-(methyloxy)-2,3-dihydro-1H-indole hydrogen chloride (94.5 g, 509 mmol) in CH₂Cl₂ (250 mL) was added dropwise to a mixture of α-bromoacetylchloride (120 g, 764 mmol) and K₂CO₃ (78 g, 560 mmol) in CH₂Cl₂ (750 mL) at 0° C. After the addition, the suspension was stirred at 0° C. for 1.5 hours. The reaction was washed with water and filtered. The residue (presumed to be K₂CO₃) was rinsed with DCM (2×100 ml). The organic layers were separated, combined, dried over Na₂SO₄, filtered, and concentrated to provide a brown solid (135 g, 98%).

The brown solid (135 g, 499 mmol) was dissolved in DCM (500 ml), cooled to 0° C., then treated with K₂CO₃ (139 g, 999 mmol), and 650 ml of 2 M dimethyl amine in THF. The reaction was stirred at 0° C. for 1 hour and filtered. The resulting solid was washed with DCM. The combined filtrates were washed with water, dried over Na₂SO₄, filtered, and concentrated to provide N,N-dimethyl-2-[5-(methyloxy)-2,3-dihydro-1H-indol-1-yl]-2-oxoethanamine as a grey solid (111 g, 95%). ESIMS (M+H)+=235.

Step B/Intermediate B100: N,N-dimethyl-2-[5-(methyloxy)-6-nitro-2,3-dihydro-1H-indol-1-yl]-2-oxoethanamine (First Alternate Synthesis)

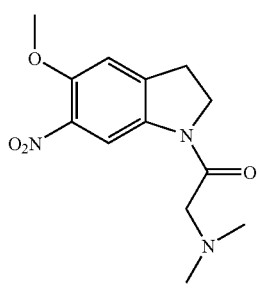

To a solution of NaNO₃ (43.9 g, 516 mmol) in TFA (250 mL) was added N,N-dimethyl-2-[5-(methyloxy)-2,3-dihydro-1H-indol-1-yl]-2-oxoethanamine (11.6 g, 49 mmol) in TFA (50 mL) at 0° C. and the mixture was stirred at 0° C. for 1.5 h. The reaction mixture was poured into ice-water (1000 mL), the TFA and some water was removed by reduced pressure (the volume was reduced to 400 mL), the reaction mixture was adjusted to pH=11 by addition of 2N NaOH (the mixture became cloudy), and the aqueous layer was extracted with CHCl₃ (2×300 mL), and washed with water. The organic layer was separated, dried over with Na₂SO₄, and the solvents were removed under reduced pressure to yield N,N-dimethyl-2-[5-(methyloxy)-6-nitro-2,3-dihydro-1H-indol-1-yl]-2-oxoethanamine (130 g, 99%). 1H NMR (400 MHz, DMSO-d₆) δ ppm 2.24 (s, 6 H), 3.15-3.24 (m, 4 H), 3.86 (s, 3 H), 4.18 (t, J=8.5 Hz, 2 H), 7.31 (s, 1 H), 8.45 (s, 1 H).

This protocol could be repeated to generate larger quantities of N,N-dimethyl-2-[5-(methyloxy)-6-nitro-2,3-dihydro-1H-indol-1-yl]-2-oxoethanamine which could be carried forward in the synthetic sequence as blended batches.

Step C/Intermediate B95: 1-[(dimethylamino)acetyl]-5-(methyloxy)-2,3-dihydro-1H-indol-6-amine (First Alternate Synthesis)

A suspension of N,N-dimethyl-2-[5-(methyloxy)-6-nitro-2,3-dihydro-1 H-indol-1-yl]-2-oxoethanamine (26.6 g, 95 mmol), iron(III)chloride (3.09 g, 19.05 mmol), activated carbon (25 g, 95 mmol), and hydrazine hydrate (37.4 mL, 762 mmol) in methanol (500 mL) was warmed to 65° C. and maintained overnight. The reaction was filtered through celite while still warm and all methanol was removed under reduced pressure. The solids were partitioned between ethyl acetate (ca 1 L) and saturated sodium chloride (ca 1 L) and the aqueous layer was washed twice with ethyl acetate (ca 500 mL). The combined organic layers were dried over sodium sulfate, taken to a residue under reduced pressure, and the derived solids triturated with hexanes/diether ether and filtered to afford 1-[(dimethylamino)acetyl]-5-(methyloxy)-2,3-dihydro-1H-indol-6-amine (16.46 g, 69.3% yield) as an off-white solid: NMR: ¹H NMR (400 MHz, DMSO-d₆) δ ppm 2.23 (s, 6 H), 2.95 (t, J=8.25 Hz, 2 H), 3.11 (s, 2H), 3.69 (s, 3 H), 4.07 (s, 2 H), 4.61 (s, 2 H), 6.68 (s, 1 H), 7.53 (s, 1 H).

Intermediate B95 (Second Alternative Synthesis): 1-[(dimethylamino)acetyl]-5-(methyloxy)-2,3-dihydro-1H-indol-6-amine

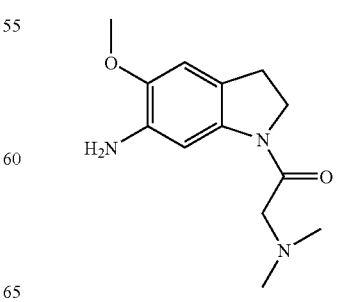

Step A/Intermediate B96 (Second Alternative Synthesis): 5-(methyloxy)-2,3-dihydro-1H-indole

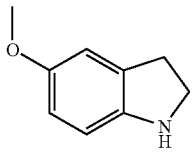

At room temperature, to a solution of 5-(methyloxy)-1H-indole (12 g, 81.5 mmol, 1.0 eq) in acetic acid (150 mL) was added sodium cyanoborohydride (10.25 g, 163 mmol, 2.0 eq) in small portions, and the mixture was stirred overnight. The solvent was evaporated under reduced pressure and the residue was dissolved in ethyl acetate. The organic layer was washed with saturated aqueous sodium hydrogencarbonate solution and brine, and dried over $Na_2SO_4$. The solvent was removed under reduced pressure to give 5-(methyloxy)-2,3-dihydro-1H-indole (8.91 g, 45% yield) $^1$H NMR ($CDCl_3$, 300 MHz) δ 6.76 (s, 1H), 6.60 (s, 2H), 3.54 (t, 2H), 3.01 (t, 2H).

Step B/Intermediate B97 (Second Alternative Synthesis): 1-acetyl-5-(methyloxy)-2,3-dihydro-1H-indole

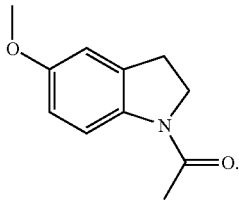

To a solution 5-(methyloxy)-2,3-dihydro-1H-indole (8.9 g, 59.8 mmol, 1.0 eq) in acetic acid (120 mL) was added dropwise acetic anhydride (6.1 g, 59.8 mmol, 1.0 eq). The mixture was heated at 60° C. for 15 minutes. The reaction was quenched by pouring into water (100 mL). After cooling, a grey precipitate was formed, the precipitate was filtered by a Buchner funnel and rinsed with water to afford 1-acetyl-5-(methyloxy)-2,3-dihydro-1H-indole (10.5 g, 91% yield). $^1$H-NMR ($CDCl_3$, 300 MHz) δ 8.13 (d, J=6.3 Hz, 1 H), 6.74-6.71 (m, 2 H), 4.05 (t, 2 H), 3.78 (s, 3 H), 3.17 (t, 2H), 2.21 (s, 3 H).

Step C/Intermediate B98 (Second Alternative Synthesis): 1-acetyl-5-(methyloxy)-6-nitro-2,3-dihydro-1H-indole

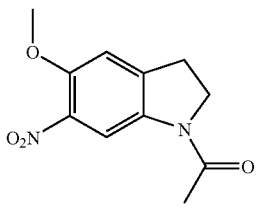

To a solution of 5-(methyloxy)-2,3-dihydro-1H-indole (10.4 g, 54.4 mmol, 1.0 eq) in acetic anhydride (150 mL) was added dropwise fuming nitric acid (3.43 g, 54.4 mmol, 1.0 eq) at 0° C., then the mixture was stirred for 1 hour at r. t. After stirring for 1 hour the yellow precipitate which formed was filtered via Buchner funnel and washed with water and dried in vacuo to give 1-acetyl-5-(methyloxy)-6-nitro-2,3-dihydro-1H-indole as a yellow solid (8.0 g, 62% yield). $^1$H-NMR ($CDCl_3$, 300 MHz) δ 8.43 (s, 1H), 7.31 (s, 1H), 4.13 (t, 2H), 3.87 (s, 3H), 3.22 (t, 2H), 2.14 (s, 3H).

Step D/Intermediate B99 (Second Alternative Synthesis): 5-(methyloxy)-6-nitro-2,3-dihydro-1H-indole

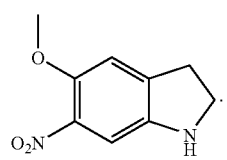

To the solution of conc. HCl (20 mL) in methanol (40 mL) was added 1-acetyl-5-(methyloxy)-6-nitro-2,3-dihydro-1H-indole (7.8 g, 33 mmol) and the resulting mixture was refluxed for 4 hours. After cooling, the solvent was removed in vacuo, the residue was neutralized with saturated aqueous sodium hydrogencarbonate solution, and a brown precipitate formed. The precipitate was filtered via Buchner funnel, washed with water, and dried under reduced pressure to give 5-(methyloxy)-6-nitro-2,3-dihydro-1H-indole as a brown solid (6.1 g, 94% yield). $^1$H-NMR (DMSO, 300 MHz) δ 7.11 (s, 1H), 6.87 (s, 1H), 5.59 (brs, 1H), 3.78 (s, 3H), 3.43 (t, 2H), 2.97 (t, 2H).

Step E/Intermediate B100 (Second Alternative Synthesis): N,N-dimethyl-2-[5-(methyloxy)-6-nitro-2,3-dihydro-1H-indol-1-yl]-2-oxoethanamine

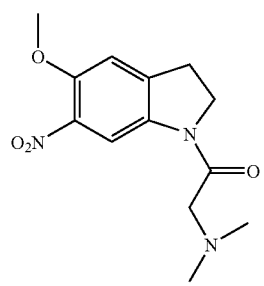

To a solution of 5-(methyloxy)-6-nitro-2,3-dihydro-1H-indole (1.00 g, 5.2 mmol) in dichloromethane (50 mL) was added polymer supported diisopropylethylamine (Argonaut Technologies Inc., 4.0 g, ca 15 mmol base) and bromoacetylchloride (0.650 mL, 7.82 mmol). The resulting solution was stirred for three hours and filtered through a plug of celite. Dichloromethane was removed under reduced pressure and the residue was dissolved in tetrahydrofuran (50 mL). To the solution was added dimethylamine as a 2.0M solution in tetrahydrofuran (60 mmol, Aldrich) and the resulting solution was stirred overnight. The next morning the volatiles were removed under reduced pressure and the residue was purified via chromatography on SiO$_2$ (0-10% MeOH/CH$_2$CL$_2$ with 0.2% NH$_3$) to afford N,N-dimethyl-2-[5-(methyloxy)-6-nitro-2,3-dihydro-1H-indol-1-yl]-2-oxoethanamine as a yellow solid (1.20 g, 4.33 mmol, 84% yield). 1H NMR (400 MHz, CDCl$_3$) δ ppm 2.59 (s, 6 H), 3.24 (t, J=8.24 Hz, 2 H), 3.52 (s, 2 H), 3.89 (s, 3 H), 4.19 (t, J=8.52 Hz, 2 H), 6.89 (s, 1 H), 8.60 (s, 1 H).

Step F/Intermediate B95 (Second Alternative Synthesis): 1-[(dimethylamino)acetyl]-5-(methyloxy)-2,3-dihydro-1H-indol-6-amine To a solution of N,N-dimethyl-2-[5-(methyloxy)-6-nitro-2,3-dihydro-1H-indol-1-yl]-2-oxoethanamine (1.0 g, 3.58 mmol) in methanol (30 mL) was added activated carbon (1.0 g), iron (III) chloride (0.120 mg, 0.2 equiv.) and hydrazine hydrate (0.800 mL, 25 mmol, 7.0 equiv.). The resulting slurry was warmed to 60° C. and maintained overnight. The next morning the reaction was filtered, taken to a residue under reduced pressure, and partitioned between ethyl acetate and brine. The organic layer was dried over sodium sulfate. Volatiles were removed and the derived 1-[(dimethylamino)acetyl]-5-(methyloxy)-2,3-dihydro-1H-indol-6-amine was isolated as a white solid of sufficient purity for use in subsequent transformations (0.550 g, 2.20 mmol, 62% yield). 1H NMR (400 MHz, DMSO-d$_6$) δ ppm 2.23 (s, 6 H), 2.95 (t, J=8.43 Hz, 2 H), 3.11 (s, 2 H), 3.68 (s, 3 H), 4.05 (t, J=8.25 Hz, 2 H), 4.61 (s, 2 H), 6.68 (s, 1 H), 7.53 (s, 1 H).

Intermediate B101: 5-methyl-2-(methyloxy)-4-{4-[2-(methylsulfonyl)ethyl]-1-piperazinyl}aniline

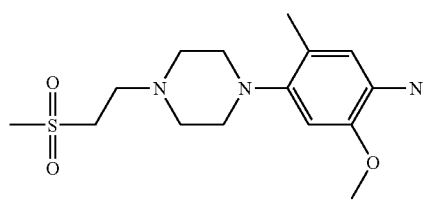

Step A/Intermediate B102:
1-bromo-2-methyl-5-(methyloxy)-4-nitrobenzene

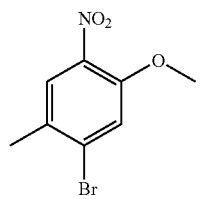

To 2-methyl-5-(methyloxy)-4-nitroaniline (18.3 g, 100.45 mmol) in 200 mL of acetonitrile was added t-butylnitrite (23.8 g, 231 mmol). To the stirring solution was added copper (II) bromide (53.85 g, 241 mmol) over 30 minutes. The mixture was stirred for 3 hour. The acetonitrile was rotovaped down. The crude product was partitioned between ether and 1N HCl (aq). The ether layer was washed several times with 1N HCl (aq), dried (Na$_2$SO$_4$), filtered, and rotovaped down. The crude product was taken up as a suspension in 1:10 ether/hexanes and filtered. The solids were washed with 1:10 ether/hexanes, and dried under vacuum to give 1-bromo-2-methyl-5-(methyloxy)-4-nitrobenzene (19 g, 77.22 mmol, 77%) as a yellow solid. $^1$H NMR (400 MHz, CDCl$_3$) δ ppm 7.75 (s, 1 H), 7.26 (s, 1 H), 3.93 (s, 3 H), 2.37 (s, 3 H).

Step B/Intermediate B103: 1,1-dimethylethyl 4-[2-methyl-5-(methyloxy)-4-nitrophenyl]-1-piperazinecarboxylate

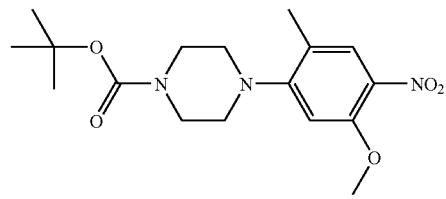

to a stirred solution of 1-bromo-2-methyl-5-(methyloxy)-4-nitrobenzene (9 g, 36.6 mmol) in 180 mL of Dioxane was added Pd$_2$(dba)$_2$ (2.14 g, 2.34 mmol), XANTPHOS (2.12 g, 3.65 mmol), cesuim carbonte (50 g, 153.6 mmol) and 1,1-dimethylethyl 1-piperazinecarboxylate (13.6 g, 73.15 mmol). The resulting slurry was warmed to 60° C. for 24 hours. The dioxane was removed under reduced pressure and the crude mixture was taken up in ether and filtered to remove cesium carbonate. The ether was, washed with water, dried (Na$_2$SO$_4$), filtered, and rotovaped down. The crude product was purified by flash chromatography to give 1,1-dimethylethyl 4-[2-methyl-5-(methyloxy)-4-nitrophenyl]-1-piperazinecarboxylate (4.83 g, 13.75 mmol, 38%). $^1$H NMR (400 MHz, CDCl$_3$) δ ppm 7.81 (s, 1 H), 6.56 (s, 1 H), 3.92 (s, 3 H), 3.52-3.63 (m, 4 H), 2.88-2.99 (m, 4 H), 2.25 (s, 3 H), 1.47 (s, 9 H).

Step C/Intermediate B104:
1-[2-methyl-5-(methyloxy)-4-nitrophenyl]piperazine

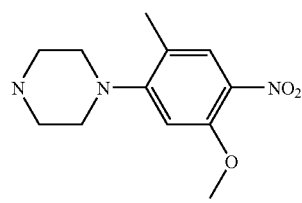

To a stirred solution of 1,1-dimethylethyl 4-[2-methyl-5-(methyloxy)-4-nitrophenyl]-1-piperazinecarboxylate (4.8 g, 13.67 mmol) in 80 mL of dichloromethane was added trifluoroacetic acid (~5.5 mL). The mixture stirred at room temperature for 24 hours. The solvent was rotovaped down. The crude product was taken up in 50 mL of methanol and neutralized with 0.5 N sodium methoxide. 12 g of Silica gel was added and the solvent was rotovaped down. The crude product was purified by flash chromatography to give 1-[2-methyl-5-(methyloxy)-4-nitrophenyl]piperazine (3.43 g, 13.53 mmol, 98%). $^1$H NMR (400 MHz, DMSO-d$_6$) δ ppm 7.75 (s, 1 H), 6.69 (s, 1 H), 3.88 (s, 3 H), 3.08-3.18 (m, 8 H), 2.15-2.21 (m, 3 H).

Step D/Intermediate B105: 1-[2-methyl-5-(methyloxy)-4-nitrophenyl]-4-[2-(methylsulfonyl)ethyl]piperazine

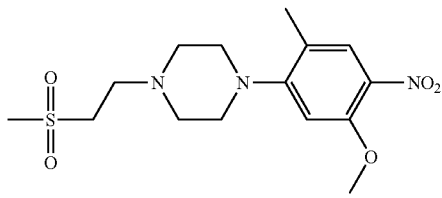

To 1-[2-methyl-5-(methyloxy)-4-nitrophenyl]piperazine (0.300 g, 1.2 mmol) in 10 mL of dioxane was added, ethenyl methyl sulfone (0.32 g, 3 mmol). The mixture was heated to 120° C. 1 hour. The solvent was rotovaped down and the crude product was purified by flash chromatography, followed by a wash of the solids with 30% ether in hexanes to give 1-[2-methyl-5-(methyloxy)-4-nitrophenyl]-4-[2-(methylsulfonyl)ethyl]piperazine (0.257 g, 0.72 mmol, 60%). $^1$H NMR (400 MHz, CDCl$_3$) δ ppm 7.80 (s, 1 H), 6.54 (s, 1 H), 3.93 (s, 3 H), 3.18-3.30 (m, 2 H), 2.99-3.10 (m, 9 H), 2.71-2.82 (m, 4 H), 2.23 (s, 3 H).

Step E/Intermediate B101: 5-methyl-2-(methyloxy)-4-{4-[2-(methylsulfonyl)ethyl]-1-piperazinyl}aniline 1-[2-methyl-5-(methyloxy)-4-nitrophenyl]-4-[2-(methylsulfonyl)ethyl]piperazine (0.257 g, 0.72 mmol) was placed in a 40 mL high vial and dissolved in 10 mL of 1:1 ethyl acetate/methanol. 5 wt % Platinum(sulfided)/C (0.165 g, 0.043 mmol) was added followed quickly by a screw cap septum. The vial was evacuated and filled with nitrogen six times to remove any oxygen. The vial was then pressurized with hydrogen (balloon) and the solution stirred overnight. The next morning the vessel was evacuated and filled with nitrogen six times to remove any hydrogen. The solution was filtered through celite and evaporated to afford 5-methyl-2-(methyloxy)-4-{4-[2-(methylsulfonyl)ethyl]-1-piperazinyl}aniline (0.194 g, 0.59mmol, 82%). $^1$ H NMR (400 MHz, CHLOROFORM-δ ppm 6.54 (s, 2 H), 3.80 (s, 3 H), 3.30-3.37 (m, 2H), 3.07 (s, 3 H), 2.91-2.98 (m, 6 H), 2.82-2.90 (m, 4 H), 2.15 (s, 3 H).

Intermediate B106: 3-methyl-4-[4-(1-methylethyl)-1-piperazinyl]-2-(methyloxy)aniline

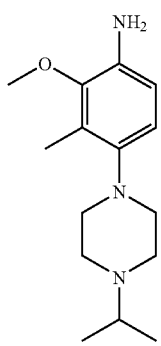

Step A/Intermediate B107: 2-chloro-4-fluoro-3-methyl-1-nitrobenzene

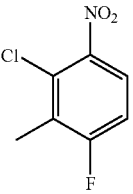

To a ice-cooled solution of 1-chloro-3-fluoro-2-methylbenzene (1 mL, 8.24 mmol) in sulfuric acid (18 M, 10 mL) was added K$_2$NO$_3$ (0.87 g, 8.65 mmol) as a solution in sulfuric acid(18 M, 10 mL). The reaction mixture was stirred at 0° C. for 2 h. The reaction mixture was poured into ice, and extracted with ethyl acetate. The combined organic layers were dried over Na$_2$SO$_4$, filtered, taken to a residue under reduced pressure, and purified via chromatography on SiO$_2$ to afford 2-chloro-4-fluoro-3-methyl-1-nitrobenzene (1.4 g crude) of sufficient purity for use in the next transformation.

Step B/Intermediate B108: 1-(3-chloro-2-methyl-4-nitrophenyl)-4-(1-methylethyl)piperazine

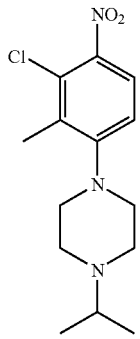

To the solution of 2-chloro-4-fluoro-3-methyl-1-nitrobenzene (12.5 g, 64.8 mmol, 1.2 equiv.) and isopropylpiperazine (10.8 g, 53.98 mmol, 1 equiv.) in 90 mL of anhydrous DMSO was added powdered K$_2$CO$_3$ (37 g, 269 mmol, 5 equiv.). The mixture was stirred at 40-50° C. overnight before it was poured into 200 mL of ice-water. The precipitates were collected and purified via chromatography on SiO$_2$ to afford 1-(3-chloro-2-methyl-4-nitrophenyl)-4-(1-methylethyl)piperazine as a yellow solid (12.7 g, 79% Yield). 1H NMR (400 MHz, CDCl$_3$) δ ppm 0.95-1.05 (d, J=6.53 Hz, 6H), 2.31 (s, 3H), 2.60-2.72 (m, 5H), 2.89-2.95 (m, 4H), 6.87 (d, J=8 Hz, 1H), 7.62 (d, J=8 Hz, 1H).

Step C/Intermediate B109: 1-(1-methylethyl)-4-[2-methyl-3-(methyloxy)-4-nitrophenyl]piperazine

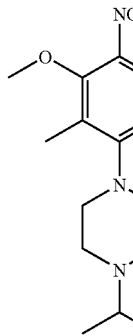

To a solution of 1-(3-chloro-2-methyl-4-nitrophenyl)-4-(1-methylethyl)piperazine (12.6 g, 42.4 mmol, 1 equiv) in 120 mL of DMF was added sodium methoxide (1.12 g, 21 mmol, 0.5 equiv) at 0° C. After stirring for 1 hour at room temperature, additional sodium methoxide was added (4.61 g, 85 mmol, 2 equiv, ×2) at 0° C. The mixture was warmed to 35° C. overnight. The next morning, the mixture was diluted with water, dried, and taken to a residue under reduced pressure. Recrystallization from ethyl acetate afforded 1-(1-methylethyl)-4-[2-methyl-3-(methyloxy)-4-nitrophenyl]piperazine (10.8 g, yield 87.1%) of sufficient purity for use in subsequent chemical transformations. 1H NMR (400 MHz, CDCl$_3$) δ ppm 1.12 (d, J=6.53 Hz, 6H), 2.27 (s, 3H), 2.68-2.74 (m, 4H), 2.98-3.09 (m, 4H), 3.89 (s, 3H), 6.78 (d, J=9.2 Hz, 1H), 7.74 (d, J=9.2 Hz, 1H).

Step D/Intermediate B106: 3-methyl-4-[4-(1-methylethyl)-1-piperazinyl]-2-(methyloxy)aniline A mixture of 1-(1-methylethyl)-4-[2-methyl-3-(methyloxy)-4-nitrophenyl]piperazine (5.5 g, 18.7 mmol) and Raney Ni (2 g) in 200 mL of MeOH was stirred under an atmosphere of H$_2$ overnight. The mixture was filtered and taken to a residue under reduced pressure to afford 3-methyl-4-[4-(1-methylethyl)-1-piperazinyl]-2-(methyloxy)aniline as a white solid (4.50 g, 91% yield). $^1$H NMR (400 MHz, CDCl$_3$) δ ppm 1.10 (d, J=6.4 Hz, 6H), 2.24 (s, 3H), 2.73-2.67 (m, 5H), 2.89 (m, 4H), 3.63 (s, 2H), 3.73 (s, 3H), 6.58 (d, J=8.4 Hz, 1H), 6.71 (d, J=8.4 Hz, 1H).

Intermediate B110: 5-methyl-4-[4-(1-methylethyl)-1-piperazinyl]-2-(methyloxy)aniline

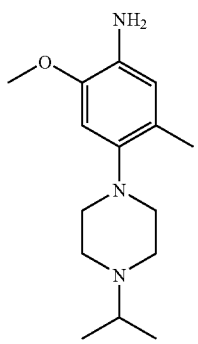

Step A/Intermediate B111:
5-fluoro-4-methyl-2-nitrophenol

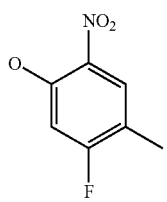

3-fluoro-4-methylphenol (3.66 g, 29.0 mmol) was dissolved in dichloroethane (32 mL) and tetrabutylammonium bromide (0.935 g, 2.90 mmol) was added. Nitric acid 70% (3.7 mL, 58 mmol) was diluted with water (33 mL) to make a 7% nitric acid solution. This solution was added to the reaction mixture which was then stirred at room temperature for 4 h at which time the reaction was judged complete by TLC. The reaction was poured into water and extracted with dichloromethane (3×). The combined organic layers were dried over magnesium sulfate, filtered and concentrated in vacuo. The resulting residue was absorbed onto silica gel and purified by chromatography on SiO$_2$ to give 5-fluoro-4-methyl-2-nitrophenol as a yellow solid (2.83 g, 57%). 1H NMR (400 MHz, DMSO-d$_6$) δ ppm 11.10 (s, 1 H), 7.89 (d, J=8.1 Hz, 1 H), 6.85 (d, J=11.0 Hz, 1 H), 2.13 (s, 3 H).

Step B/Intermediate B112:
1-fluoro-2-methyl-5-(methyloxy)-4-nitrobenzene

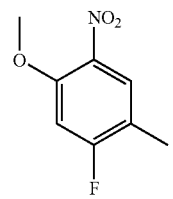

5-fluoro-4-methyl-2-nitrophenol (2.83 g, 16.5 mmol) was dissolved in N,N-dimethylformamide (25 mL). Potassium carbonate (3.4 g, 25 mmol) and iodomethane (1.2 mL, 20 mmol) were added and the mixture was stirred at room temperature overnight. The mixture was then poured into water and stirred until solids crashed out. The solids were filtered and air dried to give 1-fluoro-2-methyl-5-(methyloxy)-4-nitrobenzene without further purification (2.76 g, 90%). 1H NMR (400 MHz, DMSO-d$_6$) δ ppm 7.92 (d, J=8.1 Hz, 1 H), 7.25 (d, J=11.7 Hz, 1 H), 3.89 (s, 3H), 2.19 (d, J=1.5 Hz, 3 H).

Step C/Intermediate B113: 1-(1-methylethyl)-4-[2-methyl-5-(methyloxy)-4-nitrophenyl]piperazine

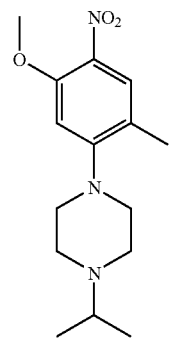

To a solution of 1-fluoro-2-methyl-5-(methyloxy)-4-nitrobenzene (1.3 g, 7.03 mmol) in dimethylsulfoxide was added potassium carbonate (1.9 g, 14.0 mmol) and isopropylpiperazine (2.0 mL, 14 mmol). The resulting suspension was warmed at 70° C. for 12 hours, poured into water, and extracted with diethyl ether. The ether layers were washed with aqueous saturated sodium chloride, dried over sodium sulfate, taken to a residue under reduced pressure, and purified by chromatography on SiO$_2$ to afford 1-(1-methylethyl)-4-[2-methyl-5-(methyloxy)-4-nitrophenyl]piperazine (1.78 g, 86% yield) as a yellow solid. 1H NMR (400 MHz, CDCl$_3$)

δ ppm. 1.11 (d, J=6.60 Hz, 6 H), 2.24 (s, 3 H), 2.72 (s, 4 H), 2.79 (s, 1 H), 3.06 (s, 4 H), 3.93 (s, 3 H), 6.57 (s, 1 H), 7.81 (s, 1 H).

Step D/Intermediate B110: 5-methyl-4-[4-(1-methylethyl)-1-piperazinyl]-2-(methyloxy)aniline To a solution of 1-(1-methylethyl)-4-[2-methyl-5-(methyloxy)-4-nitrophenyl]piperazine (1.78 g, 6.08 mmol) in methanol (75 mL) was added hydrazine (1.33 mL, 7.0 mmol), iron (III) chloride (0.200 g, 1.22 mmol) and activated charcoal (2 g). The resulting slurry was warmed to 60° C. and maintained overnight. The next morning the slurry was filtered and concentrated to a residue. The residue was partitioned between ethyl acetate and sat. NaCl(aq). The organic layer was washed twice with saturated brine, dried over sodium sulfate, and taken to a residue under reduced pressure to afford 5-methyl-4-[4-(1-methylethyl)-1-piperazinyl]-2-(methyloxy)aniline (1.50 g, 94% yield) of sufficient purity for use directly in the next step. 1H NMR (400 MHz, DMSO-$d_6$) δ ppm 0.98 (d, J=6.60 Hz, 6 H), 2.04 (s, 3 H), 2.52 (s, 4 H), 2.64 (dt, J=12.92, 6.55 Hz, 1 H), 2.68-2.72 (m, 4 H), 3.69 (s, 3 H), 4.28 (s, 2 H), 6.41 (s, 1 H), 6.55 (s, 1 H).

Intermediate B114: 2-(methyloxy)-4-{1'-[2-(methylsulfonyl)ethyl]-4,4'-bipiperidin-1-yl}aniline

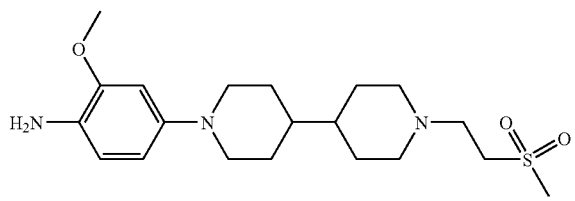

Step A/Intermediate B115: 1,1-dimethylethyl 4,4'-bipiperidine-1-carboxylate

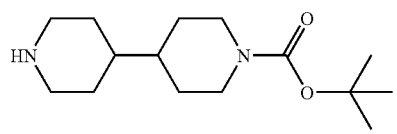

To 4,4'-bipiperidine (5.48 g, 32.6 mmol) in tetrahydrofuran (160 mL) and chloroform (160 mL) was added BOC-ON (4.01 g, 16.2 mmol) in tetrahydrofuran (90 mL) dropwise over an 8 hour period. The reaction was then concentrated and purified by chromatograpy on $SiO_2$. The residue was taken up in 1M $KHSO_4$ (250 mL) and washed with diethyl ether (three times). Potassium carbonate (38.0 g, 275 mmol) was added to the aqueous layer which was subsequently extracted with chloroform (three times), dried ($MgSO_4$), and concentrated to provide 1,1-dimethylethyl 4,4'-bipiperidine-1-carboxylate (1.98 g, 7.40 mmol, 45%). 1H NMR (400 MHz, $CDCl_3$) δ ppm 1.06-1.18 (m, 6 H), 1.42 (s, 9 H), 1.58-1.69 (m, 6 H), 2.50-2.61 (m, 4 H), 3.06 (d, J=12.1 Hz, 2 H), 4.08 (br s, 1 H).

Step B/Intermediate B116: 1,1-dimethylethyl 1'-[3-(methyloxy)-4-nitrophenyl]-4,4'-bipiperidine-1-carboxylate

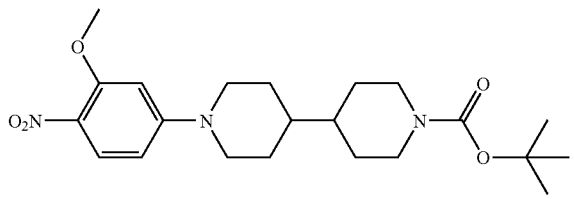

1,1-dimethylethyl 1'-[3-(methyloxy)-4-nitrophenyl]-4,4'-bipiperidine-1-carboxylate (2.32 g, 5.50 mmol, 75%) was prepared in an analogous manner to that of 1-(3-chloro-2-methyl-4-nitrophenyl)-4-(1-methylethyl)piperazine (Intermediate B108). 1H NMR (400 MHz, DMSO-$d_6$) δ ppm 0.92-1.03 (m, 2 H), 1.10-1.21 (m, 3 H), 1.27-1.39 (m, 10 H), 1.60 (d, J=12.3 Hz, 2 H), 1.70 (d, J=11.2 Hz, 2 H), 2.58 (bs, 2 H), 2.88 (t, J=12.0 Hz, 2H), 3.32, (s, 1H), 3.85 (s, 3 H), 3.91 (d, J=12.5 Hz 2 H), 4.03 (d, J=13.4 Hz, 2 H), 6.43 (d, J=2.4 Hz, 1 H), 6.53 (dd, J=9.4, 2.3 Hz 1 H), 7.82 (d, J=9.5 Hz, 1 H).

Step C/Intermediate B117: 1-[3-(methyloxy)-4-nitrophenyl]-4,4'-bipiperidine

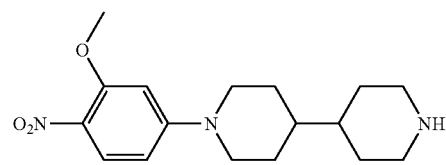

1-[3-(methyloxy)-4-nitrophenyl]-4,4'-bipiperidine (1.63 g, 5.10 mmol, 100%) was prepared in an analogous manner to that of 1-[3-(methyloxy)-4-nitrophenyl]piperazine (Intermediate B50). 1H NMR (400 MHz, DMSO-$d_6$) δ ppm 1.03-1.07 (m, 2 H), 1.09-1.19 (m, 3 H), 1.31 (m, 1 H), 1.59 (d, J=12.1 Hz, 2 H), 1.73 (d, J=12.1 Hz, 2.42 (t, J=11.9 Hz, 2 H), 2.82-2.91 (m, 2 H), 2.95 (d, J=12.1 Hz, 2 H), 3.36 (bs, 1H), 3.88 (s, 3 H), 4.06 (d, J=13.2 Hz, 2 H), 6.46 (d, J=2.6 Hz, 1 H), 6.55 (dd, J=9.5, 2.6 Hz, 1H), 7.85 (d, J=9.5 Hz, 1 H).

Step D/Intermediate B118: 1-[3-(methyloxy)-4-nitrophenyl]-1'-[2-(methylsulfonyl)ethyl]-4,4'-bipiperidine

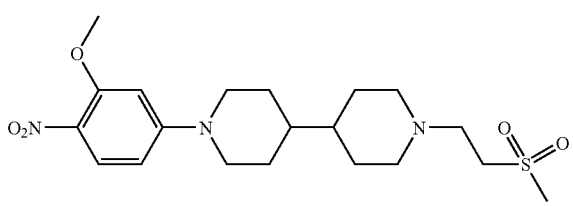

1-[3-(methyloxy)-4-nitrophenyl]-1'-[2-(methylsulfonyl)ethyl]-4,4'-bipiperidine (0.602 g, 1.41 mmol, 83%) was prepared in an analogous manner to that of 1-[2-methyl-5-(methyloxy)-4-nitrophenyl]-4-[2-(methylsulfonyl)ethyl]

piperazine (Intermediate 105). 1H NMR (400 MHz, DMSO-d$_6$) δ ppm 0.95-1.04 (m, 1 H), 1.08-1.19 (m, 4 H), 1.25-1.35 (m, 1 H), 1.60 (d, J=11.2 Hz, 2 H), 1.71 (d, J=10.8 Hz, 2 H), 1.82 (t, J=11.5 Hz, 2 H), 2.60 (t, J=6.8 Hz, 2 H), 2.79-2.89 (m, 4 H), 2.96 (s, 3 H), 3.21 (t, J=6.8 Hz, 2 H), 3.85 (s, 3 H), 4.02 (d, J=13.2 Hz, 2 H), 6.43 (d, J=2.4 Hz), 1H), 6.52 (dd, J=9.5, 2.4 Hz, 1 H) 7.82 (d, J=9.3 Hz, 1 H).

Step E/Intermediate B114: 2-(methyloxy)-4-{1'-[2-(methylsulfonyl)ethyl]-4,4'-bipiperidin-1-yl}aniline 2-(methyloxy)-4-{1'-[2-(methylsulfonyl)ethyl]-4,4'-bipiperidin-1-yl}aniline (0.457 g, 1.16 mmol, 78%) was prepared in an analogous manner to that of 4-[(3S)-3-methyl-4-morpholinyl]-2-(methyloxy)aniline (Intermediate B38). 1H NMR (400 MHz, DMSO-d$_6$) δ ppm 1.00-1.04 (m, 1 H), 1.06-1.13 (m, 2 H), 1.15-1.25 (m, 3 H), 1.65 (m, 4 H), 1.83 (t, J=11.1 Hz, 2 H), 2.33-2.42 (m, 2 H), 2.61 (t, J=6.7 Hz, 2 H), 2.84-2.90 (m, 2 H), 2.97 (s, 3 H), 3.21 (t, J=6.8 Hz, 2 H), 3.36 (d, J=11.4 Hz, 2 H), 3.68 (s, 3 H), 4.14 (bs, 2 H), 6.23 (dd, J=8.3, 2.3 Hz, 1 H), 6.41-6.46 (m, 2 H).

Intermediate B119: 2-(methyloxy)-4-{4-[4-(methylsulfonyl)-1-piperazinyl]-1-piperidinyl}aniline

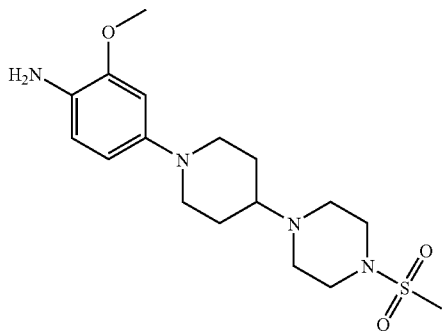

Step A/Intermediate B120: 1-{1-[3-(methyloxy)-4-nitrophenyl]-4-piperidinyl}piperazine

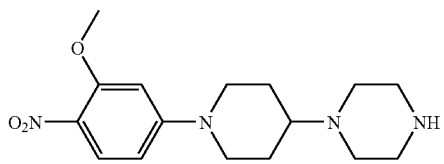

To a solution of 1-[4-amino-3-(methyloxy)phenyl]-4-piperidinone (Intermediate B40, 17.35 g, 69.3 mmol, from multiple batches) in toluene (600 mL) was added sequentially, triethylamine (25 mL, 179.4 mmol), 1-Boc-piperazine (25.36 g, 136.2 mmol), and acetic acid (6.0 mL, 105.9 mmol). The solution was stirred at room temperature for 30 minutes. Sodium triacetoxyborohydride (12.2 g, 57.6 mmol) was added in one portion and stirred for 30 minutes. This was repeated twice for the complete addition of sodium triacetoxyborohydride (24.4 g, 115.1 mmol). The reaction was stirred for three hours and then quenched with a saturated solution of sodium bicarbonate (600 mL) and stirred 2 days. The solution was separated and extracted with dichloromethane, dried with magnesium sulfate, filtered and concentrated. The resultant solid, 1,1-dimethylethyl 4-{1-[3-(methyloxy)-4-nitrophenyl]-4-piperidinyl}-1-piperazinecarboxylate, was dissolved in dichloromethane (600 mL) and cooled to 0° C. Trifluoroacetic acid (110 mL) was added; the reaction was warmed to room temperature and stirred overnight. The reaction was cooled to 0° C. and quenched with 6N sodium hydroxide (320 mL) dropwise. The solution was separated and extracted with dichloromethane (x3), dried with magnesium sulfate, filtered and concentrated. Purification by flash chromatography provided 1-{1-[3-(methyloxy)-4-nitrophenyl]-4-piperidinyl}piperazine(18.03 g, 56.10 mmol, 81%) as a yellow solid. 1H NMR (400 MHz, DMSO-d$_6$) δ ppm 1.41 (qd, J=12.0, 3.7 Hz, 2 H) 1.77-1.84 (m, 2 H) 2.38-2.47 (m, 5 H) 2.67-2.73 (m, 4 H) 2.88-2.98 (m, 2H), 3.32 (br. s., 1 H) 3.88 (s, 3 H) 4.03 (d, J=12.8 Hz, 2 H) 6.48 (d, J=2.6 Hz, 1 H) 6.56 (dd, J=9.5, 2.6 Hz, 1 H) 7.85 (d, J=9.2 Hz, 1 H).

Step B/Intermediate B121: 1-{1-[3-(methyloxy)-4-nitrophenyl]-4-piperidinyl}-4-(methylsulfonyl)piperazine

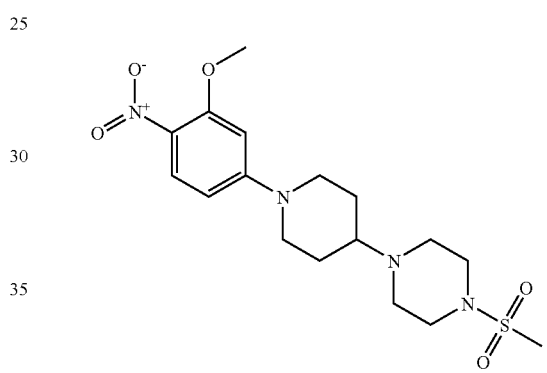

To a suspension of 1-{1-[3-(methyloxy)-4-nitrophenyl]-4-piperidinyl}piperazine (5.0 g, 11.6 mmol), methane sulfonyl chloride (1.4 mL, 17.5 mmol) and dichloromethane (200 mL) was added triethylamine (8.1 mL, 58.2 mmol). The reaction was stirred at room temperature and monitored by TLC. After complete consumption of the starting material the clear yellow solution was concentrated onto silica gel and purified by chromatography to afford 1-{1-[3-(methyloxy)-4-nitrophenyl]-4-piperidinyl}-4-(methylsulfonyl)piperazine as a yellow solid (3.54 g, 76%). 1H NMR (400 MHz, DMSO-d6) δ 7.85 (d, J=9.5 Hz, 1H), 6.57 (dd, J=9.2, 2.6 Hz, 1H), 6.48 (d, J=2.6 Hz, 1H), 4.09-4.00 (m, 2H), 3.89 (s, 3H), 3.10-3.03 (m, 4H), 2.99-2.90 (m, 2H), 2.84 (s, 3H), 2.61-2.52 (m, 5H), 1.85-1.77 (m, 2H), 1.50-1.37 (m, 2H).

Step C/Intermediate B119: 2-(methyloxy)-4-{4-[4-(methylsulfonyl)-1-piperazinyl]-1-piperidinyl}aniline NaBH$_4$ (1.18 g, 31.1 mmol) was added carefully in portions (exothermic) to a suspension of 1-{1-[3-(methyloxy)-4-nitrophenyl]-4-piperidinyl}-4-(methylsulfonyl)piperazine (3.54 g, 8.9 mmol), NiCL$_2$.6H$_2$O (1.06 g, 4.4 mmol), MeOH (100 mL) and THF (50 mL) at 0° C. The ice bath was removed and the reaction mixture was warmed to room temperature. The reaction mixture was concentrated onto silica gel and flash chromatography afforded 2-(methyloxy)-4-{4-[4-(methylsulfonyl)-1-piperazinyl]-1-piperidinyl}aniline (2.93 g, 90%) as a colourless solid. 1H NMR (400 MHz, DMSO-d6) δ 6.49-6.46 (m, 2H), 6.27 (dd, J=8.5, 2.6 Hz, 1H), 4.18 (bs, 2H), 3.71 (s, 3H), 3.44-3.38 (m, 2H), 3.11-3.04 (m, 4H), 2.84 (s, 3H), 2.61-2.54 (m, 6H complicated by DMSO peak), 2.35-2.26 (m, 1H), 1.80-1.77 (m, 2H), 1.56-1.46 (m, 2 H).

Intermediate B122: 4-{4-[4-(2-fluoroethyl)-1-piperazinyl]-1-piperidinyl}-2-(methyloxy)aniline

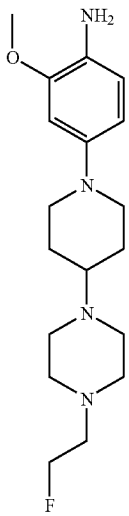

Step A/Intermediate B123: 1-(2-fluoroethyl)-4-{1-[3-(methyloxy)-4-nitrophenyl]-4-piperidinyl}

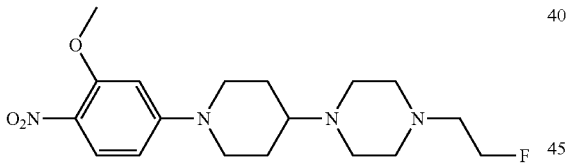

To a solution of 1-{1-[3-(methyloxy)-4-nitrophenyl]-4-piperidinyl}piperazine (intermediate 8120, 18.03 g, 56.10 mmol and 2.23 g, 6.96 mmol from separate batches) in tetrahydrofuran was added 1-Iodo-2-fluoroethane (7.38 mL, 90.79 mmol). The reaction was stirred at 85° C. overnight. The solution was transferred to a sealed tube. Upon addition of 1-Iodo-2-fluoroethane (7.38 mL, 90.79 mmol), the reaction was stirred at 85° C. for an additional 5 hours. The solvent was removed in vacuo and the residue was taken up in water and extracted with dichloromethane (×3), dried with magnesium sulfate, filtered and concentrated. Purification by flash chromatography provided 1-(2-fluoroethyl)-4-{1-[3-(methyloxy)-4-nitrophenyl]-4-piperidinyl}piperazine (15.94 g, 43.50 mmol, 69%) as a yellow solid. 1H NMR (400 MHz, DMSO-d$_6$) δ ppm 1.38 (qd, J=11.9, 3.7 Hz, 2 H) 1.79 (d, J=10.8 Hz, 2 H) 2.32-2.42 (m, J=7.0, 3.7 Hz, 9 H) 2.52 (dt, J$_{HF}$=28.6 Hz, J=4.9 Hz 2 H) 2.86-2.95 (m, 2H) 3.85 (s, 3 H) 3.99 (d, J=13.4 Hz, 2 H) 4.46 (dt, J$_{HF}$=47.8 Hz J=4.9 Hz 2 H), 6.45 (d, J=2.4 Hz, 1 H) 6.54 (dd, J=9.5, 2.6 Hz, 1 H) 7.82 (d, J=9.3 Hz, 1 H).

Step B/Intermediate B122: 4-{4-[4-(2-fluoroethyl)-1-piperazinyl]-1-piperidinyl}-2-(methyloxy)aniline A solution of 1-(2-fluoroethyl)-4-{1-[3-(methyloxy)-4-nitrophenyl]-4-piperidinyl}piperazine (15.94 g, 43.50 mmol) in tetrahydrofuran (200 mL) and methanol (300 mL) was cooled to 0° C. Nickel(II) chloridehexahydrate (5.18 g, 21.80 mmol) was added in one portion. The solution was stirred for 30 minutes followed by portion-wise addition of sodium borohydride (3.29 g, 87.00 mmol). Prior to warming the reaction to room temperature additional nickel (II) chloridehexahydrate (5.18 g, 21.80 mmol) and sodium borohydride (3.29 g, 87.00 mmol) were added to the reaction. The solvent was removed in vacuo and the residue was taken up in dichloromethane, filtered through celite, and washed with ethyl acetate. Purification by flash chromatography provided 4-{4-[4-(2-fluoroethyl)-1-piperazinyl]-1-piperidinyl}-2-(methyloxy)aniline (13.46 g, 40.10 mmol, 92%) as a white solid. 1H NMR (400 MHz, DMSO-d$_6$) δ ppm 1.46 (qd, J=11.9, 3.6 Hz, 2 H) 1.76 (d, J=12.1 Hz, 2 H) 2.12-2.20 (m, 1 H) 2.35-2.45 (m, 10 H) 2.53 (dt, J$_{HF}$=28.6 Hz, J=4.9 Hz, 2 H) 3.37 (d, J=12.1 Hz, 2 H) 3.68 (s, 3 H) 4.14 (br. s., 2 H) 4.47 (dt, J$_{HF}$=47.9 Hz, J=4.94 Hz, 2 H) 6.24 (dd, J=8.2, 2.4 Hz, 1 H) 6.43 (d, J=2.4 Hz, 1 H) 6.45 (d, J=8.4 Hz, 1 H).

Intermediate B124: 2-(methyloxy)-4-(4-{4-[2-(methylsulfonyl)ethyl]-1-piperazinyl}-1-piperidinyl)aniline

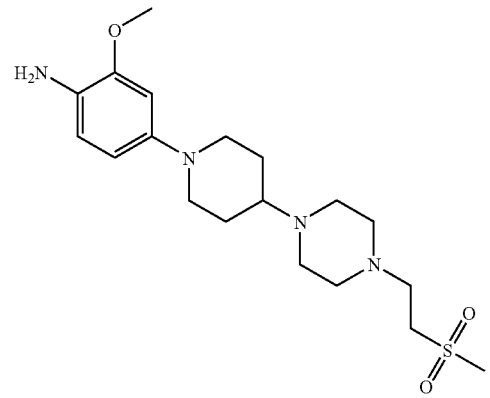

Step A/Intermediate B125: 1-{1-[3-(methyloxy)-4-nitrophenyl]-4-piperidinyl}-4-[2-(methylsulfonyl)ethyl]piperazine

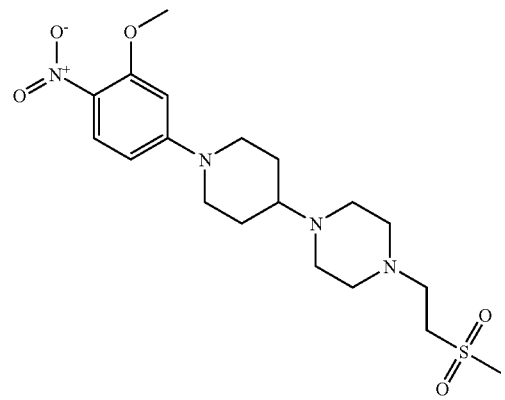

To a suspension of 1-{1-[3-(methyloxy)-4-nitrophenyl]-4-piperidinyl}piperazine (Intermediate B120, 10.0 g, 23.27 mmol) and 1,4-dioxane (400 mL) was added MeOH (~100 mL) to enhance solubility. Methyl vinyl sulfone (6.1 mL, 69.8 mmol) and Na$_2$CO$_3$ (7.4 g, 69.8 mmol) were added and the resultant mixture was heated at 80° C. overnight. The solvent was evaporated and the residue was taken up in DCM (300 mL) and filtered to remove salts. The filtrate was concentrated in vacuo to afford 1-{1-[3-(methyloxy)-4-nitrophenyl]-4-piperidinyl}-4-[2-(methylsulfonyl)ethyl]piperazine (9.9 g, >95%) which was carried forward with no further purification. MS (ES+, m/z) 427 (M+1).

Step B/Intermediate 124: 2-(methyloxy)-4-(4-{4-[2-(methylsulfonyl)ethyl]-1-piperazinyl}-1-piperidinyl)aniline NaBH$_4$ (2.64 g, 69.8 mmol) was added carefully in portions (exothermic) to a suspension of 1-{1-[3-(methyloxy)-4-nitrophenyl]-4-piperidinyl}-4-[2-(methylsulfonyl)ethyl]piperazine (9.9 g, 23.3 mmol), NiCL$_2$.6H$_2$O (1.66 g, 7 mmol), MeOH (120 mL) and THF (60 mL) at 0° C. The ice bath was removed and the reaction mixture was stirred at room temperature overnight (~16 h). The reaction mixture was concentrated onto silica gel and flash chromatography afforded the 2-(methyloxy)-4-(4-{4-[2-(methylsulfony)]-1-piperazinyl}-1-piperidinyl)aniline (6.24 g, 68%) as a brown solid. 1H NMR (400 MHz, DMSO-d6) δ 6.49-6.44 (m, 2H), 6.26 (dd, J=8.4, 2.6 Hz, 1H), 4.18 (bs, 2H), 3.71 (s, 3H), 3.43-3.36 (m, 2H), 3.25 (t, J=6.8 Hz, 2H), 3.00 (s, 3H), 2.65 (t, J=6.8 Hz, 2H), 2.47-2.36 (m, 10H complicated by DMSO), 2.23-2.15 (m, 1H), 1.82-1.75 (m, 2H), 1.54-1.43 (m, 2H).

Intermediate B127: 1-acetyl-5-(methyloxy)-2,3-dihydro-1H-indol-6-amine

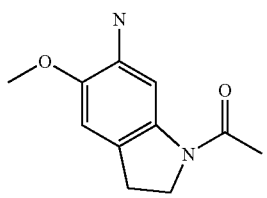

A mixture of 1-acetyl-5-(methyloxy)-6-nitro-2,3-dihydro-1H-indole Intermediate B98 (0.56 g, 2.37 mmol) and 10% Pd on carbon (500 mg) in EtOH (100 mL) was stirred overnight under 1 atm of H$_2$ gas, then was filtered through a pad of Celite. The filtrate was concentrated to dryness. The residue was dissolved in CH$_2$Cl$_2$ and purified by silica gel chromatography using 30-60% EtOAc/CH$_2$Cl$_2$ to obtain 1-acetyl-5-(methyloxy)-2,3-dihydro-1H-indol-6-amine as a white solid (327 mg, 67%). $^1$H NMR (400 MHz, DMSO-d$_6$) δ ppm 2.09 s, 3H), 2.98 (t, J=8.33 Hz 2H), 3.70 (s, 3H), 3.99 (t, J=8.33 Hz, 2H), 4.62 (s, 2H), 6.69 (s, 1H), 7.52 (s, 1H); ESIMS (M+H)$^+$= 207.

Intermediate B128: 1-[(diethylamino)acetyl]-5-(methyloxy)-2,3-dihydro-1H-indol-6-amine

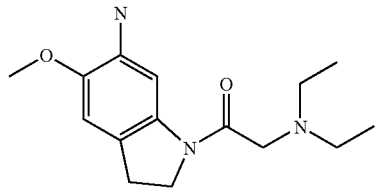

StepA/Intermediate B129: N,N-diethyl-2-[5-(methyloxy)-6-nitro-2,3-dihydro-1H-indol-1-yl]-2-oxoethanamine

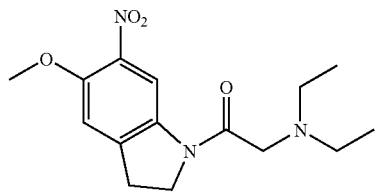

A mixture of 5-(methyloxy)-6-nitro-2,3-dihydro-1H-indole (Intermediate B99, 433 mg, 2.23 mol), bromoacetyl chloride (386 mg, 2.45 mmol) and K$_2$CO$_3$ (924 mg, 6.69 mmol) in THF (50 mL) was stirred for 40 min and then Et$_2$NH (326 mg, 4.46 mmol) was added. The reaction mixture was stirred for 1 day, additional Et$_2$NH (0.3 mL) was added, stirring was continued for an additional 24 h, then the reaction was heated at 60° C. for 2 h. The resulting mixture was diluted with EtOAc (200 mL), washed with water (150 mL) and a saturated NaCl solution (100 mL), and back extracted with EtOAc (100 mL). The organic layers were combined, dried (Na$_2$SO$_4$), and concentrated to obtain N,N-diethyl-2-[5-(methyloxy)-6-nitro-2,3-dihydro-1H-indol-1-yl]-2-oxoethanamine (687 mg, 100%). ESIMS (M+H)$^+$=307.97.

StepB/Intermediate B128: 1-[(diethylamino)acetyl]-5-(methyloxy)-2,3-dihydro-1H-indol-6-amine A mixture of N,N-diethyl-2-[5-(methyloxy)-6-nitro-2,3-dihydro-1 H-indol-1-yl]-2-oxoethanamine (0.68 g, 2.2 mol) and 10% Pd on carbon (0.06 g) in EtOH (150 mL) was stirred under 1 atm of H$_2$ for 20 h, then filtered through a pad of Celite. The filtrate was concentrated, the residue dissolved in CH$_2$Cl$_2$ and purified by silica gel chromatography using 0-10% MeOH (containing 0.2% NH$_3$)/CH$_2$Cl$_2$ to obtain 1-[(diethylamino)acetyl]-5-(methyloxy)-2,3-dihydro-1H-indol-6-amine as a brown solid (281 mg, 46%). $^1$H NMR (400 MHz, DMSO-d$_6$) δ ppm 0.98 (t, J=7.14 Hz, 6H), 2.57 (q, J=7.02 Hz 4H), 2.97 (t, J=8.24 Hz 2H), 3.28 (s, 2H), 3.71 (s, 3H), 4.12 (t, J=8.24 Hz, 2H), 4.62 (s, 2H), 6.70 (s, 1H), 7.54 (s, 1H); ESIMS (M+H)$^+$=278.19.

Intermediate B130: 5-(methyloxy)-1-(1-pyrrolidinylacetyl)-2,3-dihydro-1H-indol-6-amine

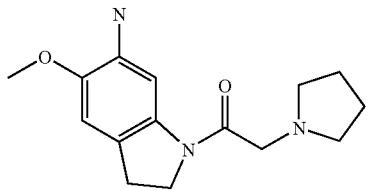

Step A/Intermediate B131: 5-(methyloxy)-6-nitro-1-(1-pyrrolidinylacetyl)-2,3-dihydro-1H-indole

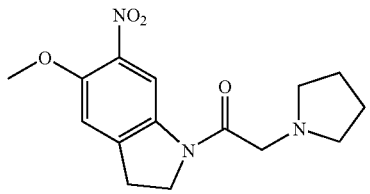

To a 0° C. slurry of 5-(methyloxy)-6-nitro-2,3-dihydro-1H-indole hydrogen chloride (Intermediate B99, 743 mg, 3.22 mmol) and DIPEA (2.8 mL, 16.11 mmol) was added bromoacetyl chloride (0.3 mL, 3.54 mmol) dropwise. After stirring at rt for 40 min pyrrolidine (1 mL, 12.89 mmol) was added and the reaction mixture was stirred overnight. The resulting mixture was concentrated and the residue was partitioned between EtOAc (200 mL) and water (200 mL). The organic layer was washed with a saturated NaCl solution (100 mL). The aqueous layers were back-extracted with EtOAc (100 mL). The organic layers were combined, dried ($Na_2SO_4$) and concentrated to obtain 5-(methyloxy)-6-nitro-1-(1-pyrrolidinylacetyl)-2,3-dihydro-1H-indole as a brown solid (754 mg, 77%). $^1$H NMR (400 MHz, DMSO-$d_6$) δ ppm 1.71 (br s, 4H), 2.58 (br s, 4H), 3.23 (t, J=8.42 Hz 2H), 3.40 (s, 2H), 3.89 (s, 3H), 4.10 (t, J=8.42 Hz, 2H), 7.34 (s, 1H), 8.38 (s, 1H); ESIMS (M+H)$^+$=305.97.

Step B/Intermediate B130: 5-(methyloxy)-1-(1-pyrrolidinylacetyl)-2,3-dihydro-1H-indol-6-amine To a solution of 5-(methyloxy)-6-nitro-1-(1-pyrrolidinylacetyl)-2,3-dihydro-1H-indole (750 mg, 2.46 mmol) in THF (20 mL) and MeOH (40 mL) was added $NiCl_2 \cdot 6H_2O$ (source: Riedel De Haiën) (175 mg, 0.74 mmol), followed by addition of $NaBH_4$ (280 mg, 7.4 mmol) in small portions. After stirring overnight the reaction mixture was concentrated onto Celite and purified by silica gel chromatography using 0-10% MeOH (containing 0.2% $NH_3$)/$CH_2Cl_2$ to obtain 5-(methyloxy)-1-(1-pyrrolidinylacetyl)-2,3-dihydro-1H-indol-6-amine as a brown solid (364 mg, 54%). $^1$H NMR (400 MHz, DMSO-$d_6$) δ ppm 1.70 (br s, 4H), 2.56 (br s, 4H), 2.97 (t, J=8.24 Hz, 2H), 3.71 (s, 3H), 4.06 (t, J=8.33 Hz 2H), 4.63 (s, 2H), 6.70 (s, 1H), 7.54 (s, 1H) a $CH_2$ signal with 2 protons is missing, may overlap with water peak in sample; ESIMS (M+H)$^+$=276.11.

Intermediate B132: 5-(methyloxy)-1-[(4-methylphenyl)sulfonyl]-2,3-dihydro-1H-indol-6-amine

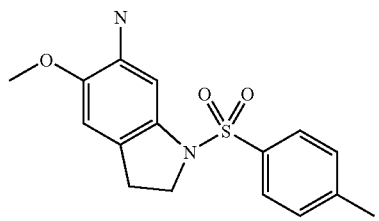

Step A/Intermediate B133: 5-(methyloxy)-1-[(4-methylphenyl)sulfonyl]-6-nitro-2,3-dihydro-1H-indole

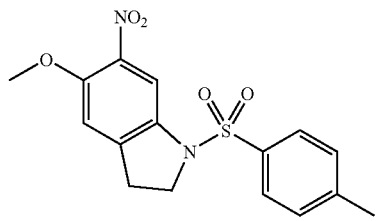

A 0° C. slurry of 5-(methyloxy)-6-nitro-2,3-dihydro-1H-indole hydrogen chloride (Intermediate B99, 12.0 g, 52 mmol) in THF (500 mL) was treated with DIPEA (27 mL, 156 mmol) and DMAP (6.3 g, 52 mmol), and then allowed to warm to rt with stirring overnight. The resulting mixture was concentrated, the residue was partitioned between $CH_2Cl_2$ (600 mL) and a 1N HCl solution (300 mL). The organic layer was washed with a saturated NaCl solution, dried ($Na_2SO_4$) and concentrated to about 50 mL volume. $Et_2O$ was added and the resulting slurry was filtered to obtain 5-(methyloxy)-1-[(4-methylphenyl)sulfonyl]-6-nitro-2,3-dihydro-1H-indole as a yellow solid (15.7 g, 87%). $^1$H NMR (400 MHz, DMSO-$d_6$) δ ppm 2.35 (s, 3H), 2.95 (t, J=8.42 Hz 2H), 3.84 (s, 3H), 3.93 (t, J=8.33 Hz 2H), 7.25 (s, 1H), 7.39 (d, J=8.24 Hz, 2H), 7.70 (d, J=8.06 Hz, 2H); ESIMS (M+H)$^+$=349.11.

Step B/Intermediate B132: 5-(methyloxy)-1-[(4-methylphenyl)sulfonyl]-2,3-dihydro-1H-indol-6-amine A yellow slurry of 5-(methyloxy)-1-[(4-methylphenyl)sulfonyl]-6-nitro-2,3-dihydro-1H-indole (16.1 g, 46 mmol) and $NiCl_2 \cdot 6H_2O$ (3.29 g, 13.9 mmol) in THF (150 mL) and MeOH (300 mL) was treated with $NaBH_4$ (5.2 g, 139 mmol) in small portions. The resulting mixture was stirred for 1 h, concentrated onto Celite and purified by column chromatography using 0-10% MeOH (containing 0.2% $NH_3$)/$CH_2Cl_2$ to obtain 5-(methyloxy)-1-[(4-methylphenyl)sulfonyl]-2,3-dihydro-1H-indol-6-amine as white solid (11.94 g, 81%). $^1$H NMR (400 MHz, DMSO-$d_6$) δ ppm 2.33 (s, 3H), 2.63 (t, J=8.15 Hz, 2H), 3.66 (s, 3H), 3.77 (t, J=8.06 Hz 2H), 4.79 (s, 2H), 6.58 (s, 1H), 6.94 (s, 1H), 7.34 (d, J=7.87 Hz, 2H), 7.62 (d, J=7.87 Hz, 2H); ESIMS (M+H)$^+$=320.12.

Intermediate B134: 5-(methyloxy)-1-[(methyloxy)acetyl]-2,3-dihydro-1H-indol-6-amine

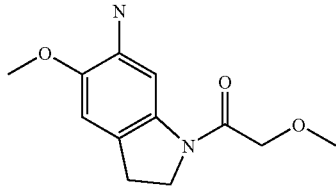

Step A/Intermediate B135: 5-(methyloxy)-1-[(methyloxy)acetyl]-6-nitro-2,3-dihydro-1H-indole

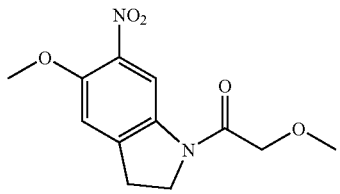

A slurry of 5-(methyloxy)-6-nitro-2,3-dihydro-1H-indole (Intermediate B99, 3.2 g, 13.87 mmol) in THF (100 mL) was treated with diisopropylethylamine (4.83 mL, 27.7 mmol), followed by (methyloxy)acetyl chloride (1.903 mL, 20.81 mmol). The resulting yellow slurry was stirred at rt for 3 days, then diluted with CH$_2$Cl$_2$ (300 mL), washed with water (150 mL), a saturated NaCl solution (150 mL), dried (Na$_2$SO$_4$) and concentrated to obtain 5-(methyloxy)-1-[(methyloxy)acetyl]-6-nitro-2,3-dihydro-1H-indole as an orange solid (3.96 g). $^1$H NMR (400 MHz, DMSO-d$_6$) δ ppm 3.24 (t, J=8.42 Hz 2H), 3.36 (s, 3H), 3.89 (s, 3H), 4.07 (t, J=8.42 Hz 2H), 4.19 (s, 2H), 7.35 (s, 1H), 8.47 (s, 1H); ESIMS (M+H)$^+$=266.87.

Step B/Intermediate B134: 5-(methyloxy)-1-[(methyloxy)acetyl]-2,3-dihydro-1H-indol-6-amine A slurry of 5-(methyloxy)-1-[(methyloxy)acetyl]-6-nitro-2,3-dihydro-1H-indole (3.96 g, 14.87 mmol) and NiCl$_2$.6H$_2$O (1.061 g, 4.46 mmol) in THF (50 mL) and MeOH (100 mL) was treated with NaBH$_4$ (1.69 g, 44.6 mmol) in small portions. After 5 minutes the reaction mixture was concentrated onto Celite and purified by silica gel chromatography using THF. The crude product was triturated using CH$_2$Cl$_2$ and Et$_2$O to obtain 5-(methyloxy)-1-[(methyloxy)acetyl]-2,3-dihydro-1H-indol-6-amine as a white solid (884 mg, 25%). $^1$H NMR (400 MHz, DMSO-d$_6$) δ ppm 2.98 (t, J=8.24 Hz, 2H), 3.34 (s, 3H), 3.71 (s, 3H), 3.93 (t, J=8.33 Hz 2H), 4.12 (s, 2H), 4.67 s, 2H), 6.71 (s, 1H), 7.54 (s, 1H); ESIMS (M+H)$^+$=237.4.

Intermediate B136: 1-[2-(dimethylamino)ethyl]-5-(methyloxy)-2,3-dihydro-1H-indol-6-amine

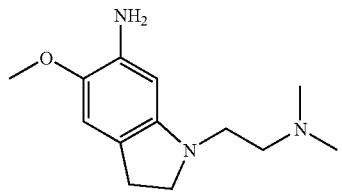

A 1.0M solution of lithium aluminum hydride in diethyl ether (Aldrich, 11 mL, 11 mmol, 10 equiv.) was added dropwise to a solution of 1-[(dimethylamino)acetyl]-5-(methyloxy)-2,3-dihydro-1H-indol-6-amine (0.280 g, 1.12 mmol) in diethyl ether (10 mL). The solids failed to dissolve, so anhydrous tetrahydrofuran was added (10 mL) and the solution was maintained at 50° C. for 12 hours. The solution was cooled, poured into ice water, diluted with ethyl acetate, and the organic layer was dried, taken to a residue under reduced pressure, and purified by chromatography on SiO$_2$ to afford 1-[2-(dimethylamino)ethyl]-5-(methyloxy)-2,3-dihydro-1H-indol-6-amine (0.065 g, 25% Yield). $^1$H NMR (400 MHz, CDCl$_3$) δ ppm 6.66 (s, 1 H), 6.05 (s, 1 H), 3.77 (s, 3 H), 3.28 (t, J=8.07 Hz, 2 H), 3.16 (t, J=6.97 Hz, 2 H), 2.86 (t, J=8.25 Hz, 2H), 2.64 (s, 2 H), 2.39 (s, 6 H).

Intermediate B137: 1-[3-(dimethylamino)propanoyl]-5-(methyloxy)-2,3-dihydro-1H-indol-6-amine

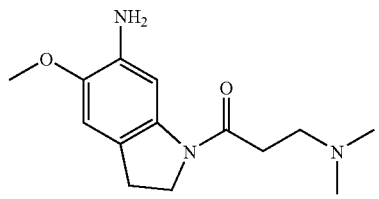

Step A/Intermediate B138: N,N-dimethyl-3-[5-(methyloxy)-6-nitro-2,3-dihydro-1H-indol-1-yl]-3-oxo-1-propanamine

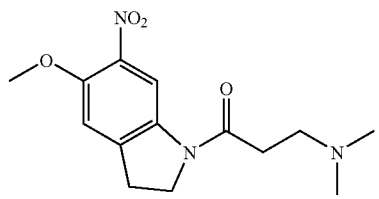

A suspension of 5-(methyloxy)-6-nitro-2,3-dihydro-1H-indole (1.50 g, 7.73 mmol) and polymer supported diisopropylethylamine (4.1 g, 16 mmol) in dichloromethane (100 mL) was cooled to 0° C. and 2-propenoyl chloride (0.750 mL, 9.3 mmol) was added dropwise. The solution was warmed slowly to room temperature and all solids were observed to dissolve. The mixture was filtered through celite, the celite washed twice with dichloromethane, and the combined filtrates were concentrated under reduced pressure to give a crude residue which was dissolved directly in a 1.0M dimethyl amine solution in tetrahydrofuran (40 mL). The solution was maintained at 60° C. for 12 hours, cooled, taken to a residue under reduced pressure, and purified by chromatography on $SiO_2$ to afford N,N-dimethyl-3-[5-(methyloxy)-6-nitro-2,3-dihydro-1H-indol-1-yl]-3-oxo-1-propanamine (1.52 g, 67% Yield). $^1$H NMR (400 MHz, $CDCl_3$) δ ppm 8.68 (s, 1 H), 6.91 (s, 1 H), 4.15 (t, J=8.43 Hz, 2 H), 3.91 (s, 3 H), 3.26 (t, J=8.43 Hz, 2 H), 2.81 (t, J=7.33 Hz, 2 H), 2.66 (t, J=7.15 Hz 2 H), 2.27-2.41 (m, 6H). U24644/64/1

Step B/Intermediate B137: 1-[3-(dimethylamino)propanoyl]-5-(methyloxy)-2,3-dihydro-1H-indol-6-amine To N,N-dimethyl-3[5-(methyloxy)-6-nitro-2,3-dihydro-1H-indol-1-yl]-3-oxo-1-propanamine (1.52 g, 5.4 mmol) in MeOH (50 mL) was added iron (III) chloride (0.220 g, 1.35 mmol, Aldrich) and activated carbon (2.0 g, Aldrich). The reaction mixture was stirred at 64° C. for 20 min before the dropwise addition of hydrazine hydrate (1.2 mL, 37.5 mmol, Aldrich) over 5 min. The reaction was kept stirring at 64° C. for additional 12 h. Filtration removed the solids and the filtrate was concentrated and purified via chromatography on $SiO_2$ (0-10% 2 M $NH_3$ in MeOH/DCM) to afford 1-[3-(dimethylamino)propanoyl]-5-(methyloxy)-2,3-dihydro-1H-indol-6-amine (0.270 g, 19% Yield). $^1$H NMR (400 MHz, $CDCl_3$) δ ppm 7.72 (s, 1 H), 6.63 (s, 1 H), 3.95-4.15 (m, 2 H), 3.81 (s, 3 H), 3.76 (s, 2 H), 3.10 (t, J=8.43 Hz, 2 H), 2.83-2.96 (m, 2 H), 2.70 (t, J=7.15 Hz, 2 H), 2.41 (s, 6 H).

Intermediate B139: 1-[(dimethylamino)acetyl]-3,3-dimethyl-5-(methyloxy)-2,3-dihydro-1H-indol-6-amine

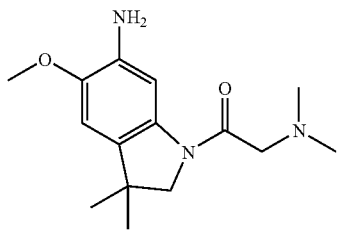

Step A/Intermediate B140: 1-acetyl-3,3-dimethyl-5-(methyloxy)-6-nitro-2,3-dihydro-1H-indole

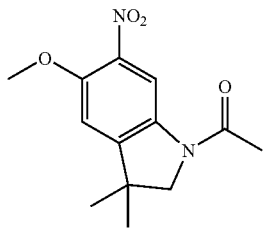

A solution of 1-acetyl-3,3-dimethyl-5-(methyloxy)-2,3-dihydro-1H-indole (2.44 g, 11.13 mmol, see PCT Int. Appl. (2001), WO 2001023374 A1 20010405) in trifluoroacetic acid (50 mL) was stirred at 0° C. and potassium nitrate (1.181 g, 11.68 mmol) was added in one portion. The reaction was maintained at 0° C. for 3 hours and poured into water. The solids were collected via filtration to afford 1-acetyl-3,3-dimethyl-5-(methyloxy)-6-nitro-2,3-dihydro-1H-indole (2.545 g, 87% yield) as a yellow solid. $^1$H NMR (400 MHz, DMSO-$d_6$) δ ppm 8.41 (s, 1 H), 7.34 (s, 1 H), 3.91 (s, 3 H), 2.15 (s, 2 H), 1.36 (s, 6 H). Note: proton resonance corresponding to acetyl was extremely broad and/or not evident for a variety of lots.

Step B/Intermediate B141: 3,3-dimethyl-5-(methyloxy)-6-nitro-2,3-dihydro-1H-indole

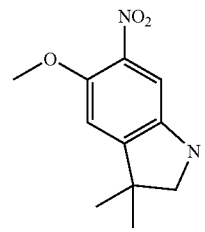

A solution of 1-acetyl-3,3-dimethyl-5-(methyloxy)-6-nitro-2,3-dihydro-1H-indole (2.55 g, 9.65 mmol) in methanol (75 mL) was treated with 4.0N HCl in dioxane (19.30 mL, 77 mmol) and maintained at 70° C. for 16 hours. The solution was concentrated under reduced pressure, solids were triturated with diethyl ether and the slurry was filtered to afford 3,3-dimethyl-5-(methyloxy)-6-nitro-2,3-dihydro-1H-indole (2.340 g, 94% yield) as an orange solid. $^1$H NMR (400 MHz, DMSO-$d_6$) δ ppm 7.68 (s, 1 H), 7.36 (s, 1 H), 3.89 (s, 3 H), 3.41 (s, 2 H), 1.33 (s, 6 H).

Step C/Intermediate B142: {2-[3,3-dimethyl-5-(methyloxy)-6-nitro-2,3-dihydro-1H-indol-1-yl]-2-oxoethyl}dimethylamine

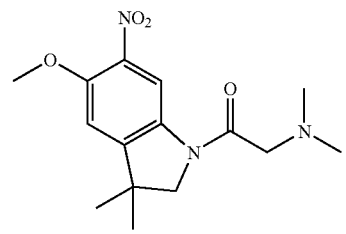

A solution of 3,3-dimethyl-5-(methyloxy)-6-nitro-2,3-dihydro-1H-indole (2.38 g, 10.71 mmol), Hunig's base (9.33 mL, 53.5 mmol) and bromo-acetylchloride (1.159 mL, 13.92 mmol) in tetrahydrofuran (100 mL) was maintained at 0° C. for 2 hours. Dimethylamine (2.0M in THF, 42.8 mL, 86 mmol) was added to the solution and the reaction was warmed to room temperature and maintained for 5 hours. The reaction was poured into saturated sodium bicarbonate, the organic layer was dried over sodium sulfate, filtered, and purified by column chromatography to afford {2-[3,3-dimethyl-5-(methyloxy)-6-nitro-2,3-dihydro-1H-indol-1-yl]-2-oxoethyl}dimethylamine (2.14 g, 65.0% yield) as an orange solid. $^1$H NMR (400 MHz, DMSO-d$_6$) δ ppm 8.44 (s, 1 H), 7.35 (s, 1 H), 3.97 (s, 2 H), 3.92 (s, 3 H), 3.21 (s, 2 H), 2.26 (s, 6H), 1.34 (s, 6 H).

StepD/Intermediate B139: 1-[(dimethylamino)acetyl]-3,3-dimethyl-5-(methyloxy)-2,3-dihydro-1H-indol-6-amine A suspension of {2-[3,3-dimethyl-5-(methyloxy)-6-nitro-2,3-dihydro-1H-indol-1-yl]-2-oxoethyl}dimethylamine (2.20 g, 7.16 mmol), hydrazine hydrate (2.81 mL, 57.3 mmol), iron(III)chloride (0.232 g, 1.432 mmol), and activated carbon (2 g, 7.16 mmol) was warmed at 65° C. for 16 hours. The solution was filtered while still warm through celite, taken to a residue under reduced pressure, and partitioned between chloroform and saturated sodium bicarbonate. The organic layer was washed with saturated sodium chloride (aq), dried over sodium sulfate, filtered, taken to a residue under reduced pressure, and purified by column chromatography to afford 1-[(dimethylamino)acetyl]-3,3-dimethyl-5-(methyloxy)-2,3-dihydro-1 H-indol-6-amine (1.41 g, 71% yield) as a light yellow solid. $^1$H NMR (400 MHz, DMSO-d$_6$) δ ppm 7.49 (s, 1 H), 6.69 (s, 1 H), 4.62 (s, 2 H), 3.82 (s, 2 H), 3.73 (s, 3 H), 3.12 (s, 2 H), 2.23 (s, 6 H), 1.22 (s, 6 H).

Intermediate B143: 5-(methyloxy)-1-(1-methyl-L-prolyl)-2,3-dihydro-1H-indol-6-amine

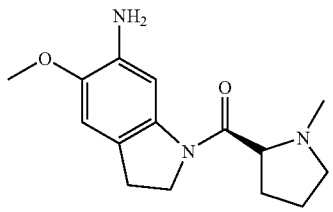

Step A/Intermediate B144: 5-(methyloxy)-1-(1-methyl-L-prolyl)-6-nitro-2,3-dihydro-1 H-indole

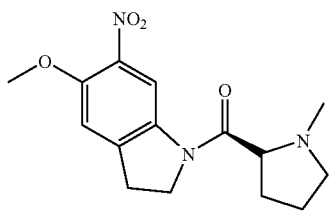

A solution of 5-(methyloxy)-6-nitro-2,3-dihydro-1H-indole (2.7 g, 11.71 mmol), 1-methyl-L-proline (Acros, 1.739 g, 13.46 mmol), HATU (5.79 g, 15.22 mmol), and DIPEA (6.13 mL, 35.1 mmol) in N,N-Dimethylformamide (DMF) (25 mL) was stirred at room temperature overnight. The next morning the solution had completely solidified. The solids were diluted with ethyl acetate/THF and washed with saturated sodium bicarbonate until all solids had dissolved. The organic layer was dried over sodium sulfate, filtered, concentrated onto celite, and purified by column chromatography to afford 5-(methyloxy)-1-(1-methyl-L-prolyl)-6-nitro-2,3-dihydro-1H-indole (3.4 g, 95% yield) as a yellow solid. $^1$H NMR (400 MHz, DMSO-d$_6$) δ ppm 8.51 (s, 1 H), 7.35 (s, 1 H), 4.20-4.31 (m, 1 H), 4.10-4.20 (m, 1 H), 3.88 (s, 3 H), 3.56-3.70 (m, 1 H), 3.25 (t, J=8.43 Hz, 2 H), 3.15-3.21 (m, 1 H), 2.52-.64 (m, 1H), 2.45 (s, 3 H), 2.21-2.35 (m, 1 H), 1.75-1.93 (m, 3 H).

Step B/Intermediate B143: 5-(methyloxy)-1-(1-methyl-L-prolyl)-2,3-dihydro-1H-indol-6-amine A suspension of 5-(methyloxy)-1-(1-methyl-L-prolyl)-6-nitro-2,3-dihydro-1H-indole (2.50 g, 8.19 mmol) in methanol (100 mL)/tetrahydrofuran (100 mL) was warmed to 65° C. and maintained until all solids had dissolved. The solution was cooled, purged with nitrogen for 40 minutes, and 10% palladium on carbon (1.1 g, 8.19 mmol) was added and the suspension was maintained under 40 psi of H$_2$ gas with rapid stirring for 24 hours. The solution was carefully purged with nitrogen, filtered through a pad of celite, and all solvents removed under reduced pressure to afford 5-(methyloxy)-1-(1-methyl-L-prolyl)-2,3-dihydro-1H-indol-6-amine (2.23 g, 99% yield). $^1$H NMR (400 MHz, DMSO-d$_6$) δ ppm 7.57 (s, 1 H), 6.70 (s, 1 H), 4.76 (s, 2 H), 4.06-4.17 (m, 1 H), 3.93-4.06 (m, 1 H), 3.70 (s, 3 H), 3.46 (s, 1 H), 3.06-3.18 (m, 1 H), 2.98 (t, J=8.25 Hz, 2 H), 2.41-2.47 (m, 1 H), 2.37 (s, 3 H), 2.12-2.29 (m, 1 H), 1.66-1.92 (m, 3 H).

Intermediate B145: 5-(methyloxy)-1-(1-methyl-D-propyl)-2,3-dihydro-1H-indol-6-amine

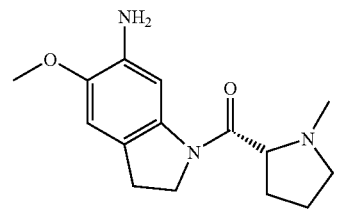

Step A/Intermediate B146: 1-methyl-D-proline

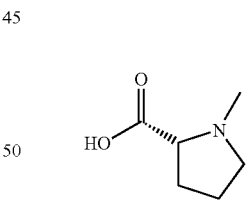

To a solution of D-proline (30 g, 260.7 mmol, 1 eq) and 37% aqueous formaldehyde (80.5 mL, 782 mmol, 3eq) in H$_2$O (900 mL) was added 10% Pd/C (30 g) under N$_2$. The mixture was stirred at 50° C. under H$_2$ (30 psi) overnight. The mixture was heated to boiling and filtered to remove the catalyst. The solution was concentrated under reduced pressure, and then water (150 mL) was added to the mixture and concentrated, the procedure was repeated three times so as to remove unreacted formaldehyde. The crude product was resuspended in ACN/H$_2$O (1:1, v/v) and lyophilized. The solid product was recrystallized from EtOH/acetone, filtered, liberally washed with acetone, and dried under reduced pressure to give 1-methyl-D-proline (12.3 g, 40%) as white solid. $^1$H NMR (400 MHz, MeOHD) δ ppm 1.95-1.99 (s, 1H), 2.1-2.2(s, 2H), 2.4-2.5 (m, 1H), 3.05-3.15(m,1H),3.3-3.35(s, 1H),3.65-3.75(m, 1H),3.75-3.85(m,1H).

Step B/Intermediate B147: 5-(methyloxy)-1-(1-methyl-D-prolyl)-6-nitro-2,3-dihydro-1H-indole

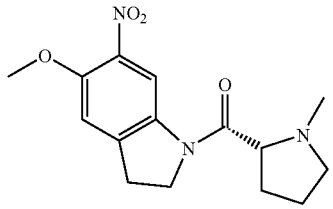

A solution of 5-(methyloxy)-6-nitro-2,3-dihydro-1H-indole (4.35 g, 18.86 mmol), 1-methyl-D-proline (2.436 g, 18.86 mmol), HATU (9.32 g, 24.52 mmol), and DIPEA (9.88 mL, 56.6 mmol) in N,N-dimethylformamide (25 mL) was stirred at room temperature overnight. The solution was poured into ethyl acetate/saturated sodium bicarbonate and the organic layer was washed three times with saturated sodium chloride (aq). The organic layer was dried over sodium sulfate, filtered, taken to a residue under reduced pressure, and purified by column chromatography to afford 5-(methyloxy)-1-(1-methyl-D-propyl)-6-nitro-2,3-dihydro-1H-indole (3.62 g, 11.86 mmol, 62.9% yield) as a pale brown oil. $^1$H NMR (400 MHz, DMSO-$d_6$) δ ppm 8.52 (s, 1 H), 7.37 (s, 1 H), 4.21-4.34 (m, 1 H), 4.05-4.21 (m, 1 H), 3.90 (s, 3 H), 3.78-3.88 (m, 1 H), 3.22-3.31 (m, 2 H), 3.16 (d, J=3.01 Hz, 1 H), 2.64-2.81 (m, 1 H), 2.54 (s, 3H), 2.30-2.44 (m, 1 H), 1.67-2.09 (m, 3 H).

Step C/Intermediate B145: 5-(methyloxy)-1-(1-methyl-D-propyl)-2,3-dihydro-1H-indol-6-amine A suspension of 5-(methyloxy)-1-(1-methyl-D-prolyl)-6-nitro-2,3-dihydro-1H-indole (3.62 g, 11.86 mmol) in tetrahydrofuran (50.0 mL)/methanol (50 mL) was warmed to 60° C. and maintained until all solids dissolved. The solution was cooled, degassed by bubbling with $N_2$ gas for 20 minutes, added to a pressure flask containing 10% palladium on carbon (1.1 g, 8.19 mmol), and maintained under 60 psi $H_2$ gas for 24 hours. The solution was purged with nitrogen, filtered through celite, the celite washed with methanol, and all volatiles removed under reduced pressure to afford 5-(methyloxy)-1-(1-methyl-D-propyl)-2,3-dihydro-1H-indol-6-amine (2.35 g, quantitative yield) as a pale yellow solid. $^1$H NMR (400 MHz, DMSO-$d_6$) δ ppm 7.57 (s, 1 H), 6.72 (s, 1 H), 4.69 (s, 2 H), 4.06-4.17 (m, 1 H), 3.93-4.06 (m, 1 H), 3.71 (s, 3 H), 3.64 (s, 1 H), 3.32 (s, 1 H), 3.21 (d, J=10.83 Hz, 1 H), 3.00 (t, J=8.03 Hz, 2 H), 2.49 (t, 3 H), 2.30 (d, J=8.23 Hz, 1 H), 1.65-1.96 (m, 3 H).

Intermediate B148: 1-[(dimethylamino)acetyl]-2,3-dihydro-1H-indol-6-amine

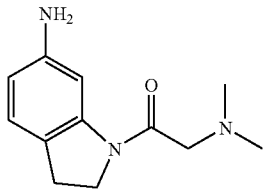

Step A/Intermediate B149: N,N-dimethyl-2-(6-nitro-2,3-dihydro-1H-indol-1-yl)-2-oxoethanamine

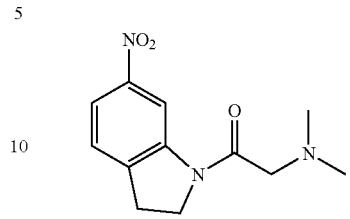

A suspension of 6-nitro-2,3-dihydro-1H-indole (10 g, 60.9 mmol) and potassium carbonate (16.84 g, 122 mmol) in dichloromethane (250 mL) was treated with bromoacetyl-chloride (6.33 mL, 76 mmol) and stirred for 25 minutes. Water was added and the organic layer was dried over sodium sulfate, filtered, taken to a residue under reduced pressure. The residue was redissolved in THF and 2.0M dimethyl amine in THF (Aldrich, 152 mL, 305 mmol) was added. The solution was stirred overnight, diluted with saturated sodium bicarbonate, and the organic layer was dried over sodium sulfate, filtered, taken to a residue under reduced pressure, and purified by column chromatography to afford N,N-dimethyl-2-(6-nitro-2,3-dihydro-1H-indol-1-yl)-2-oxoethanamine (13.6 g, 54.6 mmol, 90% yield) as a pale yellow solid. $^1$H NMR (400 MHz, DMSO-$d_6$) δ ppm 8.80 (d, J=2.01 Hz, 1 H), 7.90 (dd, J=8.23, 2.21 Hz, 1 H), 7.48 (d, J=8.23 Hz, 1 H), 4.26 (t, J=8.53 Hz 2 H), 3.18-3.31 (m, 4 H), 2.28 (s, 6 H).

Step B/Intermediate B148: 1-[(dimethylamino)acetyl]-2,3-dihydro-1H-indol-6-amine A suspension of N,N-dimethyl-2-(6-nitro-2,3-dihydro-1H-indol-1-yl)-2-oxoethanamine (13.6 g, 54.6 mmol), hydrazine hydrate (21.42 mL, 436 mmol), iron (III) chloride (1.768 g, 10.91 mmol), activated carbon (15 g), and methanol (100 mL) was maintained at 65° C. for 12 hours, cooled, and filtered through celite (rinsed with additional methanol). Filtrates were concentrated, redissolved in ethyl acetate, and washed twice with saturated aqueous sodium chloride and sodium bicarbonate. The organic layer was dried over sodium sulfate, filtered, and concentrated to afford 1-[(dimethylamino)acetyl]-2,3-dihydro-1H-indol-6-amine (9.6 g, 80% yield) as a white solid. $^1$H NMR (400 MHz, DMSO-$d_6$) δ ppm 7.44 (d, J=1.40 Hz, 1 H), 6.83 (d, J=8.03 Hz, 1 H), 6.20 (dd, J=7.93, 2.11 Hz, 1 H), 4.94 (s, 2 H), 4.06 (t, J=8.43 Hz, 2 H), 3.14 (s, 2 H), 2.91 (t, J=8.33 Hz, 2 H), 2.25 (s, 6 H).

Intermediate B150: 5-chloro-1-[(dimethylamino)acetyl]-2,3-dihydro-1H-indol-6-amine

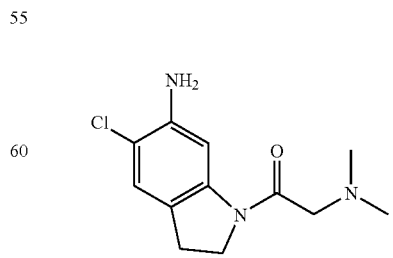

A solution of 1-[(dimethylamino)acetyl]-2,3-dihydro-1H-indol-6-amine (3.0 g, 13.68 mmol) in acetonitrile (150 mL)

was treated with N-chlorosuccinimide (2.010 g, 15.05 mmol) and stirred at room temperature for 15 minutes. The solution was poured into chloroform/saturated sodium bicarbonate (aq.) and the organic layer was dried over sodium sulfate, filtered, taken to a residue under reduced pressure, and purified by column chromatography to afford 5-chloro-1-[(dimethylamino)acetyl]-2,3-dihydro-1H-indol-6-amine (0.510 g, 15% yield) as a pale yellow solid. $^1$H NMR (400 MHz, DMSO-d$_6$) δ ppm 7.66 (s, 1 H), 7.01 (s, 1 H), 5.21 (s, 2 H), 4.08 (t, J=8.33 Hz, 2 H), 3.16 (s, 2 H), 2.95 (t, J=8.33 Hz, 2 H), 2.25 (s, 6 H).

Intermediate B151: 1-{[ethyl(methyl)amino]acetyl}-6-(methyloxy)-1,2,3,4-tetrahydro-7-quinolinamine

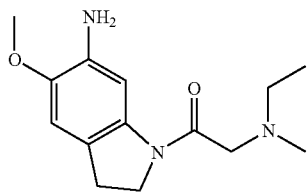

Step A/Intermediate B152:
3-chloro-N-(4-hydroxyphenyl)propanamide

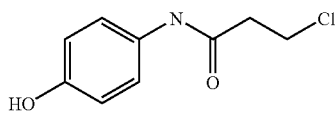

The solution of 4-aminophenol (250 g, 2.29 mol, 1 equiv) in CH$_2$Cl$_2$ (2L) and saturated NaHCO$_3$ (2L) was stirred for 5 min at 25° C., then 3-chloropropanoyl chloride (314 g, 2.52 mol 1.1 equiv) was added dropwise and the reaction was stirred for an additional 3 h at 25° C. The solids were filtered and dried under high vacuum to afford 3-chloro-N-(4-hydroxyphenyl)propanamide was used to the next step directly. (250 g, crude). $^1$H NMR (400 MHz, DMSO) δ, 2.96-2.99 (m, 2 H), 4.06-4.10 (m, 2 H), 6.88-6.92 (m 2 H), 7.57-7.60 (m, 2 H), 9.38-9.39 (br, 1 H), 10.1 (br, 1 H).

Step B/Intermediate B153:
6-hydroxy-3,4-dihydro-2(1 H)-quinolinone

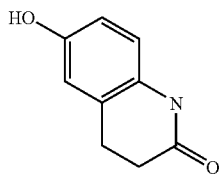

A mixture of 3-chloro-N-(4-hydroxyphenyl)propanamide (122 g, 0.61 mol) and AlCl$_3$ (327 g, 2.45 mol) were slowly heated with vigorous stirring at 180° C. (a thick melt formed) and after 5 hours the liquid was poured over ice. The solids were collected by filtration, washed with water, and recrystallized from MeOH to afford 6-hydroxy-3,4-dihydro-2(1H)-quinolinone (80 g, 40% yield). $^1$H NMR (400 MHz, DMSO) δ, 2.32-2.36 (m, 2 H), 2.74 (t, 2 H, J=7.2 Hz), 6.50 (m, 1 H), 6.54 (d, 1 H, J=2.8 Hz), 662(d, 1 H, J=8.4 Hz), 9.00 (br, 1 H), 9.78 (br, 1 H).

Step C/Intermediate B154:
6-(methyloxy)-3,4-dihydro-2(1H)-quinolinone

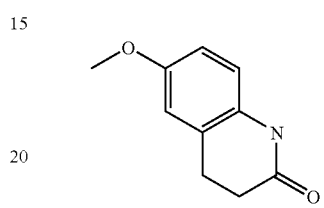

To 6-hydroxy-3,4-dihydro-2(1H)-quinolinone (90.8 g, 0.56 mol, 1 equiv) in CH$_3$CN (2 L) was added potassium carbonate (230.67 g, 1.67 mol, 3 equiv). The mixture was stirred for 1 h at 25° C., then MeI (75 g, 0.53 mol, 0.95 equiv) was added and the mixture was maintained at 60° C. for 12 hours. The mixture was filtered and the filtrate was taken to a residue under reduce pressure. The crude 6-(methyloxy)-3,4-dihydro-2(1H)-quinolinone was directly use to the next step. (128 g, crude) $^1$H NMR (400 MHz, DMSO) δ, 2.34-2.38 (m, 2 H), 2.79 (t, 2 H, J=7.2 Hz), 3.65 (s, 3 H), 6.67 (m, 1H), 6.72-6.75 (m, 2 H), 9.86 (br, 1 H). This procedure was reproduced multiple times to prepare >300 g quantities of 6-(methyloxy)-3,4-dihydro-2(1H)-quinolinone.

Step D/Intermediate B155: 6-(methyloxy)-7-nitro-3,4-dihydro-2(1H)-quinolinone

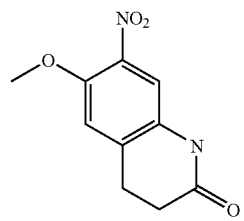

To a solution of 6-(methyloxy)-3,4-dihydro-2(1H)-quinolinone (209 g, 1.18 mol) in TFA (1500 mL) was added NaNO$_2$ (96 g, 1.41 mol, 1.2 equiv) at 0° C., then the temperature was raised to 25° C. and the mixture was stirred for 4 hours. The mixture was poured into ice and the yellow precipitate was collected via filtration and dried under high vacuum at 50° C. The crude product was recrystallized from ethyl acetate to afford 6-(methyloxy)-7-nitro-3,4-dihydro-2(1H)-quinolinone (75.6 g, 29%). $^1$H NMR (400 MHz, DMSO) δ 2.39-2.43 (m, 2 H), 2.92(t, 2 H, J=7.2 Hz), 3.82 (s, 3 H), 7.22 (s, 1 H), 7.32 (s, 1 H), 10.11(br, 1 H).

Step E/Intermediate B156: 6-(methyloxy)-7-nitro-1,2,3,4-tetrahydroquinoline

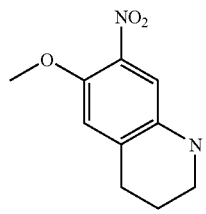

To a stirred solution of 6-(methyloxy)-7-nitro-3,4-dihydro-2(1H)-quinolinone (75 g of, 0.34 mol, 1 equiv) in THF (1L) was added BH$_3$.DMS (10 M, 150 mL, 1.5 mol, 4.4equiv) dropwise at 25° C. After the addition, the mixture was stirred for 6 h at 60° C. The reaction was cooled and quenched with excess MeOH, concentration under reduced pressure and purified via chromatography on SiO$_2$ t afford 6-(methyloxy)-7-nitro1,2,3,4-tetrahydroquinoline (51.5 g, 73% yield). $^1$H NMR (400 MHz, DMSO) δ 1.73-1.80 (m, 2 H), 2.71 (t, 2 H, J=6.4 Hz), 3.13-3.16 (m, 2 H), 3.75 (s, 3H), 5.83(br, 1 H), 6.88(s, 1 H), 6.95(s, 1 H).

Step F/Intermediate B157: N-ethyl-N-methyl-2-[6-(methyloxy)-7-nitro-3,4-dihydro-1(2H)-quinolinyl]-2-oxoethanamine

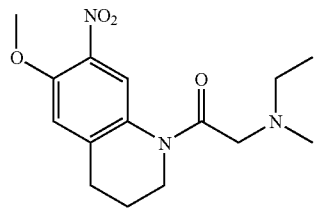

A solution of 6-(methyloxy)-7-nitro-1,2,3,4-tetrahydroquinoline (3.00 g, 14.41 mmol), Hunig's Base (12.55 mL, 72.0 mmol), and bromo-acetylchloride (1.500 mL, 18.01 mmol) was stirred at room temperature for 2 hours, at which time quinoline was observed to still remain. Additional bromo-acetylchloride (1.500 mL, 18.01 mmol) was added, the reaction was stirred an additional 5 hours, N-ethylmethylamine (12.38 mL, 144 mmol) was added, and the reaction was maintained for 16 hours at room temperature. The reaction was poured into saturated aqueous sodium bicarbonate and diluted with ethyl acetate. The organic layer was dried over sodium sulfate, taken to a residue under reduced pressure, and the residue was purified by silica gel chromatography to afford N-ethyl-N-methyl-2-[6-(methyloxy)-7-nitro-3,4-dihydro-1(2H)-quinolinyl]-2-oxoethanamine (2.02 g, 45.6% yield) as a dark red solid. $^1$H NMR (400 MHz, DMSO-d$_6$) δ ppm 8.35 (s, 1 H), 7.18 (s, 1 H), 3.89 (s, 3 H), 3.75 (s, 2 H), 3.30 (s, 2 H), 2.81 (t, J=6.12 Hz, 2 H), 2.36-2.47 (m, 2 H), 2.19 (s, 3 H), 1.80-1.97 (m, 2 H), 0.86-1.02 (m, 3 H).

Step G/Intermediate B151: 1-{[ethyl(methyl)amino]acetyl}-6-(methyloxy)-1,2,3,4-tetrahydro-7-quinolinamine A solution of N-ethyl-N-methyl-2-[6-(methyloxy)-7-nitro-3,4-dihydro-1(2 H)-quinolinyl]-2-oxoethanamine (2.02 g, 6.57 mmol) and 10% palladium on carbon (1.05 g) in methanol (55 mL) was maintained under 40 psi of H$_2$ gas in a pressure flask for 24 hours. The solution was purged with nitrogen, filtered through celite, taken to a residue under reduced pressure, and purified by column chromatography to afford 1-{[ethyl(methyl)amino]acetyl}-6-(methyloxy)-1,2,3,4-tetrahydro-7-quinolinamine (1.16 g, 64% yield) as a dark orange oil. $^1$H NMR (400 MHz, DMSO-d$_6$) δ ppm 6.82 (s, 1H), 6.56 (s, 1 H), 4.54 (s, 2 H), 3.72 (s, 3 H), 3.61 (t, J=5.82 Hz, 2 H), 3.25 (s, 2 H), 2.57 (t, J=6.22 Hz, 2 H), 2.43 (q, J=7.02 Hz, 2 H), 2.20 (s, 3 H), 1.70-1.89 (m, 2 H), 0.84-1.03 (m, 3 H).

Intermediate B158: 1-[(dimethylamino)acetyl]-6-(ethyloxy)-1,2,3,4-tetrahydro-7-quinolinamine

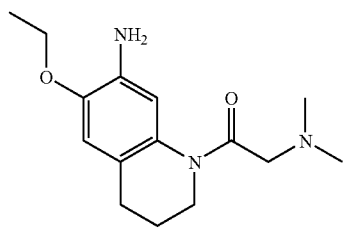

Step A/Intermediate B159: 6-(ethyloxy)-3,4-dihydro-2(1H)-quinolinone

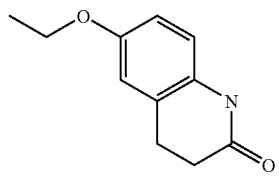

To 6-hydroxy-3,4-dihydro-2(1 H)-quinolinone (90.2 g, 0.55 mol, 1 equiv) in DMF (1.8 L) was added potassium carbonate (228 g, 1.65 mol, 3 equiv). The slurry was stirred for 45 min. at 25° C., then iodoethane (114 g, 0.73 mol, 1.33 equiv) was added and stirring was continued for 12 hours. The mixture was filtered, the filtrate was poured into water, and the white precipitate was collected via filtration, washed with water (500 mL), and dried under high vacuum to provide 6-(ethyloxy)-3,4-dihydro-2(1H)-quinolinone (72.3 g, 69%). $^1$H NMR (400 MHz, DMSO) δ, 1.25 (t, J=7.2 Hz, 3H), 2.35 (m, 2 H), 2.78 (m, 2H), 3.90(m, 2H), 6.70-6.73 (m, 3H), 9.83 (br, 1H).

StepB/Intermediate B160: 6-(ethyloxy)-7-nitro-3,4-dihydro-2(1H)-quinolinone

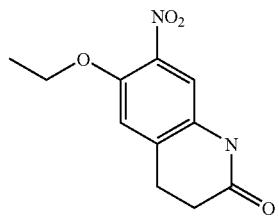

To the solution of 6-ethoxy-3,4-dihydroquinolin-2(1H)-one (72.3 g, 0.38 mol, 1 equiv) in TFA (800 mL) was added NaNO$_2$ (33.7 g, 0.496 mol, 1.3 equiv) at 0° C. The solution was allowed to warm to room temperature and stirring was continued for 4 hours. The mixture was poured into ice and the yellow precipitate was isolated via filtration and dried under high vacuum at 50° C. The crude product was recrystallized from ethyl acetate to afford 6-(ethyloxy)-7-nitro-3,4-dihydro-2(1H)-quinolinone (69.2 g, 77% yield). $^1$H NMR (400 MHz, DMSO) δ 1.31 (t, J=6.8 Hz, 3H), 2.45-2.49 (m, 2 H), 2.95 (t, 2 H, J=6.4 Hz), 4.13-4.15 (m, 2 H), 7.25 (s, 1 H), 7.34 (s, 1 H), 10.16 (bs, 1H).

Step C/Intermediate B161:
6-(ethyloxy)-7-nitro-1,2,3,4-tetrahydroquinoline

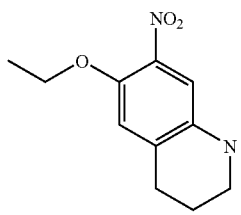

To a stirred solution of 6-ethoxy-3,4-dihydroquinolin-2 (1H)-one (69 g of, 0.29 mol, 1 equiv) in THF (1 L) was added BH$_3$.DMS (10 M, 120 mL, 1.2 mol, 4 equiv) dropwise at 25° C. The mixture was stirred for 4 h at 60° C. The reaction was cooled and quenched carefully with excess MeOH, then the mixture was concentrated under reduced pressure and the resultant solid suspended in a mixture of Et$_2$O and EtOAc and filtered to afford 6-(ethyloxy)-7-nitro-1,2,3,4-tetrahydroquinoline (26.7 g, 42% yield) as an orange solid. $^1$H NMR (400 MHz, DMSO) δ 1.24 (t, J=6.8 Hz, 3 H), 1.73-1.77 (m, 2 H), 2.68 (t, J=6.4 Hz, 2 H), 3.95-4.01 (m, 2 H), 5.81 (s, 1 H), 6.85 (s, 1 H), 6.89 (s, 1 H).

Step D/Intermediate B162: {2-[6-(ethyloxy)-7-nitro-3,4-dihydro-1(2H)-quinolinyl]-2-oxoethyl}dimethylamine

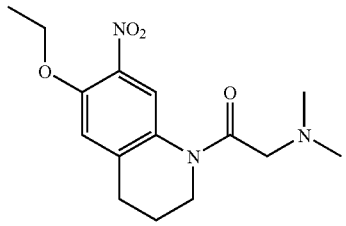

A suspension of 6-(ethyloxy)-7-nitro-1,2,3,4-tetrahydroquinoline (5.0 g, 22.50 mmol) and potassium carbonate (6.22 g, 45.0 mmol) in dichloromethane (100 mL) was treated with bromoacetylchloride (2.336 mL, 28.1 mmol) and stirred for 25 minutes. Water was added and the organic layer was dried over sodium sulfate, filtered, taken to a residue under reduced pressure, redissolved in THF, and 2.0M dimethyl amine in THF (67.5 mL, 135 mmol) was added. The solution was stirred overnight, diluted with saturated sodium bicarbonate, and the organic layer was dried over sodium sulfate, filtered, taken to a residue under reduced pressure, and purified by column chromatography to afford {2-[6-(ethyloxy)-7-nitro-3,4-dihydro-1(2H)-quinolinyl]-2-oxoethyl}dimethylamine (5.8 g, 84% yield) as a pale yellow oil. $^1$H NMR (400 MHz, DMSO-d$_6$) δ ppm 8.34 (s, 1 H), 7.16 (s, 1 H), 4.17 (q, J=6.96 Hz, 2 H), 3.74 (t, J=5.62 Hz, 2 H), 3.21 (s, 2 H), 2.80 (t, J=6.32 Hz, 2 H), 2.21 (s, 6 H), 1.76-2.01 (m, 2 H), 1.33 (t, J=6.92 Hz, 3 H).

Step E/Intermediate B158: 1-[(dimethylamino)acetyl]-6-(ethyloxy)-1,2,3,4-tetrahydro-7-quinolinamine A solution of {2-[6-(ethyloxy)-7-nitro-3,4-dihydro-1(2H)-quinolinyl]-2-oxoethyl}dimethylamine (5.8 g, 18.87 mmol) in degassed methanol (50.0 mL) was added to a suspension of 10% Pd/C (3.0 g, 16.36 mmol) in degassed methanol (5 mL) and maintained under a 50 psi hydrogen gas with rapid stirring for 16 hours. The suspension was purged with nitrogen, filtered through celite, all volatiles removed, and the resulting residue was purified by flash column chromatography to afford 1-[(dimethylamino)acetyl]-6-(ethyloxy)-1,2,3,4-tetrahydro-7-quinolinamine (2.85 g, 63%) as a viscous yellow liquid which solidified upon standing for 10 hours. $^1$H NMR (400 MHz, DMSO-d$_6$) δ ppm 6.80 (s, 1 H), 6.55 (s, 1 H), 4.52 (s, 2 H), 3.95 (q, J=6.89 Hz, 2 H), 3.61 (t, J=6.02 Hz, 2 H), 3.15 (s, 2 H), 2.55 (t, J=6.52 Hz 2 H), 2.20 (s, 6 H), 1.73-1.86 (m, 2 H), 1.32 (t, J=7.02 Hz, 3 H).

Intermediate B163: 2-methyl-6-(methyloxy)-1,2,3,4-tetrahydro-7-isoquinolinamine

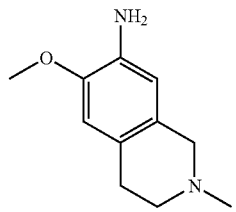

Step A/Intermediate B164: ethyl {2-[3-(methyloxy)phenyl]ethyl}carbamate

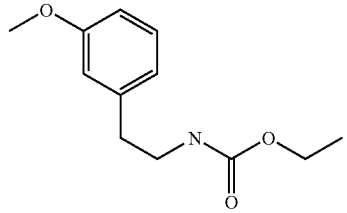

To a solution of {2-[3-(methyloxy)phenyl]ethyl}amine (20 g, 132.3 mmol) and triethylamine (20 g, 198 mmol) in dichloromethane (150 mL) was added ethyl chloridocarbonate (17.7 g, 163 mmol) dropwise at 0° C. After being stirred for 1 h the solvent was removed under vacuum and the residue was washed with ethyl acetate. Following filtration, the filtrate was concentrated to afford ethyl {2-[3-(methyloxy)phenyl]ethyl}carbamate (32 g, crude, 100%). $^1$H NMR(CDCl3) δ: 7.15-7.25 (1H), 6.7-6.8 (3H), 4.72 (1H), 3.75 (3H), 3.4 (2H), 2.75 (2H), 2.0 (3H), 1.15-1.3(2H).

Step B/Intermediate B165:
6-(methyloxy)-3,4-dihydro-1(2H)-isoquinolinone

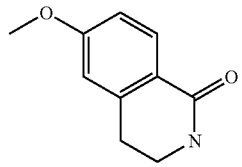

A mixture of {2-[3-(methyloxy)phenyl]ethyl}carbamate (30 g crude) and polyphosphoric acid (116 g) was maintained at 120-140° C. for 1 hr. After cooling to room temperature, water was added. The solution was adjusted to pH=9 with 6N sodium hydroxide and the organic products extracted with ethyl acetate. The combined organic layers were concentrated under reduced pressure and the residue was purified by column chromatography to afford 6-(methyloxy)-3,4-dihydro-1 (2H)-isoquinolinone (10 g, 40%). $^1$H NMR(CDCl$_3$) δ 8.0 (1H), 6.85 (1H), 6.7 (1H), 6.35 (1H), 3.85 (3H), 3.55 (2H), 2.95 (2H).

Step C/Intermediate B166: 2-methyl-6-(methyloxy)-3,4-dihydro-1(2H)-isoquinolinone

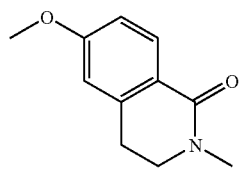

To a solution of 6-(methyloxy)-3,4-dihydro-1(2H)-isoquinolinone (5 g, 28.2 mmol) in THF (300 mL) was added NaH (1.35 g, 34.1 mmol) and the mixture was stirred for 30 min, then MeI (4.82 g, 33.87 mmol) was added. Stirring was maintained for 3 hours and then the solution was diluted with sat. NH$_4$Cl (aq) and extracted with dichloromethane. The combined organic layer was concentrated under reduced pressure to afford 6-methoxy-2-methyl-3,4-dihydroisoquinolin-1(2H)-one(6.3 g, 100%).

Step D/Intermediate B167: 2-methyl-6-(methyloxy)-7-nitro-3,4-dihydro-1(2H)-isoquinolinone

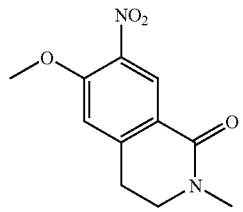

To a solution of 2-methyl-6-(methyloxy)-3,4-dihydro-1 (2H)-isoquinolinone (5 g, 26.17 mmol) in H$_2$SO$_4$(2.17 mL) was added HNO$_3$ (1.95 g, 31.4 mmol) dropwise at −20° C. The mixture was stirred for 2 h at −20° C. The reaction was diluted with water and the aqueous layer was extracted with dichloromethane. The combined organic layer was concentrated under reduced pressure to afford 2-methyl-6-(methyloxy)-7-nitro-3,4-dihydro-1(2H)-isoquinolinone (4.7 g, 75.8%).

Step E/Intermediate B168: 2-methyl-6-(methyloxy)-7-nitro-1,2,3,4-tetrahydroisoquinoline

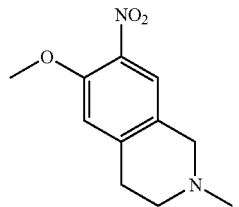

To a solution of 2-methyl-6-(methyloxy)-7-nitro-3,4-dihydro-1(2H)-isoquinolinone (4.7 g, 20 mmol) in THF (500 mL) was added 2.0 M BH$_3$ in THF (49.8 mL, 100 mmol). The resulting solution was heated at reflux for 20 h. The mixture was quenched via careful addition of MeOH (50 mL), the resulting solution was concentrated under reduced pressure and the residue was heated at 80° C. with 2N HCl for 3 h. The reation was cooled, adjusted to basic pH via cautious addition of aqueous NH$_4$OH, and extracted with dichloromethane. The combined organic layers were dried and concentrated under reduced pressure to give 6-methoxy-2-methyl-7-nitro-1,2,3,4-tetrahydroisoquinoline (3 g crude, 67%).

Step F/Intermediate B163: 2-methyl-6-(methyloxy)-1,2,3,4-tetrahydro-7-isoquinolinamine A solution of 2-methyl-6-(methyloxy)-7-nitro-1,2,3,4-tetrahydroisoquinoline and Pd(OH)$_2$(1 g) in MeOH(100 mL) was stirred under H$_2$ at room temperature for 5 h. The solution was filtered and all solvents were removed under reduced pressure to give 2-methyl-6-(methyloxy)-1,2,3,4-tetrahydro-7-isoquinolinamine (2 g, 77.2%). $^1$H NMR (400 MHz, CDCl$_3$) δ ppm 6.51 (s, 1 H), 6.38 (s, 1 H), 3.81 (s, 3 H), 3.64 (s, 2 H), 3.43 (s, 2 H), 2.81 (t, J=5.77 Hz, 2 H), 2.64 (t, J=5.90 Hz, 2 H), 2.42 (s, 3H).

Intermediate B169: 2-[(dimethylamino)acetyl]-6-(methyloxy)-1,2,3,4-tetrahydro-7-isoquinolinamine

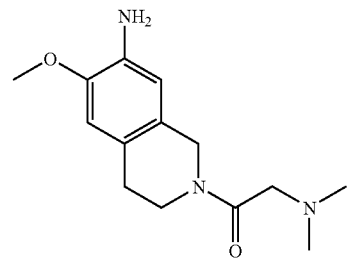

Step A/Intermediate B170: 6-(methyloxy)-7-nitro-3,4-dihydro-1(2H)-isoquinolinone

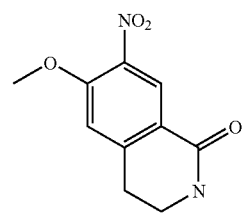

To a solution of 6-(methyloxy)-3,4-dihydro-1(2H)-isoquinolinone (3.4 g, 17.8 mmol) in H$_2$SO$_4$ (45 mL) at −20° C. was added HNO$_3$ (1.58 mL, 21.3 mmol) dropwise. The mixture was allowed to stir for 3 h at −20° C. The mixture was poured into ice water and the aqueous layer was extracted with dichloromethane. The combined organic layers were concentrated under reduced pressure to give 6-(methyloxy)-7-nitro-3,4-dihydro-1(2H)-isoquinolinone (3.0 g, 71%). $^1$H NMR (CDCl$_3$) δ 8.55 (1H), 6.88 (1H), 6.2 (1H), 4.0 (3H), 3.6 (2H), 3.05 (2H).

Step B/Intermediate B171: 6-(methyloxy)-7-nitro-1,2,3,4-tetrahydroisoquinoline

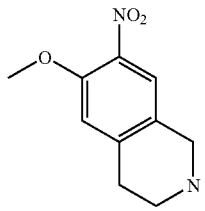

A solution of 6-(methyloxy)-7-nitro-3,4-dihydro-1(2H)-isoquinolinone (7 g, 31.5 mmol) in THF (800 mL) was treated with 2M BH$_3$ in THF(78.8 mL, 157.6 mmol) and heated to reflux for 20 h. Methanol (100 mL) was added and the solution was concentrated under reduced pressure. The resulting residue was heated with 2N HCl for 3 hr., cooled, basified via careful addition of aqueous ammonium hydroxide, and extracted with dichloromethane. The organic layer was dried, filtered, and taken to a residue under reduced pressure to afford 6-(methyloxy)-7-nitro-1,2,3,4-tetrahydroisoquinoline (5.5 g crude, 84.5% pure).

Step C/Intermediate B172: N,N-dimethyl-2-[6-(methyloxy)-7-nitro-3,4-dihydro-2(1H)-isoquinolinyl]-2-oxoethanamine

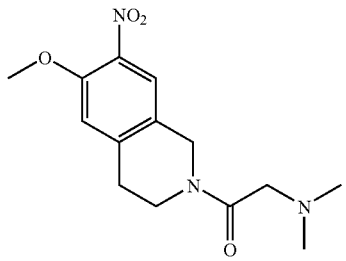

A suspension of 6-(methyloxy)-7-nitro-1,2,3,4-tetrahydroisoquinoline (1.25 g, 6.00 mmol), bromoacetyl chloride (0.75 mL, 9.01 mmol), and polymer supported diisopropylethylamine (4.7 g, 18 mmol) was stirred for 4 hours, filtered, and taken to a residue under reduced pressure. The residue was redissolved in 2.0M methylamine in tetrahydrofuran (15 mL) and stirred overnight. The solution was concentrated under reduced pressure and purified by column chromatography to afford N,N-dimethyl-2-[6-(methyloxy)-7-nitro-3,4-dihydro-2(1H)-isoquinolinyl]-2-oxoethanamine as a mixture of apparent rotameric forms in DMSO (0.90 g, 3.07 mmol).

Step D/Intermediate B169: 2-[(dimethylamino)acetyl]-6-(methyloxy)-1,2,3,4-tetrahydro-7-isoquinolinamine A suspension of N,N-dimethyl-2-[6-(methyloxy)-7-nitro-3,4-dihydro-2(1H)-isoquinolinyl]-2-oxoethanamine (0.9 g, 3.07 mmol), hydrazine hydrate (0.67 mL, 21.5 mmol), iron (III)chloride (0.125 g, 0.77 mmol), activated carbon (1 g), and methanol (100 mL) was maintained at 65° C. for 12 hours, cooled, and filtered through celite (rinsed with additional methanol). Filtrates were concentrated, redissolved in ethyl acetate, and washed twice with saturated aqueous sodium chloride and sodium bicarbonate. The organic layer was dried over sodium sulfate, filtered, and concentrated to afford 2-[(dimethylamino)acetyl]-6-(methyloxy)-1,2,3,4-tetrahydro-7-isoquinolinamine (0.214 g, 26%) as a white solid. $^1$H NMR/80° C. (400 MHz, DMSO-d$_6$) δ ppm 6.56 (s, 1 H), 6.41 (s, 1 H), 4.49 (s, 2 H), 4.38 (s, 2 H), 3.73 (3.64 (s, 2 H), 3.11 (s, 2 H), 2.66 (s, 2 H), 2.20 (s, 6 H).

Intermediate B173: 6-(methyloxy)-2-(1-propyl-4-piperidinyl)-1,2,3,4-tetrahydro-7-isoquinolinamine

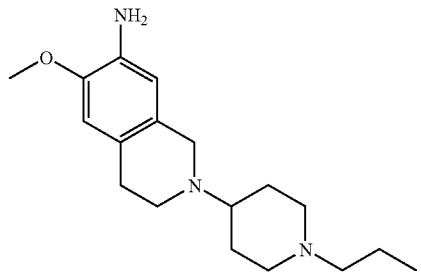

Step A/Intermediate B174: 6-(methyloxy)-7-nitro-2-(1-propyl-4-piperidinyl)-1,2,3,4-tetrahydroisoquinoline

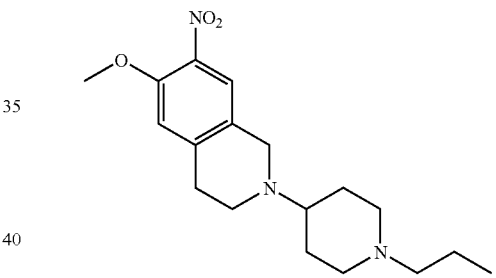

A mixture of 1-propyl-4-piperidinone (01.25 mL, 8.3 mmol), 6-(methyloxy)-7-nitro-1,2,3,4-tetrahydroisoquinoline (1.0 g, 4.8 mmol), acetic acid (0.55 mL) and triethylamine (1.3 mL) in 1,2-dichloroethane (5 mL) was stirred for 30 minutes. Sodium triacetoxyborohydride (1.8 g, 2.8 mmol) was added. After stirring for 12 hours the reaction was quenched by the addition of saturated NaHCO$_3$ (aq). The reaction was diluted with dichloromethane and the layers were separated. The aqueous phase was extracted with dichloromethane. The combined organic layers were washed with water, dried over MgSO$_4$ and concentrated onto silica gel. The crude material was purified by flash column chromatography to give 6-(methyloxy)-7-nitro-2-(1-propyl-4-piperidinyl)-1,2,3,4-tetrahydroisoquinoline (1.43 g, 89%). $^1$H NMR (400 MHz, CDCl$_3$) δ ppm 7.60 (s, 1 H), 6.78 (s, 1 H), 3.91 (s, 3 H), 3.73 (s, 2 H), 3.07 (d, J=9.17 Hz, 2 H), 2.91 (t, J=5.87 Hz, 2 H), 2.83 (t, J=5.68 Hz 2 H), 2.47-2.60 (m, 1 H), 2.29-2.42 (m, 2 H), 2.04 (d, J=10.63 Hz, 2 H), 1.68-1.94 (m, 4 H), 1.49-1.66 (m, 2 H), 0.91 (t, J=7.33 Hz, 3 H).

Step B/Intermediate B173: 6-(methyloxy)-2-(1-propyl-4-piperidinyl)-1,2,3,4-tetrahydro-7-isoquinolinamine A suspension of 6-(methyloxy)-7-nitro-2-(1-propyl-4-piperidinyl)-1,2,3,4-tetrahydroisoquinoline (1.43 g, 4.35 mmol), hydrazine hydrate (1.0 mL, 30.5 mmol), iron(III)chloride (0.180 g, 1.09 mmol), activated carbon (2 g), and methanol (50 mL) was maintained at 65° C. for 12 hours, cooled, and filtered through celite (rinsed with additional methanol). Filtrates were concentrated, redissolved in ethyl acetate, and washed twice with saturated aqueous sodium chloride and sodium bicarbonate. The organic layer was dried over sodium sulfate, filtered, and concentrated to afford 6-(methyloxy)-2-(1-propyl-4-piperidinyl)-1,2,3,4-tetrahydro-7-isoquinolinamine (0.550 g, 42%). $^1$H NMR (400 MHz, CDCl$_3$) δ ppm 6.49 (s, 1 H), 6.37 (s, 1 H), 3.80 (s, 3 H), 3.64 (s, 4 H), 2.99-3.15 (m, 2 H), 2.70-2.85 (m, 4 H), 2.49 (s, 1 H), 2.33 (s, 2 H), 2.01 (s, 2 H), 1.89 (s, 2 H), 1.77 (s, 2 H), 1.56 (s, 2 H), 0.91 (t, J=7.33 H, 3 H).

Intermediate B175: 2-[{2-[6-amino-5-(methyloxy)-2,3-dihydro-1H-indol-1-yl]-2-oxoethyl}(ethyl)amino]ethanol

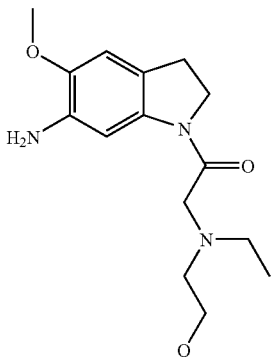

Step A/Intermediate B176: 1-(bromoacetyl)-5-(methyloxy)-6-nitro-2,3-dihydro-1H-indole

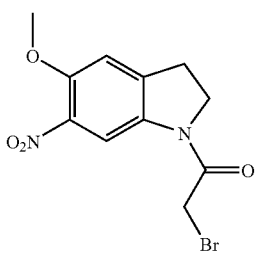

A solution of 5-(methyloxy)-6-nitro-2,3-dihydro-1H-indole (33.6 g, 173 mmol) in CH$_2$Cl$_2$ (150 mL) was added dropwise to a mixture of bromoacetylchloride (54.5 g, 346 mmol) and K$_2$CO$_3$ (53.0 g, 381 mmol) in CH$_2$Cl$_2$ (150 mL). The resulting solution was stirred at 0° C. for 1 hour, then warmed up RT for 4 hours. Water (150 mL) was added and the mixture was extracted with CH$_2$Cl$_2$ (2×100 mL). The organic phase was dried over Na$_2$SO$_4$, the solvent was removed to yield the 1-(bromoacetyl)-5-(methyloxy)-6-nitro-2,3-dihydro-1H-indole (54.2 g, 99%). $^1$HNMR (400 MHz, DMSO) δ ppm 2.47(s, 2H), 3.25 (m, 2 H), 3.87 (s, 3 H), 4.21 (m, 2 H), 7.34 (s, 1 H), 8.42 (s, 1 H).

Step B/Intermediate B177: 2-[{2-[6-amino-5-(methyloxy)-2,3-dihydro-1H-indol-1-yl]-2-oxoethyl}ethyl)amino]ethanol

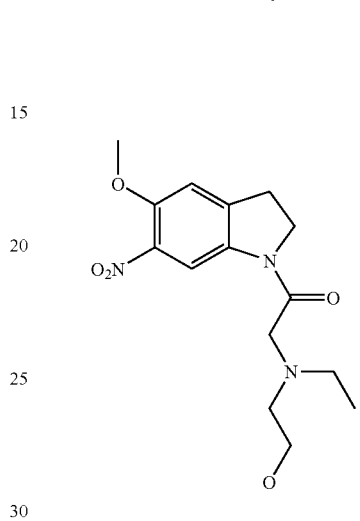

The 1-(bromoacetyl)-5-(methyloxy)-6-nitro-2,3-dihydro-1H-indole (4.0 g, 12.7 mmol) was dissolved in 50 mL of dicholomethane, then K$_2$CO$_3$ (4.4 g, 31.7 mmol) and 2-(ethylamino)ethanol (2.3 g, 25.4 mmol) in 10 mL dichloromethane were added, the reaction was stirred at RT for 3 hours. After filtration, the organic layers were washed with water (2×100 mL)and dried over Na$_2$SO$_4$. The solvent was removed to yield the 2-[{2-[6-amino-5-(methyloxy)-2,3-dihydro-1H-indol-1-yl]-2-oxoethyl}(ethyl)amino]ethanol as a yellow solid (3.77 g, 92%).$^1$HNMR (400 MHz, DMSO-d$_6$) δ ppm: 0.94 (t, J=7.14 Hz,3 H), 2.45 (s, 2 H), 2.60 (m, 4 H), 3.18 (t, J=8.42 Hz, 2 H), 3.40 (t, J=6.13 Hz,2H), 3.84 (s, 3 H), 4.19 (t, J=8.51 Hz, 2 H), 7.29 (s, 1 H), 8.43 (s, 1 H).

Step C/Intermediate B175: 2-[{2-[6-amino-5-(methyloxy)-2,3-dihydro-1H-indol-1-yl]-2-oxoethyl}(ethyl)amino]ethanol The 2-[{2-[6-amino-5-(methyloxy)-2,3-dihydro-1H-indol-1-yl]-2-oxoethyl}(ethyl)amino]ethanol (3.77 g, 11.7 mmol) was dissolved in 10 mL of EA, 25 mL of MeOH and 15 mL of THF, then 0.8 g 10% Pd/C was added and the reaction was stirred at RT overnight under H$_2$ pressure (65 psi). The catalyst was removed by filtration and the solvent was evaporated under reduced pressure to yield the 2-[{2-[6-amino-5-(methyloxy)-2,3-dihydro-1H-indol-1-yl]-2-oxoethyl}(ethyl)amino]ethanol as a yellow solid, (3.43 g, 99%). $^1$H NMR (400 MHz, DMSO-d$_6$) δ ppm: 0.95 (t, J=6.96 Hz,3H), 2.61(m, 2H), 2.94 (t, J=8.15 Hz, 2 H), 3.35 (m, 4 H), 3.68(s, 3H), 4.05 (t, H=7.97 Hz,2 H), 4.61 (s, 2H), 6.66 (s, 1 H), 7.51 (s, 1 H).

Intermediate B178: 1-{[ethyl(methyl)amino]acetyl}-5-(methyloxy)-2,3-dihydro-1H-indol-6-amine

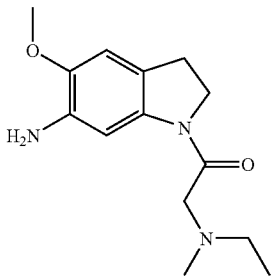

The 1-(bromoacetyl)-5-(methyloxy)-6-nitro-2,3-dihydro-1H-indole (4.0 g, 12.7 mmol) was dissolved in 50 mL of dichloromethane, then $K_2CO_3$ (4.4 g, 31.7 mmol) and N-methylethanamine(1.5 g, 25.4 mmol) in 10 mL dichloromethane were added and the reaction was stirred at RT for 3 hours. After filtration, the organic layers were washed with water (2×100 mL) and dried over $Na_2SO_4$. The solvent was was removed under reduced pressure and the derived residue (3.4 g, 11.59 mmol) was dissolved in 10 mL of EA, 25 mL of MeOH and 15 mL of THF, then 0.8 g 10% Pd/C was added, the reaction was stirred at RT overnight under $H_2$ pressure (65 psi). The catalyst was removed via filteration, and the solvent was evaporated under reduced pressure to afford 1-{[ethyl(methyl)amino]acetyl}-5-(methyloxy)-2,3-dihydro-1H-indol-6-amine as a yellow solid, 3.0 g (97%). $^1$HNMR (400 MHz, DMSO-$d_6$) δ ppm: 0.97 (t, J=7.14 Hz, 3H), 2.20 (s, 3H), 2.46(m, 2H), 2.94 (t, 2 H), 3.16(s, 2H), 3.68 (s, 3H), 4.06 (t, J=8.42 Hz, 2 H), 4.60 (s, 2H), 6.67 (s, 1 H), 7.52 (s, 1 H).

Intermediate B179: 5-(methyloxy)-1-{[methyl(propyl)amino]acetyl}-2,3-dihydro-1H-indol-6-amine

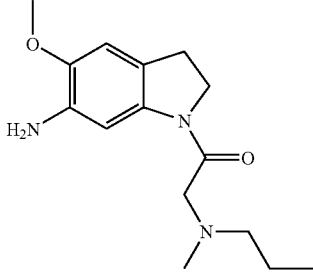

The 1-(bromoacetyl)-5-(methyloxy)-6-nitro-2,3-dihydro-1H-indole (4.0 g, 12.7 mmol) was dissolved in 50 mL of dichloromethane, then $K_2CO_3$ (4.4 g, 31.7 mmol) and N-methyl-1-propanamine (1.9 g, 25.4 mmol) in 10 mL dichloromethane were added, the reaction was stirred at RT for 3 hours. After filtration, the organic layers were washed with water (2×100 mL) and dried over $Na_2SO_4$. The solvent was removed under reduced pressure and the resulting residue was dissolved in 10 mL of EA, 25 mL of MeOH and 15 mL of THF, then 0.8 g 10% Pd/C was added and the reaction was stirred at RT overnight under $H_2$ pressure (65 psi). The catalyst was removed via filteration and the solvent was removed under reduced pressure to afford 5-(methyloxy)-1-{[methyl(propyl)amino]acetyl}-2,3-dihydro-1H-indol-6-amine as a yellow solid, 3.0 g (96%). $^1$HNMR (400 MHz, DMSO-$d_6$) δ ppm: 0.81 (t, J=7.14 Hz, 3H), 1.40 (m, 2H), 2.21 (s, 3H), 2.35(m, 2H), 2.94 (t, J=8.24 Hz, 2 H), 3.17(s, 2H), 3.70 (s, 3H), 4.07 (t, J=8.33 Hz, 2 H), 4.60 (s, 2H), 6.67 (s, 1 H), 7.52 (s, 1 H).

Intermediate B180: 1-({methyl[2-(methyloxy)ethyl]amino}acetyl)-5-(methyloxy)-2,3-dihydro-1H-indol-6-amine

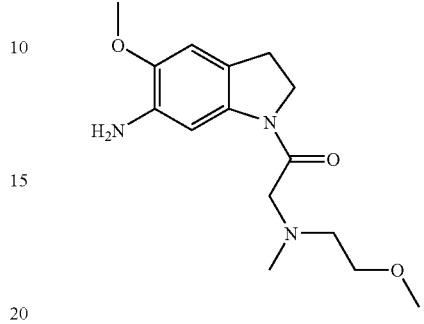

The 1-(bromoacetyl)-5-(methyloxy)-6-nitro-2,3-dihydro-1H-indole (4.0 g, 12.7 mmol) was dissolved in 50 mL of dichloromethane, then $K_2CO_3$ (4.4 g, 31.7 mmol) and N-methyl-2-(methyloxy)ethanamine (1.4 g, 15.2 mmol) in 10 mL dichloromethane were added, the reaction was stirred at RT overnight. The reaction mixture was diluted with 100 mL of water, the organic solvents were washed with water (2×100 mL), and dried over $Na_2SO_4$. The solvent was removed under reduced pressure and the resulting residue was dissolved in 10 mL of EA, 25 mL of MeOH and 15 mL of THF, then 0.8 g 10% Pd/C was added, and the reaction was stirred at RT overnight under a balloon of $H_2$ pressure. The catalyst was removed via filtration and the solvent was evaporated under reduced pressure to yield the 1-({methyl[2-(methyloxy)ethyl]amino}acetyl)-5-(methyloxy)-2,3-dihydro-1H-indol-6-amine as a white solid (3.1 g, 89%). $^1$HNMR (400 MHz, DMSO-$d_6$) δ ppm: 2.28(s, 3H), 2.62 (t, J=5.77 Hz, 2H), 2.94 (t, J=8.24 Hz 2 H), 3.19 (s, 3H), 3.25(s, 2H), 3.41 (t, J=5.77 Hz, 2 H), 3.68(s, 3H), 4.04 (t, J=8.33 Hz,2H), 4.61 (s, 2H), 6.67 (s, 1 H), 7.52 (s, 1 H).

Intermediate B181: 1-{2-[6-amino-5-(methyloxy)-2,3-dihydro-1H-indol-1-yl]-2-oxoethyl}-3-pyrrolidinol

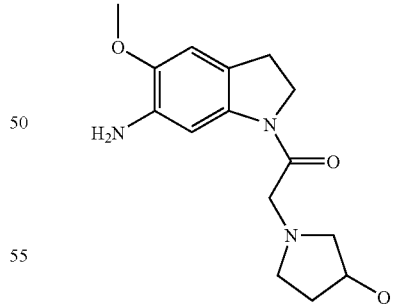

The 1-(bromoacetyl)-5-(methyloxy)-6-nitro-2,3-dihydro-1H-indole (4.0 g, 12.7 mmol) was dissolved in 50 mL of dichloromethane, then $K_2CO_3$ (4.4 g, 31.7 mmol) and 3-pyrrolidinol (1.33 g, 15.2 mmol) in 10 mL dichloromethane were added, and the reaction was stirred at RT overnight. The reaction mixture was diluted with 100 mL of water, the organic solvents were washed with water (2×100 mL), dried over $Na_2SO_4$, and the solvent was removed under reduced pressure. The resulting residue was dissolved in 10 mL of EA, 25 mL of MeOH and 15 mL of THF, then 0.8 g 10% Pd/C was added, and the reaction was stirred at RT overnight under a balloon of $H_2$ pressure. The catalyst was removed via filtration and the solvent was evaporated under reduced pressure to yield the 1-{2-[6-amino-5-(methyloxy)-2,3-dihydro-1H-indol-1-yl]-2-oxoethyl}-3-pyrrolidinol as a white solid (3.0 g, 92%). $^1$H NMR (400 MHz, DMSO-$d_6$) δ ppm: 1.60 (m, 1 H), 1.97 (m, 1 H), 2.47(s, 1H), 2.59 (m, 1 H), 2.72 (m, 1 H), 2.85 (m, 1 H), 2.96 (m, 4 H), 3.50(s, 2H), 3.68(s, 3H), 4.00 (t, J=8.33 Hz, 2 H), 4.86 (s, 2H), 6.68 (s, 1 H), 7.51 (s, 1 H).

Intermediate B182: 1-{2-[6-amino-5-(methyloxy)-2,3-dihydro-1H-indol-1-yl]-2-oxoethyl}-3-piperidinol

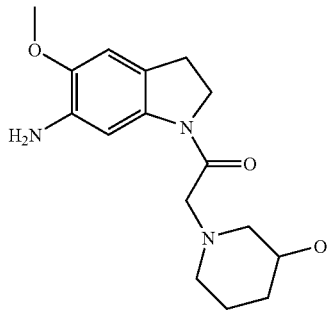

The 1-(bromoacetyl)-5-(methyloxy)-6-nitro-2,3-dihydro-1H-indole (4.0 g, 12.7 mmol) was dissolved in 50 mL of dichloromethane, then $K_2CO_3$ (4.4 g, 31.7 mmol) and 3-piperidinol (1.54 g, 15.2 mmol) in 10 mL dichloromethane were added, the reaction was stirred at RT overnight. The reaction mixture was diluted with 100 mL of water, the organic solvents were washed with water (2×100 mL), dried over $Na_2SO_4$ and the solvent was removed under reduced pressure. The resulting residue was dissolved in 10 mL of EA, 25 mL of MeOH and 15 mL of THF, then 0.8 g 10% Pd/C was added, the reaction was stirred at RT overnight under balloon $H_2$ pressure. The catalyst was removed via filtration and the solvent was removed under reduced pressure to yield 1-{2-[6-amino-5-(methyloxy)-2,3-dihydro-1H-indol-1-yl]-2-oxoethyl}-3-piperidinol as a white solid (3.0 g, 92%). $^1$HNMR (400 MHz, DMSO-$d_6$) δ ppm: 1.09 (m, 1 H), 1.44 (m, 1 H), 1.62 (m, 1 H), 1.74 (m, 1H), 2.14(br, 1H), 2.47(s, 1H), 2.74(br, 2H), 2.95 (m, 4H), 3.50(s, 2H), 3.68(s, 3H), 4.04 (t, J=6.13 Hz,2 H), 4.71 (s, 2H), 6.68 (s, 1 H), 7.51 (s, 1 H).

Intermediate B183: 6-(methyloxy)-1-(1-pyrrolidinylacetyl)-1,2,3,4-tetrahydro-7-quinolinamine

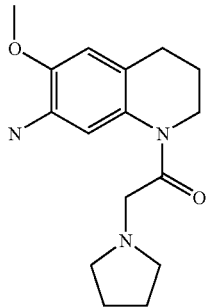

Step A : Intermediate B184: 6-(methyloxy)-7-nitro-1-(1-pyrrolidinylacetyl)-1,2,3,4-tetrahydroquinoline

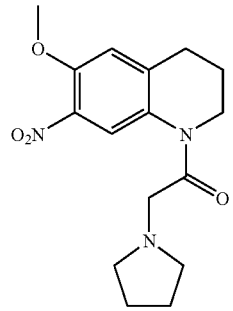

A solution of 6-(methyloxy)-7-nitro-1,2,3,4-tetrahydroquinoline (4.5 g, 21.6 mmol) in $CH_2Cl_2$ (40 mL) was added dropwise to a mixture of bromoacetylchloride (6.8 g, 43.2 mmol) and $K_2CO_3$ (6.6 g, 47.5 mmol) in $CH_2Cl_2$ (40 mL). The resulting solution was stirred at 0° C. for 1 hour, then warmed up to RT for 4 hours. Water (50 mL) was added and extracted with $CH_2Cl_2$(2×50 mL). The organic phase was dried over $Na_2SO_4$, the solvent was removed under reduced pressure, and the resulting residue was dissolved in 50 mL of dicholomethane. Potassium carbonate (6.2 g, 44.4 mmol) and pyrrolidine (4.0 g, 55.4 mmol) in 10 mL dicholomethane were added and the reaction was stirred at RT for 3 hours. After filtration, the organic layers were washed with water (2×100 mL), and dried over $Na_2SO_4$. The solvent was removed to yield the 6-(methyloxy)-7-nitro-1-(1-pyrrolidinylacetyl)-1,2,3,4-tetrahydroquinoline as a yellow solid (6.8 g, 97%). $^1$HNMR (400 MHz, DMSO-$d_6$) δ ppm 1.66 (br. s., 4 H), 1.85 (d, J=6.04 Hz, 2 H), 2.49 (br. s., 4 H), 2.79 (t, J=6.00 Hz, 2 H), 3.35 (br. s, 2 H), 3.71 (br. s., 2 H), 3.86 (s, 3 H), 7.16 (s, 1 H), 8.39 (s, 1 H)

Step B: Intermediate B183: 6-(methyloxy)-1-(1-pyrrolidinylacetyl)-1,2,3,4-tetrahydro-7-quinolinamine The 6-(methyloxy)-7-nitro-1-(1-pyrrolidinylacetyl)-1,2,3,4-tetrahydroquinoline (6.9 g, 21.6 mmol) was dissolved in 10 mL of EA, 25 mL of MeOH and 15 mL of THF, then 1.0 g 10% Pd/C was added, the reaction was stirred at RT overnight under a balloon of $H_2$ pressure. The catalyst was removed via filtration and the solvent was evaporated under reduced pressure to yield 6-(methyloxy)-1-(1-pyrrolidinylacetyl)-1,2,3,4-tetrahydro-7-quinolinamine as a white solid, 6.0 g (95%). $^1$HNMR (400 MHz, DMSO-$d_6$) δ ppm: 1.09 (m, 1 H), 1.44 (m, 1 H), 1.62 (m, 1 H), 1.74 (m, 1 H), 2.14(br, 1H), 2.47(s, 1H), 2.74(br, 2H), 2.95 (m, 4 H), 3.50(s, 2H), 3.68(s, 3H), 4.04 (t, J=6.13 Hz, 2 H), 4.71 (s, 2H), 6.68 (s, 1 H), 7.51 (s, 1 H).

Intermediate B185: 5-(methyloxy)-1-(4-morpholinylacetyl)-2,3-dihydro-1H-indol-6-amine

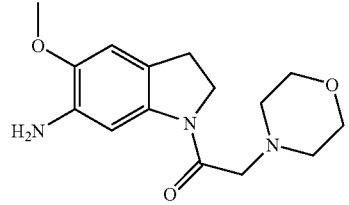

Step A/Intermediate B186: 5-(methyloxy)-1-(4-morpholinylacetyl)-6-nitro-2,3-dihydro-1H-indole

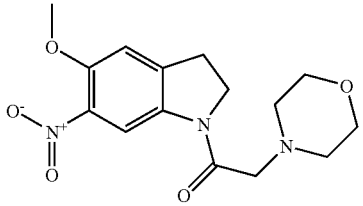

To a solution of 5-(methyloxy)-6-nitro-2,3-dihydro-1H-indole (0.5 g, 2.57 mmols) and polymer-bound diisopropyl ethylamine (2.10 g, 7.73 mmol) in dichloromethane (50 mL) was added bromoacetyl chloride (0.49 g, 3.11 mmol) via a dropwise addition. After stirring for 2 hrs at room temperature the solids were removed by vacuum filtration. The filtrate was concentrated under reduced pressure, maintained under high vacuum for several hours, redissolved in THF (20 mL) and to this crude mixture was added potassium carbonate (1.06 g, 7.68 mmols), catalytic KI, and morpholine (0.67 g, 7.68 mmols). After overnight stirring, the reaction was diluted with dichloromethane (50 mL), washed with water (25 mL), filtered through a cotton plug and concentrated by rotary evaporation to provide 5-(methyloxy)-1-(4-morpholinylacetyl)-6-nitro-2,3-dihydro-1H-indole (0.56 g, 67% over two steps). ESIMS (M+H)$^+$=322.

Step B/Intermediate B185: 5-(methyloxy)-1-(4-morpholinylacetyl)-2,3-dihydro-1H-indol-6-amine To a solution of 5-(methyloxy)-1-(4-morpholinylacetyl)-6-nitro-2,3-dihydro-1H-indole (0.56 g, 1.74 mmol) in absolute ethanol (100 mL) and DMA (20 mL) was added tin(II) chloride dihydrate (2.36 g, 10.45 mmol) and 1M HCl (1.0 mL). After overnight stirring, reaction was quenched with excess saturated NaHCO$_3$ solution, stirred for one hr, filtered through celite which was and rinsed with methanol. After organic solvent removal, the aqueous layers were extracted with dichloromethane (2×200 mL), the combined organic layers were adsorbed to silica gel and purified by column chromatography (DCM to 5% MeOH/DCM+0.1% NH$_4$OH) to afford 5-(methyloxy)-1-(4-morpholinylacetyl)-2,3-dihydro-1H-indol-6-amine. ESIMS (M+H)+=292.

Intermediate B187: 1-{[4-(1-methylethyl)-1-piperazinyl]acetyl}-5-(methyloxy)-2,3-dihydro-1H-indol-6-amine

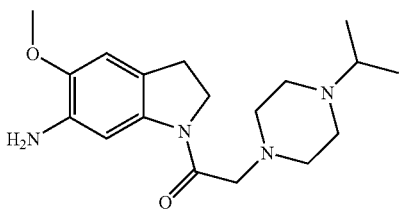

Step A/Intermediate B188: 1-{[4-(1-methylethyl)-1-piperazinyl]acetyl}-5-(methyloxy)-6-nitro-2,3-dihydro-1H-indole

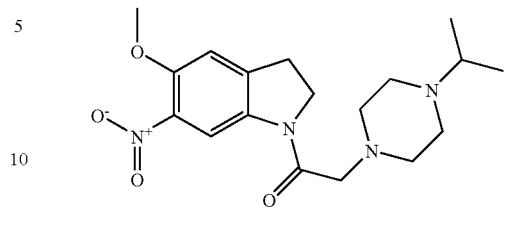

To a solution of 5-(methyloxy)-6-nitro-2,3-dihydro-1H-indole (0.5 g, 2.57 mmols) and polymer-bound diisopropyl ethylamine (2.10 g, 7.73 mmol) in dichloromethane (50 mL) was added bromoacetyl chloride (0.49 g, 3.11 mmol) via a dropwise addition. After stirring for two hrs at room temperature, the solids were removed by vacuum filtration. The filtrate was concentrated under reduced pressure, maintained under high vacuum for several hours, redissolved in THF (20 mL) and to this crude mixture was added potassium carbonate (1.06 g, 7.68 mmols), catalytic KI, and isopropyl piperazine (0.99 g, 7.68 mmols). After overnight stirring, the reaction was diluted with dichloromethane (50 mL), washed with water (25 mL), filtered through a cotton plug and concentrated by rotary evaporation to provide 1-{[4-(1-methylethyl)-1-piperazinyl]acetyl}-5-(methyloxy)-6-nitro-2,3-dihydro-1H-indole (0.60 g, 64% yield). ESIMS (M+H)+=363.

Step B/Intermediate B187: 1-{[4-(1-methylethyl)-1-piperazinyl]acetyl}-5-(methyloxy)-2,3-dihydro-1H-indol-6-amine To a solution of 1-{[4-(1-methylethyl)-1-piperazinyl]acetyl}-5-(methyloxy)-6-nitro-2,3-dihydro-1H-indole (0.60 g, 1.66 mmol) in absolute ethanol (100 mL) and DMA (20 mL) was added tin(II)chloride dihydrate (2.24 g, 9.93 mmols) and 1M HCl(1.0 mL). After overnight stirring, reaction was quenched with excess saturated NaHCO$_3$ solution, stirred for one hr, and filtered through celite which was rinsed with methanol. After organic solvent removal, the aqueous layer was extracted with dichloromethane (2×200 mL), organic layers combined, adsorbed to silica gel and purified by column chromatography (DCM to 5% MeOH/DCM+0.1% NH$_4$OH) to afford 1-{[4-(1-methylethyl)-1-piperazinyl]acetyl}-5-(methyloxy)-2,3-dihydro-1H-indol-6-amine. ESIMS (M+H)$^+$=333.

Intermediate B189: 5-(methyloxy)-1-[3-(4-morpholinyl)propanoyl]-2,3-dihydro-1H-indol-6-amine

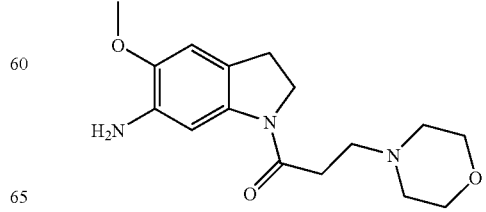

Step A/Intermediate B190: 5-(methyloxy)-1-[3-(4-morpholinyl)propanoyl]-6-nitro-2,3-dihydro-1H-indole

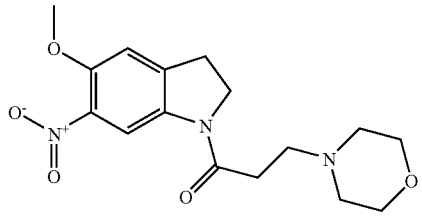

To a solution of 5-(methyloxy)-6-nitro-2,3-dihydro-1H-indole (1.0 g, 5.15 mmol) and polymer-bound diisopropyl ethylamine (4.20 g, 15.46 mmol) in dichloromethane (200 mL) was added acryloyl chloride (0.51 g, 5.67 mmol) via a dropwise addition. After stirring overnight at rt, the solids were removed by vacuum filtration and washed with dichloromethane. The filtrate was concentrated under reduced pressure, and stored under vacuum for several hours. A portion of the crude mixture (0.4 g, 1.61 mmol) was redissolved in absolute ethanol (25 mL) and to this was added morpholine (0.41 g, 4.84 mmol). After heating at 60° C. for 3 hr, the reaction was concentrated under reduced pressure and solids were recrystallized from ethyl acetate/hexanes to provide 5-(methyloxy)-1-[3-(4-morpholinyl)propanoyl]-6-nitro-2,3-dihydro-1H-indole (0.44 g, 54%). ESIMS (M+H)$^+$=336.

Step B/Intermediate B189: 5-(methyloxy)-1-[3-(4-morpholinyl)propanoyl]-2,3-dihydro-1H-indol-6-amine To a solution of 5-(methyloxy)-1-[3-(4-morpholinyl)propanoyl]-6-nitro-2,3-dihydro-1H-indole (0.44 g, 1.31 mmols) in absolute ethanol (150 mL) and DMA (20 mL) was added tin(II)chloride dihydrate (1.77 g, 7.84 mmols) and 1M HCl (3.0 mL). After overnight stirring, reaction was quenched with excess saturated Na HCO3 solution, stirred for one hr. and filtered through celite which was rinsed with methanol. After organic solvent removal, the aqueous layer was extracted with dichloromethane (2×200 mL), the organic layers were combined, adsorbed to silica gel and purified by column chromatography (DCM to 5% MeOH/DCM+0.1% NH$_4$OH) to afford 5-(methyloxy)-1-[3-(4-morpholinyl)propanoyl]-2,3-dihydro-1H-indol-6-amine. ESIMS (M+H)+=306.

Intermediate B191: 1-{3-[4-(1-methylethyl)-1-piperazinyl]propanoyl}-5-(methyloxy)-2,3-dihydro-1H-indol-6-amine

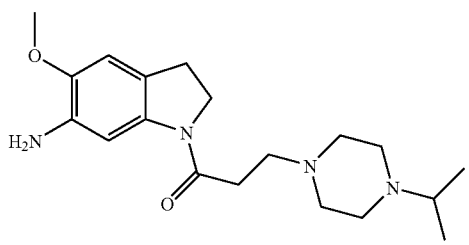

Step A/Intermediate B192: 1-{3-[4-(1-methylethyl)-1-piperazinyl]propanoyl}-5-(methyloxy)-6-nitro-2,3-dihydro-1H-indole

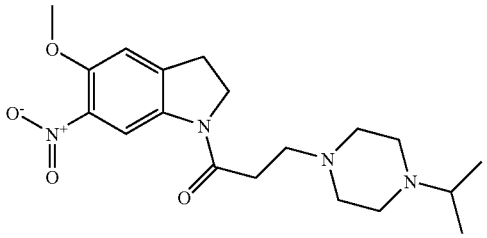

To a solution of 5-(methyloxy)-6-nitro-2,3-dihydro-1H-indole (1.0 g, 5.15 mmol) and polymer-bound diisopropyl ethylamine (4.20 g, 15.46 mmol) in dichloromethane (200 mL) was added acryloyl chloride (0.51 g, 5.67 mmol) via a dropwise addition. After stirring overnight at rt, the solids were removed by vacuum filtration and washed with dichloromethane. The filtrate was concentrated under reduced pressure and maintained under vacuum for several hours. A portion of this crude mixture (0.52 g, 2.1 mmol) was redissolved in absolute ethanol (25 mL) and to this was added isopropylpiperazine (0.81 g, 6.29 mmol). After heating at 60° C. for 3 hrs, the reaction was concentrated under reduced pressure and solids were recrystallized from ethyl acetate/hexanes to provide 1-{3-[4-(1-methylethyl)-1-piperazinyl]propanoyl}-5-(methyloxy)-6-nitro-2,3-dihydro-1H-indole (0.62 g, 79%). ESIMS (M+H)$^+$=377.

Step B/Intermediate B191: 1-{3-[4-(1-methylethyl)-1-piperazinyl]propanoyl}-5-(methyloxy)-2,3-dihydro-1H-indol-6-amine To a solution of 1-{3-[4-(1-methylethyl)-1-piperazinyl]propanoyl}-5-(methyloxy)-6-nitro-2,3-dihydro-1H-indole (0.62 g, 1.65 mmol) in absolute ethanol (150 mL) and DMA (10 mL) was added tin (II) chloride dihydrate (2.23 g, 7.84 mmol) and 1M HCl(3.0 mL). After overnight stirring, reaction was quenched with excess saturated NaHCO$_3$ solution, stirred for one hr, and filtered through a celite pad which was rinsed with methanol. After organic solvent removal, the aqueous layer was extracted with dichloromethane (2×200 mL), the organic layers were combined, adsorbed to silica gel and purified by column chromatography (DCM to 5% MeOH/DCM+0.1% NH$_4$OH) to afford 1-{3-[4-(1-methylethyl)-1-piperazinyl]propanoyl}-5-(methyloxy)-2,3-dihydro-1H-indol-6-amine. ESIMS (M+H)+=347.

Intermediate B193: 1-[(2S)-2-(dipropylamino)propanoyl]-5-(methyloxy)-2,3-dihydro-1H-indol-6-amine

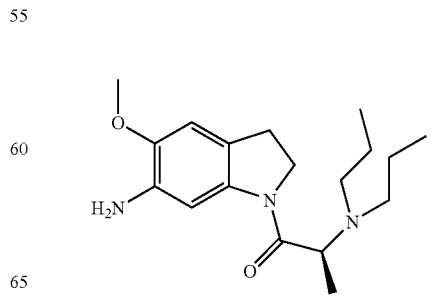

Step A/Intermediate B194: N-{(1S)-1-methyl-2-[5-(methyloxy)-6-nitro-2,3-dihydro-1H-indol-1-yl]-2-oxoethyl}-N-propyl-1-propanamine

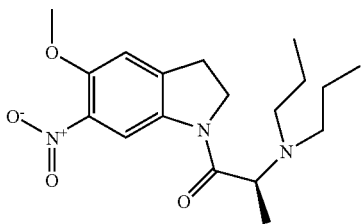

To a solution of 5-(methyloxy)-6-nitro-2,3-dihydro-1H-indole (0.8 g, 4.12 mmol) in THF (200 mL) was added EDC hydrochloride (2.37 g, 12.4 mmol), HOBT (1.67 g, 12.4 mmol), and N,N-dipropyl-L-alanine (2.14 g, 12.4 mmol). After stirring at rt for 5 days, the reaction was diluted with ethyl acetate (100 mL), washed with saturated NaHCO$_3$ (200 mL) and 1M NaOH (200 mL). The organic layer was separated, adsorbed onto silica gel, and purified by column chromatography (DCM to 5% MeOH/DCM) to provide N-{(1S)-1-methyl-2-[5-(methyloxy)-6-nitro-2,3-dihydro-1H-indol-1-yl]-2-oxoethyl}-N-propyl-1-propanamine (0.6 g, 42%). ESIMS (M+H)$^+$=350.

Step B/Intermediate B193: 1-[(2S)-2-(dipropylamino)propanoyl]-5-(methyloxy)-2,3-dihydro-1H-indol-6-amine

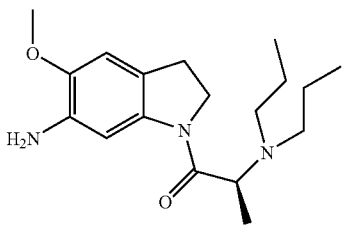

A solution of N-{(1S)-1-methyl-2-[5-(methyloxy)-6-nitro-2,3-dihydro-1H-indol-1-yl]-2-oxoethyl}-N-propyl-1-propanamine (0.6 g, 1.72 mmols) in absolute ethanol (50 mL) was maintained under 45 psi H$_{2(g)}$ with catalytic 10% Pd/C for 16 hours. The catalyst was removed by vacuum filtration through a celite pad and rinsed with methanol. The filtrate was collected, concentrated under reduced pressure, and dried under high vacuum to give 1-[(2S)-2-(dipropylamino)propanoyl]-5-(methyloxy)-2,3-dihydro-1H-indol-6-amine. ESIMS (M+H)$^+$=320.

Intermediate B195: 1-[6-amino-5-(methyloxy)-2,3-dihydro-1H-indol-1-yl]-2-methyl-1-oxo-2-propanol

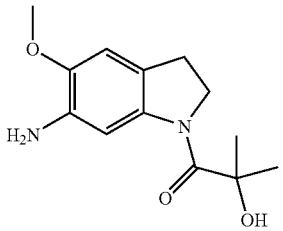

Step A/Intermediate B196: 2-methyl-1-[5-(methyloxy)-6-nitro-2,3-dihydro-1H-indol-1-yl]-1-oxo-2-propanol

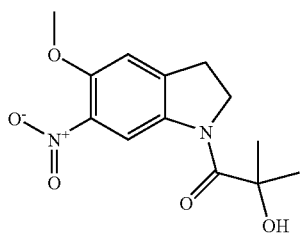

To a solution of 5-(methyloxy)-6-nitro-2,3-dihydro-1H-indole hydrochloride (1 g, 4.34 mmol) in DMF (50 mL) was added HATU (9.89 g, 26.0 mmol), 2-hydroxy-2-methylpropanoic acid (0.677 g, 6.50 mmol), and DIPEA (2.272 mL, 13.01 mmol). After stirring overnight at rt, the solvent was removed, the residue was redissolved in DCM (100 mL), washed with 1M HCl (100 mL), adsorbed to silica gel, and purified by column chromatography (10% to 40% ethyl acetate/hexanes) to afford 2-methyl-1-[5-(methyloxy)-6-nitro-2,3-dihydro-1H-indol-1-yl]-1-oxo-2-propanol (0.84 g, 69%). ESIMS (M+H)+=281.

Step B/Intermediate B195: 1-[6-amino-5-(methyloxy)-2,3-dihydro-1H-indol-1-yl]-2-methyl-1-oxo-2-propanol A solution of 2-methyl-1-[5-(methyloxy)-6-nitro-2,3-dihydro-1H-indol-1-yl]-1-oxo-2-propanol (840 mg, 3.00 mmol) in ethyl acetate (100 mL) and Ethanol (50 mL) was degassed with N$_2$ and to this was added 10% Pd/C (31.9 mg, 0.300 mmol). The reaction was maintained at 50 psi H$_{2(g)}$ overnight at rt on the Fisher-Porter apparatus. The catalyst was removed by vacuum filtration, rinsed with ethyl acetate (200 mL), and the filtrate was concentrated under reduced pressure to provide 1-[6-amino-5-(methyloxy)-2,3-dihydro-1H-indol-1-yl]-2-methyl-1-oxo-2-propanol (0.7 g, 93%). ESIMS (M+H)+=251. $^1$H NMR (400 MHz, DMSO-d6) δ ppm 1.36 (s, 6H) 2.91 (t, J=8.03 Hz, 2 H) 3.71 (s, 3 H) 4.31 (t, J=8.03 Hz, 2 H) 4.57 (s, 2 H) 5.36 (s, 1 H), 6.70 (s, 1 H) 7.57 (s, 1 H).

Intermediate B197: 1-[(2R)-2-(dimethylamino)propanoyl]-5-(methyloxy)-2,3-dihydro-1H-indol-6-amine

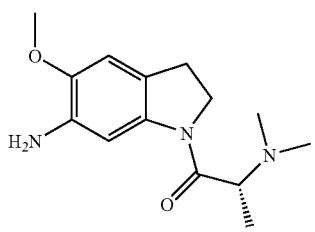

Step A/Intermediate B198: N,N-dimethyl-D-alanine

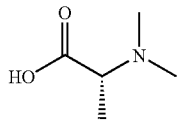

To a solution of D-alanine (30 g, 336 mmol) and 37% aqueous formaldehyde (90.5 mL, 930 mmol) in $H_2O$ (900 mL) was added 10% Pd/C (30 g) under $N_2$, the mixture was stirred at 50° C. under $H_2$ (30 psi) overnight. The mixture was heated to boiling and filtered to remove the catalyst. The solution was concentrated under reduced pressure, and then water (150 mL) was added to the mixture and concentrated, the procedure was repeated 3 times in order to remove any unreacted formaldehyde. The crude product was resuspended in $ACN/H_2O$ (1:1, v/v) and lyophilized. The solid product was recrystallized from EtOH/acetone, filtered, liberally washed with acetone, and dried under reduced pressure to give N,N-dimethyl-D-alanine (30.4 g, 77.07%) as white, very hygroscopic solid. $^1H$ NMR (400 MHz, MeOHD) δ ppm 1.41-1.49 (m, 3H), 2.8-2.85 (s, 6H), 3.6-3.65 (m, 1H), 4.9-4.95 (s, 1H)

Step B/Intermediate B199: 1-[(2R)-N,N-dimethyl-1-[5-(methyloxy)-6-nitro-2,3-dihydro-1H-indol-1-yl]-1-oxo-2-propanamine

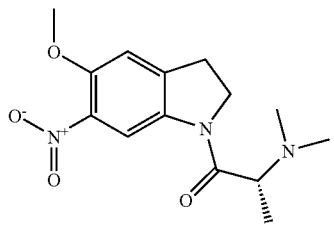

To a solution of 5-(methyloxy)-6-nitro-2,3-dihydro-1H-indole hydrogen chloride (2 g, 8.67 mmol) in N,N-dimethylformamide (100 mL) was added N,N-dimethyl-D-alanine (1.524 g, 13.01 mmol), PyBOP (13.54 g, 26.0 mmol), and DIPEA (15.14 mL, 87 mmol). After stirring overnight at rt, the solvent was removed and the residue was suspended in dichloromethane (150 mL), washed with water (100 mL), concentrated on the rotovap, and purified by column chromatography (DCM to 5% MeOH/DCM) to provide 1-[(2R)-N,N-dimethyl-1-[5-(methyloxy)-6-nitro-2,3-dihydro-1H-indol-1-yl]-1-oxo-2-propanamine (2.2 g, 86%). ESIMS $(M+H)^+=294$.

Step C/Intermediate B197: 1-[(2R)-2-(dimethylamino)propanoyl]-5-(methyloxy)-2,3-dihydro-1H-indol-6-amine To a solution of (2R)-N,N-dimethyl-1-[5-(methyloxy)-6-nitro-2,3-dihydro-1H-indol-1-yl]-1-oxo-2-propanamine (2.2 g, 7.50 mmol) in ethyl acetate (250 mL) was added Pd/C (0.798 g, 0.750 mmol) and the reaction maintained under 50 psi of $H_{2(g)}$ overnight on the Fisher-Porter. The crude material was filtered through a celite pad, washed with ethyl acetate, concentrated on the rotovap, and placed under high vacuum overnight to afford 1-[(2R)-2-(dimethylamino)propanoyl]-5-(methyloxy)-2,3-dihydro-1H-indol-6-amine (1.4 g, 71%). ESIMS $(M+H)+=264$.

Intermediate B200: 1-[(2S)-2-(dimethylamino)propanoyl]-5-(methyloxy)-2,3-dihydro-1H-indol-6-amine

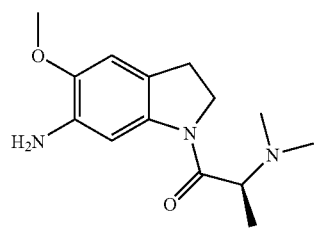

Step A/Intermediate B201: N,N-dimethyl-L-alanine

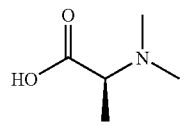

To a solution of L-alanine (30 g, 360 mmol) and 37% aqueous formaldehyde (90 mL, 930 mmol) in $H_2O$ (900 mL) was added 10% Pd/C (30 g) under $N_2$, the mixture was stirred at 50° C. under $H_2$ (30psi) overnight. The mixture was heated to boiling and filtered to remove the catalyst. The solution was concentrated under reduced pressure, and then water (150 mL) was added to the mixture and concentrated, the procedure was repeated for 3 times in order to remove any unreacted formaldehyde. The crude product was resuspended in $ACN/H_2O$ (1:1, v/v) and lyophilized. The solid product was recrystallized from EtOH/acetone, filtered, liberally washed with acetone, and dried under reduced pressure to give N,N-dimethyl-L-alanine (30.4 g, 77.07%) as white, very hygroscopic solid. $^1H$ NMR (400 MHz, MeOD) δ ppm 1.41-1.49 (d, J=7.2 Hz,3H), 2.8-2.85 (s, 6H), 3.6-3.65 (q, J=7.2 Hz,1H), 4.7-4.95 (br, 1H).

Step B/Intermediate B202: (2S)-N,N-dimethyl-1-[5-(methyloxy)-6-nitro-2,3-dihydro-1H-indol-1-yl]-1-oxo-2-propanamine

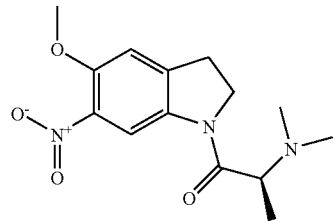

To a solution of 5-(methyloxy)-6-nitro-2,3-dihydro-1H-indole hydrogen chloride (2 g, 8.67 mmol) in N,N-dimethylformamide (100 mL) was added N,N-dimethyl-L-alanine (1.524 g, 13.01 mmol), PyBOP (13.54 g, 26.0 mmol), and DIPEA (15.14 mL, 87 mmol). After stirring overnight at rt, the solvent removed, residue suspended in dichloromethane (150 mL), washed with water (100 mL), concentrated on the rotovap, and purified by column chromatography (DCM to 5% MeOH/DCM) to give (2S)-N,N-dimethyl-1-[5-(methyloxy)-6-nitro-2,3-dihydro-1H-indol-1-yl]-1-oxo-2-propanamine (2.2 g, 86%). ESIMS (M+H)+=294.

Step C/Intermediate B200: 1-[(2S)-2-(dimethylamino)propanoyl]-5-(methyloxy)-2,3-dihydro-1H-indol-6-amine To a solution of (2S)-N,N-dimethyl-1-[5-(methyloxy)-6-nitro-2,3-dihydro-1H-indol-1-yl]-1-oxo-2-propanamine (2.2 g, 7.50 mmol) in Ethyl acetate (250 mL) was added Pd/C (0.798 g, 0.750 mmol) and the reaction was maintained under 50 psi of H$_{2(g)}$ overnight on the Fisher-Porter apparatus. The reaction was filtered through a celite pad which was washed with ethyl acetate, concentrated by rotary evaporation, and high maintained under vacuum for 12 hours to afford 1-[(2S)-2-(dimethylamino)propanoyl]-5-(methyloxy)-2,3-dihydro-1H-indol-6-amine (1.5 g, 76%). ESIMS (M+H)$^+$=264.

Intermediate B203: 2-[6-amino-5-(methyloxy)-2,3-dihydro-1H-indol-1-yl]-N,N-dimethylacetamide

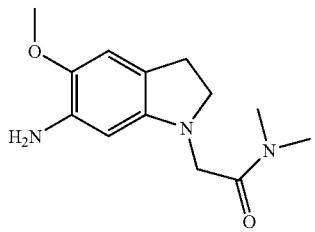

Step A/Intermediate B204: N,N-dimethyl-2-[5-(methyloxy)-6-nitro-2,3-dihydro-1H-indol-1-yl]acetamide

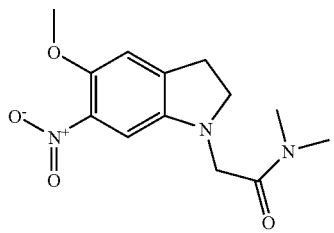

To a solution of 5-(methyloxy)-6-nitro-2,3-dihydro-1H-indole (0.7 g, 3.61 mmol) in THF (100 mL) was added 2-chloro-N,N-dimethylacetamide (1.11 g, 10.8 mmol), and potassium carbonate (2.98 g, 21.6 mmol). After heating at 65° C. for 4 days, the reaction was diluted with ethyl acetate (100 mL) and washed with water (100 mL). The organic layer was separated, adsorbed onto silica gel, and purified by column chromatography (DCM to 2% MeOH/DCM) to provide N,N-dimethyl-2-[5-(methyloxy)-6-nitro-2,3-dihydro-1H-indol-1-yl]acetamide (0.16 g, 16%). ESIMS (M+H)+=280.

Step B/Intermediate B203: 2-[6-amino-5-(methyloxy)-2,3-dihydro-1H-indol-1-yl]-N,N-dimethylacetamide A solution of N,N-dimethyl-2-[5-(methyloxy)-6-nitro-2,3-dihydro-1H-indol-1-yl]acetamide (0.16 g, 1.72 mmol) in absolute ethanol (50 mL) and ethyl acetate (5 mL) was hydrogenated overnight at 45 psi with catalytic 10% Pd/C. The catalyst was removed by vacuum filtration through a celite pad which was rinsed with methanol. The filtrate was concentrated under reduced pressure and dried under high vacuum to provide 2-[6-amino-5-(methyloxy)-2,3-dihydro-1H-indol-1-yl]-N,N-dimethylacetamide. This was then carried forward without any further purification.

Intermediate B205: 1-[(dimethylamino)acetyl]-6-(methyloxy)-2,3-dihydro-1H-indol-5-amine

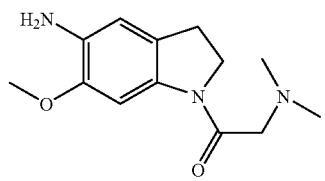

Step A/Intermediate B206: 1-acetyl-6-(methyloxy)-2,3-dihydro-1H-indole

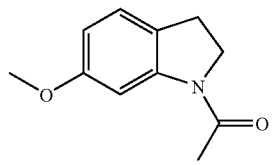

To a solution of 6-(methyloxy)-1H-indole (5.0 g, 34 mmols) in acetic acid (150 mL) was added NaBH$_3$CN (5.12 g, 81.6 mmol) in several small portions. After stirring overnight at rt, the solvent was removed, the residue redissolved in ethyl acetate (300 mL), washed with saturated NaHCO$_3$ (600 mL), filtered through a cotton plug and concentrated under reduced pressure to provide the crude indoline. ESIMS (M+H)+=150. The residue was then dissolved in glacial acetic acid (150 mL) and acetic anhydride (3.45 g, 33.86 mmol) was added. After stirring at rt for two hrs, the solvent was removed, residue resuspended in ethyl acetate (200 mL), washed with saturated NaHCO$_3$ (600 mL). The aqueous layer was extracted with ethyl acetate (200 mL). The organic layers were combined, filtered through a cotton plug, and concentrated under reduced pressure to provide 1-acetyl-6-(methyloxy)-2,3-dihydro-1H-indole which was used without any further purification. ESIMS (M+H)$^+$=192.

Step B/Intermediate B207: 6-(methyloxy)-5-nitro-2,3-dihydro-1H-indole

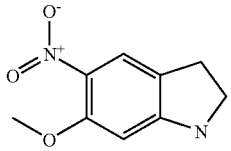

To a solution of 1-acetyl-6-(methyloxy)-2,3-dihydro-1H-indole (2.0 g, 10.5 mmol) in acetic anhydride (150 mL) at 0° C. was added 70% nitric acid (1.03 g, 11.5 mmol) via a dropwise addition. After stirring the reaction at 0° C. for 2 hrs, the contents were allowed to warm to rt, the precipitate was filtered and washed with water. The filtrate was neutralized with 5.0 M NaOH, extracted with ethyl acetate (2×200 mL). The organic layers were combined, adsorbeded onto silica gel and purified by column chromatography (DCM to 2% MeOH/DCM). The derived residue was subsequently dissolved in methanol (200 mL), followed by the addition of 4M HCl(29 mL, 116 mmol). After heating at 60° C. for 3 hrs, the solvent was removed by rotary evaporation, the residue redissolved in THF (300 mL), washed with saturated NaHCO$_3$ (300 mL) and the aqueous layer was extracted with THF (200 mL). The combined organic layers were filtered through a cotton plug, concentrated under reduced pressure, and placed under high vacuum for several hours to give 6-(methyloxy)-5-nitro-2,3-dihydro-1H-indole (1.1 g, 54% over two steps). ESIMS (M+H)+=195. 1H NMR (400 MHz, DMSO-d6) δ ppm 2.90 (t, J=8.42 Hz, 2 H) 3.58 (t, J=8.52 Hz, 2 H) 3.75-3.79 (m, 3 H) 6.10 (s, 1 H) 7.14 (s, 1 H) 7.65 (s, 1H).

Step C/Intermediate B208: N,N-dimethyl-2-[6-(methyloxy)-5-nitro-2,3-dihydro-1 H-indol-1-yl]-2-oxoethanamine

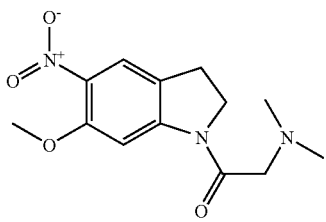

To a solution of 6-(methyloxy)-5-nitro-2,3-dihydro-1H-indole (1.1 g, 5.67 mmol) and potassium carbonate (2.34 g, 17.17 mmol) in THF (250 mL) was added bromoacetyl chloride (0.98 g, 6.23 mmols) via a dropwise addition. After stirring 2 hrs at rt, catalytic Kl was added followed by a 2.0M solution of dimethylamine in tetrahydrofuran (17 mL). After overnight stirring, the reaction was diluted with ethyl acetate and washed with water (200 mL). The organic layer was adsorbed onto silica gel and purified by column chromatography (DCM to 10% MeOH/DCM) to afford N,N-dimethyl-2-[6-(methyloxy)-5-nitro-2,3-dihydro-1H-indol-1-yl]-2-oxoethanamine (0.55 g, 35% over two steps). ESIMS (M+H)+=280.

Step D/Intermediate B205: 1-[(dimethylamino)acetyl]-6-(methyloxy)-2,3-dihydro-1H-indol-5-amine

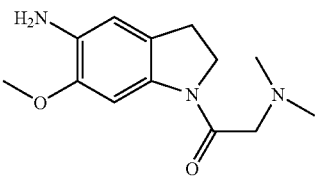

A solution of N,N-dimethyl-2-[6-(methyloxy)-5-nitro-2,3-dihydro-1H-indol-1-yl]-2-oxoethanamine (0.16 g, 1.72 mmol) in absolute ethanol (50 mL) was maintained under 45 psi H$_{2(g)}$ with catalytic 10% Pd/C for 12 hours. The catalyst was removed by vacuum filtration through a celite pad and rinsed with methanol. The filtrate was concentrated under reduced pressure and dried under high vacuum to provide 1-[(dimethylamino)acetyl]-6-(methyloxy)-2,3-dihydro-1H-indol-5-amine. This was then carried forward without any further purification. ESIMS (M+H)+=250.

Intermediate B210: 2-(methyloxy)-4-{[2-(4-methyl-1-piperazinyl)ethyl]oxy}aniline

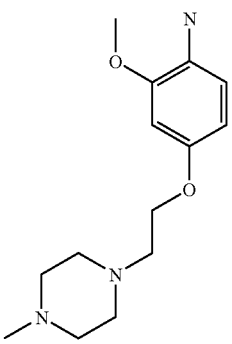

Step A\Intermediate B211: 1-methyl-4-(2-{[3-(methyloxy)-4-nitrophenyl]oxy}ethyl)piperazine

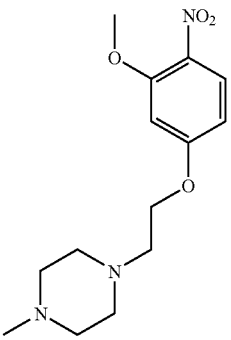

To a solution of 4-fluoro-2-(methyloxy)-1-nitrobenzene (1 g, 5.8 mmol) in 20 mL of anhydrous DMF was added 2-(4-methyl-1-piperazinyl)ethanol (1.09 g, 7.6 mmol). Sodium hydride (60%) (467 mg, 11.68 mmol) was added portionwise. The reaction was stirred at rt for 30 min at which time the reaction was diluted with ethyl acetate and washed with water and a saturated sodium chloride solution. Solvents were removed under reduced pressure to give 1.7 g of crude 1-methyl-4-(2-{[3-(methyloxy)-4-nitrophenyl]oxy}ethyl)piperazine as a yellow solid. ESIMS (M+H)+=296.

Step B\Intermediate B210: 2-(methyloxy)-4-{[2-(4-methyl-1-piperazinyl)ethyl]oxy}aniline 1-methyl-4-(2-{[3-(methyloxy)-4-nitrophenyl]oxy}ethyl)piperazine (1.7 g, 5.76 mmol) was dissolved in methanol (75 mL) and cycled through the H-Cube using a Pd/C cartridge. After an hour of cycling through the system the solvent was removed under reduced pressure to afford 2-(methyloxy)-4-{[2-(4-methyl-1-piperazinyl)ethyl]oxy}aniline as a purple sticky solid (1.3 g, 4.9 mmol). $^1$H NMR (400 MHz, DMSO-$d_6$) δ ppm 2.14 (s, 3 H) 2.18-2.48 (m, 8 H) 2.61 (t, J=5.96 Hz, 2 H), 3.73 (s, 3 H) 3.93 (t, J=5.91 Hz, 2 H) 4.23 (br. s., 2 H) 6.28 (dd, J=8.43, 2.57 Hz, 1) 6.45 (d, J=2.57 Hz, 1 H) 6.49-6.57 (m, 1 H).

Intermediate B212: 2-(methyloxy)-4-[4-(methylsulfonyl)-1-piperazinyl]aniline

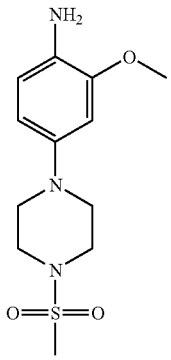

Step A\Intermediate B213: 1-[3-(methyloxy)-4-nitrophenyl]-4-(methylsulfonyl)piperazine

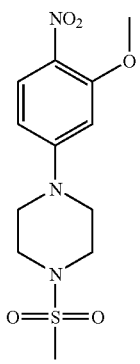

To a solution of 4-fluoro-2-(methyloxy)-1-nitrobenzene (1 g, 5.8 mmol) in 10 mL of DMSO were added 1-(methylsulfonyl)piperazine (1.15 g, 7.02 mmol), and potassium carbonate (2.42 g, 17.5 mmol). The mixture was heated at 80° C. for 16 h at which time it was poured into 100 mL of water. The resulting precipitate was filtered, washed with water and let air dry for a several hours. The solids were dried under high vacuum overnight to afford 1-[3-(methyloxy)-4-nitrophenyl]-4-(methylsulfonyl)piperazine (1.09 g, 3.46 mmol, 60%) as a yellow solid. ESIMS (M+H)+=316.

Step B\Intermediate B212: 2-(methyloxy)-4-[4-(methylsulfonyl)-1-piperazinyl]aniline 1-[3-(Methyloxy)-4-nitrophenyl]-4-(methylsulfonyl)piperazine (1.09 g, 3.46 mmol) was suspended in 5 mL THF and 10 mL MeOH in a 100 mL round bottom flask. NiCl$_2$·6H$_2$O (0.247 g, 1.04 mmol) was added, followed by slow addition of NaBH$_4$ (0.392 g, 10.38 mmol). The reaction mixture was adsorbed on SiO$_2$ and purified via column chromatography to afford 2-(methyloxy)-4-[4-(methylsulfonyl)-1-piperazinyl]aniline. (0.925 g, 3.24 mmol, 93%). $^1$H NMR (400 MHz, DMSO-$d_6$) δ ppm 2.91 (s, 3 H) 2.99-3.07 (m, 4 H) 3.19-3.27 (m, 4 H) 3.75 (s, 3 H) 4.28 (s, 2 H) 6.33 (dd, J=8.39, 2.43 Hz, 1 H) 6.49-6.58 (m, 2 H). ESIMS M+H)+=285.

Intermediate B214: 2-(methyloxy)-4-{[3-(4-methyl-1-piperazinyl)propyl]oxy}aniline

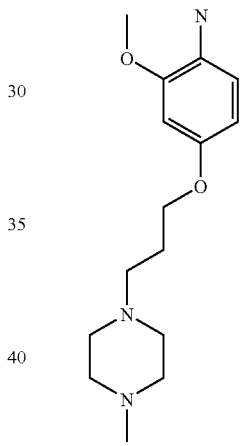

Step A\Intermediate B215 1-methyl-4-(3-{[3-(methyloxy)-4-nitrophenyl]oxy}propyl)piperazine

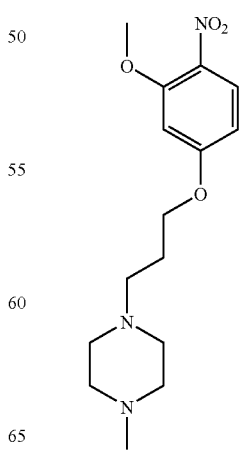

To a solution of 4-fluoro-2-(methyloxy)-1-nitrobenzene (1 g, 5.8 mmol) in 20 mL of anhydrous DMF was added 3-(4-methyl-1-piperazinyl)-1-propanol (1.2 g, 7.59 mmol). Sodium hydride (60%) (467 mg, 11.68 mmol) was added portionwise and the reaction was stirred at rt for 90 min at which time it was quenched with a solution of saturated NH$_4$Cl (5 mL) and most of the DMF was removed under reduced pressure. The residue was diluted with ethyl acetate and washed with a minimum amount of water and a saturated sodium chloride solution, dried over Na$_2$SO$_4$ and filtered. Solvents were removed under reduced pressure to give 1-methyl-4-(3-{[3-(methyloxy)-4-nitrophenyl]oxy}propyl)piperazine as a yellow solid (1.8 g total isolated, some residual DMF in product) (ESIMS (M+H)$^+$=311)

Step B\Intermediate B214: 2-(methyloxy)-4-{[3-(4-methyl-1-piperazinyl)propyl]oxy}aniline 1-methyl-4-(3-{[3-(methyloxy)-4-nitrophenyl]oxy}propyl)piperazine (1.8 g, 5.8 mmol) was dissolved in methanol (75 mL) and cycled through the H-Cube using a Pd/C cartridge. After 60 min of cycling through the system, the solvent was removed under reduced pressure. NMR indicates starting material still present so residue was dissolved in ethanol and 5% platinum on carbon (200 mg) was added and subjected to a H$_2$ balloon for 16 h. At this time the reaction mixture was filtered through celite which was washed with methanol. The solvents were evaporated under reduced pressure to afford 2-(methyloxy)-4-{[3-(4-methyl-1-piperazinyl)propyl]oxy}aniline (1.1 g, 3.75 mmol). $^1$H NMR (400 MHz, DMSO-d$_6$) δ ppm 1.83 (d, J=5.68 Hz, 2 H) 2.41-2.51 (m, 3 H overlaying with DMSO peak) 2.51-2.99 (m, 10 H) 3.68 (s, 3 H) 3.83 (t, J=6.23 Hz, 2 H) 6.24 (dd, J=8.42, 2.56 Hz, 1 H) 6.39 (d, J=2.47 Hz 1 H) 6.49 (d, J=8.42 Hz, 1 H). ESIMS (M+H)$^+$=311.

Intermediate B216: 2-(methyloxy)-4-{[(1-propyl-4-piperidinyl)methyl]oxy}aniline

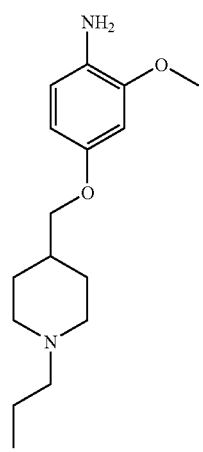

Step A\Intermediate B217: 4-({[3-(methyloxy)-4-nitrophenyl]oxy}methyl)-1-propylpiperidine

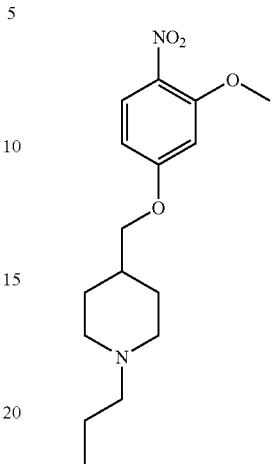

To a solution of 4-fluoro-2-(methyloxy)-1-nitrobenzene (1 g, 5.8 mmol) in 20 mL of anhydrous DMF was added 1,1-dimethylethyl 4-(hydroxymethyl)-1-piperidinecarboxylate (1.5 g, 7.0 mmol). Sodium hydride (60%) (448 mg, 11.68 mmol) was added portionwise. Reaction was stirred at rt for 60 min at which time the reaction was diluted with ethyl acetate and washed with a minimum amount of a saturated solution of sodium bicarbonate, water and a saturated sodium chloride solution, dried over Na$_2$SO$_4$ and filtered. Solvents were removed under reduced pressure and the resulting residue was dissolved in dichloromethane (20 mL) and trifluoroacetic acid (4.5 mL, 58.4 mmol) was added and the mixture was stirred for 30 min at rt. Solvents were removed under reduced pressure and the resulting residue was dissolved in acetonitrile (20 mL) and 1-iodopropane (0.63 mL, 6.4 mmol) and potassium carbonate (2.4 g, 17.52 mmol) were added and stirred at rt for 16 h. Subsequently the reaction mixture was diluted with ethyl acetate and washed with a saturated sodium bicarbonate solution, water and a saturated sodium chloride solution. The organic layer was dried over Na$_2$SO$_4$ and filtered. Solvents were removed under reduced pressure and the residue was purified by SiO$_2$ chromatography to afford 4-({[3-(methyloxy)-4-nitrophenyl]oxy}methyl)-1-propylpiperidine (0.9 g, 2.92 mmol). (ESIMS (M+H)$^+$=309)

Step B\Intermediate B216: 2-(methyloxy)-4-{[(1-propyl-4-piperidinyl)methyl]oxy}aniline To a solution of 4-({[3-(methyloxy)-4-nitrophenyl]oxy}methyl)-1-propylpiperidine (0.913 g, 3.0 mmol) in 20 mL of ethanol was added 5% platinum on carbon (100 mg) and subjected to a H$_2$ balloon for 40 h. At this time reaction mixture was filtered through celite which was rinsed with methanol. Solvents were evaporated under reduced pressure to afford 2-(methyloxy)-4-{[3-(4-methyl-1-piperazinyl)propyl]oxy}aniline (0.769 g, 2.77 mmol). $^1$H NMR (400 MHz, DMSO-d$_6$) δ ppm 0.87 (t, J=7.38 Hz, 3 H) 1.30-1.49 (m, 2 H) 1.48-1.63 (m, 2 H) 1.73-1.93 (m, 3 H) 2.55-2.77 (m, 2 H) 3.06-3.51 (m, 4 H) 3.65-3.76 (m, 5 H) 4.02-4.54 (m, 2 H), 6.28 (dd, J=8.43, 2.57 Hz, 1 H) 6.44 (d, J=2.47 Hz, 1 H) 6.48-6.57 (m, 1 H). ESIMS (M+H)$^+$=279.

Intermediate B218: 2-(methyloxy)-4-[4-(methylsulfonyl)hexahydro-1H-1,4-diazepin-1-yl]aniline

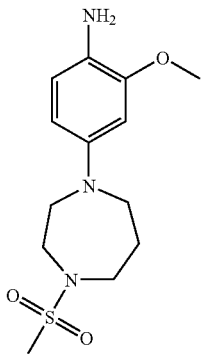

Step A\Intermediate B219: 1-[3-(methyloxy)-4-nitrophenyl]hexahydro-1H-1,4-diazepine (TFA salt)

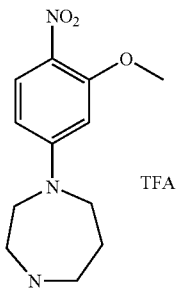

To a solution of 4-fluoro-2-(methyloxy)-1-nitrobenzene (2.32 g, 13.56 mmol) in DMSO (50 mL) was added 1,1-dimethylethyl hexahydro-1H-1,4-diazepine-1-carboxylate (3.0 g, 15 mmol) and potassium carbonate (5.6 g, 41 mmol). Reaction was heated at 80° C. for 16 h at which time the reaction was diluted with ethyl acetate and washed with a saturated solution of sodium bicarbonate, water and a saturated sodium chloride solution, dried over $Na_2SO_4$ and filtered. Solvents were removed under reduced pressure and the resulting residue was dissolved in dichloromethane (50 mL) and trifluoroacetic acid (12.2 mL, 158.7 mmol) was added and let stir for 40 min at rt. Subsequently, the reaction was diluted with ethyl acetate and washed with a saturated solution of sodium bicarbonate, water and a saturated sodium chloride solution, dried over $Na_2SO_4$ and filtered. Solvents were removed under reduced pressure to afford 1-[3-(methyloxy)-4-nitrophenyl]hexahydro-1H-1,4-diazepine as the TFA salt. (7.6 g, 15.8 mmol). ESIMS $(M+H)^+=253$.

Step B\Intermediate B220: 1-[3-(methyloxy)-4-nitrophenyl]-4-(methylsulfonyl)hexahydro-1H-1,4-diazepine

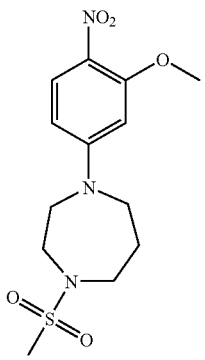

1-[3-(methyloxy)-4-nitrophenyl]hexahydro-1H-1,4-diazepine (as the TFA salt) (1.0 g, 2.08 mmol) was dissolved in dichloromethane (10 mL) and triethylamine (0.87 mL, 6.25 mmol). Methanesulfonyl chloride (0.24 mL, 3.12 mmol) was added slowly and stirred at rt for 30 min. At this time the reaction mixture was diluted with dichloromethane and washed with a saturated bicarbonate solution, water and a saturated sodium chloride solution, dried over $Na_2SO_4$ and filtered. Solvents were removed under reduced pressure to afford 1-[3-(methyloxy)-4-nitrophenyl]-4-(methylsulfonyl)hexahydro-1H-1,4-diazepine. (0.737 g, 2.24 mmol) as a yellow/brown solid. ESIMS $(M+H)^+=330$.

Step C\Intermediate B218: 2-(methyloxy)-4-[4-(methylsulfonyl)hexahydro-1H-1,4-diazepin-1-yl]aniline 1-[3-(methyloxy)-4-nitrophenyl]-4-(methylsulfonyl)hexahydro-1H-1,4-diazepine (0.737g, 2.24 mmol) was suspended in 5 mL THF and 10 mL MeOH in a 100 mL round bottom flask. $NiCl_2 \cdot 6H_2O$ (159 mg, 0.672 mmol) was added followed by slow addition of $NaBH_4$ (254 mg, 6.72 mmol). Reaction mixture was adsorbed onto $SiO_2$ and purified via column chromatography to afford 2-(methyloxy)-4-[4-(methylsulfonyl)hexahydro-1H-1,4-diazepin-1-yl]aniline (340 mg, 51%) $^1$H NMR (400 MHz, DMSO-$d_6$) δ ppm 1.82-1.94 (m, 2 H) 2.80 (s, 3 H) 3.17 (t, J=5.82 Hz, 2 H) 3.36-3.43 (m, 2 H) 3.49 (dd, J=10.68, 3.99 Hz, 4 H) 3.75 (br. s., 3 H) 4.01-4.15 (m, 2 H) 6.10-6.20 (m, 1 H) 6.26-6.35 (m, 1 H) 6.48-6.59 (m, 1 H). ESIMS $(M+H)^+$ 301

Intermediate B221: 4-[4-(1-methylethyl)hexahydro-1H-1,4-diazepin-1-yl]-2-(methyloxy)aniline

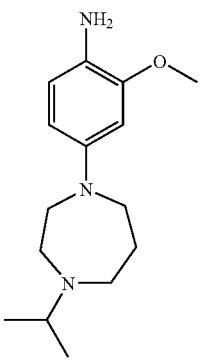

Step A\Intermediate B222 1-(1-methylethyl)-4-[3-(methyloxy)-4-nitrophenyl]hexahydro-1H-1,4-diazepine

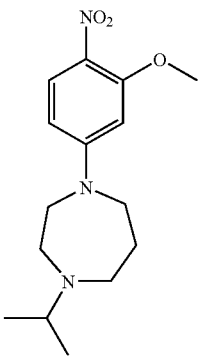

1-[3-(methyloxy)-4-nitrophenyl]hexahydro-1H-1,4-diazepine (580 mg, 2.3 mmol) was dissolved in acetonitrile (10 mL). Potassium carbonate (952 mg, 6.9 mmol) and 1-iodopropane (0.344 mL, 3.45 mmol) were added. Reaction was stirred at it for 60 h. At this time the reaction mixture was diluted with dichloromethane and washed with a saturated sodium bicarbonate solution, water and a saturated sodium chloride solution, dried over $Na_2SO_4$ and filtered. Solvents were removed under reduced pressure and purified by $SiO_2$ chromatography to afford 1-(1-methylethyl)-4-[3-(methyloxy)-4-nitrophenyl]hexahydro-1H-1,4-diazepine (0.565 g, 1.92 mmol). ESIMS $(M+H)^+$=295.

Step B\Intermediate B221: 4-[4-(1-methylethyl)hexahydro-1H-1,4-diazepin-1-yl]-2-(methyloxy)aniline 1-(1-methylethyl)-4-[3-(methyloxy)-4-nitrophenyl]hexahydro-1H-1,4-diazepine (0.565 g, 1.92 mmol) was suspended in 5 mL THF and 10 mL MeOH. $NiCl_2 \cdot 6H_2O$ (138 mg, 0.576 mmol) was added followed by slow addition of $NaBH_4$ (218 mg, 5.76 mmol). The reaction mixture was adsorbed on $SiO_2$ and purified via column chromatography to afford 4-[4-(1-methylethyl)hexahydro-1H-1,4-diazepin-1-yl]-2-(methyloxy)aniline (364 mg, 1.38 mmol). $^1$H NMR (400 MHz, DMSO-$d_6$) δ ppm 0.89-1.06 (m, 6 H) 1.71-1.88 (m, 2 H) 2.69 (br. s., 2 H) 2.81-2.97 (m, 1 H) 3.23-3.47 (m, 6H) 3.66-3.77 (m, 3 H) 3.82-4.27 (m, 2 H) 6.08 (br. s., 1 H) 6.25 (br. s., 1 H) 6.49 (br. s., 1 H). ESIMS $(M+H)^+$=264.

Intermediate B223: 4-(4-methylhexahydro-1H-1,4-diazepin-1-yl)-2-(methyloxy)aniline

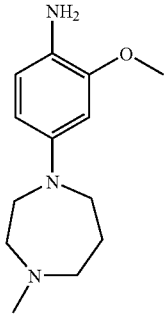

Step A\Intermediate B224: 1-methyl-4-[3-(methyloxy)-4-nitrophenyl]hexahydro-1H-1,4-diazepine

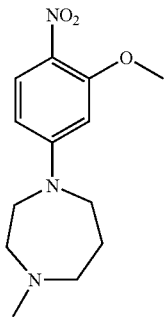

To a solution of 4-fluoro-2-(methyloxy)-1-nitrobenzene (1.0 g, 5.85 mmol) in 15 mL of DMSO was added 1-methylhexahydro-1H-1,4-diazepine (0.8 mL, 6.42 mmol) and potassium carbonate (2.4 g, 17.4 mmol). The reaction mixture was heated at 80° C. for 16 h at which time the reaction was diluted with ethyl acetate and washed with a saturated solution of sodium bicarbonate, water and a saturated sodium chloride solution, dried over $Na_2SO_4$ and filtered. Solvents were removed under reduced pressure to give 1-methyl-4-[3-(methyloxy)-4-nitrophenyl]hexahydro-1H-1,4-diazepine (1.77 g, 6.67 mmol) as a yellow solid containing residual DMSO. ESIMS $(M+H)^+$=266

Step B\Intermediate B223: 4-(4-methylhexahydro-1H-1,4-diazepin-1-yl)-2-(methyloxy)aniline To a solution of 1-methyl-4-[3-(methyloxy)-4-nitrophenyl]hexahydro-1H-1,4-diazepine (1.77 g, 6.67 mmol) in 15 mL of ethanol (with 1 mL DMF added to aid solubility) was added 5% platinum on carbon (200 mg) and subjected to a $H_2$ balloon for 16 h. At this time the reaction mixture was filtered through celite and washed with methanol. Solvents were evaporated under reduced pressure to afford 4-(4-methylhexahydro-1H-1,4-diazepin-1-yl)-2-(methyloxy)aniline (1.46 g, 6.2 mmol, contains residual DMF). $^1$H NMR (400 MHz, DMSO-$d_6$) δ ppm 1.85 (ddd, J=11.55, 6.05, 5.87 Hz, 2 H) 2.24 (s, 3 H) 2.39-2.47 (m, 2 H) 2.54-2.60 (m, 2 H) 3.28-3.36 (m, 2 H) 3.36-3.42 (m, 2H) 3.73 (s, 3 H) 3.93 (s, 2 H) 6.07 (dd, J=8.43, 2.66 Hz, 1 H) 6.23 (d, J=2.57 Hz, 1 H) 6.49 (d, J=8.43 Hz, 1 H)

Intermediate B225: 2-[3-(dimethylamino)propanoyl]-6-(methyloxy)-1,2,3,4-tetrahydro-7-isoquinolinamine

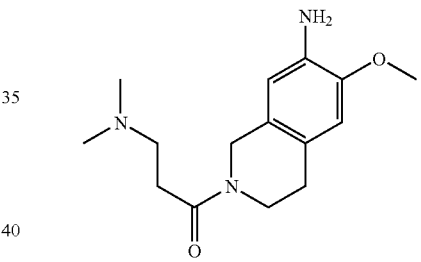

Step A/Intermediate B226: 2-acryloyl-6-(methyloxy)-7-nitro-1,2,3,4-tetrahydroisoquinoline

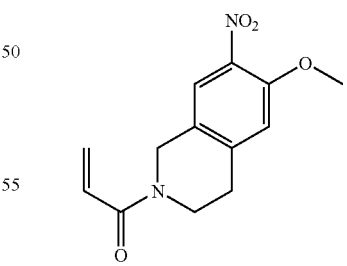

A solution of 6-(methyloxy)-7-nitro-1,2,3,4-tetrahydroisoquinoline (1.6 g, 7.7 mmol) in dichloromethane (30 mL) was treated with acryloyl chloride (1.9 mL, 23 mmol, TCl), triethylamine (3.2 mL, 23 mmol, Aldrich), and catalytic 4-dimethylaminopyridine (50 mg 0.41 mmol, Aldrich). The mixture was stirred for 16 h, diluted with excess water, and extracted with ethyl acetate. The organic layer was separated, dried over magnesium sulfate, filtered, and concentrated to provide 2-acryloyl-6-(methyloxy)-7-nitro-1,2,3,4-tetrahydroisoquinoline (1.7 g, 84%). $^1$H NMR (400 MHz, DMSO-$d_6$) is complicated due to amide rotomers δ ppm 2.86-2.95 (two triplets at 2.88 and 2.93, 2 H), 3.72-3.82 (two triplets at 3.74 and 3.80, 2 H), 3.89 (m, 3 H), 4.63-4.80 (two singlets at 4.65 and 4.77, 2 H), 5.73 (app d, J=10.3 Hz, 1 H), 6.16 (dd, J=16.7, 2.4 Hz, 1 H), 6.89 (dd, J=16.9, 10.3 Hz, 1 H), 7.21 (s, 1 H), 7.78-7.84 (two singlets at 7.79 and 7.83, 1 H); ESIMS (M+H)$^+$=263.

Step B/Intermediate B227: N,N-dimethyl-3-[6-(methyloxy)-7-nitro-3,4-dihydro-2(1 H)-isoquinolinyl]-3-oxo-1-propanamine

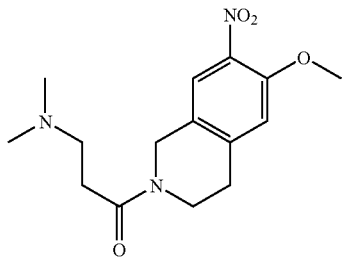

A solution of 2-acryloyl-6-(methyloxy)-7-nitro-1,2,3,4-tetrahydroisoquinoline (0.8 g, 3 mmol) in methanol (10 mL) was treated with dimethyl amine (10 mL, 2 M in THF, 20 mmol, Aldrich) and heated at 65° C. in a sealed tube for 16 h. The mixture was cooled, concentrated, and partitioned between ethyl acetate and saturated aqueous ammonium chloride. The organic layer was separated, dried over magnesium sulfate, filtered, and purified by chromatography on SiO$_2$ (dichloromethane to 20% methanol/dichloromethane) to give N,N-dimethyl-3-[6-(methyloxy)-7-nitro-3,4-dihydro-2(1 H)-isoquinolinyl]-3-oxo-1-propanamine (0.65 g, 71%). ESIMS (M+H)$^+$=308.

Step C/Intermediate B225: 2-[3-(dimethylamino)propanoyl]-6-(methyloxy)-1,2,3,4-tetrahydro-7-isoquinolinamine A solution of N,N-dimethyl-3-[6-(methyloxy)-7-nitro-3,4-dihydro-2(1H)-isoquinolinyl]-3-oxo-1-propanamine (0.65 g, 2.1 mmol) in ethanol (10 mL) was treated with 10% palladium on carbon (70 mg, Aldrich), and stirred under 60 psi of hydrogen pressure for 16 h in a Fischer-Porter apparatus. The pressure was released, the reaction vessel evacuated, and back-filled with nitrogen twice. The mixture was filtered through celite and the filtrate was concentrated to provide 2-[3-(dimethylamino)propanoyl]-6-(methyloxy)-1,2,3,4-tetrahydro-7-isoquinolinamine (0.58 g, 2.1 mmol, 99%). $^1$H NMR (400 MHz, DMSO-$d_6$) is complicated due to amide rotomers d ppm 2.14 (s, 6 H), 2.46-2.52 (m, signals beneath DMSO, 4 H), 2.55-2.73 (m, two triplets at 2.58 and 2.69, 2 H), 3.58-3.63 (m, 2 H), 3.72 (s, 3 H), 4.37-4.48 (two singlets at 4.38 and 4.45, 2 H), 4.54-4.61 (two broad singlets at 4.55 and 4.58, 2 H), 6.38-6.42 (two singlets at 6.39 and 6.41, 1 H), 6.56-6.59 (two singlets at 6.56 and 6.57, 1 H); ESIMS (M+H)$^+$=278.

Intermediate B228: 6-(methyloxy)-2-[3-(4-morpholinyl)propanoyl]-1,2,3,4-tetrahydro-7-isoquinolinamine

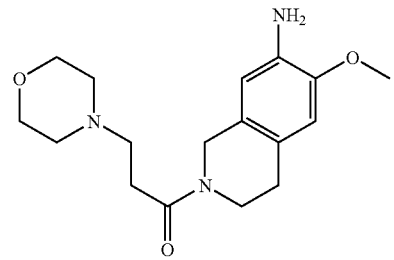

Step A/Intermediate B229: 6-(methyloxy)-2-[3-(4-morpholinyl)propanoyl]-7-nitro-1,2,3,4-tetrahydroisoquinoline

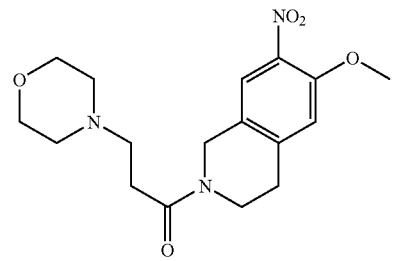

A solution of 2-acryloyl-6-(methyloxy)-7-nitro-1,2,3,4-tetrahydroisoquinoline (425 mg, 1.62 mmol) in methanol (5 mL) was treated with morpholine (1.00 mL, 11.5 mmol, Aldrich) and heated at 65° C. in a sealed tube for 16 h. The mixture was cooled, concentrated, and partitioned between ethyl acetate and saturated aqueous ammonium chloride. The organic layer was separated, dried over magnesium sulfate, filtered, and purified by chromatography on SiO$_2$ (dichloromethane to 25% methanol/dichloromethane) to give 6-(methyloxy)-2-[3-(4-morpholinyl)propanoyl]-7-nitro-1,2,3,4-tetrahydroisoquinoline. This material was taken directly to the next step without a determination of yield. $^1$H NMR (400 MHz, DMSO-$d_6$) is complicated by amide rotomers δ ppm 2.32-2.41 (m, 4 H), 2.52-2.62 (m, 4 H), 2.79-2.97 (two app triplets at 2.83 and 2.94, 2 H), 3.48-3.58 (m, 4 H), 3.63-3.72 (m, 2 H), 3.89 (s, 3 H), 4.55-4.69 (two singlets at 4.57 and 4.67, 2 H), 7.18-7.21 (m, 1 H), 7.80 (s, 1 H); ESIMS (M+H)$^+$=350.

Step B/Intermediate B228: 6-(methyloxy)-2-[3-(4-morpholinyl)propanoyl]-1,2,3,4-tetrahydro-7-isoquinolinamine 6-(methyloxy)-2-[3-(4-morpholinyl)propanoyl]-7-nitro-1,2,3,4-tetrahydroisoquinoline (assumed 1.62 mmol from previous reaction) was dissolved in dimethylformamide (3.0 mL) and diluted with ethanol (10 mL). The solution was treated with tin (II) chloride dihydrate (2.2 g, 9.6 mmol, Aldrich), hydrochloric acid (1.0 mL, 1.0 mmol, 1 M in water), and stirred for 16 h. Excess saturated aqueous sodium bicarbonate was added carefully and the observed white suspension was stirred for 1 h. The mixture was filtered through celite. The filtrate was concentrated and purified by chromatography on $SiO_2$ (dichloromethane to 20% methanol/dichloromethane) to give 6-(methyloxy)-2-[3-(4-morpholinyl)propanoyl]-1,2,3,4-tetrahydro-7-isoquinolinamine (350 mg, 1.10 mmol, 68% over two steps) which was slightly contaminated with DMF. 1H NMR (400 MHz, DMSO-$d_6$) is complicated by amide rotomers d ppm 2.31-2.41 (m, 4 H), 2.52-2.71 (m, 6 H), 3.50-3.57 (m, 4 H), 3.57-3.62 (m, 2 H), 3.72 (s, 3 H), 4.37-4.47 (two singlets at 4.38 and 4.45, 2 H), 4.54-4.61 (two broad singlets at 4.56 and 4.59, 2 H), 6.38-6.41 (two singlets at 6.39 and 6.40, 1 H), 6.55-6.58 (two singlets at 6.56 and 6.57, 1 H); ESIMS (M+H)$^+$=320.

Intermediate B230: 2-{3-[4-(1-methylethyl)-1-piperazinyl]propanoyl}-6-(methyloxy)-1,2,3,4-tetrahydro-7-isoquinolinamine

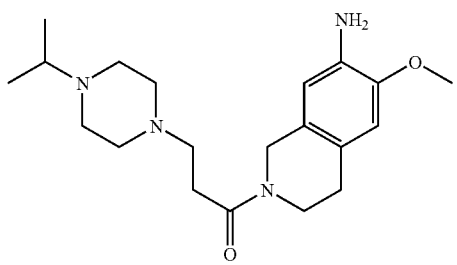

Step A/Intermediate B231: 2-{3-[4-(1-methylethyl)-1-piperazinyl]propanoyl}-6-(methyloxy)-7-nitro-1,2,3,4-tetrahydroisoquinoline

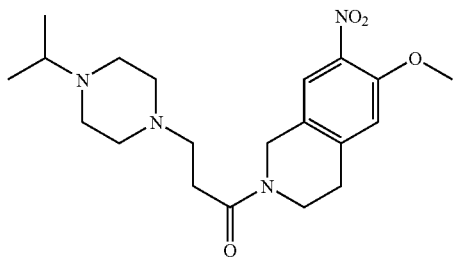

A solution of 2-acryloyl-6-(methyloxy)-7-nitro-1,2,3,4-tetrahydroisoquinoline (425 mg, 1.62 mmol) in methanol (5 mL) was treated with 1-isopropylpiperzine (1.0 mL, 7.0 mmol, Oakwood Products) and heated at 65° C. in a sealed tube for 16 h. The mixture was cooled, concentrated, and partitioned between ethyl acetate and saturated aqueous ammonium chloride. The organic layer was separated, dried over magnesium sulfate, filtered, and purified by chromatography on $SiO_2$ (dichloromethane to 25% methanol/dichloromethane) to give 2-{3-[4-(1-methylethyl)-1-piperazinyl]propanoyl}-6-(methyloxy)-7-nitro-1,2,3,4-tetrahydroisoquinoline (285 mg, 0.731 mmol, 45%). ESIMS (M+H)$^+$=391.

Step B/Intermediate B230: 2-{3-[4-(1-methylethyl)-1-piperazinyl]propanoyl}-6-(methyloxy)-1,2,3,4-tetrahydro-7-isoquinolinamine A solution of 2-{3-[4-(1-methylethyl)-1-piperazinyl]propanoyl}-6-(methyloxy)-7-nitro-1,2,3,4-tetrahydroisoquinoline (285 g, 0.731 mmol) in ethanol (10 mL) was treated with 10% palladium on carbon (30 mg, Aldrich), and stirred under 60 psi of hydrogen pressure for 16 h in a Fischer-Porter apparatus. The pressure was released, the reaction vessel evacuated, and back-filled with nitrogen twice. The mixture was filtered through celite and the filtrate was concentrated to provide 2-{3-[4-(1-methylethyl)-1-piperazinyl]propanoyl}-6-(methyloxy)-1,2,3,4-tetrahydro-7-isoquinolinamine (0.26 g, 0.72 mmol, 99%). $^1$H NMR (400 MHz, DMSO-$d_6$) is complicated due to amide rotomers δ ppm 0.92-0.98 (m, 6 H), 2.30-2.71 (m, some signals underneath DMSO, 15 H), 3.56-3.63 (m, 2 H), 3.72 (s, 3 H), 4.37-4.47 (two singlets at 4.38 and 4.45, 2 H), 4.53-4.59 (two broad singlets at 4.55 and 4.58, 2 H), 6.38-6.42 (two singlets at 6.39 and 6.41, 1 H), 6.55-6.58 (two singlets at 6.56 and 6.57, 1 H); ESIMS (M+H)$^+$=361.

Intermediate B232: 2-[3-(dimethylamino)propyl]-6-(methyloxy)-1,2,3,4-tetrahydro-7-isoquinolinamine

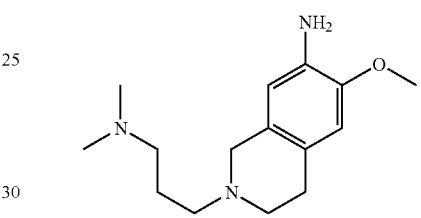

A solution of 2-[3-(dimethylamino)propanoyl]-6-(methyloxy)-1,2,3,4-tetrahydro-7-isoquinolinamine (335 mg, 1.21 mmol) in tetrahydrofuran (10 mL) was treated with lithium aluminum hydride (10 mL, 1 M in diethyl ether, 10 mmol, Aldrich). The mixture was refluxed for 16 h, cooled, quenched carefully via sequential addition of water (0.4 mL), 15% aqueous sodium hydroxide (0.4 mL), and then water (1.2 mL) again. The mixture was stirred vigorously for 1 h and then filtered through a pad of celite. The filtrate was concentrated to provide 2-[3-(dimethylamino)propyl]-6-(methyloxy)-1,2,3,4-tetrahydro-7-isoquinolinamine (284 mg, 1.08 mmol, 90%). $^1$H NMR (400 MHz, DMSO-$d_6$) δ ppm 1.55-1.65 (m, J=7.2, 7.2, 7.2, 7.2 Hz, 2 H), 2.11 (s, 6 H), 2.19-2.24 (m, 2 H), 2.36-2.41 (m, 2 H), 2.54 (t, J=6.0 Hz, 2 H), 2.63 (t, J=5.4 Hz, 2 H), 3.34-3.41 (m, 2 H), 3.70 (s, 3 H), 4.44 (s, 2 H), 6.28 (s, 1 H), 6.48 (s, 1 H); ESIMS (M+H)$^+$=264.

Intermediate B233: 1-[3-(dimethylamino)propanoyl]-6-(methyloxy)-1,2,3,4-tetrahydro-7-quinolinamine

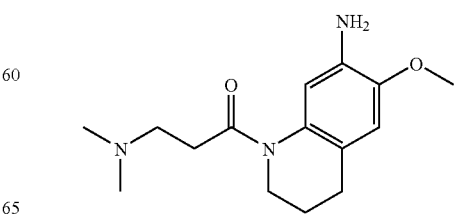

Step A/Intermediate B234: 1-acryloyl-6-(methyloxy)-7-nitro-1,2,3,4-tetrahydroquinoline

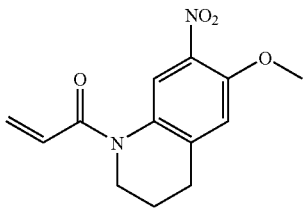

A mixture of 6-(methyloxy)-7-nitro-1,2,3,4-tetrahydroquinoline (0.19 g, 0.91 mmol) and triethylamine (0.5 mL, 3.6 mmol, Aldrich) in dichloromethane was treated with dropwise addition of acryloyl chloride (0.3 mL, 3.7 mmol, Pfaltz and Bauer). A catalytic amount of 4-dimethylaminopyridine was added and the reaction stirred overnight. The mixture was diluted with saturated aqueous ammonium chloride and extracted with ethyl acetate. The organic layer was dried over magnesium sulfate, filtered, and concentrated to give 1-acryloyl-6-(methyloxy)-7-nitro-1,2,3,4-tetrahydroquinoline which was taken directly to the next step without determination of yield. ESIMS $(M+H)^+=263$.

Step B/Intermediate B235: N,N-dimethyl-3-[6-(methyloxy)-7-nitro-3,4-dihydro-1(2H)-quinolinyl]-3-oxo-1-propanamine

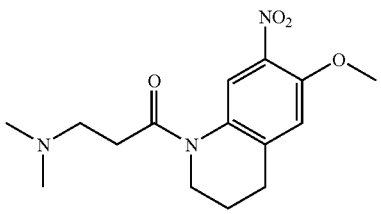

1-acryloyl-6-(methyloxy)-7-nitro-1,2,3,4-tetrahydroquinoline (crude from previous reaction, assumed 0.91 mmol) was dissolved in methanol (5 mL), treated with excess dimethyl amine (5.0 mL, 10 mmol, 2 M in THF, Aldrich), and the reaction heated in a sealed tube at 65° C. for 16 h. The mixture was cooled, concentrated, and partitioned between ethyl acetate and saturated aqueous sodium bicarbonate. The aqueous layer was separated and then back-extracted with dichloromethane. The organic layers were combined, dried over magnesium sulfate, filtered, and concentrated to give N,N-dimethyl-3-[6-(methyloxy)-7-nitro-3,4-dihydro-1(2H)-quinolinyl]-3-oxo-1-propanamine which was taken directly to the next step without determination of yield. $^1$H NMR (400 MHz, DMSO-$d_6$) δ ppm 1.83-1.94 (m, 2 H), 2.18 (bs, 6 H), 2.56-2.71 (m, 4 H), 2.80 (t, J=6.4 Hz, 2 H), 3.71 (t, J=6.0 Hz, 2 H), 3.90 (s, 3 H), 7.20 (s, 1 H), 8.27 (very broad singlet due to amide rotomers, 1 H); ESIMS $(M+H)^+=308$.

Step C/Intermediate B233: 1-[3-(dimethylamino)propanoyl]-6-(methyloxy)-1,2,3,4-tetrahydro-7-quinolinamine N,N-dimethyl-3-[6-(methyloxy)-7-nitro-3,4-dihydro-1 (2H)-quinolinyl]-3-oxo-1-propanamine (crude from previous reaction, assumed 0.91 mmol) was dissolved in methanol (10 mL), treated with 10% palladium on carbon (50 mg, Aldrich), and stirred under 60 psi of hydrogen pressure for 16 h in a Fischer-Porter apparatus. The pressure was released, the reaction vessel evacuated, and back-filled with nitrogen twice. The mixture was filtered through celite and the filtrate was concentrated to provide 1-[3-(dimethylamino)propanoyl]-6-(methyloxy)-1,2,3,4-tetrahydro-7-quinolinamine (0.24 g, 93% over three steps). $^1$H NMR (400 MHz, DMSO-$d_6$) δ ppm 1.74-1.85 (m, 2 H), 2.09 (bs, 6 H), 2.51-2.60 (m, some signals may be underneath DMSO, 6 H), 3.58 (t, J=6.4 Hz, 2 H), 3.74 (s, 3 H), 4.60 (bs, 2 H), 6.60 (s, broadening due to amide rotomers, 2 H); ESIMS $(M+H)^+=278$.

Intermediate B236: 1-[(dimethylamino)acetyl]-6-(methyloxy)-1,2,3,4-tetrahydro-7-quinolinamine

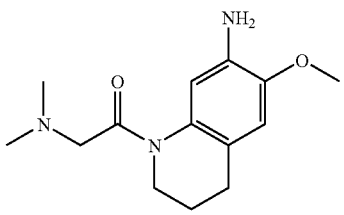

Step A/Intermediate B237: 1-(bromoacetyl)-6-(methyloxy)-7-nitro-1,2,3,4-tetrahydroquinoline

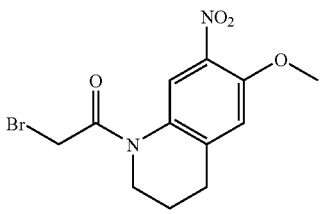

A mixture of 6-(methyloxy)-7-nitro-1,2,3,4-tetrahydroquinoline (0.19 g, 0.91 mmol) and triethylamine (0.5 mL, 3.7 mmol, Aldrich) in dichloromethane was treated with dropwise addition of bromoacetyl chloride (0.33 mL, 4.0 mmol, Fluka). A catalytic amount of 4-dimethylaminopyridine was added and the reaction stirred overnight. The mixture was diluted with saturated aqueous ammonium chloride and extracted with dichloromethane. The organic layer was dried over magnesium sulfate, filtered, and concentrated to give 1-(bromoacetyl)-6-(methyloxy)-7-nitro-1,2,3,4-tetrahydroquinoline which was taken directly to the next step without determination of yield. RF=0.3 (50% EtOAc/hexanes).

Step B/Intermediate B238: N,N-dimethyl-2-[6-(methyloxy)-7-nitro-3,4-dihydro-1(2H)-quinolinyl]-2-oxoethanamine

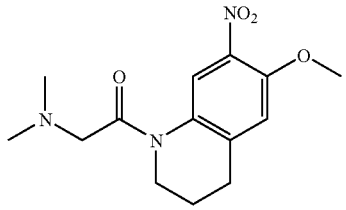

1-(bromoacetyl)-6-(methyloxy)-7-nitro-1,2,3,4-tetrahydroquinoline (crude from previous reaction, assumed 0.91 mmol) was treated with excess dimethyl amine (4.5 mL, 9.0 mmol, 2 M in THF, Aldrich), and the reaction stirred for 16 h. The mixture was partitioned between ethyl acetate and saturated aqueous sodium bicarbonate.

The organic layer was dried over magnesium sulfate, filtered, and concentrated to give N,N-dimethyl-2-[6-(methyloxy)-7-nitro-3,4-dihydro-1 (2H)-quinolinyl]-2-oxoethanamine which was taken directly to the next step without determination of yield. $^1$H NMR (400 MHz, DMSO-$d_6$) δ ppm 1.85-1.95 (m, 2 H), 2.22 (s, 6 H), 2.82 (t, J=6.6 Hz, 2 H), 3.22 (bs, 2 H), 3.72-3.79 (m, 2 H), 3.89 (s, 3 H), 7.19 (s, 1 H), 8.37 (bs, 1 H); ESIMS (M+H)$^+$=294.

Step C/Intermediate B236: 1-[(dimethylamino)acetyl]-6-(methyloxy)-1,2,3,4-tetrahydro-7-quinolinamine N,N-dimethyl-2-[6-(methyloxy)-7-nitro-3,4-dihydro-1 (2H)-quinolinyl]-2-oxoethanamine (crude from previous reaction, assumed 0.91 mmol) was dissolved in methanol (5 mL), treated with 10% palladium on carbon (40 mg, Aldrich), and stirred under 60 psi of hydrogen pressure for 16 h in a Fischer-Porter apparatus. The pressure was released, the reaction vessel evacuated, and back-filled with nitrogen twice. The mixture was filtered through celite, the filtrate was concentrated and purified by chromatography on SiO$_2$ (0 to 20% methanol/dichloromethane) to provide 1-[(dimethylamino)acetyl]-6-(methyloxy)-1,2,3,4-tetrahydro-7-quinolinamine (0.18 g, 0.68 mmol, 75% over three steps). $^1$H NMR (400 MHz, CDCl$_3$) δ ppm 1.88-1.97 (m, J=6.5, 6.5, 6.5, 6.5 Hz, 2 H), 2.35 (s, 6 H), 2.65 (m, 2 H), 3.24 (s, 2 H), 3.74-3.80 (m, 2 H), 3.84 (s, 3 H), 6.55 (s, 1 H), 6.76 (very broad singlet due to amide rotomers, 1 H), aniline NH$_2$ not visible probably due to fast exchange.

Intermediate B239: 6-(methyloxy)-1-(1-piperidinylacetyl)-1,2,3,4-tetrahydro-7-quinolinamine

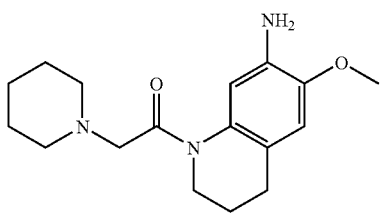

Step A/Intermediate B240: 6-(methyloxy)-7-nitro-1-(1-piperidinylacetyl)-1,2,3,4-tetrahydroquinoline

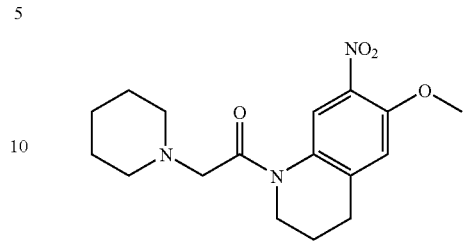

1-(bromoacetyl)-6-(methyloxy)-7-nitro-1,2,3,4-tetrahydroquinoline (0.66 g, 2.0 mmol) was dissolved in tetrahydrofuran (10 mL), treated with piperidine (0.2 mL, 2.0 mmol, Aldrich) and potassium carbonate (0.83 g, 6.0 mmol, Aldrich). The reaction was stirred for 12 h. The mixture was partitioned between ethyl acetate and saturated aqueous ammonium chloride. The organic layer was separated, dried over magnesium sulfate, filtered, and purified by chromatography on SiO$_2$ (0 to 20% methanol/dichloromethane spiked with aqueous ammonia) to provide 6-(methyloxy)-7-nitro-1-(1-piperidinylacetyl)-1,2,3,4-tetrahydroquinoline (0.50 g, 75%). $^1$H NMR (400 MHz, DMSO-$d_6$) δ ppm 1.34-1.60 (m, 6 H), 1.86-1.95 (m, 2 H), 2.29-2.40 (m, 4 H), 2.77-2.86 (m, 2 H), 3.21 (bs, 2 H), 3.70-3.78 (m, 2 H), 3.89 (s, 3 H), 7.19 (s, 1 H), 8.38 (bs, 1 H).

Step B/Intermediate B239: 6-(methyloxy)-1-(1-piperidinylacetyl)-1,2,3,4-tetrahydro-7-quinolinamine 6-(methyloxy)-7-nitro-1-(1-piperidinylacetyl)-1,2,3,4-tetrahydroquinoline (0.50 g, 1.5 mmol) was dissolved in a mixture of methanol (10 mL) and water (0.2 mL), treated with 10% palladium on carbon (75 mg, Aldrich), and stirred under 60 psi of hydrogen pressure for 16 h in a Fischer-Porter apparatus. The pressure was released, the reaction vessel evacuated, and back-filled with nitrogen twice. The mixture was filtered through celite and the filtrate was concentrated to provide 6-(methyloxy)-1-(1-piperidinylacetyl)-1,2,3,4-tetrahydro-7-quinolinamine (0.43 g, 93%). $^1$H NMR (400 MHz, DMSO-$d_6$) δ ppm 1.30-1.62 (m, 6 H), 1.78-1.88 (m, 2 H), 2.29-2.41 (m, 4 H), 2.53-2.63 (m, 2 H), 3.18 (s, 2 H), 3.58-3.66 (m, 2 H), 3.72 (s, 3 H), 4.53 (s, 2 H), 6.56 (s, 1 H). 6.86 (very broad singlet due to amide rotomers, 1H).

Intermediate B241: 2-(2-fluoroethyl)-6-(methyloxy)-1,2,3,4-tetrahydro-7-isoquinolinamine

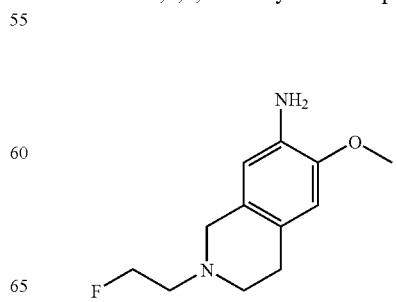

Step A/Intermediate B242: 2-(2-fluoroethyl)-6-(methyloxy)-7-nitro-1,2,3,4-tetrahydroisoquinoline

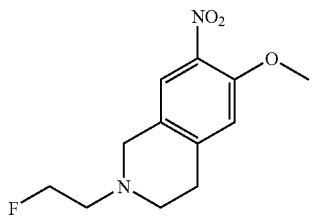

6-(methyloxy)-7-nitro-1,2,3,4-tetrahydroisoquinoline (222 mg, 1.07 mmol) was taken in acetonitrile (5 mL), treated with 1-iodo-2-fluoroethane (0.40 g, 2.3 mmol) and potassium carbonate (500 mg, 3.62 mmol, Aldrich). The mixture was heated at 65° C. for 16 h, cooled, and partitioned between ethyl acetate and water. The organic layer was separated, dried over magnesium sulfate, filtered, and concentrated to provide 2-(2-fluoroethyl)-6-(methyloxy)-7-nitro-1,2,3,4-tetrahydroisoquinoline which was taken directly to the next step without determination of yield. $^1$H NMR (400 MHz, CDCl$_3$) δ ppm 2.89-3.04 (m, 6 H), 3.77 (s, 2 H), 3.94 (s, 3 H), 4.62-4.80 (dt, J$_{HF}$=47.6, J=4.6 Hz, 2 H), 6.82 (s, 1 H), 7.63 (s, 1 H); ESIMS (M+H)$^+$=255.

Step B/Intermediate B241: 2-(2-fluoroethyl)-6-(methyloxy)-1,2,3,4-tetrahydro-7-isoquinolinamine 2-(2-fluoroethyl)-6-(methyloxy)-7-nitro-1,2,3,4-tetrahydroisoquinoline (assumed 1.07 mmol from previous reaction) was dissolved in ethyl acetate (5 mL), treated with 10% palladium on carbon (50 mg, Aldrich), and then diluted with methanol (10 mL). The mixture was stirred under 60 psi of hydrogen pressure for 16 h in a Fischer-Porter apparatus. The pressure was released, the reaction vessel evacuated, and back-filled with nitrogen twice. The mixture was filtered through celite and the filtrate was concentrated to provide 2-(2-fluoroethyl)-6-(methyloxy)-1,2,3,4-tetrahydro-7-isoquinolinamine (239 mg, 100%). $^1$H NMR (400 MHz, CDCl$_3$) δ ppm 2.80-2.93 (m, 6 H), 3.51 (bs, 2 H), 3.61 (s, 2 H), 3.80 (s, 3 H), 4.58-4.75 (dt, J$_{HF}$=47.6, J=4.9 Hz, 2 H), 6.37 (s, 1 H), 6.50 (s, 1 H).

Intermediate B243: 2-(1-methylethyl)-6-(methyloxy)-1,2,3,4-tetrahydro-7-isoquinolinamine

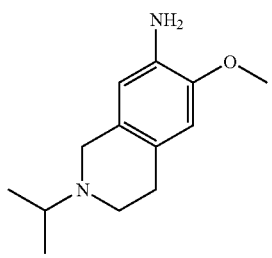

Step A/Intermediate B244: 2-(1-methylethyl)-6-(methyloxy)-7-nitro-1,2,3,4-tetrahydroisoquinoline

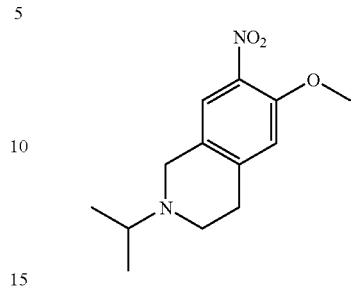

6-(methyloxy)-7-nitro-1,2,3,4-tetrahydroisoquinoline (222 mg, 1.07 mmol) was taken in acetonitrile (5 mL), treated with 2-iodopropane (0.8 mL, 5.0 mmol) and potassium carbonate (600 mg, 4.35 mmol, Aldrich). The mixture was heated at 65° C. for 16 h, cooled, and partitioned between ethyl acetate and water. The organic layer was separated, dried over magnesium sulfate, filtered, concentrated, and purified by chromatography on SiO$_2$ (0 to 20% methanol/dichloromethane spiked with aqueous ammonia) to provide 2-(1-methylethyl)-6-(methyloxy)-7-nitro-1,2,3,4-tetrahydro isoquinoline (0.24 g, 88%). $^1$H NMR (400 MHz, CDCl$_3$) δ ppm 1.16 (d, J=6.4 Hz, 6 H), 2.76-2.84 (m, 2 H), 2.90-3.00 (m, 3 H), 3.70 (s, 2 H), 3.93 (s, 3 H), 6.80 (s, 1 H), 7.64 (s, 1 H); ESIMS (M+H)$^+$=251.

Step B/Intermediate B243: 2-(1-methylethyl)-6-(methyloxy)-1,2,3,4-tetrahydro-7-isoquinolinamine 2-(1-methylethyl)-6-(methyloxy)-7-nitro-1,2,3,4-tetrahydroisoquinoline (0.24 g, 0.94 mmol) was dissolved in ethyl acetate (5 mL), treated with 10% palladium on carbon (50 mg, Aldrich), and then diluted with methanol (10 mL). The mixture was stirred under 60 psi of hydrogen pressure for 16 h in a Fischer-Porter apparatus. The pressure was released, the reaction vessel evacuated, and back-filled with nitrogen twice. The mixture was filtered through celite and the filtrate was concentrated to provide 2-(1-methylethyl)-6-(methyloxy)-1,2,3,4-tetrahydro-7-isoquinolinamine (206 mg, 0.94 mmol, 100%). $^1$H NMR (400 MHz, CDCl$_3$) δ ppm 1.13 (d, J=6.6 Hz, 6 H), 2.71-2.81 (m, 4 H), 2.87 (tt, J=6.5, 6.5 Hz, 1 H), 3.59 (s, 2 H), 3.63 (bs, 2 H), 3.81 (s, 3 H), 6.40 (s, 1 H), 6.50 (s, 1 H).

Intermediate B245: 6-(methyloxy)-2-(1-methylpropyl)-1,2,3,4-tetrahydro-7-isoquinolinamine

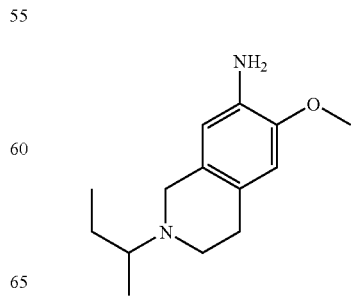

Step A/Intermediate B246 : 6-(methyloxy)-2-(1-methylpropyl)-7-nitro-1,2,3,4-tetrahydroisoquinoline

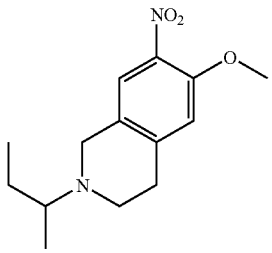

6-(methyloxy)-7-nitro-1,2,3,4-tetrahydroisoquinoline (222 mg, 1.07 mmol) was dissolved in acetonitrile (5 mL), treated with 2-iodobutane (0.40 mL, 3.5 mmol) and potassium carbonate (500 mg, 3.62 mmol, Aldrich). The mixture was heated at 65° C. for 16 h, cooled, and partitioned between ethyl acetate and water. The organic layer was separated, dried over magnesium sulfate, filtered, concentrated, and purified by chromatography on SiO$_2$ (0 to 20% methanol/dichloromethane spiked with aqueous ammonia) to provide 6-(methyloxy)-2-(1-methylpropyl)-7-nitro-1,2,3,4-tetrahydro isoquinoline (0.23 g, 0.89 mmol, 82%). $^1$H NMR (400 MHz, CDCl$_3$) δ ppm 0.96 (t, J=7.2 Hz, 3 H), 1.06-1.18 (m, 3 H), 1.37-1.48 (m, 1 H), 1.63 (m, signal overlapped with H$_2$O, 1 H), 2.64-3.08 (m, 5 H), 3.63-3.85 (m, 2 H), 3.93 (s, 3 H), 6.81 (s, 1 H), 7.63 (s, 1 H); ESIMS (M+H)$^+$=265.

Step B/Intermediate B245: 6-(methyloxy)-2-(1-methylpropyl)-1,2,3,4-tetrahydro-7-isoquinolinamine 6-(methyloxy)-2-(1-methylpropyl)-7-nitro-1,2,3,4-tetrahydroisoquinoline (0.23 g, 0.87 mmol) was dissolved in ethyl acetate (5 mL), treated with 10% palladium on carbon (50 mg, Aldrich), and then diluted with methanol (10 mL). The mixture was stirred under 60 psi of hydrogen pressure for 16 h in a Fischer-Porter apparatus. The pressure was released, the reaction vessel evacuated, and back-filled with nitrogen twice. The mixture was filtered through celite and the filtrate was concentrated to provide 6-(methyloxy)-2-(1-methylpropyl)-1,2,3,4-tetrahydro-7-isoquinolinamine (196 mg, 96%). 1H NMR (400 MHz, CDCl$_3$) δ ppm 0.90 (t, J=7.4 Hz, 3 H), 1.02 (d, J=6.6 Hz, 3 H), 1.28-1.40 (m, 1 H), 1.59-1.69 (m, 1 H), 2.56-2.75 (m, 5 H), 3.48-3.67 (m, 4 H), 3.77 (s, 3 H), 6.35 (s, 1 H), 6.47 (s, 1 H).

Intermediate B247: 1-acetyl-6-(methyloxy)-1,2,3,4-tetrahydro-7-quinolinamine

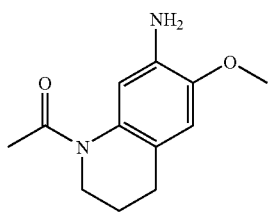

Step A/Intermediate B248: 1-acetyl-6-(methyloxy)-7-nitro-1,2,3,4-tetrahydroquinoline

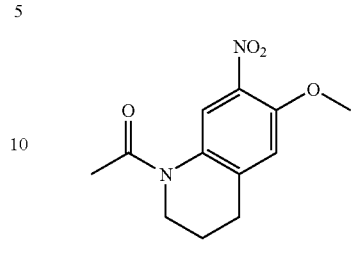

A solution of 1-acetyl-6-(methyloxy)-1,2,3,4-tetrahydroquinoline (500 mg, 2.44 mmol, Aldrich) in trifluoroacetic acid (4 mL, Aldrich) was treated with sodium nitrite (169 mg, 2.45 mmol, added slowly in about 4 portions, Aldrich). The dark brown reaction was stirred for 2 h and then poured over ice. The mixture was extracted with ethyl acetate and the organic layer was separated, dried over magnesium sulfate, filtered, concentrated, and purified by chromatography on SiO$_2$ (0 to 100% ethyl acetate/hexanes) to give 1-acetyl-6-(methyloxy)-7-nitro-1,2,3,4-tetrahydroquinoline (357 mg, 59%). $^1$H NMR (400 MHz, DMSO-d$_6$) is complicated due to amide rotamers δ ppm 1.83-1.94 (m, 2 H), 2.14-2.25 (m, 3 H), 2.76-2.85 (m, 2 H), 3.64-3.73 (m, 2 H), 3.86-3.92 (m, 3 H), 7.14-7.25 (m, 1 H), 8.38 (very broad singlet, 1H).

Step B/Intermediate B247: 1-acetyl-6-(methyloxy)-1,2,3,4-tetrahydro-7-quinolinamine A solution of 1-acetyl-6-(methyloxy)-7-nitro-1,2,3,4-tetrahydroquinoline (350 mg, 1.40 mmol) in ethyl acetate (20 mL) was taken in a Fischer Porter apparatus and treated with 10% palladium on carbon (100 mg, Aldrich). After rinsing the sides of the flask with ethyl acetate, methanol (30 mL) was added and the mixture was stirred under 60 psi hydrogen pressure for 16 h. The pressure was released, the reaction vessel evacuated, and back-filled with nitrogen twice. The mixture was filtered through celite and the filtrate was concentrated to provide 1-acetyl-6-(methyloxy)-1,2,3,4-tetrahydro-7-quinolinamine (270 mg, 1.23 mmol, 88%). $^1$H NMR (400 MHz, DMSO-d$_6$) δ ppm 1.74-1.86 (m, 2 H), 2.06-2.13 (m, 3 H), 2.53-2.61 (m, 2 H), 3.56-3.61 (m, 2 H), 3.73 (s, 3 H), 4.55 (bs, 2 H), 6.46-6.91 (m, broadened signals caused by amide rotomers, 2 H).

Intermediate B249: 7-amino-6-(methyloxy)-3,4-dihydro-2(1H)-quinolinone

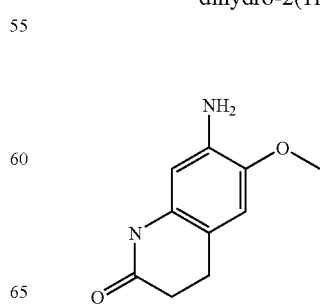

Step A/Intermediate B250: 6-(methyloxy)-7-nitro-3,4-dihydro-2(1H)-quinolinone

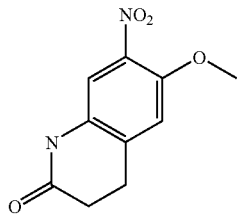

A solution of 6-(methyloxy)-3,4-dihydro-2(1H)-quinolinone (400 mg, 2.25 mmol, Precursor Chemicals) in trifluoroacetic acid (4 mL, Aldrich) was treated with sodium nitrite (156 mg, 2.26 mmol, added slowly in about 4 portions, Aldrich). The dark brown reaction was stirred for 1 h after which an aliquot was taken out, diluted with water and extracted with ethyl acetate. TLC analysis of the ethyl acetate layer revealed that starting material remained. More sodium nitrite (50 mg, 0.72 mmol) was added and the reaction stirred for another 2 h at which point some precipitation was observed in the reaction. The reaction was poured over ice and then extracted with ethyl acetate. The organic layer, which still had undissolved solids in it, was concentrated to give 6-(methyloxy)-7-nitro-3,4-dihydro-2(1H)-quinolinone (372 mg, 70%) as a white powder. $^1$H NMR (400 MHz, DMSO-$d_6$) δ ppm 2.45-2.49 (m, 2 H), 2.98 (t, J=7.5 Hz, 2 H), 3.88 (s, 3 H), 7.29 (s, 1 H), 7.38 (s, 1 H), 10.18 (bs, 1 H).

Step B/Intermediate B249: 7-amino-6-(methyloxy)-3,4-dihydro-2(1H)-quinolinone

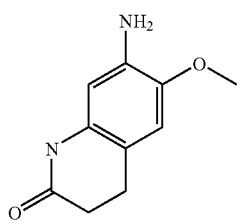

6-(methyloxy)-7-nitro-3,4-dihydro-2(1H)-quinolinone (485 mg, 2.18 mmol) was taken in ethyl acetate (10 mL) and methanol (50 mL). Dimethylformamide (10 mL) was added and the mixture heated to ensure dissolution. 10% palladium on carbon (581 mg, Aldrich) was added and the reaction stirred under 60 psi hydrogen pressure for 16 h. The pressure was released, the reaction vessel evacuated, and back-filled with nitrogen twice. The mixture was filtered through celite and the filtrate was concentrated to provide 7-amino-6-(methyloxy)-3,4-dihydro-2(1H)-quinolinone (387 mg, 2.02 mmol, 92%). $^1$H NMR (400 MHz, DMSO-$d_6$) δ ppm 2.32-2.37 (m, 2 H), 2.66-2.72 (m, 2 H), 3.69 (s, 3 H), 4.63 (s, 2 H), 6.20 (s, 1 H), 6.60 (s, 1 H), 9.70 (s, 1 H); ESIMS (M+H)$^+$=193.

Intermediate B251: 1-[(dimethylamino)acetyl]-4,4-dimethyl-6-(methyloxy)-1,2,3,4-tetrahydro-7-quinolinamine

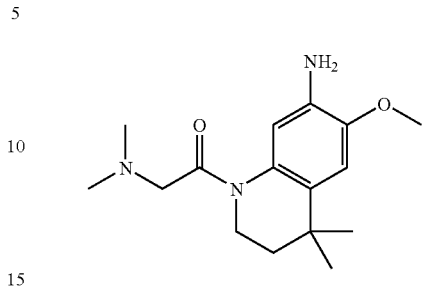

Step A/Intermediate B252: 3-methyl-N-[4-(methyloxy)phenyl]-2-butenamide

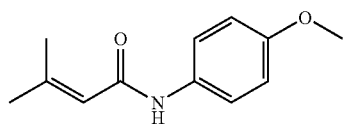

A mixture of p-anisidine (10 g, 81 mmol, Aldrich) and potassium carbonate (13.5 g, 97.5 mmol, Aldrich) in acetone (125 mL) was cooled to 0° C. and treated with dimethyl acryloyl chloride (10.2 mL, 89.3 mmol). The mixture was allowed to warm to room temperature overnight. The reaction was diluted with water and extracted with dichloromethane. The organic layer was separated, dried over magnesium sulfate, filtered, concentrated, and purified by chromatography on SiO$_2$ (0 to 100% ethyl acetate/dichloromethane) to give 3-methyl-N[4-(methyloxy)phenyl]-2-butenamide (12.4 g, 67%) as a light violet solid. $^1$H NMR (400 MHz, DMSO-$d_6$) δ ppm 1.84 (s, 3 H), 2.13 (s, 3 H), 3.71 (s, 3 H), 5.82 (s, 1 H), 6.85 (d, J=9.0 Hz, 2 H), 7.52 (d, J=9.0 Hz, 2 H), 9.67 (s, 1 H); ESIMS (M+H)$^+$=206.

Step B/Intermediate B253: 4,4-dimethyl-6-(methyloxy)-3,4-dihydro-2(1H)-quinolinone

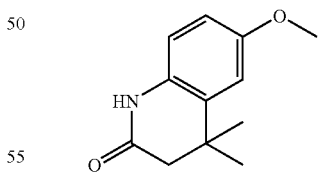

A solution of 3-methyl-N-[4-(methyloxy)phenyl]-2-butenamide (5.8 g, 28 mmol) in dichloromethane (250 mL) was treated with aluminum trichloride (13 g, 97 mmol, Aldrich). The mixture was refluxed for 7 h, cooled, and then poured over ice. The organic layer was separated, dried over magnesium sulfate, filtered, and concentrated to give 4,4-dimethyl-6-(methyloxy)-3,4-dihydro-2(1H)-quinolinone (4.5 g, 77%). $^1$H NMR (400 MHz, DMSO-$d_6$) δ ppm 1.20 (s, 6 H), 2.29 (s, 2 H), 3.71 (s, 3 H), 6.72-6.81 (m, 2 H), 6.83 (d, J=2.6 Hz, 1 H), 9.97 (s, 1 H).

Step C/Intermediate B254: 4,4-dimethyl-6-(methyloxy)-7-nitro-3,4-dihydro-2(1H)-quinolinone

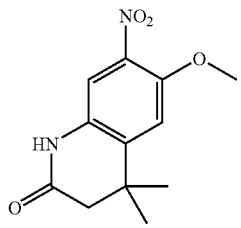

A solution of 4,4-dimethyl-6-(methyloxy)-3,4-dihydro-2(1H)-quinolinone (4.45 g, 21.7 mmol) in trifluoroacetic acid (110 mL) was treated at 0° C. with sodium nitrite (1.9 g, 28 mmol, Aldrich). The dark brown mixture was allowed to warm to room temperature overnight. Analysis of an aliquot of the reaction mixture by $^1$H NMR revealed that starting material still remained. Another 1.15 g (16.7 mmol) of sodium nitrite was added as three installments of 300/500/350 mg at room temperature and the reaction stirred for 3/3/20 h respectively. The reaction mixture was concentrated, dissolved in dichloromethane, and washed with saturated aqueous sodium bicarbonate. The organic layer was separated and the aqueous layer, filtered (due to emulsions), and back-extracted with dichloromethane. The combined organic layers were dried over magnesium sulfate, filtered, concentrated, and triturated with dichloromethane/diethyl ether/hexanes. The mixture was filtered to obtain pure product (3.6 g) and the filtrate was purified by column chromatography on SiO$_2$ (0 to 100% ethyl acetate/dichloromethane) to obtain another 350 mg of 4,4-dimethyl-6-(methyloxy)-7-nitro-3,4-dihydro-2(1H)-quinolinone (a total of 3.97 g, 15.8 mmol, 73%). $^1$H NMR (400 MHz, DMSO-d$_6$) δ ppm 1.28 (s, 6 H), 2.39 (s, 2 H), 3.92 (s, 3 H), 7.21 (s, 1 H), 7.40 (s, 1 H), 10.25 (s, 1 H).

Step D/Intermediate B255: 4,4-dimethyl-6-(methyloxy)-7-nitro-1,2,3,4-tetrahydroquinoline

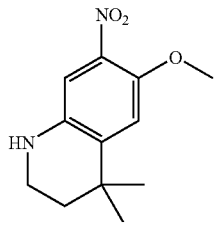

A solution of 4,4-dimethyl-6-(methyloxy)-7-nitro-3,4-dihydro-2(1H)-quinolinone (2.5 g, 10 mmol) in tetrahydrofuran (45 mL) was treated with borane-dimethylsulfide complex (20.5 mL, 41 mmol, 2 M in THF, Acros Organics). The mixture was heated at reflux for 16 h, cooled, quenched carefully via dropwise of excess methanol, concentrated, and purified by column chromatography on SiO$_2$ (0 to 100% ethyl acetate/dichloromethane) to obtain 4,4-dimethyl-6-(methyloxy)-7-nitro-1,2,3,4-tetrahydroquinoline (1.33 g, 5.63 mmol, 56%). $^1$H NMR (400 MHz, DMSO-d$_6$) δ ppm 1.26 (s, 6 H), 1.58-1.65 (m, 2 H), 3.13-3.21 (m, 2 H), 3.79 (s, 3 H), 5.95 (bs, 1 H), 6.96 (s, 1 H), 7.06 (s, 1 H).

Step E/Intermediate B256: 1-(bromoacetyl)-4,4-dimethyl-6-(methyloxy)-7-nitro-1,2,3,4-tetrahydroquinoline

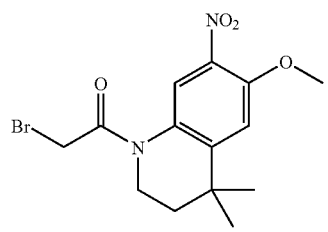

4,4-dimethyl-6-(methyloxy)-7-nitro-1,2,3,4-tetrahydroquinoline (1.32 g, 5.59 mmol) was dissolved in tetrahydrofuran (50 mL). This solution was treated with potassium carbonate (1.54 g, 11.2 mmol, Aldrich) and cooled to 0° C. Bromoacetyl chloride (0.93 mL, 11 mmol, Fluka) was added (white precipitation observed) and the reaction stirred for 15 min. The reaction mixture was then diluted with water and extracted with ethyl acetate. The organic layer was dried over magnesium sulfate, filtered, and concentrated to give 1-(bromoacetyl)-4,4-dimethyl-6-(methyloxy)-7-nitro-1,2,3,4-tetrahydroquinoline (assumed 5.59 mmol, 100%). This material was analyzed by $^1$H NMR (amide rotamers were observed) and taken to bromide displacement reactions directly without further purification. $^1$H NMR (400 MHz, DMSO-d$_6$) δ ppm 1.33 (s, 6 H), 1.75-1.86 (m, 2 H), 3.72-3.82 (m, 2 H), 3.95 (s, 3 H), 4.31-4.69 (two singles at 4.37 and 4.63, 2 H), 7.27 (s, 1 H), 8.28 (very broad singlet, 1 H).

Step F/Intermediate B257: {2-[4,4-dimethyl-6-(methyloxy)-7-nitro-3,4-dihydro-1(2H)-quinolinyl]-2-oxoethyl}dimethylamine

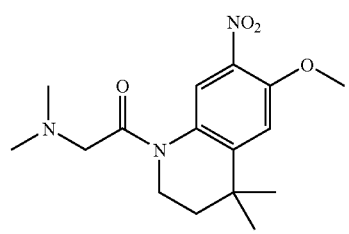

A solution of 1-(bromoacetyl)-4,4-dimethyl-6-(methyloxy)-7-nitro-1,2,3,4-tetrahydroquinoline (1.0 g, 2.8 mmol) in tetrahydrofuran (35 mL) was treated with potassium carbonate (1.3 g, 9.4 mmol) and dimethyl amine (10 mL, 20 mmol, 2 M in THF, Aldrich). The mixture was heated in sealed tube at 55° C. for 1h, cooled, diluted with water, and extracted with ethyl acetate. The organic layer was separated, dried over magnesium sulfate, filtered, and concentrated to give {2-[4,4-dimethyl-6-(methyloxy)-7-nitro-3,4-dihydro-1(2H)-quinolinyl]-2-oxoethyl}dimethylamine which was taken directly to the next step. ESIMS (M+H)$^+$=322.

Step G/Intermediate B251: 1-[(dimethylamino)acetyl]-4,4-dimethyl-6-(methyloxy)-1,2,3,4-tetrahydro-7-quinolinamine {2-[4,4-dimethyl-6-(methyloxy)-7-nitro-3,4-dihydro-1(2H)-quinolinyl]-2-oxoethyl}dimethylamine (assumed 2.8 mmol) was dissolved in a mixture of ethyl acetate (50 mL) and water (5 mL) and transferred to a Fischer Porter apparatus. 10% Palladium on carbon (500 mg, Aldrich) was added followed by methanol (5 mL) and the mixture stirred under 60 psi hydrogen pressure for 2 h. The pressure was released, the reaction vessel evacuated, and back-filled with nitrogen twice. The mixture was filtered through celite and the filtrate was concentrated to provide 1-[(dimethylamino)acetyl]-4,4-dimethyl-6-(methyloxy)-1,2,3,4-tetrahydro-7-quinolinamine (724 mg, 2.49 mmol, 89% over three steps). $^1$H NMR (400 MHz, DMSO-$d_6$) δ ppm 1.20 (s, 6 H), 1.62-1.68 (m, 2 H), 2.20 (s, 6 H), 3.17 (s, 2 H), 3.62-3.69 (m, 2 H), 3.75 (s, 3 H), 4.58 (bs, 2 H), 6.56-6.94 (s at 6.71 on top of a very broad singlet caused by amide rotomers, 2 H); ESIMS (M+H)$^+$ =292.

Intermediate B258: 4,4-dimethyl-6-(methyloxy)-1-(1-pyrrolidinylacetyl)-1,2,3,4-tetrahydro-7-quinolinamine

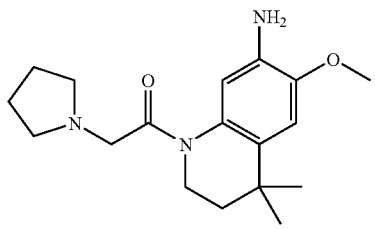

Step A/Intermediate B259: 4,4-dimethyl-6-(methyloxy)-7-nitro-1-(1-pyrrolidinylacetyl)-1,2,3,4-tetrahydroquinoline

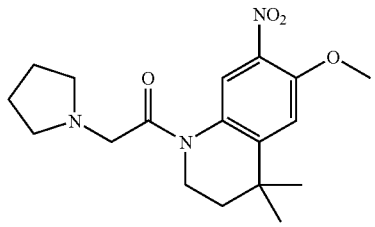

A solution of 1-(bromoacetyl)-4,4-dimethyl-6-(methyloxy)-7-nitro-1,2,3,4-tetrahydroquinoline (1.0 g, 2.8 mmol) in tetrahydrofuran (35 mL) was treated with potassium carbonate (1.3 g, 9.4 mmol) and pyrrolidine (1.5 mL, 18 mmol, Aldrich). The mixture was heated in sealed tube at 55° C. for 1 h, cooled, diluted with water, and extracted with ethyl acetate. The organic layer was separated, dried over magnesium sulfate, filtered, and concentrated to give 4,4-dimethyl-6-(methyloxy)-7-nitro-1-(1-pyrrolidinylacetyl)-1,2,3,4-tetrahydroquinoline which was taken directly to the next step. ESIMS (M+H)$^+$=348.

Step B/Intermediate B258: 4,4-dimethyl-6-(methyloxy)-1-(1-pyrrolidinylacetyl)-1,2,3,4-tetrahydro-7-quinolinamine 4,4-dimethyl-6-(methyloxy)-7-nitro-1-(1-pyrrolidinylacetyl)-1,2,3,4-tetrahydroquinoline (assumed 2.8 mmol) was dissolved in a mixture of ethyl acetate (50 mL) and water (5 mL) and transferred to a Fischer Porter apparatus. 10% Palladium on carbon (500 mg, Aldrich) was added followed by methanol (5 mL) and the mixture stirred under 60 psi hydrogen pressure for 2 h. The pressure was released, the reaction vessel evacuated, and back-filled with nitrogen twice. The mixture was filtered through celite and the filtrate was concentrated to provide 4,4-dimethyl-6-(methyloxy)-1-(1-pyrrolidinylacetyl)-1,2,3,4-tetrahydro-7-quinolinamine (790 mg, 89% over three steps). 1H NMR (400 MHz, DMSO-$d_6$) δ ppm 1.19 (s, 6 H), 1.61-1.71 (m, 6 H), 2.50-2.54 (m, signal underneath DMSO, 4 H), 3.32-3.35 (m, signal underneath H$_2$O, 2 H), 3.62-3.69 (m, 2 H), 3.75 (s, 3 H), 4.58 (bs, 2 H), 6.62-7.00 (s at 6.71 on top of a very broad singlet caused by amide rotomers, 2 H).

Intermediate B260: 7-amino-4,4-dimethyl-6-(methyloxy)-3,4-dihydro-2(1H)-quinolinone

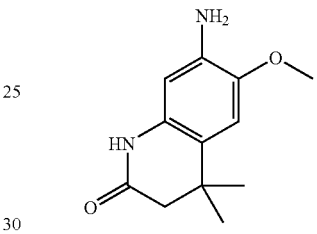

4,4-dimethyl-6-(methyloxy)-7-nitro-3,4-dihydro-2(1H)-quinolinone (250 mg, 1.00 mmol) was dissolved in ethyl acetate (10 mL) and transferred to a Fischer Porter apparatus. 10% Palladium on carbon (250 mg, Aldrich) was added followed by methanol (20 mL) and the mixture stirred under 60 psi hydrogen pressure for 16 h. The pressure was released, the reaction vessel evacuated, and back-filled with nitrogen twice. The mixture was filtered through celite and the filtrate was concentrated to provide 7-amino-4,4-dimethyl-6-(methyloxy)-3,4-dihydro-2(1H)-quinolinone (213 mg, 0.92 mmol, 92%). $^1$H NMR (400 MHz, DMSO-$d_6$) δ ppm 1.16 (s, 6 H), 2.22 (s, 2 H), 3.72 (s, 3 H), 4.66 (s, 2 H), 6.20 (s, 1 H), 6.67 (s, 1 H), 9.76 (s, 1 H).

Intermediate B261: 6-(methyloxy)-1-(1-methyl-L-prolyl)-1,2,3,4-tetrahydro-7-quinolinamine

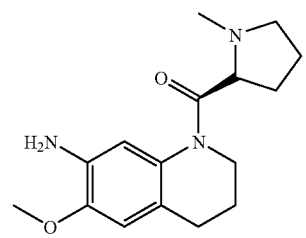

A solution of 6-(methyloxy)-7-nitro-1,2,3,4-tetrahydroquinoline (3.0 g, 14.41 mmol), 1-methyl-L-proline (2.140 g, 16.57 mmol), HATU (7.12 g, 18.73 mmol), and DIPEA (6.29 mL, 36.0 mmol) in N,N-Dimethylformamide (DMF) (25 mL) was stirred for 2.5 days at room temperature. Reaction was poured into ethyl acetate and washed successively with 5% lithium chloride (aq) and saturated sodium chloride (aq). The organic layer was dried over sodium sulfate, filtered, and purified by column chromatography (10% MeOH/CH$_2$Cl$_2$) to afford 6-(methyloxy)-1-(1-methyl-L-prolyl)-7-nitro-1,2,3,4-tetrahydroquinoline (2.09 g, 6.54 mmol, 45.4% yield). The residue was suspended in ethanol (300 mL) and N,N-dimethylacetamide (50 mL) was added followed by tin(II)chloride dihydrate (6.78 g, 30.1 mmol) and 1.0M HCl (2.505 mL, 2.505 mmol). After overnight stirring the reaction was quenched with excess saturated NaHCO$_3$ (300 mL) and allowed to stir at rt for 30 min. The solids were removed through a celite pad, rinsed with MeOH, and evaporated. The aqueous layer was extracted with DCM (2×100 mL). The combined organic layers were filtered through a cotton plug, and concentrated by rotary evaporation to provide 6-(methyloxy)-1-(1-methyl-L-prolyl)-1,2,3,4-tetrahydro-7-quinolinamine (1.1 g, 26% over two steps). ESIMS (M+H)+=290.

Intermediate B262: N$^1$-[5-amino-2-methyl-4-(methyloxy)phenyl]-N$^1$,N$^2$,N$^2$-trimethylglycinamide

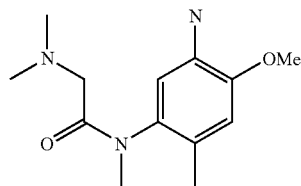

Step A/Intermediate B263:
N,2-dimethyl-4-(methyloxy)aniline

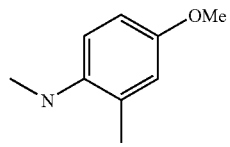

A suspension of [2-methyl-4-(methyloxy)phenyl]amine (5 ml, 39.2 mmol), paraformaldehyde (5.88 g, 196 mmol), and sodium methoxide (10.58 g, 196 mmol) in methanol (100 ml) was maintained at 50° C. for 5 hours, cooled, and sodium borohydride (7.41 g, 196 mmol) was added portionwise. The resulting suspension was re-heated to 50° C. and maintained for 16 hours. The reaction was cooled, poured into ethyl acetate/saturated sodium bicarbonate, and the organic layer was dried over sodium sulfate, filtered, taken to a residue under reduced pressure, and purified by column chromatography to afford N,2-dimethyl-4-(methyloxy)aniline (5.40 g, 35.7 mmol, 91% yield) as a pale orange oil. $^1$H NMR (400 MHz, DMSO-d$_6$) δ ppm 6.55-6.68 (m, 2 H), 6.34-6.40 (m, 1 H), 4.47-4.66 (m, 1 H), 3.62 (s, 3 H), 2.66 (d, J=5.0 Hz, 3 H), 2.04 (s, 3 H).

Step B/Intermediate B264: N$^1$,N$^2$,N$^2$-trimethyl-N$^1$-[2-methyl-4-(methyloxy)phenyl]glycinamide

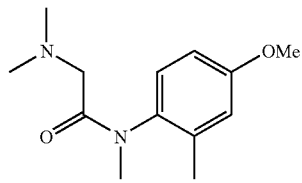

A suspension of N,2-dimethyl-4-(methyloxy)aniline (5.10 g, 33.7 mmol) and potassium carbonate (9.32 g, 67.5 mmol) in tetrahydrofuran (150 ml) was treated with bromoacetylchloride (3.50 ml, 42.2 mmol), stirred for 45 minutes, and dimethyl amine in tetrahydrofuran (67.5 ml, 135 mmol) was added. The solution was stirred for 3 hours, additional dimethyl amine in tetrahydrofuran (67.5 ml, 135 mmol) was added, and the solution was warmed to 50° C. and maintained overnight. The solution was cooled, poured into ethyl acetate/saturated sodium bicarbonate, and the organic layer was separated, dried over sodium sulfate, filtered, taken to a residue under reduced pressure, and purified by column chromatography to afford N1,N2,N2-trimethyl-N1-[2-methyl-4-(methyloxy)phenyl]glycinamide (5.10 g, 21.58 mmol, 64.0% yield) as a yellow oil. $^1$H NMR (400 MHz, DMSO-d$_6$); two protons likely obstructed by DMSO; δ ppm 7.13 (d, J=8.6 Hz, 1 H), 6.90 (d, J=2.6 Hz, 1 H), 6.77-6.84 (m, 1 H), 3.76 (s, 3 H), 3.00 (s, 3 H), 2.13 (s, 3 H), 2.08 (s, 6 H).

Step C/Intermediate B265: N$^1$,N$^2$,N$^2$-trimethyl-N$^1$-[2-methyl-4-(methyloxy)-5-nitrophenyl]glycinamide

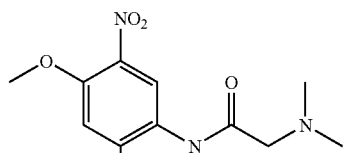

A 0° C. solution of N1,N2,N2-trimethyl-N1-[2-methyl-4-(methyloxy)phenyl]glycinamide (4.9 g, 20.74 mmol) in TFA (20 mL) was treated with sodium nitrite (2.003 g, 29.0 mmol). The resulting thick mixture was stirred at rt. After 5 h water (20 mL) and EtOAc (200 mL) were added and the mixture was poured into a saturated NaHCO$_3$ solution (300 mL). The layers were separated. The aqueous layer was treated with a few g of K$_2$CO$_3$ to obtain pH=8, then was extracted with EtOAc (2×125 mL) and CHCl$_3$ (2×125 mL). The combined organic layers were washed with a saturated NaCl solution (100 mL), dried (Na$_2$SO$_4$), concentrated onto Celite and purified by silica gel chromatography to obtain N$^1$,N$^2$,N$^2$-trimethyl-N$^1$-[2-methyl-4-(methyloxy)-5-nitrophenyl]glycinamide as an orange solid (1.87 g, 32% Yield). ESIMS (M+H)+=282.52.

Step D/Intermediate B262: N$^1$-[5-amino-2-methyl-4-(methyloxy)phenyl]-N$^1$,N$^2$,N$^2$-trimethylglycinamide 10% palladium on carbon (0.25 g, 8.52 mmol) was placed under N$_2$ atm. MeOH (10 mL) was added, followed by a solution of N1,N2,N2-trimethyl-N1-[2-methyl-4-(methyloxy)-5-nitrophenyl]glycinamide (1.86 g, 6.61 mmol) in MeOH (90 mL). The slurry was purged with $N_2$, then was placed under $H_2$ atm via a rubber balloon and maintained at rt for 2 days. The resulting mixture was filtered through Celite. The filtrate was concentrated. The oily residue was taken up into $Et_2O$ and concentrated again to obtain $N^1$-[5-amino-2-methyl-4-(methyloxy)phenyl]-$N^1,N^2,N^2$-trimethylglycinamide as a white foamy solid (1.41 g, 85%). $^1$H NMR (400 MHz, DMSO-$d_6$) δ ppm 2.00 (s, 3H), 2.11 (s, 6H), 2.58 (d, J=15.57 Hz, 1H), 2.77 (d J=15.57 Hz, 1H), 2.97 (s, 3H), 3.77 (s, 3H), 4.70 (s, 2H), 6.41 (s, 1H), 6.72 (s, 1H); ESIMS (M+H)+=252.10.

Intermediate B266: $N^1$-[3-amino-4-(methyloxy)phenyl]-$N^1,N^2,N^2$-trimethylglycinamide

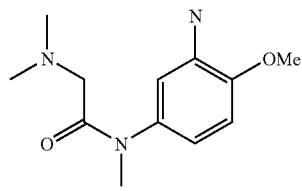

Step A/Intermediate B267: 1,1-dimethylethyl [5-(methylamino)-2-(methyloxy)phenyl]carbamate

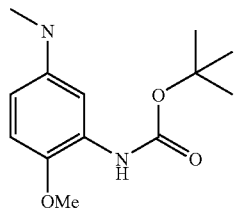

A suspension of 1,1-dimethylethyl [5-amino-2-(methyloxy)phenyl]carbamate (1.94 g, 8.14 mmol), paraformaldehyde (1.222 g, 40.7 mmol), and sodium methoxide (2.199 g, 40.7 mmol) in methanol (50 ml) was maintained at 50° C. for 16 hours, cooled, sodium borohydride (0.924 g, 24.42 mmol) was added portionwise, and the solution was re-heated to 50° C. and maintained for an additional 24 hours. The solution was cooled, diluted with ethyl acetate, saturated sodium bicarbonate, and the organic layer was dried over sodium sulfated, filtered, taken to a residue under reduced pressure, and purified by column chromatography to afford 1,1-dimethylethyl [5-(methylamino)-2-(methyloxy)phenyl]carbamate (2.15 g, 8.52 mmol, quant. Yield) as a pale yellow oil. $^1$H NMR (400 MHz, DMSO-$d_6$) δ ppm 7.58 (s, 1 H), 7.10 (d, J=1.6 Hz, 1 H), 6.76 (d, J=8.8 Hz, 1 H), 6.14 (dd, J=8.7, 2.7 Hz, 1H), 5.07-5.31 (m, 1 H), 3.61-3.74 (m, 3 H), 2.60 (d, J=4.4 Hz, 3 H), 1.44 (s, 9 H).

Step B/Intermediate B268: 1,1-dimethylethyl [5-[(N,N-dimethylglycyl)(methyl)amino]-2-(methyloxy)phenyl]carbamate

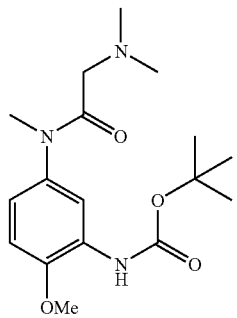

A suspension of 1,1-dimethylethyl [5-(methylamino)-2-(methyloxy)phenyl]carbamate (2.15 g, 8.52 mmol) and potassium carbonate (2.355 g, 17.04 mmol) in tetrahydrofuran (75 ml) was treated with bromoacetylchloride (0.779 ml, 9.37 mmol), stirred for 45 minutes, and dimethyl amine in THF (17.04 ml, 34.1 mmol) was added. The solution was stirred at room temperature for 8 hours, poured into saturated sodium bicarbonate/ethyl acetate, and the organic layer was separated, dried over sodium sulfate, filtered, taken to a residue under reduced pressure, and purified by column chromatography to afford 1,1-dimethylethyl [5-[(N,N-dimethylglycyl)(methyl)amino]-2-(methyloxy)phenyl]carbamate (2.25 g, 6.67 mmol, 78% yield) as a yellow oil. $^1$H NMR (400 MHz, DMSO-$d_6$) δ ppm 8.05 (br. s., 1 H), 7.60 (br. s., 1 H), 6.88-7.10 (m, 2 H), 3.82 (s, 3 H), 3.08 (s, 3 H), 2.80 (br. s., 2 H), 2.11 (s, 6 H), 1.36-1.54 (m, 9 H)

Step C/Intermediate B266: $N^1$-[3-amino-4-(methyloxy)phenyl]-$N^1,N^2,N^2$-trimethylglycinamide A solution of 1,1-dimethylethyl [5-[(N,N-dimethylglycyl)(methyl)amino]-2-(methyloxy)phenyl]carbamate (2.01 g, 5.96 mmol) in 1,4-dioxane (40 ml) was treated with 4.0M HCl in dioxanes (7.45 ml, 29.8 mmol) and stirred for 3 hours. Additional 4.0M HCl in dioxanes (7.45 ml, 29.8 mmol) was added and the reaction was stirred for 16 hours. The solution was poured into ethyl acetate, diluted with water, and neutralized by careful addition of solid potassium carbonate. The aqueous layer was washed with chloroform and the organic layers were combined, dried over sodium sulfate, filtered, and taken to a residue under reduced pressure to afford N1-[3-amino-4-(methyloxy)phenyl]-N1,N2,N2-trimethylglycinamide (1.19 g, 5.01 mmol, 84% yield) as a tan oil. $^1$H NMR (400 MHz, DMSO-$d_6$) δ ppm 6.78 (d, J=8.2 Hz, 1 H), 6.48 (d, J=2.4 Hz, 1 H), 6.41 (d, J=8.2 Hz, 1 H), 4.91 (br. s., 2 H), 3.77 (s, 3 H), 3.05 (s, 3 H), 2.82 (s, 2 H), 2.12 (s, 6 H).

Intermediate B269

1-[(dimethylamino)acetyl]-6-methyl-1,2,3,4-tetrahydro-7-quinolinamine

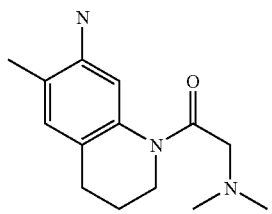

Step A/Intermediate B270: N,N-dimethyl-2-(6-methyl-7-nitro-3,4-dihydro-1(2H) quinolinyl)-2-oxoethanamine

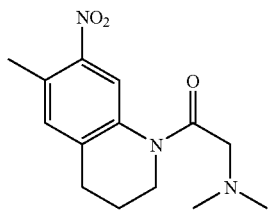

To a bright orange solution of 6-methyl-7-nitro-1,2,3,4-tetrahydroquinoline (2 g, 10.41 mmol)—(see Achvlediani, R.; Natsvlishvili, M.; Baberkina, E.; Khachidze, M.; Abesadze, I.; Suvorov, N. Synthesis of 1H-pyrrolo[3,2-g]- and 1H-pyrrolo[2,3-g]quinoline. Izvestiya Akademii Nauk Gruzii, Seriya Khimicheskaya (1996), 22(1-4), 43-47.)—in THF (50 mL) was added $K_2CO_3$ (4.31 g, 31.2 mmol). The resulting mixture was cooled to 0° C. and was treated with bromoacetyl chloride (1.040 mL, 12.49 mmol) dropwise. The reaction mixture was stirred for 20 min. EtOAc (100 mL) and water (100 mL) were then added. The organic layer was dried ($Na_2SO_4$) and concentrated. The crude 1-(bromoacetyl)-6-methyl-7-nitro-1,2,3,4-tetrahydroquinoline (3.26 g, 10.41 mmol) was dissolved in THF (50mL). A 2M $Me_2NH$ solution in THF (50 mL) was added. The resulting slurry was filtered, the solids were rinsed with THF. The filtrate was concentrated onto Celite and purified by silica gel chromatography using 1-10% MeOH (containing 0.2% $NH_3$)/$CH_2Cl_2$ to afford as a yellow solid (2.09 g, 72%). $^1$H NMR (400 MHz, DMSO-$d_6$) δ ppm 1.81-1.97 (m, 2H), 2.24 (s, 6H), 2.47 (s, 3H), 2.80 (t, J=6.89 Hz, 2H), 3.25 (s, 2H), 3.68-6.85 (m, 2H), 7.29 (s, 1H), 8.54 (br s, 1H); ESIMS (M+H)+=278.40.

Step B/Intermediate B269: 1-[(dimethylamino)acetyl]-6-methyl-1,2,3,4-tetrahydro-7-quinolinamine 10% Pd on carbon (0.5 g, 17.37 mmol) was placed under $N_2$ atm. MeOH (20 mL) was added, followed by a solution of N,N-dimethyl-2-(6-methyl-7-nitro-3,4-dihydro-1(2H)-quinolinyl)-2-oxoethanamine (2.07 g, 7.46 mmol) in MeOH (80 mL). The mixture was placed under $H_2$ atm via balloon and maintained for 1 day. The resulting mixture was filtered through a pad of Celite using MeOH. The filtrate was concentrated, the residue was taken up into $Et_2O$ and concentrated again to afford 1-[(dimethylamino)acetyl]-6-methyl-1,2,3,4-tetrahydro-7-quinolinamine as a grey solid (1.55 g, 84%). $^1$H NMR (400 MHz, DMSO-$d_6$) δ ppm 1.71-1.87 (m, 2H), 1.99 (s, 3H), 2.20 (s, 6H), 2.45-2.58 (m, 2H), 3.18 (s, 2H), 3.61 (t, J=6.13 Hz, 2H), 4.66 (br s, 2H), 6.69 (s, 1H), 6.78 (br s, 1H); ESIMS (M+H)+=248.17.

Intermediate B271

(2R)-1-[(dimethylamino)acetyl]-2-methyl-5-(methyloxy)-2,3-dihydro-1H-indol-6-amine

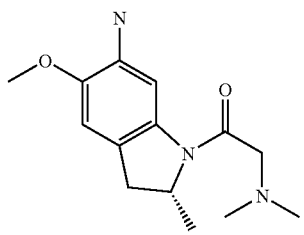

Step A/Intermediate B272: (2R)-1-acetyl-2-methyl-5-(methyloxy)-6-nitro-2,3-dihydro-1H-indole

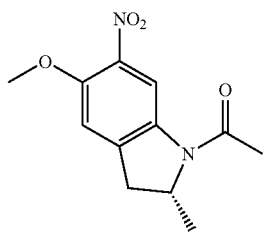

A solution of (2R)-1-acetyl-2-methyl-5-(methyloxy)-2,3-dihydro-1H-indole (100 mg, 0.487 mmol)—see (Arp, Forrest O.; Fu, Gregory C. Kinetic Resolutions of Indolines by a Nonenzymatic Acylation Catalyst. Journal of the American Chemical Society (2006), 128(44), 14264-14265.)—in TFA (2 mL) at 0° C. was treated with sodium nitrite (33.6 mg, 0.487 mmol). The resulting red solution was stirred at 0° C. for 1 h. $H_2O$ (20 mL) was added, the resulting slurry was filtered and the solids were washed with water to afford (2R)-1-acetyl-2-methyl-5-(methyloxy)-6-nitro-2,3-dihydro-1H-indole as a yellow solid (85 mg, 70%). $^1$H NMR (400 MHz, DMSO-$d_8$) δ ppm 1.22 (d, J=6.41 Hz, 3H), 2.22 (s, 3H), 2.76 (d, J=17.21 Hz, 1H), 3.45 (dd, J=17.12, 8.88 Hz, 1H), 3.89 (s, 3H), 4.59-4.74 (m, 1H), 7.35 (s, 1H), 8.40 (s, 1H); ESIMS (M+H)+=251.00.

This procedure was repeated on 5 g of (2R)-1-acetyl-2-methyl-5-(methyloxy)-2,3-dihydro-1H-indole to obtain 5.8 g of (2R)-1-acetyl-2-methyl-5-(methyloxy)-6-nitro-2,3-dihydro-1H-indole.

Step B/Intermediate B273: (2R)-2-methyl-5-(methyloxy)-6-nitro-2,3-dihydro-1H-indole hydrogen chloride

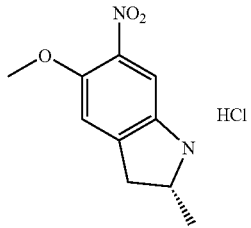

A slurry of (2R)-1-acetyl-2-methyl-5-(methyloxy)-6-nitro-2,3-dihydro-1H-indole (5.78 g, 23.10 mmol) in MeOH (50 mL) and a 4N HCl solution in dioxane (57.7 mL, 231 mmol) was heated at 70° C. for 8 h. The resulting mixture was allowed to cool to rt and concentrated to afford (2R)-2-methyl-5-(methyloxy)-6-nitro-2,3-dihydro-1H-indole hydrogen chloride as a brown sticky solid (5.47 g, 97%). $^1$H NMR (400 MHz, DMSO-d$_6$) δ ppm 1.38 (d, J=6.59 Hz, 3H), 2.82 (dd, J=16.85, 7.69 Hz, 1H), 3.32 (dd, J=16.85, 8.06 Hz, 1H), 3.90 (s, 3H), 4.09-4.26 (m, 1H), 7.39 (s, 1H), 7.60 (s, 1H); ESIMS (M+H)+=209.00.

Step C/Intermediate B274: N,N-dimethyl-2-[(2R)-2-methyl-5-(methyloxy)-6-nitro-2,3-dihydro-1H-indol-1-yl]-2-oxoethanamine

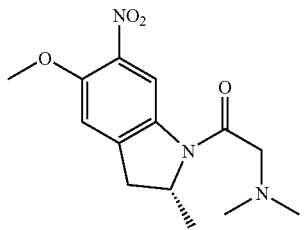

A 0° C. slurry of (2R)-2-methyl-5-(methyloxy)-6-nitro-2,3-dihydro-1H-indole hydrogen chloride (4.55 g, 18.60 mmol) and K$_2$CO$_3$ (10.28 g, 74.4 mmol) in THF (200 mL) was treated with bromoacetyl chloride (3.10 mL, 37.2 mmol). After 2 h the reaction mixture was allowed to warm to rt. A 2M Me$_2$NH solution in THF (55.8 mL, 112 mmol) was added and the reaction mixture was stirred at rt for 18 h. The resulting thick slurry was filtered and the solids were rinsed with EtOAc. The filtrate was concentrated onto Celite and purified by silica gel chromatography using 1-10% MeOH (containing 0.2% NH$_3$)/CH$_2$Cl$_2$ to obtain N,N-dimethyl-2-[(2R)-2-methyl-5-(methyloxy)-6-nitro-2,3-dihydro-1H-indol-1-yl]-2-oxoethanamine as an orange solid (2.92 g, 54%). $^1$H NMR (400 MHz, DMSO-d$_6$) δ ppm 1.23 (d, J=6.04 Hz, 3H), 2.28 (s, 6H), 2.75 (d, J=17.03 Hz, 1H), 3.14 (d, J=14.83 Hz, 1H), 3.44 (d, J=14.65 Hz, 2H), 3.90 (s, 3H), 4.77-4.92 (m, 1H), 7.36 (s, 1H), 8.43 (s, 1H); ESIMS (M+H)+=294.01.

Step D/Intermediate B271: (2R)-1-[(dimethylamino)acetyl]-2-methyl-5-(methyloxy)-2,3-dihydro-1H-indol-6-amine 10% palladium on carbon (0.25 g, 8.52 mmol) was placed under N$_2$ atm. MeOH (10 mL) was added, followed by a solution of N,N-dimethyl-2-[(2R)-2-methyl-5-(methyloxy)-6-nitro-2,3-dihydro-1H-indol-1-yl]-2-oxoethanamine (2.92 g, 9.96 mmol) in MeOH (190 mL). The slurry was purged with N$_2$, then was placed under H$_2$ atm via a rubber balloon and maintained at rt for 2 days. The resulting mixture was filtered through a pad of Celite and the filtrate was concentrated. The oily residue was taken up into Et$_2$O and concentrated again to obtain (2R)-1-[(dimethylamino)acetyl]-2-methyl-5-(methyloxy)-2,3-dihydro-1H-indol-6-amine as a beige solid (2.43 g, 93%). $^1$H NMR (400 MHz, DMSO-d$_6$) δ ppm 1.17 (d, J=5.86 Hz, 3H), 2.26 (s, 6H), 2.44 (d, J=14.83 Hz, 1H), 3.02 (d, J=14.28 Hz, 1H), 3.10-3.27 (m, 1H), 3.36 (d, J=14.28 Hz, 1H), 3.72 (s, 3H), 4.52-4.77 (m, 3H), 6.72 (s, 1H), 7.48 (s, 1H); ESIMS (M+H)+=264.23.

Intermediate B275

(2S)-1-[(dimethylamino)acetyl]-2-methyl-5-(methyloxy)-2,3-dihydro-1H-indol-6-amine

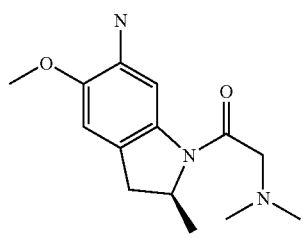

Step A/Intermediate B276: (2S)-1-acetyl-2-methyl-5-(methyloxy)-6-nitro-2,3-dihydro-1H-indole

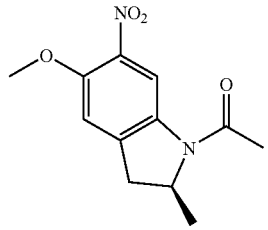

A 0° C. orange solution of (2S)-1-acetyl-2-methyl-5-(methyloxy)-2,3-dihydro-1H-indole (5.19 g, 25.3 mmol) in TFA (30 mL) was treated with NaNO$_2$ (1.745 g, 25.3 mmol) portion wise. After 2 h more NaNO$_2$ (800 mg, 11.6 mmol) was added. After 1 h the resulting mixture was poured into water (450 mL). The resulting slurry was filtered and the solids were washed with water. The solids were dissolved in CH$_2$Cl$_2$. The layers were separated, the organic layer was dried (Na$_2$SO$_4$) and concentrated to afford (2S)-1-acetyl-2-methyl-5-(methyloxy)-6-nitro-2,3-dihydro-1H-indole as a green solid (5.73 g, 91%). $^1$H NMR (400 MHz, DMSO-d$_6$) δ ppm 1.23 (d, J=6.23 Hz, 3H), 2.22 (s, 3H), 2.76 (d, J=17.21 Hz, 1H), 3.45 (dd, J=17.03, 8.97 Hz, 1H), 3.89 (s, 3H), 4.58-4.78 (m, 1H), 7.35 (s, 1H), 8.41 (s, 1H); ESIMS (M+H)+=251.02.

Step B/Intermediate B277: (2S)-2-methyl-5-(methyloxy)-6-nitro-2,3-dihydro-1H-indole hydrogen chloride

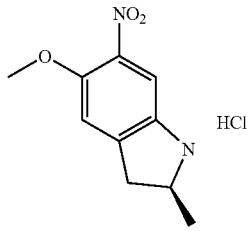

A slurry of (2S)-1-acetyl-2-methyl-5-(methyloxy)-6-nitro-2,3-dihydro-1H-indole (5.7 g, 22.78 mmol) in MeOH (50 mL) and a 4N HCl solution in dioxane (56.9 mL, 228 mmol) was heated at 70° C. for 10 h. The resulting mixture was allowed to cool to rt and concentrated to afford (2S)-2-methyl-5-(methyloxy)-6-nitro-2,3-dihydro-1H-indole hydrogen chloride as a beige solid (5.55 g, 100%). $^1$H NMR (400 MHz, DMSO-d$_6$) δ ppm 1.39 (d, J=6.41 Hz, 3H), 2.84 (dd, J=16.94, 7.60 Hz, 1H), 3.34 (dd, J=16.85, 8.06 Hz, 1H), 3.90 (s, 3H), 4.12-4.27 (m, 1H), 7.41 (s, 1H), 7.66 (s, 1H); ESIMS (M+H)+=209.00.

Step C/Intermediate B278: N,N-dimethyl-2-[(2S)-2-methyl-5-(methyloxy)-6-nitro-2,3-dihydro-1H-indol-1-yl]-2-oxoethanamine

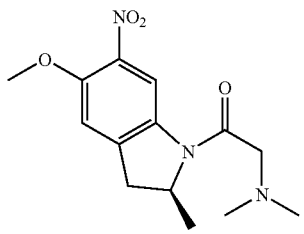

A slurry of (2S)-2-methyl-5-(methyloxy)-6-nitro-2,3-dihydro-1H-indole hydrogen chloride (4.43 g, 18.11 mmol) and K$_2$CO$_3$ (10.01 g, 72.4 mmol) in THF (200 mL) at 0° C. was treated with bromoacetyl chloride (3.02 mL, 36.2 mmol). After 2 h the resulting mixture was allowed to warm to rt. A 2M Me$_2$NH solution in THF (54.3 mL, 109 mmol) was added. After 18 h the resulting thick slurry was filtered and the solids were washed with EtOAc. The filtrate was concentrated onto Celite and purified by silica gel chromatography using 1-10% MeOH (containing 0.2% NH$_3$)/CH$_2$Cl$_2$. The foamy oily product was chased using CH$_2$Cl$_2$ and hexanes, CH$_2$Cl$_2$ and Et$_2$O, then Et$_2$O to obtain N,N-dimethyl-2-[(2S)-2-methyl-5-(methyloxy)-6-nitro-2,3-dihydro-1H-indol-1-yl]-2-oxoethanamine as an orange solid (2.50 g, 47%). $^1$H NMR (400 MHz, DMSO-d$_6$) δ ppm 1.23 (d, J=6.04 Hz, 3H), 2.28 (s, 6H), 2.75 (d, J=17.21 Hz, 1H), 3.14 (d, J=14.65 Hz, 1H), 3.44 (d, J=14.65 Hz, 2H), 3.90 (s, 3H), 4.75-4.92 (m, 1H), 7.37 (s, 1H), 8.43 (s, 1H); ESIMS (M+H)+=293.88.

Step D/Intermediate B275: (2S)-1-[(dimethylamino)acetyl]-2-methyl-5-(methyloxy)-2,3-dihydro-1H-indol-6-amine 10% palladium on carbon (0.25 g, 8.52 mmol) was placed under N$_2$ atm. MeOH (10 mL) was added, followed by a solution of N,N-dimethyl-2-[(2S)-2-methyl-5-(methyloxy)-6-nitro-2,3-dihydro-1H-indol-1-yl]-2-oxoethanamine (2.50 g, 8.52 mmol) in MeOH (190 mL). The slurry was purged with N$_2$, then was placed under H$_2$ atm via a rubber balloon and maintained at rt for 2 days. The resulting mixture was filtered through a pad of Celite and the filtrate was concentrated. The oily residue was taken up into Et$_2$O and concentrated again to obtain (2S)-1-[(dimethylamino)acetyl]-2-methyl-5-(methyloxy)-2,3-dihydro-1H-indol-6-amine as a beige solid (2.10 g, 94%).

$^1$H NMR (400 MHz, DMSO-d$_8$) δ ppm 1.17 (d, J=5.68 Hz, 3H), 2.26 (s, 6H), 2.44 (d, J=15.02 Hz, 1H), 3.03 (d, J=14.28 Hz, 1H), 3.10-3.25 (m, 1H), 3.36 (d, J=14.28 Hz, 1H), 3.72 (s, 3H), 4.54-4.76 (m, 3H), 6.72 (s, 1H), 7.48 (s, 1H); ESIMS (M+H)+=264.20.

Intermediate B279

N1-[5-amino-2-methyl-4-(methyloxy)phenyl]-N2,N2-dimethylglycinamide

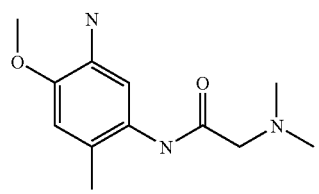

Step A/Intermediate B280: N-[2-methyl-4-(methyloxy)phenyl]acetamide

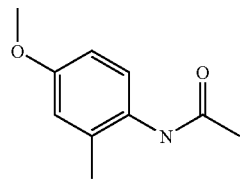

2-methyl-4-(methyloxy)aniline (5 ml, 39 mmol) was dissolved in acetic acid (40 ml) and acetic anhydride (3.7 ml, 39 mmol) was added dropwise. Reaction was heated to 60° C. After 30 min, most of the solvent was removed under reduced pressure and the residue diluted with EtOAc. A saturated solution of sodium bicarbonate was added until solution was pH 8. Organics were then washed with water and a saturated brine solution and dried over sodium sulfate. Solvents were removed under reduced pressure to afford N-[2-methyl-4-(methyloxy)phenyl]acetamide (6.37 g, 35.5 mmol) as a pink fluffy solid. $^1$H NMR (400 MHz, DMSO-d$_6$) δ ppm 1.95-2.06 (m, 3 H) 2.14 (s, 3 H) 3.71 (s, 3 H) 6.70 (dd, J=8.71, 2.84 Hz, 1 H) 6.77 (d, J=2.75 Hz, 1 H) 7.18 (d, J=8.61 Hz, 1 H) 9.16 (s, 1 H)

Step B/Intermediate B281:
N[2-methyl-4-(methyloxy)-5-nitrophenyl]acetamide

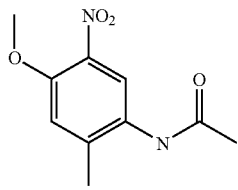

N-[2-methyl-4-(methyloxy)phenyl]acetamide (1.95 g, 10.88 mmol) was dissolved in TFA (20 mL) and cooled to 0° C. in an ice bath. Potassium nitrate (1.210 g, 11.97 mmol) was added slowly. The reaction was monitored by tlc and quenched by pouring into ice and diluting with EtOAc. A solution of saturated sodium bicarbonate was added until solution was a neutral pH. Organics were washed with water and saturated brine solution and dried over sodium sulfate. Solvents were removed under reduced pressure to afford a yellow solid. Efforts to dissolve the solid in ethyl acetate resulted in a suspension that was let sit for several hours. Hexanes were added and the solids filtered to afford N-[2-methyl-4-(methyloxy)-5-nitrophenyl]acetamide (1.13 g, 5.04 mmol) as yellow fluffy solid. The filtrate was purified via $SiO_2$ chromatography to afford N-[2-methyl-4-(methyloxy)-5-nitrophenyl]acetamide (1.02 g, 4.55 mmol) as a yellow solid. $^1$H NMR (400 MHz, DMSO-$d_6$) δ ppm 2.00-2.11 (m, 3 H) 2.29 (s, 3 H) 3.90 (s, 3 H) 7.24 (s, H) 7.99 (s, 1 H) 9.42 (s, 1 H)

Step C/Intermediate B282:
2-methyl-4-(methyloxy)-5-nitroaniline HCl salt

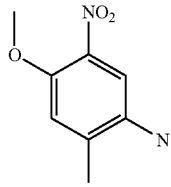

A slurry of N-[2-methyl-4-(methyloxy)-5-nitrophenyl]acetamide (1 g, 4.46 mmol) in methanol (20 ml) and 4M HCl in dioxane (8.92 ml, 35.7 mmol) was heated at 60° C. for 18 h. The reaction mixture was cooled in an ice bath and solids were filtered and washed with cold methanol to afford 2-methyl-4-(methyloxy)-5-nitroaniline HCl salt (0.516 g, 2.36 mmol) as a white solid. $^1$H NMR (400 MHz, DMSO-$d_6$) δ ppm 2.38 (s, 3 H) 3.91 (s, 3 H) 7.31 (s, 1 H) 7.87 (s, 1 H) 9.39 (br. s., 2 H)

Step D/Intermediate B283: $N^2,N^2$-dimethyl-$N^1$-[2-methyl-4-(methyloxy)-5-nitrophenyl]glycinamide

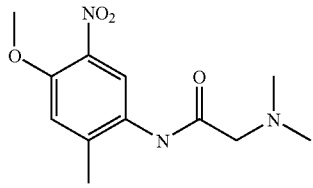

A mixture of 2-methyl-4-(methyloxy)-5-nitroaniline HCl salt (500 mg, 2.287 mmol) and Hunig's Base (1.198 ml, 6.86 mmol) was stirred in THF (20 ml). Bromoacetyl chloride (0.211 ml, 2.52 mmol) was added and the reaction let stir at rt for 40 min. LCMS analysis indicated complete conversion to the acyl bromide so a 2M solution of dimethylamine in THF (4.6 ml, 9.15 mmol) was added and let stir at rt overnight. The reaction was diluted with EtOAc and washed with a saturated brine solution. Aqueous layers were re-extracted with EtOAc. Organics were combined and dried over sodium sulfate and filtered. Solvents were removed under reduced pressure to afford $N^2,N^2$-dimethyl-$N^1$-[2-methyl-4-(methyloxy)-5-nitrophenyl]glycinamide (0.642 mg, 2.4 mmol). ESIMS (M+H)$^+$=268.

Step E/Intermediate B279: N1-[5-amino-2-methyl-4-(methyloxy)phenyl]-N2,N2-dimethylglycinamide $N^2,N^2$-dimethyl-$N^1$-[2-methyl-4-(methyloxy)-5-nitrophenyl]glycinamide (0.642 mg, 2.4 mmol) was suspended in methanol (20 ml) and Pd/C (65 mg) was added. The reaction vessel was subjected to $H_2$ at 60 psi on a Fisher Porter apparatus. After stirring overnight, the reaction was not complete so more Pd (from a new bottle) was added and the vessel resubjected to $H_2$ at 60 psi on a Fisher Porter apparatus for an additional 18 h. Pd/C was removed from the reaction by filtering through a pad of celite and washing with MeOH. Solvents were removed under reduced pressure and the residue was purified by $SiO_2$ chromatography to afford N1-[5-amino-2-methyl-4-(methyloxy)phenyl]-N2,N2-dimethylglycinamide (435 mg, 1.83 mmol) as a orange solid. $^1$H NMR (400 MHz, DMSO-$d_6$) δ ppm 2.05 (s, 3 H) 2.30 (s, 6 H) 3.00 (s, 2 H) 3.72 (s, 3 H) 4.54 (s, 2 H) 6.62 (s, 1 H) 6.90 (s, 1 H) 8.97 (s, 1 H).

Intermediate B280

1-[(dimethylamino)acetyl]-$N^5,N^5$-dimethyl-2,3-dihydro-1H-indole-5,6-diamine

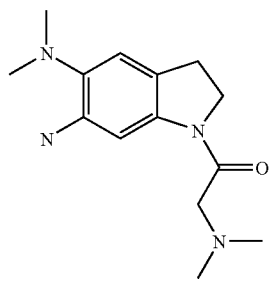

Step A/Intermediate B281:
1-acetyl-5-fluoro-6-nitro-2,3-dihydro-1H-indole

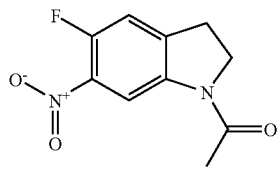

To a solution of 5-fluoro-1H-indole (5.0 g, 37 mmols) in acetic acid (300 ml) was added sodium cyanoborohydride (2.79 g, 44 mmols). After stirring overnight at rt, the reaction was concentrated under reduced pressure, redissolved in ethyl acetate (300 ml) and the pH was adjusted to 8 with saturated sodium bicarbonate. The organic layer was separated, filtered through a cotton plug, evaporated, and placed on the high vacuum for one hour prior to the next synthetic step. The crude material was then dissolved in acetic acid (100 ml), followed by the addition of acetic anhydride (3.5 ml, 37 mmols). After heating at 60 C for one hour, the reaction was poured into ice, stirred for one hour, solid was removed by vacuum filtration, rinsed with water and allowed to dry overnight under house vacuum. Next, to a solution of the 1-acetyl-5-fluoro-2,3-dihydro-1H-indole (500 mg, 2.79 mmol) in sulfuric acid (10 ml) at OC was added nitric acid (0.196 ml, 3.07 mmols) by a slow dropwise addition. After stirring 30 min at OC, the reaction was quenched by pouring into ice water. The solids were removed by vacuum filtration, redissolved in dichloromethane (50 ml), adsorbed to silica gel, and purified by LC(25% to 75% ethyl acetate/hexanes). The lower Rf spot was isolated and the structure was determined to be the desired regioisomer by IR profiling. 1H NMR (400 MHz, DMSO-$d_6$) δ ppm 2.18 (s, 3 H) 3.25 (t, J=8.63 Hz, 2 H) 4.18 (t, J=8.53 Hz, 2 H) 7.50 (d, J=11.24 Hz, 1 H) 8.64 (d, J=7.22 Hz, 1 H).

Step B/Intermediate B282:
5-fluoro-6-nitro-2,3-dihydro-1H-indole

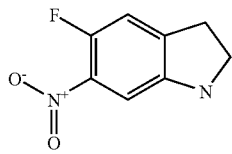

A solution of 1-acetyl-5-fluoro-6-nitro-2,3-dihydro-1H-indole (1.22 g, 5.44 mmol) and 4.0 M HCl/dioxane (6.80 ml, 27.2 mmol) in tetrahydrofuran (50 ml) and methanol (100 ml) was heated overnight at 50 C. The reaction was quenched with saturated NaHCO$_3$ (200 ml), solvent removed, aqueous layer extracted with dichloromethane (250 ml), organic layer adsorbed to silica gel and purified by LC (20-75% ethyl acetate/hexanes) to afford the indoline (0.9 g, 91%). ESIMS (M+H)+=183.

Step C/Intermediate B283: 1-[(dimethylamino) acetyl]-N,N-dimethyl-6-nitro-2,3-dihydro-1H-indol-5-amine

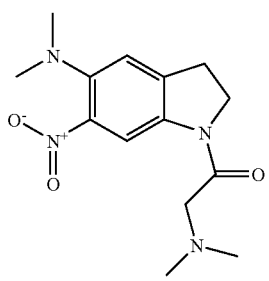

To a solution of 5-fluoro-6-nitro-2,3-dihydro-1H-indole (0.9 g, 4.94 mmol) and potassium carbonate (2.049 g, 14.82 mmol) in tetrahydrofuran (300 ml) was added bromoacetyl chloride (0.414 ml, 4.94 mmol) and the reaction was stirred at rt for 30 min. To this reaction was added 2.0M dimethylamine in THF (7.41 ml, 14.82 mmol) and the mixture was stirred overnight at rt. The solvent removed, water added (200 ml), aqueous layer extracted with dichloromethane (2×250 ml), organic layers adsorbed to silica gel and purified by LC (DCM to 10% MeOH/DCM) to give the title compound (1 g, 69%). ESIMS (M+H)+=293.

Step D/Intermediate B280: 1-[(dimethylamino) acetyl]-$N^5$,$N^5$-dimethyl-2,3-dihydro-1H-indole-5,6-diamine To an N$_2$ degassed solution of 1-[(dimethylamino)acetyl]-N,N-dimethyl-6-nitro-2,3-dihydro-1H-indol-5-amine (1.00 g, 3.42 mmol) and 10% Pd/C (3.64 g, 3.42 mmol) in ethanol (100 ml) was added H$_2$ and the reaction was stirred at rt overnight on the Fisher Porter at 50 psi. The reaction was filtered through celite, rinsed with methanol (100 ml), concentrated by rotary evaporation, and high vacced prior to the next reaction to give the title compound (0.9 g, 100%). ESIMS (M+H)+=263.

General Protocol II: 4-Chloro Displacements of 2,4-dichloro-7-[(4-methylphenyl)sulfonyl]-7H-pyrrolo[2,3-d]pyrimidine

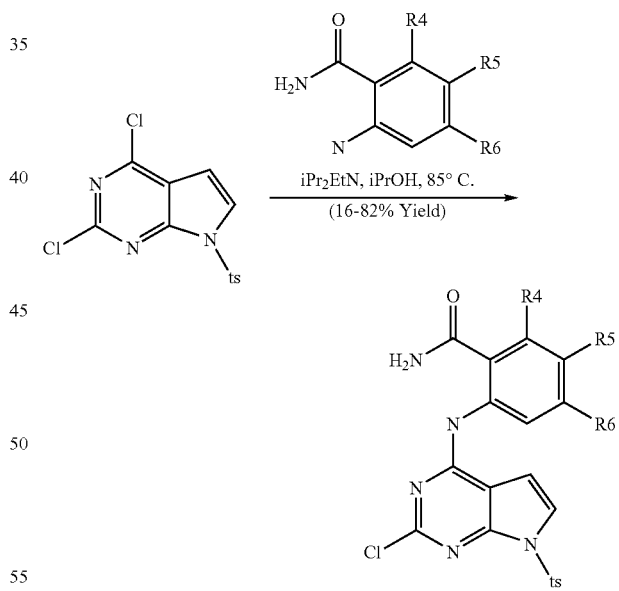

A mixture of the 2-amino carboxamide (1-3 equiv.), 2,4-dichloro-7-[(4-methylphenyl)sulfonyl]-7H-pyrrolo[2,3-d]pyrimidine (1 equiv.) (commercially available from CiventiChem, Cary, N.C.) and diisopropylethylamine (5 equiv.) in 2-propanol was heated at reflux until a thick white precipitate formed (1-7 days). Following cooling to room temperature, the precipitate was collected and washed with either diethylether to afford analytically pure 4-anilino pyrrolopyridimines as white solids.

Intermediate C1: 2-({2-chloro-7-[(4-methylphenyl)sulfonyl]-7H-pyrrolo[2,3-d]pyrimidin-4-yl}amino)benzamide

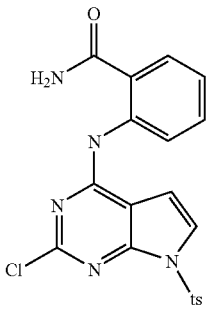

Using General Protocol II and starting with 2,4-dichloro-7-[(4-methylphenyl)sulfonyl]-7H-pyrrolo[2,3-d]pyrimidine (6.91 g) and 2-aminobenzamide (11.8 g), 2-({2-chloro-7-[(4-methylphenyl)sulfonyl]-7H-pyrrolo[2,3-d]pyrimidin-4-yl}amino)benzamide was isolated as a white solid (6.2 g, 70% Yield); 1H NMR (400 MHz, DMSO-$d_6$) δ ppm 2.36 (s, 3 H), 6.67 (d, J=4.03 Hz, 1 H), 7.17 (td, J=7.59, 1.10 Hz, 1 H), 7.47 (d, J=8.05 Hz, 2 H), 7.57 (td, J=7.87, 1.46 Hz, 1 H), 7.75 (d, J=4.03 Hz, 1 H), 7.78 (s, 1 H), 7.83 (dd, J=8.05, 1.46 Hz, 1 H), 7.98 (dt, J=8.69, 1.97 Hz, 2 H), 8.30 (s, 1 H), 8.44 (dd, J=8.33, 1.01 Hz, 1 H), 12.32 (s, 1 H).

Intermediate C2: 3-({2-chloro-7-[(4-methylphenyl)sulfonyl]-7H-pyrrolo[2,3-d]pyrimidin-4-yl}amino)-2-naphthalenecarboxamide

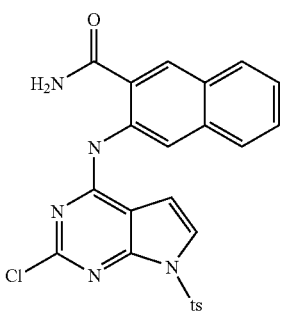

Using General Protocol II (but using methanol in place of dimethylether) and starting with 2,4-dichloro-7-[(4-methylphenyl)sulfonyl]-7H-pyrrolo[2,3-d]pyrimidine (2.5 g, 13.2 mmol) and 3-amino-2-naphthalenecarboxamide (3.00 g, 8.8 mmol), 3-({2-chloro-7-[(4-methylphenyl)sulfonyl]-7H-pyrrolo[2,3-d]pyrimidin-4-yl}amino)-2-naphthalenecarboxamide was isolated as a white solid (2.56 g, 59% Yield); 1H NMR (400 MHz, DMSO-$d_6$) δ ppm 2.35 (s, 3 H), 6.69 (d, J=4.03 Hz, 1 H), 7.42-7.51 (m, 3 H), 7.58 (t, J=7.51 Hz, 1 H), 7.72 (d, J=4.03 Hz, 1 H), 7.78-7.85 (m, 2 H), 7.90 (d, J=8.06 Hz, 1 H), 7.97 (d, J=8.42 Hz, 2 H), 8.40 (s, 2 H), 8.69 (s, 1 H), 11.90 (s, 1 H).

Intermediate C3: 2-({2-chloro-7-[(4-methylphenyl)sulfonyl]-7H-pyrrolo[2,3-d]pyrimidin-4-yl}amino)-6-methylbenzamide

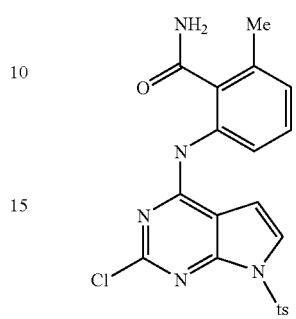

Using General Protocol II and starting with 2,4-dichloro-7-[(4-methylphenyl)sulfonyl]-7H-pyrrolo[2,3-d]pyrimidine (2.79 g, 8.2 mmol) and 2-amino-6-methylbenzamide (0.830 g, 5.46 mmol), 2-({2-chloro-7-[(4-methylphenyl)sulfonyl]-7H-pyrrolo[2,3-d]pyrimidin-4-yl}amino)-6-methylbenzamide was isolated as a yellow solid (0.960 g, 38% yield); 1H NMR (400 MHz, DMSO-$d_6$) δ ppm 2.32 (s, 3 H), 2.36 (s, 3 H), 6.49 (s, 1 H), 7.18-7.24 (m, 2 H), 7.30 (s, 1 H), 7.44-7.47 (m, 4 H), 7.56 (d, J=4.03 Hz, 1 H), 7.95 (d, J=8.43 Hz, 2 H).

Intermediate C4: 2-({2-chloro-7-[(4-methyl phenyl)sulfonyl]-7H-pyrrolo[2,3-d]pyrimidin-4-yl}amino)-5-methylbenzamide

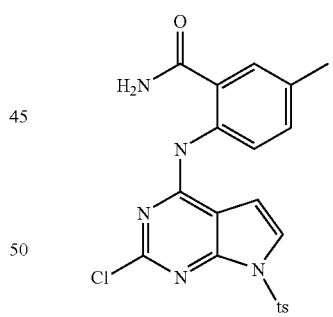

Using General Protocol II and starting with 2,4-dichloro-7-[(4-methylphenyl)sulfonyl]-7H-pyrrolo[2,3-d]pyrimidine (3.00 g, 8.8 mmol) and 2-amino-5-methylbenzamide (3.30 g, 22.0 mmol), 2-({2-chloro-7-[(4-methylphenyl)sulfonyl]-7H-pyrrolo[2,3-d]pyrimidin-4-yl}amino)-5-methylbenzamide was isolated as white solid (3.30 g, 82% Yield); 1H NMR (400 MHz, DMSO-$d_6$) δ ppm 2.30 (s, 3 H), 2.35 (s, 3 H), 6.64 (d, J=4.03 Hz, 1 H), 7.37 (dd, J=8.60, 1.65 Hz, 1 H), 7.46 (d, J=8.05 Hz, 2 H), 7.64 J=1.65 Hz, 1 H), 7.70 (s, 1 H), 7.71 (d, J=4.03 Hz, 1 H), 7.97 (dt, J=8.69, 1.97 Hz, 2 H), 8.19 (s, 1 H), 8.22 (d, J=8.42 Hz, 1 H), 12.02 (s, 1 H).

Intermediate C5: 2-({2-chloro-7-[(4-methylphenyl)sulfonyl]-7H-pyrrolo[2,3-d]pyrimidin-4-yl}amino)-4-methylbenzamide

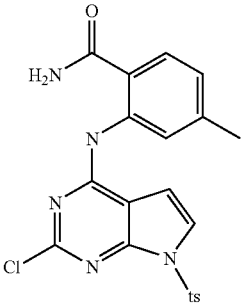

Using General Protocol II and starting with 2,4-dichloro-7-[(4-methylphenyl)sulfonyl]-7H-pyrrolo[2,3-d]pyrimidine (3.0 g, 8.8 mmol) and 2-amino-4-methylbenzamide (2.0 g, 13.2 mmol), 2-({2-chloro-7-[(4-methylphenyl)sulfonyl]-7H-pyrrolo[2,3-d]pyrimidin-4-yl}amino)-4-methylbenzamide was isolated as a white solid (2.81 g, 70% Yield): 1H NMR (400 MHz, DMSO-$d_6$) δ ppm 2.34 (s, 3 H), 2.36 (s, 3 H), 6.65 (d, J=3.84 Hz, 1 H), 6.98 (s, 1 H), 7.47 (d, J=8.05 Hz, 2 H), 7.70 (s, 1 H), 7.74 (s, 1 H), 7.75 (d, J=2.93 Hz, 1 H), 7.98 (d, J=8.42 Hz, 2 H), 8.25 (s, 1 H), 8.33 (s, 1 H), 12.52 (s, 1 H).

Intermediate C6: 2-({2-chloro-7-[(4-methylphenyl)sulfonyl]-7H-pyrrolo[2,3-d]pyrimidin-4-yl}amino)-6-(methyloxy)benzamide

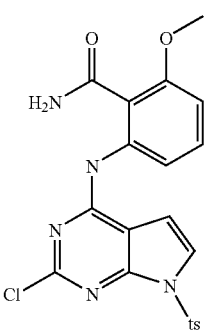

Using General Protocol II with 2,4-dichloro-7-[(4-methylphenyl)sulfonyl]-7H-pyrrolo[2,3-d]pyrimidine (3.00 g, 8.8 mmol) and 2-amino-6-(methyloxy)benzamide (3.10 g, 18.7 mmol), 2-({2-chloro-7-[(4-methylphenyl)sulfonyl]-7H-pyrrolo[2,3-d]pyrimidin-4-yl}amino)-6-(methyloxy)benzamide was isolated as white solid (1.15 g, 28% Yield); 1H NMR (400 MHz, DMSO-$d_6$) δ ppm 2.34 (s, 3 H), 3.81 (s, 3 H), 6.55 (s, 1 H), 6.94 (d, J=7.87 Hz, 1 H), 7.37-7.49 (m, 4 H), 7.63 (d, J=4.03 Hz, 3 H), 7.94 (d, J=8.24 Hz, 2 H), 10.98 (s, 1 H).

Intermediate C7: 2-{(2-chloro-7-[(4-methylphenyl)sulfonyl]-7H-pyrrolo[2,3-d]pyrimidin-4-yl}amino)-5-(methyloxy)benzamide

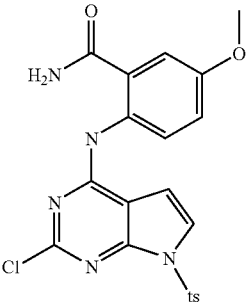

Using General Protocol II and starting with 2,4-dichloro-7-[(4-methylphenyl)sulfonyl]-7H-pyrrolo[2,3-d]pyrimidine (1.64 g, 4.82 mmol) and 2-amino-5-(methyloxy)benzamide (1.0 g, 6.00 mmol), 2-({2-chloro-7-[(4-methylphenyl)sulfonyl]-7H-pyrrolo[2,3-d]pyrimidin-4-yl}amino)-5-(methyloxy)benzamide was isolated as a white solid (1.83 g, 81% Yield); 1H NMR (400 MHz, DMSO-$d_6$) δ ppm 2.36 (s, 3 H), 3.79 (s, 3 H), 6.61 (s, 1 H), 7.15 (dd, J=8.97, 2.93 Hz, 1 H), 7.31 (d, J=2.93 Hz, 1 H), 7.46 (d, J=8.05 Hz, 2 H), 7.67 (d, J=4.03 Hz, 2 H), 7.96 (ddd, J=8.60, 2.01, 1.83 Hz, 2 H), 8.08 (d, J=8.78 Hz, 1 H), 8.15 (s, 1 H), 11.48 (s, 1 H).

Intermediate C8: 2-({2-chloro-7-[(4-methylphenyl)sulfonyl]-7H-pyrrolo[2,3-d]pyrimidin-4-yl}amino)-4-(methyloxy)benzamide

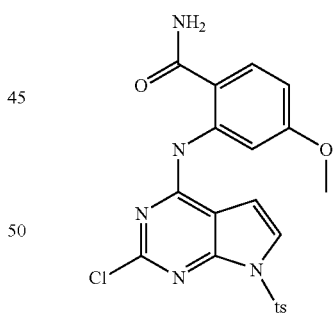

Using General Protocol II and starting with 2,4-dichloro-7-[(4-methylphenyl)sulfonyl]-7H-pyrrolo[2,3-d]pyrimidine (4.0 g, 11.7 mmol) and 2-amino-4-(methyloxy)benzamide (4.5 g, 26.8 mmol), 2-({2-chloro-7-[(4-methylphenyl)sulfonyl]-7H-pyrrolo[2,3-d]pyrimidin-4-yl}amino)-4-(methyloxy)benzamide was isolated as a yellow solid (0.1.58 g, 29% yield); 1H NMR (400 MHz, DMSO-$d_6$) δ ppm 2.33 (s, 3 H), 4.28 (s, 3 H), 6.62 (t, J=3.48 Hz, 1 H), 6.68 (ddd, J=6.00, 2.88, 2.66 Hz, 1 H), 7.41-7.46 (m, 2 H), 7.64 (s, 1 H), 7.74 (t, J=3.48 Hz, 1 H), 7.81-7.87 (m, 1 H), 7.92-7.98 (m, 2 H), 8.22 (s, 1 H), 8.32 (t, J=2.66 Hz, 1 H), 13.13 (s, 1 H).

Intermediate C9: 2-({2-chloro-7-[(4-methylphenyl)sulfonyl]-7H-pyrrolo[2,3-d]pyrimidin-4-yl}amino)-4,5-bis(methyloxy)benzamide

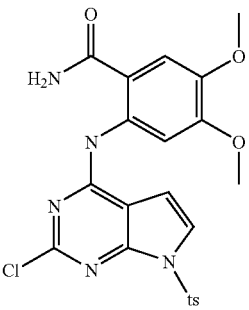

Using General Protocol II and starting with 2,4-dichloro-7-[(4-methylphenyl)sulfonyl]-7H-pyrrolo[2,3-d]pyrimidine (3.0 g, 8.8 mmol) and 2-amino-4,5-bis(methyloxy)benzamide (3.7 g, 18.9 mmol), 2-({2-chloro-7-[(4-methylphenyl)sulfonyl]-7H-pyrrolo[2,3-d]pyrimidin-4-yl}amino)-4,5-bis(methyloxy)benzamide was isolated as a white solid (2.75 g, 62% Yield); 1H NMR (400 MHz, DMSO-$d_6$) δ ppm 2.34 (s, 3 H), 3.77 (s, 3 H), 3.80 (s, 3 H), 6.60 (d, J=3.85 Hz, 1 H), 7.38 (s, 1 H), 7.44 (d, J=8.61 Hz, 2 H), 7.62 (s, 1 H), 7.71 (d, J=4.03 Hz, 1 H), 7.95 (d, J=8.42 Hz, 2 H), 8.21 (s, 1 H), 8.32 (s, 1 H), 12.70 (s, 1 H)

Intermediate C10: 2-({2-chloro-7-[(4-methylphenyl)sulfonyl]-7H-pyrrolo[2,3-d]pyrimidin-4-yl}amino)-6-fluorobenzamide

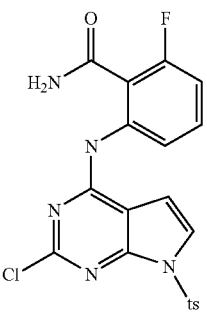

A mixture of 2-amino-6-fluorobenzamide (10 g, 64.9 mmol, Piedmont or Ryan Scientific) and 2,4-dichloro-7-[(4-methylphenyl)sulfonyl]-7H-pyrrolo[2,3-d]pyrimidine (17.7 g, 51.7 mmol) was taken up into trifluoroethanol (400 mL) and trifluoroacetic acid (20 mL, 260 mmol). The resulting yellow slurry was heated at 80° C. After heating for 30 minutes a clear brown solution was obtained, which was heated at 80° C. for 18 h, then at the reflux temperature for an additional 6 h. The resulting slurry was cooled to 0° C. and filtered. The filtrate was concentrated down to 200 mL volume, heated at 80C for 20 h, cooled to 0° C., then filtered. The two crops of solids were combined, taken up into isopropanol (150 mL), heated at the reflux temperature for 4 h, then filtered to give 13 g (55%) of 2-({2-chloro-7-[(4-methylphenyl)sulfonyl]-7H-pyrrolo[2,3-d]pyrimidin-4-yl}amino)-6-fluorobenzamide as a pale yellow solid; 1H NMR (400 MHz, DMSO-$d_6$) δ ppm 2.36 (s, 3 H), 6.71 (d, J=3.66 Hz, 1 H), 7.12-7.17 (m, 1 H), 7.45-7.48 (m, 2 H), 7.49-7.52 (m, 1 H), 7.61 (d, J=7.87 Hz, 1 H), 7.67 (d, J=4.03 Hz, 1 H), 7.80 (s, 1 H), 7.89 (s, 1 H), 7.95-7.98 (m, 2 H), 10.47 (s, 1 H).

Intermediate C11: 2-({2-chloro-7-[(4-methylphenyl)sulfonyl]-7H-pyrrolo[2,3-d]pyrimidin-4-yl}amino)-5-fluorobenzamide

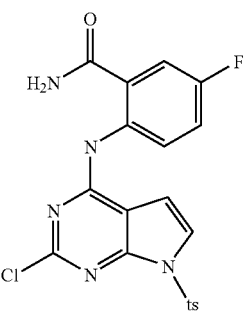

Using General Protocol II and starting with 2,4-dichloro-7-[(4-methylphenyl)sulfonyl]-7H-pyrrolo[2,3-d]pyrimidine (3.0 g, 8.8 mmol) and 2-amino-5-fluorobenzamide (4.0 g, 26 mmol), 2-({2-chloro-7-[(4-methylphenyl)sulfonyl]-7H-pyrrolo[2,3-d]pyrimidin-4-yl}amino)-5-fluorobenzamide was isolated as a white solid (3.05 g, 76% Yield); 1H NMR (400 MHz, DMSO-$d_6$) δ ppm 2.36 (s, 3 H), 6.68 (d, J=4.03 Hz, 1 H), 7.42-7.50 (m, 3 H), 7.65 (dd, J=9.51, 3.11 Hz, 1 H), 7.72 (d, J=3.84 Hz, 1 H), 7.83 (s, 1 H), 7.97 (dt, J=8.65, 1.90 Hz, 2 H), 8.26 (s, 1 H), 8.30 (dd, J=9.15, 5.12 Hz, 1 H), 11.81 (s, 1 H).

Intermediate C12: 2-({2-chloro-7-[(4-methylphenyl)sulfonyl]-7H-pyrrolo[2,3-d]pyrimidin-4-yl}amino)-4-fluorobenzamide

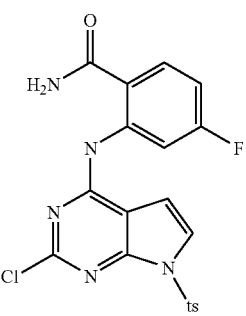

Using General Protocol II and starting with 2,4-dichloro-7-[(4-methylphenyl)sulfonyl]-7H-pyrrolo[2,3-d]pyrimidine (3.0 g, 8.8 mmol) and 2-amino-4-fluorobenzamide (3.50 g, 23 mmol), 2-({2-chloro-7-[(4-methylphenyl)sulfonyl]-7H-pyrrolo[2,3-d]pyrimidin-4-yl}amino)-4-fluorobenzamide was isolated as a white solid (1.75 g, 43% Yield); 1H NMR (400 MHz, DMSO-$d_6$) δ ppm 2.36 (s, 3 H), 6.67 (d, J=4.03 Hz, 1 H), 6.98-7.04 (m, 1 H), 7.47 (d, J=8.23 Hz, 2 H), 7.80 (d, J=4.03 Hz, 1 H), 7.89 (s, 1 H), 7.93-8.01 (m, 3 H), 8.40 (s, 1 H), 8.47 (dd, J=11.89, 2.74 Hz, 1 H), 12.95 (s, 1 H).

Intermediate C13: 2-({2-chloro-7-[(4-methylphenyl)sulfonyl]-7H-pyrrolo[2,3-d]pyrimidin-4-yl}amino)-4,5-difluorobenzamide

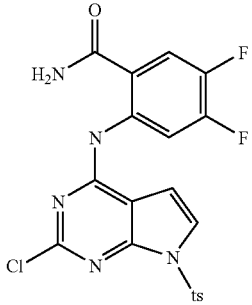

Using General Protocol II and starting with 2,4-dichloro-7-[(4-methylphenyl)sulfonyl]-7H-pyrrolo[2,3-d]pyrimidine (3.0 g, 8.8 mmol) and 2-amino-4,5-difluorobenzamide (4.15 g, 23.9 mmol), 2-({2-chloro-7-[(4-methylphenyl)sulfonyl]-7H-pyrrolo[2,3-d]pyrimidin-4-yl}amino)-4,5-difluorobenzamide was isolated as a white solid (1.80 g, 43% Yield); 1H NMR (400 MHz, DMSO-$d_6$) δ ppm 2.34 (s, 3H), 6.67 (d, J=4.03 Hz, 1 H), 7.46 (d, J=8.61 Hz, 2 H), 7.76 (d, J=4.03 Hz, 1 H), 7.92-8.01 (m, 4 H), 8.35 9s, 1 H), 8.55 (dd, J=13.55, 7.69 Hz, 1 H), 12.50 (s, 1 H).

Intermediate C14: 5-chloro-2-({2-chloro-7-[(4-methylphenyl)sulfonyl]-7H-pyrrolo[2,3-d]pyrimidin-4-yl}amino)benzamide

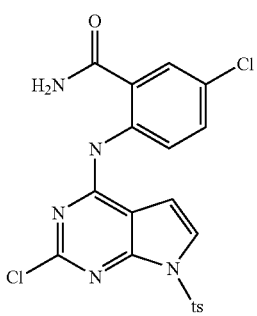

Using General Protocol II and starting with 2,4-dichloro-7-[(4-methylphenyl)sulfonyl]-7H-pyrrolo[2,3-d]pyrimidine (2.5 g, 7.3 mmol) and 2-amino-5-chlorobenzamide (3.73 g, 22 mmol), 5-chloro-2-({2-chloro-7-[(4-methylphenyl)sulfonyl]-7H-pyrrolo[2,3-d]pyrimidin-4-yl}amino)benzamide was isolated as a yellow solid (2.0 g, 57% Yield); 1H NMR (400 MHz, DMSO-$d_6$) δ ppm 2.36 (s, 3 H), 6.70 (d, J=4.03 Hz, 1 H), 7.47 (d, J=8.23 Hz, 2 H), 7.64 (dd, J=8.87, 2.47 Hz, 1 H), 7.76 (d, J=3.84 Hz, 1 H), 7.88 (d, J=2.38 Hz, 2 H), 7.98 (d, J=8.60 Hz, 2 H), 8.38 (s, 1 H), 8.41 (d, J=8.97 Hz, 1 H), 12.14 (s, 1 H).

Intermediate C15: 4-chloro-2-({2-chloro-7-[(4-methylphenyl)sulfonyl]-7H-pyrrolo[2,3-d]pyrimidin-4-yl}amino)benzamide

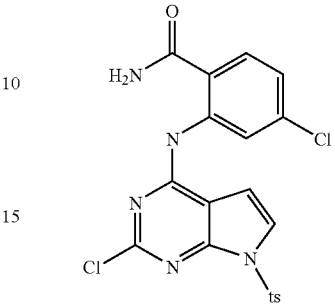

Using General Protocol II and starting with 2,4-dichloro-7-[(4-methylphenyl)sulfonyl]-7H-pyrrolo[2,3-d]pyrimidine (3.0 g, 8.8 mmol) and 2-amino-4-chlorobenzamide (3.0 g, 17.6 mmol), 4-chloro-2-({2-chloro-7-[(4-methylphenyl)sulfonyl]-7H-pyrrolo[2,3-d]pyrimidin-4-yl}amino)benzamide was isolated as a yellow solid (0.650 g, 16% Yield); 1H NMR (400 MHz, DMSO-$d_6$) δ ppm 2.36 (s, 3 H), 6.68 (d, J=4.03 Hz, 1 H), 7.23 (dd, J=8.51, 2.10 Hz, 1 H), 7.47 (d, J=8.23 Hz, 2 H), 7.79 (d, J=4.03 Hz, 1 H), 7.87 (d, J=8.42 Hz, 1 H), 7.91 (s, 1 H), 7.98 (d, J=8.42 Hz, 2 H), 8.41 (s, 1 H), 8.66 (d, J=2.20 Hz, 1 H), 12.65 (s, 1 H).

Intermediate C16: 5-bromo-2-({2-chloro-7-[(4-methylphenyl)sulfonyl]-7H-pyrrolo[2,3-d]pyrimidin-4-yl}amino)benzamide

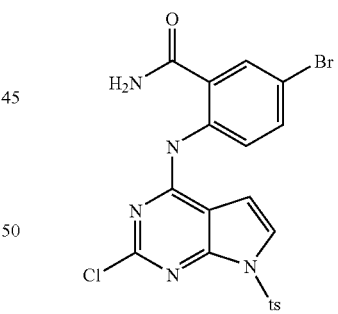

Using General Protocol II and starting with 2,4-dichloro-7-[(4-methylphenyl)sulfonyl]-7H-pyrrolo[2,3-d]pyrimidine (4.0 g, 11.7 mmol) and 2-amino-5-bromobenzamide (7.6 g, 35.2 mmol), 5-bromo-2-({2-chloro-7-[(4-methylphenyl)sulfonyl]-7H-pyrrolo[2,3-d]pyrimidin-4-yl}amino)benzamide was isolated as a yellow solid (2.1 g, 35% Yield); 1H NMR (400 MHz, DMSO-$d_6$) δppm 2.36 (s, 3 H), 6.70 (d, J=3.66 Hz, 1 H), 7.46 (d, J=8.42 Hz, 2 H), 7.74-7.78 (m, 2 H), 7.88 (s, 1 H), 7.97 (d, J=8.42 Hz, 2 H), 8.00 (d, J=2.20 Hz, 1 H), 8.35 (d, J=8.79 Hz, 1 H), 8.39 (s, 1 H), 12.16 (s, 1 H).

Intermediate C17: 2-({2-chloro-7-[(4-methylphenyl) sulfonyl]-7H-pyrrolo[2,3-d]-4pyrimidin-4-yl}amino)-4,6-difluorobenzamide

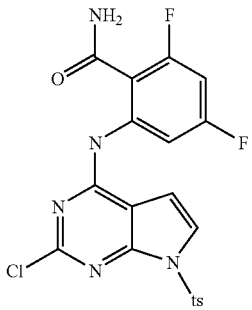

To a solution of 2,4-dichloro-7-[(4-methylphenypsulfonyl]-7h-pyrrolo[2,3-d]pyrimidine (5.9 g, 17.21 mmol) and 2-amino-4,6-difluorobenzamide (2.96 g, 17.21 mmol) in trifluoroethanol (100 mL) was added trifluoroacetic acid (4 mL, 51.6 mmol) and the resulting solution was heated at 75° C. under a water cooled reflux condensor. After overnight stirring LCMS analysis indicates starting materials still remain, so an additional aliquot of trifluoroacetic acid (5 mL) was added and heating was continued for an additional 24 hours. The reaction was cooled and 2-({2-chloro-7-[(4-methylphenyl)sulfonylj-7H-pyrrolo[2,3-d]pyrimidin-4-yl}amino)-4,6-difluorobenzamide was collected as a yellow solid via filtration (1.91 g, 23% yield); 1H NMR (400 MHz, DMSO-$d_6$) δ ppm 2.36 (s, 3 H), 6.75 (d, J=4.03 Hz, 1 H), 7.17 (ddd, J=11.09, 8.89, 2.38 Hz, 1 H), 7.47 (d, J=7.70 Hz, 2 H), 7.74 (d, J=4.03 Hz, 1 H), 7.83 (d, J=11.00 Hz, 1 H), 7.94- 7.99 (m, 3 H), 7.99 (s, 1 H), 11.08 (s, 1 H).

Intermediate C18: 6-({2-chloro-7-[(4-methylphenyl) sulfonyl]-7H-pyrrolo[2,3-d]pyrimidin-4-yl}amino)-2,3-difluorobenzamide

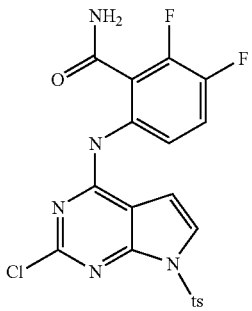

To a pressure flask is added 6-amino-2,3-difluorobenzamide (0.700 g, 4.07 mmol), 2,4-dichloro-7-[(4-methylphenyl)sulfonyl]-7H-pyrrolo[2,3-d]pyrimidine (1.4 g, 4.07 mmol), trifluoroethanol (30 mL) and trifluoroacetic acid (1.6 mL, 20.4 mmol). The resulting clear solution was stirred overnight. The next morning all precipitates were collected to afford analytically pure 6-({2-chloro-7-[(4-methylphenyl) sulfonyl]-7H-pyrrolo[2,3-d]pyrimidin-4-yl}amino)-2,3-difluorobenzamide as a white solid (1.07 g, 55% yield). 1H NMR (400 MHz, DMSO-$d_6$) δ ppm 2.36 (s, 3 H), 6.74 (s, 1 H), 7.41-7.48 (m, 3 H), 7.49-7.60 (m, 1 H), 7.64 (d, J=3.67 Hz, 1 H), 7.82 (s, 1 H), 7.96 (d, J=8.43 Hz, 3 H), 10.13 (s, 1 H).

Intermediate C19: 4-chloro-2-({2-chloro-7-[(4-methylphenyl)sulfonyl]-7H-pyrrolo[2,3-d]pyrimidin-4-yl}amino)-6-fluorobenzamide

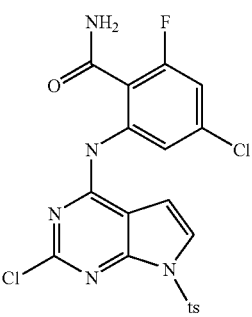

To a pressure flask was added 2-amino-4-chloro-6-fluorobenazmide (1.0 g, 5.32 mmol), 2,4-dichloro-7-[(4-methylphenyl)sulfonyl]-7H-pyrrolo[2,3-d]pyrimidine (1.64 g, 4.84 mmol), trifluoroethanol (40 mL) and trifluoroacetic acid (1.9 mL, 24.2 mmol). The resulting clear solution was stirred overnight. The next morning all precipitates were collected to afford analytically pure 4-chloro-2-({2-chloro-7-[(4-methylphenyl)sulfonyl]-7H-pyrrolo[2,3-d]pyrimidin-4-yl}amino)-6-fluorobenzamide (0.785 g, 33% yield). 1H NMR (400 MHz, DMSO-$d_6$) δ ppm 2.34 (s, 3 H), 6.76 (d, J=4.03 Hz, 1 H), 7.35 (dd, J=9.89, 1.83 Hz, 1H), 7.45 (d, J=8.24 Hz, 2 H), 7.70 (d, J=3.85 Hz, 1 H), 7.87 (s, 1 H), 7.90 (s, 1 H), 7.95 (d, J=8.42 Hz, 3 H), 10.73 (s, 1 H).

General Protocol III: Synthesis of 2,4-bisanilinopyrrolopyrimidines

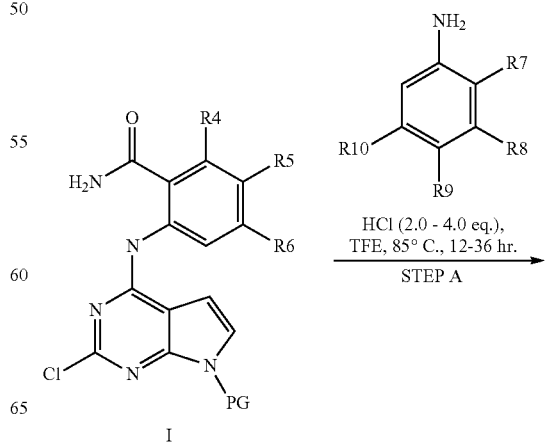

-continued

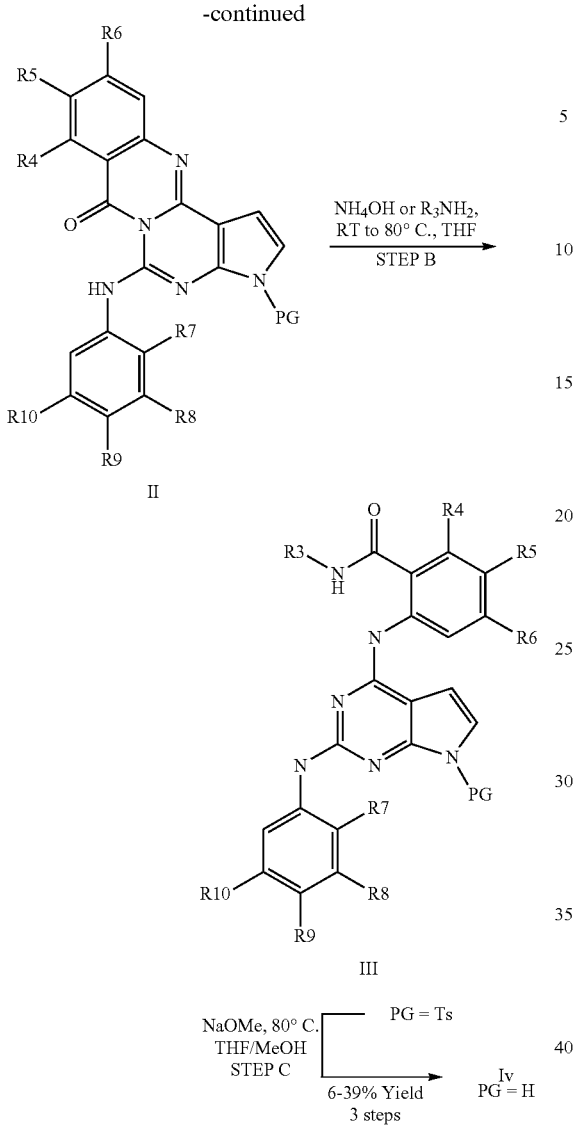

Step A: To a suspension of the 2-chloro-4-anilino-7-[(4-methylphenyl)sulfonyl]-7H-pyrrolo[2,3-d]pyrimidine (i, Intermediates C1-C19, 300 mg-6 g) in trifluoroethanol (7-300 mL) was added an aniline (1.25-1.75 equiv., Intermediates B1-B124), hydrochloric acid as a 4.0M solution in dioxane (4 equiv.), and catalytic potassium iodide (<10 mg). The resulting slurry was stirred at ~85° C. in a pressure vial until all solids had completely dissolved 12-36 hr.) The resulting solution was cooled to room temperature and diluted with dichloromethane and saturated sodium bicarbonate as to adjust the aqueous layer to pH>10. The organic layer was dried over sodium sulfate, filtered, and the solvents removed under reduced pressure to afford the corresponding 3-[(4-methylphenyl)sulfonyl]-5-(phenylamino)pyrrolo[2',3':4,5]pyrimido[6,1-b]quinazolin-7(3H)-ones (ii).

Step B: Tetracyclic ii was suspended in tetrahydrofuran (12-20 mL) and either 27% aqueous ammonium hydroxide (50 mL) or another primary amine (i.e. 4-fluorobenzylamine, 2-15 equiv.) was added. The resulting solution was warmed to ~80° C. in a pressure vessel until all solids had dissolved (1-10 hr.) After cooling to room temperature, the vessel was cautiously opened and the organic layer was dried with solid sodium sulfate, filtered, and concentrated under reduced pressure to afford adequately pure intermediate iii.

Step C: These solids (iii) were dissolved in a 1:1 mixture of tetrahydrofuran and methanol and solid sodium methoxide was added. The resulting suspension was stirred at room temperature (or 80° C. in a pressure vessel) until all starting materials were judged consumed by thin layer chromatography. Upon cooling to room temperature saturated sodium bicarbonate (10 mL) and ethyl acetate (20 mL) were added. The organic layer was subsequently washed with 2.0N sodium hydroxide and brine, dried over sodium sulfate, filtered, stripped onto celite, and purified by chromatography on $SiO_2$ (80 g $SiO_2$, 0% to 10% MeOH/$CH_2CL_2$ with 0.2% added $NH_3$) to afford the final bisanilinopyrrolopyrimidines (6-39% yield, 3 steps, Examples 1-115) as yellow or white solids.

Example 1

2-[(2-{[2-methyl-4-(1-propyl-1,2,5,6-tetrahydro-3-pyridinyl)phenyl]amino}-1H-pyrrolo[2,3-d]pyrimidin-4-yl)amino]benzamide

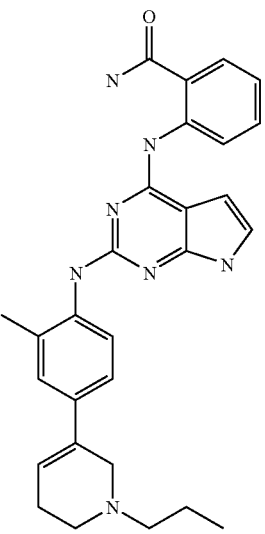

According to General Protocol III, 2-[(2-{[2-methyl-4-(1-propyl-1,2,5,6-tetrahydro-3-pyridinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)benzamide (0.25 g, 51 mmol), 27% aqueous ammonium hydroxide, and 2-methyl-4-(1-propyl-1,2,5,6-tetrahydro-3-pyridinyl)aniline (0.26 g, 1.14 mmol) and isolated as a yellow solid (0.056 g). 1H NMR (400 MHz, DMSO-$d_6$) δ ppm 0.88 (t, J=7.3 Hz, 3 H), 1.46-1.63 (m, 2 H), 2.19-2.31 (m, 5 H), 2.39-2.46 (m, 2 H), 2.50-2.59 (m, 2 H), 3.21-3.40 (m, 2 H), 6.11 (s, 1 H), 6.22 (dd, J = 3.2, 1.7 Hz, 1H), 6.87-6.99 (m, 2 H), 7.15-7.24 (m, 2 H), 7.28 (t, J =7.8 Hz, 1 H), 7.56 (d, J=8.4 Hz, 1 H), 7.69 (s, 1 H), 7.78 (d, J=8.1 Hz, 1 H), 8.05 (s, 1 H), 8.25 (s, 1 H), 8.92 (d, J=8.4 Hz, 1 H), 11.21 (s, 1 H), 12.01 (s, 1 H); ESIMS (M+H)$^+$=482.

Example 2

2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide

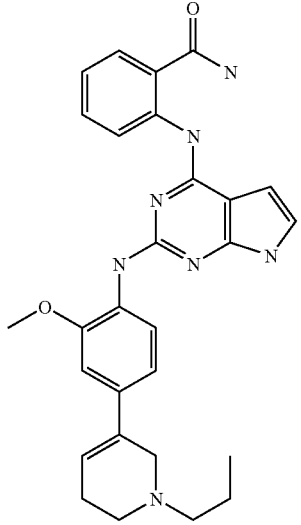

According to General Protocol III, 2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)benzamide (3.0 g, 6.8 mmol), 27% aqueous ammonium hydroxide, and 2-(methyloxy)-4-(1-propyl-1,2,5,6-tetrahydro-3-pyridinyl)aniline (1.84 g, 7.48 mmol) and isolated as a yellow solid (2.53 g). 1H NMR (400 MHz, DMSO-$d_6$) δ ppm 0.89 (t, J=7.4 Hz, 3 H), 1.51-1.60 (m, 2 H), 2.26 (s, 2 H), 2.38-2.44 (m, 2 H), 2.49-2.55 (m, 2 H), 3.23-3.29 (m, J=2.0, 1.3, 1.1 Hz, 2 H), 3.90 (s, 3 H), 6.11-6.16 (m, 1 H), 6.28 (dd, J=3.5, 1.8 Hz, 1 H), 6.94 (dd, J=8.4, 1.8 Hz, 1 H), 7.00-7.05 (m, 3 H), 7.47-7.52 (m, 1 H), 7.55 (s, 1 H), 7.74 (s, 1 H), 7.82 (dd, J=8.1, 1.5 Hz, 1 H), 8.29 (d, J=0.7 Hz, 1 H), 8.30-8.34 (m, 1 H), 8.92 (dd, J=8.4, 1.1 Hz, 1 H), 11.42 (s, 1 H), 12.00 (s, 1 H); ESIMS (M+H)$^+$=498.

Example 3

2-[(2-{[2-(methyloxy)-4-(1-propyl-3-piperidinyl)phenyl]amino}-1H-pyrrolo[2,3-d]pyrimidin-4-yl)amino]benzamide

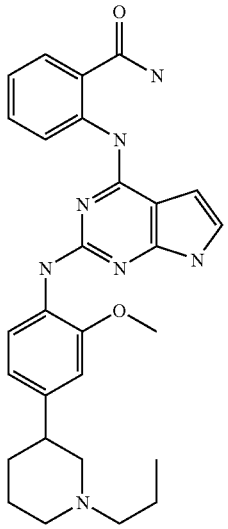

According to General Protocol III, 2-[(2-{[2-(methyloxy)-4-(1-propyl-3-piperidinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)benzamide (0.350 g, 0.79 mmol), 27% aqueous ammonium hydroxide and [2-2-(methyloxy)-4-(1-propyl-3-piperidinyl)aniline (0.21 g, 0.87 mmol) and isolated as a yellow solid (0.054 g). 1H NMR (400 MHz, DMSO-$d_6$) δ ppm 0.80-0.87 (m, 3 H), 1.39-1.50 (m, 3 H), 1.52-1.62 (m, 1 H), 1.66-1.74 (m, 1 H), 1.79-1.84 (m, 1 H), 1.88-1.98 (m, 2 H), 2.20-2.29 (m, 2 H), 2.64-2.74 (m, 1 H), 2.82-2.91 (m, 2 H), 3.85 (s, 3 H), 6.27 (dd, J=2.7, 1.8 Hz, 1 H), 6.80 (d, J=7.9 Hz, 1 H), 6.90 (s, 1 H), 6.97-7.05 (m, 2 H), 7.45-7.52 (m, 2 H), 7.71-7.76 (m, 1 H), 7.79-7.86 (m, 1 H), 8.17 (d, J=8.1 Hz, 1 H), 8.26-8.33 (m, 1 H), 8.92 (d, J=8.4 Hz, 1 H), 11.35-11.42 (m, 1 H), 11.97-12.05 (m, 1 H); ESIMS (M+H)$^+$=500.

Example 4

2-[(2-{[2-(methyloxy)-4-(1-methyl-1,2,5,6-tetrahydro-3-pyridinyl)phenyl]amino}-1H-pyrrolo[2,3-d]pyrimidin-4-yl)amino]benzamide

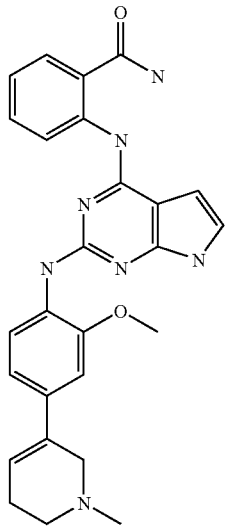

According to General Protocol III, 2-[(2-{[2-(methyloxy)-4-(1-methyl-1,2,5,6-tetrahydro-3-pyridinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)benzamide (0.5 g, 1.13 mmol), 27% aqueous ammonium hydroxide and 2-(methyloxy)-4-(1-methyl-1,2,5,6-tetrahydro-3-pyridinyl)aniline (0.27 g, 1.25 mmol) and isolated as a yellow solid (0.075g). 1H NMR (400 MHz, DMSO-$d_6$) δ ppm 2.27 (s, 2 H), 2.34 (s, 3 H), 2.44-2.47 (m, 2 H), 3.20 (s, 2 H), 3.90 (s, 3 H), 6.09-6.16 (m, 1 H), 6.29 (dd, J=3.2, 1.9 Hz, 1 H), 6.94 (dd, J=8.5, 1.7 Hz, 1 H), 6.99-7.07 (m, 3 H), 7.46-7.53 (m, 1 H), 7.54 (s, 1 H), 7.73 (s, 1 H), 7.82 (dd, J=8.0, 1.2 Hz, 1 H), 8.28 (s, 1 H), 8.33 (d, J=8.4 Hz, 1 H), 8.92 (d, J=8.2 Hz, 1 H), 11.41 (s, 1 H), 11.99 (s, 1 H); ESIMS (M-H)$^+$=468.

Example 5

2-[(2-{[2-(methyloxy)-4-(1-methyl-3-piperidinyl)phenyl]amino}-1H-pyrrolo[2,3-d]pyrimidin-4-yl)amino]benzamide

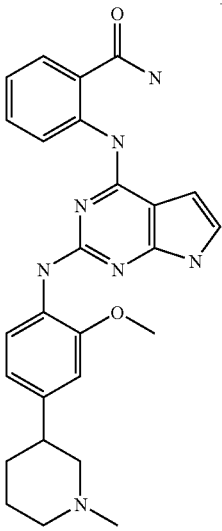

According to General Protocol III, 2-[(2-{[2-(methyloxy)-4-(1-methyl-3-piperidinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)benzamide (0.5 g, 1.13 mmol), 27% aqueous ammonium hydroxide, and 2-(methyloxy)-4-(1-methyl-3-piperidinyl)aniline (0.27 g, 1.24 mmol) and isolated as a yellow solid (0.114 g). 1H NMR (400 MHz, DMSO-$d_6$) δ ppm 1.36-1.47 (m, 1 H), 1.58 (d, J=13.7 Hz, 1 H), 1.70 (d, J=14.8 Hz, 1 H), 1.81 (d, J=7.5 Hz, 1 H), 1.89 (s, 1 H), 1.92 (d, J=4.9 Hz, 1 H), 2.20 (s, 3 H), 2.65-2.76 (m, 1 H), 2.76-2.87 (m, 2 H), 3.85 (s, 3 H), 6.24-6.32 (m, 1 H), 6.79 (d, J=9.1 Hz, 1 H), 6.89 (d, J=0.9 Hz, 1 H), 6.95-6.99 (m, 1 H), 7.01 (t, J=7.5 Hz, 1 H), 7.43-7.51 (m, 2 H), 7.73 (s, 1 H), 7.76-7.85 (m, 1 H), 8.18 (d, J=7.9 Hz, 1 H), 8.23-8.33 (m, 1 H), 8.92 (d, J=8.6 Hz, 1 H), 11.36 (s, 1 H), 11.98 (s, 1 H); ESIMS (M+H)$^+$=472.

Example 6

2-[(2-{[4-[1-(1-methylethyl)-1,2,5,6-tetrahydro-3-pyridinyl]-2-(methyloxy)phenyl]amino}-1H-pyrrolo[2,3-d]pyrimidin-4-yl)amino]benzamide

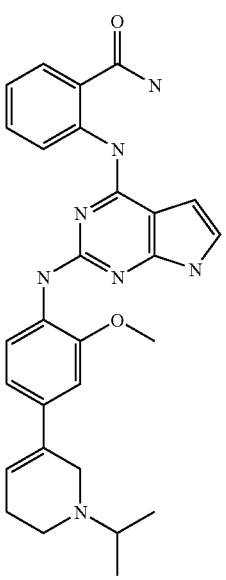

According to General Protocol III, 2-[(2-{[4-[1-(1-methylethyl)-1,2,5,6-tetrahydro-3-pyridinyl]-2-(methyloxy)phenyl]amino}-1H-pyrrolo[2,3-d]pyrimidin-4-yl)amino]benzamide (0.083 g, 0.167 mmol) was prepared from 2-({2-chloro-7-[(4-methylphenyl)sulfonyl]-7H-pyrrolo[2,3-d]pyrimidin-4-yl}amino)benzamide (0.25 g, 0.57 mmol), 27% aqueous ammonium hydroxide, and 4-[1-(1-methylethyl)-1,2,5,6-tetrahydro-3-pyridinyl]-2-(methyloxy)aniline. 1H NMR (400 MHz, DMSO-$d_6$) δ ppm 1.04 (d, J=6.4 Hz, 6 H), 2.17-2.27 (m, 2 H), 2.50-2.57 (m, 2 H), 2.78-2.89 (m, 1 H), 3.31-3.38 (m, 2 H), 3.88 (s, 3 H), 6.09 (s, 1 H), 6.24-6.30 (m, 1 H), 6.89-6.95 (m, 1 H), 6.96-7.04 (m, 3 H), 7.48 (t, J=7.9 Hz, 1 H), 7.53 (s, 1 H), 7.72 (s, 1 H), 7.81 (d, J=7.1 Hz, 1 H), 8.24-8.32 (m, 2 H), 8.90 (d, J=8.4 Hz, 1 H), 11.39 (s, 1 H), 11.98 (s, 1 H); ESIMS (M+)$^+$=498.

Example 7

2-[(2-{[4-[4-(1-methylethyl)-1-piperazinyl]-2-(methyloxy)phenyl]amino}-1H-pyrrolo[2,3-d]pyrimidin-4-yl)amino]benzamide

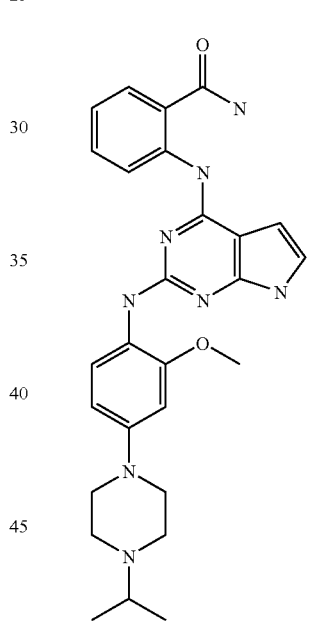

According to General Protocol III, 2-[(2-{[4-[4-(1-methylethyl)-1-piperazinyl]-2-(methyloxy)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)benzamide (0.5 g, 1.13 mmol), 27% aqueous ammonium hydroxide, and 4-[4-(1-methylethyl)-1-piperazinyl]-2-(methyloxy)aniline (0.31 g, 1.25 mmol) and isolated as a yellow solid (0.123 g). 1H NMR (400 MHz, DMSO-$d_6$) δ ppm 1.00 (d, J=6.6 Hz, 6 H), 2.57 (s, 4 H), 2.66 (d, J=5.9 Hz, 1 H), 3.09 (s, 4 H), 3.80 (s, 3 H), 6.23 (s, 1 H), 6.45-6.49 (m, 1 H), 6.62 (d, J=1.8 Hz, 1 H), 6.91-6.94 (m, 1 H), 6.99 (t, J=7.3 Hz, 1 H), 7.38-7.45 (m, 2 H), 7.69-7.73 (m, 1 H), 7.80 (d, J=7.3 Hz, 1 H), 7.88 (d, J=8.8 Hz, 1 H), 8.27 (s, 1 H), 8.94 (d, J=7.7 Hz, 1 H), 11.27 (s, 1 H), 11.94-11.97 (m, 1 H); ESIMS (M+H)$^+$=501.

Example 8

2-[(2-{[2-(methyloxy)-4-(4-propyl-1-piperazinyl)phenyl]amino}-1H-pyrrolo[2,3-d]pyrimidin-4-yl)amino]benzamide

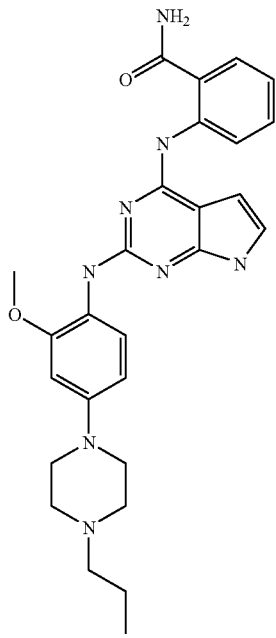

According to General Protocol III, 2-[(2-{[2-(methyloxy)-4-(4-propyl-1-piperazinyl)phenyl]amino}-1H-pyrrolo[2,3-d]pyrimidin-4-yl)amino]benzamide (0.106 g, 31% yield) was prepared from 2-({2-chloro-7-[(4-methylphenyl)sulfonyl]-7H-pyrrolo[2,3-d]pyrimidin-4-yl}amino)benzamide (0.300 g, 0.68 mmol), 27% aqueous ammonium hydroxide, and 2-(methyloxy)-4-(4-propyl-1-piperazinyl)aniline (0.250 g, 1.02 mmol); 1H NMR (400 MHz, DMSO-$d_6$) δ ppm 0.85 (t, J=7.42 Hz, 3 H), 1.40-1.50 (m, 2 H), 2.20-2.30 (m, 2 H), 2.49 (s, 4 H), 3.08 (s, 4 H), 3.79 (s, 3 H), 6.22 (dd, J=3.39, 1.74 Hz, 1 H), 6.46 (d, J=8.79 Hz, 1 H), 6.61 (d, J=2.38 Hz, 1 H), 6.91 (dd, J=3.39, 2.29 Hz, 1 H), 6.94-7.02 (m, 1 H), 7.36 (s, 1 H), 7.42 (t, J=7.69 Hz, 1 H), 7.69 (s, 1 H), 7.79 (d, J=8.06 Hz, 1 H), 7.88 (d, J=8.61 Hz, 1 H), 8.25 (s, 1 H), 8.92 (d, J=8.24 Hz, 1 H), 11.25 (s, 1H), 11.94 (s, 1 H). ESIMS (M+H)+=501.

Example 9

2-[(2-{[2-(methyloxy)-5-(4-methyl-1-piperazinyl)phenyl]amino}-1H-pyrrolo[2,3-d]pyrimidin-4-yl)amino]benzamide

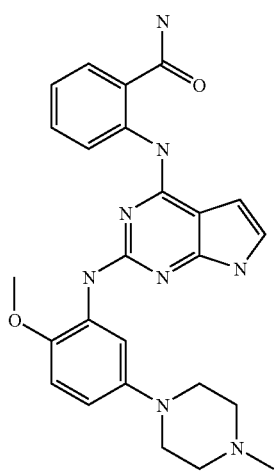

According to General Protocol III, 2-[(2-{[2-(methyloxy)-5-(4-methyl-1-piperazinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)benzamide (0.23 g, 0.52 mmol), 27% aqueous ammonium hydroxide, and 2-(methyloxy)-5-(4-methyl-1-piperazinyl)aniline (0.15 g, 0.68 mmol) and isolated as a yellow solid (0.112 g): 1H NMR (400 MHz, DMSO-$d_6$) δ ppm 2.19 (s, 3 H) 2.39-2.48 (m, 4 H) 2.96-3.05 (m, 4 H) 3.78 (s, 3 H) 6.26-6.28 (m, 1 H) 6.45 (dd, J=8.79, 2.75 Hz, 1 H) 6.84 (d, J=8.79 Hz, 1 H) 6.95-7.03 (m, 2 H) 7.42-7.50 (m, 2 H) 7.72 (s, 1 H) 7.80 (m, 1 H) 8.12 (m, 1 H) 8.28 (s, 1 H) 8.90 (d, J=8.42 Hz, 1 H) 11.38 (s, 1 H) 12.01 (s, 1 H). ESIMS (M+H)+=473.

Example 10

2-[(2-{[5-[4-(1-methylethyl)-1-piperazinyl]-2-(methyloxy)phenyl]amino}-1H-pyrrolo[2,3-d]pyrimidin-4-yl)amino]benzamide

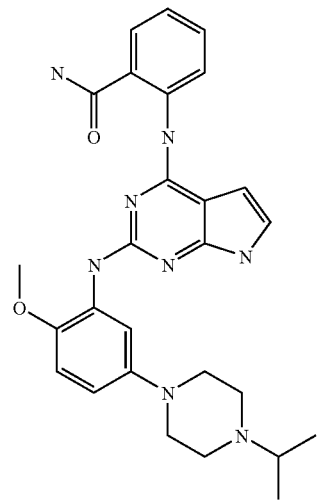

According to General Protocol III, 2-[(2-{[5-[4-(1-methylethyl)-1-piperazinyl]-2-(methyloxy)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)benzamide (0.30 g, 0.65 mmol), 27% aqueous ammonium hydroxide, and 5-[4-(1-methylethyl)-1-piperazinyl]-2-(methyloxy)aniline (0.20 g, 0.8 mmol) and isolated as a yellow-green solid (0.099 g, 43% over 3 steps). 1H NMR (400 MHz, DMSO-$d_6$) δ ppm 0.96-1.04 (m, 6 H) 2.55 (s, 4 H) 2.64 (s, 1 H) 3.00 (s, 4 H), 3.78 (s, 3 H) 6.27 (m, 1 H) 6.44 (m, 1 H) 6.84 (d, J=8.97 Hz, 1 H) 6.97-7.02 (m, 2 H) 7.45 (s, 1 H) 7.46-7.51 (m, 1 H) 7.72 (s, 1 H) 7.81 (m, 1 H) 8.14 (d, J=2.56 Hz, 1 H) 8.28 (s, 1 H) 8.91 (d, J=8.42 Hz, 1 H) 11.38 (s, 1 H) 12.02 (s, 1 H). ESIMS (M+H)+=501.

Example 11

2-[(2-{[2-methyl-4-(4-morpholinyl)phenyl]amino}-1H-pyrrolo[2,3-d]pyrimidin-4-yl)amino]benzamide

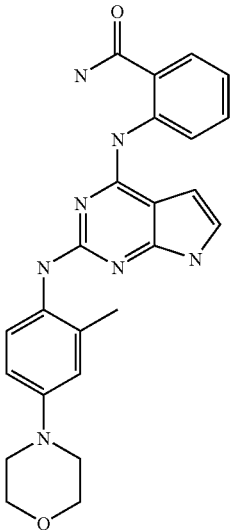

According to General Protocol III, 2-[(2-{[2-methyl-4-(4-morpholinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)benzamide (0.300 g, 0.680 mmol), 27% aqueous ammonium hydroxide, and 2-methyl-4-(4-morpholinyl) aniline (0.144 g, 0.750 mmol) and isolated as a yellow solid (0.110 g, 37% Yield); 1H NMR (400 MHz, DMSO-$d_6$) δ ppm 2.17 (s, 3 H), 3.02-3.12 (m, 4 H), 3.70-3.79 (m, 4 H), 6.19 (d, J=1.28 Hz, 1 H), 6.77 (d, J=8.42 Hz, 1 H), 6.81 (s, 1 H), 6.83-6.89 (m, 1 H), 6.93 (t, J=7.23 Hz, 1 H), 7.22-7.33 (m, 2 H), 7.68 (s, 1 H), 7.78 (d, J=8.05 Hz, 1 H), 7.93 (s, 1 H), 8.24 (s, 1 H), 8.92 (d, J=8.60 Hz, 1 H), 11.14 (s, 1 H), 11.98 (s, 1 H). ESI-MS (M+H) 444. Retention time 1.77 minutes.

Example 12

2-[(2-{[2-(methyloxy)-4-(4-morpholinyl)phenyl]amino}-1H-pyrrolo[2,3-d]pyrimidin-4-yl)amino]benzamide

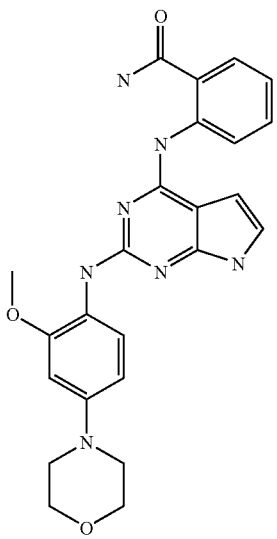

According to General Protocol III, 2-[(2-{[2-(methyloxy)-4-(4-morpholinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)benzamide (0.378 g, 0.86 mmol), 27% aqueous ammonium hydroxide, and 2-(methyloxy)-4-(4-morpholinyl)aniline (0.220 g, 0.902 mmol) and isolated as a yellow solid (0.130 g, 33% Yield); 1H NMR (400 MHz, DMSO-$d_6$) δ ppm 3.06-3.11 (m, 4 H), 3.72-3.77 (m, 4 H), 3.82 (s, 3 H), 6.24 (dd, J=3.48, 1.83 Hz, 1 H), 6.49 (dd, J=8.78, 2.56 Hz, 1 H), 6.65 (d, J=2.38 Hz, 1 H), 6.94 (dd, J=3.38, 2.29 Hz, 1 H), 6.96-7.03 (m, 1 H), 7.40 (s, 1 H), 7.41-7.47 (m, 1 H), 7.71 (s, 1 H), 7.81 (dd, J=7.96, 1.37 Hz, 1 H), 7.94 (d, J=8.78 Hz, 1 H), 8.27 (s, 1 H), 8.94 (d, J=8.05 Hz, 1 H), 11.28 (s, 1 H), 11.97 (s, 1 H). ESI-MS (M+H) 460. Retention time 1.75 minutes.

Example 13

2-{[2-({5-[(N,N-dimethylglycyl)amino]-2-methylphenyl}amino)-1H-pyrrolo[2,3-d]pyrimidin-4-yl]amino}benzamide

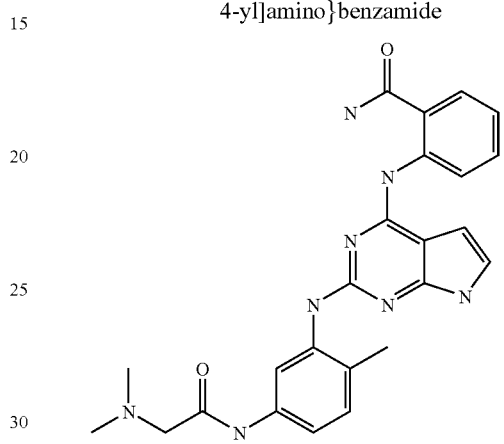

According to General Protocol III, 2-{[2-({5-[(N,N-dimethylglycyl)amino]-2-methylphenyl}amino)-1H-pyrrolo[2,3-d]pyrimidin-4-yl]amino}benzamide was prepared from 2-({2-chloro-7-[(4-methylphenyl)sulfonyl]-7H-pyrrolo[2,3-d]pyrimidin-4-yl}amino)benzamide (0.300 g, 0.680 mmol), 27% aqueous ammonium hydroxide, and $N^1$-(3-amino-4-methylphenyl)-$N^2$,$N^2$-dimethylglycinamide (0.176 g, 0.850 mmol) and isolated as a yellow solid (0.121 g, 39% Yield); 1H NMR (400 MHz, DMSO-$d_6$) δ ppm 2.16 (s, 3 H), 2.22 (s, 6 H), 3.00 (s, 2 H), 6.22 (dd, J=3.38, 1.92 Hz, 1 H), 6.88-6.95 (m, 2 H), 7.11 (d, J=8.23 Hz, 1 H), 7.24 (t, J=7.50 Hz, 1 H), 7.38 (dd, J=8.14, 1.92 Hz, 1 H), 7.70 (s, 1 H), 7.73 (d, J=2.01 Hz, 1 H), 7.77 (dd, J=8.05, 1.28 Hz, 1 H), 8.16 (s, 1 H), 8.25 (s, 1 H), 8.89 (d, J=8.05 Hz, 1 H), 9.57 (s, 1 H), 11.21 (s, 1 H), 12.04 (s, 1 H). ESI-MS (M+H) 459. Retention time 1.19 minutes.

Example 14

2-{[2-({2-methyl-5-[(1-pyrrolidinylacetyl)amino]phenyl}amino)-1H-pyrrolo[2,3-d]pyrimidin-4-yl]amino}benzamide

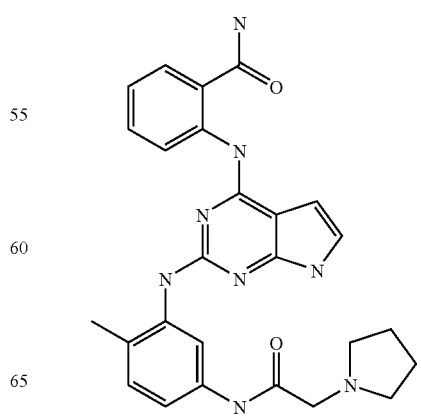

According to General Protocol III, 2-{[2-({2-methyl-5-[(1-pyrrolidinylacetyl)amino]phenyl}amino)-1H-pyrrolo[2,3-d]pyrimidin-4-yl]amino}benzamide was prepared from 2-({2-chloro-7-[(4-methylphenyl)sulfonyl]-7H-pyrrolo[2,3-d]pyrimidin-4-yl}amino)benzamide (0.300 g, 0.68 mmol), 27% aqueous ammonium hydroxide, and N-(3-amino-4-methylphenyl)-2-(1-pyrrolidinyl)acetamide (0.20 g, 1.02 mmol) and isolated as a yellow solid (0.112 g); 1H NMR (400 MHz, DMSO-$d_6$) δppm 1.66-1.67 (m, 4 H) 2.15 (s, 3 H) 2.52 (m, 4 H) 3.16 (s, 2 H) 6.20-6.22 (m, 1 H) 6.88-6.92 (m, 2 H) 7.10 (d, J=8.24 Hz, 1 H) 7.20-7.25 (m, 1 H) 7.35-7.37 (m, 1 H) 7.67-7.70 (m, 2 H) 7.75-7.77 (m, 1 H) 8.14 (s, 1 H) 8.24 (s, 1 H) 8.88 (d, J=8.42 Hz, 1 H) 9.54 (s, 1 H) 11.19 (s, 1 H) 12.02 (s, 1 H). ESIMS (M+H)+=485.

Example 15

2-[(2-{[5-[(N,N-dimethylglycyl)amino]-2-(methyloxy)phenyl]amino}-1H-pyrrolo[2,3-d]pyrimidin-4-yl)amino]benzamide

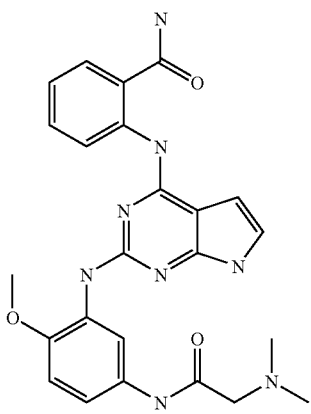

According to General Protocol III, 2-[(2-{[5-[(N,N-dimethylglycyl)amino]-2-(methyloxy)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)benzamide (0.30 g, 0.68 mmol), 27% aqueous ammonium hydroxide, and $N^1$-[3-amino-4-(methyloxy)phenyl]-$N^2$,$N^2$-dimethylglycinamide (0.23 g, 1.02 mmol) and isolated as a yellow solid (0.115 g); 1H NMR (400 MHz, DMSO-$d_6$) δ ppm 2.24 (s, 6 H) 2.99 (s, 2 H) 3.80 (s, 3 H) 6.26-6.27 (m, 1 H) 6.92-6.94 (m, 1 H) 6.95-7.01 (m, 2 H) 7.31-7.34 (m, 1 H) 7.37-7.43 (m, 1 H) 7.56 (s, 1 H) 7.71 (s, 1 H) 7.80 (dd, J=7.87, 1.10 Hz, 1 H) 8.16-8.17 (m, 1 H) 8.26 (s, 1 H) 8.90 (d, J=8.42 Hz, 1 H) 9.39 (s, 1 H) 11.31 (s, 1 H) 12.03 (s, 1 H). ESIMS (M+H)+=475.

Example 16

2-{[2-({5-[(N,N-dimethylglycyl)amino]-2-[(trifluoromethyl)oxy]phenyl}amino)-1H-pyrrolo[2,3-d]pyrimidin-4-yl]amino}benzamide

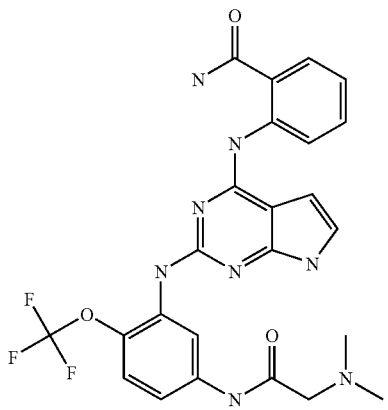

According to General Protocol III, 2-{[2-({5-[(N, N-dimethylglycyl)amino]-2-[(trifluoromethyl)oxy]phenyl}amino)-1H-pyrrolo[2,3-d]pyrimidin-4-yl]amino}benzamide was prepared from 2-({2-chloro-7-[(4-methylphenyl)sulfonyl]-7H-pyrrolo[2,3-d]pyrimidin-4-yl}amino)benzamide (0.300 g, 0.680 mmol), 27% aqueous ammonium hydroxide, and $N^1$-{3-amino-4-[(trifluoromethyl)oxy]phenyl}-$N^2$,$N^2$-dimethylglycinamide (0.180 g, 0.850 mmol) and isolated as a yellow solid (0.135 g, 38% Yield); 1H NMR (400 MHz, DMSO-$d_6$) δ ppm 2.22 (s, 6 H), 3.02 (s, 2 H), 6.25 (dd, J=3.48, 1.83 Hz, 1 H), 6.91-6.98 (m, 2 H), 7.24-7.33 (m, 2 H), 7.50 (dd, J=8.88, 2.47 Hz, 1 H), 7.70 (s, 1 H), 7.78 (dd, J=7.87, 1.28 Hz, 1 H), 8.07 (d, J=2.56 Hz, 1 H), 8.26 (s, 1 H), 8.33 (s, 1 H), 8.87 (d, J=8.42 Hz, 1 H), 9.79 (s, 1 H), 11.30 (s, 1 H), 12.08 (s, 1 H). ESI-MS (M+H) 529. Retention time 1.76 minutes.

Example 17

2-{[2-({5-[(N,N-dimethylglycyl)amino]-2-fluorophenyl}amino)-1H-pyrrolo[2,3-d]pyrimidin-4-yl]amino}benzamide

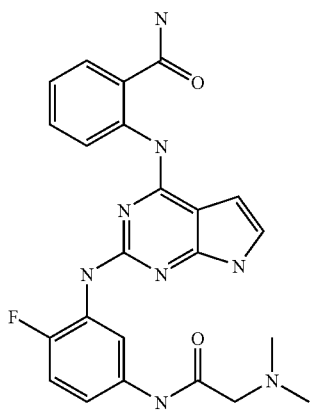

According to General Protocol III, 2-{[2-({5-[(N,N-dimethylglycyl)amino]-2-fluorophenyl}amino)-1H-pyrrolo[2,3-d]pyrimidin-4-yl]amino}benzamide was prepared from 2-({2-chloro-7-[(4-methylphenyl)sulfonyl]-7H-pyrrolo[2,3-d]pyrimidin-4-yl}amino)benzamide (0.300 g, 0.68 mmol), 27% aqueous ammonium hydroxide, and N¹-(3-amino-4-fluorophenyl)-N²,N²-dimethylglycinamide (0.22 g, 1.04 mmol) and isolated as a yellow solid (0.056 g); 1H NMR (400 MHz, DMSO-d$_6$) δ ppm 2.24 (s, 6 H) 3.02 (s, 2 H) 5.74 (s, 1 H) 6.25-6.26 (m, 1 H) 6.91-6.98 (m, 3 H) 7.11-7.19 (m, 1 H) 7.31 (s, 2 H) 7.35-7.43 (m, 1 H) 7.70-7.81 (m, 2 H) 7.96 (dd, J=7.41, 2.47 Hz, 1 H) 9.69 (s, 1 H) 11.31 (s, 1 H) 12.08 (s, 1 H). ESIMS (M+H)+=463.

Example 18

2-{[2-({2-chloro-5-[(N,N-dimethylglycyl)amino]phenyl}amino)-1H-pyrrolo[2,3-d]pyrimidin-4-yl]amino}benzamide

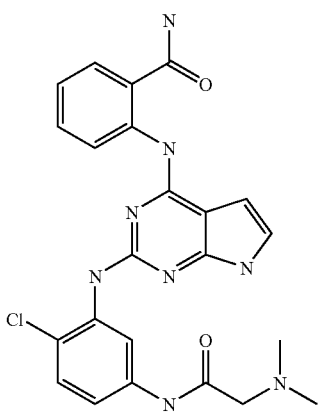

According to General Protocol III, 2-{[2-({2-chloro-5-[(N,N-dimethylglycyl)amino]phenyl}amino)-1H-pyrrolo[2,3-d]pyrimidin-4-yl]amino}benzamide was prepared from 2-({2-chloro-7-[(4-methylphenyl)sulfonyl]-7H-pyrrolo[2,3-d]pyrimidin-4-yl}amino)benzamide (0.30 g, 0.68 mmol), 27% aqueous ammonium hydroxide, and N¹-(3-amino-4-chlorophenyl)-N²,N²-dimethylglycinamide (0.23 g, 1.01 mmol) and isolated as a yellow solid (0.114 g); 1H NMR (400 MHz, DMSO-d$_6$) δppm 2.22 (s, 6 H) 3.03 (s, 2 H) 6.24-6.26 (m, 1 H) 6.91-6.97 (m, 2 H) 7.28 (m, 1 H) 7.37 (d, J=8.79 Hz, 1 H) 7.47-7.50 (m, 1 H) 7.70 (s, 1 H) 7.77-7.79 (m, 1 H) 8.07 (d, J=2.38 Hz, 1 H) 8.14 (s, 1 H) 8.25 (s, 1 H) 8.85 (d, J=8.61 Hz, 1 H), 9.77 (s, 1 H) 11.32 (s, 1 H) 12.07 (s, 1 H). ESIMS (M+H)+=479.

Example 19

2-{[2-({2-(methyloxy)-4-[(methylsulfonyl)methyl]phenyl}amino)-1H-pyrrolo[2,3-d]pyrimidin-4-yl]amino}benzamide

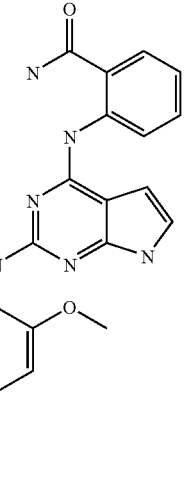

According to General Protocol III, 2-{[2-({2-(methyloxy)-4-[(methylsulfonyl)methyl]phenyl}amino)-1H-pyrrolo[2,3-d]pyrimidin-4-yl]amino}benzamide was prepared from 2-({2-chloro-7-[(4-methylphenyl)sulfonyl]-7H-pyrrolo[2,3-d]pyrimidin-4-yl}amino)benzamide (0.250 g, 0.567 mmol), 27% aqueous ammonium hydroxide, and 2-(methyloxy)-4-[(methylsulfonyl)methyl]aniline (0.146 g, 0.680 mmol) and isolated as a white solid (0.075 g, 24% Yield); 1H NMR (400 MHz, DMSO-d$_6$) δ ppm 2.87 (s, 3 H), 3.85 (s, 3 H), 4.39 (s, 2 H), 6.27 (s, 1 H), 6.94-7.06 (m, 4 H), 7.42-7.53 (m, 1 H), 7.60 (s, 1 H), 7.71 (s, 1 H), 7.80 (d, J=8.06 Hz, 1 H), 8.27 (s, 1 H), 8.34 (d, J=8.42 Hz, 1 H), 8.89 (d, J=8.42 Hz, 1 H), 11.40 (s, 1 H), 11.98 (s, 1 H). ESI-MS (M+H) 467. Retention time 1.74 minutes.

Example 20

2-{[2-({2-(methyloxy)-5-[(methylsulfonyl)methyl]phenyl}amino)-1H-pyrrolo[2,3-d]pyrimidin-4-yl]amino}benzamide

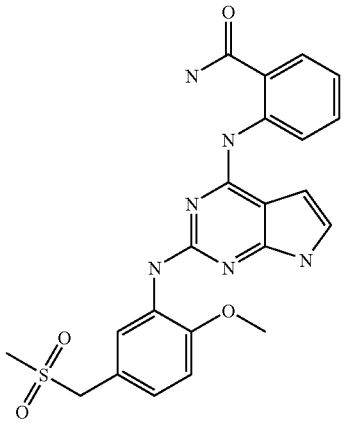

According to General Protocol III, 2-{[2-({2-(methyloxy)-5-[(methylsulfonyl)methyl]phenyl}amino)-1H-pyrrolo[2,3-d]pyrimidin-4yl]amino}benzamide was prepared from 2-({2-chloro-7-[(4-methylphenyl)sulfonyl]-7H-pyrrolo[2,3-d]pyrimidin-4-yl}amino)benzamide (0.250 g, 0.567 mmol), 27% aqueous ammonium hydroxide, and 2-(methyloxy)-5-[(methylsulfonyl)methyl]aniline (0.146 g, 0.680 mmol) and isolated as a yellow solid (0.051 g, 16% Yield); 1H NMR (400 MHz, DMSO-$d_6$) δ ppm 2.86 (s, 3 H), 3.87 (s, 3 H), 4.32 (s, 2 H), 6.29 (s, 1 H), 6.97-7.07 (m, 4 H), 7.48 (t, J=7.78 Hz, 1 H), 7.65 (s, 1 H), 7.73 (s, 1 H), 7.82 (d, J=7.50 Hz, 1 H), 8.22-8.33 (m, 2 H), 8.87 (d, J=8.42 Hz, 1 H), 11.31 (s, 1 H), 11.99 (s, 1 H). ESI-MS (M+H) 467. Retention time 1.78 minutes.

Example 21

N-methyl-2-[(2-{[2-(methyloxy)-4-(1-methyl-1,2,5,6-tetrahydro-3-pyridinyl)phenyl]amino}-1H-pyrrolo[2,3-d]pyrimidin-4-yl)amino]benzamide

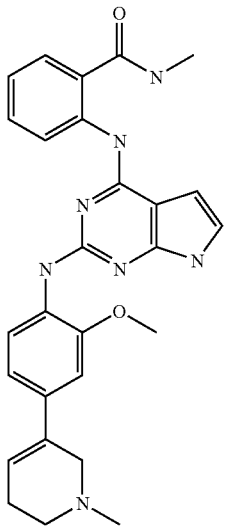

According to General Protocol III, N-methyl-2-[(2-{[2-(methyloxy)-4-(1-methyl-1,2,5,6-tetrahydro-3-pyridinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)benzamide (0.50 g, 1.13 mmol), methylamine (0.93 mL, 30 mmol), and 2-(methyloxy)-4-(1-methyl-1,2,5,6-tetrahydro-3-pyridinyl)aniline (0.27 g, 1.25 mmol) and isolated as a yellow solid (0.099 g). 1H NMR (400 MHz, DMSO-$d_6$) δ ppm 2.27 (d, J=4.0 Hz, 2 H), 2.34 (s, 3 H), 2.44-2.47 (m, 2 H), 2.81 (d, J=4.4 Hz, 3 H), 3.20 (d; J=1.8 Hz, 2 H), 3.90 (s, 3 H), 6.10-6.15 (m, 1 H), 6.31-6.35 (m, 1 H), 6.91-6.95 (m, 1 H), 6.99-7.08 (m, 3 H), 7.47-7.55 (m, 2 H), 7.72-7.78 (m, 1 H), 8.31-8.36 (m, 1 H), 8.70-8.77 (m, 1 H), 8.81-8.86 (m, 1 H), 11.39-11.44 (m, 1 H), 11.62-11.67 (m, 1 H); ESIMS (M+H)$^+$=484.

Example 22

N-methyl-2-[(2-{[2-(methyloxy)-4-(1-methyl-3-piperidinyl)phenyl]amino}-1H-pyrrolo[2,3-d]pyrimidin-4-yl)amino]benzamide

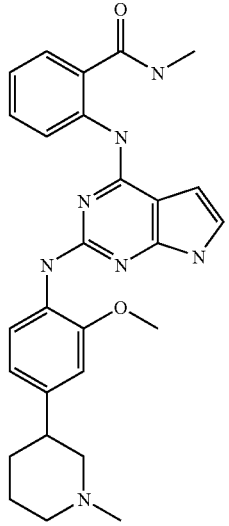

According to General Protocol III, N-methyl-2-[(2-{[2-(methyloxy)-4-(1-methyl-3-piperidinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)benzamide (0.50 g, 1.13 mmol), methyl amine (0.96 mL, 30 mmol), and 2-(methyloxy)-4-(1-methyl-3-piperidinyl)aniline (0.27 g, 1.24 mmol) and isolated as a yellow solid (0.152 g); 1H NMR (400 MHz, DMSO-$d_6$) δ ppm 1.62-1.74 (m, 2 H), 1.76-1.84 (m, 3 H), 1.86-1.91 (m, 1 H), 2.18 (s, 3 H), 2.72-2.84 (m, 6 H), 3.85 (s, 3 H), 6.30 (dd, J=3.3, 1.8 Hz, 1 H), 6.75-6.81 (m, 1 H), 6.89 (d, J=1.6 Hz, 1 H), 6.96-6.99 (m, 1 H), 7.04 (t, J=7.7 Hz, 1 H), 7.41-7.51 (m, 2 H), 7.69-7.76 (m, 1 H), 8.19 (d, J=8.2 Hz, 1 H), 8.73 (d, J=4.8 Hz, 1 H), 8.83 (d, J=8.4 Hz, 1 H), 11.36 (s, 1 H), 11.63 (s, 1 H); ESIMS (M+H)$^+$=486.

Example 23

N-methyl-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide

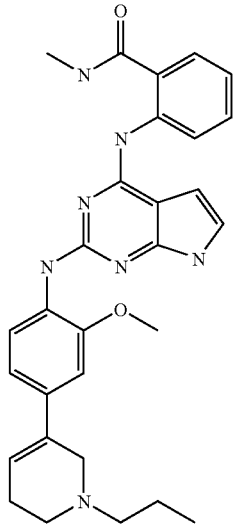

According to General Protocol III, N-methyl-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)benzamide (0.300 g, 0.68 mmol), methyl amine (2mL of a 2.0M solution in THF, Aldrich), and 2-(methyloxy)-4-(1-propyl-1,2,5,6-tetrahydro-3-pyridinyl)aniline (0.234 g, 0.95 mmol) and isolated as a yellow solid (0.065 g, 19% Yield); 1H NMR (400 MHz, DMSO-d$_6$) δ ppm 0.89 (t, J=7.32 Hz, 3 H), 1.50-1.61 (m, 2 H), 2.27 (s, 2 H), 2.45 (s, 2 H), 2.54 (s, 2 H), 2.81 (d, J=4.39 Hz, 3 H), 3.29 (s, 2 H), 3.90 (s, 3 H), 6.14 (s, 1 H), 6.33 (dd, J=3.20, 1.74 Hz, 1 H), 6.94 (d, J=8.42 Hz, 1 H), 7.01 (s, 2 H), 7.05 (t, J=7.50 Hz, 1 H), 7.50 (t, J=7.78 Hz, 1 H), 7.54 (s, 1 H), 7.74 (d, J=7.87 Hz, 1 H), 8.34 (d, J=8.42 Hz, 1 H), 8.74 (d, J=4.21 Hz, 1 H), 8.84 (d, J=8.42 Hz, 1 H), 11.42 (s, 1 H), 11.65 (s, 1 H). ESI-MS (M+H) 512. Retention time 1.52 minutes.

Example 24

N-methyl-2-[(2-{[2-(methyloxy)-4-(1-propyl-3-piperidinyl)phenyl]amino}-1H-pyrrolo[2,3-d]pyrimidin-4-yl)amino]benzamide

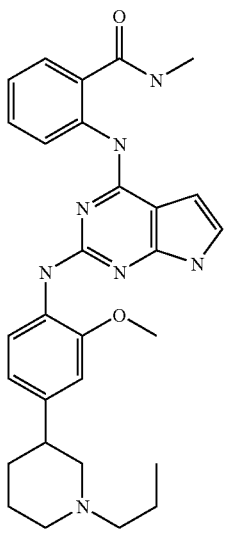

According to General Protocol III, N-methyl-2-[(2-{[2-(methyloxy)-4-(1-propyl-3-piperidinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)benzamide (0.35 g, 0.79 mmol), methyl amine (30 mmol), and 2-(methyloxy)-4-(1-propyl-3-piperidinyl)aniline (0.21 g, 0.87 mmol) and isolated as a yellow solid (0.077 g). 1H NMR (400 MHz, DMSO-d$_6$) δ ppm 0.87 (t, J=7.33 Hz, 3 H), 1.56 (s, 3 H), 1.69 (s, 1 H), 1.78-1.89 (m, 2 H), 2.69 (s, 1 H), 2.81 (d, J=4.77 Hz, 4 H), 3.16 (s, 2 H), 3.31 (s, 2 H), 3.87 (s, 3 H), 6.31 (d, J=1.47 Hz, 1 H), 6.32 (s, 1 H), 6.81 (d, J=8.07 Hz, 1 H), 6.92 (s, 1 H), 6.95-7.01 (m, 1 H), 7.04 (t, J=7.33 Hz, 1 H), 7.44-7.53 (m, 3 H), 8.24 (d, J=8.07 Hz, 1 H), 8.73 (d, J=4.40 Hz, 1 H), 8.83 (d, J=8.07 Hz, 1 H), 11.36 (s, 1 H), 11.65 (s, 1 H) with ca 70 mol % TsOH impurity present. ESIMS (M+H)$^+$=514.

Example 25

N-methyl-2-[(2-{[4-[4-(1-methylethyl)-1-piperazinyl]-2-(methyloxy)phenyl]amino}-1H-pyrrolo[2,3-d]pyrimidin-4yl)amino]benzamide

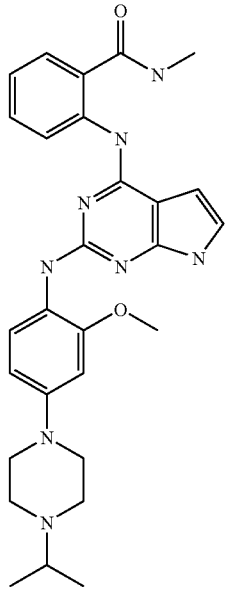

According to General Protocol III, N-methyl-2-[(2-{[4-[4-(1-methylethyl)-1-piperazinyl]-2-(methyloxy)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)benzamide (0.25 g, 0.54 mmol), methyl amine (30 mmol), and 4-[4-(1-methylethyl)-1-piperazinyl]-2-(methyloxy)aniline (0.150 g, 0.60 mmol) and isolated as a yellow solid (0.140 g). 1H NMR (400 MHz, DMSO-d$_6$) δ ppm 1.00 (d, J=6.6 Hz, 6 H), 2.58 (s, 4H), 2.61-2.70 (m, 1 H), 2.81 (d, J=4.0 Hz, 3 H), 3.09 (s, 4 H), 3.80 (s, 3 H), 6.27 (d, J=1.8 Hz, 1 H), 6.46 (d, J=2.2 Hz, 1 H), 6.62 (d, J=1.8 Hz, 1 H), 6.89-6.96 (m, 1 H), 7.01 (t, J=7.5 Hz, 1 H), 7.35-7.45 (m, 2 H), 7.72 (d, J=7.3 Hz, 1 H), 7.89 (d, J=9.2 Hz, 1 H), 8.68-8.75 (m, 1 H), 8.87 (d, J=8.4 Hz, 1 H), 11.26 (s, 1 H), 11.63 (s, 1 H); ESIMS (M+H)$^+$=515.

Example 26

2-{[2-({5-[(N,N-dimethylglycyl)amino]-2-methylphenyl}amino)-1H-pyrrolo[2,3-d]pyrimidin-4-yl]amino}-N-(2-hydroxyethyl)benzamide

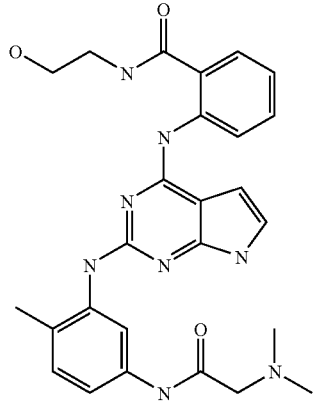

253

Step A/Intermediate D1: $N^2,N^2$-dimethyl-$N^1$-[4-methyl-3-({3-[(4-methylphenyl)sulfonyl]-7-oxo-3,7-dihydropyrrolo[2',3':4,5]pyrimido[6,1-b]quinazolin-5-yl}amino)phenyl]glycinamide

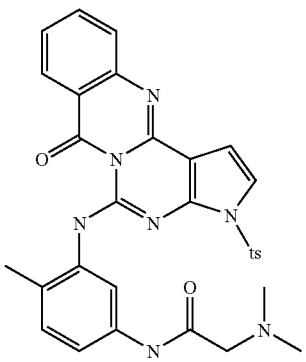

To a pressurized vessel was added 2-({2-chloro-7-[(4-methylphenyl)sulfonyl]-7H-pyrrolo[2,3-d]pyrimidin-4-yl}amino)benzamide (1.0 g, 2.27 mmol), $N^1$-(3-amino-4-methylphenyl)-$N^2,N^2$-dimethylglycinamide (0.590 g, 2.83 mmol), potassium iodide (<10 mg) and hydrochloric acid as a 4.0M solution in dioxanes (ca 4 mL). The resulting suspension was stirred until all solids had completely dissolved (24 hr.) The reaction was poured into into saturated sodium bicarbonate and diluted with dichloromethane. The organic layer was dried over sodium sulfate, volatiles removed under reduced pressure, and the solids triturated with diethyl ether to afford $N^2,N^2$-dimethyl-$N^1$-[4-methyl-3-({3-[(4-methylphenyl)sulfonyl]-7-oxo-3,7-dihydropyrrolo[2',3':4,5]pyrimido[6,1-b]quinazolin-5-yl}amino)phenyl]glycinamide (1.11 g, 18.7 mmol, 82% yield) of sufficient purity for use in subsequent transformations. ESIMS (M+H)=596.

Step B: 2-{[2-({5-[(N,N-dimethylglycyl)amino]-2-methylphenyl}amino)-1H-pyrrolo[2,3-d]pyrimidin-4-yl]amino}-N-(2-hydroxyethyl)benzamide According to General Protocol III (Steps B & C), 2-{[2-({5-[(N,N-dimethylglycyl)amino]-2-methylphenyl}amino)-1H-pyrrolo[2,3-d]pyrimidin-4-yl]amino}-N-(2-hydroxyethyl)benzamide was prepared starting with $N^2,N^2$-dimethyl-$N^1$-[4-methyl-3-({3-[(4-methylphenyl)sulfonyl]-7-oxo-3,7-dihydropyrrolo[2',3':4,5]pyrimido[6,1-b]quinazolin-5-yl}amino)phenyl]glycinamide (0.200 g, 0.340 mmol) and ethanolamine (0.100 mL, 1.68 mmol) a yellow solid (0.071 g, 42% Yield); 1H NMR (400 MHz, DMSO-$d_6$) δ ppm 2.14 (s, 3 H), 2.21 (s, 6 H), 2.98 (s, 2 H), 3.30-3.38 (m, 2 H), 3.51 (q, J=5.80 Hz, 2 H), 4.73 (t, J=5.77 Hz, 1 H), 6.22 (dd, J=3.48, 1.83 Hz, 1 H), 6.87-6.92 (m, 1 H), 6.92-6.96 (m, 1 H), 7.09 (d, J=8.06 Hz, 1 H), 7.18-7.26 (m, 1 H), 7.36 (dd, J=8.15, 1.92 Hz, 1 H), 7.69-7.72 (m, 2 H), 8.12 (s, 1 H), 8.67 (t, J=5.31 Hz, 1 H), 8.82 (d, J=8.42 Hz, 1 H), 9.54 (s, 1 H), 11.19 (s, 1 H), 11.62 (s, 1 H). ESI-MS (M+H) 503. Retention time 1.21 minutes.

254

Example 27

2-{[2-({5-[(N,N-dimethylglycyl)amino]-2-methylphenyl}amino)-1H-pyrrolo[2,3-d]pyrimidin-4-yl]amino}-N-[(4-fluorophenyl)methyl]benzamide

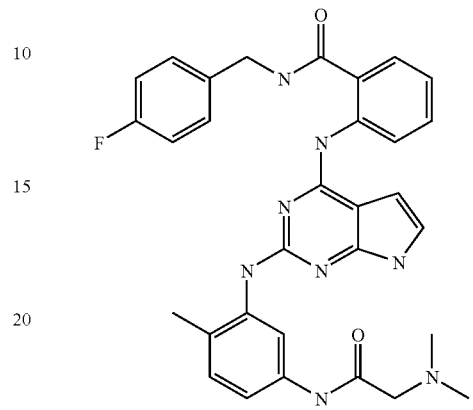

In a manner analogous to Example 26, 2-{[2-({5-[(N,N-dimethylglycyl)amino]-2-methylphenyl}amino)-1H-pyrrolo[2,3-d]pyrimidin-4-yl]amino}-N-[(4-fluorophenyl)methyl]benzamide was prepared from $N^2,N^2$-dimethyl-$N^1$-[4-methyl-3-({3-[(4-methylphenyl)sulfonyl]-7-oxo-3,7-dihydropyrrolo[2',3':4,5]pyrimido[6,1-b]quinazolin-5-yl}amino)phenyl]glycinamide (0.150 g, 0.27 mmol) and 4-fluoro benzylamine (0.5 mL) isolated as a yellow solid (0.055 g, 39% Yield); 1H NMR (400 MHz, DMSO-$d_6$) δ ppm 2.16 (s, 3 H), 2.23 (s, 6 H), 3.01 (s, 2 H), 4.49 (d, J=6.04 Hz, 2 H), 6.21 (dd, J=3.29, 1.83 Hz, 1 H), 6.91 (dd, J=3.20, 2.29 Hz, 1 H), 6.97 (t, J=7.50 Hz, 1 H), 7.08-7.17 (m, 3 H), 7.22-7.31 (m, 1 H), 7.33-7.42 (m, 3 H), 7.73 (d, J=1.65 Hz, 1 H), 7.78 (dd, J=8.05, 0.91 Hz, 1 H), 8.15 (s, 1 H), 8.84 (d, J=8.23 Hz, 1 H), 9.29 (t, J=6.04 Hz, 1 H), 9.58 (s, 1 H), 11.21 (s, 1 H), 11.56 (s, 1 H). ESI-MS (M+H) 567. Retention time 1.57 minutes.

Example 28

2-{[2-({5-[(N,N-dimethylglycyl)amino]-2-methylphenyl}amino)-1H-pyrrolo[2,3-d]pyrimidin-4-yl]amino}-N-hydroxybenzamide

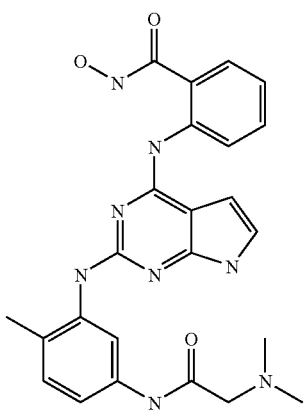

255

In a manger analogous to Example 26, 2-{[2-({5-[(N,N-dimethylglycyl)amino]-2-methylphenyl}amino)-1H-pyrrolo[2,3-d]pyrimidin-4-yl]amino}-N-hydroxybenzamide was prepared from $N^2,N^2$-dimethyl-$N^1$-[4-methyl-3-({3-[(4-methylphenyl)sulfonyl]-7-oxo-3,7-dihydropyrrolo[2',3':4,5]pyrimido[6,1-b]quinazolin-5-yl}amino)phenyl]glycinamide (0.400 g, 0.67 mmol) and 50% aqueous hydroxylamine (20 mL), and isolated as a yellow solid (0.026 g, 8% Yield); 1H NMR (400 MHz, DMSO-$d_6$) δ ppm 2.14 (s, 3 H), 2.21 (s, 6 H), 2.99 (s, 2 H), 6.23 (dd, J=3.48, 1.83 Hz 1 H), 6.85-6.94 (m, 2 H), 7.09 (d, J=8.42 Hz, 1 H), 7.22 (t, J=7.60 Hz, 1 H), 7.35 (dd, J=8.33, 2.66 Hz, 1 H), 7.54 (dd, J=8.24, 1.46 Hz, 1 H), 7.72 (d, J=1.83 Hz, 1 H), 8.13 (s, 1 H), 8.80 (d, J=7.87 Hz, 1 H), 9.27 (s, 1 H), 9.55 (s, 1 H), 11.20 (s, 1 H), 11.27 (s, 1 H). ESI-MS (M+H) 475. Retention time 110 minutes.

Example 29

3-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]-2-naphthalenecarboxamide

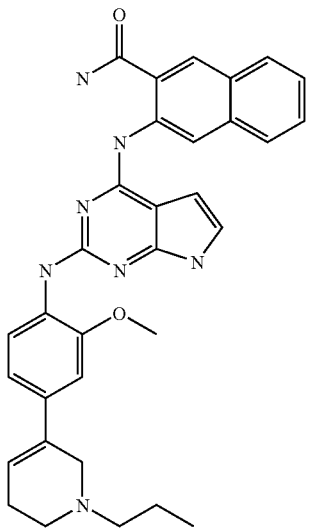

According to General Protocol III, 3-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]-2-naphthalenecarboxamide was prepared from 3-({2-chloro-7-[(4-methylphenyl)sulfonyl]-7H-pyrrolo[2,3-d]pyrimidin-4-yl}amino)-2-naphthalenecarboxamide (0.300 g, 0.611 mmol), 27% aqueous ammonium hydroxide, and 2-(methyloxy)-4-(1-propyl-1,2,5,6-tetrahydro-3-pyridinyl)aniline (0.188 g, 0.764 mmol) and isolated as a yellow solid (0.075 g, 22% Yield); 1H NMR (400 MHz, DMSO-$d_6$) δ ppm 0.91 (t, J=7.14 Hz, 3 H), 1.55 (s, 2 H), 2.30 (s, 2 H), 2.44 (s, 2 H), 2.55 (s, 2 H), 3.28 (s, 2 H), 3.90 (s, 3 H), 6.19 (s, 1 H), 6.28-6.35 (m, 1 H), 6.92 (d, J=10.25 Hz, 1 H), 6.98-7.04 (m, 1 H), 7.05-7.10 (m, 1 H), 7.36-7.46 (m, 1 H), 7.48-7.56 (m, 1 H), 7.71 (s, 1 H), 7.74 (d, J=8.78 Hz, 1 H), 7.86 (d, J=8.23 Hz, 1 H), 7.92 (s, 1 H), 8.16-8.23 (m, 1 H), 8.44 (s, 1 H), 8.53 (s, 1 H), 9.22 (s, 1 H), 11.37 (s, 1 H), 11.67 (s, 1 H). ESI-MS (M+H) 548. Retention time 1.77 minutes.

256

Example 30

3-{[2-({5-[(N,N-dimethylglycyl)amino]-2-methylphenyl}amino)-1H-pyrrolo[2,3-d]pyrimidin-4-yl]amino}-2-naphthalenecarboxamide

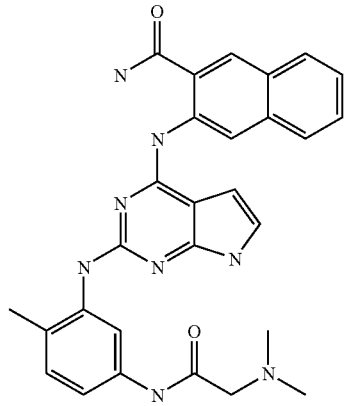

According to General Protocol III, 3-{[2-({5-[(N,N-dimethylglycyl)amino]-2-methylphenyl}amino)-1H-pyrrolo[2,3-d]pyrimidin-4-yl]amino}-2-naphthalenecarboxamide was prepared from 3-({2-chloro-7-[(4-methylphenyl)sulfonyl]-7H-pyrrolo[2,3-d]pyrimidin-4-yl}amino)-2-naphthalenecarboxamide (0.300 g, 0.610 mmol), 27% aqueous ammonium hydroxide, and $N^1$-(3-amino-4-methylphenyl)-$N^2,N^2$-dimethylglycinamide (0.151 g, 0.732 mmol) and isolated as a yellow solid (0.057 g, 18% Yield); 1H NMR (400 MHz, DMSO-$d_6$) δ ppm 2.11 (s, 6 H), 2.21 (s, 3 H), 2.89 (s, 2 H), 6.26 (s, 1 H), 6.95 (s, 1 H), 7.19 (d, J=8.23 Hz, 1 H), 7.36 (t, J=6.95 Hz, 1 H), 7.43-7.55 (m, 3 H), 7.79 (d, J=8.78 Hz, 1 H), 7.81 (s, 1 H), 7.90 (s, 1 H), 8.25 (s, 1 H), 8.40 (s, 1 H), 8.52 (s, 1 H), 9.25 (s, 1 H), 9.55 (s, 1 H), 11.23 (s, 1 H), 11.79 (s, 1 H). ESI-MS (M+H) 509. Retention time 1.63 minutes.

Example 31

2-methyl-6-[(2-{[4-[4-(1-methylethyl)-1-piperazinyl]-2-(methyloxy)phenyl]amino}-1H-pyrrolo[2,3-d]pyrimidin-4-yl)amino]benzamide

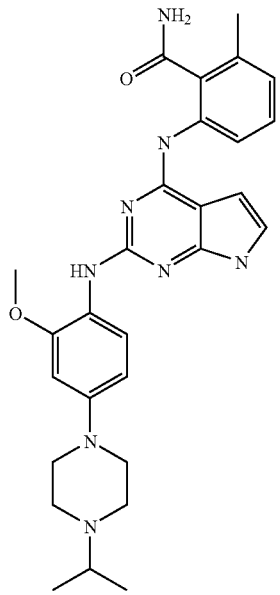

According to General Protocol III, 2-methyl-6-[(2-{[4-[4-(1-methylethyl)-1-piperazinyl]-2-(methyloxy)phenyl]amino}-1H-pyrrolo[2,3-d]pyrimidin-4-yl)amino]benzamide (0.028 g, 8% Yield) was prepared from 2-({2-chloro-7-[(4-methylphenyl)sulfonyl]-7H-pyrrolo[2,3-d]pyrimidin-4-yl}amino)-6-methylbenzamide (0.300 g, 0.66 mmol), 27% aqueous ammonium hydroxide, and 4-[4-(1-methylethyl)-1-piperazinyl]-2-(methyloxy)aniline (0.213 g, 0.857 mmol). 1H NMR (400 MHz, DMSO-$d_6$) δ ppm 1.00 (d, J=6.60 Hz, 6 H), 2.35 (s, 3 H), 2.57 (s, 4 H), 2.66 (s, 1 H), 3.05 (s, 4 H), 3.80 (s, 3 H), 6.15 (dd, J=3.48, 2.02 Hz, 1 H), 6.38 (dd, J=8.80, 2.57 Hz, 1 H), 6.59 (d, J=2.57 Hz, 1 H), 6.81-6.89 (m, 1 H), 7.01 (d, J=7.70 Hz, 1 H), 7.13 (s, 1 H), 7.27 (t, J=7.88 Hz, 1 H), 7.70 (s, 1 H), 7.70-7.77 (m, J=12.46 Hz, 1 H), 7.83 (d, J=7.70 Hz, 1 H), 8.00 (d, J=8.80 Hz, 1 H), 8.66 (s, 1 H), 11.18 (s, 1 H). ESIMS (M+H)=516.

Example 32

5-methyl-2-[(2-{[2-methyl-4-(1-propyl-1,2,5,6-tetrahydro-3-pyridinyl)phenyl]amino}-1H-pyrrolo[2,3-d]pyrimidin-4-yl)amino]benzamide

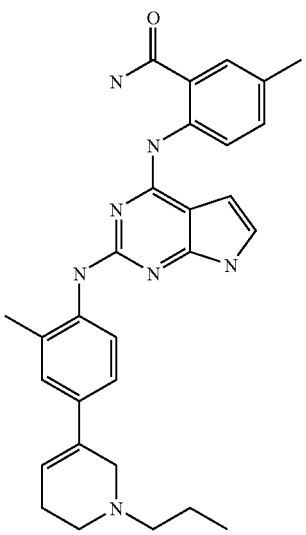

According to General Protocol III, 5-methyl-2-[(2-{[2-methyl-4-(1-propyl-1,2,5,6-tetrahydro-3-pyridinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-5-methylbenzamide (0.300 g, 0.66 mmol), 27% aqueous ammonium hydroxide, and 2-methyl-4-(1-propyl-1,2,5,6-tetrahydro-3-pyridinyl)aniline (0.230$_9$, 1.00 mmol) and isolated as a yellow solid (0.080 g, 25% Yield); 1H NMR (400 MHz, DMSO-$d_6$) δ ppm 0.89 (t, J=7.41 Hz, 3 H), 1.50-1.61 (m, 2 H), 2.23 (s, 3 H), 2.26 (s, 3 H), 2.30 (s, 2 H), 2.43 (s, 2 H), 2.53 (s, 2 H), 3.27 (s, 2 H), 6.12 (s, 1 H), 6.21 (dd, J=3.48, 2.01 Hz, 1 H), 6.91 (dd, J=3.48, 2.38 Hz, 1 H), 7.10 (dd, J=8.97, 1.65 Hz, 1 H), 7.20 (d, J=8.23 Hz, 1 H), 7.23 (d, J=2.01 Hz, 1 H), 7.56 (d, J=8.60 Hz, 1 H), 7.62 (d, J=1.28 Hz, 1 H), 7.65 (s, 1 H), 8.03 (s, 1 H), 8.21 (s, 1 H), 8.76 (d, J=8.60 Hz, 1 H), 11.20 (s, 1 H), 11.83 (s, 1 H). ESI-MS (M+H) 496. Retention time 1.38 minutes.

Example 33

5-methyl-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide

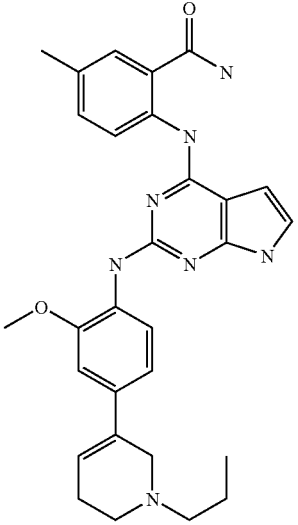

According to General Protocol III, 5-methyl-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-5-methylbenzamide (0.25 g, 0.55 mmol), 27% aqueous ammonium hydroxide, and 2-(methyloxy)-4-(1-propyl-1,2,5,6-tetrahydro-3-pyridinyl)aniline (0.16 g, 0.66 mmol) and isolated as a yellow solid (0.098 g); 1H NMR (400 MHz, DMSO-$d_6$) δ ppm 0.89 (t, J=7.3 Hz, 3 H), 1.49-1.59 (m, 2 H), 2.25 (d, J=4.4 Hz, 2 H), 2.30 (s, 3 H), 2.39-2.44 (m, 2 H), 2.50-2.54 (m, 2 H), 3.26 (d, J=1.5 Hz, 2 H), 3.90 (s, 3 H), 6.10-6.17 (m, 1 H), 6.26 (dd, J=3.6, 1.9 Hz, 1 H), 6.93 (dd, J=8.4, 1.8 Hz, 1 H), 6.97-7.02 (m, 2 H), 7.31 (dd, J=8.6, 1.6 Hz, 1 H), 7.50 (s, 1 H), 7.65 (d, J=1.3 Hz, 1 H), 7.67 (s, 1 H), 8.22 (s, 1 H), 8.32 (d, J=8.4 Hz, 1 H), 8.75 (d, J=8.4 Hz, 1 H), 11.38 (s, 1 H), 11.77 (s, 1 H); ESIMS (M+H)$^+$=512.

Example 34

2-{[2-({5-[(N,N-dimethylglycyl)amino]-2-methylphenyl}amino)-1H-pyrrolo[2,3-d]pyrimidin-4-yl]amino}-5-methylbenzamide

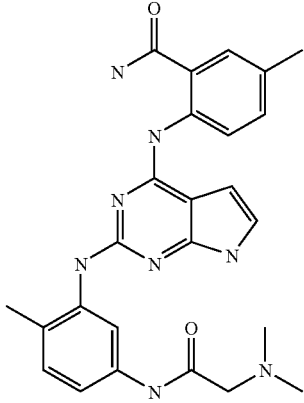

According to General Protocol III, 2-{[2-({5-[(N,N-dimethylglycyl)amino]-2-methylphenyl}amino)-1H-pyrrolo[2,3-d]pyrimidin-4-yl]amino}-5-methylbenzamide was prepared from 2-({2-chloro-7-[(4-methylphenyl)sulfonyl]-7H-pyrrolo[2,3-d]pyrimidin-4-yl}amino)-5-methylbenzamide (0.300 g, 0.66 mmol), 27% aqueous ammonium hydroxide, and $N^1$-(3-amino-4-methylphenyl)-$N^2$,$N^2$-dimethylglycinamide (0.170 g, 0.82 mmol) and isolated as a yellow solid (0.019 g, 6% Yield); 1H NMR (400 MHz, DMSO-$d_6$) δ ppm 2.14 (s, 3 H), 2.21 (s, 6 H), 2.23 (s, 3 H), 2.99 (s, 2 H), 6.19 (s, 1 H), 6.88 (s, 1 H), 7.03 (d, J=8.42 Hz, 1 H), 7.10 (d, J=8.42 Hz, 1 H), 7.35 (d, J=7.14 Hz, 1 H), 7.59 (s, 1 H), 7.62 (s, 1 H), 7.72 (s, 1 H), 8.09 (s, 1 H), 8.18 (s, 1 H), 8.74 (d, J=8.42 Hz, 1 H), 9.55 (s, 1 H), 11.16 (s, 1 H), 11.86 (s, 1 H). ESI-MS (M+H) 473. Retention time 1.32 minutes.

Example 35

4-methyl-2-[(2-{[2-methyl-4-(1-propyl-1,2,5,6-tetrahydro-3-pyridinyl)phenyl]amino}-1H-pyrrolo[2,3-d]pyrimidin-4-yl)amino]

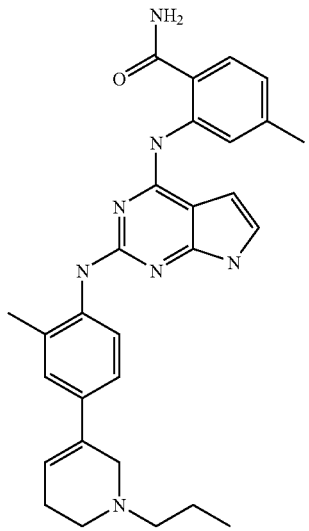

According to General Protocol III, 4-methyl-2-[(2-{[2-methyl-4-(1-propyl-1,2,5,6-tetrahydro-3-pyridinyl)phenyl]amino}-1H-pyrrolo[2,3-d]pyrimidin-4-yl)amino]benzamide (0.067 g, 21% yield) was prepared from 2-({2-chloro-7-[(4-methylphenyl)sulfonyl]-7H-pyrrolo[2,3-d]pyrimidin-4-yl}amino)-4-methylbenzamide (0.300 g, 0.66 mmol), 27% aqueous ammonium hydroxide, and 2-methyl-4-(1-propyl-1,2,5,6-tetrahydro-3-pyridinyl)aniline (0.227 g, 0.99 mmol); 1H NMR (400 MHz, DMSO-$d_6$) ppm 0.89 (t, J=7.41 Hz, 3 H), 1.50-1.59 (m, 2 H), 2.14 (s, 3 H), 2.24 (s, 3 H), 2.27 (s, 2 H), 2.41 (s, 2 H), 2.53 (s, 2 H), 3.24 (s, 2 H), 6.10 (s, 1 H), 6.24 (dd, J=3.48, 1.83 Hz, 1 H), 6.73 (dd, J=8.23, 1.46 Hz, 1 H), 6.93 (dd, J=3.48, 2.38 Hz, 1 H), 7.20 (dd, J=8.32, 2.10 Hz, 1 H), 7.25 (d, J=1.83 Hz, 1 H), 7.53 (d, J=8.23 Hz, 1 H), 7.60 (s, 1 H), 7.68 (d, J=8.05 Hz, 1H), 8.08 (s, 1 H), 8.18 (s, 1 H), 8.68 (s, 1 H), 11.19 (s, 1 H), 12.19 (s, 1 H). ESIMS (M+H)+=512.

Example 36

2-(methyloxy)-6-[(2-{[2-(methyloxy)-4-(1-propyl-3-piperidinyl)phenyl]amino}-1H-pyrrolo[2,3-d]pyrimidin-4-yl)amino]benzamide

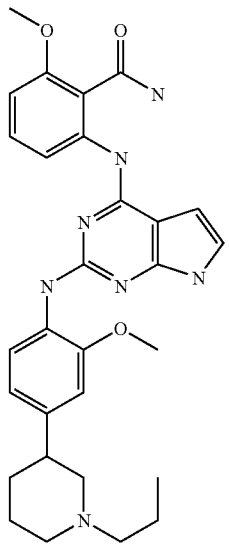

According to General Protocol III, 2-(methyloxy)-6-[(2-{[2-(methyloxy)-4-(1-propyl-3-piperidinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-6-(methyloxy)benzamide (0.25 g, 0.53 mmol), 27% aqueous ammonium hydroxide, and [2-2-(methyloxy)-4-(1-propyl-3-piperidinyl)aniline (0.15 g, 0.62 mmol) and isolated as a yellow solid (0.079 g). 1H NMR (400 MHz, DMSO-$d_6$) δ ppm 0.86 (t, J=7.52 Hz, 3 H), 1.44-1.56 (m, 4 H), 1.64 (d, J=12.83 Hz, 2 H), 1.78 (dd, J=19.25, 7.52 Hz, 3 H), 1.84 (s, 1 H), 2.76 (s, 1 H), 3.04 (s, 2 H), 3.85 (s, 3 H), 3.86 (s, 3 H), 6.23 (dd, J=3.30, 1.83 Hz, 1 H), 6.77 (s, 1 H), 6.79 (s, 1 H), 6.90 (s, 1 H), 6.97 (dd, J=3.30, 2.20 Hz, 1 H), 7.34-7.43 (m, 2 H), 7.89 (s, 2 H), 8.20-8.30 (m, 2 H), 11.10 (s, 1 H), 11.33 (s, 1 H) with ca 40 mol % TsOH impurity present. ESIMS (M+H)+=530.

Example 37

5-(methyloxy)-2-[(2-{[2-methyl-4-(1-propyl-1,2,5,6-tetrahydro-3-pyridinyl)phenyl]amino}-1H-pyrrolo[2,3-d]pyrimidin-4-yl)amino]benzamide

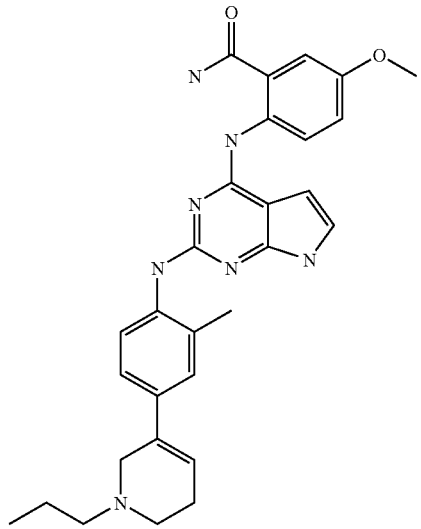

261

According to General Protocol III, 5-(methyloxy)-2-[(2-{[2-methyl-4-(1-propyl-1,2,5,6-tetrahydro-3-pyridinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-5-(methyloxy)benzamide (0.300 g, 0.637 mmol), 27% aqueous ammonium hydroxide, and 2-methyl-4-(1-propyl-1,2,5,6-tetrahydro-3-pyridinyl)aniline (0.142 g, 0.701 mmol) and isolated as a yellow solid (0.114 g, 27% Yield); 1H NMR (400 MHz, DMSO-$d_6$) δ ppm 0.88 (t, J=6.68 Hz, 3 H), 1.21 (s, 2 H), 1.54 (dd, J=14.82, 3.66 Hz, 2 H), 1.82 (s, 2 H), 2.18-2.29 (m, 5 H), 2.43 (s, 2 H), 3.76 (s, 3 H), 6.10 (s, 1 H), 6.18 (s; 1 H), 6.88 (d, J=3.29 Hz, 2 H), 7.19 (d, J=6.40 Hz, 1 H), 7.22 (s, 1 H), 7.33 (s, 1 H), 7.56 (d, J=7.68 Hz, 1 H), 7.71 (s, 1 H), 7.97 (s, 1 H), 8.26 (s, 1 H), 8.74 (d, J=8.78 Hz, 1 H), 11.17 (s, 1 H), 11.55 (s, 1 H). ESI-MS (M+H) 512. Retention time 1.26 minutes.

Example 38

5-(methyloxy)-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide

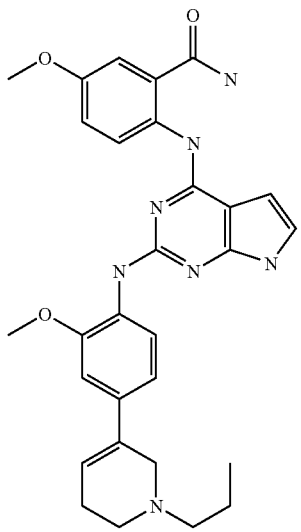

According to General Protocol III, 5-(methyloxy)-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-5-(methyloxy)benzamide (0.250 g, 0.53 mmol), 27% aqueous ammonium hydroxide, and 2-(methyloxy)-4-(1-propyl-1,2,5,6-tetrahydro-3-pyridinyl)aniline (0.16 g, 0.64 mmol) and isolated as a yellow solid (0.063 g). 1H NMR (400 MHz, DMSO-$d_6$) δ ppm 0.89 (t, J=7.4 Hz, 3 H), 1.49-1.59 (m, 2 H), 2.25 (dt, J=2.9, 1.5 Hz, 2 H), 2.38-2.44 (m, 2 H), 2.49-2.53 (m, 2 H), 3.25 (s, 2 H), 3.80 (s, 3 H), 3.89 (s, 3 H), 6.09-6.16 (m, 1 H), 6.25 (dd, J=3.5, 1.8 Hz, 1 H), 6.92 (dd, J=8.4, 2.0 Hz, 1 H), 6.97 (dd, J=3.5, 2.2 Hz, 1 H), 7.00 (d, J=1.8 Hz, 1 H), 7.11 (dd, J=9.2, 3.0 Hz, 1 H), 7.36 (d, J=2.9 Hz, 1 H), 7.46 (s, 1 H), 7.69-7.74 (m, 1 H), 8.23-8.28 (m, 1 H), 8.33 (d, J=8.6 Hz, 1 H), 8.70 (d, J=9.1 Hz, 1 H), 11.35 (s, 1 H), 11.43 (s, 1 H); ESIMS (M+H)$^+$=528.

262

Example 39

2-[(2-{[4-[(3S)-3-methyl-4-morpholinyl]-2-(methyloxy)phenyl]amino}-1H-pyrrolo[2,3-d]pyrimidin-4-yl) amino]-4-(methyloxy)benzamide

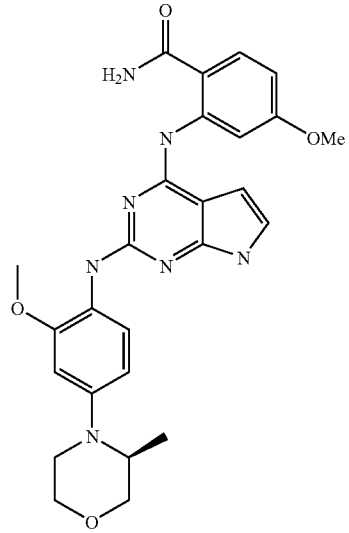

According to General Protocol III, 2-[(2-{[4-[(3S)-3-methyl-4-morpholinyl]-2-(methyloxy)phenyl]amino}-1H-pyrrolo[2,3-d]pyrimidin-4-yl)amino]-4-(methyloxy)benzamide (0.103 g, 32% yield) was prepared from 2-({2-chloro-7-[(4-methylphenyl)sulfonyl]-7H-pyrrolo[2,3-d]pyrimidin-4-yl}amino)-4-(methyloxy)benzamide (0.300 g, 0.64 mmol), 27% aqueous ammonium hydroxide, and 4-[(3S)-3-methyl-4-morpholinyl]-2-(methyloxy)aniline (0.184 g, 0.83 mmol); 1H NMR (400 MHz, DMSO-$d_6$) δ ppm 0.92 (d, J=6.23 Hz, 3 H), 2.94-3.05 (m, 2 H), 3.52-3.61 (m, 2 H), 3.64-3.73 (m, 2 H), 3.76 (s, 3 H), 3.79 (s, 3 H), 3.83 (d, J=10.80 Hz, 1 H), 6.18-6.26 (m, 1 H), 6.44 (d, J=8.61 Hz, 1 H), 6.52-6.56 (m, 1 H), 6.59 (s, 1 H), 6.93 (s, 1 H), 7.29 (s, 1 H), 7.48 (s, 1 H), 7.77 (d, J=8.79 Hz, 1 H), 7.98 (d, J=8.42 Hz, 1 H), 8.08 (s, 1 H), 8.63 (s, 1 H), 11.28 (s, 1 H), 12.40 (s, 1 H). ESIMS (M+H)+= 504.

Example 40

2-fluoro-6-[(2-{[2-methyl-4-(1-propyl-1,2,5,6-tetrahydro-3-pyridinyl)phenyl]amino}-1H-pyrrolo[2,3-d]pyrimidin-4-yl)amino]benzamide

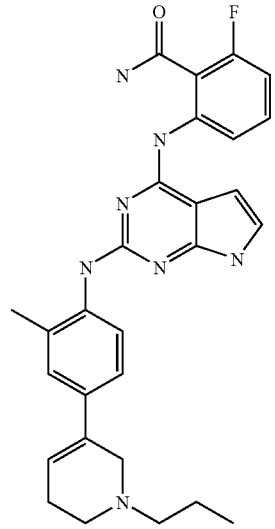

According to General Protocol III, 2-fluoro-6-[(2-{[2-methyl-4-(1-propyl-1,2,5,6-tetrahydro-3-pyridinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-6-fluorobenzamide (0.300 g, 0.650 mmol), 27% aqueous ammonium hydroxide, and 2-methyl-4-(1-propyl-1,2,5,6-tetrahydro-3-pyridinyl)aniline (0.188 g, 0.82 mmol) and isolated as a yellow solid (0.065 g, 20% Yield); 1H NMR (400 MHz, DMSO-$d_6$) δ ppm 0.89 (t, J=7.32 Hz, 3 H), 1.49-1.60 (m, 2 H), 2.23 (s, 3 H), 2.27 (s, 2 H), 2.43 (s, 2 H), 2.53 (s, 2 H), 3.25 (s, 2 H), 6.11 (s, 1 H), 6.20 (s, 1 H), 6.81-6.91 (m, 1 H), 6.94 (s, 1 H), 7.19 (d, J=8.60 Hz, 1 H), 7.22 (s, 1 H), 7.24-7.33 (m, 1 H), 7.58 (d, J=8.42 Hz, 1 H), 8.00 (s, 1 H), 8.04 (s, 1 H), 8.10 (s, 1 H), 8.48 (d, J=8.23 Hz, 1 H), 10.52 (s, 1 H), 11.27 (s, 1 H). ESI-MS (M+H) 500. Retention time 1.32 minutes.

Example 41

2-fluoro-6-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide

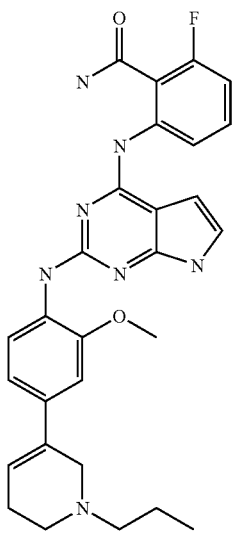

According to General Protocol III, 2-fluoro-6-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-6-fluorobenzamide (0.270 g, 0.590 mmol), 27% aqueous ammonium hydroxide, and 2-(methyloxy)-4-(1-propyl-1,2,5,6-tetrahydro-3-pyridinyl)aniline (0.175 g, 0.710 mmol) and isolated as a yellow solid (0.067 g, 22% Yield); 1H NMR (400 MHz, DMSO-$d_6$) δ ppm 0.89 (t, J=7.41 Hz, 3 H), 1.50-1.61 (m, 2 H), 2.27 (s, 2 H), 2.44 (s, 2 H), 2.55 (s, 2 H), 3.27 (s, 2 H), 3.89 (s, 3 H), 6.13 (s, 1H), 6.26 (dd, J=3.20, 1.74 Hz, 1 H), 6.92 (m, 2 H), 6.96-7.02 (m, 2 H), 7.43-7.50 (m, 1 H), 7.53 (s, 1 H), 8.01 (s, 1 H), 8.07 (s, 1 H), 8.31 (d, J=8.42 Hz, 1 H), 8.40 (d, J=8.42 Hz, 1 H), 10.42 (s, 1 H), 11.43 (s, 1 H). ESI-MS (M+H) 516. Retention time 1.50 minutes.

Example 42

2-fluoro-6-[(2-{[2-(methyloxy)-4-(1-propyl-4-piperidinyl)phenyl]amino}-1H-pyrrolo[2,3-d]pyrimidin-4-yl)amino]benzamide

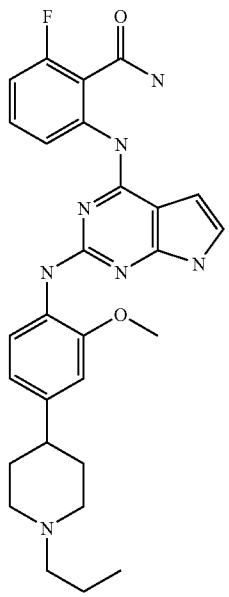

According to General Protocol III, 2-fluoro-6-[(2-{[2-methyloxy)-4-(1-propyl-4-piperidinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-6-fluorobenzamide (0.30 g, 0.65 mmol), 27% aqueous ammonium hydroxide, and 2-(methyloxy)-4-(1-propyl-4-piperidinyl)aniline (0.18 g, 0.72 mmol) and isolated as a yellow solid (0.117 g); 1H NMR (400 MHz, DMSO-$d_6$) δ ppm 0.85 (t, J=7.5 Hz, 3H), 1.45 (dq, J=14.9, 7.4 Hz, 2 H), 1.64-1.75 (m, 4 H), 1.88-1.98 (m, 2 H), 2.19-2.27 (m, 2 H), 2.42 (dt, J=7.4, 3.8 Hz, 1 H), 2.95 (d, J=11.0 Hz, 2 H), 3.84 (s, 3 H), 6.23 (dd, J=3.5, 2.0 Hz, 1 H), 6.76 (dd, J=8.4, 1.5 Hz, 1 H), 6.87 (d, J=1.5 Hz, 1 H), 6.90-7.00 (m, 2 H), 7.39-7.48 (m, 2 H), 8.01 (s, 1 H), 8.08 (s, 1 H), 8.17 (d, J=8.1 Hz, 1 H), 8.42 (d, J=8.4 Hz, 1 H), 10.42 (s, 1 H), 11.39 (s, 1 H); ESIMS (M+H)$^+$=518.

Example 43

2-fluoro-6-[(2-{[4-{4-[(3S)-3-fluoro-1-pyrrolidinyl]-1-piperidinyl}-2-(methyloxy)phenyl]amino}-1H-pyrrolo[2,3-d]pyrimidin-4-yl)amino]benzamide

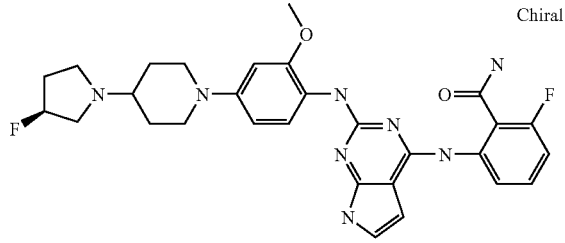

According to General Protocol III, 2-fluoro-6-[(2-{[4-{4-[(3S)-3-fluoro-1-pyrrolidinyl]-1-piperidinyl}-2-(methyloxy)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-6-fluorobenzamide (0.30 g, 0.65 mmol), 27% aqueous ammonium hydroxide, and 4-{4-[(3S)-3-fluoro-1-pyrrolidinyl]-1-piperidinyl}-2-(methyloxy)aniline (0.23 g, 0.78 mmol) to afford 2-fluoro-6-[(2-{[4-{4-[(3S)-3-fluoro-1-pyrrolidinyl]-1-piperidinyl}-2-(methyloxy)phenyl]amino}-1H-pyrrolo[2,3-d]pyrimidin-4-yl)amino]benzamide (0.1 g, 27% over 3 steps) as a yellow-green solid. 1H NMR (400 MHz, DMSO-$d_6$) δ ppm 1.49 (s, 2 H) 1.86 (s, 3 H) 2.11 (s, 2 H) 2.33 (s, 1 H) 2.58-2.69 (m, 3 H) 2.77-2.83 (m, 2 H) 3.54 (d, J=12.09 Hz, 2 H) 3.77 (s, 3 H) 5.08-5.22 (dt, J=5.62, 56.21 Hz, 1H) 6.15-6.18 (m, 1 H) 6.44 (d, J=8.79 Hz, 1 H) 6.59 (s, 1 H) 6.84-6.92 (m, 2 H) 7.33-7.40 (m, 3 H) 7.86 (d, J=8.61 Hz, 1 H) 8.05 (s, 1 H) 8.45 (d, J=8.42 Hz, 1 H) 10.41 (s, 1 H) 11.26 (s, 1 H). ESIMS (M+H)+=563.

Example 44

2-fluoro-6-[(2-{[4-{4-[(3R)-3-fluoro-1-pyrrolidinyl]-1-piperidinyl}-2-(methyloxy)phenyl]amino}-1H-pyrrolo[2,3-d]pyrimidin-4-yl)amino]benzamide

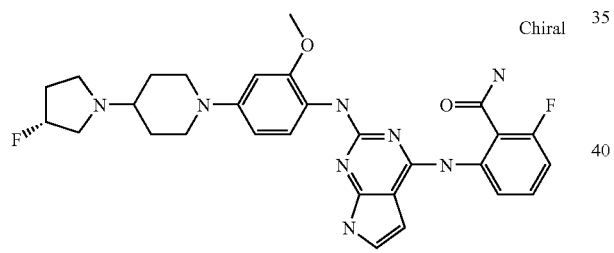

In a manner completely analogous to Example 43, 2-fluoro-6-[(2-{[4-{4-[(3R)-3-fluoro-1-pyrrolidinyl]-1-piperidinyl}-2-(methyloxy)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl)amino)-6-fluorobenzamide, 27% aqueous ammonium hydroxide, and 4-{4-[(3R)-3-fluoro-1-pyrrolidinyl]-1-piperidinyl}-2-(methyloxy)aniline to afford 2-fluoro-6-[(2-{[4-{4-[(3R)-3-fluoro-1-pyrrolidinyl]-1-piperidinyl}-2-(methyloxy)phenyl]amino}-1H-pyrrolo[2,3-d]pyrimidin-4-yl)amino]benzamide (0.1 g, 27% over 3 steps) as a yellow-green solid. ESIMS (M+H)+=563. 1H NMR (400 MHz, DMSO-$d_6$) δ ppm 1.43-1.53 (m, 2 H) 1.82-1.91 (m, 3 H) 2.06-2.15 (m, 2 H) 2.30-2.38 (m, 1 H) 2.58-2.69 (m, 3 H) 2.77-2.83 (m, 2 H) 3.54 (d, J=12.45 Hz, 2 H) 3.77 (s, 3 H) 5.08-5.22 (dt, J=6.22, 56 Hz, 1 H) 6.15-6.18 (m, 1 H) 6.44 (dd, J=8.70, 2.11 Hz, 1 H) 6.57-6.60 (m, 1 H) 6.84-6.92 (m, 2 H) 7.32-7.40 (m, 2 H) 7.86 (d, J=8.97 Hz, 1 H) 7.96 (s, 1 H) 8.05 (s, 1 H) 8.45 (d, J=8.42 Hz, 1 H) 10.41 (s, 1 H) 11.26 (s, 1 H).

Example 45

2-[(2-{[4-(1,4'-bipiperidin-1'-yl)-2-(methyloxy)phenyl]amino}-1H-pyrrolo[2,3-d]pyrimidin-4-yl)amino]-6-fluorobenzamide

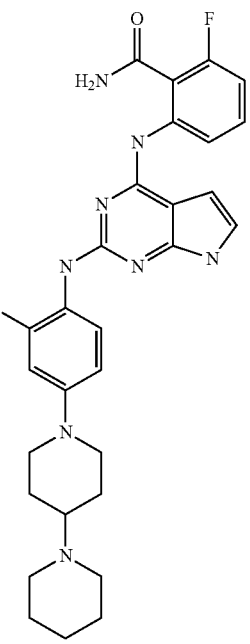

According to General Protocol III, 2-[(2-{[4-(1,4'-bipiperidin-1'-yl)-2-(methyloxy)phenyl]amino}-1H-pyrrolo[2,3-d]pyrimidin-4-yl)amino]-6-fluorobenzamide (0.187 g, 51% yield) was prepared from 2-({2-chloro-7-[(4-methylphenyl)sulfonyl]-7H-pyrrolo[2,3-d]pyrimidin-4-yl}amino)-6-fluorobenzamide (0.300 g, 0.65 mmol), 27% aqueous ammonium hydroxide, and 4-(1,4'-bipiperidin-1'-yl)-2-(methyloxy)aniline (0.250 g, 0.850 mmol); 1H NMR (400 MHz, DMSO-$d_6$) δ ppm 1.32-1.42 (m, 2 H), 1.45-1.51 (m, 4 H), 1.55 (d, J=15.40 Hz, 2 H), 1.79 (d, J=11.00 Hz, 2 H), 2.25-2.36 (m, 1 H), 2.46 (s, 4 H), 2.54-2.66 (m, 2 H), 3.66 (d, J=12.83 Hz, 2 H), 3.80 (s, 3 H), 6.20 (dd, J=3.67, 1.83 Hz, 1 H), 6.46 (dd, J=8.80, 2.57 Hz; 1 H), 6.61 (d, J=2.57 Hz, 1 H), 6.90 (d, J=1.47 Hz, 1 H), 6.91-6.95 (m, 1 H), 7.36 (s, 1 H), 7.40 (td, J=8.62, 6.97 Hz, 1 H), 7.88 (d, J=8.43 Hz, 1 H), 7.99 (s, 1 H), 8.08 (s, 1 H), 8.47 (d, J=8.43 Hz, 1 H), 10.44 (s, 1 H), 11.29 (s, 1 H). ESIMS (M+H)+=559.

Example 46

2-fluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide

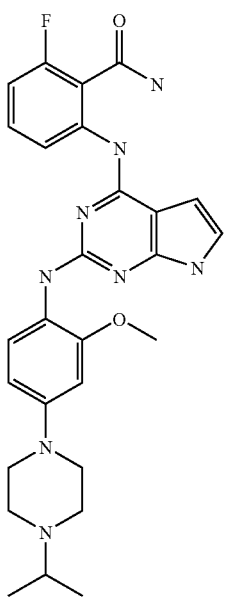

According to General Protocol III, 2-fluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-6-fluorobenzamide (0.30 g, 0.65 mmol), 27% aqueous ammonium hydroxide, and 4-[4-(1-methylethyl)-1-piperazinyl]-2-methyloxy)aniline (0.18 g, 0.72 mmol) and isolated as a yellow solid (0.083 g); 1H NMR (400 MHz, DMSO-$d_6$) δ ppm 1.00 (d, J=5.5 Hz, 6 H), 2.58 (s, 4 H), 2.66 (d, J=1.8 Hz, 1 H), 3.08 (s, 4 H), 3.80 (s, 3 H), 6.20 (dd, J=3.7, 1.8 Hz, 1 H), 6.45 (dd, J=8.8, 1.5 Hz, 1 H), 6.61 (d, J=1.8 Hz, 1 H), 6.88-6.94 (m, 2 H), 7.37-7.43 (m, 2 H), 7.88 (d, J=8.8 Hz, 1 H), 8.01 (s, 1 H), 8.09 (s, 1 H), 8.48 (d, J=8.4 Hz, 1 H), 10.44 (s, 1 H), 11.30 (s, 1 H); ESIMS (M+H)$^+$=519.

Example 46

Alternative Preparation 2-fluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide

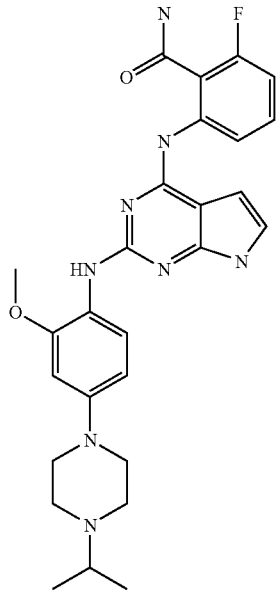

Step A/Intermediate D66: 8-fluoro-5-{[4-[4-(1-methylethyl)-1-piperazinyl]-2-(methyloxy)phenyl]amino}-3-[(4-methylphenyl)sulfonyl]pyrrolo[2',3':4,5]pyrimido[6,1-b]quinazolin-7(3H)-one

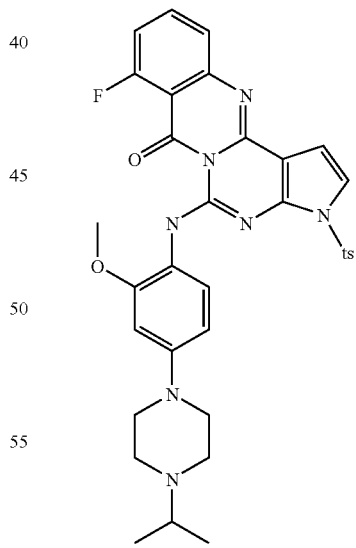

To a solution of 2-({2-chloro-7-[(4-methylphenyl)sulfonyl]-7H-pyrrolo[2,3-d]pyrimidin-4-yl}amino)-6-fluorobenzamide (5.50 g, 11.98 mmol), [4-[4-(1-methylethyl)-1-piperazinyl]-2-(methyloxy)phenyl]amine (4.5 g, 18 mmol, 1.50 equiv.), and potassium iodide (<20 mg) in trifluoroethanol (200 mL) in a 300 mL sealed tube was added hydrochloric acid as a 4.0M solution in dioxane (12 mL, 48 mmol, 4 equiv.). The vessel was sealed and the resulting suspension was stirred rapidly at 80° C. for 12 hours. TLC/LCMS analysis indicates starting material still remains, so additional hydrochloric acid (5 mL as a 4.0M solution in dioxane) and potassium iodide (<20 mg) were added and heating was continued. Three such reactions were cooled and poured directly in saturated sodium bicarbonate/methylene chloride. The organic layer was collected, concentrated under reduced pressure, and then resuspended in diethylether. Sonication for 10 minutes was followed by filtration to give crude 8-fluoro-5-{[4-[4-(1-methylethyl)-1-piperazinyl]-2-(methyloxy)phenyl]amino}-3-[(4-methylphenyl)sulfonyl]pyrrolo[2',3':4,5]pyrimido[6,1-b]quinazolin-7(3H)-one as an orange solid with sufficient purity for use in the next transformation (23.5 g, ca 99% yield, purity 85-90%). ESIMS (M+H)+=655.

Step B/Intermediate D67: 2-fluoro-6-({2-{[4-[4-(1-methylethyl)-1-piperazinyl]-2-(methyloxy)phenyl]amino}-7-[(4-methylphenyl)sulfonyl]-7H-pyrrolo[2,3-d]pyrimidin-4-yl}amino)benzamide

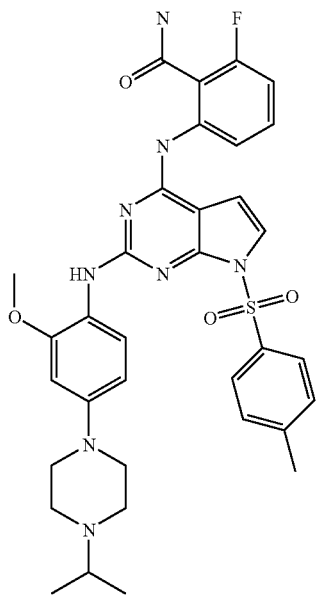

To a solution of 8-fluoro-5-{[4-[4-(1-methylethyl)-1-piperazinyl]-2-(methyloxy)phenyl]amino}-3-[(4-methylphenyl)sulfonyl]pyrrolo[2',3':4,5]pyrimido[6,1-b]quinazolin-7(3H)-one (7.6 g, 11.6 mmol) in tetrahydrofuran (350 mL) was added 27% ammonium hydroxide (500 mL). The resulting biphasic mixture, was rapidly stirred for 24 hours, at which time no starting material was evident by TLC/LCMS. Three such reactions were combined, diluted with EtOAc, and the organic layers washed with saturated sodium chloride, dried over sodium sulfate, and taken to a residue under reduced pressure to give 2-fluoro-6-({2-{[4-[4-(1-methylethyl)-1-piperazinyl]-2-(methyloxy)phenyl]amino}-7-[(4-methylphenyl)sulfonyl]-7H-pyrrolo[2,3-d]pyrimidin-4-yl}amino)benzamide (19.3 g, 28.7 mmol, 80% Yield). $^1$H NMR (400 MHz, DMSO-$d_6$) δ ppm 10.36 (s, 1 H), 8.04 (d, J=8.2 Hz, 1 H), 7.87-7.99 (m, 4 H), 7.79 (br. s., 2 H), 7.26-7.47 (m, 4 H), 6.87-7.06 (m, 1 H), 6.63 (d, J=2.4 Hz, 1 H), 6.47-6.58 (m, 2 H), 3.70-3.85 (m, 3 H), 3.05-3.19 (m, 4 H), 2.66 (quin, J=6.5 Hz, 1 H), 2.54-2.63 (m, 4 H), 2.32 (s, 3 H), 1.00 (d, J=6.6 Hz, 6 H). ESIMS (M+H)+=673.

Stage C/Example 46 (alternative preparation):
2-fluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide To a suspension of the 2-fluoro-6-({2-{[4-[4-(1-methylethyl)-1-piperazinyl]-2-(methyloxy)phenyl]amino}-7-[(4-methylphenyl)sulfonyl]-7H-pyrrolo[2,3-d]pyrimidin-4-yl}amino)benzamide (15.7 g, 23.4 mmol) in methanol (250 mL) and tetrahydrofuran (125 ml) was added $K_2CO_3$ (32.3g 234 mmol in 125 ml of water), The reaction mixture was stirred at 85° C. for 6 hours. The organic layer was subsequently washed with water and brine, dried over sodium sulfate, filtered, stripped onto celite, and purified by chromatography on $SiO_2$ (400 g $SiO_2$, 0% to 10% MeOH/$CH_2CL_2$ with 0.1% added $NH_3$) to afford the 2-fluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide (11.2 g, 92%) as a yellow solid. $^1$H NMR (400 MHz, DMSO-$d_6$) δ ppm 1.01 (d, J=6.59 Hz, 6 H), 2.59 (d, J=3.85 Hz, 4 H), 2.67 (m, J=6.41 Hz, 1 H), 3.10 (br. s., 4 H), 3.81 (s, 3H), 6.22 (s., 1 H), 6.47 (d, J=8.79 Hz, 1 H), 6.63 (d, J=1.28 Hz, 1 H), 6.89-6.98 (m, 2 H), 7.36-7.46 (m, 2 H), 7.90 (d, J=8.61 Hz, 1 H), 8.02 (s., 1 H), 8.10 (s, 1 H), 8.50 (d, J=8.42 Hz, 1 H), 10.47 (s, 1 H), 11.31 (s., 1 H). MS(ESI): m/z 519 (M+1)+.

Example 47

2-fluoro-6-[(2-{[4-[4-(1-methylethyl)-1-piperazinyl]-2,5-bis(methyloxy)phenyl]amino}-1H-pyrrolo[2,3-d]pyrimidin-4-yl)amino]benzamide

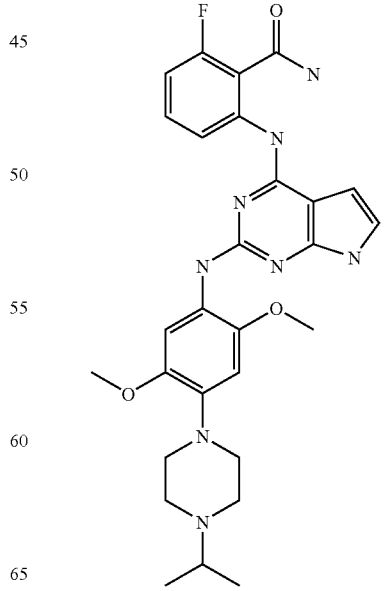

According to General Protocol III, 2-fluoro-6-[(2-{[4-[4-(1-methylethyl)-1-piperazinyl]-2,5-bis(methyloxy)phenyl]amino}-1H-pyrrolo[2,3-d]pyrimidin-4-yl)amino]benzamide (0.065 g) was prepared from 2-({2-chloro-7-[(4-methylphenyl)sulfonyl]-7H-pyrrolo[2,3-d]pyrimidin-4-yl}amino)-6-fluorobenzamide (0.300 g, 0.65 mmol), 27% aqueous ammonium hydroxide, and 4-[4-(1-methylethyl)-1-piperazinyl]-2,5-bis(methyloxy)aniline (0.20 g, 0.72 mmol). 1H NMR (400 MHz, DMSO-$d_6$) δ ppm 1.00 (d, J=5.9 Hz, 6 H), 2.57 (s, 4 H), 2.62-2.69 (m, 1 H), 2.95 (s, 4 H), 3.71 (s, 3 H), 3.78 (s, 3 H), 6.22 (dd, J=3.3, 1.8 Hz, 1 H), 6.60 (s, 1 H), 6.91 (dd, J=10.8, 8.2 Hz, 1H), 6.95-7.00 (m, 1 H), 7.34-7.41 (m, 1 H), 7.43 (s, 1 H), 7.95 (s, 1 H), 8.00 (s, 1 H), 8.08 (s, 1 H), 8.45 (d, J=8.4 Hz, 1 H), 10.45 (s, 1 H), 11.34 (s, 1 H); ESIMS (M+H)$^+$=549.

Example 48

2-fluoro-6-[(2-{[5-fluoro-4-[4-(1-methylethyl)-1-piperazinyl]-2-(methyloxy)phenyl]amino}-1H-pyrrolo[2,3-d]pyrimidin-4-yl)amino]benzamide

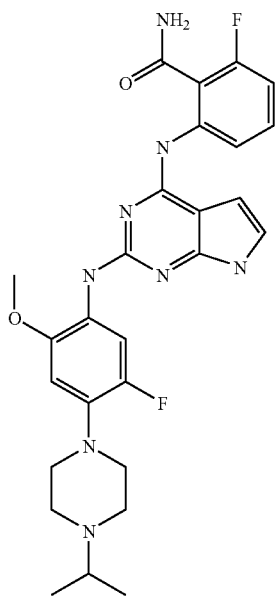

According to General Protocol III, 2-fluoro-6-[(2-{[5-fluoro-4-[4-(1-methylethyl)-1-piperazinyl]-2-(methyloxy)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-6-fluorobenzamide (0.200 g, 0.44 mmol), 27% aqueous ammonium hydroxide, and 5-fluoro-4-[4-(1-methylethyl)-1-piperazinyl]-2-(methyloxy)aniline (0.144 g, 0.54 mmol) and isolated as a yellow solid (0.071 g, 24% yield); 1H NMR (400 MHz, DMSO-$d_6$) δ ppm 1.00 (d, J=6.60 Hz, 6 H), 2.58 (s, 4 H), 2.68 (d, J=6.97 Hz, 1 H), 2.98 (s, 4 H), 3.85 (s, 3 H), 6.26 (dd, J=3.30, 1.83 Hz, 1 H), 6.67 (d, J=8.43 Hz, 1 H), 6.95 (dd, J=11.36, 8.43 Hz, 1 H), 7.00 (dd, J=3.67, 2.20 Hz, 1 H), 7.39-7.49 (m, 2 H), 8.00 (s, 1 H), 8.06 (s, 1 H), 8.19 (s, 1 H), 8.37 (d, J=8.43 Hz, 1 H), 10.39 (s, 1 H), 11.43 (s, 1 H). ESIMS (M+H)+=537.

Example 49

2-fluoro-6-[(2-{[4-[(3S)-3-methyl-4-morpholinyl]-2-(methyloxy)phenyl]amino}-1H-pyrrolo[2,3-d]pyrimidin-4-yl)amino]benzamide

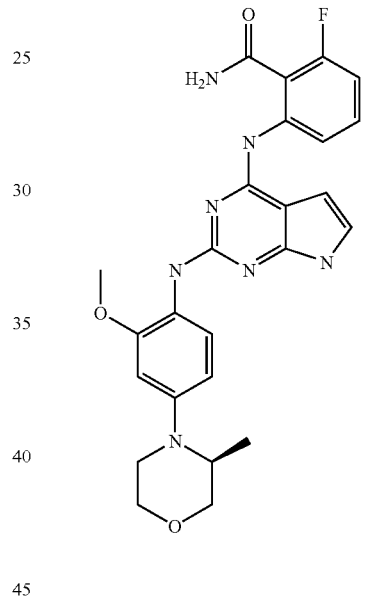

According to General Protocol III, 2-fluoro-6-[(2-{[4-[(3S)-3-methyl-4-morpholinyl]-*(methyloxy)phenyl*] *amino*}-1 H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-6-fluorobenzamide (0.200 g, 0.44 mmol), 27% aqueous ammonium hydroxide, and 4-[(3S)-3-methyl-4-morpholinyl]-2-(methyloxy)aniline (0.120 g, 0.54 mmol) and isolated as a yellow solid (0.043 g, 20% yield); 1H NMR (400 MHz, DMSO-$d_6$) δ ppm 0.94 (d, J=6.23 Hz, 3 H), 2.94-3.02 (m, 1 H), 3.02-3.12 (m, 1 H), 3.54-3.65 (m, 2 H), 3.72 (s, 1 H), 3.74 (d, J=6.23 Hz, 1 H), 3.80 (s, 3 H), 3.86 (d, J=11.36 Hz, 1 H), 6.21 (s, 1 H), 6.47 (d, J=8.80 Hz, 1 H), 6.61 (s, 1 H), 6.87-6.98 (m, 2 H), 7.36-7.45 (m, 2 H), 7.93 (d, J=8.43 Hz, 1 H), 8.00 (s, 1 H), 8.08 (s, 1 H), 8.46 (d, J=8.43 Hz, 1 H), 10.44 (s, 1 H), 11.30 (s, 1 H). ESIMS (M+H)+=492.

Example 50

2-fluoro-6-[(2-{[3-methyl-4-[4-(1-methylethyl)-1-piperazinyl]-2-(methyloxy)phenyl]amino}-1H-pyrrolo[2,3-d]pyrimidin-4-yl)amino]benzamide

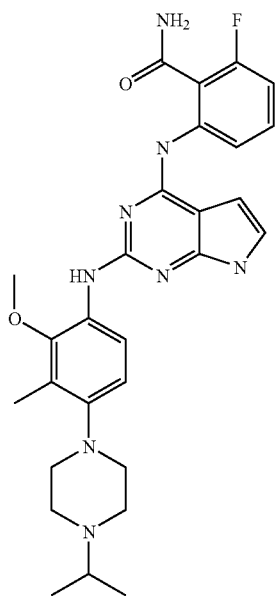

According to General Protocol III, 2-fluoro-6-[(2-{[3-methyl-4-[4-(1-methylethyl)-1-piperazinyl]-2-(methyloxy)phenyl]amino}-1 H-pyrrolo[2,3-d]pyrimidin-4-yl)amino]benzamide (0.101 g, 29% Yield) was prepared from 2-({2-chloro-7-[(4-methylphenyl)sulfonyl]-7H-pyrrolo[2,3-d]pyrimidin-4-yl}amino)-6-fluorobenzamide (0.300 g, 0.654 mmol), 27% aqueous ammonium hydroxide, and 3-methyl-4-[4-(1-methylethyl)-1-piperazinyl]-2-(methyloxy)aniline (0.258 g, 0.981 mmol). 1H NMR (400 MHz, DMSO-$d_6$) δ ppm 0.97 (d, J=6.23 Hz, 6 H), 2.15 (s, 3 H), 2.55 (s, 4 H), 2.60-2.69 (m, 1 H), 2.77 (s, 4 H), 3.63 (s, 3 H), 6.19 (dd, J=3.20, 1.74 Hz, 1 H), 6.75 (d, J=8.79 Hz, 1 H), 6.85-6.95 (m, 2 H), 7.33-7.40 (m, 1 H), 7.55 (s, 1 H), 7.86 (s, 1 H), 7.97 (s, 1 H), 8.04 (s, 1 H), 8.42 (d, J=8.42 Hz, 1 H), 10.41 (s, 1 H), 11.30 (s, 1 H). ESIMS (M+H)=533.

Example 51

2-fluoro-6-[(2-{[3-fluoro-4-[4-(1-methylethyl)-1-piperazinyl]-2-(methyloxy)phenyl]amino}-1H-pyrrolo[2,3-d]pyrimidin-4-yl)amino]benzamide

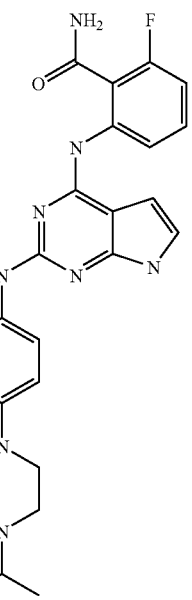

According to General Protocol III, 2-fluoro-6-[(2-{[3-fluoro-4-[4-(1-methylethyl)-1-piperazinyl]-2-(methyloxy)phenyl]amino}-1H-pyrrolo[2,3-d]pyrimidin-4-yl)amino]benzamide (0.151 g, 37% Yield) was prepared from 2-({2-chloro-7-[(4-methylphenyl)sulfonyl]-7H-pyrrolo[2,3-d]pyrimidin-4-yl}amino)-6-fluorobenzamide (0.350 g, 0.76 mmol), 27% aqueous ammonium hydroxide, and 3-fluoro-4-[4-(1-methylethyl)-1-piperazinyl]-2-(methyloxy)aniline (0.304 g, 1.14 mmol). 1H NMR (400 MHz, DMSO-$d_6$) δ ppm 1.00 (d, J=6.60 Hz, 6 H), 2.58 (s, 4 H), 2.62-2.74 (m, 1 H), 2.95 (s, 4 H), 3.81 (s, 3 H), 6.23 (dd, J=3.48, 2.02 Hz, 1 H), 6.70 (t, J=9.16 Hz, 1 H), 6.92 (dd, J=11.00, 8.80 Hz, 1 H), 6.97 (dd, J=3.67, 2.20 Hz, 1 H), 7.36-7.43 (m, 1 H), 7.72-7.80 (m, 2 H), 8.00 (s, 1 H), 8.06 (s, 1 H), 8.43 (d, J=8.43 Hz, 1 H), 10.45 (s, 1 H), 11.34 (s, 1 H). ESIMS (M+H)=537.

Example 52

2-fluoro-6-({2-[(5-methyl-2-(methyloxy)-4-{4-[2-(methylsulfonyl)ethyl]-1-piperazinyl}phenyl)amino]-1H-pyrrolo[2,3-d]pyrimidin-4-yl}amino)benzamide

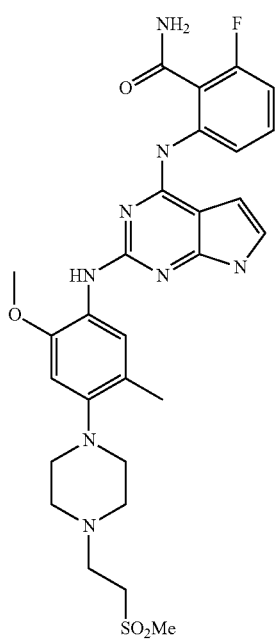

According to General Protocol III, 2-fluoro-6-({2-[(5-methyl-2-(methyloxy)-4-{4-[2-(methylsulfonyl)ethyl]-1-piperazinyl}phenyl)amino]-1H-pyrrolo[2,3-d]pyrimidin-4-yl}amino)benzamide (0.107 g, 40% Yield) was prepared from 2-({2-chloro-7-[(4-methylphenyl)sulfonyl]-7H-pyrrolo[2,3-d]pyrimidin-4-yl}amino)-6-fluorobenzamide (0.200 g, 0.45 mmol), 27% aqueous ammonium hydroxide, and 5-methyl-2-(methyloxy)-4-{4-[2-(methylsulfonyl)ethyl]-1-piperazinyl}aniline (0.160 g, 0.49 mmol). 1H NMR (400 MHz, DMSO-$d_6$) δ ppm 2.16 (s, 3 H), 2.59 (s, 4 H), 2.72-2.80 (m, 2 H), 2.84 (d, J=8.07 Hz, 4 H), 3.06 (s, 3 H), 3.31-3.35 (m, 2 H), 3.81 (s, 3 H), 6.22 (dd, J=3.30, 1.83 Hz, 1 H), 6.71 (s, 1 H), 6.92 (dd, J=11.55, 8.25 Hz, 1 H), 6.95-6.99 (m, 1 H), 7.38-7.45 (m, 2 H), 7.96 (s, 1 H), 8.01 (s, 1 H), 8.09 (s, 1 H), 8.43 (d, J=8.80 Hz, 1 H), 10.44 (s, 1 H), 11.31 (s, 1 H). ESIMS (M+H)=597.

Example 53

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluorobenzamide

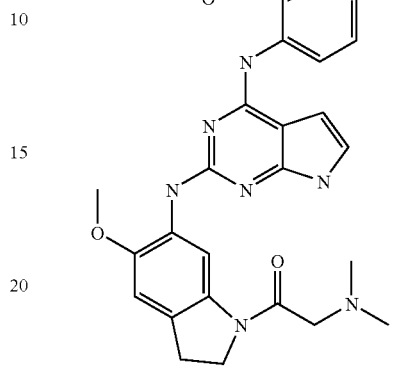

According to General Protocol III, 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluorobenzamide was prepared from 2-({2-chloro-7-[(4-methylphenyl)sulfonyl]-7H-pyrrolo[2,3-d]pyrimidin-4-yl}amino)-6-fluorobenzamide (0.350 g, 0.763 mmol), 27% aqueous ammonium hydroxide, and 1-[(dimethylamino)acetyl]-5-(methyloxy)-2,3-dihydro-1H-indol-6-amine (0.240 g, 0.96 mmol) and isolated as a yellow solid (110 mg, 28% yield). 1H NMR (400 MHz, DMSO-$d_6$) δ ppm 2.24 (s, 6 H), 3.11 (t, J=8.25 Hz, 2 H), 3.31 (s, 3 H), 3.76 (s, 2 H), 4.17 (t, J=8.25 Hz, 2 H), 6.21 (dd, J=3.48, 1.65 Hz, 1 H), 6.80-6.90 (m, 1 H), 6.90-7.01 (m, 2 H), 7.25-7.37 (m, 1 H), 7.59 (s, 1 H), 8.01 (s, 1 H), 8.09 (s, 1 H), 8.50 (d, J=8.43 Hz, 1 H), 8.60 (s, 1 H), 10.53 (s, 1 H), 11.28 (s, 1 H). ESIMS (M+H)=519.

Example 53

Alternative Preparation

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluorobenzamide

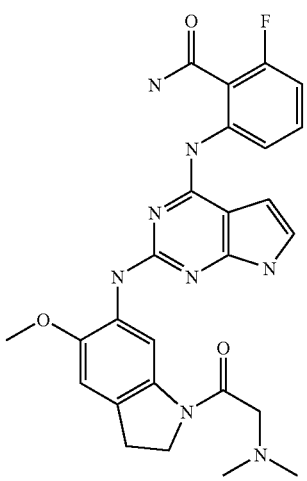

Step A/Intermediate D75: 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluorobenzamide

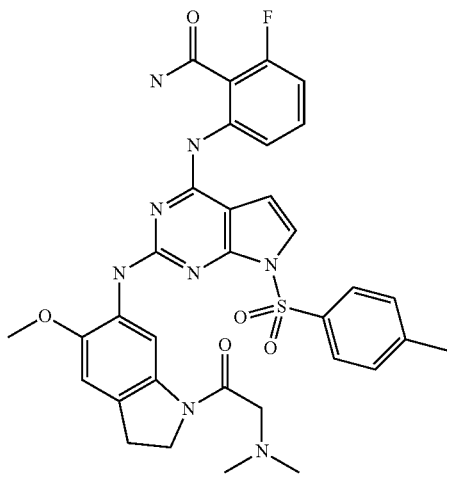

A mixture of 2-({2-chloro-7-[(4-methylphenyl)sulfonyl]-7H-pyrrolo[2,3-d]pyrimidin-4-yl}amino)-6-fluorobenzamide (11 g, 24 mmol), 1-[(dimethylamino)acetyl]-5-(methyloxy)-2,3-dihydro-1H-indol-6-amine (5 g, 20 mmol), a 4M HCl solution in dioxane (25 mL, 100 mmol) and 2,2,2-trifluoroethanol (250 mL) was heated at 80° C. for 16 h. The resulting mixture was allowed to cool to rt and diluted with a 27% aqueous $NH_4OH$ solution (250 mL) and THF (250 mL). The reaction mixture was stirred at rt overnight. The resulting slurry was filtered and the solids were triturated using $H_2O$ (300 mL), $Et_2O$ (300 mL) and finally EtOAc (300 mL). The solids were dissolved in THF, concentrated onto Celite and purified by silica gel chromatography using 0-10% MeOH (containing 0.2% $NH_3$)/$CH_2Cl_2$. The solids obtained following chromatography were triturated using a mixture of MeOH and $CH_2Cl_2$ to afford 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluorobenzamide as a beige solid (6.8 g, 51%).

Step B/Example 53 (Alternative Preparation): 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluorobenzamide A mixture of 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluorobenzamide (6.7 g, 10 mmol), a solution of NaOMe (0.5M in MeOH, 200 mL, 100 mmol) and THF (400 mL) was stirred at rt overnight. The resulting mixture was filtered through a pad of silica gel, which was rinsed with a solution of $NH_3$ (2N in MeOH). The filtrate was concentrated. The residue was dissolved in THF and purified by silica gel chromatography using 0-10% MeOH (containing 0.2% $NH_3$)/THF. The crude product was dissolved in a mixture of THF and MeOH (200 mL) and washed with a 2N NaOH solution (200 mL) and a saturated NaCl solution (100 mL). The organic layer was dried ($Na_2SO_4$), concentrated and triturated using $Et_2O$ to obtain 2.18 g of 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluorobenzamide as a beige solid. The impure fractions from the column were combined and concentrated. The residue was dissolved in THF. MeOH (100 mL) was added, followed by NaOMe (2.6 g). After 2 h the resulting mixture was diluted with EtOAc (100 mL) and a 2N NaOH solution (200 mL). The organic layer was washed with a saturated NaCl solution (200 mL), dried ($Na_2SO_4$) and concentrated down to about 20 mL volume. The resulting slurry was filtered and the solids were washed with $Et_2O$ to obtain 0.95 g of 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluorobenzamide as a light brown solid (combined yield 3.13 g, 61%). $^1$H NMR (400 MHz, DMSO-$d_6$) δ ppm 2.24 (s, 6 H), 3.11 (t, J=8.25 Hz, 2 H), 3.31 (s, 3 H), 3.76 (s, 2 H), 4.17 (t, J=8.25 Hz, 2 H), 6.21 (dd, J=3.48, 1.65 Hz, 1 H), 6.80-6.90 (m, 1 H), 6.90-7.01 (m, 2 H), 7.25-7.37 (m, 1 H), 7.59 (s, 1 H), 8.01 (s, 1 H), 8.09 (s, 1 H), 8.50 (d, J=8.43 Hz, 1 H), 8.60 (s, 1 H), 10.53 (s, 1 H), 11.28 (s, 1 H). ESIMS (M+H)=519.

Example 54

5-fluoro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide

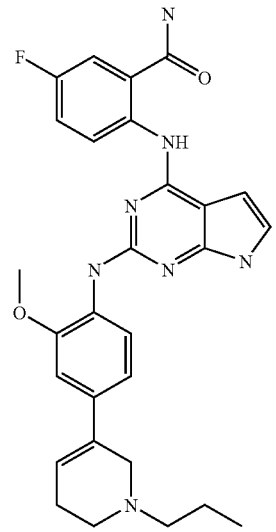

According to General Protocol III, 5-fluoro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-5-fluorobenzamide (4.0 g, 8.71 mmol), 27% aqueous ammonium hydroxide, and 2-(methyloxy)-4-(1-propyl-1,2,5,6-tetrahydro-3-pyridinyl)aniline (2.5 g, 10 mmol) and isolated as a yellow solid (1.5 g); 1H NMR (400 MHz, DMSO-$d_5$) δppm 0.89 (t, J=7.33 Hz, 3 H) 1.61 (s, 2 H) 2.25 (s, 2 H) 2:44-2.50 (m, 6H) 3.89 (s, 3H) 6.19(s, 1H) 6.94-6.96 (m, 1H) 6.26 (dd, J=3.39, 1.74 Hz, 1H) 6.99-7.01 (m, 2H) 7.07 (d, J=8.42 Hz, 1H) 7.34-7.38 (m, 1H) 7.43 (d, J=8.24 Hz, 1H) 7.56 (s, 1H) 7.67 (dd, J=9.89, 2.93 Hz, 1H) 7.85 (s, 1H) 8.31 (s, 2H) 8.89 (dd, J=9.34, 5.49 Hz, 1H) 11.40 (s, 1H) 11.73 (s, 1H). ESIMS (M+H)+=516.

Example 55

5-fluoro-2-[(2-{[2-(methyloxy)-4-(1-methyl-1,2,5,6-tetrahydro-3-pyridinyl) phenyl]amino}-1H-pyrrolo[2,3-d]pyrimidin-4-yl)amino]benzamide

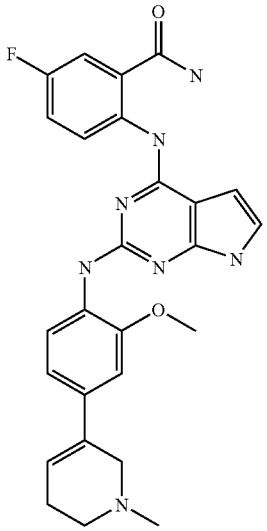

According to General Protocol III, 5-fluoro-2-[(2-{[2-(methyloxy)-4-(1-methyl-1,2,5,6-tetrahydro-3-pyridinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-5-fluorobenzamide (0.25 g, 0.57 mmol), 27% aqueous ammonium hydroxide, and 2-(methyloxy)-4-(1-methyl-1,2,5,6-tetrahydro-3-pyridinyl)aniline (0.14 g, 0.63 mmol) and isolated as a yellow solid (0.159 g). 1H NMR (400 MHz, DMSO-$d_6$) δ ppm 2.27 (s, 2H), 2.30 (s, 2H), 2.39 (s, 3H), 2.54 (t, J=5.50 Hz, 2H), 3.90 (s, 3H), 6.15 (t, J=4.03 Hz, 1H), 6.28 (dd, J=3.30, 1.83 Hz, 1H), 6.95 (dd, J=8.43, 1.83 Hz, 1H), 6.98-7.04 (m, 1H), 7.09 (d, J=7.70 Hz, 1H), 7.33-7.42 (m, 1H), 7.46 (d, J=8.07 Hz, 1H), 7.56 (s, 1H), 7.69 (dd, J=9.90, 2.93 Hz, 1H), 7.86 (s, 1H), 8.32 (d, J=8.43 Hz, 1H), 8.91 (dd, J=9.35, 5.32 Hz, 1H), 11.42 (s, 1H), 11.74 (s, 1H); ESIMS (M+H)$^+$=488.

Example 56

5-fluoro-2-[(2-{[2-(methyloxy)-4-(1-methyl-3-piperidinyl)phenyl]amino}-1H-pyrrolo[2,3-d]pyrimidin-4-yl)amino]benzamide

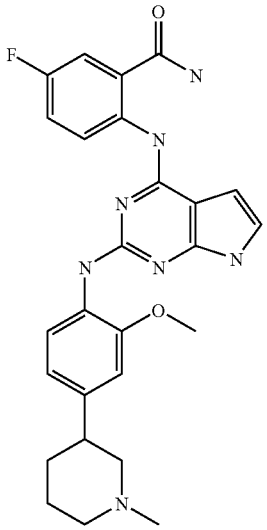

According to General Protocol III, 5-fluoro-2-[(2-{[2-(methyloxy)-4-(1-methyl-3-piperidinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-5-fluorobenzamide (0.26 g, 0.57 mmol), 27% aqueous ammonium hydroxide, and 2-(methyloxy)-4-(1-methyl-3-piperidinyl)aniline (0.14 g, 0.62 mmol) and isolated as a yellow solid (0.139 g); 1H NMR (400 MHz, DMSO-$d_6$) δ ppm 1.34-1.45 (m, 1H), 1.51-1.63 (m, 1H), 1.65-1.73 (m, 1H), 1.76-1.81 (m, 1H), 1.83-1.93 (m, 2H), 2.17 (s, 3H), 2.66-2.73 (m, 1H), 2.74-2.83 (m, 2H), 3.83 (s, 3H), 6.24 (dd, J=3.4, 1.9 Hz, 1H), 6.78 (dd, J=8.4, 1.5 Hz, 1H), 6.87 (d, J=1.5 Hz, 1H), 6.96 (dd, J=3.4, 2.3 Hz, 1H), 7.28-7.37 (m, 1H), 7.48 (s, 1H), 7.66 (dd, J=9.9, 3.1 Hz, 1H), 7.83 (s, 1H), 8.14 (d, J=8.1 Hz, 1H), 8.30 (s, 1H), 8.90 (dd, J=9.2, 5.4 Hz, 1H), 11.34 (s, 1H), 11.71 (s, 1H); ESIMS (M+H)$^+$=490.

Example 57

5-fluoro-2-[(2-{[2-(methyloxy)-5-(1-propyl-1,2,5,6-tetrahydro-3-pyridinyl)phenyl]amino}-1H-pyrrolo[2,3-d]pyrimidin-4-yl)amino]benzamide

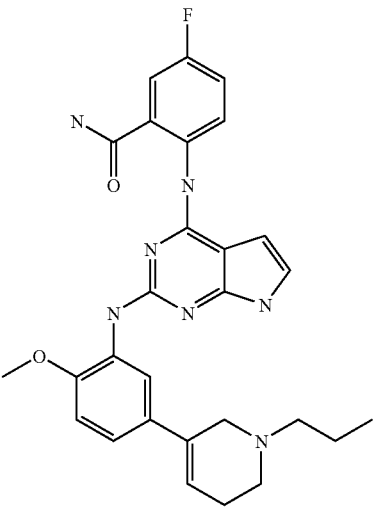

According to General Protocol III, 5-fluoro-2-[(2-{[2-(methyloxy)-5-(1-propyl-1,2,5,6-tetrahydro-3-pyridinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-5-fluorobenzamide (0.30 g, 0.65 mmol), 27% aqueous ammonium hydroxide, and 2-(methyloxy)-5-(1-propyl-1,2,5,6-tetrahydro-3-pyridinyl)aniline (0.19 g, 0.77 mmol) to afford 5-fluoro-2-[(2-{[2-(methyloxy)-5-(1-propyl-1,2,5,6-tetrahydro-3-pyridinyl)phenyl]amino}-1H-pyrrolo[2,3-d]pyrimidin-4-yl)amino]benzamide (0.026 g, 7.7% over 3 steps) as a pale yellow solid. 1H NMR (400 MHz, DMSO-$d_6$) δ ppm 0.85 (t, J=7.33 Hz, 3H) 1.43-1.54 (m, 2H) 2.22 (bs, 2H) 2.37 (bs, 2H) 2.47-2.50 (m, 2H) 3.20 (bs, 2H) 3.85 (s, 3H) 6.04 (s, 1H), 6.27-6.28 (m,1H) 6.95 (s, 2H) 6.99-7.05 (m, 1H) 7.25-7.33 (m, 1H) 7.53 (s, 1H) 7.69 (dd, J=9.90, 3.30 Hz, 1H) 7.87 (s, 1H) 8.31-8.33 (m, 2H) 8.89-8.93 (m, 1H) 11.39 (s, 1H) 11.84 (s, 1H). ESIMS (M+H)+=516.

Example 58

5-fluoro-2-[(2-{[4-[1-(1-methylethyl)-4-piperidinyl]-2-(methyloxy)phenyl]amino}-1H-pyrrolo[2,3-d]pyrimidin-4-yl)amino]benzamide

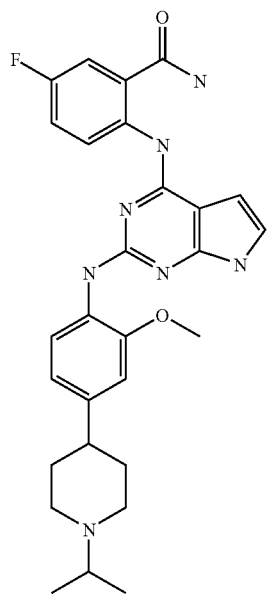

According to General Protocol III, 5-fluoro-2-[(2-{[4-[1-(1-methylethyl)-4-piperidinyl]-2-(methyloxy)phenyl]amino}-1H-pyrrolo[2,3-d]pyrimidin-4-yl)amino]benzamide (0.102 g, 0.197 mmol) was prepared from 2-({2-chloro-7-[(4-methylphenyl)sulfonyl]-7H-pyrrolo[2,3-d]pyrimidin-4-yl}amino)-5-fluorobenzamide (0.25 g, 0.54 mmol), 27% aqueous ammonium hydroxide, and 4-[1-(1-methylethyl)-4-piperidinyl]-2-(methyloxy)aniline (0.15 g, 0.60 mmol). 1H NMR (400 MHz, DMSO-$d_6$) δ ppm 0.98 (d, J=6.2 Hz, 6H), 1.59-1.70 (m, 2H), 1.71-1.79 (m, 2H), 2.14-2.24 (m, 2H), 2.36-2.45 (m, 1H), 2.64-2.74 (m, 1H), 2.83-2.92 (m,.2H), 3.85 (s, 3H), 6.25 (dd, J=3.7, 1.8 Hz, 1H), 6.79 (dd, J=8.4, 1.8 Hz, 1H), 6.88 (d, J=1.8 Hz, 1H), 6.97 (dd, J=3.7, 2.2 Hz, 1H), 7.32-7.37 (m, 1H), 7.48 (s, 1H), 7.68 (dd, J=9.9, 2.9 Hz, 1H), 7.86 (s, 1H), 8.16 (d, J=8.1 Hz, 1H), 8.32 (s, 1H), 8.93 (dd, J=9.2, 5.5 Hz, 1H), 11.37 (s, 1H), 11.73 (s, 1H); ESIMS (M+H)$^+$=518.

Example 59

5-fluoro-2-{[2-({2-(methyloxy)-4-[4-(4-morpholinyl)-1-piperidinyl]phenyl}amino)-1H-pyrrolo[2,3-d]pyrimidin-4-yl]amino}benzamide

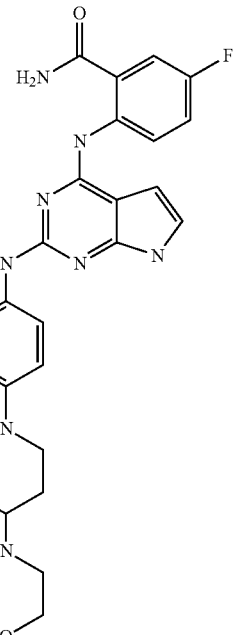

According to General Protocol III, 5-fluoro-2-{[2-({2-(methyloxy)-4-[4-(4-morpholinyl)-1-piperidinyl]phenyl}amino)-1H-pyrrolo[2,3-d]pyrimidin-4-yl]amino}benzamide was prepared from 2-({2-chloro-7-[(4-methylphenyl)sulfonyl]-7H-pyrrolo[2,3-d]pyrimidin-4-yl}amino)-5-fluorobenzamide (0.250 g, 0.545 mmol), 27% aqueous ammonium hydroxide, and 2-(methyloxy)-4-[4-(4-morpholinyl)-1-piperidinyl]aniline (0.190 g, 0.654 mmol) and isolated as a yellow solid (0.144 g, 47% yield); 1H NMR (400 MHz, DMSO-$d_6$) δ ppm 1.44-1.55 (m, 2H), 1.85 (d, J=12.09 Hz, 2H), 2.19 (s, 2H), 2.24 (d, J=17.03 Hz, 2H), 2.61 (t, J=12.82 Hz, 2H), 3.51-3.59 (m, 4H), 3.66 (d, J=11.72 Hz, 2H), 3.78 (s, 3H), 6.19-6.25 (m, 1H), 6.48 (dd, J=8.70, 2.29 Hz, 1H), 6.61 (d, J=2.38 Hz, 1H), 6.91 (s, 1H), 6.91 (d, J=3.30 Hz, 1H), 7.28 (d, J=17.03 Hz, 1H), 7.36 (s, 1H), 7.65 (dd, J=9.89, 2.93 Hz, 1H), 7.82 (s, 1H), 7.85 (d, J=8.79 Hz, 1H), 8.29 (s, 1H), 8.93 (dd, J=9.16, 5.49 Hz, 1H), 11.24 (s, 1H), 11.71 (s, 1H).

Example 60

5-fluoro-2-[(2-{[4-[4-(1-methylethyl)-1-piperazinyl]-2-(methyloxy)phenyl]amino}-1H-pyrrolo[2,3-d]pyrimidin-4-yl)amino]benzamide

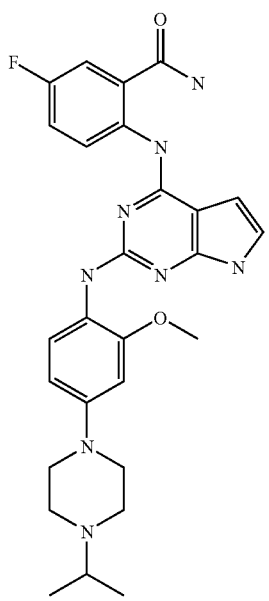

According to General Protocol III, 5-fluoro-2-[(2-{[4-[4-(1-methylethyl)-1-piperazinyl]-2-(methyloxy)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-5-fluorobenzamide (0.250 g, 0.54 mmol), 27% aqueous ammonium hydroxide, and 4-[4-(1-methylethyl)-1-piperazinyl]-2-(methyloxy)aniline (0.15 g, 0.60 mmol) and isolated as a yellow solid (0.131 g). 1H NMR (400 MHz, DMSO-$d_6$) δ ppm 1.00 (d, J=6.2 Hz, 6H), 2.58 (s, 4H), 2.65 (s, 1H), 3.09 (s, 4H), 3.80 (s, 3H), 6.22 (d, J=2.6 Hz, 1H), 6.48 (d, J=8.1 Hz, 1H), 6.62 (d, J=1.5 Hz, 1H), 6.90-6.94 (m, 1H), 7.25-7.32 (m, 1H), 7.40 (s, 1H), 7.67 (dd, J=10.3, 2.6 Hz, 1H), 7.86 (d, J=8.4 Hz, 2H), 8.32 (s, 1H), 8.95 (dd, J=9.5, 5.9 Hz, 1H), 11.27 (s, 1H), 11.74 (s, 1H); ESIMS (M+H)$^+$=519.

Example 61

5-fluoro-2-[(2-{[4-[(3S)-3-methyl-4-morpholinyl]-2-(methyloxy)phenyl]amino}-1H-pyrrolo[2,3-d]pyrimidin-4-yl)amino]benzamide

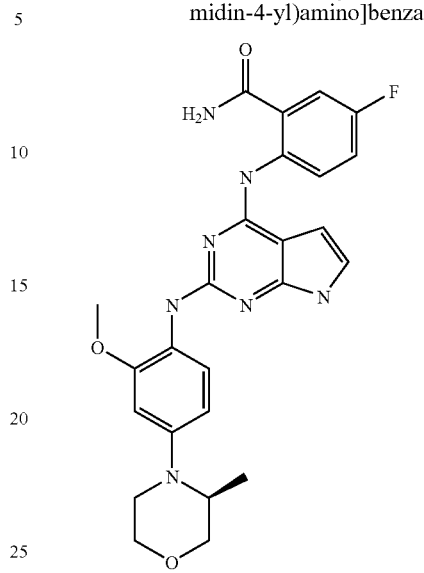

According to General Protocol III, 5-fluoro-2-[(2-{[4-[(3S)-3-methyl-4-morpholinyl]-2-(methyloxy)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-5-fluorobenzamide (0.500 g, 1.09 mmol), 27% aqueous ammonium hydroxide, and 4-[(3S)-3-methyl-4-morpholinyl]-2-(methyloxy)aniline (0.350 g, 1.63 mmol) and isolated as a yellow solid (0.211 g, 39% yield); 1H NMR (400 MHz, DMSO-$d_6$) δ ppm 0.95 (d, J=6.60 Hz, 3H), 3.01 (ddd, J=12.19, 9.07, 3.30 Hz, 1H), 3.06-3.11 (m, 1H), 3.55-3.65 (m, 2H), 3.70-3.78 (m, 2H), 3.81 (s, 3H), 3.87 (ddd, J=11.09, 3.21, 2.93 Hz, 1H), 6.23 (dd, J=3.48, 2.02 Hz, 1H), 6.50 (dd, J=8.80, 2.20 Hz, 1H), 6.62 (d, J=2.20 Hz, 1H), 6.86-6.96 (m, 1H), 7.21-7.32 (m, 1H), 7.40 (s, 1H), 7.67 (dd, J=9.90, 2.93 Hz, 1H), 7.84 (s, 1H), 7.91 (d, J=8.80 Hz, 1H), 8.31 (s, 1H), 8.94 (dd, J=9.35, 5.32 Hz, 1H), 11.27 (s, 1H), 11.72 (s, 1H). ESIMS (M+H)+=492.

Example 62

2-{[2-({5-[(N,N-dimethylglycyl)amino]-2-methylphenyl}amino)-1H-pyrrolo[2,3-d]pyrimidin-4-yl]amino}-5-fluorobenzamide

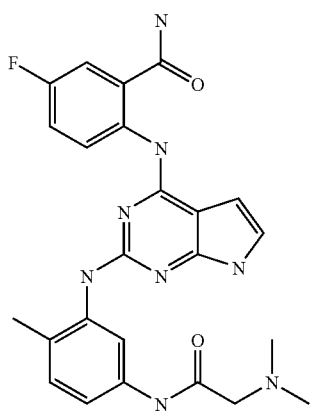

291

According to General Protocol III, 2-{[2-({5-[(N,N-dimethylglycyl)amino]-2-methylphenyl}amino)-1H-pyrrolo[2,3-d]pyrimidin-4-yl]amino}-5-fluorobenzamide was prepared from 2-({2-chloro-7-[(4-methylphenyl)sulfonyl]-7H-pyrrolo[2,3-d]pyrimidin-4-yl}amino)-5-fluorobenzamide (0.30 g, 0.65 mmol), 27% aqueous ammonium hydroxide, and N$^1$-(3-amino-4-methylphenyl)-N$^2$,N$^2$-dimethylglycinamide (0.20 g, 0.98 mmol) and isolated as a yellow solid (0.045 g); 1H NMR (400 MHz, DMSO-d$_6$) δ ppm 2.14 (s, 3H) 2.21 (s 6H) 2.99 (s, 2H) 6.19 (dd, J=3.48, 2.01 Hz, 1H) 6.90 (dd, J=3.39, 2.29 Hz, 1H) 7.02-7.12 (m, 2H) 7.34 (dd, J=8.33, 2.11 Hz, 1H) 7.64 (dd, J=9.98, 3.02 Hz, 1H) 7.72 (d, J=2.01 Hz, 1H) 7.83 (s, 1H) 8.15 (s, 1H) 8.29 (s, 1H) 8.89 (dd, J=9.34, 5.49 Hz, 1H) 9.57 (s, 1H) 11.20 (s, 1H) 11.83 (s, 1H). ESIMS (M+H)+=477.

Example 63

2-{[2-({5-[(N,N-dimethylglycyl)amino]-2-[(trifluoromethyl)oxy]phenyl}amino)-1H-pyrrolo[2,3-d]pyrimidin-4-yl]amino}-5-fluorobenzamide

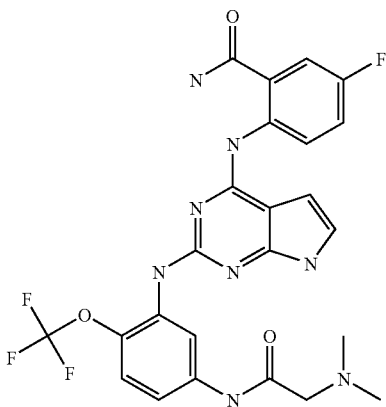

According to General Protocol III, 2-{[2-({5-[(N,N-dimethylglycyl)amino]-2-[(trifluoromethyl)oxy]phenyl}amino)-1H-pyrrolo[2,3-d]pyrimidin-4-yl]amino}-5-fluorobenzamide was prepared from 2-({2-chloro-7-[(4-methylphenyl)sulfonyl]-7H-pyrrolo[2,3-d]pyrimidin-4-yl}amino)-5-fluorobenzamide (0.300 g, 0.65 mmol), 27% aqueous ammonium hydroxide, and N$^1$-{3-amino-4-[(trifluoromethyl)oxy]phenyl}-N$^2$,N$^2$-dimethylglycinamide (0.172 g, 0.82 mmol) and isolated as a yellow solid (0.137 g, 39% Yield); 1H NMR (400 MHz, DMSO-d$_6$) δ ppm 2.23 (s, 6H), 3.02 (s, 2H), 6.25 (dd, J=3.20, 1.74 Hz, 1H), 6.92-7.00 (m, 1H), 7.10-7.18 (m, 1H), 7.31 (d, J=8.60 Hz, 1H), 7.49 (dd, J=8.87, 2.47 Hz, 1H), 7.67 (dd, J=9.97, 3.02 Hz, 1H), 7.87 (s, 1H), 8.07 (d, J=2.38 Hz, 1H), 8.33 (s, 1H), 8.38 (s, 1H), 8.90 (dd, J=9.33, 5.49 Hz, 1H), 9.83 (s, 1H), 11.33 (s, 1H), 11.89 (s, 1H). ESI-MS (M+H) 547. Retention time 1.78 minutes.

292

Example 64

2-[(2-{[5-{[3-(dimethylamino)propyl]oxy}-2-(methyloxy)phenyl]amino}-1H-pyrrolo[2,3-d]pyrimidin-4-yl)amino]-5-fluorobenzamide

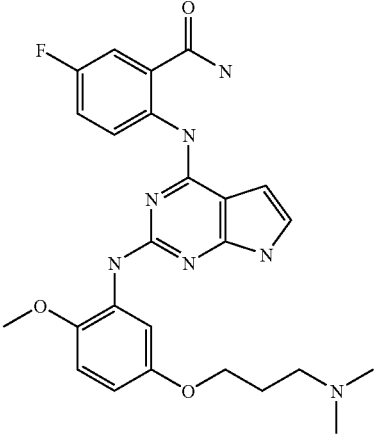

According to General Protocol III, 2-[(2-{[5-{[3-(dimethylamino)propyl]oxy}-2-(methyloxy)phenyl]amino}-1H-pyrrolo[2,3-d]pyrimidin-4-yl)amino]-5-fluorobenzamide (0.149 g) was prepared from 2-({2-chloro-7-[(4-methylphenyl)sulfonyl]-7H-pyrrolo[2,3-d]pyrimidin-4-yl}amino)-5-fluorobenzamide (0.30 g, 0.65 mmol), 27% aqueous ammonium hydroxide, and 5-{[3-(dimethylamino)propyl]oxy}-2-(methyloxy)aniline (0.17 g, 0.78 mmol). 1H NMR (400 MHz, DMSO-d$_6$) δ ppm 1.83 (qd, J=6.8, 6.6 Hz, 2H), 2.14 (s, 6H), 2.36 (t, J=7.3 Hz, 2H), 3.82 (s, 3H), 3.91 (t, J=6.4 Hz, 2H), 6.29 (d, J=3.3 Hz, 1H), 6.45 (dd, J=8.8, 2.9 Hz, 1H), 6.88 (d, J=9.2 Hz, 1H), 6.96-7.07 (m, 1H), 7.32-7.39 (m, 1H), 7.51 (s, 1H), 7.69 (dd, J=9.9, 3.3 Hz, 1H), 7.86 (s, 1H), 8.09 (d, J=2.9 Hz, 1H), 8.32 (s, 1H), 8.89 (dd, J=9.3, 5.3 Hz, 1H), 11.46 (s, 1H), 11.74 (s, 1H); ESIMS (M+H)$^+$=494.

Example 65

Step A/Intermediate D2: 9-fluoro-5-{[4-[4-(1-methylethyl)-1-piperazinyl]-2-(methyloxy)phenyl]amino}-3-[(4-methylphenyl)sulfonyl]pyrrolo[2',3':4,5]pyrimido[6,1-b]quinazolin-7(3H)-one

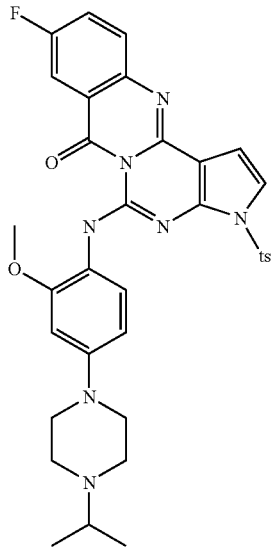

To a pressurized vessel was added 2-({2-chloro-7-[(4-methylphenyl)sulfonyl]-7H-pyrrolo[2,3-d]pyrimidin-4-yl}amino)-5-fluorobenzamide (3.0 g, 6.54 mmol), 4-[4-(1-methylethyl)-1-piperazinyl]-2-(methyloxy)aniline (2.11 g, 8.5 mmol), potassium iodide (<10 mg) and hydrochloric acid as a 4.0M solution in dioxanes (ca 10 mL). The resulting suspension was stirred until all solids had completely dissolved (24 hr.) The reaction was poured into into saturated sodium bicarbonate and diluted with dichloromethane. The organic layer was dried over sodium sulfate, volatiles removed under reduced pressure, and the solids triturated with diethyl ether to afford 9-fluoro-5-{[4-[4-(1-methylethyl)-1-piperazinyl]-2-(methyloxy)phenyl]amino}-3-[(4-methylphenyl)sulfonyl]pyrrolo[2',3':4,5]pyrimido[6,1-b]quinazolin-7(3H)-one (3.27 g, 76% yield) of sufficient purity for use in subsequent transformations. ESIMS (M+H)=656.

Step B: 5-fluoro-N-methyl-2-[(2-{[4-[4-(1-methylethyl)-1-piperazinyl]-2-(methyloxy)phenyl]amino}-1H-pyrrolo[2,3-d]pyrimidin-4-yl)amino]benzamide

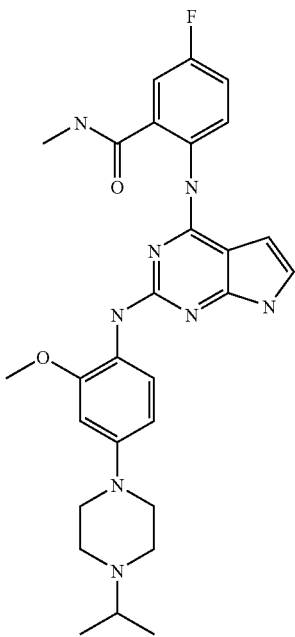

According to General Protocol III (Steps B & C), 5-fluoro-N-methyl-2-[(2-{[4-[4-(1-methylethyl)-1-piperazinyl]-2-(methyloxy)phenyl]amino}-1H-pyrrolo[2,3-d]pyrimidin-4-yl)amino]benzamide was prepared from 9-fluoro-5-[{4-[4-(1-methylethyl)-1-piperazinyl]-2-(methyloxy)phenyl]amino}-3-[(4-methylphenyl)sulfonyl]pyrrolo[2',3':4,5]pyrimido[6,1-b]quinazolin-7(3H)-one (0.048 g, 0.01 mmol) and methyl amine and isolated as a pale yellow solid (0.022 g, 43%). 1H NMR (400 MHz, CDCl₃) δ ppm 1.03-1.10 (m, 6H) 2.66-2.74 (m, 4H) 2.78-2.79 (m, 1H) 2.95-3.00 (m, 3H) 3.11-3.17 (m, 4H) 3.85 (s, 3H) 6.16 (s, 1H) 6.45-6.57 (m, 3H) 6.74 (m, 1H) 7.07 (s, 1H) 7.10-7.18 (m, 2H) 8.17-8.22 (m, 1H) 8.74 (s, 1H) 8.85 (m, 1H) 1.64 (m, 1H). ESIMS (M+H)+=533.

Example 66

5-fluoro-N-(2-hydroxyethyl)-2-[(2-{[4-[4-(1-methylethyl)-1-piperazinyl]-2-(methyloxy)phenyl]amino}-1H-pyrrolo[2,3-d]pyrimidin-4-yl)amino]benzamide

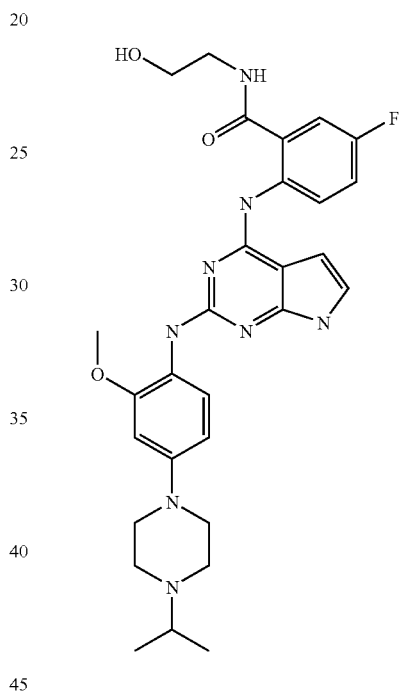

According to General Protocol III (Steps B and C) 5-fluoro-N-(2-hydroxyethyl)-2-[(2-{[4-[4-(1-methylethyl)-1-piperazinyl]-2-(methyloxy)phenyl]amino}-1H-pyrrolo[2,3-d]pyrimidin-4-yl)amino]benzamide was prepared from ethanolamine (0.115 mL, 1.91 mmol) and 9-fluoro-5-{[4-[4-(1-methylethyl)-1-piperazinyl]-2-(methyloxy)phenyl]amino}-3-[(4-methylphenyl)sulfonyl]pyrrolo[2',3':4,5]pyrimido[6,1-b]quinazolin-7(3H)-one (0.250 g, 0.382 mmol) as a pale yellow solid (0.088 g, 41% yield); 1H NMR (400 MHz, DMSO-d₆) δ ppm 0.97 (d, J=6.04 Hz, 6H), 2.55 (s, 4H), 2.64 (ddd, J=6.18, 3.30, 3.16 Hz, 1H), 3.06 (s, 4H), 3.28-3.34 (m, 2H), 3.49 (q, J=5.86 Hz, 2H), 3.77 (s, 3H), 4.72 (t, J=5.13 Hz, 1H), 6.22 (s, 1H), 6.44 (d, J=8.97 Hz, 1H), 6.59 (s, 1H), 6.89 (s, 1H), 7.25 (td, J=8.56, 3.57 Hz, 1H), 7.33 (s, 1H), 7.61 (dd, J=9.80, 3.57 Hz, 1H), 7.85 (d, J=8.42 Hz, 1H), 8.72 (t, J=5.49 Hz, 1H), 8.80 (dd, J=9.52, 5.49 Hz, 1H), 11.22 (s, 1H), 11.23 (s, 1H). ESIMS (M+H)+=563.

Example 67

N-(2-amino-2-oxoethyl)-4-fluoro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide

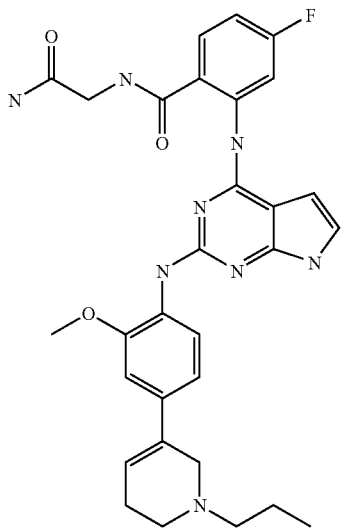

Step A/Intermediate D3: N-(2-amino-2-oxoethyl)-4-fluoro-2-({2-{[2-(methyloxy)-4-(1-propyl-1,2,5,6-tetrahydro-3-pyridinyl)phenyl]amino}-7-[(4-methylphenyl)sulfonyl]-7H-pyrrolo[2,3-d]pyrimidin-4-yl}amino)benzamide

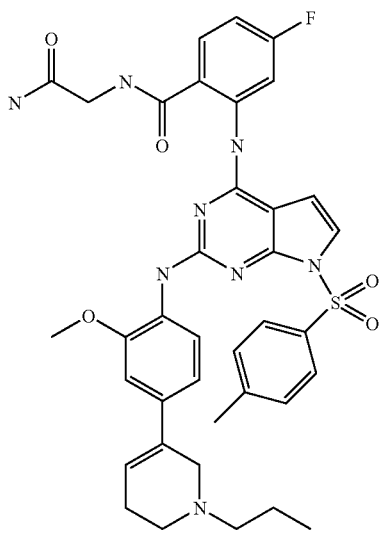

To a solution of 9-fluoro-5-{[2-(methyloxy)-4-(1-propyl-1,2,5,6-tetrahydro-3-pyridinyl)phenyl]amino}-3-[(4-methylphenyl)sulfonyl]pyrrolo[2',3':4,5]pyrimido[6,1-b]quinazolin-7(3H)-one (0.2 g, 0.31 mmol) in anhydrous dimethylacetamide (20 mL, Aldrich) was added potassium carbonate (1.27 g, 9.19 mmol, J. T. Baker) and glycinamide hydrochloride (0.34 g, 3.07 mmol, Aldrich). After heating at 90° C. for 4 hrs, the solvent was removed under reduced pressure, residue partitioned between dichloromethane (100 mL) and water (50 mL), organic layer removed and aqueous layer was extracted with an additional 50 mL dichloromethane. Combined organic layers were adsorbed to silica gel and purified by column chromatography (dichloromethane to 10% methanol/dichloromethane) to give N-(2-amino-2-oxoethyl)-4-fluoro-2-({2-{[2-(methyloxy)-4-(1-propyl-1,2,5,6-tetrahydro-3-pyridinyl)phenyl]amino}-7-[(4-methylphenyl)sulfonyl]-7H-pyrrolo[2,3-d]pyrimidin-4-yl}amino)benzamide (0.1 g, 45%). ESIMS (M+H)+=727.

Step B: N-(2-amino-2-oxoethyl)-4-fluoro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide According to General Protocol III (Steps B & C), N-(2-amino-2-oxoethyl)-4-fluoro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide was prepared from N-(2-amino-2-oxoethyl)-4-fluoro-2-({2-{[2-(methyloxy)-4-(1-propyl-1,2,5,6-tetrahydro-3-pyridinyl)phenyl]amino}-7-[(4-methylphenyl)sulfonyl]-7H-pyrrolo[2,3-d]pyrimidin-4-yl}amino)benzamide (0.1 g, 0.14 mmol) and isolated as a pale yellow solid (0.021 g, 27%). 1H NMR (400 MHz, DMSO-$d_6$) δ ppm 0.83-0.91 (m, 3H) 1.49-1.51 (m, 2H) 2.23 (bs, 2H) 2.39 (m, 2H) 2.48 (bs, 2H) 3.23 (bs, 2H) 3.81-3.82 (m, 2H), 3.86 (s, 3H) 6.10 (bs, 1H) 6.26-6.31 (m, 1H) 6.84-6.91 (m, 2H) 6.99 (s, 2H) 7.05 (s, 1H) 7.43 (s, 1H) 7.64 (s, 1H) 7.89-7.91 (m, 1H) 8.15 (d, J=8.63 Hz, 1H) 8.76 (d, J=11.77 Hz, 1H) 8.95 (s, 1H) 11.40 (s, 1H) 11.89 (s, 1H). ESIMS (M+H)+=573.

Example 68

5-bromo-2-[(2-{[4-[4-(1-methylethyl)-1-piperazinyl]-2-(methyloxy)phenyl]amino}-1H-pyrrolo[2,3-d]pyrimidin-4-yl)amino]benzamide

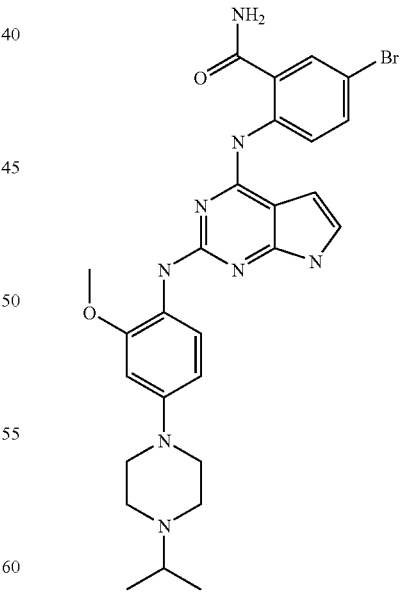

According to General Protocol III/Step A & B, 5-bromo-2-({2-chloro-7-[(4-methylphenyl)sulfonyl]-7H-pyrrolo[2,3-d]pyrimidin-4-yl}amino)benzamide (1.5 g, 3.69 mmol), 27% aqueous ammonium hydroxide, and 4-[4-(1-methylethyl)-1-piperazinyl]-2-(methyloxy)aniline (0.550 g, 3.32 mmol)

were combined to afford 5-bromo-2-({2-{[4-[4-(1-methylethyl)-1-piperazinyl]-2-(methyloxy)phenyl]amino}-7-[(4-methylphenyl)sulfonyl]-7H-pyrrolo[2,3-d]pyrimidin-4-yl}amino)benzamide as a pale yellow solid (1.78 g). An aliquot of 5-bromo-2-({2-{[4-[4-(1-methylethyl)-1-piperazinyl]-2-(methyloxy)phenyl]amino}-7-[(4-methylphenyl)sulfonyl]-7H-pyrrolo[2,3-d]pyrimidin-4-yl}amino)benzamide (0.340 g) was detosylated according to the General Protocol III/Step C to afford 5-bromo-2-[(2-{[4-[4-(1-methylethyl)-1-piperazinyl]-2-(methyloxy)phenyl]amino}-1H-pyrrolo[2,3-d]pyrimidin-4-yl)amino]benzamide (0.204 g, 58% yield, 3 steps); 1H NMR (400 MHz, DMSO-d$_6$) δ ppm 0.98 (d, J=6.41 Hz, 6H), 2.56 (s, 4H), 2.63 (d, J=6.23 Hz, 1H), 3.07 (s, 4H), 3.26 (s, 3H), 6.19 (dd, J=3.30, 1.83 Hz, 1H), 6.45 (d, J=8.97 Hz, 1H), 6.59 (d, J=2.01 Hz, 1H), 6.91 (d, J=2.20 Hz, 1H), 7.41 (s, 1H), 7.51 (dd, J=9.06, 2.29 Hz, 1H), 7.75-7.84 (m, 2H), 7.96 (d, J=2.20 Hz, 1H), 8.35 (s, 1H), 8.88 (d, J=8.97 Hz, 1H), 11.26 (s, 1H), 11.85 (s, 1H). ESIMS (M+H)+=580.

Example 69

2-{[2-({2-ethyl-4-[4-(1-methylethyl)-1-piperazinyl]phenyl}amino)-1H-pyrrolo[2,3-d]pyrimidin-4-yl]amino}-4-fluorobenzamide

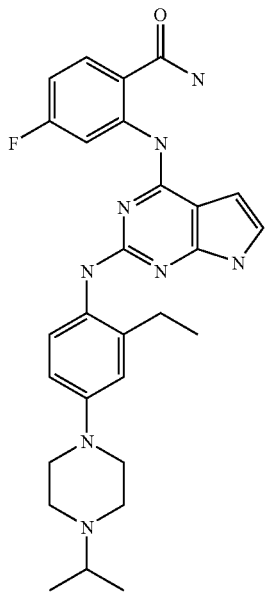

According to General Protocol III, the 2-{[2-({2-ethyl-4-[4-(1-methylethyl)-1-piperazinyl]phenyl}amino)-1H-pyrrolo[2,3-d]pyrimidin-4-yl]amino}-4-fluorobenzamide (0.093 g, 0.180 mmol) was prepared from 2-({2-chloro-7-[(4-methylphenyl)sulfonyl]-7H-pyrrolo[2,3-d]pyrimidin-4-yl}amino)-5-fluorobenzamide (0.30 g, 0.65 mmol), 27% aqueous ammonium hydroxide, and 2-ethyl-4-[4-(1-methylethyl)-1-piperazinyl]aniline (0.18 g, 0.72 mmol). 1H NMR (400 MHz, DMSO-d$_6$) δ ppm 0.98 (d, J=6.0 Hz, 6H), 1.05 (t, J=7.2 Hz, 3H), 2.50-2.59 (m, 6H), 2.64 (d, J=5.7 Hz, 1H), 3.07 (s, 4H), 6.18 (s, 1H), 6.72 (d, J=1.8 Hz, 1H), 6.75 (d, J=19.0 Hz, 2H), 6.87 (s, 1H), 7.13 (d, J=8.4 Hz, 1H), 7.69 (s, 1H), 7.84 (t, J=7.1 Hz, 1H), 8.01 (s, 1H), 8.24 (s, 1H), 8.75 (d, J=11.9 Hz, 1H), 11.15 (s, 1H); ESIMS (M+H)$^+$=517.

Example 70

4-fluoro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide

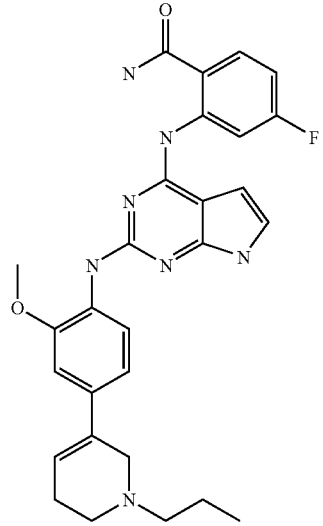

According to General Protocol III, 4-fluoro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-4-fluorobenzamide (0.300 g, 0.65 mmol), 27% aqueous ammonium hydroxide, and 2-(methyloxy)-4-(1-propyl-1,2,5,6-tetrahydro-3-pyridinyl)aniline (0.200 g, 0.810 mmol) and isolated as a yellow solid (0.069 g, 21% Yield); 1H NMR (400 MHz, DMSO-d$_6$) δ ppm 0.88 (t, J=7.42 Hz, 3H), 1.54 (s, 2H), 2.26 (s, 2H), 2.41 (s, 2H), 2.52 (s, 2H), 3.25 (s, 2H), 3.87 (s, 3H), 6.13 (s, 1H), 6.27 (dd, J=3.39, 1.92 Hz, 1H), 6.83 (td, J=8.42, 2.56 Hz, 1H), 6.92 (d, J=9.89 Hz, 1H), 6.98-7.04 (m, 2H), 7.67 (s, 1H), 7.75 (s, 1H), 7.90 (dd, J=8.79, 6.78 Hz, 1H), 8.17 (d, J=8.06 Hz, 1H), 8.29 (s, 1H), 8.83 (dd, J=12.64, 2.56 Hz, 1H), 11.42 (s, 1H), 12.41 (s, 1H). ESI-MS (M+H) 516. Retention time 1.65 minutes.

Example 71

4-fluoro-2-[(2-{[2-(methyloxy)-4-(1-propyl-3-piperidinyl)phenyl]amino}-1H-pyrrolo[2,3-d]pyrimidin-4-yl)amino]benzamide

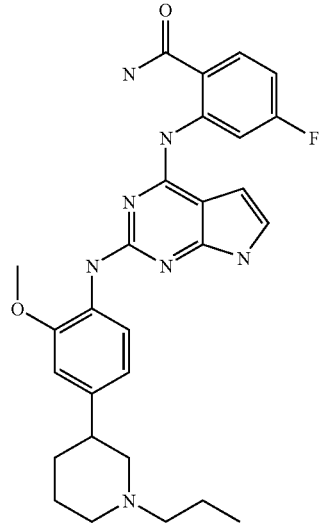

According to General Protocol III, 4-fluoro-2-[(2-{[2-(methyloxy)-4-(1-propyl-3-piperidinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-4-fluorobenzamide (0.300 g, 0.650 mmol), 27% aqueous ammonium hydroxide, and 2-(methyloxy)-4-(1-propyl-3-piperidinyl)aniline (0.200 g, 0.810 mmol) and isolated as a yellow solid (0.100 g, 30% Yield); 1H NMR (400 MHz, DMSO-d$_6$) δ ppm 0.84 (t, J=7.32 Hz, 3H), 1.36-1.47 (m, 2H), 1.52-1.62 (m, 1H), 1.69-1.97 (m, 4H), 2.19-2.31 (m, 2H), 2.64-2.74 (m, 2H), 2.81-2.92 (m, 2H), 3.84 (s, 3H), 6.26 (dd, J=3.29, 2.01 Hz, 1H), 6.76-6.86 (m, 2H), 6.91 (s, 1H), 6.96-7.02 (m, 1H), 7.61 (s, 1H), 7.75 (s, 1H), 7.90 (dd, J=8.78, 6.40 Hz, 1H), 8.02 (d, J=8.23 Hz, 1H), 8.30 (s, 1H), 8.83 (dd, J=12.62, 2.38 Hz, 1H), 11.38 (s, 1H), 12.40 (s, 1H). ESI-MS (M+H) 518. Retention time 1.60 minutes.

Example 72

4-fluoro-2-[(2-{[4-[1-(1-methylethyl)-1,2,3,6-tetrahydro-4-pyridinyl]-2-(methyloxy)phenyl]amino}-1H-pyrrolo[2,3-d]pyrimidin-4-yl)amino]benzamide

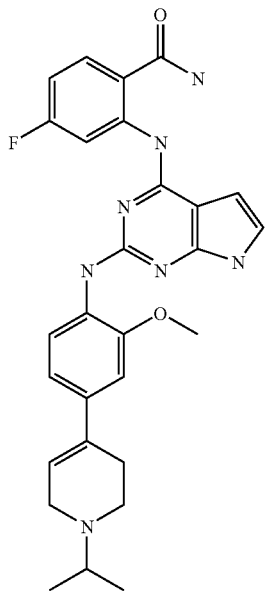

According to General Protocol III, 4-fluoro-2-[(2-{[4-[1-(1-methylethyl)-1,2,3,6-tetrahydro-4-pyridinyl]-2-(methyloxy)phenyl]amino}-1H-pyrrolo[2,3-d]pyrimidin-4-yl)amino]benzamide (0.078 g) was prepared from 2-({2-chloro-7-[(4-methylphenyl)sulfonyl]-7H-pyrrolo[2,3-d]pyrimidin-4-yl}amino)-5-fluorobenzamide (0.25 g, 0.54 mmol), 27% aqueous ammonium hydroxide, and 4-[1-(1-methylethyl)-1,2,3,6-tetrahydro-4-pyridinyl]-2-(methyloxy)aniline (0.15 g, 0.60 mmol). 1H NMR (400 MHz, DMSO-d$_5$) δ ppm 1.00 (d, J=6.4 Hz, 6H), 2.40-2.46 (m, 2H), 2.63 (t, J=5.3 Hz, 2H), 2.72 (dt, J=13.0, 6.4 Hz, 1H), 3.09-3.15 (m, 2H), 3.88 (s, 3H), 6.10 (s, 1H), 6.26 (s, 1H), 6.93-7.04 (m, 3H), 7.31-7.40 (m, 1H), 7.54 (s, 1H), 7.67 (dd, J=9.8, 2.5 Hz, 1H), 7.85 (s, 1H), 8.27-8.33 (m, 2H), 8.91 (dd, J=9.0, 5.5 Hz, 1H), H), 11.40 (s, 1H), 11.73 (s, 1H); ESIMS (M+)$^+$=516.

Example 73

4-fluoro-2-[(2-{[2-(methyloxy)-4-(1-propyl-4-piperidinyl)phenyl]amino}-1H-pyrrolo[2,3-d]pyrimidin-4-yl)amino]benzamide

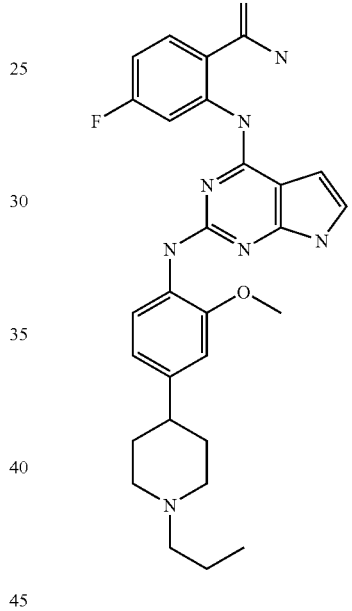

According to General Protocol III, 4-fluoro-2-[(2-{[2-(methyloxy)-4-(1-propyl-4-piperidinyl)phenyl]amino}-1H-pyrrolo[2,3-d]pyrimidin-4-yl)amino]benzamide (0.135 g) was prepared from 2-({2-chloro-7-[(4-methylphenyl)sulfonyl]-7H-pyrrolo[2,3-d]pyrimidin-4-yl}amino)-5-fluorobenzamide (0.18 g, 0.72 mmol), 27% aqueous ammonium hydroxide, and 2-(methyloxy)-4-(1-propyl-4-piperidinyl)aniline (0.30 g, 0.65 mmol). 1H NMR (400 MHz, DMSO-d$_6$) δ ppm 0.86 (t, J=7.3 Hz, 3H), 1.40-1.50 (m, J=14.8, 7.7, 7.5, 7.5 Hz, 2H), 1.65-1.77 (m, 4H), 1.89-1.98 (m, 2H), 2.20-2.27 (m, 2H), 2.40-2.46 (m, 1H), 2.95 (d, J=11.4 Hz, 2H), 3.84 (s, 3H), 6.26 (dd, J=3.5, 2.0 Hz, 1H), 6.79 (dd, J=8.1, 1.8 Hz, 1H), 6.83 (td, J=8.4, 2.6 Hz, 1H), 6.89 (d, J=1.5 Hz, 1H), 6.98-7.02 (m, 1H), 7.61 (s, 1H), 7.76 (s, 1H), 7.90 (dd, J=9.0, 6.4 Hz, 1H), 8.02 (d, J=8.4 Hz, 1H), 8.30 (s, 1H), 8.84 (dd, J=12.6, 2.7 Hz, 1H), 11.39 (s, 1H), 12.40 (s, 1H); ESIMS (M+H)$^+$=518.

303
Example 74

4-fluoro-2-[(2-{[4-[(3S)-3-hydroxy-1-piperidinyl]-2-(methyloxy)phenyl]amino}-1H-pyrrolo[2,3-d]pyrimidin-4-yl)amino]benzamide

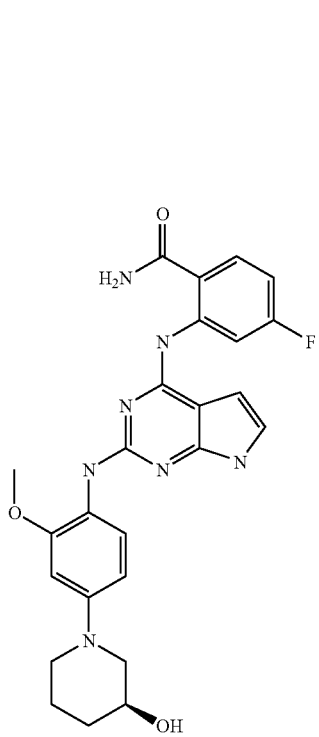

According to General Protocol III, 4-fluoro-2-[(2-{[4-[(3S)-3-hydroxy-1-piperidinyl]-2-(methyloxy)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-4-fluorobenzamide (0.300 g, 0.654 mmol), 27% aqueous ammonium hydroxide, and (3S)-1-[4-amino-3-(methyloxy)phenyl]-3-piperidinol (0.200 g, 0.920 mmol) and isolated as a yellow solid (0.156 g, 49% yield); 1H NMR (400 MHz, DMSO-$d_6$) δ ppm 1.17-1.27 (m, 1H), 1.49-1.59 (m, 1H), 1.70-1.74 (m, 1H), 1.83-1.91 (m, 1H), 2.41-2.45 (m, 1H), 2.58 (td, J=11.45, 2.93 Hz, 1H), 3.41 (td, J=7.97, 4.03 Hz, 1H), 3.50-3.56 (m, 1H), 3.59 (td, J=8.93, 5.04 Hz, 1H), 3.78 (s, 3H), 4.76 (d, J=4.58 Hz, 1H), 6.22 (dd, J=3.48, 1.47 Hz, 1H), 6.44 (dd, J=8.88, 2.47 Hz, 1H), 6.58 (d, J=2.38 Hz, 1H), 6.76-6.84 (m, 1H), 6.93 (dd, J=3.39, 2.11 Hz, 1H), 7.50 (s, 1H), 7.71 (d, J=8.79 Hz, 2H), 7.88 (dd, J=8.79, 6.59 Hz, 1H), 8.26 (s, 1H), 8.84 (d, J=2.56 Hz, 1H), 11.26 (s, 1H), 12.34 (s, 1H). ESIMS (M+H)+=492.

304
Example 75

4-fluoro-2-[(2-{[4-{4-[(3S)-3-fluoro-1-pyrrolidinyl]-1-piperidinyl}-2-(methyloxy)phenyl]amino}-1H-pyrrolo[2,3-d]pyrimidin-4-yl)amino]benzamide

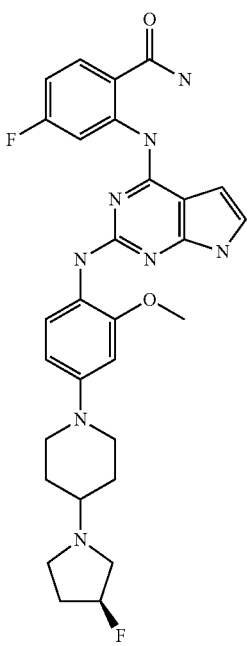

According to General Protocol III, 4-fluoro-2-[(2-{[4-{4-[(3S)-3-fluoro-1-pyrrolidinyl]-1-piperidinyl}-2-(methyloxy)phenyl]amino}-1H-pyrrolo[2,3-d]pyrimidin-4-yl)amino]benzamide (0.188 g) was prepared from 2-({2-chloro-7-[(4-methylphenyl)sulfonyl]-7H-pyrrolo[2,3-d]pyrimidin-4-yl}amino)-5-fluorobenzamide (0.30 g, 0.65 mmol), 27% aqueous ammonium hydroxide, and 4-{4-[(3S)-3-fluoro-1-pyrrolidinyl]-1-piperidinyl}-2-(methyloxy)aniline (0.21 g, 0.72 mmol). 1H NMR (400 MHz, DMSO-$d_6$) δ ppm 1.44-1.55 (m, 2H), 1.73-1.93 (m, 3H), 2.07-2.16 (m, 2H), 2.36 (q, J=6.8 Hz, 1H), 2.59-2.71 (m, 3H), 2.81 (d, J=6.6 Hz, 2H), 3.51-3.60 (m, 2H), 3.78 (s, 3H), 5.07-5.26 (m, 1H), 6.22 (d, J=3.5 Hz, 1H), 6.47 (dd, J=8.8, 2.4 Hz, 1H), 6.61 (d, J=2.4 Hz, 1H), 6.79 (td, J=8.4, 2.6 Hz, 1H), 6.92-6.95 (m, 1H), 7.51 (s, 1H), 7.72 (d, J=8.4 Hz, 2H), 7.88 (dd, J=8.6, 6.8 Hz, 1H), 8.26 (s, 1H), 8.84 (dd, J=12.6, 2.2 Hz, 1H), 11.27 (s, 1H), 12.35 (s, 1H); ESIMS (M+H)+=563.

Example 76

4-fluoro-2-[(2-{[4-{4-[(3R)-3-fluoro-1-pyrrolidinyl]-1-piperidinyl}-2-(methyloxy)phenyl]amino}-1H-pyrrolo[2,3-d]pyrimidin-4-yl)amino]benzamide

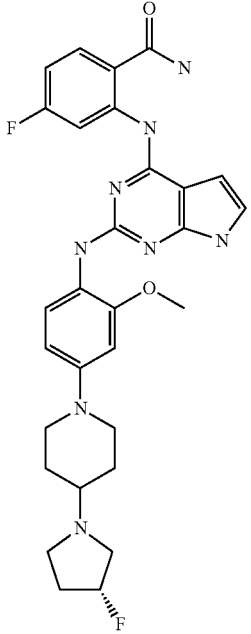

In a manner completely analogous to Example 75, 4-fluoro-2-[(2-{[4-{4-[(3R)-3-fluoro-1-pyrrolidinyl]-1-piperidinyl}-2-(methyloxy)phenyl]amino}-1H-pyrrolo[2,3-d]pyrimidin-4-yl)amino]benzamide (0.142 g) was prepared from 2-({2-chloro-7-[(4-methylphenyl)sulfonyl]-7H-pyrrolo[2,3-d]pyrimidin-4-yl}amino)-5-fluorobenzamide (0.300 g, 0.65 mmol), 27% aqueous ammonium hydroxide, and 4-{4-[(3R)-3-fluoro-1-pyrrolidinyl]-1-piperidinyl}-2-(methyloxy)aniline (0.40 g, 0.72 mmol). ESIMS (M+H)⁺= 563.

Example 77

2-[(2-{[4-(3,3-difluoro-1,4'-bipiperidin-1'-yl)-2-(methyloxy)phenyl]amino}-1H-pyrrolo[2,3-d]pyrimidin-4-yl)amino]-4-fluorobenzamide

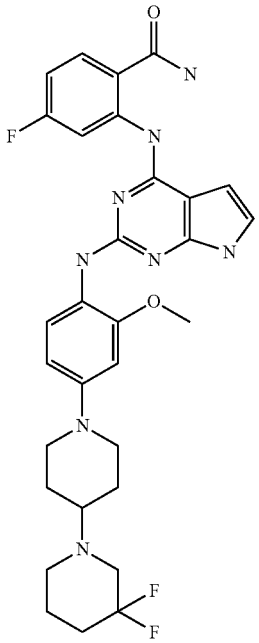

According to General Protocol III, 2-[(2-{[4-(3,3-difluoro-1,4'-bipiperidin-1'-yl)-2-(methyloxy)phenyl]amino}-1H-pyrrolo[2,3-d]pyrimidin-4-yl)amino]-4-fluorobenzamide (0.060 g) was prepared from 2-({2-chloro-7-[(4-methylphenyl)sulfonyl]-7H-pyrrolo[2,3-d]pyrimidin-4-yl}amino)-5-fluorobenzamide (0.2 g, 0.65 mmol), 27% aqueous ammonium hydroxide, and 4-{4-[(3S)-3-fluoro-1-pyrrolidinyl]-1-piperidinyl}-2-(methyloxy)aniline (0.23 g, 0.72 mmol). 1H NMR (400 MHz, DMSO-d₆) δ ppm 1.55-1.65 (m, 4H), 1.76-1.88 (m, 4H), 2.50-2.51 (m, 2H), 2.52-2.54 (m, 1H), 2.57-2.67 (m, 2H), 2.75 (t, J=11.5 Hz, 2H), 3.68 (d, J=11.7 Hz, 2H), 3.79 (s, 3H), 6.24 (dd, J=3.5, 2.0 Hz, 1H), 6.48 (dd, J=8.6, 2.7 Hz, 1H), 6.62 (d, J=2.6 Hz, 1H), 6.80 (td, J=8.3, 2.7 Hz, 1H), 6.94-6.96 (m, 1H), 7.52 (s, 1H), 7.73 (d, J=8.8 Hz, 2H), 7.89 (dd, J=9.0, 6.4 Hz, 1H), 8.28 (s, 1H), 8.85 (dd, J=12.8, 2.6 Hz, 1H), 11.28 (s, 1H), 12.36 (s, 1H); ESIMS (M+H)⁺=595.

Example 78

4-fluoro-2-{[2-({2-(methyloxy)-4-[4-(4-morpholinyl)-1-piperidinyl]phenyl}amino)-1H-pyrrolo[2,3-d]pyrimidin-4-yl]amino}benzamide

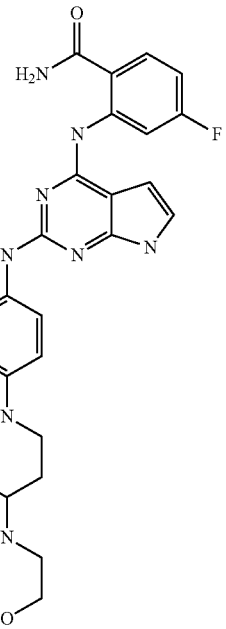

According to General Protocol III, above 4-fluoro-2-{[2-({2-(methyloxy)-4-[4-(4-morpholinyl)-1-piperidinyl]phenyl}amino)-1H-pyrrolo[2,3-d]pyrimidin-4-yl]amino}benzamide was prepared from 2-({2-chloro-7-[(4-methylphenyl)sulfonyl]-7H-pyrrolo[2,3-d]pyrimidin-4-yl}amino)-4-fluorobenzamide (0.250 g, 0.545 mmol), 27% aqueous ammonium hydroxide, and 2-(methyloxy)-4-[4-(4-morpholinyl)-1-piperidinyl]aniline (0.190 g, 0.654 mmol) and isolated as a yellow solid (0.107 g, 35% yield); 1H NMR (400 MHz, DMSO-d₆) δ ppm 1.44-1.55 (m, 2H), 1.85 (d, J=12.09 Hz, 2H), 2.22 (t, J=10.62 Hz, 1H), 2.46 (s, 4H), 2.61 (t, J=11.99 Hz, 2H), 3.50-3.58 (m, 4H), 3.65 (d, J=12.45 Hz, 2H), 3.77 (s, 3H), 6.22 (d, J=3.48 Hz, 1H), 6.46 (dd, J=8.79, 2.38 Hz, 1H), 6.61 (d, J=2.38 Hz, 1H), 6.79 (td, J=8.33, 2.56 Hz, 1H), 6.94 (d, J=3.48 Hz, 1H), 7.50 (s, 1H), 7.72 (d, J=8.42 Hz, 2H), 7.84-7.90 (m, 1H), 8.26 (s, 1H), 8.84 (s, 1H), 11.27 (s, 1H), 12.34 (s, 1H). ESIMS (M+H)+=561.

Example 79

4-fluoro-2-[(2-{[4-[4-(1-methylethyl)-1-piperazinyl]-2-(methyloxy)phenyl]amino}-1H-pyrrolo[2,3-d]pyrimidin-4-yl)amino]benzamide

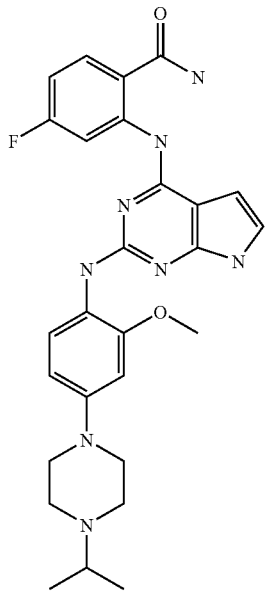

According to General Protocol III, 4-fluoro-2-[(2-{[4-[4-(1-methylethyl)-1-piperazinyl]-2-(methyloxy)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-4-fluorobenzamide (0.250 g, 0.55 mmol), 27% aqueous ammonium hydroxide, and 4-[4-(1-methylethyl)-1-piperazinyl]-2-(methyloxy)aniline (0.15 g, 0.60 and isolated as a yellow solid (0.096 g). 1H NMR (400 MHz, DMSO-d$_6$) δ ppm 1.00 (d, J=6.2 Hz, 6H), 2.58 (s, 4H), 2.66 (d, J=5.1 Hz, 1H), 3.09 (s, 4H), 3.79 (s, 3H), 6.23 (s, 1H), 6.47 (d, J=8.1 Hz, 1H), 6.62 (d, J=2.2 Hz, 1H), 6.77-6.84 (m, 1H), 6.93-6.98 (m, 1H), 7.54 (s, 1H), 7.70-7.76 (m, 2H), 7.86-7.92 (m, 1H), 8.28 (t, J=5.1 Hz, 1H), 8.84 (dd, J=13.0, 2.0 Hz, 1H), 11.28 (s, 1H), 12.36 (s, 1H); ESIMS (M+H)+=519.

Example 80

4-fluoro-{[2-({2-(methyloxy)-4-[4-(2-methylpropyl)-1-piperazinyl]phenyl}amino)-1H-pyrrolo[2,3-d]pyrimidin-4-yl]amino}benzamide

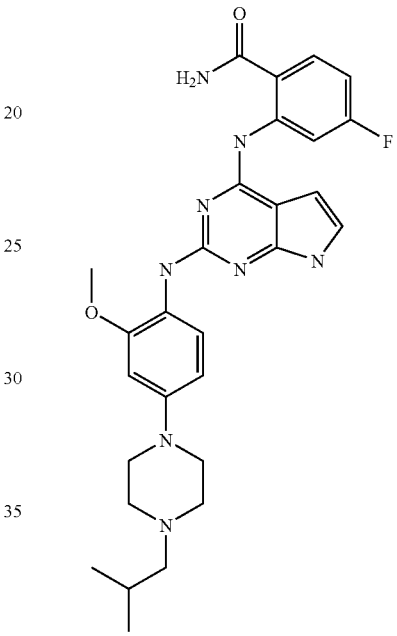

According to General Protocol III, 4-fluoro-2-{[2-({2-(methyloxy)-4-[4-(2-methylpropyl)-1-piperazinyl]phenyl}amino)-1H-pyrrolo[2,3-d]pyrimidin-4-yl]amino}benzamide was prepared from 2-({2-chloro-7-[(4-methylphenyl)sulfonyl]-7H-pyrrolo[2,3-d]pyrimidin-4-yl}amino)-4-fluorobenzamide (0.300 g, 0.650 mmol), 27% aqueous ammonium hydroxide, and 2-(methyloxy)-4-[4-(2-methylpropyl)-1-piperazinyl]aniline (0.260 g, 0.980 mmol) and isolated as a yellow solid (0.054 g, 16% yield); 1H NMR (400 MHz, DMSO-d$_6$) δ ppm 0.85 (d, J=6.41 Hz, 6H), 1.78 (dt, J=13.69, 6.80 Hz, 1H), 2.06 (d, J=7.69 Hz, 2H), 2.45 (s, 4H), 3.08 (s, 4H), 3.77 (s, 3H), 6.21 (dd, J=3.39, 1.92 Hz, 1H), 6.45 (dd, J=8.52, 2.47 Hz, 1H), 6.61 (d, J=2.38 Hz, 1H), 6.75-6.84 (m, 1H), 6.93 (dd, J=3.48, 2.38 Hz, 1H), 7.52 (s, 1H), 7.72 (d, J=8.61 Hz, 2H), 7.87 (dd, J=8.79, 6.59 Hz, 1H), 8.26 (s, 1H), 8.83 (dd, J=12.73, 2.47 Hz, 1H), 11.27 (s, 1H), 12.35 (s, 1H). ESIMS (M+H)+=533.

Example 81

2-[(2-{[4-[4-(cyclopropylmethyl)-1-piperazinyl]-2-(methyloxy)phenyl]amino}-1H-pyrrolo[2,3-d]pyrimidin-4-yl)amino]-4-fluorobenzamide

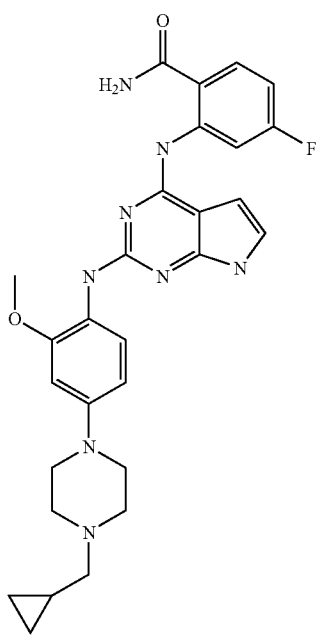

Example 82

4-fluoro-2-[(2-{[4-[4-(1-methylethyl)-1-piperazinyl]-2,5-bis(methyloxy)phenyl]amino}-1H-pyrrolo[2,3-d]pyrimidin-4-yl)amino]benzamide

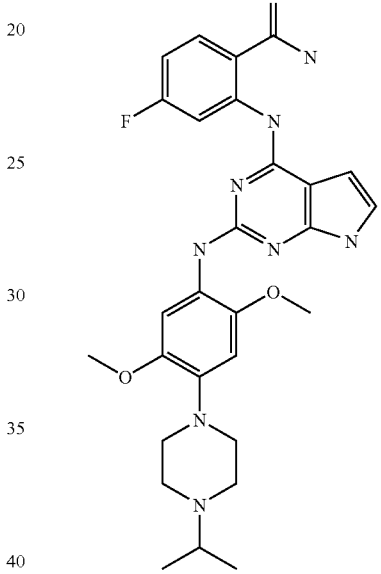

According to General Protocol III, 2-[(2-{[4-[4-(cyclopropylmethyl)-1-piperazinyl]-2-(methyloxy)phenyl]amino}-1H-pyrrolo[2,3-d]pyrimidin-4-yl)amino]-4-fluorobenzamide was prepared from 2-({2-chloro-7-[(4-methylphenyl)sulfonyl]-7H-pyrrolo[2,3-d]pyrimidin-4-yl}amino)-4-fluorobenzamide (0.300 g, 0.654 mmol), 27% aqueous ammonium hydroxide, and 4-[4-(cyclopropylmethyl)-1-piperazinyl]-2-(methyloxy)aniline (0.203 g, 1.2 mmol) and isolated as a yellow solid (0.131 g, 38% yield); 1H NMR (400 MHz, DMSO-$d_6$) δ ppm 0.08 (d, J=4.21 Hz, 2H), 0.46 (d, J=8.61 Hz, 2H), 0.80-0.87 (m, 1H), 2.20 (d, J=7.33 Hz, 2H), 2.51-2.61 (m, 4H), 3.05-3.15 (m, 4H), 3.77 (s, 3H), 6.15-6.26 (m, 1H), 6.46 (d, J=9.16 Hz, 1H), 6.61 (s, 1H), 6.79 (t, J=8.06 Hz, 1H), 6.92-6.95 (m, 1H), 7.53 (s, 1H), 7.69-7.76 (m, 2H), 7.82-7.94 (m, 1H), 8.27 (s, 1H), 8.83 (dd, J=12.09, 3.11 Hz, 1H), 11.27 (s, 1H), 12.35 (s, 1H). ESIMS (M+H)+=531.

According to General Protocol III, 4-fluoro-2-[(2-{[4-[4-(1-methylethyl)-1-piperazinyl]-2,5-bis(methyloxy)phenyl]amino}-1H-pyrrolo[2,3-d]pyrimidin-4-yl)amino]benzamide (0.098 g) was prepared from 2-({2-chloro-7-[(4-methylphenyl)sulfonyl]-7H-pyrrolo[2,3-d]pyrimidin-4-yl}amino)-5-fluorobenzamide (0.30 g, 0.65 mmol), 27% aqueous ammonium hydroxide, and 4-[4-(1-methylethyl)-1-piperazinyl]-2,5-bis(methyloxy)aniline (0.20 g, 0.72 mmol). 1H NMR (400 MHz, DMSO-$d_6$) δ ppm 1.00 (d, J=6.6 Hz, 6H), 2.57 (s, 4H), 2.62-2.70 (m, 1H), 2.97 (s, 4H), 3.71 (s, 3H), 3.77 (s, 3H), 6.25 (dd, J=3.5, 2.0 Hz, 1H), 6.61 (s, 1H), 6.81 (td, J=8.3, 2.7 Hz, 1H), 6.99 (dd, J=3.7, 2.2 Hz, 1H), 7.62 (s, 1H), 7.69-7.77 (m, 2H), 7.90 (dd, J=8.8, 6.6 Hz, 1H), 8.29 (s, 1H), 8.84 (dd, J=12.6, 2.7 Hz, 1H), 11.34 (s, 1H), 12.39 (s, 1H); ESIMS (M+H)+=549.

Example 83

4-fluoro-2-[(2-{[2-(methyloxy)-4-(4-morpholinyl)phenyl]amino}-1H-pyrrolo[2,3-d]pyrimidin-4-yl)amino]benzamide

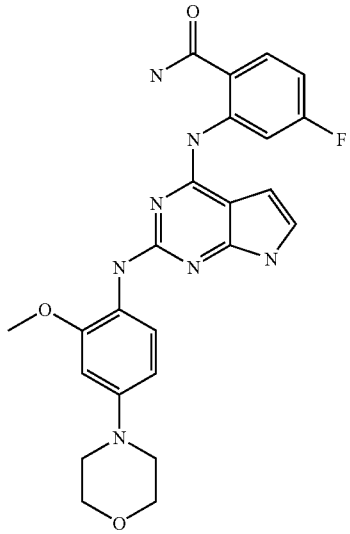

According to General Protocol III, 4-fluoro-2-[(2-{[2-(methyloxy)-4-(4-morpholinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4yl}amino)-4-fluorobenzamide (0.300 g, 0.65 mmol), 27% aqueous ammonium hydroxide, and 2-(methyloxy)-4-(4-morpholinyl)aniline (0.208g, 0.78 mmol) and isolated as a yellow solid (0.229 g, 111% Yield); 1H NMR (400 MHz, DMSO-$d_6$) δ ppm 3.05-3.10 (m, 4H), 3.72-3.77 (m, 4H), 3.80 (s, 3H), 6.24 (dd, J=3.67, 1.83 Hz, 1H), 6.49 (dd, J=8.80, 2.57 Hz, 1H), 6.65 (d, J=2.57 Hz, 1H), 6.80 (td, J=8.43, 2.57 Hz, 1H), 6.95 (dd, J=3.30, 2.20 Hz, 1H), 7.55 (s, 1H), 7.74 (s, 1H), 7.76 (d, J=8.80 Hz, 1H), 7.89 (dd, J=8.80, 6.60 Hz, 1H), 8.28 (s, 1H), 8.84 (dd, J=12.65, 2.75 Hz, 1H), 11.29 (s, 1H), 12.36 (s, 1H). ESIMS (M+H)+=478.

Example 84

4-fluoro-2-[(2-{[4-[(3S)-3-methyl-4-morpholinyl]-2-(methyloxy)phenyl]amino}-1H-pyrrolo[2,3-d]pyrimidin-4-yl)amino]benzamide

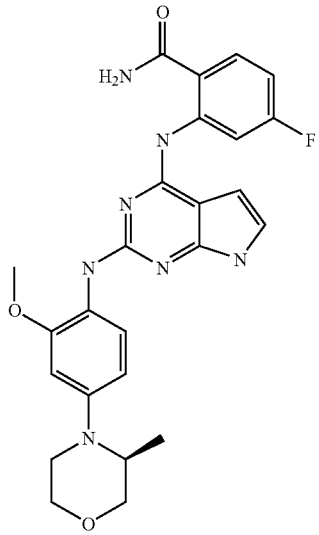

According to General Protocol III, 4-fluoro-2-[(2-{[4-[(3S)-3-methyl-4-morpholinyl]-2-(methyloxy)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-4-fluorobenzamide (0.500 g, 1.09 mmol), 27% aqueous ammonium hydroxide, and 4-[(3S)-3-methyl-4-morpholinyl]-2-(methyloxy)aniline (0.350 g, 1.63 mmol) and isolated as a yellow solid (0.228 g, 43% yield); 1H NMR (400 MHz, DMSO-$d_6$) δ ppm 0.96 (d, J=6.23 Hz, 3H), 2.98-3.10 (m, 2H), 3.55-3.64 (m, 2H), 3.69-3.77 (m, 2H), 3.80 (s, 3H), 3.86 (dt, J=10.91, 2.98 Hz, 1H), 6.25 (dd, J=3.30, 1.83 Hz, 1H), 6.48 (dd, J=8.80, 2.57 Hz, 1H), 6.61 (d, J=2.57 Hz, 1H), 6.81 (td, J=8.34, 2.75 Hz, 1H), 6.92-7.01 (m, 1H), 7.53 (s, 1H), 7.74 (s, 1H), 7.80 (d, J=8.80 Hz, 1H), 7.90 (dd, J=8.80, 6.60 Hz, 1H), 8.28 (s, 1H), 8.85 (dd, J=12.65, 2.75 Hz, 1H), 11.30 (s, 1H), 12.37 (s, 1H). ESIMS (M+H)+=492.

Example 85

2-{[2-({5-[(N,N-dimethylglycyl)amino]-2-methylphenyl}amino)-1H-pyrrolo[2,3-d]pyrimidin-4-yl]amino}-4-fluorobenzamide

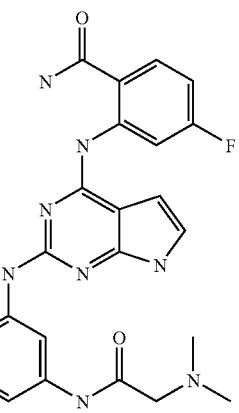

According to General Protocol III, 2-{[2-({5-[(N,N-dimethylglycyl)amino]-2-methylphenyl}amino)-1H-pyrrolo[2,3-d]pyrimidin-4-yl]amino}-4-fluorobenzamide was prepared from 2-({2-chloro-7-[(4-methylphenyl)sulfonyl]-7H-pyrrolo[2,3-d]pyrimidin-4yl}amino)-4-fluorobenzamide (0.300 g, 0.650 mmol), 27% aqueous ammonium hydroxide, and $N^1$-(3-amino-4-methylphenyl)-$N^2$,$N^2$-dimethylglycinamide (0.170 g, 0.82 mmol) and isolated as a yellow solid (0.026 g, 8% Yield); 1H NMR (400 MHz, DMSO-$d_6$) δ ppm 2.16 (s, 3H), 2.22 (s, 6H), 2.98 (s, 2H), 6.23 (d, J=1.65 Hz, 1H), 6.73 (t, J=7.50 Hz, 1H), 6.91-6.97 (m, 1H), 7.10 (d, J=8.05 Hz, 1H), 7.35 (d, J=8.05 Hz, 1H), 7.68-7.74 (m, 1H), 7.74-7.78 (m, 1H), 7.86 (dd, J=8.69, 6.50 Hz, 1H), 8.24-8.28 (m, 1H), 8.29 (s, 1H), 8.79 (d, J=10.79 Hz, 1H), 9.52 (s, 1H), 11.26 (s, 1H), 12.42 (s, 1H). ESI-MS (M+H) 477. Retention time 1.45 minutes.

Example 86

2-[(2-{[5-{[(2S)-3-(dimethylamino)-2-hydroxypropyl]oxy}-2-(methyloxy)phenyl]amino}-1H-pyrrolo[2,3-d]pyrimidin-4-yl)amino]-4-fluorobenzamide

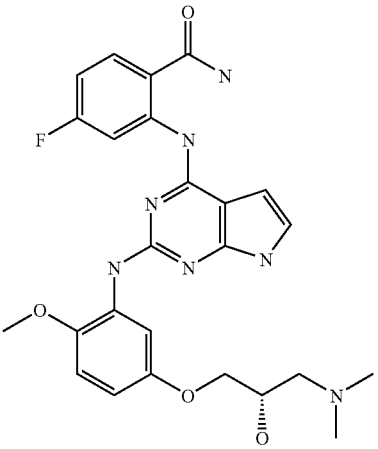

According to General Protocol III, 2-[(2-{[5-{[(2S)-3-(dimethylamino)-2-hydroxypropyl]oxy}-2-(methyloxy)phenyl]amino}-1H-pyrrolo[2,3-d]pyrimidin-4-yl)amino]-4-fluorobenzamide (0.099 g) was prepared from 2-({2-chloro-7-[(4-methylphenyl)sulfonyl]-7H-pyrrolo[2,3-d]pyrimidin-4-yl}amino)-5-fluorobenzamide (0.30 g, 0.65 mmol), 27% aqueous ammonium hydroxide, and (2S)-1-{[3-amino-4-(methyloxy)phenyl]oxy}-3-(dimethylamino)-2-propanol (0.38 g, 1.3 mmol). 1H NMR (400 MHz, DMSO-$d_6$) δ ppm 2.17 (s, 6H), 2.26 (dd, J=12.1, 6.6 Hz, 1H), 2.33-2.40 (m, 1H), 3.75-3.81 (m, 1H), 3.82 (s, 3H), 3.84-3.91 (m, 2H), 4.75 (d, J=3.7 Hz, 1H), 6.30 (d, J=3.7 Hz, 1H), 6.48 (dd, J=8.8, 2.9 Hz, 1H), 6.84 (td, J=8.4, 2.6 Hz, 1H), 6.90 (d, J=8.8 Hz, 1H), 7.04-7.06 (m, 1H), 7.65 (s, 1H), 7.77 (t, J=6.8 Hz, 1H), 7.92 (dd, J=8.6, 6.4 Hz, 1H), 8.02 (d, J=2.9 Hz, 1H), 8.29-8.33 (m, 1H), 8.86 (dd, J=12.5, 2.6 Hz, 1H), 11.59 (s, 1H), 12.45 (s, 1H); ESIMS (M+H)$^+$=510.

Example 87

4-fluoro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]-N-[(1S)-1-methylpropyl]benzamide

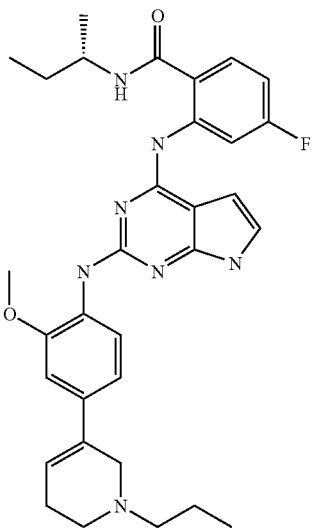

According to General Protocol III, 4-fluoro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]-N-[(1S)-1-methylpropyl]benzamide was prepared from 10-fluoro-5-{[2-(methyloxy)-4-(1-propyl-1,2,5,6-tetrahydro-3-pyridinyl)phenyl]amino}-3-[(4-methylphenyl)sulfonyl]pyrrolo[2',3':4,5]pyrimido[6,1-b]quinazolin-7(3H)-one (0.200 g, available in a manner analgous to Example 70), [(1S)-1-methylpropyl]amine (2.5 mL, General Protocol III/Step B performed neat), and 2-(methyloxy)-4-(1-propyl-1,2,5,6-tetrahydro-3-pyridinyl)aniline (0.075 g); 1H NMR (400 MHz, DMSO-$d_6$) δ ppm 0.88 (q, J=7.58 Hz, 6H), 1.15 (d, J=6.60 Hz, 3H), 1.48-1.59 (m, 4H), 2.23-2.31 (m, 2H), 2.40 (d, J=3.67 Hz, 1H), 2.43 (d, J=7.33 Hz, 1H), 2.52 (d, J=2.57 Hz, 1H), 2.54 (s, 1H), 3.26 (s, 2H), 3.89 (s, 3H), 3.94-4.04 (m, 1H), 6.13 (s, 1H), 6.29 (dd, J=3.30, 1.83 Hz, 1H), 6.87 (td, J=8.43, 2.57 Hz, 1H), 6.93 (dd, J=8.62, 1.65 Hz, 1H), 7.00-7.04 (m, 2H), 7.65 (s, 1H), 7.87 (dd, J=8.80, 6.60 Hz, 1H), 8.19 (d, J=8.43 Hz, 1H), 8.46 (d, J=8.43 Hz, 1H), 8.75 (s, 1H), 11.43 (s, 1H), 11.94 (s, 1H). ESIMS (M+H)+=572.

Example 88

4-fluoro-2-[(2-{[4-[4-(1-methylethyl)-1-piperazinyl]-2-(methyloxy)phenyl]amino}-1H-pyrrolo[2,3-c]pyrimidin-4-yl)amino]-6-(methyloxy)benzamide

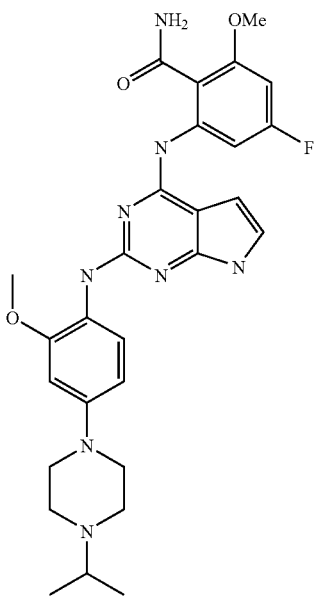

According to General Protocol III, 4-fluoro-2-[(2-{[4-[4-(1-methylethyl)-1-piperazinyl]-2-(methyloxy)phenyl]amino}-1H-pyrrolo[2,3-d]pyrimidin-4-yl)amino]-6-(methyloxy)benzamide was prepared from 2-({2-chloro-7-[(4-methylphenyl)sulfonyl]-7H-pyrrolo[2,3-d]pyrimidin-4-yl}amino)-4,6-difluorobenzamide (0.300 g, 0.63 mmol), 27% aqueous ammonium hydroxide, and 4-[4-(1-methylethyl)-1-piperazinyl]-2-(methyloxy)aniline (0.204 g, 0.82 mmol) and isolated as a yellow solid (0.051 g, 15% yield); 1H NMR (400 MHz, DMSO-$d_6$) δ ppm 1.01 (d, J=6.60 Hz, 6H), 2.59 (s, 4H), 2.69 (s, 1H), 3.09 (s, 4H), 3.79 (s, 3H), 3.86 (s, 3H), 6.20 (dd, J=3.48, 2.02 Hz, 1H), 6.45 (dd, J=8.80, 2.57 Hz, 1H), 6.58-6.64 (m, 2H), 6.94 (d, J=3.67 Hz, 1H), 7.47 (s, 1H), 7.76 (d, J=8.43 Hz, 1H), 7.96 (d, J=2.93 Hz, 2H), 8.43 (dd, J=12.10, 2.57 Hz, 1H), 11.27 (s, 1H), 12.01 (s, 1H). ESIMS (M+H)+=549.

Example 89

2,4-difluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide

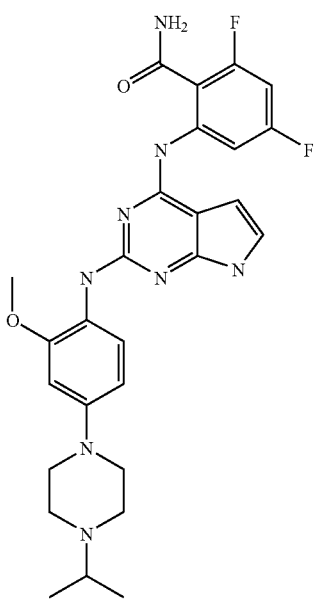

Step A: 2,4-difluoro-6-({2-{[4-[4-(1-methylethyl)-1-piperazinyl]-2-(methyloxy)phenyl]amino}-7-[(4-methylphenyl)sulfonyl]-7H-pyrrolo[2,3-d]pyrimidin-4-yl}amino)benzamide

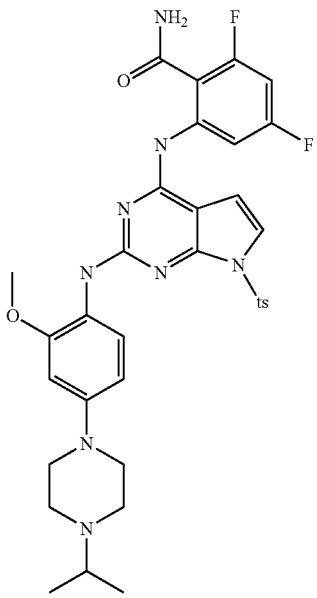

According to General Protocol III (Steps A & B), 2,4-difluoro-6-({2-{[4-[4-(1-methylethyl)-1-piperazinyl]-2-(methyloxy)phenyl]amino}-7-[(4-methylphenyl)sulfonyl]-7H-pyrrolo[2,3-d]pyrimidin-4-yl}amino)benzamide was prepared from 2-({2-chloro-7-[(4-methylphenyl)sulfonyl]-7H-pyrrolo[2,3-d]pyrimidin-4-yl}amino)-4,6-difluorobenzamide (0.750 g, 1.57 mmol), 27% aqueous ammonium hydroxide, and 4-[4-(1-methylethyl)-1-piperazinyl]-2-(methyloxy)aniline (1.17g, 4.72 mmol) and was isolated following purification on silica gel prior to tosyl hydrolysis. (0.650 g, 78% yield, 2 steps). 1H NMR (400 MHz, DMSO-$d_6$) δ ppm 0.98 (d, J=6.41 Hz, 6H), 2.31 (s, 3H), 2.56 (s, 4H), 2.60-2.68 (m, 1H), 3.11 (s, 4H), 3.75 (s, 3H), 6.43 (dd, J=3.75, 2.29 Hz, 1H), 6.51 (d, J=7.51 Hz, 1H), 6.62 (s, 1H), 6.89-6.96 (m, 1H), 7.31 (s, 1H), 7.33 (dd, J=3.30, 2.01 Hz, 2H), 7.55 (s, 1H), 7.90 (d, J=7.14 Hz, 2H), 7.96 (s, 1H), 8.07 (s, 1H), 8.13 (s, 1H), 8.24 (d, J=12.82 Hz, 1H), 11.09 (s, 1H).

Step B

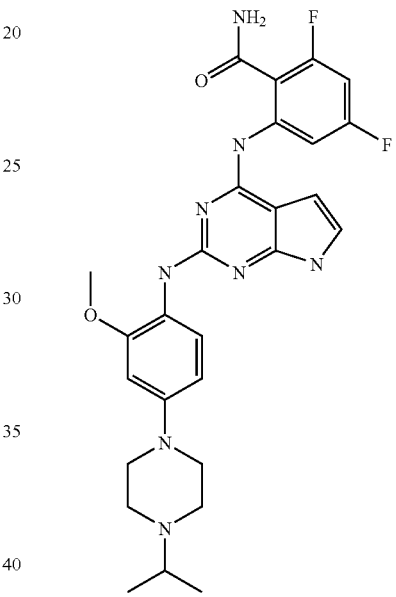

Alternative Detosylation Protocol I:
2,4-difluoro-6-({2-{[4-[4-(1-methylethyl)-1-piperazinyl]-2-(methyloxy)phenyl]amino}-7-[(4-methylphenyl)sulfonyl]-7H-pyrrolo[2,3-d]pyrimidin-4-yl}amino)benzamide (175 mg, 0.254 mmol) was suspended in a mixture of dioxane (10 mL) and aqueous 2.0N NaOH (5 mL) and stirred rapidly under microwave heating (120° C.) for 10 minutes. After cooling, the reaction mixture was diluted with ethyl acetate and washed with saturated sodium chloride. The organic layer was dried over sodium sulfate, taken to a residue under reduced pressure, and purified by chromatography on $SiO_2$ to afford 2,4-difluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide as a pale yellow solid (85 mg, 63% yield); 1H NMR (400 MHz, DMSO-$d_6$) δ ppm 1.00 (d, J=6.60 Hz, 6H), 2.52-2.61 (m, 4H), 2.66 (d, J=6.23 Hz, 1H), 3.08 (d, J=5.50 Hz, 4H), 3.78 (s, 3H), 6.18 (dd, J=3.67, 1.83 Hz, 1H), 6.45 (dd, J=8.80, 2.57 Hz, 1H), 6.61 (d, J=2.57 Hz, 1H), 6.89 (ddd, J=11.36, 8.80, 2.57 Hz, 1H), 6.93-6.98 (m, 1H), 7.59 (s, 1H), 7.68 (d, J=8.80 Hz, 1H), 8.01 (d, J=1.47 Hz, 1H), 8.15 (s, 1H), 8.56 (d, J=11.73 Hz, 1H), 11.08 (s, 1H), 11.32 (s, 1H). ESIMS (M+H)+=537.

Example 89 (Alternative Preparation)

2,4-difluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide

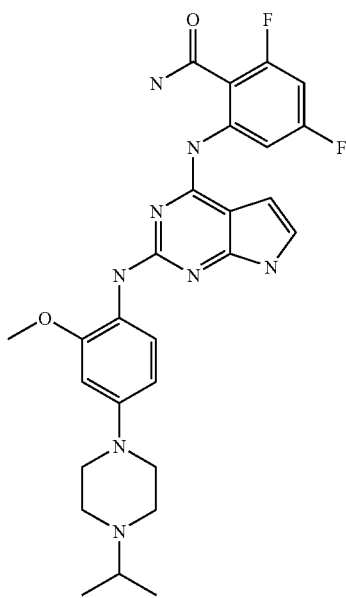

Step A/Intermediate D70: 2,4-difluoro-6-({2-{[4-[4-(1-methylethyl)-1-piperazinyl]-2-(methyloxy)phenyl]amino}-7-[(4-methylphenyl)sulfonyl]-7H-pyrrolo[2,3-d]pyrimidin-4-yl}amino)benzamide

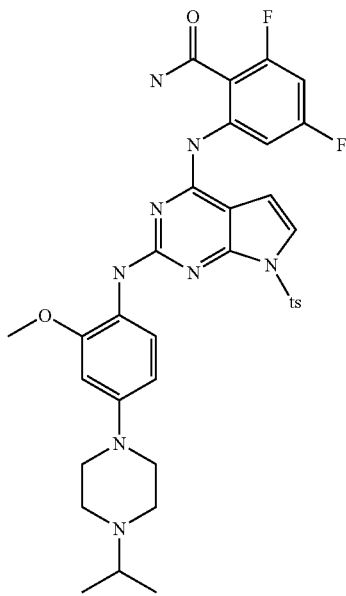

A suspension of 2-({2-chloro-7-[(4-methylphenyl)sulfonyl]-7H-pyrrolo[2,3-d]pyrimidin-4-yl}amino)-4,6-difluorobenzamide (2.71 g, 5.68 mmol), 4-[4-(1-methylethyl)-1-piperazinyl]-2-(methyloxy)aniline (2.12 g, 8.52 mmol), potassium iodide (catalytic), and sulfuric acid (2.72 ml, 51 mmols) in trifluoroethanol (150 ml) was heated at 90C for 4 hrs. The reaction was diluted with 1:1 THF:ethyl acetate (300 ml) and washed with saturated $NaHCO_3$ (300 ml). The organic layer was removed and concentrated by rotary evaporation. The solids were then added to THF (300 ml) followed by ammonium hydroxide (300 ml) and the resulting mixture was stirred at rt overnight. Next, the crude reaction was adsorbed to silica gel and purified by LC (DCM to 5% MeOH/DCM) to afford 2,4-difluoro-6-({2-{[4-[4-(1-methylethyl)-1-piperazinyl]-2-(methyloxy)phenyl]amino}-7-[(4-methylphenyl)sulfonyl]-7H-pyrrolo[2,3-d]pyrimidin-4-yl}amino)benzamide (1.5 g, 38% over two steps). ESIMS (M+H)+=691.

Step B/Example 89 (Alternative Preparation)

2,4-difluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide To a solution of 2,4-difluoro-6-({2-{[4-[4-(1-methylethyl)-1-piperazinyl]-2-(methyloxy)phenyl]amino}-7-[(4-methylphenyl)sulfonyl]-7H-pyrrolo[2,3-d]pyrimidin-4-yl}amino)benzamide (1.5 g, 2.17 mmols) in 1,4-dioxane (100 ml) and 2-propanol (2 ml) was added 1.0M potassium hydroxide (21 ml, 21.7 mmol) and the reaction was heated at 80C overnight. The resulting solution was diluted with ethyl acetate, washed with water, adsorbed onto silica gel and purified by LC (DCM to 10% MeOH/DCM) to afford 2,4-difluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide (1.0 g, 86%). ESIMS (M+H)+=537. $^1$H NMR (400 MHz, DMSO-$d_6$) δ ppm 1.00 (d, J=6.60 Hz, 6H) 2.54-2.60 (m, 4H) 2.64-2.72 (m, 1H) 3.05-3.11(m, 4H) 3.78 (s, 3H) 6.18 (dd, J=3.48, 2.02 Hz, 1H) 6.45 (dd, J=8.62, 2.38 Hz, 1H) 6.61 (d, J=2.57 Hz, 1H) 6.86-6.92 (m, 1H) 6.96 (dd, J=3.67, 2.20 Hz, 1H) 7.59 (s, 1H) 7.68 (d, J=8.80 Hz, 1H) 8.01 (br. s., 1H) 8.16 (s, 1H) 8.53-8.59 (m, 1H) 11.08 (s, 1H) 11.32 (s, 1H).

Example 90

2,4-difluoro-6-[(2-{[4-[(3S)-3-methyl-4-morpholinyl]-2-(methyloxy)phenyl]amino}-1H-pyrrolo[2,3-d]pyrimidin-4-yl)amino]benzamide

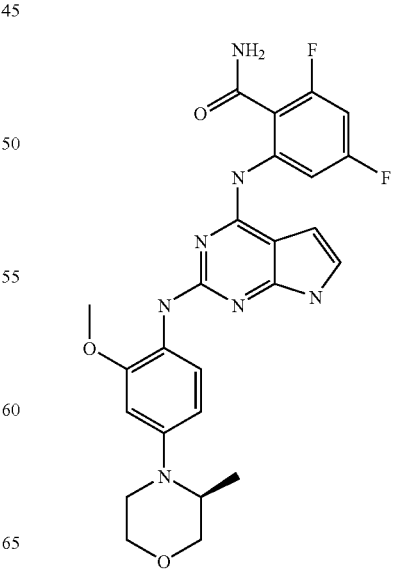

Step A: 2,4-difluoro-6-({2-{[4-[(3S)-3-methyl-4-morpholinyl]-2-(methyloxy)phenyl]amino}-7-[(4-methylphenyl)sulfonyl]-7H-pyrrolo[2,3-d]pyrimidin-4-yl}amino)benzamide

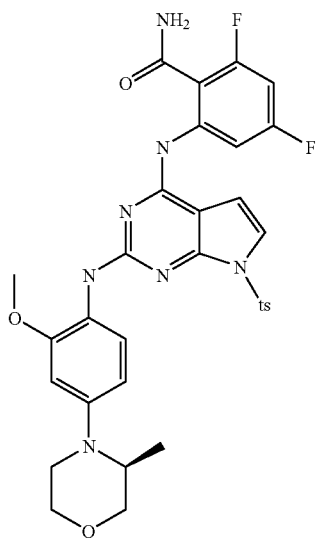

According to General Protocol III (Steps A & B), 2,4-difluoro-6-({2-{[4-[(3S)-3-methyl-4-morpholinyl]-2-(methyloxy)phenyl]amino}-7-[(4-methylphenyl)sulfonyl]-7H-pyrrolo[2,3-d]pyrimidin-4-yl}amino)benzamide was prepared from 2-({2-chloro-7-[(4-methylphenyl)sulfonyl]-7H-pyrrolo[2,3-d]pyrimidin-4-yl}amino)-4,6-difluorobenzamide (0.300 g, 0.630 mmol), 27% aqueous ammonium hydroxide, and 4-[(3S)-3-methyl-4-morpholinyl]-2-(methyloxy)aniline (0.182 g, 0.820 mmol) and was isolated following purification on silica gel prior to tosyl hydrolysis. (208 mg, 50% yield, 2 steps). ESIMS (M+H)=663.

Step B/Example 90: 2,4-difluoro-6-[(2-{[4-[(3S)-3-methyl-4-morpholinyl]-2-(methyloxy)phenyl]amino}-1H-pyrrolo[2,3-d]pyrimidin-4-yl)amino]benzamide 2,4-difluoro-6-({2-{[4-[(3S)-3-methyl-4-morpholinyl]-2-(methyloxy)phenyl]amino}-7-[(4-methylphenyl)sulfonyl]-7H-pyrrolo[2,3-d]pyrimidin-4-yl}amino)benzamide (200 mg, 0.301 mmol) was suspended in a mixture of dioxane (10 mL) and aqueous 2.0N NaOH (5 mL) and stirred rapidly under microwave heating (120° C.) for 10 minutes.

After cooling, the reaction mixture was diluted with ethyl acetate and washed with saturated sodium chloride. The organic layer was dried over sodium sulfate, taken to a residue under reduced pressure, and purified by chromatography on SiO₂ to afford 2,4-difluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide as a pale yellow solid (74 mg, 48% yield); 1H NMR (400 MHz, DMSO-d₆) δ ppm 0.95 (d, J=6.60 Hz, 3H), 2.97-3.09 (m, 2H), 3.55-3.62 (m, 2H), 3.69-3.76 (m, 2H), 3.79 (s, 3H), 3.82-3.89 (m, 1H), 6.19 (dd, J=3.30, 1.83 Hz, 1H), 6.46 (dd, J=8.80, 2.57 Hz, 1H), 6.60 (d, J=2.57 Hz, 1H), 6.89 (ddd, J=11.46, 9.07, 2.57 Hz, 1H), 6.97 (dd, J=3.67, 2.20 Hz, 1H), 7.58 (s, 1H), 7.75 (d, J=8.43 Hz, 1H), 8.01 (s, 1H), 8.15 (s, 1H), 8.56 (d, J=12.83 Hz, 1H), 11.07 (s, 1H), 11.33 (s, 1H). ESIMS (M+H)+=510.

Example 91

2,4-difluoro-6-[(2-{[5-methyl-4-[4-(1-methylethyl)-1-piperazinyl]-2-(methyloxy)phenyl]amino}-1H-pyrrolo[2,3-d]pyrimidin-4-yl)amino]benzamide

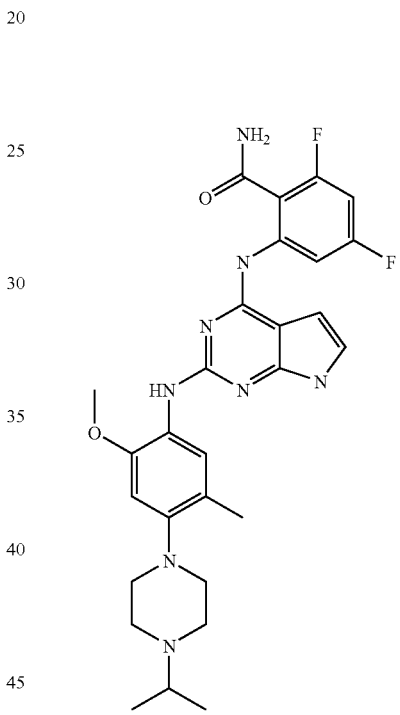

In a manner analogous to that described for Example 90, 2,4-difluoro-6-[(2-{[5-methyl-4-[4-(1-methylethyl)-1-piperazinyl]-2-(methyloxy)phenyl]amino}-1H-pyrrolo[2,3-d]pyrimidin-4-yl)amino]benzamide (0.182g, 53% Yield) was prepared from 2-({2-chloro-7-[(4-methylphenyl)sulfonyl]-7H-1-pyrrolo[2,3-d]pyrimidin-4-yl}amino)-4,6-difluorobenzamide (0.300 g, 0.63 mmol), 27% aqueous ammonium hydroxide, and 5-methyl-4-[4-(1-methylethyl)-1-piperazinyl]-2-(methyloxy)aniline (0.290 g, 1.100 mmol). 1H NMR (400 MHz, DMSO-d₆) δ ppm 1.00 (d, J=6.60 Hz, 6H), 2.15 (s, 3H), 2.58 (s, 4H), 2.64-2.70 (m, 1H), 2.83 (s, 4H), 3.78 (s, 3H), 6.21 (dd, J=3.67, 1.83 Hz, 1H), 6.72 (s, 1H), 6.90 (ddd, J=11.36, 8.80, 2.20 Hz, 1H), 6.96-7.03 (m, 1H), 7.60 (s, 1H), 7.71 (s, 1H), 8.02 (s, 1H), 8.16 (s, 1H), 8.51 (d, J=11.73 Hz, 1H), 11.08 (s, 1H), 11.34 (s, 1H). ESIMS (M+H)=552.

Example 92

2,4-difluoro-6-[(2-{[2-(methyloxy)-4-(1-propyl-4-piperidinyl)phenyl]amino}-1H-pyrrolo[2,3-d]pyrimidin-4-yl)amino]benzamide

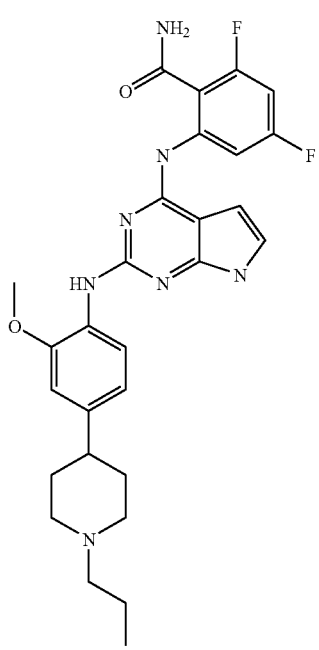

In a manner analogous to that described for Example 90, 2,4-difluoro-6-[(2-{[2-(methyloxy)-4-(1-propyl-4-piperidinyl)phenyl]amino}-1H-pyrrolo[2,3-d]pyrimidin-4-yl)amino]benzamide (0.087 g, 22% Yield) was prepared from 2-({2-chloro-7-[(4-methylphenyl)sulfonyl]-7H-pyrrolo[2,3-d]pyrimidin-4-yl}amino)-4,6-difluorobenzamide (0.350 g, 0.73 mmol), 27% aqueous ammonium hydroxide, and 2-(methyloxy)-4-(1-propyl-4-piperidinyl)aniline (0.273 g, 1.1 mmol). 1H NMR (400 MHz, DMSO-$d_6$) δ ppm 0.86 (t, J=7.33 Hz, 3H), 1.40-1.51 (m, 2H), 1.60-1.71 (m, 2H), 1.71-1.79 (m, 2H), 1.88-2.00 (m, 2H), 2.20-2.28 (m, 2H), 2.93 (s, 1H), 2.96 (d, J=9.53 Hz, 2H), 3.83 (s, 3H), 6.22 (dd, J=3.30, 1.83 Hz, 1H), 6.77 (dd, J=8.25, 1.65 Hz, 1H), 6.89 (d, J=1.83 Hz, 1H), 6.93 (ddd, J=11.46, 8.89, 2.38 Hz, 1H), 7.00 (dd, J=3.67, 2.20 Hz, 1H), 7.64 (s, 1H), 7.99 (d, J=8.07 Hz, 1H), 8.02 (s, 1H), 8.16 (s, 1H), 8.55 (s, 1H), 11.08 (s, 1H), 11.41 (s, 1H). ESIMS (M+H)=536.

Example 92 (Alternative Preparation)

2,4-difluoro-6-[(2-{[2-(methyloxy)-4-(1-propyl-4-piperidinyl)phenyl]amino}-1H-pyrrolo[2,3-d]pyrimidin-4-yl)amino]benzamide

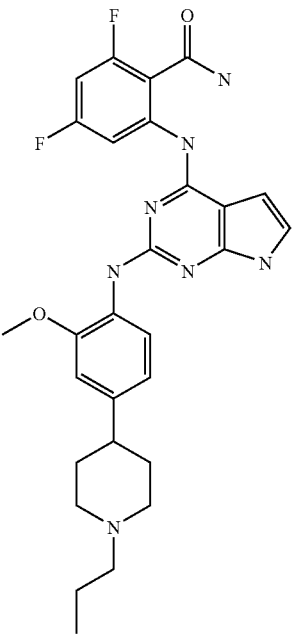

Step A/Intermediate D69: 2,4-difluoro-6-({2-{[2-(methyloxy)-4-(1-propyl-4-piperidinyl)phenyl]amino}-7-[(4-methylphenyl)sulfonyl]-7H-pyrrolo[2,3-d]pyrimidin-4-yl}amino)benzamide

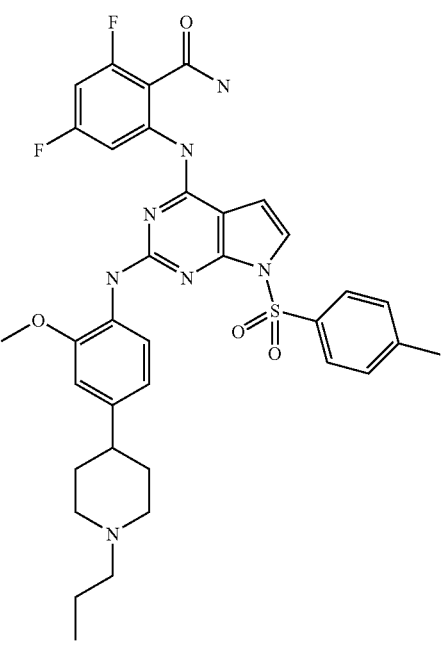

Three separate mixtures of 2-[(2-chloro-1H-pyrrolo[2,3-d]pyrimidin-4-yl)amino]-4,6-difluorobenzamide (3.50 g, 7.32 mmol), 2-(methyloxy)-4-(1-propyl-4-piperidinyl)aniline (2.7 g, 11 mmol), and 2,2,2-trifluoroethanol (150 mL) were taken in three separate sealed tubes and heated at 90° C. for 48 h. The reactions were cooled, combined, diluted with dichloromethane and treated with saturated aqueous sodium bicarbonate until no effervescence was observed. Precipitation was observed in the organic layers which was separated and concentrated. The residue was diluted with tetrahydrofuran (300 mL) and treated with excess 27% aqueous ammonia (300 mL). The suspensions were stirred for 2 h after which the solids had dissolved to form a biphasic mixture. The reaction was allowed to stir overnight at which point analysis by LCMS revealed a 77:16 ratio of 2,4-difluoro-6-({2-{[2-(methyloxy)-4-(1-propyl-4-piperidinyl)phenyl]amino}-7-[(4-methylphenyl)sulfonyl]-7H-pyrrolo[2,3-d]pyrimidin-4-yl}amino)benzamide and the starting 2-[(2-chloro-1H-pyrrolo[2,3-d]pyrimidin-4-yl)amino]-4,6-difluorobenzamide. The organic layer was separated, adsorbed onto silica and then subjected to purification by flash silica gel chromatography with a gradient from 10 to 100% of a 20:20:2:58 mixture of THF/MeOH/NH$_4$OH/DCM in DCM. After concentration of relevant fractions the solids obtained were suspended (with sonication) in a mixture of diethyl ether and small quantities of ethyl acetate. Filtration of the solids and washing with more quantities of diethyl ether and small quantities of ethyl acetate provided 2,4-difluoro-6-({2-{[2-(methyloxy)-4-(1-propyl-4-piperidinyl)phenyl]amino}-7-[(4-methylphenyl)sulfonyl]-7H-pyrrolo[2,3-d]pyrimidin-4-yl}amino)benzamide (9.5 g, 63%). $^1$H NMR (400 MHz, DMSO-d$_6$) δ ppm 0.86 (t, J=7.3 Hz, 3H), 1.37-1.50 (m, 2H), 1.63-1.82 (m, 4H), 1.90-2.01 (m, 2H), 2.18-2.27 (m, 2H), 2.33 (s, 3H), 2.91-3.00 (m, 2H), 3.81 (s, 3H), 6.51 (d, J=4.0 Hz, 1H), 6.86 (d, J=9.0 Hz, 1H), 6.93 (d, J=1.6 Hz, 1H), 6.96-7.03 (m, 1H), 7.35 (d, J=8.2 Hz, 2H), 7.40 (d, J=4.0 Hz, 1H), 7.80-7.75 (m, 1H), 7.92 (d, J=8.6 Hz, 2H), 8.00 (br. s., 1H), 8.08 (s, 1H), 8.16-8.26 (m, 2H), 11.06 (s, 1H), 1H was missing from data and by comparison to the detosylated compound below was most likely underneath the DMSO solvent peak; ESIMS (M+H)$^+$=690.

Step B/Example 92 (Alternative Preparation): 2,4-difluoro-6-[(2-{[2-(methyloxy)-4-(1-propyl-4-piperidinyl)phenyl]amino}-1H-pyrrolo[2,3-d]pyrimidin-4-yl)amino]benzamide 2,4-difluoro-6-({2-{[2-(methyloxy)-4-(1-propyl-4-piperidinyl)phenyl]amino}-7-[(4-methylphenyl)sulfonyl]-7H-pyrrolo[2,3-d]pyrimidin-4-yl}amino)benzamide (9.5 g, 13.7 mmol) was dissolved in tetrahydrofuran (100 mL) and dioxane (400 mL). A solution of KOH (35 g) in water (100 mL) was added to the reaction mixture. The mixture was heated to reflux overnight, and cooled. The organic layer was separated, dried over sodium sulfate, filtered, and adsorbed over silica. Purification by flash silica gel chromatography with a gradient from 10 to 100% of a 20:20:2:58 mixture of THF/MeOH/NH$_4$OH/DCM in DCM provided the required product which was contaminated with ~15% p-toluene sulfonic acid. The residue was dissolved in THF (~400 mL) and refluxed to dissolve most of the solid. The mixture was cooled and then washed with 2 N aqueous NaOH. The separated clear organic layer was dried over sodium sulfate, filtered and concentrated. The solid obtained was recrystallized with 20% MeOH in DCM to obtain 2,4-difluoro-6-[(2-{[2-(methyloxy)-4-(1-propyl-4-piperidinyl)phenyl]amino}-1H-pyrrolo[2,3-d]pyrimidin-4-yl)amino]benzamide (5.8 g, 79%). 1H NMR (400 MHz, DMSO-d$_6$) δ ppm 0.85 (t, J=7.4 Hz, 3H), 1.40-1.50 (m, 2H), 1.60-1.78 (m, 4H), 1.89-1.98 (m, 2H), 2.20-2.27 (m, 2H), 2.37-2.46 (m, 1H), 2.91-2.98 (m, 2H), 3.83 (s, 3H), 6.22 (dd, J=3.4, 1.9 Hz, 1H), 6.77 (dd, J=8.3, 1.6 Hz, 1H), 6.89 (d, J=1.6 Hz, 1H), 6.93 (ddd, J=11.4, 9.0, 2.6 Hz, 1H), 7.00 (dd, J=3.5, 2.2 Hz, 1H), 7.65 (s, 1H), 7.98 (d, J=8.1 Hz, 1H), 8.03 (br. s., 1H), 8.17 (s, 1H), 8.53 (d, J=11.4 Hz, 1H), 11.08 (s, 1H), 11.42 (s, 1H); ESIMS (M+H)$^+$=536.

Example 93

4-chloro-2-fluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide

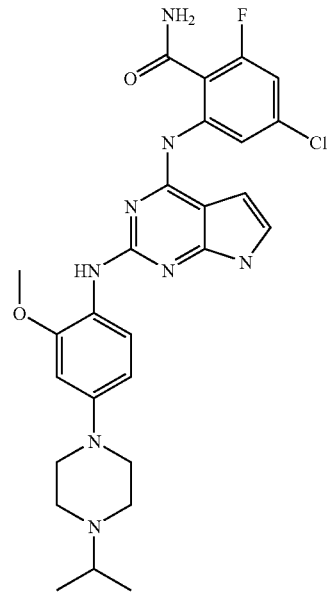

In a manner analogous to that described for Example 90, 4-chloro-2-fluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide (0.139, 28% Yield) was prepared from 4-chloro-2-({2-chloro-7-[(4-methylphenyl)sulfonyl]-7H-pyrrolo[2,3-d]pyrimidin-4-yl}amino)-6-fluorobenzamide (0.450 g, 0.91 mmol), 27% aqueous ammonium hydroxide, 4-[4-(1-methylethyl)-1-piperazinyl]-2-(methyloxy)aniline (0.455 g, 1.83 mmol). 1H NMR (400 MHz, DMSO-d$_6$) δ ppm 0.97 (d, J=6.59 Hz, 6H), 2.54 (s, 4H), 2.59-2.68 (m, 1H), 3.04 (s, 4H), 3.76 (s, 3H), 6.17 (dd, J=3.30, 1.65 Hz, 1H), 6.45 (d, J=2.01 Hz, 1H), 6.59 (d, J=2.20 Hz, 1H), 6.92-6.95 (m, 1H), 7.07 (dd, J=10.62, 2.01 Hz, 1H), 7.44 (s, 1H), 7.70 (d, J=8.42 Hz, 1H), 8.04 (s, 1H), 8.16 (s, 1H), 8.59 (s, 1H), 10.72 (s, 1H), 11.29 (s, 1H). ESIMS (M+H)=553.

Example 94

2,3-difluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide

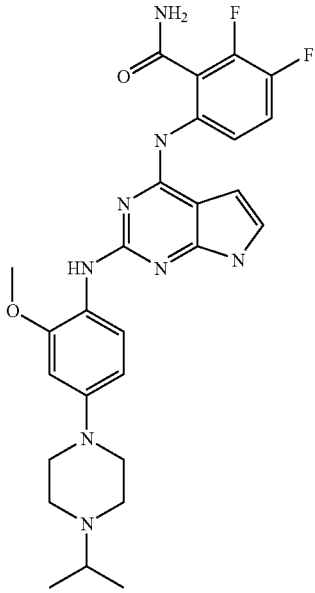

In a manner analogous to that described for Example 90, 2,3-difluoro-6-[(2-{[4-[4-(1-methylethyl)-1-piperazinyl]-2-(methyloxy)phenyl]amino}-1H-pyrrolo[2,3-d]pyrimidin-4-yl)amino]benzamide (0.072 g, 13% Yield) was prepared from 6-({2-chloro-7-[(4-methylphenyl)sulfonyl]-7H-pyrrolo[2,3-d]pyrimidin-4-yl}amino)-2,3-difluorobenzamide (0.500 g, 1.05 mmol), 27% aqueous ammonium hydroxide, and 4-[4-(1-methylethyl)-1-piperazinyl]-2-(methyloxy)aniline (0.457 g, 1.83 mmol). 1H NMR (400 MHz, DMSO-$d_6$) δ ppm 0.97 (d, J=6.59 Hz, 6H), 2.54 (s, 4H), 2.63 (ddd, J=12.64, 6.59, 6.41 Hz, 1H), 3.04 (s, 4H), 3.76 (s, 3H), 6.17 (dd, J=3.30, 1.65 Hz, 1H), 6.45 (d, J=2.01 Hz, 1H), 6.59 (d, J=2.20 Hz, 1H), 6.92-6.95 (m, 1H), 7.07 (dd, J=10.62, 2.01 Hz, 1H), 7.44 (s, 1H), 7.70 (d, J=8.42 Hz, 1H), 8.04 (s, 1H), 8.16 (s, 1H), 8.59 (s, 1H), 10.72 (s, 1H), 11.29 (s, 1H). ESIMS (M+H)=537.

Example 95

4,5-difluoro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide

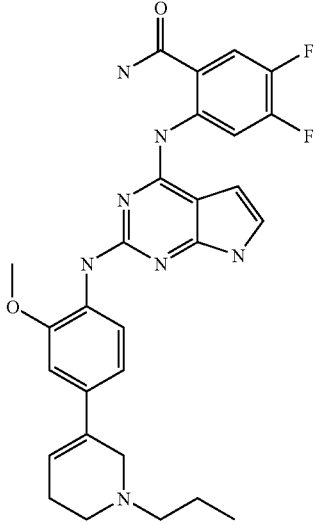

According to General Protocol III, 4,5-difluoro-2-[4(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-4,5-difluorobenzamide (0.300 g, 0.630 mmol), 27% aqueous ammonium hydroxide, and 2-(methyloxy)-4-(1-propyl-1,2,5,6-tetrahydro-3-pyridinyl)aniline (0.250 g, 0.950 mmol) and isolated as a yellow solid (0.040 g, 12% Yield); 1H NMR (400 MHz, DMSO-$d_6$) δ ppm 0.89 (t, J=7.14 Hz, 3H), 1.54 (s, 2H), 1.74 (s, 2H), 2.25 (s, 2H), 2.42 (s, 2H), 3.26 (s, 2H), 3.88 (s, 3H), 6.14 (s, 1H), 6.23-6.32 (m, 1H), 6.93 (d, J=7.69 Hz, 1H), 7.02 (s, 2H), 7.76 (s, 1H), 7.91 (dd, J=1.65, 0.92 Hz, 1H), 7.97 (dd, J=11.72, 8.79 Hz, 1H), 8.12 (d, J=8.42 Hz, 1H), 8.33 (s, 1H), 9.08 (dd, J=14.65, 7.69 Hz, 1H), 11.43 (s, 1H), 12.25 (s, 1H). ESI-MS (M+H) 533. Retention time 1.75 minutes.

Example 96

4,5-difluoro-2-[(2-{[4-[1-(1-methylethyl)-1,2,5,6-tetrahydro-3-pyridinyl]-2-(methyloxy)phenyl]amino}-1H-pyrrolo[2,3-d]pyrimidin-4-yl)amino]benzamide

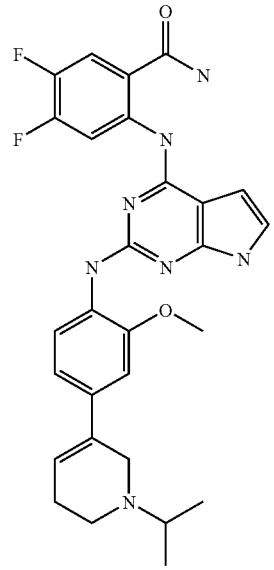

According to General Protocol III, 4,5-difluoro-2-[(2-{[4-[1-(1-methylethyl)-1,2,5,6-tetrahydro-3-pyridinyl]-2-(methyloxy)phenyl]amino}-1H-pyrrolo[2,3-d]pyrimidin-4-yl)amino]benzamide (0.119 g) was prepared from 2-({2-chloro-7-[(4-methylphenyl)sulfonyl]-7H-pyrrolo[2,3-d]pyrimidin-4-yl}amino)-4,5-difluorobenzamide (0.350 g, 0.76 mmol), 27% aqueous ammonium hydroxide, and 4-[1-(1-methylethyl)-1,2,5,6-tetrahydro-3-pyridinyl]-2-(methyloxy)aniline (0.21 g, 0.84 mmol). 1H NMR (400 MHz, DMSO-$d_6$) δ ppm 1.04 (d, J=6.4 Hz, 6H), 2.18-2.25 (m, 2H), 2.54 (t, J=5.5 Hz, 2H), 2.84 (dt, J=13.0, 6.4 Hz, 1H), 3.33 (s, 2H), 3.86 (s, 3H), 6.07-6.11 (m, 1H), 6.25 (dd, J=3.5, 1.8 Hz, 1H), 6.92 (dd, J=8.2, 1.6 Hz, 1H), 6.99-7.01 (m, 2H), 7.74 (s, 1H), 7.87-7.98 (m, 2H), 8.09 (d, J=8.2 Hz, 1H), 8.31 (s, 1H), 9.06 (dd, J=14.2, 8.0 Hz, 1H), 11.41 (s, 1H), 12.23 (s, 1H); ESIMS (M+)+=534.

Example 97

4,5-difluoro-2-[(2-{[4-[1-(1-methylethyl)-4-piperidinyl]-2-(methyloxy)phenyl]amino}-1H-pyrrolo[2,3-d]pyrimidin-4-yl)amino]benzamide

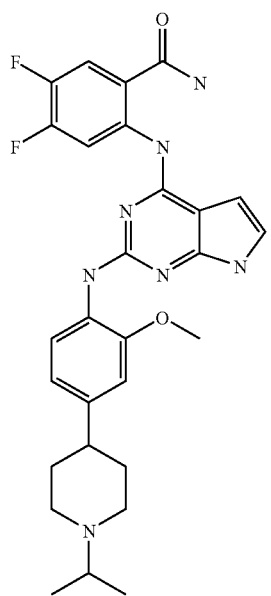

According to General Protocol III, 4,5-difluoro-2-[(2-{[4-[1-(1-methylethyl)-4-piperidinyl]-2-(methyloxy)phenyl]amino}-1H-pyrrolo[2,3-d]pyrimidin-4-yl)amino]benzamide (0.076 g) was prepared from 2-({2-chloro-7-[(4-methylphenyl)sulfonyl]-7H-pyrrolo[2,3-d]pyrimidin-4-yl}amino)-4,5-difluorobenzamide (0.225 g, 0.55 mmol), 27% aqueous ammonium hydroxide, and 4-[1-(1-methylethyl)-4-piperidinyl]-2-(methyloxy)aniline (0.150 g, 0.60 mmol). 1H NMR (400 MHz, DMSO-$d_6$) δ ppm 0.98 (d, J=6.6 Hz, 6H), 1.65 (td, J=12.0, 3.1 Hz, 2H), 1.75 (s, 1H), 1.78 (d, J=3.3 Hz, 1H), 2.14-2.24 (m, 2H), 2.34-2.45 (m, J=12.7, 5.2, 2.9 Hz, 1H), 2.64-2.74 (m, J=6.1, 6.1, 1.6 Hz, 1H), 2.83-2.91 (m, J=9.0, 2.0 Hz, 2H), 3.83 (s, 3H), 6.25 (dd, J=3.7, 1.8 Hz, 1H), 6.79 (dd, J=8.1, 1.8 Hz, 1H), 6.89 (d, J=1.8 Hz, 1H), 6.99 (dd, J=3.7, 2.2 Hz, 1H), 7.68 (s, 1H), 7.89 (s, 1H), 7.93-7.99 (m, 2H), 8.32 (d, J=1.5 Hz, 1H), 9.07 (dd, J=14.3, 8.1 Hz, 1H), 11.38 (s, 1H), 12.23 (s, 1H); ESIMS (M+H)$^+$=536.

Example 98

4,5-difluoro-2-[(2-{[2-(methyloxy)-4-(1-propyl-4-piperidinyl)phenyl]amino}-1H-pyrrolo[2,3-d]pyrimidin-4-yl)amino]benzamide

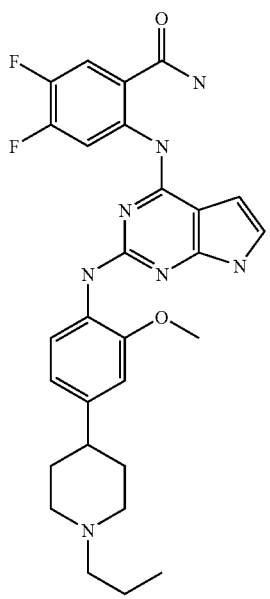

According to General Protocol III, 4,5-difluoro-2-[(2-{[2-(methyloxy)-4-(1-propyl-4-piperidinyl)phenyl]amino}-1H-pyrrolo[2,3-d]pyrimidin-4-yl)amino]benzamide (0.123 g) was prepared from 2-({2-chloro-7-[(4-methylphenyl)sulfonyl]-7H-pyrrolo[2,3-d]pyrimidin-4-yl}amino)-4,5-difluorobenzamide (0.30 g, 0.65 mmol), 27% aqueous ammonium hydroxide, and 2-(methyloxy)-4-(1-propyl-4-piperidinyl)aniline (0.180 g, 0.72 mmol). 1H NMR (400 MHz, DMSO-$d_6$) δ ppm 0.85 (t, J=7.3 Hz, 3H), 1.40-1.50 (m, 2H), 1.64-1.76 (m, 4H), 1.94 (t, J=10.6 Hz, 2H), 2.20-2.28 (m, 2H), 2.39-2.46 (m, 1H), 2.95 (d, J=11.0 Hz, 2H), 3.83 (s, 3H), 6.25 (dd, J=3.3, 1.8 Hz, 1H), 6.79 (dd, J=8.1, 1.5 Hz, 1H), 6.89 (d, J=1.5 Hz, 1H), 6.96-7.01 (m, 1H), 7.69 (s, 1H), 7.89-7.99 (m, 3H), 8.32 (s, 1H), 9.08 (dd, J=14.3, 8.1 Hz, 1H), 11.39 (s, 1H), 12.24 (s, 1H); ESIMS (M+H)$^+$=536.

Example 99

4,5-difluoro-2-[(2-{[4-hydroxy-1-piperidinyl)-2-(methyloxy)phenyl]amino}-1H-pyrrolo[2,3-d]pyrimidin-4-yl)amino]benzamide

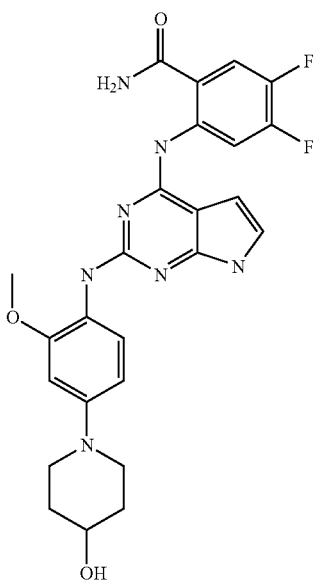

According to General Protocol III, 4,5-difluoro-2-[(2-{[4-(4-hydroxy-1-piperidinyl)-2-(methyloxy)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-4,5-difluorobenzamide (0.300 g, 0.654 mmol), 27% aqueous ammonium hydroxide, and 1-[4-amino-3-(methyloxy)phenyl]-4-piperidinol (0.220 g, 0.980 mmol) and isolated as a yellow solid (0.072 g, 22% yield); 1H NMR (400 MHz, DMSO-$d_6$) δ ppm 1.43-1.54 (m, 2H), 1.83 (d, J=6.78 Hz, 2H), 2.77 (t, J=11.81 Hz, 2H), 3.41-3.51 (m, 2H), 3.53-3.63 (m, 1H), 3.76 (s, 3H), 4.64 (d, J=4.03 Hz, 1H), 6.20 (s, 1H), 6.46 (d, J=10.80 Hz, 1H), 6.60 (s, 1H), 6.92 (s, 1H), 7.57 (s, 1H), 7.65 (d, J=8.79 Hz, 1H), 7.85 (s, 1H), 7.93 (dd, J=11.81, 9.06 Hz, 1H), 8.29 (s, 1H), 9.07 (dd, J=14.28, 7.87 Hz, 1H), 11.26 (s, 1H), 12.19 (s, 1H). ESIMS (M+H)+=510.

Example 100

2-[(2-{[4-(1,4'-bipiperidin-1'-yl)-2-(methyloxy)phenyl]amino}-1H-pyrrolo[2,3-d]pyrimidin-4-yl)amino]-4,5-difluorobenzamide

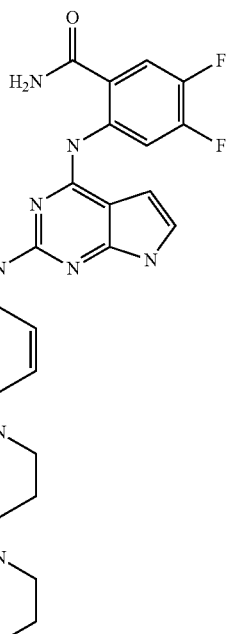

According to General Protocol III, 2-[(2-{[4-(1,4'-bipiperidin-1'-yl)-2-(methyloxy)phenyl]amino}-1H-pyrrolo[2,3-d]pyrimidin-4-yl)amino]-4,5-difluorobenzamide was prepared from 2-({2-chloro-7-[(4-methylphenyl)sulfonyl]-7H-pyrrolo[2,3-d]pyrimidin-4-yl}amino)-4,5-difluorobenzamide (0.250 g, 0.524 mmol), 27% aqueous ammonium hydroxide, and 4-(1,4'-bipiperidin-1'-yl)-2-(methyloxy)aniline (0.200 g, 0.681 mmol) and isolated as a yellow solid (0.124 g, 41% yield); 1H NMR (400 MHz, DMSO-$d_6$) δ ppm 1.32-1.42 (m, 2H), 1.47 (d, J=4.40 Hz, 4H), 1.55 (d, J=11.73 Hz, 2H), 1.78 (d, J=10.26 Hz, 2H), 2.25-2.36 (m, 1H), 2.46 (s, 4H), 2.60 (t, J=11.36 Hz, 2H), 3.68 (d, J=12.46 Hz, 2H), 3.77 (s, 3H), 6.21 (dd, J=3.67, 1.83 Hz, 1H), 6.47 (dd, J=8.98, 2.38 Hz, 1H), 6.61 (d, J=2.20 Hz, 1H), 6.90-6.97 (m, 1H), 7.60 (s, 1H), 7.66 (d, J=8.43 Hz, 1H), 7.88 (s, 1H), 7.95 (dd, J=12.10, 9.16 Hz, 1H), 8.31 (s, 1H), 9.08 (dd, J=14.11, 7.88 Hz, 1H), 11.28 (s, 1H), 12.21 (s, 1H).

Example 101

4,5-difluoro-2-{[2-({2-(methyloxy)-4-[4-(4-morpholinyl)-1-piperidinyl]phenyl}amino)-1H-pyrrolo[2,3-d]pyrimidin-4-yl]amino}benzamide

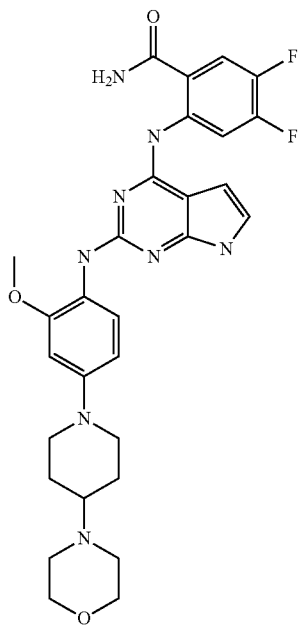

According to General Protocol III, 4,5-difluoro-2-{[2-({2-(methyloxy)-4-[4-(4-morpholinyl)-1-piperidinyl]phenyl}amino)-1H-pyrrolo[2,3-d]pyrimidin-4-yl]amino}benzamide was prepared from 2-({2-chloro-7-[(4-methylphenyl)sulfonyl]-7H-pyrrolo[2,3-d]pyrimidin-4-yl}amino)-4,5-difluorobenzamide (0.250 g, 0.524 mmol), 27% aqueous ammonium hydroxide, and 2-(methyloxy)-4-[4-(4-morpholinyl)-1-piperidinyl]aniline (0.183 g, 0.63 mmol) and isolated as a yellow solid (0.046 g, 15% yield); 1H NMR (400 MHz, DMSO-$d_6$) δ ppm 1.44-1.56 (m, 2H), 1.86 (d, J=12.09 Hz, 2H), 2.19-2.30 (m, 1H), 2.45 (s, 4H), 2.58-2.66 (m, 2H), 3.52-3.60 (m, 4H), 3.66 (d, J=12.09 Hz, 2H), 3.77 (s, 3H), 6.21 (d, J=1.65 Hz, 1H), 6.48 (d, J=8.61 Hz, 1H), 6.61 (d, J=2.38 Hz, 1H), 6.92-6.95 (m, 1H), 7.58 (s, 1H), 7.66 (d, J=8.24 Hz, 1H), 7.86 (s, 1H), 7.95 (d, J=9.16 Hz, 1H), 8.29 (s, 1H), 9.07 (dd, J=14.38, 8.33 Hz, 1H), 11.26 (s, 1H), 12.19 (s, 1H). ESIMS (M+H)+=579.

Example 102

4,5-difluoro-2-[(2-{[4-[4-(1-methylethyl)-1-piperazinyl]-2-(methyloxy)phenyl]amino}-1H-pyrrolo[2,3-d]pyrimidin-4-yl)amino]benzamide

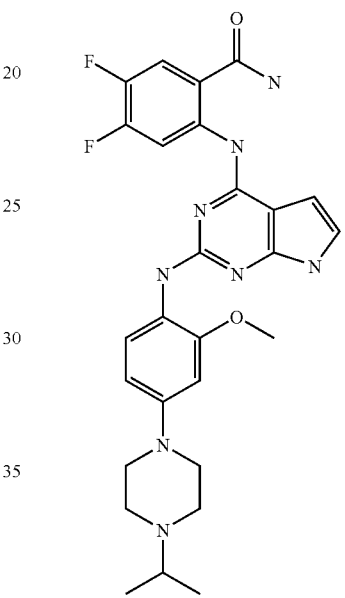

According to General Protocol III, 4,5-difluoro-2-[(2-{[4-[4-(1-methylethyl)-1-piperazinyl]-2-(methyloxy)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-4,5-difluorobenzamide (0.250 g, 0.52 mmol), 27% aqueous ammonium hydroxide, and 4-[4-(1-methylethyl)-1-piperazinyl]-2-(methyloxy)aniline (0.14 g, 0.58 mmol) and isolated as a yellow solid (0.069 g). 1H NMR (400 MHz, DMSO-$d_6$) δ ppm 0.99 (d, J=6.4 Hz, 6H), 2.56 (d, J=4.6 Hz, 4H), 2.60-2.69 (m, 1H), 3.08 (s, 4H), 3.76 (s, 3H), 6.20 (dd, J=3.2, 1.7 Hz, 1H), 6.45 (dd, J=8.9, 2.1 Hz, 1H), 6.60 (d, J=2.0 Hz, 1H), 6.90-6.97 (m, 1H), 7.59 (s, 1H), 7.61-7.67 (m, 1H), 7.82-7.88 (m, 1H), 7.93 (dd, J=12.0, 8.9 Hz, 1H), 8.26-8.33 (m, 1H), 9.05 (dd, J=14.5, 8.1 Hz, 1H), 11.26 (s, 1H), 12.19 (s, 1H); ESIMS(M+H)+=537.

Example 103

2-[(2-{[4-(4-acetyl-1-piperazinyl)-2-(methyloxy)phenyl]amino}-1H-pyrrolo[2,3-d]pyrimidin-4-yl)amino]-4,5-difluorobenzamide

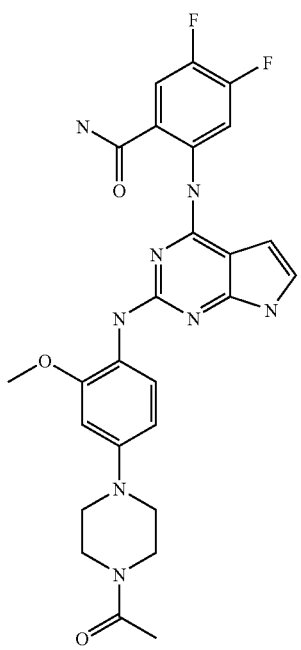

According to General Protocol III, 2-[(2-{[4-(4-acetyl-1-piperazinyl)-2-(methyloxy)phenyl]amino}-1H-pyrrolo[2,3-d]pyrimidin-4-yl)amino]-4,5-difluorobenzamide was prepared from 2-({2-chloro-7-[(4-methylphenyl)sulfonyl]-7H-pyrrolo[2,3-d]pyrimidin-4-yl}amino)-4,5-difluorobenzamide (0.20 g, 0.63 mmol), 27% aqueous ammonium hydroxide, and 4-(4-acetyl-1-piperazinyl)-2-(methyloxy)aniline (0.18 g, 0.76 mmol) and isolated as a pale green solid (0.0763 g, 23% over 3 steps). 1H NMR (400 MHz, DMSO-$d_6$) δ ppm 2.04 (s, 3H) 3.03-3.14 (m, 4H) 3.58 (q, J=4.64 Hz, 4H) 3.80 (s, 3H) 6.22 (dd, J=3.48, 2.02 Hz, 1H) 6.51 (dd, J=8.43, 2.57 Hz, 1H) 6.67 (d, J=2.57 Hz, 1H) 6.92-6.97 (m, 1H) 7.63 (s, 1H) 7.73 (d, J=8.43 Hz, 1H) 7.87 (s, 1H) 7.95 (dd, J=12.10, 8.80 Hz, 1H) 8.30 (s, 1H) 9.07 (dd, J=14.30, 8.07 Hz, 1H) 11.29 (s, 1H) 12.21 (s, 1H). ESIMS (M+H)+=537.

Example 104

4,5-difluoro-2-[(2-{[2-(methyloxy)-4-(4-morpholinyl)phenyl]amino}-1H-pyrrolo[2,3-d]pyrimidin-4-yl)amino]benzamide

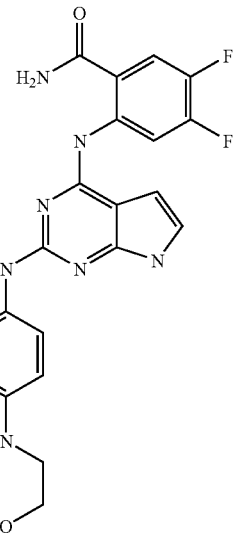

According to General Protocol III, 4,5-difluoro-2-[(2-{[2-(methyloxy)-4-(4-morpholinyl)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-4,5-difluorobenzamide (0.300 g, 0.629 mmol), 27% aqueous ammonium hydroxide, and 2-(methyloxy)-4-(4-morpholinyl)aniline (0.192 g, 0.943 mmol) and isolated as a yellow solid (0.017 g, 6% yield); 1H NMR (400 MHz, DMSO-$d_6$) δ ppm 3.03-3.10 (m, 4H), 3.70-3.76 (m, 4H), 3.77 (s, 3H), 6.20 (d, J=3.30 Hz, 1H), 6.47 (d, J=6.41 Hz, 1H), 6.63 (d, J=2.38 Hz, 1H), 6.93 (dd, J=3.39, 2.11 Hz, 1H), 7.61 (s, 1H), 7.68 (d, J=8.97 Hz, 1H), 7.85 (s, 1H), 7.93 (dd, J=11.99, 9.06 Hz, 1H), 8.28 (s, 1H), 9.05 (dd, J=14.01, 7.97 Hz, 1H), 11.27 (s, 1H), 12.19 (s, 1H). ESIMS (M+H)+=496.

Example 105

4,5-difluoro-2-[(2-{[4-[(3S)-3-methyl-4-morpholinyl]-2-(methyloxy)phenyl]amino}-1H-pyrrolo[2,3-d]pyrimidin-4-yl)amino]benzamide

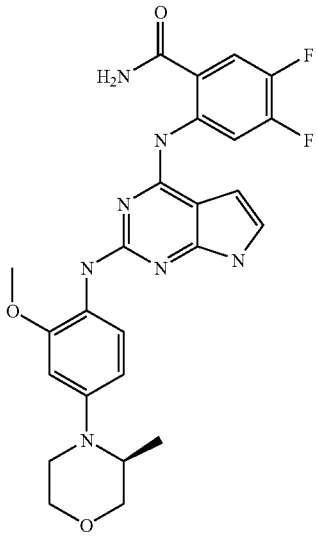

According to General Protocol III, 4,5-difluoro-2-[(2-{[4-[(3S)-3-methyl-4-morpholinyl]-2-(methyloxy)phenyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-4,5-difluorobenzamide (0.500 g, 1.05 mmol), 27% aqueous ammonium hydroxide, and 4-[(3S)-3-methyl-4-morpholinyl]-2-(methyloxy)aniline (0.341 g, 1.57 mmol) and isolated as a yellow solid (0.120 g, 20% yield); 1H NMR (400 MHz, DMSO-$d_6$) δ ppm 0.96 (d, J=6.60 Hz, 3H), 2.99-3.10 (m, 2H), 3.58 (ddd, J=6.87, 3.85, 3.57 Hz, 1H), 3.61 (d, J=3.30 Hz, 1H), 3.69-3.77 (m, 2H), 3.79 (s, 3H), 3.87 (ddd, J=11.55, 3.67, 3.48 Hz, 1H), 6.22 (dd, J=3.67, 1.83 Hz, 1H), 6.48 (dd, J=8.80, 2.57 Hz, 1H), 6.61 (d, J=2.57 Hz, 1H), 6.91-6.98 (m, 1H), 7.60 (s, 1H), 7.73 (d, J=8.80 Hz, 1H), 7.87 (s, 1H), 7.95 (dd, J=11.91, 8.98 Hz, 1H), 8.30 (s, 1H), 9.08 (dd, J=14.30, 8.07 Hz, 1H), 11.28 (s, 1H), 12.20 (s, 1H). ESIMS (M+H)+=510.

Example 106

2-{[2-({5-[(N,N-dimethylglycyl)amino]-2-methylphenyl}amino)-1H-pyrrolo[2,3-d]pyrimidin-4-yl]amino}-4,5-difluorobenzamide

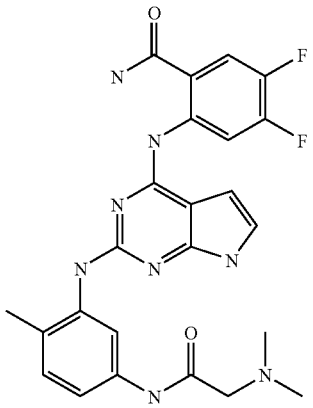

According to General Protocol III, 2-{[2-({5-[(N,N-dimethylglycyl)amino]-2-methylphenyl}amino)-1H-pyrrolo[2,3-d]pyrimidin-4-yl]amino}-4,5-difluorobenzamide was prepared from 2-({2-chloro-7-[(4-methylphenyl)sulfonyl]-7H-pyrrolo[2,3-d]pyrimidin-4-yl}amino)-4,5-difluorobenzamide (0.300 g, 0.630 mmol), 27% aqueous ammonium hydroxide, and $N^1$-(3-amino-4-methylphenyl)-$N^2,N^2$-dimethylglycinamide (0.200 g, 0.950 mmol) and isolated as a yellow solid (0.054 g, 17% Yield); 1H NMR (400 MHz, DMSO-$d_6$) δ ppm 2.17 (s, 3H), 2.22 (s, 6H), 2.99 (s, 2H), 6.20-6.24 (m, 1H), 6.94-6.97 (m, 1H), 7.13 (d, J=8.00 Hz, 1H), 7.35 (dd, J=8.42, 1.83 Hz, 1H), 7.76-7.81 (m, 1H), 7.86-7.90 (m, 1H), 7.93 (dd, J=11.72, 9.15 Hz, 1H), 8.29-8.32 (m, 1H), 8.34 (s, 1H), 9.03 (dd, J=14.46, 8.24 Hz, 1H), 9.55 (s, 1H), 11.27 (s, 1H), 12.29 (s, 1H). ESI-MS (M+H) 495. Retention time 1.57 minutes.

Example 107

4,5-difluoro-2-[(2-{[5-{[(2S)-2-hydroxy-3-(1-pyrrolidinyl)propyl]oxy}-2-(methyloxy)phenyl]amino}-1H-pyrrolo[2,3-d]pyrimidin-4-yl)amino]benzamide

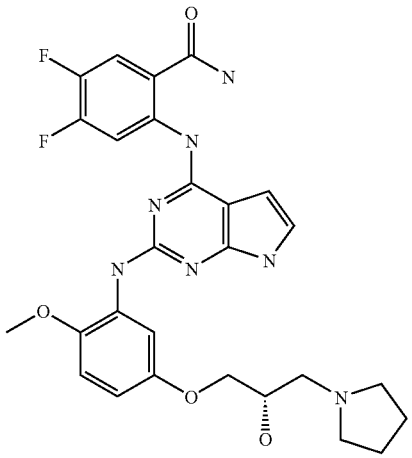

According to General Protocol III, 4,5-difluoro-2-[(2-{[5-{[(2S)-2-hydroxy-3-(1-pyrrolidinyl)propyl]oxy}-2-(methyloxy)phenyl]amino}-1H-pyrrolo[2,3-d]pyrimidin-4-yl)amino]benzamide (0.108 g) was prepared from 2-({2-chloro-7-[(4-methylphenyl)sulfonyl]-7H-pyrrolo[2,3-d]pyrimidin-4-yl}amino)-4,5-difluorobenzamide (0.30 g, 0.63 mmol), 27% aqueous ammonium hydroxide, and (2S)-1-{[3-amino-4-(methyloxy)phenyl]oxy}-3-(1-pyrrolidinyl)-2-propanol (0.21 g, 0.75 mmol). 1H NMR (400 MHz, DMSO-$d_6$) δ ppm 1.61-1.67 (m, 4H), 2.39-2.45 (m, 1H), 2.50 (d, J=2.2 Hz, 2H), 2.59 (dd, J=12.1, 5.5 Hz, 1H), 3.15 (d, J=5.5 Hz, 2H), 3.75-3.82 (m, 4H), 3.84-3.93 (m, 2H), 4.76-4.85 (m, 1H), 6.28 (dd, J=3.5, 1.6 Hz, 1H), 6.49 (dd, J=8.8, 2.9 Hz, 1H), 6.90 (d, J=8.8 Hz, 1H), 7.04 (dd, J=3.7, 2.2 Hz, 1H), 7.73 (s, 1H), 7.90 (s, 1H), 7.93-8.01 (m, 2H), 8.33 (s, 1H), 9.08 (dd, J=14.3, 8.1 Hz, 1H), 11.56 (s, 1H), 12.27 (s, 1H); ESIMS (M+H)+=554.

Example 108

5-chloro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide

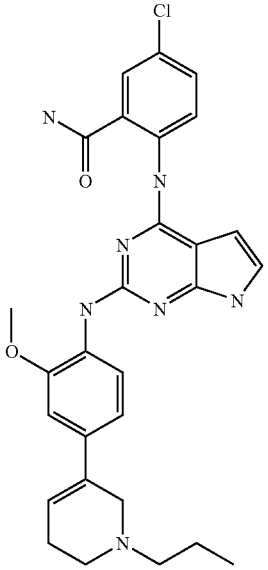

According to General Protocol III, 5-chloro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide was prepared from 5-chloro-2-({2-chloro-7-[(4-methylphenyl)sulfonyl]-7H-pyrrolo[2,3-d]pyrimidin-4-yl}amino)benzamide (0.30 g, 0.63 mmol), 27% aqueous ammonium hydroxide, and 2-(methyloxy)-4-(1-propyl-1,2,5,6-tetrahydro-3-pyridinyl)aniline (0.23 g, 0.95 mmol) and isolated as a yellow solid (0.029 g); 1H NMR (400 MHz, DMSO-$d_6$) δ ppm 0.89 (t, J=7.32 Hz, 3H) 1.50-1.61 (m, 2H) 2.27 (s, 2H) 2.54-2.55 (m, 6H) 3.89 (s, 3H) 6.15 (s, 1H) 6.28 (s, 1H) 6.93-7.03 (m, 4H) 7.51 (d, J=11.16 Hz, 1H) 7.61 (s, 1H) 7.82-7.92 (m, J=2.20 Hz, 3H) 8.26 (d, J=8.05 Hz, 1H) 8.40 (s, 1H) 8.95 (d, J=9.15 Hz, 1H) 11.44 (s, 1H) 11.91 (s, 1H). ESIMS (M+H)+=532.

Example 109

5-chloro-2-{[2-({5-[(N,N-dimethylglycyl)amino]-2-methylphenyl}amino)-1H-pyrrolo[2,3-d]pyrimidin-4-yl]amino}benzamide

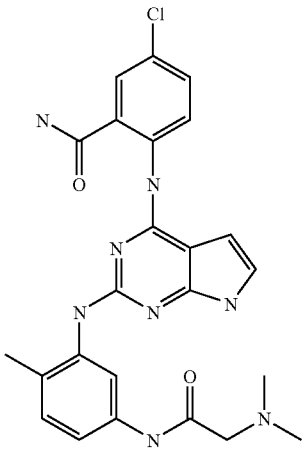

According to General Protocol III, 5-chloro-2-{[2-({5-[(N,N-dimethylglycyl)amino]-2-methylphenyl}amino)-1H-pyrrolo[2,3-d]pyrimidin-4-yl]amino}benzamide was prepared from 5-chloro-2-({2-chloro-7-[(4-methylphenyl)sulfonyl]-7H-pyrrolo[2,3-d]pyrimidin-4-yl}amino)benzamide (0.30 g, 0.63 mmol), 27% aqueous ammonium hydroxide, and $N^1$-(3-amino-4-methylphenyl)-$N^2$,$N^2$-dimethylglycinamide (0.20 g, 0.95 mmol) and isolated as a yellow solid (0.048 g); 1H NMR (400 MHz, DMSO-$d_6$) δ ppm 2.14 (s, 3H) 2.21 (s, 6H) 2.99 (s, 2H) 6.20 (dd, J=3.48, 1.83 Hz, 1H) 6.92 (dd, J=3.39, 2.29 Hz, 1H) 7.09-7.20 (m, 2H) 7.35 (dd, J=8.33, 2.11 Hz, 1H) 7.74 (d, J=2.01 Hz, 1H) 7.79-7.90 (m, 2H) 8.18 (s, 1H) 8.36 (s, 1H) 8.90 (d, J=8.97 Hz, 1H) 9.58 (s, 1H) 11.23 (s, 1H) 11.97 (s, 1H). ESIMS (M+H)+=292.

Example 110

4-chloro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide

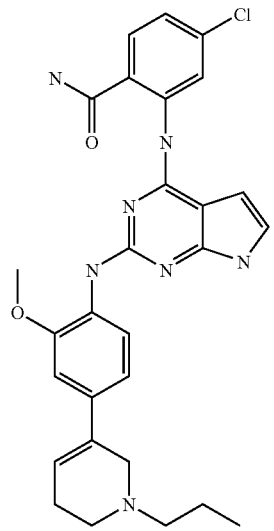

According to General Protocol III, 4-chloro-2-[(2-{[2-(methyloxy)-4-(1-propyl-1,2,5,6-tetrahydro-3-pyridinyl)phenyl]amino}-1H-pyrrolo[2,3-d]pyrimidin-4-yl)amino]benzamide was prepared from 4-chloro-2-({2-chloro-7-[(4-methylphenyl)sulfonyl]-7H-pyrrolo[2,3-d]pyrimidin-4-yl}amino)benzamide (0.30 g, 0.63 mmol), 27% aqueous ammonium hydroxide, and 2-(methyloxy)-4-(1-propyl-1,2,5,6-tetrahydro-3-pyridinyl)aniline (0.23 g, 0.95 mmol) and isolated as a yellow solid (0.033 g); 1H NMR (400 MHz, DMSO-$d_6$) δ ppm 0.87 (t, J=7.33 Hz, 3H) 1.51-1.56 (m, 2H) 2.24-2.29 (s, 2H) 2.39-2.59 (m, 6H) 3.88 (s, 3H) 6.13 (s, 1H) 6.27-6.28 (m, 1H) 6.93-6.97 (m, 1H) 7.00-7.09 (m, 3H) 7.56 (s, 1H) 7.80-7.85 (m, 2H) 8.18 (d, J=8.61 Hz, 1H) 8.35 (s, 1H) 8.99 (d, J=2.20 Hz, 1H) 11.42 (s, 1H) 12.23 (s, 1H). ESIMS (M+H)+=532.

Example 111

4-chloro-2-{[2-({5-[(N,N-dimethylglycyl)amino]-2-methylphenyl}amino)-1H-pyrrolo[2,3-c]pyrimidin-4-yl]amino}benzamide

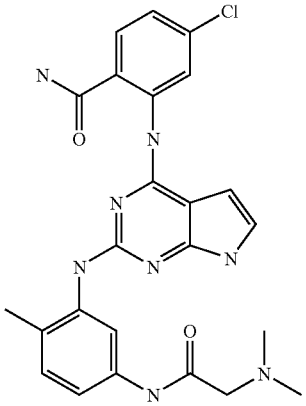

According to General Protocol III, 4-chloro-2-{[2-({5-[(N, N-dimethylglycyl)amino]-2-methylphenyl}amino)-1H-pyrrolo[2,3-d]pyrimidin-4-yl]amino}benzamide was prepared from 4-chloro-2-({2-chloro-7-[(4-methylphenyl)sulfonyl]-7H-pyrrolo[2,3-d]pyrimidin-4-yl}amino)benzamide (0.30 g, 0.63 mmol), 27% aqueous ammonium hydroxide, and $N^1$-(3-amino-4-methylphenyl)-$N^2$,$N^2$-dimethylglycinamide (0.20 g, 0.95 mmol) and isolated as a yellow solid (0.038 g); 1H NMR (400 MHz, DMSO-$d_6$) δ ppm 2.17 (s, 3H) 2.22 (s, 6H) 3.00 (s, 2H) 6.23-6.24 (m, 1H) 6.94-6.96 (m, 2H) 7.11 (d, J=8.42 Hz, 1H) 7.35-7.38 (m, 1H) 7.72-7.74 (m, 1H) 7.78 (s, 1H) 7.79-7.81 (m, 1H) 8.26 (s, 1H) 8.32 (s, 1H) 8.93 (d, J=2.20 Hz, 1H) 9.54 (s, 1H) 11.26 (s, 1H) 12.28 (s, 1H). ESIMS (M+H)+=493.

Example 112

2-fluoro-6-({2-[(2-(methyloxy)-4-{1'-[2-(methylsulfonyl)ethyl]-4,4'-bipiperidin-1-yl}phenyl)amino]-1H-pyrrolo[2,3-d]pyrimidin-4-yl}amino)benzamide

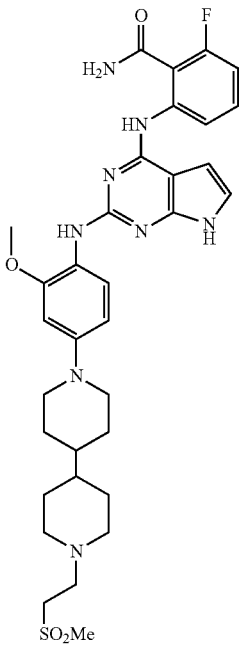

According to General Protocol III, 2-fluoro-6-({2-[(2-(methyloxy)-4-{1'-[2-(methylsulfonyl)ethyl]-4,4'-bipiperidin-1-yl}phenyl)amino]-1H-pyrrolo[2,3-d]pyrimidin-4-yl}amino)benzamide (0.180 g, 42% yield) was prepared from 2-({2-chloro-7-[(4-methylphenyl)sulfonyl]-7H-pyrrolo[2,3-d]pyrimidin-4-yl}amino)-6-fluorobenzamide (0.30 g, 0.65 mmol), 27% aqueous ammonium hydroxide, and 2-(methyloxy)-4-{1'-[2-(methylsulfonyl)ethyl]-4,4'-bipiperidin-1-yl}aniline (0.40 g, 1.0 mmol). ESIMS (M+H)+=665. 1H NMR (400 MHz, DMSO-$d_6$) δ ppm 1.05-1.36 (m, 6H), 1.66-1.75 (m, 2H), 1.75-1.81 (m, 2H), 1.85-1.94 (m, 2H), 2.52-2.59 (m, 2H), 2.66 (t, J=6.8 Hz, 2H), 2.90-2.96 (m, 2H), 3.02 (s, 3H), 3.27 (t, J=6.4 Hz, 2H), 3.63-3.70 (m, 2H), 3.81 (s, 3H), 6.21 (d, J=2.9 Hz, 1H), 6.47 (dd, J=9.0, 2.0 Hz, 1H), 6.62 (d, J=2.2 Hz, 1H), 6.89-6.97 (m, 2H), 7.38-7.46 (m, 2H), 7.89 (d, J=8.8 Hz, 1H), 8.02 (s, 1H), 8.10 (s, 1H), 8.50 (dd, J=8.4, 4.4 Hz, 1H), 10.45 (s, 1H), 11.30 (s, 1H).

Example 113

2-fluoro-6-({2-[(2-(methyloxy)-4-{4-[4-(methylsulfonyl)-1-piperazinyl]-1-piperidinyl}phenyl)amino]-1H-pyrrolo[2,3-d]pyrimidin-4-yl}amino)benzamide

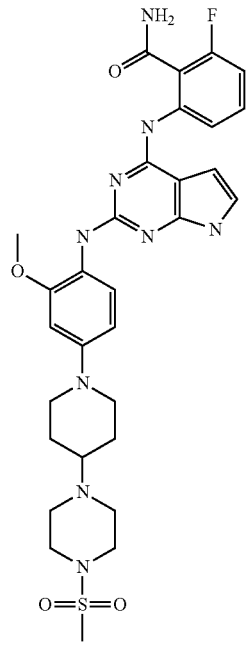

According to General Protocol III, 2-fluoro-6-({2-[(2-(methyloxy)-4-{4-[4-(methylsulfonyl)-1-piperazinyl]-1-piperidinyl}phenyl)amino]-1H-pyrrolo[2,3-d]pyrimidin-4-yl}amino)benzamide (0.346 g, 40% yield) was prepared from 2-({2-chloro-7-[(4-methylphenyl)sulfonyl]-7H-pyrrolo[2,3-d]pyrimidin-4-yl}amino)-6-fluorobenzamide (0.250 g, 0.543 mmol), 27% aqueous ammonium hydroxide, and 2-(methyloxy)-4-{4-[4-(methylsulfonyl)-1-piperazinyl]-1-piperidinyl}aniline (0.300 g, 0.815 mmol)(400 MHz, DMSO-$d_6$) δ ppm 1.48-1.56 (m, 2H), 1.79-1.82 (m, 2H), 2.34-2.39 (m, 1H), 2.57-2.62 (m, 6H), 2.82 (s, 3H), 3.05-3.08 (m, 4H), 3.62-2.65 (m, 2H), 3.77 (s, 3H), 6.17 (s, 1H), 6.43 (dd, J=2.2, 8.7 Hz, 1H), 6.59 (d, J=2.0 Hz, 1H), 6.85-6.91 (m, 2H), 7.34-7.40 (m, 2H), 7.86 (d, J=8.6 Hz, 1H), 7.97 (s, 1H), 8.05 (s, 1H), 8.44 (d, J=8.4 Hz, 1H), 10.41 (s, 1H), 11.26 (s, 1H); ESIMS (M+H)+=638.

Example 113 (Alternative Preparation)

2-fluoro-6-({2-[(2-(methyloxy)-4-{4-[4-(methylsulfonyl)-1-piperazinyl]-1-piperidinyl}phenyl)amino]-1H-pyrrolo[2,3-d]pyrimidin-4-yl}amino)benzamide

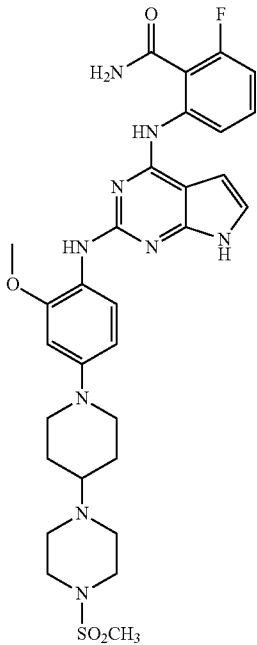

Step A/Intermediate D73: 8-fluoro-5-[(2-(methyloxy)-4-{4-[4-(methylsulfonyl)-1-piperazinyl]-1-piperidinyl}phenyl)amino]-3-[(4-methylphenyl)sulfonyl]pyrrolo[2',3':4,5]pyrimido[6,1-b]quinazolin-7(3H)-one

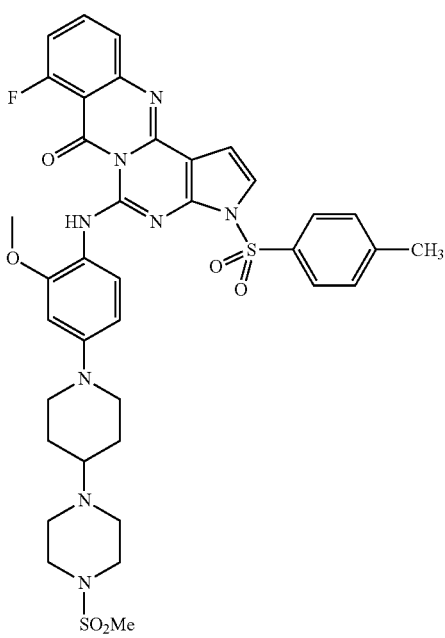

A solution of 2-(methyloxy)-4-{4-[4-(methylsulfonyl)-1-piperazinyl]-1-piperidinyl}aniline hydrochloride (3 g, 7.41 mmol) and 2-({2-chloro-7-[(4-methylphenyl)sulfonyl]-7H-pyrrolo[2,3-d]pyrimidin-4-yl}amino)-6-fluorobenzamide (3 g, 6.52 mmol) in trifluroroethanol (200 mL) and HCl in dioxane (14.16 ml, 56.6 mmol) and KI (300 mg, 1.807 mmol) was stirred at 90° C. in a 300 mL pressure vessel behind a blast shield for 15 hours. After cooling to rt, the solution was neutralized with aqueous NaHCO₃ (400 mL), the black suspension was added to CH₂Cl₂ (500 mL), and the layers separated. Addition of brine (200 mL) helped to separate the organic and aqueous layers. The organic layers were concentrated under reduced pressure and then suspended in CH2Cl2 (20 mL) and Et2O (150 mL). The solid was filtered to obtain 8-fluoro-5-[(2-(methyloxy)-4-{4-[4-(methylsulfonyl)-1-piperazinyl]-1-piperidinyl}phenyl)amino]-3-[(4-methylphenyl)sulfonyl]pyrrolo[2',3':4,5]pyrimido[6,1-b]quinazolin-7(3H)-one as brown powder (4.5 g, 5.81 mmol, 89% yield). This material was used without further purification. ESIMS (M+H)+=775.32 (100%).

Step B/Intermediate D74: 2-fluoro-6-({2-[(2-(methyloxy)-4-{4-[4-(methylsulfonyl)-1-piperazinyl]-1-piperidinyl}phenyl)amino]-7-[(4-methylphenyl)sulfonyl]-7H-pyrrolo[2,3-d]pyrimidin-4-yl}amino)benzamide

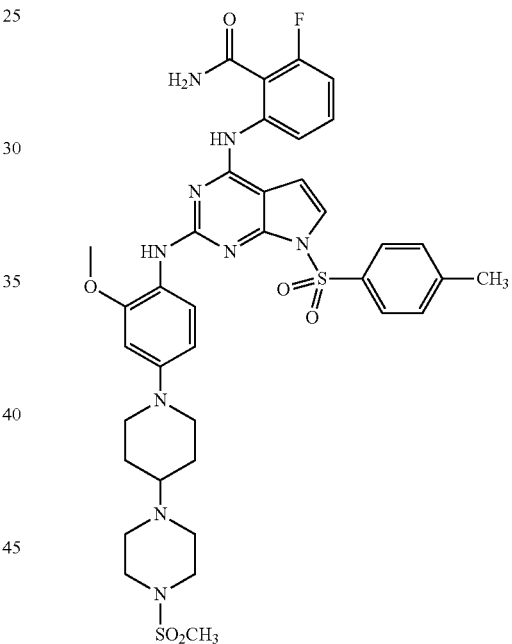

A solution of 8-fluoro-5-[(2-(methyloxy)-4-{4-[4-(methylsulfonyl)-1-piperazinyl]-1-piperidinyl}phenyl)amino]-3-[(4-methylphenyl)sulfonyl]pyrrolo[2',3':4,5]pyrimido[6,1-b]quinazolin-7(3H)-one (4.5 g, 5.81 mmol) and 30% aqueous NH₄OH (75 mL, 5.81 mmol) and tetrahydrofuran (75 mL) was stirred at rt overnight in a 200 mL rb flask. The solution was extracted with ethyl acetate (250 mL) and brine (50 mL). The organic layers were dried over MgSO4, filtered, concentrated onto Celite and purified on SiO₂ (1-10% MeOH in CH₂Cl₂ and 0.1% NH₄OH) to afford 2-fluoro-6-({2-[(2-(methyloxy)-4-{4-[4-(methylsulfonyl)-1-piperazinyl]-1-piperidinyl}phenyl)amino]-7-[(4-methylphenyl)sulfonyl]-7H-pyrrolo[2,3-d]pyrimidin-4-yl}amino)benzamide (2.78 g, 3.51 mmol, 60% yield) as a mixture with several other products. The desired product was the predominant component. The product weight was 2.78 grams. ESIMS (M+H)+=792.42 (100%). This material was used without further purification in the next step.

Step C/Example 113 (Alternative Preparation):
2-fluoro-6-({2-[(2-(methyloxy)-4-{4-[4-(methylsulfonyl)-1-piperazinyl]-1-piperidinyl}phenyl)amino]-1H-pyrrolo[2,3-d]pyrimidin-4-yl}amino)benzamide A suspension of 2-fluoro-6-({2-[(2-(methyloxy)-4-{4-[4-(methylsulfonyl)-1-piperazinyl]-1-piperidinyl}phenyl)amino]-7-[(4-methylphenyl)sulfonyl]-7H-pyrrolo[2,3-d]pyrimidin-4-yl}amino)benzamide (2.78 g, 3.51 mmol) and 1,4-dioxane (100 mL) in a 200 mL sealed flask was stirred in an 85° C. bath for 11 hours. The solution was extracted with ethyl acetate (200 mL) and brine (50 mL). The organic layers were dried over $MgSO_4$, filtered, concentrated onto Celite and purified by $SiO_2$ column chromatography (1-10% MeOH in $CH_2Cl_2$ and 0.1% $NH_4OH$) to afford 2-fluoro-6-({2-[(2-(methyloxy)-4-{4-[4-(methylsulfonyl)-1-piperazinyl]-1-piperidinyl}phenyl)amino]-1H-pyrrolo[2,3-d]pyrimidin-4-yl}amino)benzamide (1.0 g, 1.568 mmol, 44.7% yield). This material was combined in a 100mL round bottomed flask with approximately 600 mg of purified material from another batch. THF (10 mL) was added and the slurry was sonicated for 2 minutes. Ether (30 mL) was added and the slurry was sonicated for 2 minutes. The slurry was filtered and the solid collected. The solid was placed on the high vacuum pump at 0.5 torr for 2 hours to afford 2-fluoro-6-({2-[(2-(methyloxy)-4-{4-[4-(methylsulfonyl)-1-piperazinyl]-1-piperidinyl}phenyl)amino]-1H-pyrrolo[2,3-d]pyrimidin-4-yl}amino)benzamide (1.4 g, 2.195 mmol). $^1$H NMR (400 MHz, DMSO-$d_6$) δ ppm 1.48-1.56 (m, 2H), 1.79-1.82 (m, 2H), 2.34-2.39 (m, 1H), 2.57-2.62 (m, 6H), 2.82 (s, 3H), 3.05-3.08 (m, 4H), 3.62-2.65 (m, 2H), 3.77 (s, 3H), 6.17 (s, 1H), 6.43 (dd, J=2.2, 8.7 Hz, 1H), 6.59 (d, J=2.0 Hz, 1H), 6.85-6.91 (m, 2H), 7.34-7.40 (m, 2H), 7.86 (d, J=8.6 Hz, 1H), 7.97 (s, 1H), 8.05 (s, 1H), 8.44 (d, J=8.4 Hz, 1H), 10.41 (s, 1H), 11.26 (s, 1H); ESIMS (M+H)$^+$=638.

Example 114

2-fluoro-6-[(2-{[4-{4-[4-(2-fluoroethyl)-1-piperazinyl]-1-piperidinyl}-2-(methyloxy)phenyl]amino}-1H-pyrrolo[2,3-d]pyrimidin-4-yl)amino]benzamide

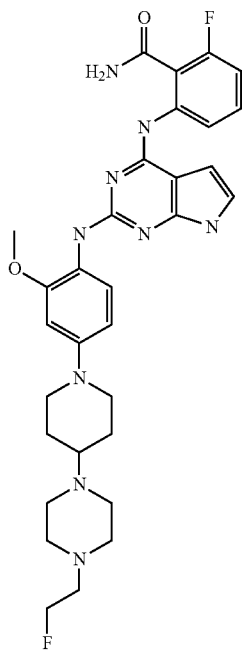

According to General Protocol III, 2-fluoro-6-[(2-{[4-{4-[4-(2-fluoroethyl)-1-piperazinyl]-1-piperidinyl}-2-(methyloxy)phenyl]amino}-1H-pyrrolo[2,3-d]pyrimidin-4-yl)amino]benzamide (0.245 g, 46% yield) was prepared from 2-({2-chloro-7-[(4-methylphenyl)sulfonyl]-7H-pyrrolo[2,3-d]pyrimidin-4-yl}amino)-6-fluorobenzamide (0.400 g, 0.87 mmol), 27% aqueous ammonium hydroxide, and 4-{4-[4-(2-fluoroethyl)-1-piperazinyl]-1-piperidinyl}-2-(methyloxy)aniline (0.496 g, 1.48 mmol). (400 MHz, DMSO-$d_6$) δ ppm 1.45-1.55 (m, 2H), 1.82-1.85 (m, 2H), 2.25-2.30 (m, 1H), 2.43-2.64 (complex m, 12H), 3.64-3.67 (m, 2H), 3.79 (s, 3H), 4.50 (dt, $J_{HF}$=47.7 Hz, J=5.0, 2H), 6.19-6.20 (m, 1H), 6.46 (dd, J=2.4, 8.8 Hz, 1H), 6.61 (sharp m, 1H), 6.88-6.94 (m, 2H), 7.37-7.43 (m, 2H), 7.88 (d, J=8.6 Hz, 1H), 8.00 (s, 1H), 8.08 (s, 1H), 8.47 (d, J=8.5 Hz, 1H), 10.43 (s, 1H), 11.29 (s, 1H); ESIMS (M+H)$^+$=606.

Example 115

2-fluoro-6-[(2-{[2-(methyloxy)-4-(4-{4-[2-(methylsulfonyl)ethyl]-1-piperazinyl}-1-piperidinyl)phenyl]amino}-1H-pyrrolo[2,3-d]pyrimidin-4-yl)amino]benzamide

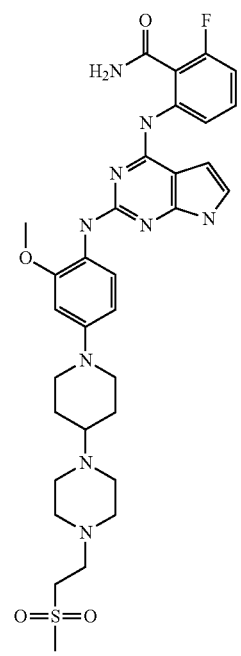

According to General Protocol III, 2-fluoro-6-[(2-{[2-(methyloxy)-4-(4-{4-[2-(methylsulfonyl)ethyl]-1-piperazinyl}-1-piperidinyl)phenyl]amino}-1H-pyrrolo[2,3-d]pyrimidin-4-yl)amino]benzamide (0.165 g, 28% yield) was prepared from 2-({2-chloro-7-[(4-methylphenyl)sulfonyl]-7H-pyrrolo[2,3-d]pyrimidin-4-yl}amino)-6-fluorobenzamide (0.400 g, 0.87 mmol), 27% aqueous ammonium hydroxide, and 2-(methyloxy)-4-(4-{4-[2-(methylsulfonyl)ethyl]-1-piperazinyl}-1-piperidinyl)aniline (0.518 g, 1.31 mmol) (400 MHz, DMSO-$d_6$) δ ppm 1.45-1.55 (m, 2H), 1.82-1.85 (m, 2H), 2.24-2.30 (m, 1H), 2.40-2.68 (complex m, 12 H complicated by DMSO peak), 3.01 (s, 3H), 3.26 (t, J=6.8, 2H), 3.63-3.66 (m, 2H), 3.79 (s, 3H), 6.19-6.20 (m, 1H), 6.46 (dd, J=2.4, 8.8 Hz, 1H), 6.61 (sharp m, 1H), 6.87-6.94 (m, 2H), 7.37-7.43 (m, 2H), 7.88 (d, J=8.8 Hz, 1H), 8.00 (s, 1H), 8.08 (s, 1H), 8.47 (d, J=8.2 Hz, 1H), 10.44 (s, 1H), 11.29 (s, 1H); ESIMS (M+H)$^+$=666.

Example 116

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluoro-N-methylbenzamide

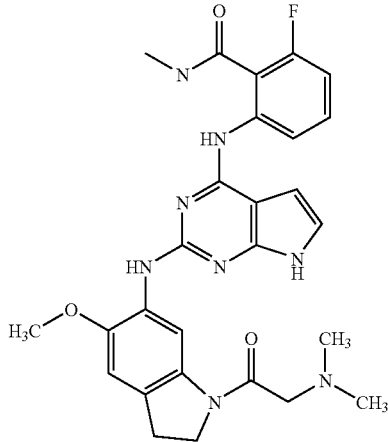

Step A/Intermediate D4: 2-({2-chloro-7-[(4-methylphenyl)sulfonyl]-7H-pyrrolo[2,3-d]pyrimidin-4-yl}amino)-6-fluorobenzoic acid

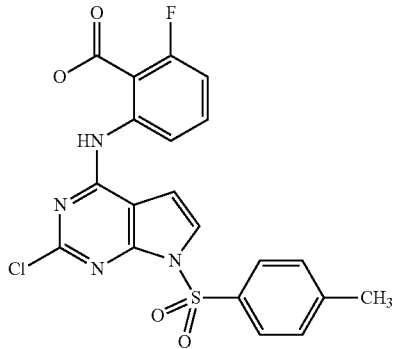

A slurry of 2,4-dichloro-7-[(4-methylphenyl)sulfonyl]-7H-pyrrolo[2,3-d]pyrimidine (50 g, 146 mmol) and 2-amino-6-fluorobenzoic acid (27.2 g, 175 mmol) (for instance from Acros Organics, Belgium) in iPrOH (1200 mL) and 30 mL of DIEA was heated to reflux. After 1 h, the solution turned a clear brown color, at which time about 450 mL of solvent were removed via distillation. The remaining mixture was treated with DIEA (90 mL) and heated to reflux for 16 hours. The reaction mixture was then further concentrated by distilling more solvent off (400 mL over 4 hours), then continued heating at reflux overnight. The resulting mixture was cooled to room temperature and concentrated under reduced pressure to obtain a thick oil which was diluted with EtOAc (1.3 L), then sequentially washed with a 1N HCl solution (2×500 mL), and a saturated NaHCO$_3$ solution (500 mL). Further dilution of the separated organic layer with a saturated NaCl solution (500 mL) led to the formation of a thick precipitate. The entire mixture was filtered and the solid was washed with Et$_2$O. The solid was dried overnight in a vacuum oven at 60° C. to obtain 2-({2-chloro-7-[(4-methylphenyl)sulfonyl]-7H-pyrrolo[2,3-d]pyrimidin-4-yl}amino)-6-fluorobenzoic acid as a yellow solid (61.63 g, 92%). $^1$H NMR (400 MHz, DMSO-d$_5$) δ ppm 2.37 (s, 3H), 6.67 (d, J=3.85 Hz, 1H), 6.71-6.81 (m, 1H), 7.31 (td, J=8.33, 6.04 Hz, 1H), 7.48 (d, J=8.24 Hz, 2H), 7.74 (d, J=4.03 Hz, 1H), 7.98 (d, J=8.42 Hz, 2H), 8.36 (d, J=8.24 Hz, 1H); ESIMS (M+H)$^+$=461.06.

Step B/Intermediate D5: 5-chloro-8-fluoro-3-[(4-methylphenyl)sulfonyl]pyrrolo[2',3':4,5]pyrimido[6,1-b]quinazolin-7(3H)-one hydrogen chloride

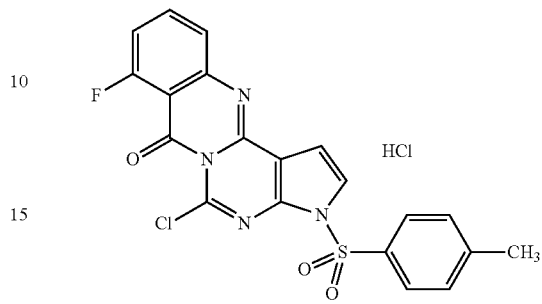

A slurry of 2-({2-chloro-7-[(4(4-methylphenyl)sulfonyl]-7H-pyrrolo[2,3-d]pyrimidin-4-yl}amino)-6-fluorobenzoic acid (33.05 g, 71.7 mmol) and THF (1000 mL) was treated with a few drops of DMF and neat oxalyl chloride (12.55 mL, 143 mmol). The resulting fine slurry was stirred at room temperature for 3 hours, then maintained at −5° C. for 17 hours. The cold slurry was filtered, the solid washed with cold THF, then dried in a vacuum oven for 4 hours at room temperature to obtain 5-chloro-8-fluoro-3-[(4-methylphenyl)sulfonyl]pyrrolo[2',3':4,5]pyrimido[6,1-b]quinazolin-7(3H)-one hydrogen chloride salt as a pale yellow solid (∼34.6 g, quantitative yield ∼100%). $^1$H NMR (400 MHz, DMSO-d$_6$) δ ppm 2.41 (s, 3H), 7.10-7.20 (m, 2H), 7.45 (d, J=8.24 Hz, 2H), 7.56 (d, J=8.24 Hz, 1H), 7.67 (d, J=3.85 Hz, 1H), 7.77 (td, J=8.20, 5.59 Hz, 1H), 8.11 (d, J=8.42 Hz, 2H); ESIMS (M+H)$^+$=442.99 (100%).

Step C/Intermediate D6: 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-methylbenzamide

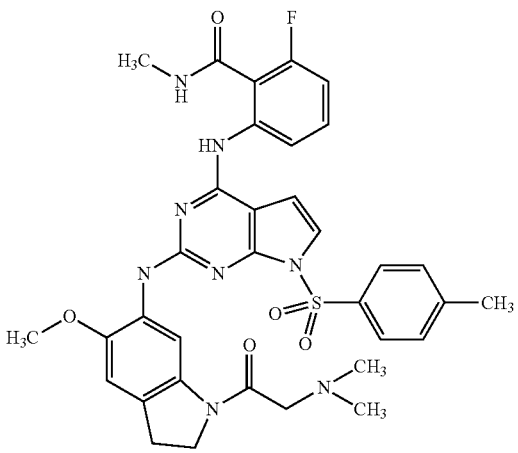

A suspension of 5-chloro-8-fluoro-3-[(4-methylphenyl)sulfonyl]pyrrolo[2',3':4,5]pyrimido[6,1-b]quinazolin-7(3H)-one hydrogen chloride (9.0 g, 18.78 mmol) and 1-[(diemthylamine)acetyl]-5-(methyloxy)-2,3-dihydro-1H-inol- 6-amine (5.85 g, 23.47 mmol) (which may be prepared as described in regard to Intermediate B95, described above) in tetrahydrofuran (600 mL) was maintained at 80° C. for 10 hours. The solution was cooled to room temperature, 2.0 M methylamine in THF (94 mL, 188 mmol) was added and the suspension was stirred vigorously for 16 hours at room temperature. Saturated sodium bicarbonate and ethyl acetate were added and all solids quickly dissolved. The organic layer was dried over sodium sulfate, filtered, stripped onto celite, and purified by chromatography on $SiO_2$ to afford 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-methylbenzamide (10.85 g, 15.80 mmol, 84%) as a yellow foam. $^1$H NMR (400 MHz, DMSO-$d_6$) δ ppm 2.23 (s, 6H), 2.32 (s, 3H), 2.73 (d, J=4.77 Hz, 3H), 3.16-3.22 (m, 4H), 3.72 (s, 3H), 4.23 (s, 2H), 6.54 (d, J=4.03 Hz, 1H), 6.89-6.97 (m, 1H), 7.03 (s, 1H), 7.20-7.32 (m, 4H), 7.90-8.01 (m, 3H), 8.20 (d, J=16.86 Hz, 2H), 8.43 (dd, J=4.58, 2.02 Hz, 1H), 10.16 (s, 1H). ESIMS (M+H)=687.

Step D/Example 116: 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluoro-N-methylbenzamide A light brown solution of 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-methylbenzamide (26 g, 37.9 mmol) prepared in multiple batches as described in Step C above, in dioxane (900 mL) was treated with a 1N aqueous KOH solution (379 mL, 379 mmol). The resulting mixture was heated in a 90° C. bath for 3 hours. The resulting mixture was allowed to cool to room temperature, then was diluted with EtOAc (500 mL). The organic layer was separated and sequentially washed with a 2N aqueous NaOH solution (2×200 mL) and a saturated NaCl solution (300 mL), then concentrated to a thick slurry. The resulting slurry was filtered and the solid washed with $Et_2O$. The filtrate was concentrated to a slurry, filtered, and combined with the previous residue to obtain 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluoro-N-methylbenzamide as a light brown solid. (16.9 g, 84%, Yield). The remaining filtrate was concentrated and purified by flash silica gel chromatography using 1-10% MeOH (0.2% $NH_3$)/$CH_2Cl_2$ affording an additional 1 g (5%). $^1$H NMR (400 MHz, DMSO-$d_6$) δ ppm 2.28 (s, 6H), 2.82 (d, J=4.40 Hz, 3H), 3.08-3.15 (m, 2H), 3.22 (s, 2H), 3.79 (s, 3H), 4.16 (t, J=8.25 Hz, 2H), 6.27 (d, J=1.83 Hz, 1H), 6.80-6.89 (m, 1H), 6.92 (d, J=2.20 Hz, 1H), 6.93 (s, 1H), 7.26-7.35 (m, 1H), 7.38 (s, 1H), 8.28 (s, 1H), 8.36 (d, J=8.43 Hz, 1H), 8.65 (s, 1H), 10.10 (s, 1H), 11.06 (s, 1H). ESIMS (M+H)=533.

Step D (alternative)/Example 116ᵅ (monohydrate preparation) 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluoro-N-methylbenzamide monohydrate A light brown solution of 2-({2-{[1-(N,N-dimethylglycyl)-5-(methoxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-methylbenzamide (19.1 kg, 27.8 mol), a method for preparation of which is described in Step C above, was suspended in dioxane (191 L, 10 volumes) and treated with a 15% aqueous KOH solution (76.4 L, 4 volumes). The mixture was heated to reflux (approximately 85° C.). Once the suspension became homogeneous, the reaction mixture was kept at reflux for 2 hours. In-process monitoring after 2 h showed completion. The heat was discontinued and the suspension was concentrated to remove approximately 80 L of solvent. Water (141 L) was added and the suspension was stirred at ambient temperature for 1 h and filtered through centrifuge. The solid was washed with water till the filtrate ran clear to obtain 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluoro-N-methylbenzamide monohydrate as a light brown solid (14.1 kg, 95% yield).

NMR analysis confirmed 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluoro-N-methylbenzamide. Powder x-ray diffraction confirmed existence of the monohydrate, characterized by the pattern shown in FIG. 1, including the peaks of Table 1.

TABLE 1

| 2 theta (deg.) | d-spacing (angstroms) |
|---|---|
| 4.8 | 18.3 |
| 5.0 | 17.5 |
| 8.3 | 10.7 |
| 8.6 | 10.3 |

Example 117

2-[(2-{[1-[2-(dimethylamino)ethyl]-5-(methyloxy)-2,3-dihydro-1H-indol-6-yl]amino}-1H-pyrrolo[2,3-d]pyrimidin-4-yl)amino]-6-fluorobenzamide

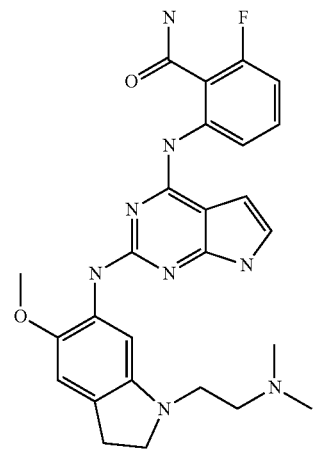

According to General Protocol III, 2-[(2-{[1-[2-(dimethylamino)ethyl]-5-(methyloxy)-2,3-dihydro-1H-indol-6-yl]amino}-1H-pyrrolo[2,3-d]pyrimidin-4-yl)amino]-6-fluorobenzamide was prepared from 2-({2-chloro-7-[(4-methylphenyl)sulfonyl]-7H-pyrrolo[2,3-d]pyrimidin-4-yl}amino)-6-fluorobenzamide (0.127 g), 27% aqueous ammonium hydroxide, and 1-[2-(dimethylamino) Ethyl]-5-(methyloxy)-2,3-dihydro-1H-indol-6-amine (0.065 g) and isolated as a yellow solid (0.044 g); $^1$H NMR (400 MHz, DMSO-$d_6$) δ ppm 11.33 (s, 1H), 10.53 (s, 1H), 8.48 (d, J=8.43 Hz, 1H), 8.10 (s, 1H), 8.01 (s, 1H), 7.54 (s, 1H), 7.36-7.47 (m, 2H), 6.97-7.02 (m, 1H), 6.86-6.94 (m, 1H), 6.82 (s, 1H), 6.23

(dd, J=3.30, 1.83 Hz, 1H), 3.74 (s, 3H), 3.24 (t, J=8.25 Hz, 2H), 2.95-3.06 (m, 2H), 2.81 (t, J=7.88 Hz, 2H), 2.36-2.45 (m, 2H), 2.13 (s, 6H). ESIMS (M+H)+=505.

Example 118

2-[(2-{[1-(N,N-dimethyl-b-alanyl)-5-(methyloxy)-2,3-dihydro-1H-indol-6-yl]amino}-1H-pyrrolo[2,3-d]pyrimidin-4-yl)amino]-6-fluorobenzamide

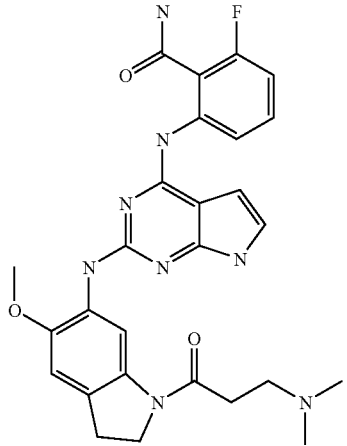

According to General Protocol III, 2-[(2-{[1-(N,N-dimethyl-b-alanyl)-5-(methyloxy)-2,3-dihydro-1H-indol-6-yl]amino}-1H-pyrrolo[2,3-d]pyrimidin-4-yl)amino]-6-fluorobenzamide was prepared from 2-({2-chloro-7-[(4-methylphenyl)sulfonyl]-7H-pyrrolo[2,3-d]pyrimidin-4-yl}amino)-6-fluorobenzamide (0.300 g), 27% aqueous ammonium hydroxide, and 1-[3-(dimethylamino)propanoyl]-5-(methyloxy)-2,3-dihydro-1H-indol-6-amine (0.200 g) and isolated as a yellow solid (0.086 g); $^1$H NMR (400 MHz, DMSO-d$_6$) δ ppm 11.25 (s, 1H), 10.50 (s, 1H), 8.58 (s, 1H), 8.47 (d, J=8.42 Hz, 1H), 8.05 (s, 1H), 7.97 (s, 1H), 7.52 (s, 1H), 7.22-7.32 (m, 1H), 6.90 (s, 2H), 6.78-6.87 (m, 1H), 6.18 (d, J=1.47 Hz, 1H), 4.10 (t, J=8.42 Hz, 2H), 3.73 (s, 3H), 3.09 (t, J=8.33 Hz, 2H), 2.46-2.58 (m, 4H), 2.12 (s, 6H). ESIMS (M+H)+=533.

Example 119

4-chloro-2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluorobenzamide

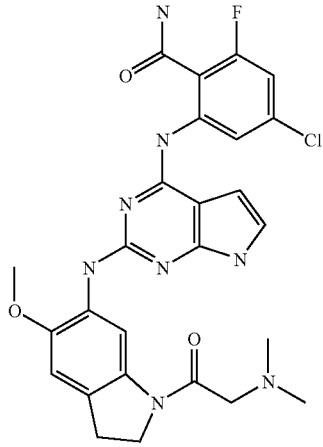

A suspension of 4-chloro-2-({2-chloro-7-[(4-methylphenyl)sulfonyl]-7H-pyrrolo[2,3-d]pyrimidin-4-yl}amino)-6-fluorobenzamide (0.450 g), 1-[(dimethylamino)acetyl]-5-(methyloxy)-2,3-dihydro-1H-indol-6-amine (0.260 g), potassium iodide (0.005 g), and hydrochloric acid as a 4.0M solution in dioxane (3 mL) in 2,2,2-trifluoroethanol (20 mL) was maintained at 80° C. in a pressure flask for 12 hours. The reaction was cooled, poured into saturated sodium bicarbonate (aq)/methylene chloride, and the organic layer was taken to a residue under reduced pressure and the derived solids triturated with diethyl ether to afford 10-chloro-5-{[1-(N,N-dimethylglycyl)-5-(methyloxy)-2,3-dihydro-1H-indol-6-yl]amino}-8-fluoro-3-[(4-methylphenyl)sulfonyl]-3,12-dihydro-7H-6I$^5$-pyrrolo[2',3':4,5]pyrimido[6,1-b]quinazolin-7-one (0.350 g) as an orange solid. Remaining filtrates were saved for the synthesis of 4-chloro-2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluoro-N-methylbenzamide below. The triturated solids were partitioned between tetrahydrofuran (30 mL) and 27% aqueous ammonium hydroxide (30 mL) and stirred vigorously for 24 hours. The solution was washed with brine/ethyl acetate, and the organic layer was dried over sodium sulfate, filtered, and taken to a residue under reduced pressure. The solids were dissolved in 1,4-dioxane (8 mL) and added to a microwave vial with 2.0N sodium hydroxide (8 mL). The mixture was maintained with rapid stirring under microwave irradiation at 120° C. for 8 minutes, cooled, poured into ethyl acetate/tetrahydrofuran/saturated sodium bicarbonate, and the organic layer was dried over sodium sulfate, taken to a residue under reduced pressure, and purified by chromatography on SiO$_2$ to afford 4-chloro-2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluorobenzamide (0.052 g); $^1$H NMR (400 MHz, DMSO-d$_6$) δ ppm 11.33 (s, 1H), 10.93 (s, 1H), 8.67 (s, 1H), 8.51 (s, 1H), 8.21 (s, 1H), 8.07 (s, 1H), 7.70 (s, 1H), 7.02 (dd, J=10.81, 2.02 Hz, 1H), 6.97-6.99 (m, 1H), 6.95 (s, 1H), 6.21 (dd, J=3.30, 1.83 Hz, 1H), 4.13 (t, J=8.62 Hz, 2H), 3.76 (s, 3H), 3.12 (s, 2H), 3.09 (t, J=8.60 Hz, 2H), 2.21 (s, 6H). ESIMS (M+H)+=553.

Example 120

4-chloro-2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluoro-N-methylbenzamide

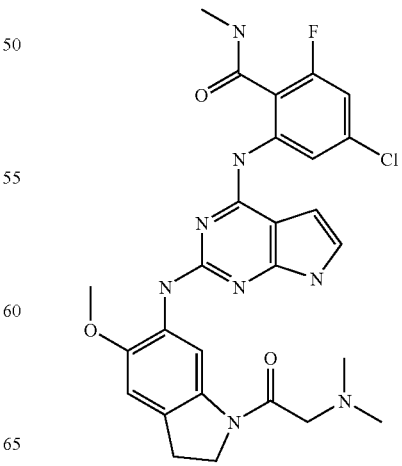

The residue obtained from concentration of the filtrates generated from the synthesis of 4-chloro-2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluorobenzamide above were dissolved in tetrahydrofuran (10 mL) and 2.0M methyl amine in THF (5 mL) was added. The resulting solution was stirred for 12 hours and then concentrated to a residue under reduced pressure. The solids were dissolved in 1,4-dioxane (8 mL) and added to a microwave vial with 2.0N sodium hydroxide (8 mL). The mixture was maintained with rapid stirring under microwave irradiation at 120° C. for 8 minutes, cooled, poured into ethyl acetate/tetrahydrofuran/saturated sodium bicarbonate, and the organic layer was dried over sodium sulfate, taken to a residue under reduced pressure, and purified by chromatography on $SiO_2$ to afford 4-chloro-2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluoro-N-methylbenzamide (0.078 g); $^1$H NMR (400 MHz, DMSO-$d_6$) δ ppm 11.31 (s, 1H), 10.53 (s, 1H), 8.62 (d, J=2.57 Hz, 1H), 8.49-8.56 (m, 2H), 7.67 (s, 1H), 7.05 (dd, J=10.26, 1.83 Hz, 1H), 6.96-7.00 (m, 1H), 6.95 (s, 1H), 6.21-6.28 (m, 1H), 4.13 (t, J=8.43 Hz, 2H), 3.76 (s, 3H), 3.13 (s, 2H), 3.09 (t, J=8.62 Hz, 2H), 2.80 (d, J=4.77 Hz, 3H), 2.21 (s, 6H). ESIMS (M+H)$^+$=567.

Example 121

2-fluoro-6-[(2-{[2-methyl-6-(methyloxy)-1,2,3,4-tetrahydro-7-isoquinolinyl]amino}-1H-pyrrolo[2,3-d]pyrimidin-4-yl)amino]benzamide

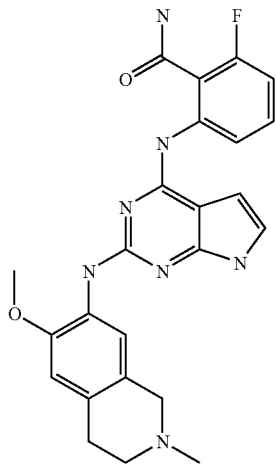

According to General Protocol III, 2-fluoro-6-[(2-{[2-methyl-6-(methyloxy)-1,2,3,4-tetrahydro-7-isoquinolinyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-6-fluorobenzamide (0.300 g), 27% aqueous ammonium hydroxide, and 2-methyl-6-(methyloxy)-1,2,3,4-tetrahydro-7-isoquinolinamine (0.165 g) and isolated as a yellow solid (0.094 g); $^1$H NMR (400 MHz, DMSO-$d_6$) δ ppm 11.34 (s, 1H), 10.38 (s, 1H), 8.36 (d, J=8.43 Hz, 1H), 8.07 (s, 1H), 7.99 (s, 1H), 7.92 (s, 1H), 7.38-7.47 (m, 1H), 6.98 (dd, J=3.67, 2.20 Hz, 1H), 6.95 (dd, J=10.63, 8.43 Hz, 1H), 6.72 (s, 1H), 6.25 (dd, J=3.67, 1.83 Hz, 1H), 3.80 (s, 3H), 3.35 (s, 2H), 2.76 (t, J=5.87 Hz, 2H), 2.56 (t, J=5.68 Hz, 2H), 2.32 (s, 3H). ESIMS (M+H)$^+$=462.

Example 122

2-fluoro-6-[(2-{[6-(methyloxy)-2-(1-propyl-4-piperidinyl)-1,2,3,4-tetrahydro-7-isoquinolinyl]amino}-1H-pyrrolo[2,3-d]pyrimidin-4-yl)amino]benzamide

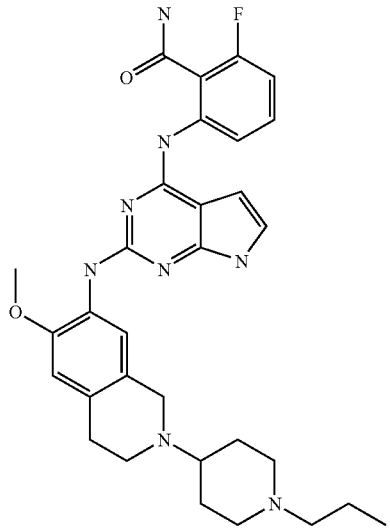

According to General Protocol III, 2-fluoro-6-[(2-{[6-(methyloxy)-2-(1-propyl-4-piperidinyl)-1,2,3,4-tetrahydro-7-isoquinolinyl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-6-fluorobenzamide (0.350 g), 27% aqueous ammonium hydroxide, and 6-(methyloxy)-2-(1-propyl-4-piperidinyl)-1,2,3,4-tetrahydro-7-isoquinolinamine (0.346 g) and isolated as a yellow solid (0.212 g); $^1$H NMR (400 MHz, DMSO-$d_6$) δ ppm 11.32 (s, 1H), 10.37 (s, 1H), 8.36 (d, J=8.43 Hz, 1H), 8.07 (s, 1H), 8.00 (s, 1H), 7.95 (s, 1H), 7.33-7.51 (m, 2H), 6.96-7.01 (m, 1H), 6.86-6.96 (m, 1H), 6.69 (s, 1H), 6.25 (dd, J=3.48, 2.02 Hz, 1H), 3.80 (s, 3H), 3.54 (s, 2H), 2.90 (d, J=11.00 Hz, 2H), 2.71 (s, 4H), 2.27-2.37 (m, 1H), 2.20 (t, J=6.97 Hz, 2H), 1.85 (t, J=12.83 Hz, 2H), 1.77 (d, J=10.63 Hz, 2H), 1.33-1.57 (m, 4H), 0.84 (t, J=7.33 Hz, 3H). ESIMS (M+H)$^+$=573.

Example 123

2-[(2-{[2-(N,N-dimethylglycyl)-6-(methyloxy)-1,2,3,4-tetrahydro-7-isoquinolinyl]amino}-1H-pyrrolo[2,3-d]pyrimidin-4-yl)amino]-6-fluorobenzamide

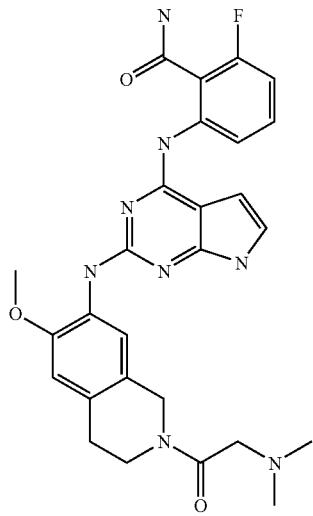

According to General Protocol III, 2-[(2-{[2-(N,N-dimethylglycyl)-6-(methyloxy)-1,2,3,4-tetrahydro-7-isoquinolinyl]amino}-1H-pyrrolo[2,3-d]pyrimidin-4-yl)amino]-6-fluorobenzamide was prepared from 2-({2-chloro-7-[(4-methylphenyl)sulfonyl]-7H-pyrrolo[2,3-d]pyrimidin-4-yl}amino)-6-fluorobenzamide (0.300 g), 27% aqueous ammonium hydroxide, and 2-[(dimethylamino)acetyl]-6-(methyloxy)-1,2,3,4-tetrahydro-7-isoquinolinamine (0.214 g) and isolated as a yellow solid (0.125 g); $^1$H 80° C. NMR (400 MHz, DMSO-$d_6$) δ ppm 11.20 (s, 1H), 10.41 (s, 1H), 8.39 (d, J=8.43 Hz, 1H), 8.14 (s, 1H), 7.80 (s, 2H), 7.48 (q, J=7.82 Hz, 1H), 7.39 (s, 1H), 6.98 (s, 1H), 6.86-6.96 (m, 1H), 6.80 (s, 1H), 6.28 (d, J=1.83 Hz, 1H), 4.53 (s, 2H), 3.85 (s, 3H), 3.73 (s, 2H), 3.32-3.44 (m, 1H), 2.81 (s, 2H), 2.22 (s, 6H), 1.09 (t, J=6.23 Hz, 1H). Many Broad/Featureless peaks due to rotameric constituents. ESIMS (M+H)$^+$=533.

Example 124

3-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-2-naphthalenecarboxamide

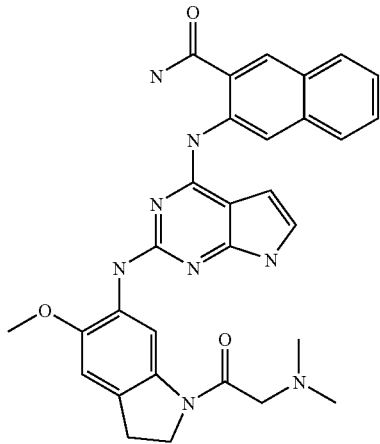

According to General Protocol III, 3-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-2-naphthalenecarboxamide was prepared from 3-({2-chloro-7-[(4-methylphenyl)sulfonyl]-7H-pyrrolo[2,3-d]pyrimidin-4-yl}amino)-2-naphthalenecarboxamide (0.300 g), 27% aqueous ammonium hydroxide, and 1-[(dimethylamino)acetyl]-5-(methyloxy)-2,3-dihydro-1H-indol-6-amine (0.175 g) and isolated as a yellow solid (0.073 g). Filtrates generated following trituration of 5-{[1-(N,N-dimethylglycyl)-5-(methyloxy)-2,3-dihydro-1H-indol-6-yl]amino}-3,14-dihydro-7H-6l$^5$-benzo[g]pyrrolo[2',3':4,5]pyrimido[6,1-b]quinazolin-7-one were saved and used below; $^1$H NMR (400 MHz, DMSO-$d_6$) δ ppm 11.77 (s, 1H), 11.21 (s, 1H), 9.28 (s, 1H), 8.58 (s, 1H), 8.49 (s, 1H), 8.36 (s, 1H), 7.87 (s, 1H), 7.76 (d, J=8.06 Hz, 1H), 7.68 (s, 1H), 7.47-7.55 (m, 1H), 7.41 (d, J=8.06 Hz, 1H), 7.34 (t, J=7.33 Hz, 1H), 6.98 (s, 1H), 6.89-6.95 (m, 1H), 6.25 (dd, J=3.11, 1.83 Hz, 1H), 4.16 (t, J=8.33 Hz, 2H), 3.75 (s, 3H), 3.17 (t, J=8.24 Hz, 2H), 2.98 (s, 2H), 1.99 (s, 6H). ESIMS (M+H)$^+$=551.

Example 125

3-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-N-methyl-2-naphthalenecarboxamide

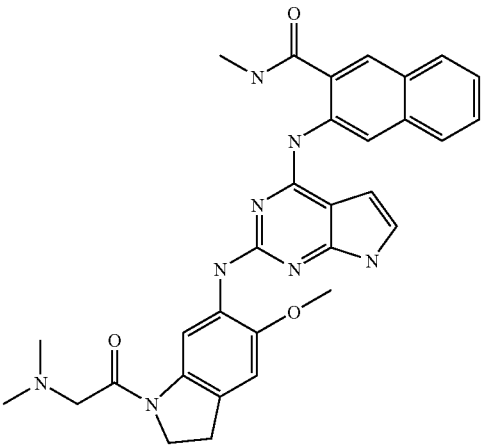

Filtrates containing 5-{[1-(N,N-dimethylglycyl)-5-(methyloxy)-2,3-dihydro-1H-indol-6-yl]amino}-3,14-dihydro-7H-6l$^5$-benzo[g]pyrrolo[2',3':4,5]pyrimido[6,1-b]quinazolin-7-one (generated above) were taken to a residue under reduced pressure, redissolved in tetrahydrofuran, and 2.0M methyl amine in tetrahydrofuran (5 mL) was added. The solution was stirred for 12 hours and all solids were evaporated under reduced pressure to generate crude 3-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-N-methyl-2-naphthalenecarboxamide of sufficient purity for direct use in the subsequent transformations. To a solution of 3-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-N-methyl-2-naphthalenecarboxamide (100 mg, 0.139 mmol) in MeOH/THF (1:1, 10 mL) was added sodium methoxide (113 mg, 2.087 mmol). The resulting solution was warmed to 80° C. for 45 minutes, cooled to room temperature, and poured into saturated aqueous NaCl (50 mL) and diluted with ethyl acetate (25 mL). The organic layer was dried over solid sodium sulfate, filtered, stripped onto celite, and purified by chromatography on SiO$_2$ to give 3-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-N-methyl-2-naphthalenecarboxamide as a yellow solid (0.055 g); $^1$H NMR (400 MHz, DMSO-$d_6$) δ ppm 11.42 (s, 1H), 11.20 (s, 1H), 9.22 (s, 1H), 8.89-9.00 (m, 1H), 8.58 (s, 1H), 8.26 (s, 1H), 7.78 (d, J=8.06 Hz, 1H), 7.66 (s, 1H), 7.46-7.54 (m, 1H), 7.40-7.46 (m, 1H), 7.34 (t, J=7.42 Hz, 1H), 6.98 (s, 1H), 6.90-6.95 (m, 1H), 6.28 (dd, J=3.02, 1.74 Hz, 1H), 4.16 (t, J=8.33 Hz, 2H), 3.74 (s, 3H), 3.16 (t, J=8.42 Hz, 2H), 2.97 (s, 2H), 2.85 (d, J=4.58 Hz, 3H), 2.00 (s, 6H). ESIMS (M+H)$^+$=565.

Example 126

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-N-ethyl-6-fluorobenzamide

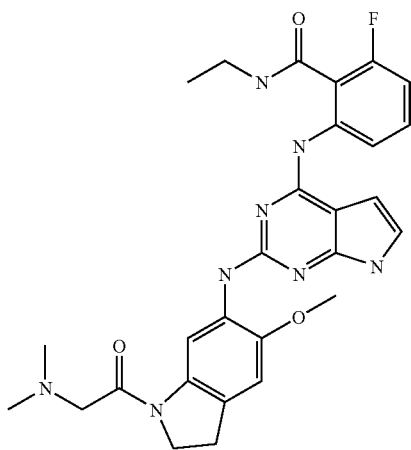

Two separate suspensions of 2-({2-chloro-7-[(4-methylphenyl)sulfonyl]-7H-pyrrolo[2,3-d]pyrimidin-4-yl}amino)-6-fluorobenzamide (6.25 g, 13.59 mmol), 1-[(dimethylamino)acetyl]-5-(methyloxy)-2,3-dihydro-1H-indol-6-amine (3.90 g, 15.63 mmol), KI (2.256 g, 13.59 mmol), and HCl (4.0M Solution in dioxane, 13.59 ml, 54.4 mmol) in 2,2,2-trifluoroethanol (200 ml) were warmed at 90° C. for 16 hours in sealed pressure flasks. The reactions were cooled, combined, and poured into dichloromethane/saturated sodium bicarbonate and the organic layers taken to a residue under reduced pressure and triturated with diethyl ether to afford 5-{[1-(N,N-dimethylglycyl)-5-(methyloxy)-2,3-dihydro-1H-indol-6-yl]amino}-8-fluoro-3-[(4-methylphenyl)sulfonyl]pyrrolo[2',3':4,5]pyrimido[6,1-b]quinazolin-7(3H)-one (15 g, 22.9 mmol, 84%). A solution of the 5-{[1-(N,N-dimethylglycyl)-5-(methyloxy)-2,3-dihydro-1H-indol-6-yl]amino}-8-fluoro-3-[(4-methylphenyl)sulfonyl]pyrrolo[2',3':4,5]pyrimido[6,1-b]quinazolin-7(3H)-one (500 mg, 0.763 mmol) and 2.0M ethylamine in tetrahydrofuran (2.67 ml, 5.34 mmol) in THF(10 ml) was stirred at room temperature for 16 hours. The crude reaction mixture was stripped onto celite and purified by chromatography on SiO$_2$ to afford 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-N-ethyl-6-fluorobenzamide (275 mg, 0.392 mmol, 51.5%) as a pale brown solid. A suspension of 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-N-ethyl-6-fluorobenzamide (0.275 g, 0.392 mmol) in 1,4 dioxane/2.0 N NaOH was heated at 120° C. for 11 minutes in a microwave. The resulting solution was poured into ethyl acetate/saturated sodium chloride and the organic layer was dried over sodium sulfate, filtered, stripped onto celite, and purified by chromatography to afford 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-N-ethyl-6-fluorobenzamide (150 mg, 0.274 mmol, 70%). $^1$H NMR (400 MHz, DMSO-d$_6$) δ ppm 11.21 (s, 1H), 9.91 (s, 1H), 8.59 (s, 1H), 8.55 (t, J=5.77 Hz, 1H), 8.27 (d, J=8.42 Hz, 1H), 7.52 (s, 1H), 7.20-7.34 (m, 1H), 6.87-6.95 (m, 2H), 6.84 (d, J=9.34 Hz, 1H), 6.22 (s, 1H), 4.13 (t, J=8.42 Hz, 2H), 3.73 (s, 3H), 3.18-3.26 (m, 2H), 3.13 (s, 2H), 3.07 (t, J=8.24 Hz, 2H), 2.21 (s, 6H), 0.97-1.13 (m, 3H). ESIMS (M+H)$^+$=547.

Example 127

2-[(2-{[1-(N,N-dimethylglycyl)-3,3-dimethyl-5-(methyloxy)-2,3-dihydro-1H-indol-6-yl]amino}-1H-pyrrolo[2,3-d]pyrimidin-4-yl)amino]-6-fluoro-N-methylbenzamide

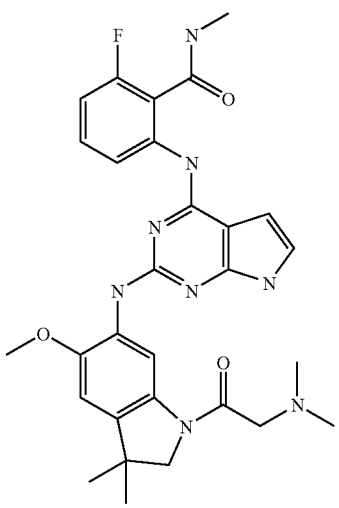

A solution of 5-chloro-8-fluoro-3-[(4-methylphenyl)sulfonyl]pyrrolo[2',3':4,5]pyrimido[6,1-b]quinazolin-7(3H)-one hydrogen chloride (500 mg, 1.043 mmol) and 1-[(dimethylamino)acetyl]-3,3-dimethyl-5-(methyloxy)-2,3-dihydro-1H-indol-6-amine (333 mg, 1.200 mmol) in THF (8 ml) was warmed to 75° C. in a sealed pressure vial for 16 hours. The solution was concentrated under reduced pressure, suspended in dichloromethane, and washed with saturated sodium bicarbonate. The organic layer was taken to a residue under reduced pressure and triturated with diethyl ether to afford 5-{[1-(N, N-dimethylglycyl)-3,3-dimethyl-5-(methyloxy)-2,3-dihydro-1H-indol-6-yl]amino}-8-fluoro-3-[(4-methylphenyl)sulfonyl]pyrrolo[2',3':4,5]pyrimido[6,1-b]quinazolin-7(3H)-one (0.472 g, 0.690 mmol, 66.2%) as a pale greenish yellow solid. A solution of 5-{[1-(N,N-dimethylglycyl)-3,3-dimethyl-5-(methyloxy)-2,3-dihydro-1H-indol-6-yl]amino}-8'-fluoro-3-[(4-methylphenyl)sulfonyl]pyrrolo[2',3':4,5]pyrimido[6,1-b]quinazolin-7(3H)-one (0.472 g, 0.690 mmol) and 2.0M methyl amine in THF (2.76 ml, 5.52 mmol) in THF (40 ml) was stirred for 3 hours at room temperature. The reaction was poured into saturated sodium bicarbonate and diluted with ethyl acetate. The organic layer was dried over sodium sulfate, filtered, taken to a residue under reduced pressure, redissolved in 1,4-dioxane (8 ml) and added to a microwave-safe vial with 2.0N NaOH (aq) (8 ml). The contents were warmed to 120° C. under microwave irradiation with rapid stirring for 12 minutes, cooled to room temperature, and poured into THF/ethyl acetate/saturated/sodium bicarbonate (aq). The organic layer was dried over sodium sulfate, filtered, stripped onto celite, and purified by column chromatography to afford 2-[(2-{[1-(N,N-dimethylglycyl)-3,3-dimethyl-5-(methyloxy)-2,3-dihydro-1H-indol-6-yl]amino}-1H-pyrrolo[2,3-d]pyrimidin-4-yl)amino]-6-fluoro-N-methylbenzamide (0.202 g, 0.360 mmol, 52.2%) as a white solid. ¹H NMR (400 MHz, DMSO-d₆) δ ppm 11.26 (s, 1H), 10.14 (s, 1H), 8.56 (s, 1H), 8.54 (d, J=4.61 Hz, 1H), 8.34 (d, J=8.43 Hz, 1H), 7.58 (s, 1H), 7.25-7.35 (m, 1H), 6.93-7.00 (m, 2H), 6.85-6.93 (m, 1H), 6.21-6.32 (m, 1H), 3.93 (s, 2H), 3.79 (s, 3H), 3.17 (s, 2H), 2.79 (d, J=4.41 Hz, 3H), 2.24 (s, 6H), 1.32 (s, 6H). ESIMS (M+H)⁺=561.

Example 128

2-fluoro-N-methyl-6-[(2-{[5-(methyloxy)-1-(1-methyl-L-prolyl)-2,3-dihydro-1H-indol-6-yl]amino}-1H-pyrrolo[2,3-d]pyrimidin-4-yl)amino]benzamide

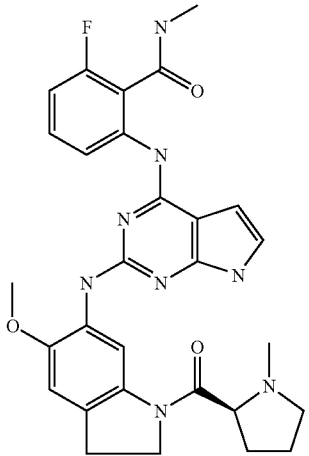

A suspension of 5-chloro-8-fluoro-3-[(4-methylphenyl)sulfonyl]pyrrolo[2',3':4,5]pyrimido[6,1-b]quinazolin-7(3H)-one hydrogen chloride (550 mg, 1.147 mmol) and 5-(methyloxy)-1-(1-methyl-L-prolyl)-2,3-dihydro-1H-indol-6-amine (363 mg, 1.320 mmol) in 2,2,2-trifluoroethanol (50 ml) was maintained at 90° C. for 2 hours. The solution was cooled, poured into dichloromethane/saturated sodium bicarbonate, and the organic layer was taken to a residue under reduced pressure. Trituration with diethyl ether affords 8-fluoro-5-{[5-(methyloxy)-1-(1-methyl-L-prolyl)-2,3-dihydro-1H-indol-6-yl]amino}-3-[(4-methylphenyl)sulfonyl]pyrrolo[2',3':4,5]pyrimido[6,1-b]quinazolin-7(3H)-one (0.390 g, 0.572 mmol, 49.9%) as a pale yellow solid contaminated with 25% of the corresponding ring-openeed trifluoroethyl ester. This mixture (0.390 g, 0.572 mmol) was directly dissolved in tetrahydrofuran (50 ml) and 2.0M MeNH₂ in THF (2.86 ml, 5.72 mmol) was added. The resulting solution was stirred at room temperature for 6 hours. The reaction was diluted with ethyl acetate, washed with saturated sodium bicarbonate (aq) and the organic layer was dried over sodium sulfate, filtered, and taken to a residue under reduced pressure. The residue was dissolved in 1,4-dioxane (8 ml)/2.0 N NaOH (aq) (8 ml) and maintained at 120° C. under microwave heating for 12 minutes. The vial was cooled and its contents were diluted with THF/EtOAc/saturated sodium chloride (aq). The organic layer was dried over sodium sulfate, filtered, stripped onto celite, and purified by column chromatography to afford 2-fluoro-N-methyl-6-[(2-{[5-(methyloxy)-1-(1-methyl-L-prolyl)-2,3-dihydro-1H-indol-6-yl]amino}-1H-pyrrolo[2,3-d]pyrimidin-4-yl)amino]benzamide (0.096 g, 0.172 mmol, 30.0%) as a grey solid. ¹H NMR (400 MHz, DMSO-d₆) δ ppm 11.27 (s, 1H), 10.14 (s, 1H), 8.69 (s, 1H), 8.55 (s, 1H), 8.35 (d, J=8.63 Hz, 1H), 7.55 (s, 1H), 7.26-7.38 (m, 1H), 6.92-6.99 (m, 2H), 6.83-6.92 (m, 1H), 6.28 (dd, J=3.31, 1.91 Hz, 1H), 4.07-4.30 (m, 2H), 3.77 (s, 3H), 3.18-3.27 (m, 1H), 3.07-3.16 (m, 2H), 2.93-3.04 (m, 1H), 2.80 (d, J=4.61 Hz, 3H), 2.26 (s, 3H), 2.11-2.21 (m, 1H), 1.77 (m, 4H). ESIMS (M+H)⁺=559.

Example 129

2-fluoro-N-methyl-6-[(2-{[5-(methyloxy)-1-(1-methyl-D-prolyl)-2,3-dihydro-1H-indol-6-yl]amino}-1H-pyrrolo[2,3-d]pyrimidin-4-yl)amino]benzamide

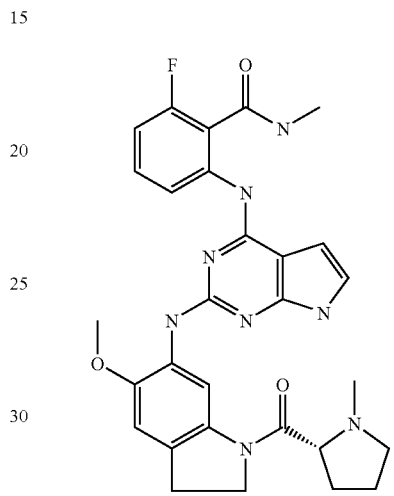

A suspension of 5-chloro-8-fluoro-3-[(4-methylphenyl)sulfonyl]pyrrolo[2',3':4,5]pyrimido[6,1-b]quinazolin-7(3H)-one hydrogen chloride (550 mg, 1.147 mmol) and 5-(methyloxy)-1-(1-methyl-D-prolyl)-2,3-dihydro-1H-indol-6-amine (363 mg, 1.320 mmol) in 2,2,2-trifluoroethanol (50 ml) was maintained at 80° C. for 2 hours. The solution was cooled, poured into saturated sodium bicarbonate/dichloromethane, and the organic layer was taken to a residue under reduced pressure. The residue was triturated with diethyl ether to afford 8-fluoro-5-{[5-(methyloxy)-1-(1-methyl-D-prolyl)-2,3-dihydro-1H-indol-6-yl]amino}-3-[(4-methylphenyl)sulfonyl]pyrrolo[2',3':4,5]pyrimido[6,1-b]quinazolin-7(3H)-one (425 mg, 0.623 mmol, 54.3%) as a pale yellow solid. To a solution of 8-fluoro-5-{[5-(methyloxy)-1-(1-methyl-D-prolyl)-2,3-dihydro-1H-indol-6-yl]amino}-3-[(4-methylphenyl)sulfonyl]pyrrolo[2',3':4,5]pyrimido[6,1-b]quinazolin-7(3H)-one (425 mg, 0.623 mmol) in tetrahydrofuran (50 ml) was added 2.0M MeNH₂ in THF (3.12 ml, 6.23 mmol) and the resulting solution was stirred at room temperature for 6 hours. The reaction was diluted with ethyl acetate, washed with saturated sodium bicarbonate (aq) and the organic layer was dried over sodium sulfate, filtered, and taken to a residue under reduced pressure. The residue was dissolved in 1,4-dioxane (8 ml)/2.0 N NaOH (aq) (8 ml) and maintained at 120° C. under microwave heating for 12 minutes. The vial was cooled and its contents were diluted with THF/EtOAc/saturated sodium chloride (aq). The organic layer was dried over sodium sulfate, filtered, stripped onto celite, and purified by column chromatography to afford 2-fluoro-N-methyl-6-[(2-{[5-(methyloxy)-1-(1-methyl-D-prolyl)-2,3-dihydro-1H-indol-6-yl]amino}-1H-pyrrolo[2,3-d]pyrimidin-4-yl)amino]benzamide (0.205 g, 0.367 mmol, 58.9%) as a grey solid. ¹H NMR (400 MHz, DMSO-d₆) δ ppm 11.27 (s, 1H), 10.15 (s, 1H), 8.69 (s, 1H), 8.55 (s, 1H), 8.35 (d, J=8.43 Hz, 1H), 7.55 (s, 1H), 7.22-7.38 (m, 1H), 6.92-6.97 (m, 2H), 6.88 (t, J=9.30 Hz, 1H), 6.28 (dd, J=3.51, 1.91 Hz, 1H), 4.08-4.26 (m, 2H), 3.78 (s, 3H), 3.17-3.23 (m, 1H), 3.12 (t, J=7.62 Hz, 2H), 2.93-3.04 (m, 1H), 2.80 (d, J=4.21 Hz, 3H), 2.26 (s, 3H), 2.11-2.22 (m, 1H), 1.70-1.85 (m, 4H). ESIMS (M+H)$^+$=559.

Example 130

2-[(2-{[1-(N,N-dimethylglycyl)-2,3-dihydro-1H-indol-6-yl]amino}-1H-pyrrolo[2,3-d]pyrimidin-4-yl)amino]-6-fluoro-N-methylbenzamide

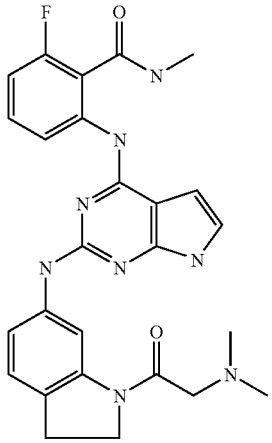

A suspension of 5-chloro-8-fluoro-3-[(4-methylphenyl)sulfonyl]pyrrolo[2',3':4,5]pyrimido[6,1-b]quinazolin-7(3H)-one hydrogen chloride (0.600 g, 1.252 mmol) and 1-[(dimethylamino)acetyl]-2,3-dihydro-1H-indol-6-amine (0.274 g, 1.252 mmol) was maintained at 70° C. in tetrahydrofuran (20 ml) in a pressure tube for 16 hours. The reaction was cooled, opened, concentrated under reduced pressure, and redissolved in methylene chloride/2,2,2-trifluoroethanol (ca 15 mL). Saturated sodium bicarbonate was added and all solids dissolve. The organic layer was dried over sodium sulfate, filtered, taken to a residue under reduced pressure, and triturated with diethyl ether to afford 5-{[1-(N,N-dimethylglycyl)-2,3-dihydro-1H-indol-6-yl]amino}-8-fluoro-3-[(4-methylphenyl)sulfonyl]pyrrolo[2',3':4,5]pyrimido[6,1-b]quinazolin-7(3H)-one (0.696 g, 1.112 mmol, 89%) as a yellow solid. A suspension of 5-{[1-(N,N-dimethylglycyl)-2,3-dihydro-1H-indol-6-yl]amino}-8-fluoro-3-[(4-methylphenyl)sulfonyl]pyrrolo[2',3':4,5]pyrimido[6,1-b]quinazolin-7(3H)-one (0.696 g, 1.112 mmol) in tetrahydrofuran (20 ml) was treated with 2.0M methyl amine/THF (3.34 ml, 6.67 mmol) and over 24 hours all solids dissolve. The solution was poured into saturated sodium bicarbonate/EtOAc and the organic layer was dried over sodium sulfate, filtered, and taken to a residue under reduced pressure. The residue was dissolved in 1,4-dioxane (8 ml)/2.0N NaOH (aq) (8 ml) and maintained at 120° C. under microwave heating for 12 minutes. The solution was cooled, poured into ethyl acetate/THF/saturated sodium chloride (aq) and the organic layer was dried over sodium sulfate, filtered, stripped onto celite, and purified by column chromatography to afford 2-[(2-{[1-(N,N-dimethylglycyl)-2,3-dihydro-1H-indol-6-yl]amino}-1H-pyrrolo[2,3-d]pyrimidin-4-yl)amino]-6-fluoro-N-methylbenzamide (0.230 g, 0.458 mmol, 41.1%) as a yellow solid. $^1$H NMR (400 MHz, DMSO-d$_6$) δ ppm 11.33 (s, 1H), 10.20 (s, 1H), 8.89 (s, 1H), 8.54 (d, J=7.62 Hz, 1H), 8.21 (s, 1H), 7.83 (d, J=7.22 Hz, 1H), 7.34-7.48 (m, 1H), 7.10 (d, J=8.23 Hz, 1H), 6.85-7.01 (m, 3H), 6.29 (dd, J=3.41, 1.81 Hz, 1H), 4.15 (t, J=8.23 Hz, 2H), 3.21 (s, 2H), 2.99-3.12 (m, 2H), 2.79 (d, J=4.61 Hz, 3H), 2.27 (s, 6H). ESIMS (M+H)$^+$=503.

Example 131

2-[(2-{[5-chloro-1-(N,N-dimethylglycyl)-2,3-dihydro-1H-indol-6-yl]amino}-1H-pyrrolo[2,3-d]pyrimidin-4-yl)amino]-6-fluoro-N-methylbenzamide

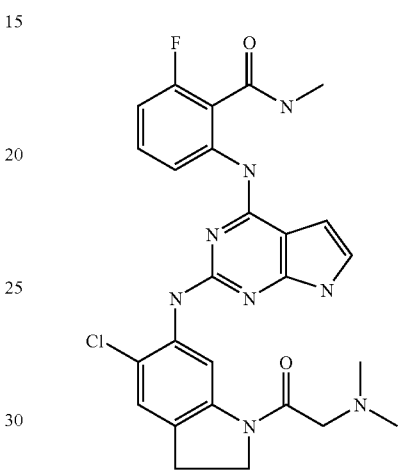

A suspension of 5-chloro-8-fluoro-3-[(4-methylphenyl)sulfonyl]pyrrolo[2',3':4,5]pyrimido[6,1-b]quinazolin-7(3H)-one hydrogen chloride (0.550 g, 1.147 mmol) and 5-chloro-1-[(dimethylamino)acetyl]-2,3-dihydro-1H-indol-6-amine (0.291 g, 1.147 mmol) in tetrahydrofuran (20 ml) was maintained at 80° C. in a pressure vessel for 16 hours. The vessel was cooled, THF removed under reduced pressure, and the solids were partitioned between methylene chloride/trifluoroethanol/saturated sodium bicarbonate. The organic layer was taken to a residue under reduced pressure and triturated with diethyl ether to afford 5-{[5-chloro-1-(N,N-dimethylglycyl)-2,3-dihydro-1H-indol-6-yl]amino}-8-fluoro-3-[(4-methylphenyl)sulfonyl]pyrrolo[2',3':4,5]pyrimido[6,1-b]quinazolin-7(3H)-one (0.550 g, 0.833 mmol, 72.6%) as a reasonably pure (ca 70-80%) green solid. A solution of 5-{[5-chloro-1-(N,N-dimethylglycyl)-2,3-dihydro-1H-indol-6-yl]amino}-8-fluoro-3-[(4-methylphenyl)sulfonyl]pyrrolo[2',3':4,5]pyrimido[6,1-b]quinazolin-7(3H)-one (0.550 g, 0.833 mmol) and 2.0M methyl amine/THF (2.500 ml, 5.00 mmol) in tetrahydrofuran (20 ml) was stirred at room temperature for 5 hours. The reaction was stripped directly onto celite and purified by column chromatography to afford the intermediate tosylate as a yellow foam. This intermediate was dissolved in 1,4-dioxane (8 ml) and added to a microwave vial with 2.0N NaOH (aq) (8 ml). Microwave heating at 120° C. for 12 minutes was followed by cooling, dilution with ethyl acetate/saturated sodium bicarbonate/THF and the resulting organic layer was dried over sodium sulfate, filtered, stripped onto celite, and purified by column chromatography to afford 2-[(2-{[5-chloro-1-(N,N-dimethylglycyl)-2,3-dihydro-1H-indol-6-yl]amino}-1H-pyrrolo[2,3-d]pyrimidin-4-yl)amino]-6-fluoro-N-methylbenzamide (0.068 g) as a pale yellow solid. $^1$H NMR (400 MHz, DMSO-d$_6$) δ ppm 11.31 (s, 1H), 10.19 (s, 1H), 8.52 (s, 1H), 8.39 (s, 1H), 8.32 (d, J=8.63 Hz, 1H), 8.15 (s, 1H), 7.33 (s, 1H), 7.20-7.30 (m, 1H), 6.92-6.97 (m, J=3.01 Hz, 1H), 6.83-6.92 (m, 1H), 6.26 (dd, J=3.41, 1.81 Hz, 1H), 4.21 (t, J=8.43 Hz, 2H), 3.20 (s, 2H), 3.09-3.17 (m, 2H), 2.80 (d, J=4.61 Hz, 3H), 2.24 (s, 6H). ESIMS (M+H)+=537.

Example 132

2-[(2{-[1-(N-ethyl-N-methylglycyl)-6-(methyloxy)-1,2,3,4-tetrahydro-7-quinolinyl]amino}-1H-pyrrolo[2,3-d]pyrimidin-4-yl)amino]-6-fluoro-N-methylbenzamide

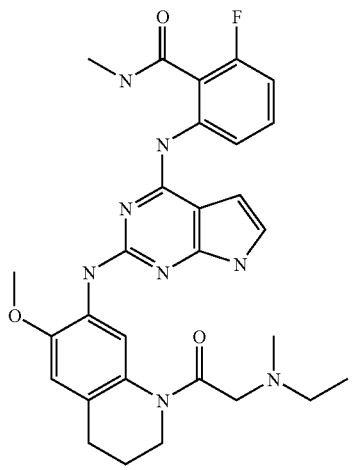

A solution of 5-chloro-8-fluoro-3-[(4-methylphenyl)sulfonyl]pyrrolo[2',3':4,5]pyrimido[6,1-b]quinazolin-7(3H)-one hydrogen chloride (500 mg, 1.043 mmol) and 1-{[ethyl(methyl)amino]acetyl}-6-(methyloxy)-1,2,3,4-tetrahydro-7-quinolinamine (289 mg, 1.043 mmol) in 2,2,2-trifluoroethanol (10 ml) was warmed to 90° C. in a pressure flask and maintained for 3 hours. The vial was cooled and its contents poured into saturated sodium bicarbonate/methylene chloride. The organic layer was dried over sodium sulfate, filtered, and taken to a residue under reduced pressure. The residue was triturated with diethyl ether to afford a yellow solid (ca 310 mg). The solid was suspended in tetrahydrofuran (100 ml) and 2.0M methyl amine in THF (5.22 ml, 10.43 mmol) was added. The solution was stirred for 16 hours and concentrated to a solid under reduced pressure to afford 2-({2-{[1-(N-ethyl-N-methylglycyl)-6-(methyloxy)-1,2,3,4-tetrahydro-7-quinolinyl]amino}-7-[(4-methylphenyl)sulfonyl]-7H-pyrrolo[2,3-d]pyrimidin-4-yl}amino)-6-fluoro-N-methylbenzamide (310 mg, 0.434 mmol, 41.6%) as a yellow solid. A solution of 2-({2-{[1-(N-ethyl-N-methylglycyl)-6-(methyloxy)-1,2,3,4-tetrahydro-7-quinolinyl]amino}-7-[(4-methylphenyl)sulfonyl]-7H-pyrrolo[2,3-d]pyrimidin-4-yl}amino)-6-fluoro-N-methylbenzamide (310 mg, 0.434 mmol) in 1,4-dioxane (8.00 ml) was added to a microwave vial along with 2.0N NaOH (aq) (8 ml). The vial was sealed and contents warmed at 120° C. for 12 minutes. The reaction was cooled, opened, and poured into ethyl acetate/THF/saturated sodium chloride. The organic layer was dried over sodium sulfate, filtered, stripped onto celite, and purified by column chromatography to afford 2-[(2-{[1-(N-ethyl-N-methylglycyl)-6-(methyloxy)-1,2,3,4-tetrahydro-7-quinolinyl]amino}-1H-pyrrolo[2,3-d]pyrimidin-4-yl)amino]-6-fluoro-N-methylbenzamide (0.085 g, 0.152 mmol, 35.0%) as a pale violet solid. 1H NMR (400 MHz, DMSO-d6) δ ppm 11.34 (s, 1H), 10.06 (s, 1H), 8.49 (d, J=4.21 Hz, 1H), 8.38 (s, 1H), 8.20 (d, J=8.24 Hz, 1H), 7.45 (s, 1H), 7.27-7.39 (m, 1H), 6.86-6.99 (m, 2H), 6.78 (s, 1H), 6.26 (s, 1H), 3.80 (s, 3H), 3.66 (t, J=5.31 Hz, 2H), 3.27 (s, 2H), 2.74 (d, J=4.39 Hz, 3H), 2.62 (s, 2H), 2.28 (s, 2H), 2.06 (s, 3H), 1.71-1.89 (m, 2H), 0.74 (s, 3H). ESIMS (M+H)+=561.

Example 133

2-[(2-{[1-(N,N-dimethylglycyl)-6-(ethyloxy)-1,2,3,4-tetrahydro-7-quinolinyl]amino}-1H-pyrrolo[2,3-d]pyrimidin-4-yl)amino]-6-fluoro-N-methylbenzamide

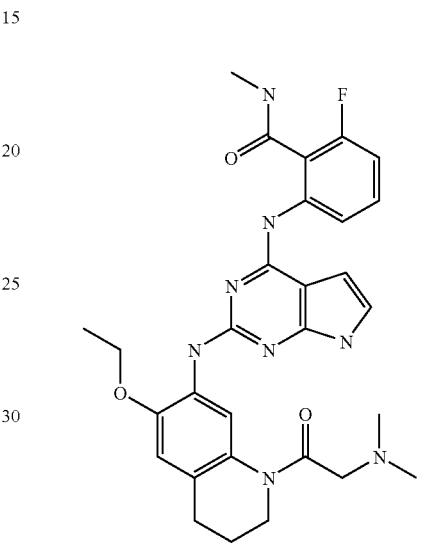

A suspension of 5-chloro-8-fluoro-3-[(4-methylphenyl)sulfonyl]pyrrolo[2',3':4,5]pyrimido[6,1-b]quinazolin-7(3H)-one (550 mg, 1.147 mmol) and 1-[(dimethylamino)acetyl]-6-(ethyloxy)-1,2,3,4-tetrahydro-7-quinolinamine (318 mg, 1.147 mmol) in tetrahydrofuran (30 mL) was stirred at 75° C. in a pressure vessel for 16 hours. All volatiles were removed and the solids were partitioned between dichloromethane and saturated sodiuim bicarbonate. The organic layer was taken to a residue under reduced pressure and the derived solids were triturated with diethyl ether to afford 5-{[1-(N,N-dimethylglycyl)-6-(ethyloxy)-1,2,3,4-tetrahydro-7-quinolinyl]amino}-8-fluoro-3-[(4-methylphenyl)sulfonyl]pyrrolo[2',3':4,5]pyrimido[6,1-b]quinazolin-7(3H)-one (548 mg, 0.801 mmol, 69.8%) as a yellow solid. A solution of 5-{[1-(N,N-dimethylglycyl)-6-(ethyloxy)-1,2,3,4-tetrahydro-7-quinolinyl]amino}-8-fluoro-3-[(4-methylphenyl)sulfonyl]pyrrolo[2',3':4,5]pyrimido[6,1-b]quinazolin-7(3H)-one (0.548 g, 0.801 mmol) in tetrahydrofuran (50 ml) was treated with methylamine in THF (2.0M) (3.21 ml, 6.41 mmol) and stirred for 16 hours. Celite was added, all volatiles were removed under reduced pressure, and the residue was purified via column chromatography to afford 2-({2-{[1-(N,N-dimethylglycyl)-6-(ethyloxy)-1,2,3,4-tetrahydro-7-quinolinyl]amino}-7-[(4-methylphenyl)sulfonyl]-7H-pyrrolo[2,3-d]pyrimidin-4-yl}amino)-6-fluoro-N-methylbenzamide (310 mg) The tosylate was dissolved in 1,4-dioxane (8 ml)/2.0N NaOH (aq) (8 ml), added to a microwave vial, and warmed under microwave heating at 120° C. for 12 minutes. The reaction was cooled, diluted with ethyl acetate/saturated sodium chloride (aq), and the organic layer was dried over sodium sulfate, filtered, stripped onto celite, and purified by column chromatography to afford 2-[(2-{[1-(N,N-dimethylglycyl)-6-(ethyloxy)-1,2,3,4-tetrahydro-7-quinolinyl]amino}-1H-pyrrolo[2,3-d]pyrimidin-4-yl)amino]-6-fluoro-N-methylbenzamide (0.110 g, 0.196 mmol, 24.48%) as a white solid. $^1$H NMR (400 MHz, DMSO-$d_6$) δ ppm 11.37 (s, 1H), 10.10 (s, 1H), 8.47-8.57 (m, 1H), 8.42 (s, 1H), 8.24 (d, J=6.82 Hz, 1H), 7.45 (s, 1H), 7.30-7.42 (m, 1H), 6.99 (d, J=3.01 Hz, 1H), 6.89-6.98 (m, 1H), 6.81 (s, 1H), 6.29 (dd, J=3.41, 1.81 Hz, 1H), 4.03-4.17 (m, 2H), 3.70 (t, J=6.72 Hz, 2H), 3.20 (s, 2H), 2.79 (d, J=4.41 Hz, 3H), 2.61-2.70 (m, 2H), 2.09 (t, J=9.43 Hz, 6H), 1.77-1.92 (m, 2H), 1.37 (t, J=6.82 Hz, 3H). ESIMS (M+H)$^+$= 561.

Example 134

2-[(2-{[1-acetyl-5-(methyloxy)-2,3-dihydro-1H-indol-6-yl]amino}-1H-pyrrolo[2,3-d]pyrimidin-4-yl)amino]-6-fluorobenzamide.

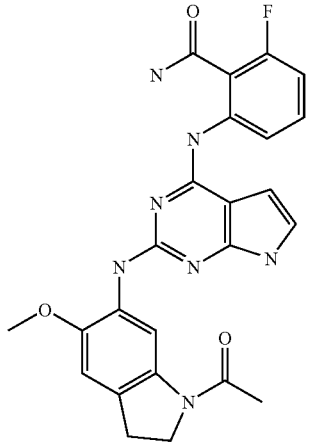

Step A/Intermediate D7: 2-({2-{[1-acetyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluorobenzamide

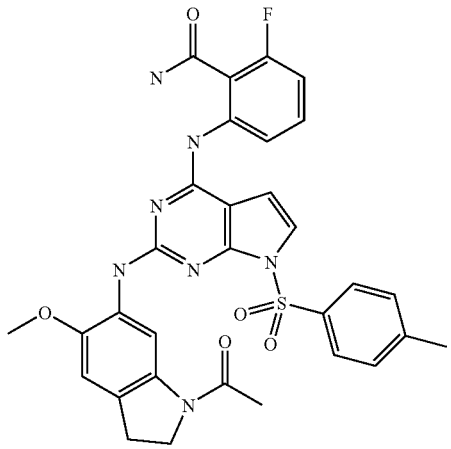

A slurry of 1-acetyl-5-(methyloxy)-2,3-dihydro-1H-indol-6-amine (212 mg, 2 mmol), 2-({2-chloro-7-[(4-methylphenyl)sulfonyl]-7H-pyrrolo[2,3-d]pyrimidin-4-yl}amino)-6-fluorobenzamide (836 mg, 1.8 mmol), KI (5.6 mg, 0.03 mmol) in 2,2,2-trifluoroethanol (10 mL) was treated with a 4 N HCl solution in dioxane (1.8 mL, 7.2 mmol). The reaction mixture was heated at 80° C. overnight in a sealed vessel, then was allowed to cool to rt Half of the reaction mixture was diluted with THF (100 mL) and a 27% aqueous NH$_4$OH solution (100 mL). After stirring at rt overnight the reaction mixture was concentrated to dryness. The residue was sonicated in CH$_2$Cl$_2$ (10 mL), then filtered. The filtrate was purified by silica gel chromatography using 8-10% THF/CH$_2$Cl$_2$ to obtain 2-({2-{[1-acetyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluorobenzamide as a yellow solid (192 mg, 34% for 2 steps). $^1$H NMR (400 MHz, DMSO-$d_6$) δ ppm 2.16 (s, 3H), 2.35 (s, 3H), 3.19 (t, J=8.33 Hz, 2H), 3.73 (s, 3H), 4.15 (t, J=8.33 Hz, 2H), 6.50 (d, J=3.85 Hz, 1H), 6.92 (t, J=9.25 Hz, 1H), 7.04 (s, 1H), 7.15-7.40 (m, 4H), 7.90-7.99 (m, 3H), 8.02 (s, 1H), 8.10 (d, J=8.61 Hz, 1H), 8.16 (s, 1H), 8.24 (s, 1H), 10.49 (s, 1H); ESIMS (M+H)$^+$= 630.13.

Step B/Example 134 2-[(2-{[1-acetyl-5-(methyloxy)-2,3-dihydro-1H-indol-6-yl]amino}-1H-pyrrolo[2,3-d]pyrimidin-4-yl)amino]-6-fluorobenzamide A solution of of 2-({2-{[1-acetyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluorobenzamide (104 mg, 0.17 mmol) in methanol (10 mL) and THF (20 mL) was treated with a solution of sodium methoxide (0.5M in MeOH, 3.3 mL, 1.7 mmol). The resulting mixture was stirred at rt for 2 days, then diluted with EtOAc (100 mL) and a saturated NaCl solution. The organic layer was washed with a saturated NaHCO$_3$ solution, concentrated onto Celite and purified by silica gel chromatography using 0-5% MeOH (containing 0.2% NH$_3$)/CH$_2$Cl$_2$ to obtain 2-[(2-{[1-acetyl-5-(methyloxy)-2,3-dihydro-1H-indol-6-yl]amino}-1H-pyrrolo[2,3-d]pyrimidin-4-yl)amino]-6-fluorobenzamide as a yellow solid (63 mg, 81%). $^1$H NMR (400 MHz, DMSO-$d_6$) δ ppm 2.13 (s, 3H), 3.09-3.19 (m, 2H), 3.78 (s, 3H), 4.06-4.15 (m, 2H), 6.23 (s, 1H), 6.88 (J=9.71 Hz, 9.34 Hz, 1H), 6.95 (s, 2H), 7.27-7.37 (m, 1H), 7.58 (s, 1H), 8.02 (s, 1H), 8.10 (s, 1H), 8.50 (d, J=8.42 Hz, 1H), 8.62 (s, 1H), 10.52 (s, 1H), 11.29 (s, 1H); ESIMS (M+H)$^+$=475.99.

Example 135

2-[(2-{[1-acetyl-5-(methyloxy)-2,3-dihydro-1H-indol-6-yl]amino}-1H-pyrrolo[2,3-d]pyrimidin-4-yl)amino]-6-fluoro-N-methylbenzamide

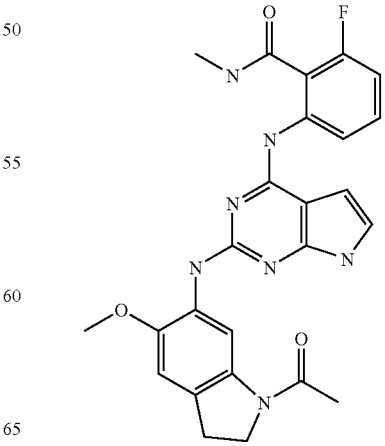

Step A/Intermediate D8: 2-({2-{[1-acetyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-methylbenzamide

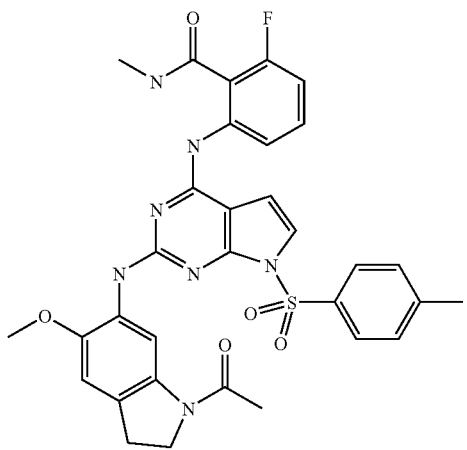

The remaining half of the reaction mixture from the preparation of 2-({2-{[1-acetyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluorobenzamide was diluted with THF (100 mL) and a solution of methylamine (2M, 9 mL), 18 mmol). The reaction mixture was stirred overnight, then concentrated to dryness. The residue was sonicated in CH$_2$Cl$_2$ (15 mL) and filtered. The filtrate was purified by silica gel chromatography using 10% THF/CH$_2$Cl$_2$ to obtain 2-({2-{[1-acetyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-methylbenzamide as a yellow solid (236 mg, 41% for 2 steps). $^1$H NMR (400 MHz, DMSO-d$_5$) δ ppm 2.16 (s, 3H), 2.34 (s, 3H), 2.75 (d, J=4.4 Hz, 3H), 3.19 (d, J=8.24 Hz, 2H), 3.73 (s, 3H), 4.15 (d, J=8.33 Hz, 2H), 6.55 (d, J=3.85 Hz, 1H), 6.94 (t, J=9.25 Hz, 1H), 7.04 (s, 1H), 7.17-7.41 (m, 4H), 7.93 (d, J=8.24 Hz, 2H), 7.98 (J=8.42 Hz, 1H), 8.16 (s, 1H), 8.19 (s, 1H), 8.36-8.52 (m, 1H), 10.16 (s, 1H); ESIMS (M+H)$^+$=644.20.

Step B/Example 135 2-[(2-{[1-acetyl-5-(methyloxy)-2,3-dihydro-1H-indol-6-yl]amino}-1H-pyrrolo[2,3-d]pyrimidin-4-yl)amino]-6-fluoro-N-methylbenzamide A solution of 2-({2-{[1-acetyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-methylbenzamide (130 mg, 0.2 mmol) in MeOH (10 mL) and THF (20 mL) was treated with a solution of sodium methoxide (0.5M in MeOH, 4 mL, 2 mmol). The resulting mixture was stirred at rt overnight, then diluted with EtOAc (100 mL) and saturated NaCl solution. The organic layer was washed with a saturated NaHCO$_3$ solution, concentrated onto Celite and purified by silica gel chromatography using 0-5% MeOH (containing 0.2% NH$_3$)/CH$_2$Cl$_2$ to obtain 2-[(2-{[1-acetyl-5-(methyloxy)-2,3-dihydro-1H-indol-6-yl]amino}-1H-pyrrolo[2,3-d]pyrimidin-4-yl)amino]-6-fluoro-N-methylbenzamide as a beige solid (73 mg, 75%). $^1$H NMR (400 MHz, DMSO-d$_6$) δ ppm 2.13 (s, 3H) 2.80 (d, J=4.4 Hz, 3H), 3.12 (t, J=8.42 Hz, 2H), 3.78 (s, 3H), 4.10 (t, J=8.42 Hz, 2H), 6.27 (d, J=1.28 Hz, 1H), 6.86-6.98 (m, 3H), 7.28-7.37 (m, 1H), 7.55 (s, 1H), 8.34 (d, J=8.61 Hz, 1H), 8.55 (br s, 1H), 8.63 (s, 1H), 10.14 (s, 1H), 11.27 (s, 1H); ESIMS (M+H)$^+$=489.98.

Example 136

2-[(2-{-[1-(N,N-diethylglycyl)-5-(methyloxy)-2,3-dihydro-1H-indol-6-yl]amino}-1H-pyrrolo[2,3-d]pyrimidin-4-yl)amino]-6-fluorobenzamide

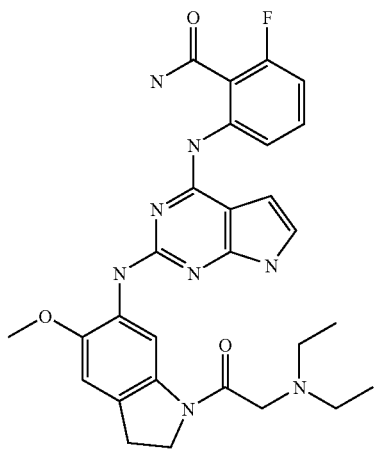

A mixture of 1-[(diethylamino)acetyl]-5-(methyloxy)-2,3-dihydro-1H-indol-6-amine (200 mg, 0.72 mmol) and 2-({2-chloro-7-[(4-methylphenyl)sulfonyl]-7H-pyrrolo[2,3-d]pyrimidin-4-yl}amino)-6-fluorobenzamide (330 mg, 0.71 mmol) and a 4 N HCl solution in dioxane (0.7 mL, 2.87 mmol) in 2,2,2-trifluoroethanol (10 mL) was heated for 8 h in a sealed vessel at 80° C. After allowing to cool to rt half of the reaction mixture was diluted with THF (80 mL) and a 27% aqueous NH$_4$OH solution (80 mL). The reaction mixture was stirred for 3 h and concentrated. The residue was taken up into CH$_2$Cl$_2$ (200 mL), concentrated onto Celite and purified by silica gel chromatography using 20% 0.5 M NH$_3$ in dioxane/THF. The product was dissolved in THF (10 mL) and THF (20 mL) and treated with a solution of sodium methoxide (0.5M in MeOH, 4 mL, 2 mmol). The reaction mixture was stirred for 2 days, concentrated onto Celite, and purified by silica gel chromatography using 4% MeOH (containing 0.2% NH$_3$)/CH$_2$Cl$_2$ then triturated using Et$_2$O (15 mL) to obtain 2-[(2-{[1-(N,N-diethylglycyl)-5-(methyloxy)-2,3-dihydro-1H-indol-6-yl]amino}-1H-pyrrolo[2,3-d]pyrimidin-4-yl)amino]-6-fluorobenzamide as a yellow solid (41 mg, 20% for 3 steps). $^1$H NMR (400 MHz, DMSO-d$_6$) δ ppm 0.99 (t, J=6.68 Hz, 6H), 2.58 (br s, 4H), 3.12 (t, J=8.15 Hz, 2H), 3.77 (s, 3H), 4.24 (t, J=8.15 Hz, 2H), 6.22 (s, 1H), 6.86 (t, J=9.43 Hz, 1H), 6.96 (s, 2H), 7.31 (q, J=7.94 Hz, 1H), 7.61 (s, 1H), 8.02 (s, 1H), 8.11 (s, 1H), 8.53 (d, J=8.24 Hz, 1H), 8.60 (s, 1H), 10.56 (s, 1H), 11.29 (s, 1H) a CH$_2$ signal with 2 protons is missing, may overlap with water peak in sample; ESIMS (M+H)$^+$=547.38.

Example 137

2-[(2-{[1-(N,N-diethylglycyl)-5-(methyloxy)-2,3-dihydro-1H-indol-6-yl]amino}-1H-pyrrolo[2,3-d]pyrimidin-4-yl)amino]-6-fluoro-N-methylbenzamide

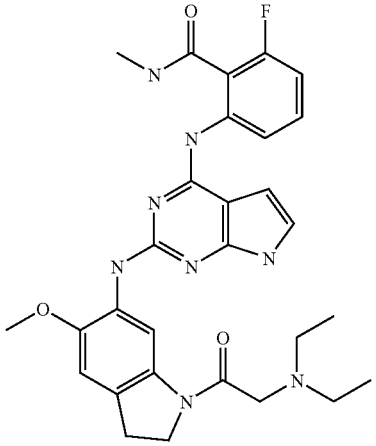

The remaining half of the reaction mixture from the preparation of 2-[(2-{[1-(N,N-diethylglycyl)-5-(methyloxy)-2,3-dihydro-1H-indol-6-yl]amino}-1H-pyrrolo[2,3-d]pyrimidin-4-yl)amino]-6-fluorobenzamide was diluted with THF (100 mL) and a solution of methylamine (1M in THF, 10 mL). After 4 h the reaction mixture was concentrated, the resulting residue was sonicated in $CH_2Cl_2$ (10 mL) and filtered. The filtrate was purified by silica gel chromatography using 0-5% MeOH (containing 0.2% $NH_3$)/$CH_2Cl_2$. The product was dissolved in THF (10 mL) and MeOH (20 mL) and treated with a solution of sodium methoxide (0.5M in MeOH, 4 mL, 2 mmol). The reaction mixture was stirred for 2 days, then concentrated onto Celite and purified by silica gel chromatography using 4% MeOH (containing 0.2% $NH_3$)/$CH_2Cl_2$ to obtain 2-[(2-{[1-(N,N-diethylglycyl)-5-(methyloxy)-2,3-dihydro-1H-indol-6-yl]amino}-1H-pyrrolo[2,3-d]pyrimidin-4-yl)amino]-6-fluoro-N-methylbenzamide as a yellow solid (60 mg, 30% for 3 steps). $^1$H NMR (400 MHz, DMSO-$d_6$) δ ppm 0.98 (t, J=7.15 Hz, 6H) 2.58 (q, J=6.72 Hz, 4H) 2.80 (d, J=4.77 Hz, 3H), 3.12 (t, J=8.43 Hz, 2H), 3.77 (s, 3H), 4.24 (t, J=8.43 Hz, 2H), 6.27 (dd, J=3.30, 1.83 Hz, 1H), 6.76-7.03 (m, 3H), 7.26-7.39 (m, 1H), 7.57 (s, 1H), 8.36 (d, J=8.43 Hz, 1H), 8.54 (s, 1H), 8.62 (s, 1H), 10.16 (s, 1H), 11.26 (s, 1H), a $CH_2$ signal with 2 protons is missing, may overlap with water peak in sample; ESIMS (M+H)$^+$=561.27.

Example 138

2-fluoro-6-[(2-{[5-(methyloxy)-1-(1-pyrrolidinylacetyl)-2,3-dihydro-1H-indol-6-yl]amino}-1H-pyrrolo[2,3-d]pyrimidin-4-yl)amino]benzamide

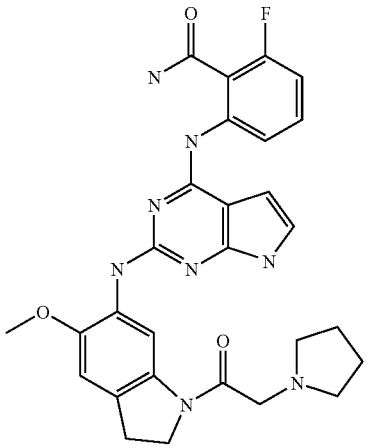

A white slurry of 5-(methyloxy)-1-(1-pyrrolidinylacetyl)-2,3-dihydro-1H-indol-6-amine (250 mg, 0.91 mmol) and 2-({2-chloro-7-[(4-methylphenyl)sulfonyl]-7H-pyrrolo[2,3-d]pyrimidin-4-yl}amino)-6-fluorobenzamide (501 mg, 1.09 mmol) in 2,2,2-trifluoroethanol was heated at 80° C. for 17 h. Half of the resulting mixture was diluted with THF (100 mL) and a 27% aqueous $NH_4OH$ solution (100 mL), and stirred for 1 day. The organic volatiles were evaporated, and the residue was diluted with $CH_2Cl_2$. The organic layer was washed with a saturated NaCl solution, dried ($Na_2SO_4$) and concentrated. The residue was dissolved in THF, concentrated onto Celite and purified by silica gel chromatography using 0-10% MeOH (containing 0.2% $NH_3$)/$CH_2Cl_2$. The crude product was taken up into THF (20 mL) and a NaOMe solution (0.5M in MeOH, 6 mL, 3 mmol) and maintained at rt for 1 day. The resulting mixture was concentrated onto Celite and purified by silica gel chromatography using 0-10% MeOH (containing 0.2% $NH_3$)/$CH_2Cl_2$ to obtain 2-fluoro-6-[(2-{[5-(methyloxy)-1-(1-pyrrolidinylacetyl)-2,3-dihydro-1H-indol-6-yl]amino}-1H-pyrrolo[2,3-d]pyrimidin-4-yl)amino]benzamide as a yellow solid (85 mg). $^1$H NMR (400 MHz, DMSO-$d_6$) δ ppm 1.64 (br s, 4H), 2.51 (br s, 4H), 3.01-3.14 (m, 2H), 3.27 (s, 2H), 3.72 (s, 3H), 4.05-4.18 (m, 2H), 6.17 (s, 1H), 6.81 (t, J=9.34 Hz, 1H), 6.90 (s, 2H), 7.20-7.32 (m, 1H), 7.55 (s, 1H), 7.96 (s, 1H), 8.05 (s, 1H), 8.46 (d, J=8.24 Hz, 1H), 8.56 (s, 1H), 10.49 (s, 1H), 11.24 (s, 1H); ESIMS (M+H)$^+$=545.25.

Example 139

2-fluoro-N-methyl-6-[(2-{[5-(methyloxy)-1-(1-pyrrolidinylacetyl)-2,3-dihydro-1H-indol-6-yl]amino}-1H-pyrrolo[2,3-d]pyrimidin-4-yl)amino]benzamide

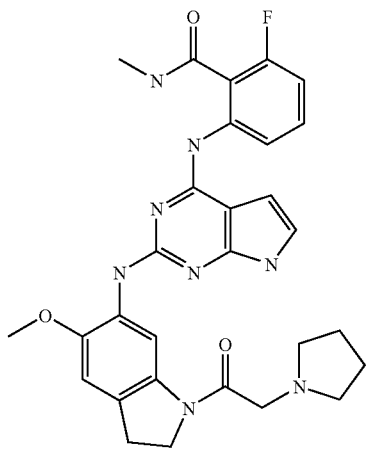

The remaining half of the reaction mixture from the preparation of 2-fluoro-6-[(2-{[5-(methyloxy)-1-(1-pyrrolidinylacetyl)-2,3-dihydro-1H-indol-6-yl]amino}-1H-pyrrolo[2,3-d]pyrimidin-4-yl)amino]benzamide was diluted with THF and a solution of $MeNH_2$ (2M in THF, 10 mL, 20 mmol). The reaction mixture was stirred at rt for 17 h. Water (20 mL) was added, followed by a solution of $MeNH_2$ (1M in THF, 6 mL, 12 mmol). The reaction mixture was stirred for 5 days, the organic volatiles were evaporated, and the residue was extracted with $CH_2Cl_2$ (200 mL). The organic layer was washed with a saturated NaCl solution (100 mL), dried ($Na_2SO_4$), concentrated onto Celite and purified by silica gel chromatography using 0-10% MeOH (containing 0.2% $NH_3$)/$CH_2Cl_2$. The crude product was taken up into THF (20 mL) and a NaOMe solution (2M in MeOH, 10 mL, 20 mmol) and maintained at rt for 1 day. Additional NaOMe solution (2M in MeOH, 6 mL, 12 mmol) was added and the reaction mixture was stirred for 3 days. The resulting mixture was diluted with EtOAc (100 mL), washed with a saturated NaHCO$_3$ solution (100 mL), and a saturated NaCl solution. The organic layer was concentrated onto Celite and purified by silica gel chromatography using 1-10% MeOH (containing 0.2% NH$_3$)/CH$_2$Cl$_2$ to obtain 2-fluoro-N-methyl-6-[(2-{[5-(methyloxy)-1-(1-pyrrolidinylacetyl)-2,3-dihydro-1H-indol-6-yl]amino}-1H-pyrrolo[2,3-d]pyrimidin-4-yl)amino]benzamide as a brown solid (48 mg). $^1$H NMR (400 MHz, DMSO-d$_6$) δ ppm 1.71 (br s, 4H), 2.78 (br s, 4H), 2.80 (br s, 3H), 3.06-3.19 (m, 2H), 3.78 (s, 3H), 4.08-4.23 (m, 2H), 6.28 (s, 1H), 6.84-7.02 (m, 3H), 7.24-7.38 (m, 1H), 7.57 (s, 1H), 8.36 (d, J=8.97 Hz, 1H), 8.55 (s, 1H), 8.64 (s, 1H), 10.16 (s, 1H), 11.27 (s, 1H); ESIMS (M+H)$^+$=559.26.

Example 140

2-fluoro-6-[(2-{[1-glycyl-5-(methyloxy)-2,3-dihydro-1H-indol-6-yl]amino}-1H-pyrrolo[2,3-d]pyrimidin-4-yl)amino]benzamide

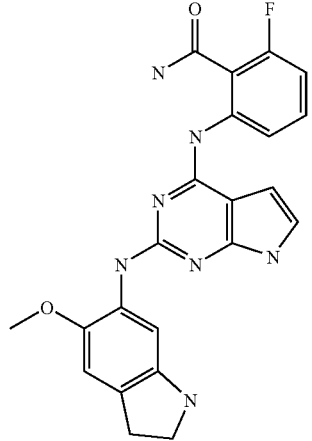

Step A/Intermediate D9: 2-fluoro-6-({2-({5-(methyloxy)-1-[(4-methylphenyl)sulfonyl]-2,3-dihydro-1H-indol-6-yl}amino)-7-[(4-methylphenyl)sulfonyl]-7H-pyrrolo[2,3-d]pyrimidin-4-yl}amino)benzamide

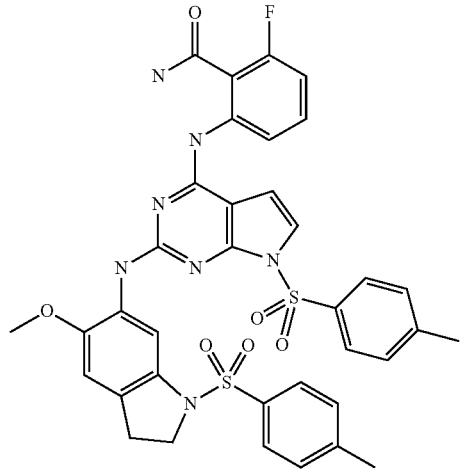

A mixture of 5-(methyloxy)-1-[(4-methylphenyl)sulfonyl]-2,3-dihydro-1H-indol-6-amine (4.0 g, 12.5 mmol), 2-({2-chloro-7-[(4-methylphenyl)sulfonyl]-7H-pyrrolo[2,3-d]pyrimidin-4-yl}amino)-6-fluorobenzamide (8.6 g, 18.79 mmol) and a 4 N solution of HCl in dioxane (16 mL, 62.5 mmol) in 2,2,2-trifluoroethanol (250 mL) was heated overnight in a sealed vessel at 80° C. The reaction mixture was diluted with a saturated NaHCO$_3$ solution, and the resulting slurry was filtered and the solids were taken up into THF (1L). The resulting slurry was filtered and the filtrate was concentrated. The resulting orange solid was dissolved in THF (250 mL), and a 27% aqueous NH$_4$OH solution (250 mL) was added and the reaction mixture was stirred overnight. The organic volatiles were evaporated, and the residue was extracted with CH$_2$Cl$_2$ (3×200 mL). The organic layers were combined, dried (Na$_2$SO$_4$), concentrated onto Celite and purified by silica gel chromatography using 0-2%THF/CH$_2$Cl$_2$ to obtain 2-fluoro-6-({2-({5-(methyloxy)-1-[(4-methylphenyl)sulfonyl]-2,3-dihydro-1H-indol-6-yl}amino)-7-[(4-methylphenyl)sulfonyl]-7H-pyrrolo[2,3-d]pyrimidin-4-yl}amino)benzamide as a yellow solid (2.8 g, 30% for 2 steps). ESIMS (M+H)$^+$=742.17.

Step B/Example D10: 2-fluoro-6-[(2-{[5-(methyloxy)-2,3-dihydro-1H-indol-6-yl]amino}-1H-pyrrolo[2,3-d]pyrimidin-4-yl)amino]benzamide

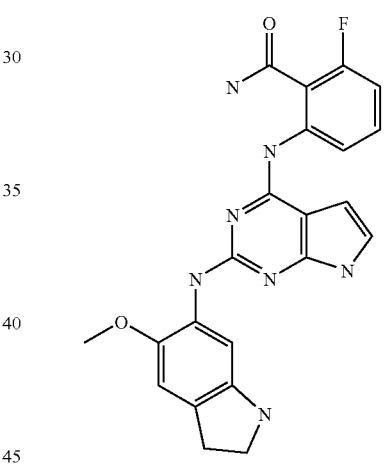

To a degassed solution of naphthalene (14 g, 109 mmol) in THF (300 mL) were added sodium cubes (2.6 g, 108 mmol). The cubes were crushed, and then stirred for 4 h. A total of 60 mL of the resulting deep green solution was added dropwise to a −78° C. solution of 2-fluoro-6-({2-({5-(methyloxy)-1-[(4-methylphenyl)sulfonyl]-2,3-dihydro-1H-indol-6-yl}amino)-7-[(4-methylphenyl)sulfonyl]-7H-pyrrolo[2,3-d]pyrimidin-4-yl}amino)benzamide (3.7 g, 4.99 mmol) in THF (100 mL). Water (5 mL) was then added, the resulting mixture was allowed to warm to rt, and filtered. The filtrate was concentrated onto Celite and purified by silica gel chromatography using 1-10% MeOH (containing 0.2% NH$_3$)/CH$_2$Cl$_2$ to obtain 2-fluoro-6-[(2-{[5-(methyloxy)-2,3-dihydro-1H-indol-6-yl]amino}-1H-pyrrolo[2,3-d]pyrimidin-4-yl)amino]benzamide as a yellow solid (710 mg, 33%). $^1$H NMR (400 MHz, DMSO-d$_6$) δ ppm 2.88 (t, J=8.33 Hz, 2H), 3.39 (t, J=8.15 Hz, 2H), 3.76 (s, 3H), 5.07 (br s, 1H), 6.24 (s, 1H), 6.83 (s, 1H), 6.89-7.02 (m, 2H), 7.40 (s, 1H), 7.50 (q, J=7.69 Hz, 1H), 7.64 (s, 1H), 8.03 (s, 1H), 8.10 (s, 1H), 8.47 (d, J=8.42 Hz, 1H), 10.46 (s, 1H), 11.39 (s, 1H); ESIMS (M+H)$^+$=434.17.

Example 141

2-fluoro-6-[(2-{[1-glycyl-5-(methyloxy)-2,3-dihydro-1H-indol-6-yl]amino}-1H-pyrrolo[2,3-d]pyrimidin-4-yl)amino]benzamide

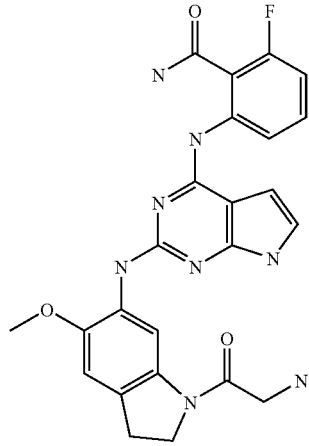

A −40° C. solution of 2-fluoro-6-[(2-{[5-(methyloxy)-2,3-dihydro-1H-indol-6-yl]amino}-1H-pyrrolo[2,3-d]pyrimidin-4-yl)amino]benzamide (70 mg, 0.16 mmol) in THF (20 mL) was treated with a solution of bromoacetyl chloride (25 mg, 0.16 mmol) in THF (1 mL). After 5 min a 27% aqueous NH₄OH solution was added and the reaction mixture was stirred at rt overnight. The resulting slurry was filtered and the solid washed with Et₂O to obtain 2-fluoro-6-[(2-{[1-glycyl-5-(methyloxy)-2,3-dihydro-1H-indol-6-yl]amino}-1H-pyrrolo[2,3-d]pyrimidin-4-yl)amino]benzamide as a grey solid (67 mg, 86%). $^1$H NMR (400 MHz, DMSO-$d_6$) δ ppm 3.07-3.19 (m, 2H), 3.44, (s, 2H), 3.78 (s, 3H), 3.97-4.10 (m, 2H), 6.23, (s, 1H), 6.82-7.04 (m, 3H), 7.27-7.41 (m, 1H), 7.60 (s, 1H), 8.02 (s, 1H), 8.10 (s, 1H), 8.51 (d, J=7.61 Hz, 1H), 8.67 (s, 1H), 10.53 (s, 1H), 11.33 (s, 1H) a CH₂ signal with 2 protons is missing, may overlap with water peak in sample; ESIMS (M+H)⁺=491.26.

Example 142

2-fluoro-6-[(2-{[1-(N-methylglycyl)-5-(methyloxy)-2,3-dihydro-1H-indol-6-yl]amino}-1H-pyrrolo[2,3-d]pyrimidin-4-yl)amino]benzamide

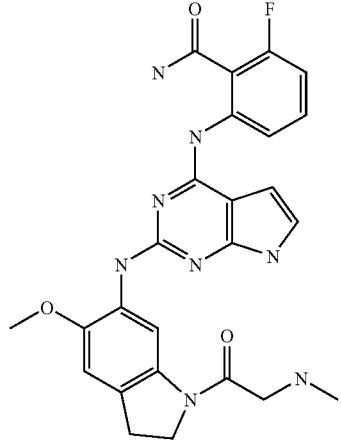

A −40° C. solution of 2-fluoro-6-[(2-{[5-(methyloxy)-2,3-dihydro-1H-indol-6-yl]amino}-1H-pyrrolo[2,3-d]pyrimidin-4-yl)amino]benzamide (250 mg, 0.58 mmol) in THF (50 mL) was treated with a solution of bromoacetyl chloride (95 mg, 0.61 mmol) in THF (1 mL). One-third of the reaction mixture was treated with a solution of methylamine (2M in THF, 4 mL, 8 mmol). After stirring overnight the resulting mixture was concentrated onto Celite and purified by silica gel chromatography using 1-10% MeOH (containing 0.2% NH₃)/CH₂Cl₂ to obtain 2-fluoro-6-[(2-{[1-(N-methylglycyl)-5-(methyloxy)-2,3-dihydro-1H-indol-6-yl]amino}-1H-pyrrolo[2,3-d]pyrimidin-4-yl)amino]benzamide as a yellow solid (54 mg, 56%). $^1$H NMR (400 MHz, DMSO-$d_6$) δ ppm 2.43 (s, 3H), 3.12-3.22 (m, 2H), 3.68 (s, 1H), 3.78 (s, 3H), 4.03-4.15 (m, 2H), 6.22 (s, 1H), 6.87 (t, J=9.34 Hz, 1H), 6.96 (s, 1H), 6.99 (s, 1H), 7.23-7.38 (m, 1H), 7.66 (s, 1H), 8.02 (s, 1H), 8.11 (s, 1H), 8.49-8.60 (m, 2H), 10.56 (s, 1H), 11.29 (s, 1H), a CH₂ signal with 2 protons is missing, may overlap with water peak in sample; ESIMS (M+H)⁺=505.07.

Example 143

2-[(2-{[1-(1-azetidinylacetyl)-5-(methyloxy)-2,3-dihydro-1H-indol-6-yl]amino}-1H-pyrrolo[2,3-d]pyrimidin-4-yl)amino]-6-fluorobenzamide

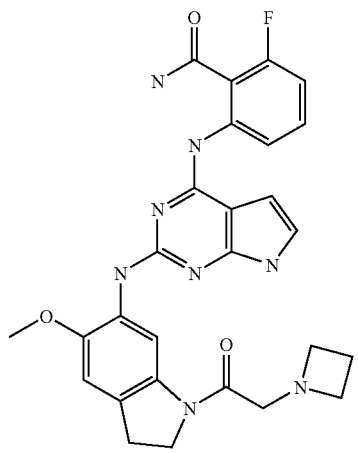

One third of the reaction mixture from the preparation of 2-fluoro-6-[(2-{[1-(N-methylglycyl)-5-(methyloxy)-2,3-dihydro-1H-indol-6-yl]amino}-1H-pyrrolo[2,3-d]pyrimidin-4-yl)amino]benzamide was treated with azetidine (0.2 mL) and maintained at rt for 17 h. The resulting mixture was concentrated onto Celite and purified by silica gel chromatography using 1-10% MeOH (containing 0.2% NH₃)/CH₂Cl₂ to obtain 2-[(2-{[1-(1-azetidinylacetyl)-5-(methyloxy)-2,3-dihydro-1H-indol-6-yl]amino}-1H-pyrrolo[2,3-d]pyrimidin-4-yl)amino]-6-fluorobenzamide as a yellow solid (72 mg). $^1$H NMR (400 MHz, DMSO-$d_6$) δ ppm 2.15-2.27 (m, 2H), 3.11-3.23 (m, 2H), 3.72 (t, J=7.42 Hz, 4H), 3.78 (s, 3H), 3.93 (s, 2H), 4.07 (t, J=8.24 Hz, 2H), 6.22 (s, 1H), 6.80-6.93 (m, 1H), 6.96 (s, 1H), 6.99 (s, 1H), 7.31 (q, J=7.69 Hz, 1H), 7.65 (s, 1H), 8.02 (s, 1H), 8.11 (s, 1H), 8.51 (s, 1H), 8.54 (s, 1H), 10.57 (s, 1H), 11.27 (s, 1H); ESIMS (M+H)⁺=531.38.

Example 144

2-fluoro-6-[(2-{[1-[N-methyl-N-(methyloxy)glycyl]-5-(methyloxy)-2,3-dihydro-1H-indol-6-yl]amino}-1H-pyrrolo[2,3-d]pyrimidin-4-yl)amino]benzamide

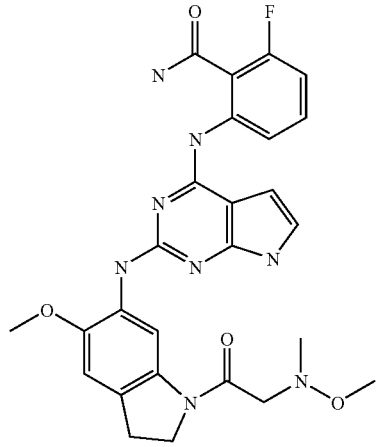

One third of the reaction mixture from the preparation of 2-fluoro-6-[(2-{[1-(N-methylglycyl)-5-(methyloxy)-2,3-dihydro-1H-indol-6-yl]amino}-1H-pyrrolo[2,3-d]pyrimidin-4-yl)amino]benzamide was treated with N,O-dimethylhydroxylamine (145 mg, 2.37 mmol) and KI (90 mg, 0.54 mmol). After 1 h the resulting mixture was concentrated onto Celite and purified by silica gel chromatography using 1-10% MeOH (containing 0.2% $NH_3$)/$CH_2Cl_2$ to obtain 2-fluoro-6-[(2-{[1-[N-methyl-N-(methyloxy)glycyl]-5-(methyloxy)-2,3-dihydro-1H-indol-6-yl]amino}-1H-pyrrolo[2,3-d]pyrimidin-4-yl)amino]benzamide as a yellow solid (43 mg 42%). $^1$H NMR (400 MHz, DMSO-$d_6$) δ ppm 2.59 (s, 3H), 3.08-3.20 (m, 2H), 3.43 (s, 3H), 3.60 (s, 2H), 3.78 (s, 3H), 4.22 (t, J=8.26 Hz, 2H), 6.23 (s, 1H), 6.81-6.92 (m, 1H), 6.95 (s, 1H), 6.97 (s, 1H), 7.28-7.40 (m, 1H), 7.61 (s, 1H), 8.02 (s, 1H), 8.10 (s, 1H), 8.51 (d, J=8.42 Hz, 1H), 8.63 (s, 1H), 10.54 (s, 1H), 11.31 (s, 1H); ESIMS (M+H)$^+$=535.18.

Example 145

2-fluoro-6-[(2-{[1-(1H-imidazol-1-ylacetyl)-5-(methyloxy)-2,3-dihydro-1H-indol-6-yl]amino}-1H-pyrrolo[2,3-d]pyrimidin-4-yl)amino]benzamide

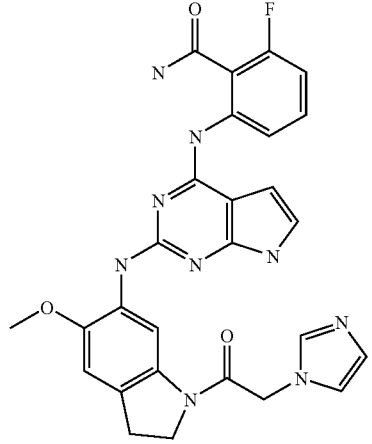

A −40° C. solution of 2-fluoro-6-[(2-{[5-(methyloxy)-2,3-dihydro-1H-indol-6-yl]amino}-1H-pyrrolo[2,3-d]pyrimidin-4-yl)amino]benzamide (70 mg, 0.16 mmol) in THF (10 mL) was treated with a solution of bromoacetyl chloride (31 mg, 0.19 mmol) in THF (1 mL), followed by imidazole (10 mL) and DIPEA (1 mL). After 3 days the resulting mixture was concentrated onto Celite and purified by silica gel chromatography using 1-10% MeOH (containing 0.2% $NH_3$)/$CH_2Cl_2$. The crude product was dissolved in THF (150 mL), diluted with EtOAc (50 mL), washed with a saturated $NaHCO_3$ solution (100 mL), a saturated NaCl solution (100 mL) and a mixture of water (50 mL) and a saturated $Na_2CO_3$ solution (50 mL). The organic layer was dried ($Na_2SO_4$) and concentrated, and the residue was triturated with $CH_2Cl_2$ to obtain 2-fluoro-6-[(2-{[1-(1H-imidazol-1-ylacetyl)-5-(methyloxy)-2,3-dihydro-1H-indol-6-yl]amino}-1H-pyrrolo[2,3-d]pyrimidin-4-yl)amino]benzamide as a white solid (72 mg, 83%). $^1$H NMR (400 MHz, DMSO-$d_6$) δ ppm 3.18 (t, J=8.15 Hz, 2H), 3.77 (s, 3H), 4.18 (t, J=8.06 Hz, 2H), 6.19 (s, 1H), 6.78-6.94 (m, 3H), 6.97 (s, 1H), 7.07 (s, 1H), 7.29 (q, J=7.69 Hz, 1H), 7.54 (s, 1H), 7.55 (s, 1H), 7.99 (s, 1H), 8.07 (s, 1H), 8.46 (d, J=8.42 Hz, 1H), 8.58 (s, 1H), 10.52 (s, 1H), 11.27 (s, 1H), a $CH_2$ signal with 2 protons is missing, may overlap with water peak in sample; ESIMS (M+H)$^+$=542.11.

Example 146

6-[(4-{[2-(aminocarbonyl)-3-fluorophenyl]amino}-1H-pyrrolo[2,3-d]pyrimidin-2-yl)amino]-N,N-dimethyl-5-(methyloxy)-2,3-dihydro-1H-indole-1-carboxamide

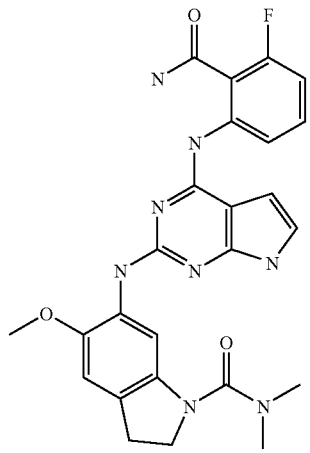

A mixture of of 2-fluoro-6-[(2-{[5-(methyloxy)-2,3-dihydro-1H-indol-6-yl]amino}-1H-pyrrolo[2,3-d]pyrimidin-4-yl)amino]benzamide (67 mg, 0.15 mmol) and CDI (30 mg, 0.18 mmol) in THF (4 mL) was stirred for 15 min, then treated with a solution of methylamine (2M in THF, 4 mL, 8 mmol) and was heated for 2 days in a sealed vessel at 80° C. More methylamine (2M in THF, 5 mL) was added and the reaction mixture was heated for 22 h. The resulting mixture was allowed to cool to rt, diluted with EtOAc (50 mL), washed with a saturated $Na_2CO_3$ solution (50 mL), water (50 mL) and a saturated NaCl solution (50 mL). The aqueous layers were back extracted with EtOAc (50 mL). The organic layers were combined and concentrated onto Celite and purified by silica gel chromatography using 1-10% MeOH (containing 0.2% $NH_3$)/$CH_2Cl_2$ to obtain 6-[(4-{[2-(aminocarbonyl)-3-fluorophenyl]amino}-1H-pyrrolo[2,3-d]pyrimidin-2-yl)amino]-N,N-dimethyl-5-(methyloxy)-2,3-dihydro-1H-indole-1-carboxamide as a yellow solid (43 mg, 55%). $^1$H NMR (400 MHz, DMSO-$d_6$) δ ppm 2.83 (s, 6H), 2.94 (t, J=8.06 Hz, 2H), 3.73-3.86 (m, 5H), 6.18-6.28 (m, 1H), 6.84-6.95 (m, 2H), 6.97 (s, 1H), 7.31-7.42 (m, 1H), 7.47 (s, 1H), 7.82 (s, 1H), 8.01 (s, 1H), 8.07 (s, 1H), 8.41 (d, J=8.24 Hz, 1H), 10.47 (s, 1H), 11.21 (s, 1H); ESIMS (M+H)$^+$=505.15.

Example 147

2-fluoro-6-[(2-{[5-(methyloxy)-1-(1-methyl-L-pro-lyl)-2,3-dihydro-1H-indol-6-yl]amino}-1H-pyrrolo[2,3-d]pyrimidin-4-yl)amino]benzamide

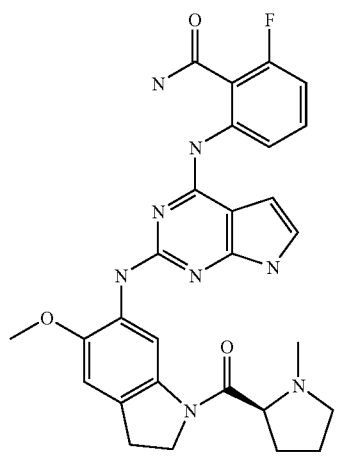

A mixture of 5-chloro-8-fluoro-3-[(4-methylphenyl)sulfonyl]pyrrolo[2',3':4,5]pyrimido[6,1-b]quinazolin-7(3H)-one hydrogen chloride (380 mg, 0.858 mmol) and 5-(methyloxy)-1-(1-methyl-L-prolyl)-2,3-dihydro-1H-indol-6-amine (236 mg, 0.858 mmol) in 2,2,2-trifluoroethanol (15 mL) was heated at 80° C. for 30 minutes, then was allowed to cool to rt, diluted with CH$_2$Cl$_2$ (100 mL), washed with a saturated NaHCO$_3$ solution (100 ml) and a saturated NaCl solution. The organic layer was dried (Na$_2$SO$_4$) and concentrated under reduced pressure. The crude product was dissolved in THF (60 mL) and was diluted with 30% aqueous NH$_4$OH solution (200 mL). The resulting mixture was heated in a sealed vessel at 80° C. After 17 h the reaction mixture was allowed to cool to rt, diluted with EtOAc (200 mL) and a saturated NaCl solution (50 mL). The organic layer was washed with a saturated NaCl solution (100 mL), dried (Na$_2$SO$_4$) and concentrated. The residue was dissolved in THF (25 mL) and MeOH (25 mL), and was treated with sodium methoxide (456 mg, 8.44 mmol). The resulting mixture was stirred at it for 20 h, then diluted with EtOAc (100 mL), washed with a saturated NaHCO$_3$ solution (100 mL), a saturated NaCl solution (50 mL), dried (Na$_2$SO$_4$), concentrated onto Celite and purified by silica gel chromatography using 1-10% MeOH (containing 0.2% NH$_3$)/CH$_2$Cl$_2$ to obtain 2-fluoro-6-[(2-{[5-(methyloxy)-1-(1-methyl-L-prolyl)-2,3-dihydro-1H-indol-6-yl]amino}-1H-pyrrolo[2,3-d]pyrimidin-4-yl)amino]benzamide as a pale yellow solid (144 mg, 32%). $^1$H NMR (400 MHz, DMSO-$d_6$) δ ppm 1.66-1.85 (m, 3H), 2.06-2.34 (m, 5H), 2.89-3.04 (m, 1H), 3.04-3.26 (m, 3H), 3.77 (s, 3H), 4.07-4.32 (m, 2H), 6.15-6.28 (m, 1H), 6.79-6.92 (m, 1H), 6.96 (br s, 2H), 7.25-7.37 (m, 1H), 7.60 (s, 1H), 8.03 (s, 1H), 8.11 (s, 1H), 8.52 (d, J=8.24 Hz, 1H), 8.67 (s, 1H), 10.55 (s, 1H), 11.30 (s, 1H); ESIMS (M+H)$^+$=545.22.

Example 148

2-fluoro-6-[(2-{[5-(methyloxy)-1-(1-methyl-L-pro-lyl)-2,3-dihydro-1H-indol-6-yl]amino}-1H-pyrrolo[2,3-d]pyrimidin-4-yl)amino]benzamide

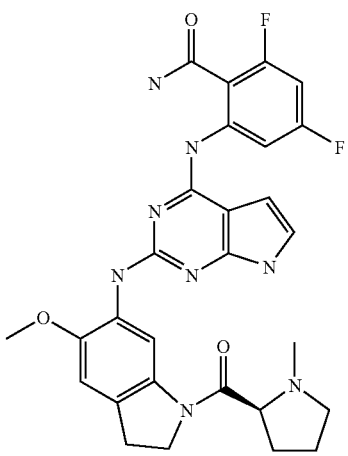

Step A/Intermediate D11: 2-({2-chloro-7-[(4-methylphenyl)sulfonyl]-7H-pyrrolo[2,3-d]pyrimidin-4-yl}amino)-4,6-difluorobenzoic acid

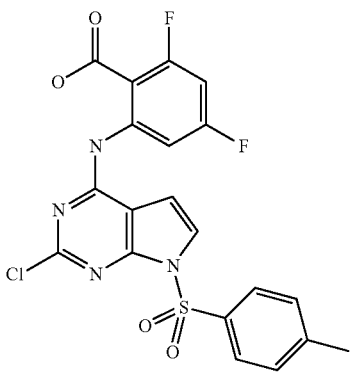

A slurry of 2,4-dichloro-7-[(4-methylphenyl)sulfonyl]-7H-pyrrolo[2,3-d]pyrimidine (10 g, 29.2 mmol) and 2-amino-4,6-difluorobenzoic acid (source: Buttpark Ltd.) (5.06 g, 29.2 mmol) in iPrOH (250 ml) and DIPEA (25.5 ml, 146 mmol) was heated at 95° C. overnight, then distilled 180 mL of solvent off over 4 h, then heated for another 2 h. After allowing to cool to rt, the reaction mixture was diluted with EtOAc (300 mL), washed with a 1N HCl solution (400 mL), a saturated NaHCO$_3$ solution (200 mL), a saturated NaCl solution (200 mL). The organic layer was diluted with Et$_2$O (200 mL). The resulting slurry was filtered, the solid dried in vacuum oven overnight at 80° C. to obtain 2-({2-chloro-7-[(4-methylphenyl)sulfonyl]-7H-pyrrolo[2,3-d]pyrimidin-4-yl}amino)-4,6-difluorobenzoic acid as a pale yellow solid (5.3 g, 38%). $^1$H NMR (400 MHz, DMSO-$d_6$) δ ppm 2.37 (s, 3H), 6.60-6.78 (m, 2H), 7.48 (d, J=8.06 Hz, 2H), 7.77 (d, J=3.85 Hz, 1H), 7.98 (d, J=8.42 Hz, 2H), 8.23-8.36 (m, 1H); ESIMS (M+H)⁺=478.94.

Step B/Intermediate D12: 5-chloro-8,10-difluoro-3-[(4-methylphenyl)sulfonyl]pyrrolo[2',3':4,5]pyrimido[6,1-b]quinazolin-7(3H)-one hydrogen chloride

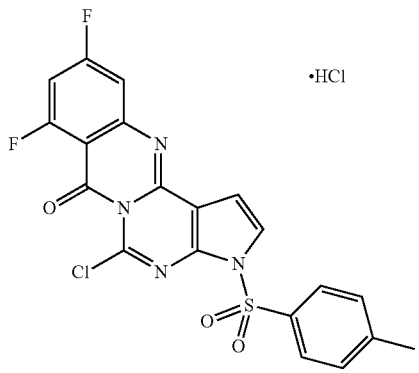

An opaque solution of 2-({2-chloro-7-[(4-methylphenyl)sulfonyl]-7H-pyrrolo[2,3-d]pyrimidin-4-yl}amino)-4,6-difluorobenzoic acid (5.3 g, 11.07 mmol) in THF (300 mL) was treated with a few drops of DMF, followed by oxalyl chloride (1M in CH₂Cl₂, 22.14 mL, 44.3 mmol). The reaction mixture was stirred for 1 h, then placed in an ice-bath for 2 h. The resulting slurry was filtered, the solid washed with CH₂Cl₂ to obtain 5-chloro-8,10-difluoro-3-[(4-methylphenyl)sulfonyl]pyrrolo[2',3':4,5]pyrimido[6,1-b]quinazolin-7(3H)-one hydrogen chloride as a white solid (5.23 g, 95%). ¹H NMR (400 MHz, THF-d₆) δ ppm 2.41 (s, 3H), 6.97-7.12 (m, 2H), 7.12-7.24 (m, 1H), 7.44 (d, J=8.24 Hz, 2H), 7.68 (d, J=3.66 Hz, 1H), 8.11 (d, J=8.42 Hz, 2H); ESIMS (M+H)⁺=460.94.

Step C/Intermediate D13: 8,10-difluoro-5-{[5-(methyloxy)-1-(1-methyl-L-prolyl)-2,3-dihydro-1H-indol-6-yl]amino}-3-[(4-methylphenyl)sulfonyl]pyrrolo[2',3':4,5]pyrimido[6,1-b]quinazolin-7(3H)-one

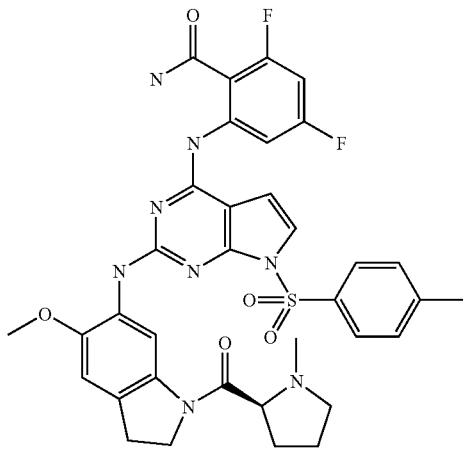

A mixture of 5-chloro-8,10-difluoro-3-[(4-methylphenyl)sulfonyl]pyrrolo[2',3':4,5]pyrimido[6,1-b]quinazolin-7(3H)-one (500 mg, 1.085 mmol) and 5-(methyloxy)-1-(1-methyl-L-prolyl)-2,3-dihydro-1H-indol-6-amine (299 mg, 1.085 mmol) in 2,2,2-trifluoroethanol (15 mL) was heated at 80° C. for 45 min. The resulting slurry was allowed to cool to rt, diluted with CH₂Cl₂ (200 mL) and a saturated NaHCO₃ solution (100 mL). The organic layer was washed with a saturated NaCl solution (100 mL), dried and concentrated. The residue was dissolved in THF (60 mL), a 27% aqueous NH₄OH solution (220 mL) was added and stirred in a sealed vessel overnight. The resulting mixture was diluted with EtOAc (100 mL) and a saturated NaCl solution (50 mL). The organic layer was washed with a saturated NaCl solution (2×100 mL), concentrated onto Celite and purified by silica gel chromatography using 1-10% MeOH (containing 0.2% NH₃)/CH₂Cl₂ to obtain 2,4-difluoro-6-({2-{[5-(methyloxy)-1-(1-methyl-L-prolyl)-2,3-dihydro-1H-indol-6-yl]amino}-7-[(4-methylphenyl)sulfonyl]-7H-pyrrolo[2,3-d]pyrimidin-4-yl}amino)benzamide as a light brown solid (276 mg, 36%). ¹H NMR (400 MHz, DMSO-d₆) δ ppm 1.72 (br s, 3H), 2.01-2.29 (m, 5H), 2.32 (s, 3H), 2.85-3.01 (m, 1H), 3.08-3.24 (m, 3H), 3.72 (s, 3H), 4.03-4.30 (m, 2H), 6.41 (d, J=4.03 Hz, 1H), 6.76-6.93 (m, 1H), 7.02 (s, 1H), 7.26-7.40 (m, 3H), 7.87-8.06 (m, 3H), 8.15 (s, 1H), 8.18-8.34 (m, 2H), 8.53 (s, 1H), 11.29 (s, 1H); ESIMS (M+H)⁺=717.36.

Step D/Example 148 2,4-difluoro-6-[(2-{[5-(methyloxy)-1-(1-methyl-L-prolyl)-2,3-dihydro-1H-indol-6-yl]amino}-1H-pyrrolo[2,3-d]pyrimidin-4-yl)amino]benzamide A slurry of 2,4-difluoro-6-({2-{[5-(methyloxy)-1-(1-methyl-L-prolyl)-2,3-dihydro-1H-indol-6-yl]amino}-7-[(4-methylphenyl)sulfonyl]-7H-pyrrolo[2,3-c]pyrimidin-4-yl}amino)benzamide (276 mg, 0.385 mmol) in dioxane (10 mL) and a 5N aqueous KOH solution (0.770 mL, 3.85 mmol) was heated at 80° C. After 5 h the reaction mixture was allowed to cool to rt, diluted with EtOAc (50 mL) and a saturated NaHCO₃ solution (50 mL). The organic layer was washed with a saturated NaCl solution (50 mL), concentrated onto Celite and purified by silica gel chromatography using 1-10% MeOH (containing 0.2% NH₃)/CH₂Cl₂ to obtain 2,4-difluoro-6-[(2-{[5-(methyloxy)-1-(1-methyl-L-prolyl)-2,3-dihydro-1H-indol-6-yl]amino}-1H-pyrrolo[2,3-d]pyrimidin-4-yl)amino]benzamide (156 mg, 72%). ¹H NMR (400 MHz, DMSO-d₆) δ ppm 1.75 (s, 3H), 1.97-2.38 (m, 5H), 2.87-3.04 (m, 1H), 3.05-3.25 (m, 3H), 3.77 (s, 3H), 4.02-4.30 (m, 2H), 6.14-6.27 (m, 1H), 6.83 (t, J=11.08 Hz, 1H), 6.92-7.04 (m, 2H), 7.81 (s, 1H), 8.04 (s, 1H), 8.19 (s, 1H), 8.50-8.63 (m, 2H), 11.22 (s, 1H), 11.35 (s, 1H); ESIMS (M+H)⁺=563.30.

Example 149

2-fluoro-6-{[2-({5-(methyloxy)-1-[(methyloxy)acetyl]-2,3-dihydro-1H-indol-6-yl}amino)-1H-pyrrolo[2,3-d]pyrimidin-4-yl]amino}benzamide

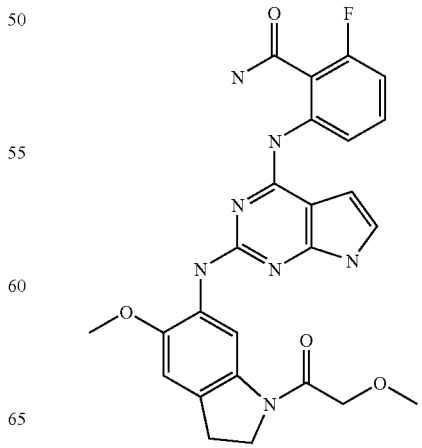

A thick white slurry of 5-chloro-8-fluoro-3-[(4-methylphenyl)sulfonyl]pyrrolo[2',3':4,5]pyrimido[6,1-b]quinazolin-7(3H)-one hydrogen chloride (400 mg, 0.835 mmol) and 5-(methyloxy)-1-[(methyloxy)acetyl]-2,3-dihydro-1H-indol-6-amine (197 mg, 0.835 mmol) in THF (15 mL) was heated at 80° C. for 17 h, cooled, then diluted with THF (20 mL) and a 30% aqueous NH$_4$OH solution (50 mL). The reaction mixture was maintained for 17 h, then diluted with EtOAc (50 mL) and a saturated NaCl solution (25 mL). The organic layer was washed with a saturated NaCl solution (3×50 mL), concentrated onto Celite and purified by silica gel chromatography using 1-10% MeOH (containing 0.2% NH$_3$)/CH$_2$Cl$_2$. The crude product was triturated using Et$_2$O, dissolved in dioxane (15 mL) and a 1N KOH solution (3.64 mL, 3.64 mmol) and then heated at 80° C. for 3 h. The resulting mixture was allowed to cool somewhat, diluted with EtOAc (100 mL) and a 2N NaOH solution (50 mL). The organic layer was washed with a 2N NaOH solution (2×50 mL), concentrated onto Celite and purified by silica gel chromatography using 1-10% MeOH (containing 0.2% NH$_3$)/CH$_2$Cl$_2$ to obtain 2-fluoro-6-{[2-({5-(methyloxy)-1-[(methyloxy)acetyl]-2,3-dihydro-1H-indol-6-yl}amino)-1H-pyrrolo[2,3-d]pyrimidin-4-yl]amino}benzamide as a yellow solid (63 mg). $^1$H NMR (400 MHz, DMSO-d$_6$) δ ppm 3.11 (t, J=8.15 Hz, 2H), 3.76 (s, 3H), 4.01 (t, J=8.33 Hz, 2H), 4.14 (s, 2H), 6.16-6.27 (m, 1H), 6.76-6.89 (m, 1H), 6.90-6.99 (m, 2H), 7.22-7.38 (m, 1H), 7.58 (s, 1H), 8.00 (s, 1H), 8.08 (s, 1H), 8.49 (d, J=8.42 Hz, 1H), 8.63 (s, 1H), 10.52 (s, 1H), 11.29 (s, 1H) a Me-O signal with 3 protons is missing, may overlap with water peak in sample; ESIMS (M+H)$^+$=506.16.

Example 150

2-fluoro-N-methyl-6-{[2-({5-(methyloxy)-1-[(methyloxy)acetyl]-2,3-dihydro-1H-indol-6-yl}amino)-1H-pyrrolo[2,3-d]pyrimidin-4-yl]amino}benzamide

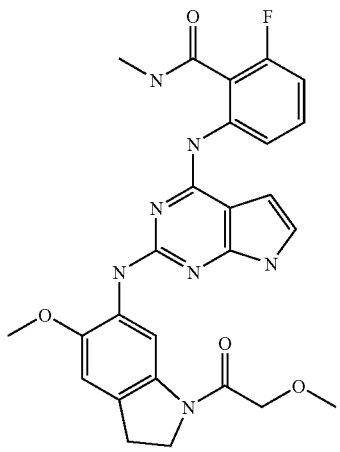

A thick white slurry of 5-chloro-8-fluoro-3-[(4-methylphenyl)sulfonyl]pyrrolo[2',3':4,5]pyrimido[6,1-b]quinazolin-7(3H)-one hydrogen chloride (400 mg, 0.835 mmol) and 5-(methyloxy)-1-[(methyloxy)acetyl]-2,3-dihydro-1H-indol-6-amine (197 mg, 0.835 mmol) in THF (15 mL) was heated at 80° C. After 17 h a methylamine solution (2 N in THF, 4.17 mL, 8.35 mmol) was added. The reaction mixture was maintained at rt for 22 h, then filtered, the solid washed with THF. The filtrate was concentrated onto Celite and purified by silica gel chromatography using 1-10% MeOH (containing 0.2% NH$_3$)/CH$_2$Cl$_2$. The crude product was dissolved in dioxane (15 mL) and a 1N KOH solution (4.38 mL, 4.38 mmol), then heated at 80° C. After 3 h the reaction mixture was allowed to cool somewhat, diluted with EtOAc (100 mL) and a 2N NaOH solution (50 mL). The organic layer was washed with a 2N NaOH solution (2×50 mL), concentrated onto Celite and purified by silica gel chromatography using 1-10% MeOH (containing 0.2% NH$_3$)/CH$_2$Cl$_2$ to obtain 2-fluoro-N-methyl-6-{[2-({5-(methyloxy)-1-[(methyloxy)acetyl]-2,3-dihydro-1H-indol-6-yl}amino)-1H-pyrrolo[2,3-d]pyrimidin-4-yl]amino}benzamide as a yellow solid (116 mg). $^1$H NMR (400 MHz, DMSO-d$_6$) δ ppm 2.80 (d, J=4.39 Hz, 3H), 3.13 (t, J=8.24 Hz, 2H), 3.79 (s, 3H), 4.04 (t, J=8.24 Hz, 2H), 4.17 (s, 2H), 6.25-6.34 (m, 1H), 6.84-7.04 (m, 3H), 7.27-7.40 (m, 1H), 7.58 (s, 1H), 8.35 (d, J=8.24 Hz, 1H), 8.50-8.61 (m, 1H), 8.68 (s, 1H), 10.16 (s, 1H), 11.30 (s, 1H), a Me-O signal with 3 protons is missing, may overlap with water peak in sample; ESIMS (M+H)$^+$=520.16.

Example 151

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-N-ethyl-4,6-difluorobenzamide

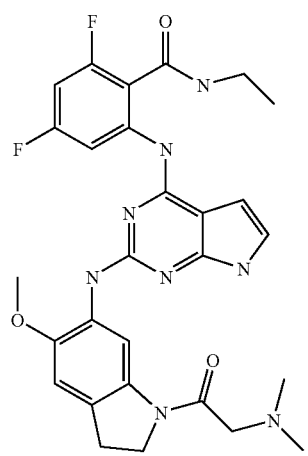

Step A\Intermediate D14: 5-{[1-(N,N-dimethylglycyl)-5-(methyloxy)-2,3-dihydro-1H-indol-6-yl]amino}-8,10-difluoro-3-[(4-methylphenyl)sulfonyl]pyrrolo[2',3':4,5]pyrimido[6,1-b]quinazolin-7(3H)-one

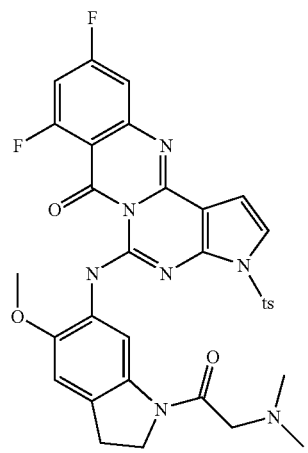

To a suspension of 2-({2-chloro-7-[(4-methylphenyl)sulfonyl]-7H-pyrrolo[2,3-d]pyrimidin-4-yl}amino)-4,6-difluorobenzamide (1.96 g, 4.1 mmol) in 2,2,2-trifluoroethanol (40 mL) was added 1-[(dimethylamino)acetyl]-5-(methyloxy)-2,3-dihydro-1H-indol-6-amine (1.33 g, 5.33 mmol), hydrochloric acid as a 4.0M solution in dioxane (4.1 mL), and catalytic potassium iodide (<10 mg). The resulting slurry was stirred at 90° C. in a pressure vial for 40 hours, at which time all solids had completely dissolved. The resulting solution was cooled to room temperature and diluted with dichloromethane and saturated sodium bicarbonate as to adjust the aqueous layer to pH>10. The organic layer was washed with water and saturated brine solution and dried over sodium sulfate. Solvents were removed under reduced pressure to afford a yellow solid that was purified via trituration from diethyl ether to afford 5-{[1-(N,N-dimethylglycyl)-5-(methyloxy)-2,3-dihydro-1H-indol-6-yl]amino}-8,10-difluoro-3-[(4-methylphenyl)sulfonyl]pyrrolo[2',3':4,5]pyrimido[6,1-b]quinazolin-7(3H)-one (2.63 g, 3.90 mmol) as a yellow solid. (ESIMS $(M+H)^+$=675)

Step B\Example 151: 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-N-ethyl-4,6-difluorobenzamide To a solution of 5-{[1-(N,N-dimethylglycyl)-5-(methyloxy)-2,3-dihydro-1H-indol-6-yl]amino}-8,10-difluoro-3-[(4-methylphenyl)sulfonyl]pyrrolo[2',3':4,5]pyrimido[6,1-b]quinazolin-7(3H)-one (300 mg, 0.445 mmol) in THF (5 mL) was added ethyl amine as a 2M solution in THF (1.11 mL, 2.22 mmol). The resulting mixture was let stir at rt for 3 h at which time it was diluted with ethyl acetate and washed with a saturated sodium bicarbonate solution, water and a saturated brine solution. Organics were dried over sodium sulfate and solvents removed under reduced pressure to afford a yellow solid, containing 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-N-ethyl-4,6-difluorobenzamide. This material was dissolved in 1,4-dioxane (5 mL) and transferred to a 20 ml microwave vessel. A solution of 2M NaOH (5 ml) was added and reaction heated in microwave at 120° C. for 8 minutes. Resulting brown solution was diluted with ethyl acetate and washed with a saturated sodium bicarbonate solution, water and a saturated brine solution. Organics were dried over sodium sulfate and solvents removed under reduced pressure to afford a yellow solid which was purified via chromatography on SiO$_2$ to afford 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-N-ethyl-4,6-difluorobenzamide (60 mg, 0.101 mmol) as an off-white solid. $^1$H NMR (400 MHz, DMSO-d$_6$) δ ppm 1.14 (t, J=7.14 Hz, 3 H) 2.18-2.31 (m, 6 H) 3.06-3.19 (m, 4H) 3.34 (dq, J=6.87, 6.65 Hz, 2 H) 3.78 (s, 3 H) 4.09-4.24 (m, 2 H) 6.25 (br. s., 1 H) 6.75-6.89 (m, 1 H) 6.93-7.03 (m, 2 H) 7.62-7.75 (m, 1 H) 8.39-8.49 (m, 1 H) 8.55 (br. s., 2 H) 10.55 (s, 1H) 11.26 (dd, J=2.56, 1.10 Hz, 1 H) (ESIMS $(M+H)^+$=565)

Example 152

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-4,6-difluoro-N-propylbenzamide

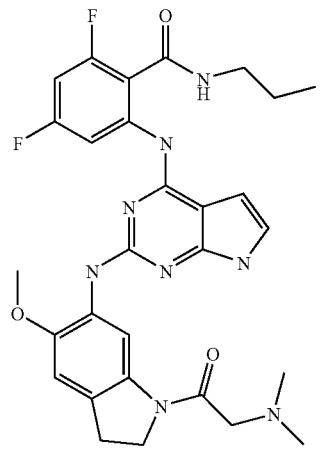

To a solution of 5-{[1-(N,N-dimethylglycyl)-5-(methyloxy)-2,3-dihydro-1H-indol-6-yl]amino}-8,10-difluoro-3-[(4-methylphenyl)sulfonyl]pyrrolo[2',3':4,5]pyrimido[6,1-b]quinazolin-7(3H)-one (300 mg, 0.445 mmol) in THF (5 mL) was added propylamine (0.183 mL, 2.22 mmol). The resulting mixture was let stir at rt for 5 h at which time it was diluted with ethyl acetate and washed with a saturated sodium bicarbonate solution, water and a saturated brine solution. Organics were dried over sodium sulfate and solvents removed under reduced pressure to afford a yellow solid, containing 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-4,6-difluoro-N-propylbenzamide. This crude material was dissolved in 1,4-dioxane (5 mL) and transferred to a 20 ml microwave vessel. A solution of 2 M NaOH (5 ml) was added and reaction heated in microwave at 120° C. for 8 minutes. Resulting brown solution was diluted with ethyl acetate and washed with a saturated sodium bicarbonate solution, water and a saturated brine solution. Organics were dried over sodium sulfate and solvents removed under reduced pressure to afford a yellow solid which was purified via chromatography on SiO$_2$ to afford 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-4,6-difluoro-N-propylbenzamide (54 mg, 0.093 mmol) as an off-white solid. $^1$H NMR (400 MHz, DMSO-d$_6$) δ ppm 0.85 (t, J=7.37 Hz, 3 H) 1.41-1.56 (m, 2 H) 2.19 (s, 6 H) 3.02-3.15 (m, 4 H) 3.19-3.25 (m, 2 H) 3.72 (s, 3H) 4.11 (t, J=8.29 Hz, 2 H) 6.17 (d, J=1.28 Hz, 1 H) 6.76-6.87 (m, 1 H) 6.88-6.97 (m, 2 H) 7.74 (s, 1 H) 8.34-8.43 (m, 1 H) 8.45 (s, 1 H) 8.61 (br. s., 1 H) 10.40 (s, 1 H) 11.28 (br. s., 1 H). (ESIMS $(M+H)^+$=579)

Example 153

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-4,6-difluoro-N-(1-methylethyl)benzamide

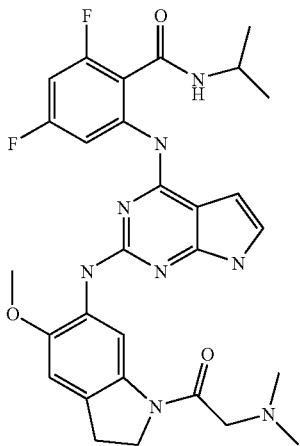

To a solution of 5-{[1-(N,N-dimethylglycyl)-5-(methyloxy)-2,3-dihydro-1H-indol-6-yl]amino}-8,10-difluoro-3-[(4-methylphenyl)sulfonyl]pyrrolo[2',3':4,5]pyrimido[6,1-b]quinazolin-7(3H)-one (300 mg, 0.445 mmol) in THF (5 mL) was added (1-methylethyl)amine (0.757 mL, 8.89 mmol). The resulting mixture was let stir at rt for 16 h at which time it was diluted with ethyl acetate and washed with a saturated ammonium chloride solution, saturated sodium bicarbonate solution, water and a saturated brine solution. Organics were dried over sodium sulfate and solvents removed under reduced pressure to afford a yellow solid, containing 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-4,6-difluoro-N-(1-methylethyl)benzamide. This crude material was dissolved in 1,4-dioxane (5 mL) and transferred to a 20 ml microwave vessel. A solution of 2 M NaOH (5 ml) was added and reaction heated in microwave at 120° C. for 8 minutes. Resulting brown solution was diluted with ethyl acetate and washed with a saturated sodium bicarbonate solution, water and a saturated brine solution. Organics were dried over sodium sulfate and solvents removed under reduced pressure to afford a yellow solid which was purified via chromatography on SiO$_2$ to afford 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-4,6-difluoro-N-(1-methylethyl)benzamide (26 mg, 0.045 mmol) as a beige solid. $^1$H NMR (400 MHz, DMSO-d$_6$) δ ppm 1.15 (d, J=6.60 Hz, 6H), 2.23 (s, 6 H), 3.07-3.19 (m, 4 H), 3.76 (s, 3 H), 4.07-4.22 (m, 3 H), 6.18-6.26 (m, 1 H), 6.80-6.91 (m, 1 H), 6.93-7.02 (m, 2 H), 7.79 (s, 1 H), 8.36-8.45 (m, 1 H), 8.46-8.56 (m, 2 H), 10.26 (s, 1 H), 11.28-11.37 (s, 1 H). (ESIMS (M+H)$^+$=579)

Example 154

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-4,6-difluoro-N-(2-methylpropyl)benzamide

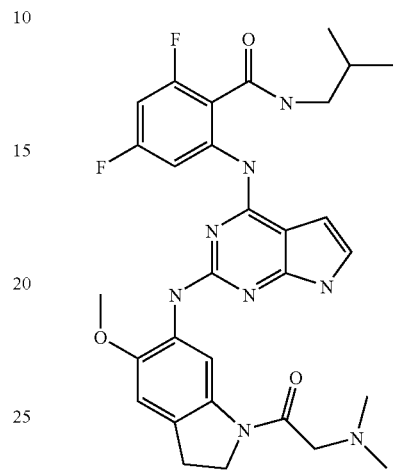

To a solution of 5-{[1-(N,N-dimethylglycyl)-5-(methyloxy)-2,3-dihydro-1H-indol-6-yl]amino}-8,10-difluoro-3-[(4-methylphenyl)sulfonyl]pyrrolo[2',3':4,5]pyrimido[6,1-b]quinazolin-7(3H)-one (300 mg, 0.445 mmol) in THF (5 mL) was added methyl-1-propanamine (0.22 mL, 2.22 mmol). The resulting mixture was let stir at rt for 6 h at which time it was diluted with ethyl acetate and washed with a saturated sodium bicarbonate solution, water and a saturated brine solution. Organics were dried over sodium sulfate and solvents removed under reduced pressure to afford a yellow solid, containing 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-4,6-difluoro-N-(2-methylpropyl)benzamide. This crude material was dissolved in 1,4-dioxane (5 mL) and transferred to a 20 ml microwave vessel. A solution of 2 M NaOH (5 ml) was added and reaction heated in microwave at 120° C. for 8 minutes. Resulting brown solution was diluted with ethyl acetate and washed with a saturated sodium bicarbonate solution, water and a saturated brine solution. Organics were dried over sodium sulfate and solvents removed under reduced pressure to afford a yellow solid which was purified via chromatography on SiO$_2$ to afford 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-4,6-difluoro-N-(2-methylpropyl)benzamide (50 mg, 0.084 mmol) as a beige solid. $^1$H NMR (400 MHz, DMSO-d$_6$) δ ppm 0.90 (d, J=6.69 Hz, 6 H) 1.84 (dt, J=13.40, 6.72 Hz, 1 H), 2.24 (s, 6 H), 3.07-3.20 (m, 6 H), 3.76 (s, 3H), 4.16 (t, J=8.34 Hz, 2 H), 6.21 (dd, J=3.21, 1.65 Hz, 1 H), 6.79-6.93 (m, 1 H), 6.93-7.01 (m, 2 H), 7.79 (s, 1 H), 8.39-8.47 (m, 1 H), 8.50 (s, 1 H), 8.63-8.74 (m, 1 H), 10.32 (s, 1 H), 11.32 (br. s., 1 H). (ESIMS (M+H)$^+$=593)

Example 155

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-4,6-difluoro-N-[(4-fluorophenyl)methyl]benzamide

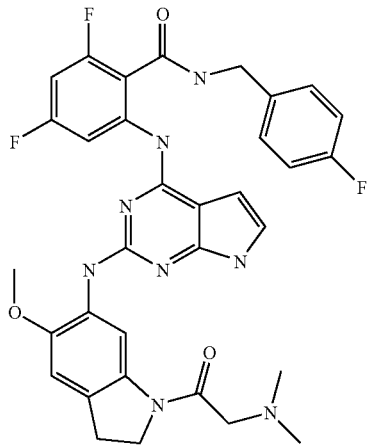

To a solution of 5-{[1-(N,N-dimethylglycyl)-5-(methyloxy)-2,3-dihydro-1H-indol-6-yl]amino}-8,10-difluoro-3-[(4-methylphenyl)sulfonyl]pyrrolo[2',3':4,5]pyrimido[6,1-b]quinazolin-7(3H)-one (300 mg, 0.445 mmol) in THF (5 mL) was added [(4-fluorophenyl)methyl]amine (1.01 mL, 8.89 mmol). The resulting mixture was let stir at rt for 16 h at which time it was diluted with ethyl acetate and washed with a saturated ammonium chloride solution, a saturated sodium bicarbonate solution, water and a saturated brine solution. Organics were dried over sodium sulfate and solvents removed under reduced pressure and purified via $SiO_2$. This lead to a yellow solid containing 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-4,6-difluoro-N-[(4-fluorophenyl)methyl]benzamide. This crude material was dissolved in 1,4-dioxane (5 mL) and transferred to a 20 ml microwave vessel. A solution of 2 M NaOH (5 ml) was added and reaction heated in microwave at 120° C. for 8 minutes. Resulting brown solution was diluted with ethyl acetate and washed with a 10% ammonium chloride solution, saturated sodium bicarbonate solution, water and a saturated brine solution. Organics were dried over sodium sulfate and solvents removed under reduced pressure to afford a yellow solid which was purified via chromatography on $SiO_2$ to afford 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-4,6-difluoro-N-[(4-fluorophenyl)methyl]benzamide (67 mg, 0.104 mmol) as an off white solid. $^1$H NMR (400 MHz, DMSO-$d_6$) δ ppm 2.23 (s, 6 H), 3.06-3.18 (m, 4 H), 3.76 (s, 3 H), 4.16 (t, J=8.29 Hz, 2 H), 4.51 (d, J=5.86 Hz, 2 H), 6.17 (d, J=1.19 Hz, 1 H), 6.81-7.01 (m, 3 H), 7.13 (t, J=8.84 Hz, 2 H), 7.38 (dd, J=8.29, 5.72 Hz, 2 H), 7.78 (s, 1 H), 8.43 (d, J=11.90 Hz, 1 H), 8.51 (s, 1 H), 9.14-9.25 (m, 1 H), 10.38 (s, 1 H), 11.32 (br. s., 1 H). (ESIMS $(M+H)^+$=645)

Example 156

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluoro-N-propylbenzamide

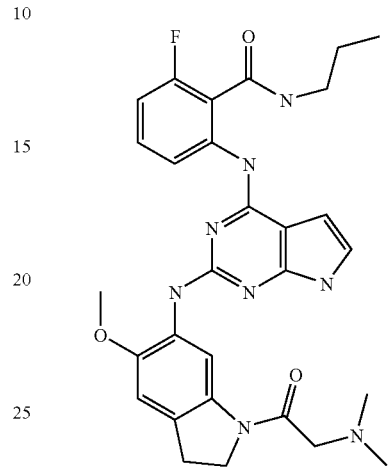

To a solution of 5-{[1-(N,N-dimethylglycyl)-5-(methyloxy)-2,3-dihydro-1H-indol-6-yl]amino}-8-fluoro-3-[(4-methylphenyl)sulfonyl]pyrrolo[2',3':4,5]pyrimido[6,1-b]quinazolin-7(3H)-one (200 mg, 0.305 mmol) in THF (5 mL) was added propylamine (0.125 mL, 1.52 mmol). The resulting mixture was let stir at rt for 3 h at which time it was diluted with ethyl acetate and washed with a saturated sodium bicarbonate solution, water and a saturated brine solution. Organics were dried over sodium sulfate and solvents removed under reduced pressure. The residue was attempted to be purified via chromatography on $SiO_2$ and afforded a solid containing 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-propylbenzamide. This crude material was dissolved in 1,4-dioxane (5 mL) and transferred to a 20 ml microwave vessel. A solution of 2M NaOH (5 ml) was added and reaction heated in microwave at 120° C. for 8 minutes. Resulting brown solution was diluted with ethyl acetate and washed with a solution of 2M NaOH, a saturated sodium bicarbonate solution, water and a saturated brine solution. Organics were dried over sodium sulfate and solvents removed under reduced pressure to afford a brown solid which was purified via chromatography on $SiO_2$ to afford 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluoro-N-propylbenzamide (68 mg, 0.121 mmol) as a beige solid. $^1$H NMR (400 MHz, DMSO-$d_6$) δ ppm 0.86 (t, J=7.38 Hz, 3 H), 1.44-1.57 (m, 2H), 2.26 (s, 6 H), 3.06-3.28 (m, 6 H), 3.18 (s, 2 H), 3.77 (s, 3 H), 4.18 (t, J=8.34 Hz, 2 H), 6.25 (dd, J=3.25, 1.79 Hz, 1 H), 6.84-7.00 (m, 3 H), 7.25-7.38 (m, 1 H), 7.57 (s, 1 H), 8.32 (d, J=8.25 Hz, 1 H), 8.55-8.67 (m, 2 H), 9.86 (s, 1 H), 11.26 (s, 1 H). (ESIMS $(M+H)^+$=561)

Example 157

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluoro-N-(2-methylpropyl)benzamide

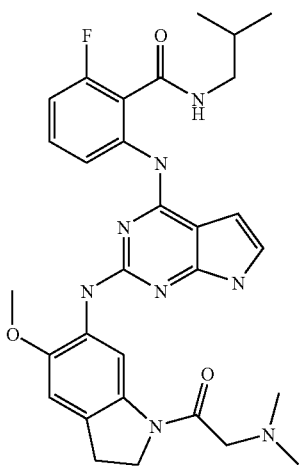

To a solution of 5-{[1-(N,N-dimethylglycyl)-5-(methyloxy)-2,3-dihydro-1H-indol-6-yl]amino}-8-fluoro-3-[(4-methylphenyl)sulfonyl]pyrrolo[2',3':4,5]pyrimido[6,1-b]quinazolin-7(3H)-one (200 mg, 0.305 mmol) in THF (5 mL) was added (2-methylpropyl)amine (0.153 mL, 1.52 mmol). The resulting mixture was let stir at rt for 16 h at which time it was diluted with ethyl acetate and washed with a saturated ammonium chloride solution, a saturated sodium bicarbonate solution, water and a saturated brine solution. Organics were dried over sodium sulfate and solvents removed under reduced pressure to afford a brown solid 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-(2-methylpropyl)benzamide. This crude material was dissolved in 1,4-dioxane (5 mL) and transferred to a 20 ml microwave vessel. A solution of 2M NaOH (5 ml) was added and reaction heated in microwave at 120° C. for 8 minutes. Resulting brown solution was diluted with ethyl acetate and washed with a saturated sodium bicarbonate solution, water and a saturated brine solution. Organics were dried over sodium sulfate and solvents removed under reduced pressure to afford a brown solid which was purified via chromatography on $SiO_2$ to afford 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluoro-N-(2-methylpropyl)benzamide (106 mg, 0.184 mmol) as a pale yellow solid. $^1$H NMR (400 MHz, DMSO-$d_6$) δ ppm 0.87 (d, J=6.68 Hz, 6 H), 1.73-1.89 (m, 1 H), 2.26 (s, 6 H), 3.05-3.23 (m, 6 H), 3.77 (s, 3 H), 4.18 (t, J=8.33 Hz, 2 H), 6.24 (br. s., 1 H), 6.83-7.00 (m, 3 H), 7.24-7.38 (m, 1 H), 7.56 (s, 1 H), 8.32 (d, J=8.42 Hz, 1 H), 8.57-8.68 (m, 2 H), 9.77 (s, 1 H), 11.26 (br. s., 1 H). (ESIMS (M+H)$^+$=575)

Example 158

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluoro-N-(1-methylethyl)benzamide

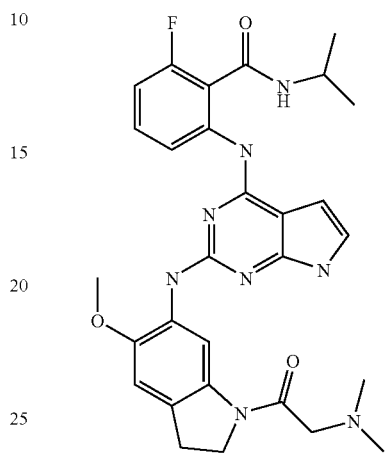

Step A\Intermediate D15: 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-(1-methylethyl)benzamide

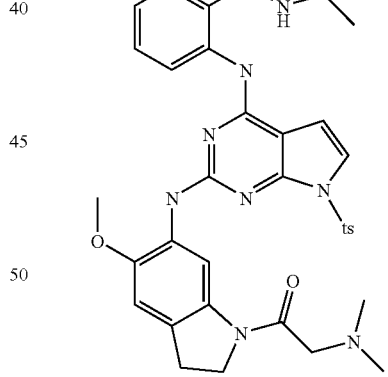

To a solution of 5-{[1-(N,N-dimethylglycyl)-5-(methyloxy)-2,3-dihydro-1H-indol-6-yl]amino}-8-fluoro-3-[(4-methylphenyl)sulfonyl]pyrrolo[2',3':4,5]pyrimido[6,1-b]quinazolin-7(3H)-one (265 mg, 0.404 mmol) in THF (5 mL) was added (1-methylethyl)amine (0.694 mL, 8.08 mmol). The resulting mixture was let stir at 40° C. for 16 h at which time it was diluted with ethyl acetate and washed with a saturated ammonium chloride solution, a saturated sodium bicarbonate solution, water and a saturated brine solution. Organics were dried over sodium sulfate and solvents removed under reduced pressure. Residue was purified via $SiO_2$ chromatography to afford 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-(1-methylethyl)benzamide. (210 mg, 0.294 mmol) as a yellow solid. (ESIMS (M+H)$^+$=715)

Step B\Example 158: 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluoro-N-(1-methylethyl)benzamide 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-(1-methylethyl)benzamide (210 mg, 0.294 mmol) was dissolved in 1,4-dioxane (10 mL) and transferred to a 20 ml microwave vessel. Water (3 mL) and a solution of 6M NaOH (3 ml) was added and reaction heated in microwave at 120° C. for 10 minutes. Resulting brown solution was diluted with ethyl acetate and washed with a saturated sodium bicarbonate solution, water and a saturated brine solution. Organics were dried over sodium sulfate and solvents removed under reduced pressure to afford a brown solid that was purified via chromatography on SiO$_2$ to afford 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-6-fluoro-N-(1-methylethyl)benzamide (120 mg, 0.214 mmol) as a yellow solid. $^1$H NMR (400 MHz, DMSO-d$_6$) δ ppm 1.11 (d, J=6.50 Hz, 6 H), 2.25 (s, 6 H), 3.05-3.22 (m, 4 H), 3.77 (s, 3 H), 4.03-4.13 (m, 1 H), 4.18 (t, J=8.29 Hz, 2 H), 6.26 (br. s., 1 H), 6.84-7.01 (m, 3 H), 7.25-7.38 (m, 1 H), 7.57 (s, 1 H), 8.25 (d, J=8.33 Hz, 1 H), 8.45 (d, J=7.60 Hz, 1 H), 8.64 (s, 1 H), 9.69 (s, 1 H), 11.25 (br. s., 1 H). (ESIMS (M+H)$^+$=561)

Example 159

6-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-2,3-difluorobenzamide

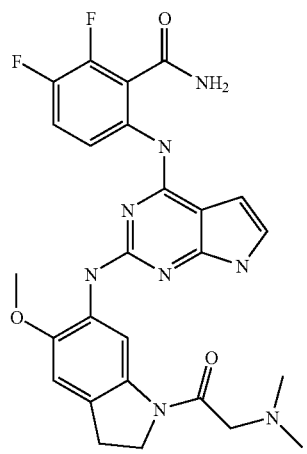

Step A\Intermediate D16: 5-{[1-(N,N-dimethylglycyl)-5-(methyloxy)-2,3-dihydro-1H-indol-6-yl]amino}-8,9-difluoro-3-[(4-methylphenyl)sulfonyl]pyrrolo[2',3':4,5]pyrimido[6,1-b]quinazolin-7(3H)-one

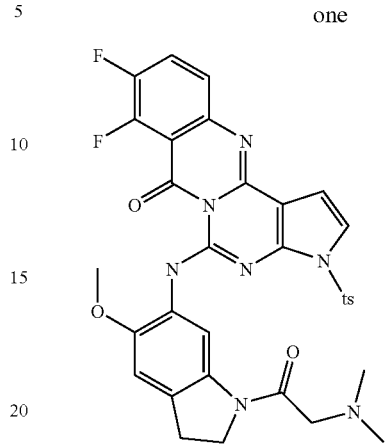

To a suspension of 6-({2-chloro-7-[(4-methylphenyl)sulfonyl]-7H-pyrrolo[2,3-d]pyrimidin-4-yl}amino)-2,3-difluorobenzamide (350 mg, 0.732 mmol) in 2,2,2-trifluoroethanol (10 ml) was added 1-[(dimethylamino)acetyl]-5-(methyloxy)-2,3-dihydro-1H-indol-6-amine (228 mg, 0.916 mmol), hydrochloric acid as a 4.0M solution in dioxane (1.47 ml, 5.86 mmol), and catalytic potassium iodide (<10 mg). The resulting slurry was stirred at 90° C. in a pressure vial for 24 hours, at which time all solids had completely dissolved. The resulting solution was cooled to room temperature and diluted with dichloromethane and saturated sodium bicarbonate as to adjust the aqueous layer to pH>10. The organic layer was washed with water and saturated brine solution, dried over sodium sulfate, filtered and solvents were removed under reduced pressure. The resulting green solid was purified via trituration with diethyl ether to afford 5-{[1-(N,N-dimethylglycyl)-5-(methyloxy)-2,3-dihydro-1H-indol-6-yl]amino}-8,9-difluoro-3-[(4-methylphenyl)sulfonyl]pyrrolo[2',3':4,5]pyrimido[6,1-b]quinazolin-7(3H)-one (533 mg, 0.791 mmol) as a yellow solid. (ESIMS (M+H)$^+$=674)

Step B\Intermediate D17: 6-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-2,3-difluorobenzamide

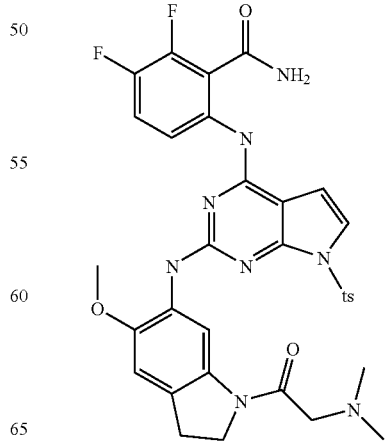

391

To a solution of 5-{[1-(N,N-dimethylglycyl)-5-(methyloxy)-2,3-dihydro-1H-indol-6-yl]amino}-8,9-difluoro-3-[(4-methylphenyl)sulfonyl]pyrrolo[2',3':4,5]pyrimido[6,1-b]quinazolin-7(3H)-one (300 mg, 0.445 mmol) in THF (5 mL) was added ammonium hydroxide (27% aqueous) (100 mL, large excess). The resulting mixture was let stir at rt for 16 h at which time it was diluted with ethyl acetate and washed with water and a saturated brine solution. Organics were dried over sodium sulfate and solvents removed under reduced pressure. The residue was purified via chromatography on SiO$_2$ and afforded 6-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-2,3-difluorobenzamide (133 mg, 0.193 mmol) as an off white solid. (ESIMS (M+H)$^+$=691)

Step C\Example 159: 6-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-2,3-difluorobenzamide 6-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-2,3-difluorobenzamide (133 mg, 0.193 mmol) was dissolved in 1,4-dioxane (10 mL) and transferred to a 20 ml microwave vessel. Water (3 mL) and a solution of 6M NaOH (3 ml) and was added and reaction heated in microwave at 120° C. for 10 minutes. Resulting brown solution was diluted with ethyl acetate and washed with a saturated sodium bicarbonate solution, water and a saturated brine solution. Organics were dried over sodium sulfate and solvents removed under reduced pressure to afford a brown solid that was purified via chromatography on SiO$_2$ to afford 6-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-2,3-difluorobenzamide (79 mg, 0.147 mmol) as a yellow solid. $^1$H NMR (400 MHz, DMSO-d$_6$) δ ppm 2.19-2.31 (m, 6 H), 3.04-3.25 (m, 4 H), 3.70-3.87 (m, 3 H), 4.18 (m, 2 H), 6.24 (d, J=0.64 Hz, 1 H), 6.95 (d, J=2.29 Hz, 2 H), 7.23-7.44 (m, 1 H), 7.54 (br. s., 1 H), 8.06-8.23 (m, 2 H), 8.24-8.38 (m, 1 H), 8.64 (br. s., 1H), 9.93 (br. s., 1 H), 11.27 (br. s., 1 H). (ESIMS (M+H)$^+$=537)

Example 160

6-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-2,3-difluoro-N-methylbenzamide

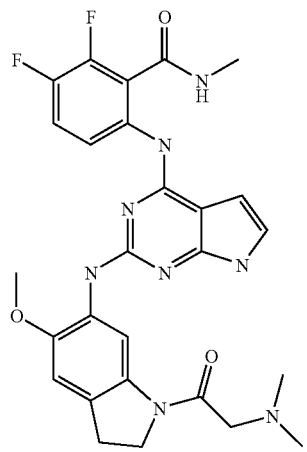

392

Step A\Intermediate D18: 6-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-2,3-difluoro-N-methylbenzamide

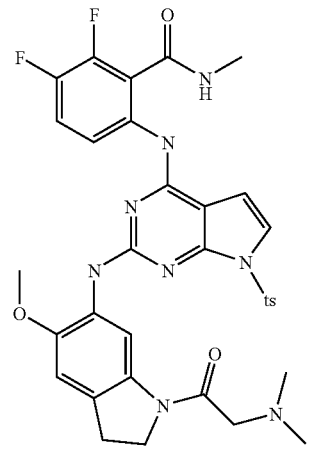

To a solution of 5-{[1-(N,N-dimethylglycyl)-5-(methyloxy)-2,3-dihydro-1H-indol-6-yl]amino}-8,9-difluoro-3-[(4-methylphenyl)sulfonyl]pyrrolo[2',3':4,5]pyrimido[6,1-b]quinazolin-7(3H)-one (300 mg, 0.445 mmol) in THF (5 mL) was added methylamine (2 M solution in THF) (2.23 mL, 4.45 mmol). The resulting mixture was let stir at rt for 10 min at which time it was diluted with ethyl acetate and washed with water and a saturated brine solution. Organics were dried over sodium sulfate and solvents removed under reduced pressure. The residue was purified via chromatography on SiO$_2$ and afforded 6-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-2,3-difluoro-N-methylbenzamide (143 mg, 0.203 mmol) as an off white solid. (ESIMS (M+H)$^+$=705)

Step B\Example 160: 6-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-2,3-difluoro-N-methylbenzamide 6-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-2,3-difluoro-N-methylbenzamide (143 mg, 0.203 mmol) was dissolved in 1,4-dioxane (10 mL) and transferred to a 20 ml microwave vessel. Water (3 mL) and a solution of 6M NaOH (3 ml) and was added and reaction heated in microwave at 120° C. for 10 minutes. Resulting brown solution was diluted with ethyl acetate and washed with a saturated sodium bicarbonate solution, water and a saturated brine solution. Organics were dried over sodium sulfate and solvents removed under reduced pressure to afford a brown solid that was purified via chromatography on SiO$_2$ to afford 6-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-2,3-difluoro-N-methylbenzamide (90 mg, 0.163 mmol) as a yellow solid. $^1$H NMR (400 MHz, DMSO-d$_6$) δ ppm 2.19-2.31 (m, 6 H), 2.77 (br. s., 3H), 3.04-3.23 (m, 4 H), 3.74-3.84 (m, 3 H), 4.17 (d, J=6.59 Hz, 2 H), 6.23-6.37 (m, 1 H), 6.86-7.02 (m, 2 H), 7.29-7.45 (m, 1 H), 7.50 (d, J=3.85 Hz, 1 H), 8.02-8.15 (m, 1

H), 8.65 (d, J=3.11 Hz, 2 H), 9.64 (d, J=3.94 Hz, 1 H), 11.23 (d, J=1.46 Hz, 1H). (ESIMS (M+H)⁺=551)

Example 161

6-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-2,3-difluoro-N-(1-methylethyl)benzamide

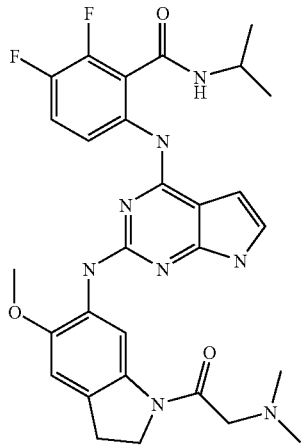

Step A\Intermediate D19: 6-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-2,3-difluoro-N-(1-methylethyl)benzamide

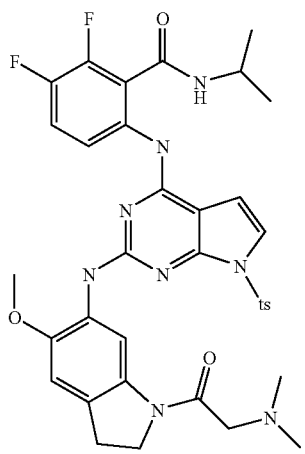

To a solution of 5-{[1-(N,N-dimethylglycyl)-5-(methyloxy)-2,3-dihydro-1H-indol-6-yl]amino}-8,9-difluoro-3-[(4-methylphenyl)sulfonyl]pyrrolo[2',3':4,5]pyrimido[6,1-b]quinazolin-7(3H)-one (300 mg, 0.445 mmol) in THF (5 mL) was added (1-methylethyl)amine (0.765 mL, 8.91 mmol). The resulting mixture was let stir at rt for 40 min at which time it was diluted with ethyl acetate and washed with water and a saturated brine solution. Organics were dried over sodium sulfate and solvents removed under reduced pressure.

The residue was purified via chromatography on SiO₂ and afforded 6-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-2,3-difluoro-N-(1-methylethyl)benzamide (101 mg, 0.138 mmol) as a yellow solid (only 85% pure by LCMS) (ESIMS (M+H)⁺=733)

Step B\Example 161: 6-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-2,3-difluoro-N-(1-methylethyl)benzamide 6-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-2,3-difluoro-N-(1-methylethyl)benzamide (101 mg, 0.138 mmol) was dissolved in 1,4-dioxane (10 mL) and transferred to a 20 ml microwave vessel. Water (3 mL) and a solution of 6M NaOH (3 ml) and was added and reaction heated in microwave at 120° C. for 10 minutes. Resulting brown solution was diluted with ethyl acetate and washed with a saturated sodium bicarbonate solution, water and a saturated brine solution. Organics were dried over sodium sulfate and solvents removed under reduced pressure to afford a brown solid that was purified via chromatography on SiO₂ to afford 6-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-2,3-difluoro-N-(1-methylethyl)benzamide (45 mg, 0.078 mmol) as a yellow solid. ¹H NMR (400 MHz, DMSO-d₆) δ ppm 1.06 (d, J=6.50 Hz, 6 H), 2.26 (s, 6 H), 3.10 (t, J=8.24 Hz, 2 H), 3.17 (s, 2 H), 3.77 (s, 3 H), 3.94-4.08 (m, 1 H), 4.17 (t, J=8.29 Hz, 2 H), 6.30 (br. s., 1 H), 6.86-6.99 (m, 2 H), 7.31-7.43 (m, 1 H), 7.50 (s, 1 H), 7.92-8.02 (m, 1 H), 8.51 (d, J=7.60 Hz, 1 H), 8.64 (s, 1 H), 9.31 (s, 1 H), 11.20 (br. s., 1 H). (ESIMS (M+H)⁺=579)

Example 162

6-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-2,3-difluorobenzamide

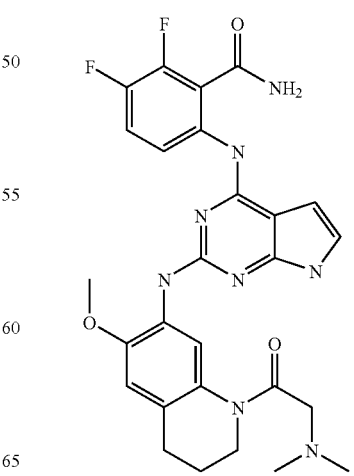

Step A\Intermediate D20: 5-{[1-(N,N-dimethylgly-cyl)-6-(methyloxy)-1,2,3,4-tetrahydro-7-quinolinyl]amino}-8,9-difluoro-3-[(4-methylphenyl)sulfonyl]pyrrolo[2',3':4,5]pyrimido[6,1-b]quinazolin-7(3H)-one

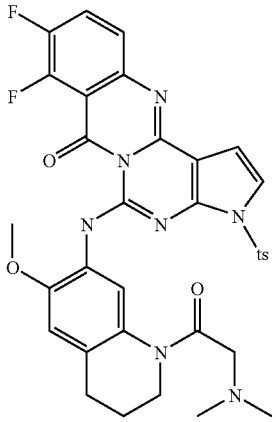

To a suspension of 6-({2-chloro-7-[(4-methylphenyl)sulfonyl]-7H-pyrrolo[2,3-d]pyrimidin-4-yl}amino)-2,3-difluorobenzamide (600 mg, 1.26 mmol) in 2,2,2-trifluoroethanol (40 ml) was added 1-[(dimethylamino)acetyl]-6-(methyloxy)-1,2,3,4-tetrahydro-7-quinolinamine (366 mg, 1.39 mmol), hydrochloric acid as a 4.0M solution in dioxane (2.51 ml, 10.1 mmol), and catalytic potassium iodide (<10 mg). The resulting slurry was stirred at 90° C. in a pressure vial for 24 hours, at which time all solids had completely dissolved. The resulting solution was cooled to room temperature and diluted with dichloromethane and saturated sodium bicarbonate as to adjust the aqueous layer to pH>10. The organic layer was washed with water and a saturated brine solution, dried over sodium sulfate, filtered and solvents were removed under reduced pressure. The resulting green solid was purified via trituration with diethyl ether to afford 5-{[1-(N,N-dimethylglycyl)-6-(methyloxy)-1,2,3,4-tetrahydro-7-quinolinyl]amino}-8,9-difluoro-3-[(4-methylphenyl)sulfonyl]pyrrolo[2',3':4,5]pyrimido[6,1-b]quinazolin-7(3H)-one (830 mg, 1.21 mmol) as a yellow solid. (ESIMS (M+H)$^+$=688)

Step B\Intermediate D21: 6-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-2,3-difluoro-N-(1-methylethyl)benzamide

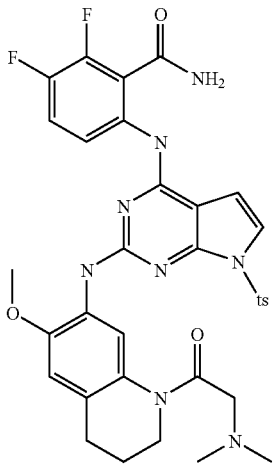

To a solution of 5-{[1-(N,N-dimethylglycyl)-6-(methyloxy)-1,2,3,4-tetrahydro-7-quinolinyl]amino}-8,9-difluoro-3-[(4-methylphenyl)sulfonyl]pyrrolo[2',3':4,5]pyrimido[6,1-b]quinazolin-7(3H)-one (270 mg, 0.393 mmol) in THF (5 mL) was added ammonium hydroxide (27% aqueous) (100 mL, large excess). The resulting mixture was let stir at rt for 16 h at which time it was diluted with ethyl acetate and washed with water and a saturated brine solution. Organics were dried over sodium sulfate and solvents removed under reduced pressure. The residue was purified via chromatography on SiO$_2$ and afforded 6-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-2,3-difluoro-N-(1-methylethyl)benzamide (110 mg, 0.156 mmol) as a yellow solid. (ESIMS (M+H)$^+$=705)

Step C\Example 162: 6-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-2,3-difluorobenzamide 6-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-2,3-difluoro-N-(1-methylethyl)benzamide (110 mg, 0.156 mmol) was dissolved in 1,4-dioxane (6 mL) and transferred to a 20 ml microwave vessel. Water (2 mL) and a solution of 6M NaOH (2 ml) and was added and reaction heated in microwave at 120° C. for 10 minutes. Resulting brown solution was diluted with ethyl acetate and washed with a saturated sodium bicarbonate solution, water and a saturated brine solution. Organics were dried over sodium sulfate and solvents removed under reduced pressure to afford a brown solid that was purified via chromatography on SiO$_2$ to afford 6-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-2,3-difluorobenzamide (53 mg, 0.096 mmol) as a tan solid. $^1$H NMR (400 MHz, DMSO-d$_6$) δ ppm 1.82-1.94 (m, 2 H), 2.12 (br. s., 6 H), 2.68 (br. s., 2 H), 3.24 (s, 2 H), 3.70 (t, J=5.95 Hz, 2 H), 3.84 (s, 3 H), 6.29 (d, J=1.10 Hz, 1 H), 6.83 (br. s., 1 H), 6.98 (br. s., 1 H), 7.38-7.51 (m, 2 H), 8.12 (br. s., 3 H), 8.42 (br. s., 1 H), 9.83 (br. s., 1 H), 11.37 (d, J=1.01 Hz, 1 H). (ESIMS (M+H)$^+$=551)

Example 163

6-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-2,3-difluoro-N-methylbenzamide

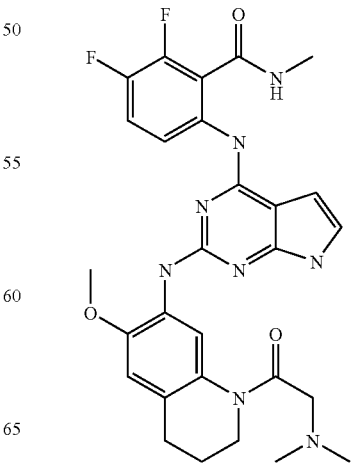

Step A\Intermediate D22: 6-({2-{[1-(N,N-dimethylglycyl)-6-(methyloxy)-1,2,3,4-tetrahydro-7-quinolinyl]amino}-7-[(4-methylphenyl)sulfonyl]-7H-pyrrolo[2,3-d]pyrimidin-4-yl}amino)-2,3-difluoro-N-methylbenzamide

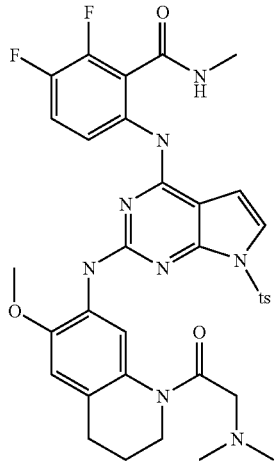

To a solution of 5-{[1-(N,N-dimethylglycyl)-6-(methyloxy)-1,2,3,4-tetrahydro-7-quinolinyl]amino}-8,9-difluoro-3-[(4-methylphenyl)sulfonyl]pyrrolo[2',3':4,5]pyrimido[6,1-b]quinazolin-7(3H)-one (270 mg, 0.393 mmol) in THF (50 mL) was added methyl amine (2M solution in THF) (1.96 mL, 3.93 mmol). The resulting mixture was let stir at rt for 1 h at which time it was diluted with ethyl acetate and washed with water and a saturated brine solution. Organics were dried over sodium sulfate and solvents removed under reduced pressure. The residue was purified via chromatography on $SiO_2$ and afforded 6-({2-{[1-(N,N-dimethylglycyl)-6-(methyloxy)-1,2,3,4-tetrahydro-7-quinolinyl]amino}-7-[(4-methylphenyl)sulfonyl]-7H-pyrrolo[2,3-d]pyrimidin-4-yl}amino)-2,3-difluoro-N-methylbenzamide (139 mg, 0.193 mmol) as a yellow solid. (ESIMS $(M+H)^+$=719)

Step B\Example 163 : 6-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-2,3-difluoro-N-methylbenzamide 6-({2-{[1-(N,N-dimethylglycyl)-6-(methyloxy)-1,2,3,4-tetrahydro-7-quinolinyl]amino}-7-[(4-methylphenyl)sulfonyl]-7H-pyrrolo[2,3-d]pyrimidin-4-yl}amino)-2,3-difluoro-N-methylbenzamide (139 mg, 0.193 mmol) was dissolved in 1,4-dioxane (6 mL) and transferred to a 20 ml microwave vessel. Water (2 mL) and a solution of 6M NaOH (2 ml) and was added and reaction heated in microwave at 120° C. for 10 minutes. Resulting brown solution was diluted with ethyl acetate and washed with a saturated sodium bicarbonate solution, water and a saturated brine solution. Organics were dried over sodium sulfate and solvents removed under reduced pressure to afford a brown solid that was purified via chromatography on $SiO_2$ to afford 6-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-2,3-difluoro-N-methylbenzamide (51 mg, 0.090 mmol) as a tan solid. $^1$H NMR (400 MHz, DMSO-$d_6$) δ ppm 1.81-1.92 (m, 2 H), 2.11 (br. s., 6H), 2.67 (br. s., 2 H), 2.74 (d, J=4.49 Hz, 3 H), 3.24 (s, 2 H), 3.69 (t, J=6.09 Hz, 2 H), 3.84 (s, 3 H), 5.76 (s, 1 H), 6.34 (d, J=1.10 Hz, 1 H), 6.82 (br. s., 1 H), 6.96 (br. s., 1 H), 7.38-7.51 (m, 2 H), 7.90-8.01 (m, 1 H), 8.38-8.48 (m, 1 H), 8.63 (d, J=4.67 Hz, 1 H), 9.58 (s, 1 H), 11.33 (br.s, 1 H). (ESIMS $(M+H)^+$=565)

Example 164

6-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-2,3-difluoro-N-(1-methylethyl)benzamide

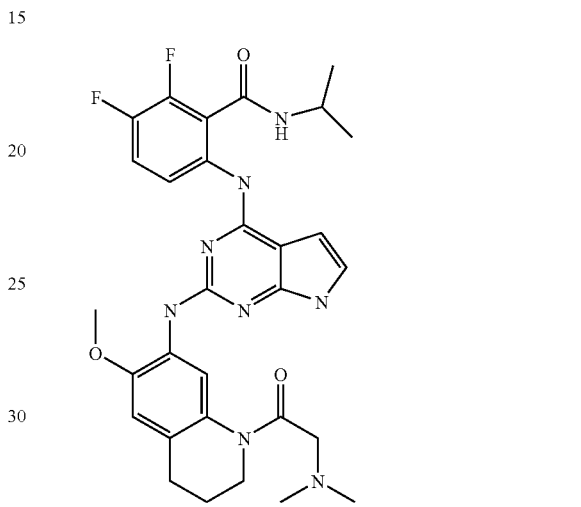

To a solution of 5-{[1-(N,N-dimethylglycyl)-6-(methyloxy)-1,2,3,4-tetrahydro-7-quinolinyl]amino}-8,9-difluoro-3-[(4-methylphenyl)sulfonyl]pyrrolo[2',3':4,5]pyrimido[6,1-b]quinazolin-7(3H)-one (300 mg, 0.436 mmol) in THF (5 mL) was added (1-methylethyl)amine (1.4 mL, 17.44 mmol). The resulting mixture was let stir at rt for 2 h at which time it was diluted with ethyl acetate and washed with water and a saturated brine solution. Organics were dried over sodium sulfate and solvents removed under reduced pressure. The residue was attempted to be purified via chromatography on $SiO_2$ and afforded a yellow solid containing about 50% 6-({2-{[1-(N,N-dimethylglycyl)-6-(methyloxy)-1,2,3,4-tetrahydro-7-quinolinyl]amino}-7-[(4-methylphenyl)sulfonyl]-7H-pyrrolo[2,3-d]pyrimidin-4-yl}amino)-2,3-difluoro-N-(1-methylethyl)benzamide mmol) as a yellow solid. This crude material was dissolved in 1,4-dioxane (6 mL) and transferred to a 20 ml microwave vessel. Water (2 mL) and a solution of 6M NaOH (2 ml) was added and reaction mixture heated in microwave at 120° C. for 10 minutes. Resulting brown solution was diluted with ethyl acetate and washed with a saturated sodium bicarbonate solution, water and a saturated brine solution. Organics were dried over sodium sulfate and solvents removed under reduced pressure to afford a brown solid that was purified via chromatography on $SiO_2$ to afford 6-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-2,3-difluoro-N-(1-methylethyl)benzamide (42 mg, 0.071 mmol) as an off white solid. $^1$H NMR (400 MHz, DMSO-$d_6$) δ ppm 1.00 (d, J=6.59 Hz, 6 H) 1.81-1.92 (m, 2 H) 2.12 (br. s., 6 H) 2.60-2.73 (m, 2 H) 3.24 (s, 2 H) 3.69 (t, J=6.04 Hz, 2 H) 3.83 (s, 3 H) 3.90-4.03 (m, 1 H) 6.34 (d, J=0.92 Hz, 1 H) 6.81 (br. s., 1 H) 6.91-6.99 (m, 1 H) 7.38-7.51

(m, 2 H) 7.74-7.87 (m, 1 H) 8.41 (d, J=7.69 Hz, 2 H), 9.29 (s, 1 H) 11.30 (br. s., 1 H) (ESIMS (M+H)+=593)

Example 165

2-[(2-{[1-(N-ethyl-N-methylglycyl)-5-(methyloxy)-2,3-dihydro-1H-indol-6-yl]amino}-1H-pyrrolo[2,3-d]pyrimidin-4-yl)amino]-6-fluoro-N-methylbenzamide

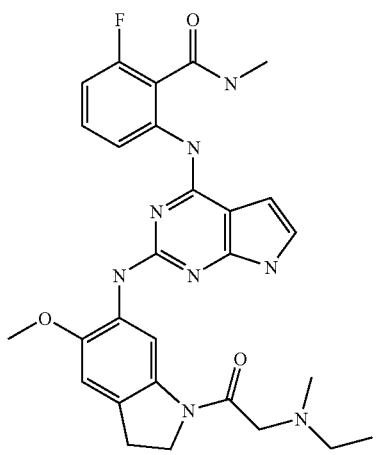

5-Chloro-8-fluoro-3-[(4-methylphenyl)sulfonyl]pyrrolo[2',3':4,5]pyrimido[6,1-b]quinazolin-7(3H)-one (0.6 g, 2.2 mmol) and 1-{[ethyl(methyl)amino]acetyl}-5-(methyloxy)-2,3-dihydro-1H-indol-6-amine (0.8 g, 1.8 mmol) were suspended in 50 ml of THF, the mixture was stirred at 82° C. overnight. The reaction mixture was cooled and diluted with 60 ml of ethyl acetate, and washed with saturated NaHCO₃, the organic phase was dried over Na₂SO₄ and the solvent was removed to yield the 5-{[1-(N-ethyl-N-methylglycyl)-5-(methyloxy)-2,3-dihydro-1H-indol-6-yl]amino}-8-fluoro-3-[(4-methylphenyl)sulfonyl]pyrrolo[2',3':4,5]pyrimido[6,1-b]quinazolin-7(3H)-one. The 5-{[1-(N-ethyl-N-methylglycyl)-5-(methyloxy)-2,3-dihydro-1H-indol-6-yl]amino}-8-fluoro-3-[(4-methylphenyl)sulfonyl]pyrrolo[2',3':4,5]pyrimido[6,1-b]quinazolin-7(3H)-one was mixed with a solution of methylamine (2M in THF, 30 mL), the reaction mixture was stirred at room temperature overnight. The reaction mixture was diluted with 50 ml of ethyl acetate, and washed with saturated NaCl, the organic layer was dried over Na₂SO₄, and the solvents removed under reduced pressure to afford the corresponding 2-({2-{[1-(N-ethyl-N-methylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-methylbenzamide. The 2-({2-{[1-(N-ethyl-N-methylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-methylbenzamide was suspended in 15 ml of dioxane, then KOH was added (it was dissolved in 5 ml of water). The reaction mixture was stirred at 92° C. for 2 hours, the reaction mixture was cooled to room temperature, the solvent was removed, the residue was re-dissolved in 50 ml of CH₂Cl₂, and washed with water (2×100 ml). The combined organic phase was washed with a saturated NH₄OH, then dried over Na₂SO₄, the solvent was removed to yield the crude product and purified by chromatography on SiO₂ (0% to 10% MeOH/CH₂Cl₂ with 0.2% added NH₃) to afford 2-[(2-{[1-(N-ethyl-N-methylglycyl)-5-(methyloxy)-2,3-dihydro-1H-indol-6-yl]amino}-1H-pyrrolo[2,3-d]pyrimidin-4-yl)amino]-6-fluoro-N-methylbenzamide as a yellow solid (0.26 g). ¹H NMR (400 MHz), DMSO-d₆) δ ppm 0.98 (t, J=6.59, 3H), 2.20 (s, 3H), 2.44 (t, J=7.33 Hz, 2H), 2.78 (d, J=3.11 Hz, 3H), 3.08 (t, J=7.51 Hz, 2H), 3.20 (s, 2H), 3.75 (s, 3H), 4.16 (t, J=7.79 Hz, 2H), 6.26 (s, 1H), 6.85-6.92 (m, 3H), 7.29 (q, J=7.05 Hz, 1H), 7.56 (s, 1H), 8.36 (d, J=8.15 Hz, 1H), 8.53 (s, 1H), 8.63 (s, 1H), 10.17 (s, 1H), 11.27 (s, 1H); ESIMS (M+H)+=547.

Example 166

2-[(2-{[1-(N-ethyl-N-methylglycyl)-5-(methyloxy)-2,3-dihydro-1H-indol-6-yl]amino}-1H-pyrrolo[2,3-d]pyrimidin-4-yl)amino]-6-fluorobenzamide

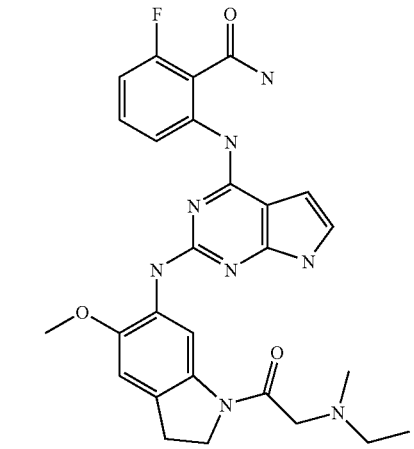

In a manner analogous to that described for Example 165, 2-[(2-{[1-(N-ethyl-N-methylglycyl)-5-(methyloxy)-2,3-dihydro-1H-indol-6-yl]amino}-1H-pyrrolo[2,3-d]pyrimidin-4-yl)amino]-6-fluorobenzamide was prepared from 5-chloro-8-fluoro-3-[(4-methylphenyl)sulfonyl]pyrrolo[2',3':4,5]pyrimido[6,1-b]quinazolin-7(3H)-one hydrogen chloride (0.40 g, 0.90 mmol), 27% aqueous ammonium hydroxide, and 1-{[ethyl(methyl)amino]acetyl}-5-(methyloxy)-2,3-dihydro-1H-indol-6-amine (0.30 g, 1.1 mmol) and isolated as a yellow solid (0.12 g). ¹H NMR (400 MHz, DMSO-d₆) δ ppm 0.98 (m, 3 H), 2.20 (s, 3 H), 2.43 (t, J=7.15 Hz, 2H), 3.07 (t, J=8.24 Hz, 2 H), 3.20 (s, 2H), 3.75 (s, 3 H), 4.18 (t, J=8.24 Hz, 2 H), 6.20 (s,1 H), 6.84 (t, J=6.88 Hz, 1H), 6.93 (s, 2H), 7.30 (q, J=6.96 Hz, 1 H), 7.58 (s, 1 H), 7.99 (s,1H), 8.08 (s,1H), 8.50 (d, J=8.42 Hz, 1H), 8.59 (s, 1 H), 10.52 (s, 1 H), 11.27 (s, 1 H); ESIMS (M+H)+=533.

Example 167

2-fluoro-N-methyl-6-[(2-{[5-(methyloxy)-1-(N-methyl-N-propylglycyl)-2,3-dihydro-1H-indol-6-yl]amino}-1H-pyrrolo[2,3-d]pyrimidin-4-yl)amino]benzamide

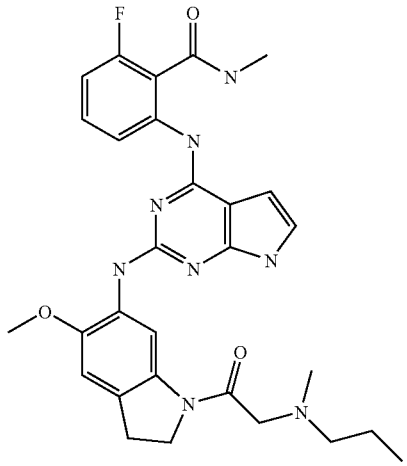

In a manner analogous to that described for Example 165, 2-fluoro-N-methyl-6-[(2-{[5-(methyloxy)-1-(N-methyl-N-propylglycyl)-2,3-dihydro-1H-indol-6-yl]amino}-1H-pyrrolo[2,3-d]pyrimidin-4-yl)amino]benzamide was prepared from 5-chloro-8-fluoro-3-[(4-methylphenyl)sulfonyl]pyrrolo[2',3':4,5]pyrimido[6,1-b]quinazolin-7(3H)-one hydrogen chloride (0.40 g, 0.90 mmol), methylamine(2M in THF), and 5-(methyloxy)-1-{[methyl(propyl)amino]acetyl}-2,3-dihydro-1H-indol-6-amine (0.30 g, 1.1 mmol) and isolated as a yellow solid (0.27 g); $^1$H NMR (400 MHz, DMSO-d$_6$) δ ppm 0.81 (t, J=7.33 Hz, 3 H), 1.41 (q, J=7.23 Hz, 2H), 2.21 (s, 3 H), 2.36 (t, J=7.33 Hz, 2H), 2.78 (d, J=4.39 Hz, 3 H), 3.08 (t, J=8.24 Hz, 2 H), 3.21 (s, 2H), 3.75 (s, 3 H), 4.18 (t, J=8.33 Hz, 2 H), 6.25 (s1 H), 6.84-6.92 (m, 3H), 7.29 (q, J=6.96 Hz, 1 H), 7.55 (s, 1 H), 8.34 (d, J=8.38 Hz, 1 H), 8.52 (s, 1 H), 8.60 (s, 1 H), 10.14 (s, 1 H), 11.25 (s, 1 H); ESIMS (M+H)$^+$=561.

Example 168

2-fluoro-6-[(2-{[5-(methyloxy)-1-(N-methyl-N-propylglycyl)-2,3-dihydro-1H-indol-6-yl]amino}-1H-pyrrolo[2,3-d]pyrimidin-4-yl)amino]benzamide

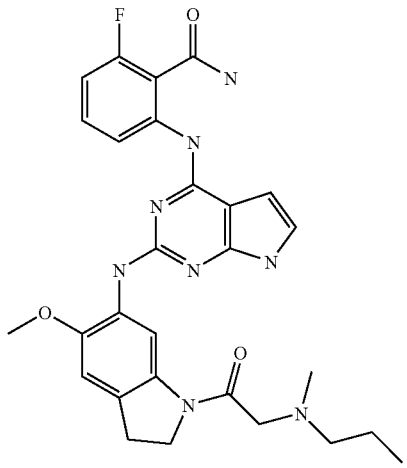

In a manner analogous to that described for Example 165, 5-chloro-8-fluoro-3-[(4-methylphenyl)sulfonyl]pyrrolo[2',3':4,5]pyrimido[6,1-b]quinazolin-7(3H)-one hydrogen chloride (0.40 g, 0.90 mmol), 27% aqueous ammonium hydroxide, and 5-(methyloxy)-1-{[methyl(propyl)amino]acetyl}-2,3-dihydro-1H-indol-6-amine (0.30 g, 1.1 mmol) and isolated as a yellow solid (0.13 g); $^1$H NMR (400 MHz, DMSO-d$_6$) δ ppm 0.81 (t, J=7.33 Hz, 3 H), 1.41 (q, J=7.14 Hz, 2H), 2.20 (s, 3 H), 2.34 (t, J=7.05 Hz, 2H), 3.09 (t, J=8.06 Hz, 2 H), 3.21 (s, 2H), 3.74 (s, 3 H), 4.18 (t, J=8.24 Hz, 2 H), 6.20 (s,1 H), 6.86 (t, J=9.61 Hz, 1H), 6.93 (s, 2H), 7.30 (m, 1 H), 7.58 (s, 1H), 8.00 (s,1H), 8.09 (s,1H), 8.51 (d, J=8.42 Hz, 1H), 8.59 (s, 1 H), 10.53 (s, 1 H), 11.28 (s, 1 H); ESIMS (M+H)$^+$=547.

Example 169

2-fluoro-N-methyl-6-[(2-{[1-{N-methyl-N-[2-(methyloxy)ethyl]glycyl}-5-(methyloxy)-2,3-dihydro-1H-indol-6-yl]amino}-1H-pyrrolo[2,3-d]pyrimidin-4-yl)amino]benzamide

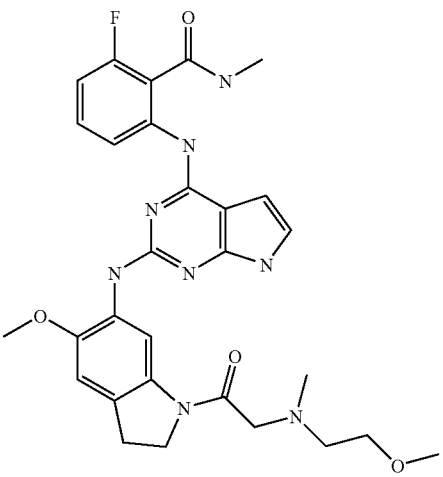

In a manner analogous to that described for Example 165, 2-fluoro-N-methyl-6-[(2-{[1-{N-methyl-N-[2-(methyloxy)Ethyl]glycyl}-5-(methyloxy)-2,3-dihydro-1H-indol-6-yl]amino}-1H-pyrrolo[2,3-d]pyrimidin-4-yl)amino]benzamide was prepared from 5-chloro-8-fluoro-3-[(4-methylphenyl)sulfonyl]pyrrolo[2',3':4,5]pyrimido[6,1-b]quinazolin-7(3H)-one hydrogen chloride (0.40 g, 0.90 mmol), methylamine(2M in THF), and 1-({methyl[2-(methyloxy)Ethyl]amino}acetyl)-5-(methyloxy)-2,3-dihydro-1H-indol-6-amine (0.30 g, 1.1 mmol) and isolated as a yellow solid (0.19 g); $^1$H NMR (400 MHz, DMSO-d$_6$) δ ppm 2.28 (s,3 H), 2.62(t, J=5.40 Hz, 2H), 2.79 (d, J=4.12 Hz, 3 H), 3.08 (t, J=7.87 Hz, 2H), 3.20 (s, 3 H), 3.29 (s,2 H), 3.41 (t, J=5.49 Hz, 2H), 3.75 (s, 3 H), 4.15 (t, J=8.06 Hz, 2 H), 6.25 (s1 H), 6.84-6.92(m, 3H), 7.31 (q, J=7.23 Hz, 1 H), 7.55 (s, 1 H), 8.36 (d, J=8.33 Hz, 1H), 8.52 (s, 1 H), 8.62 (s, 1 H), 10.15 (s, 1 H), 11.26 (s, 1 H); ESIMS (M+H)$^+$=577.

Example 170

2-fluoro-6-[(2-{[1-{N-methyl-N-[2-(methyloxy)ethyl]glycyl}-5-(methyloxy)-2,3-dihydro-1H-indol-6-yl]amino}-1H-pyrrolo[2,3-d]pyrimidin-4-yl)amino]benzamide

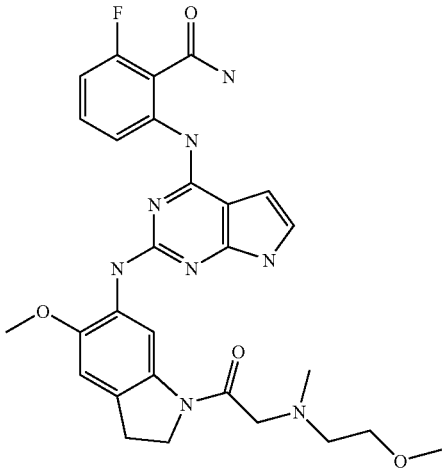

In a manner analogous to that described for Example 165, 2-fluoro-6-[(2-{[1-{N-methyl-N-[2-(methyloxy)Ethyl]glycyl}-5-(methyloxy)-2,3-dihydro-1H-indol-6-yl]amino}-1H-pyrrolo[2,3-d]pyrimidin-4-yl)amino]benzamide was prepared from 5-chloro-8-fluoro-3-[(4-methylphenyl)sulfonyl]pyrrolo[2',3':4,5]pyrimido[6,1-b]quinazolin-7(3H)-one hydrogen chloride (0.40 g, 0.90 mmol), 27% aqueous ammonium hydroxide, and 1-({methyl[2-(methyloxy)Ethyl]amino}acetyl)-5-(methyloxy)-2,3-dihydro-1H-indol-6-amine (0.30 g, 1.1 mmol) and isolated as a yellow solid (0.28 g); $^1$H NMR (400 MHz, DMSO-$d_6$) δ ppm 2.28 (br. s., 3 H), 2.62 (br. s., 2 H), 3.09 (t, J=7.51 Hz, 2 H), 3.20 (br. s., 3 H), 3.29 (br. s., 2 H), 3.41 (br. s., 2 H), 3.75 (s, 3 H), 4.16 (t, J=7.83 Hz, 2 H), 6.21 (br. s., 1 H), 6.84 (t, J=9.25 Hz, 1 H), 6.93 (br. s., 2 H), 7.29 (d, J=7.14 Hz, 1 H), 7.58 (s, 1 H), 8.00 (br. s., 1 H), 8.09 (br. s., 1 H), 8.50 (d, J=8.24 Hz, 1 H), 8.60 (s, 1 H), 10.54 (br. s., 1 H), 11.28 (br. s., 1 H). ESIMS (M+H)$^+$=563.

Example 171

4-chloro-2-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-6-fluorobenzamide

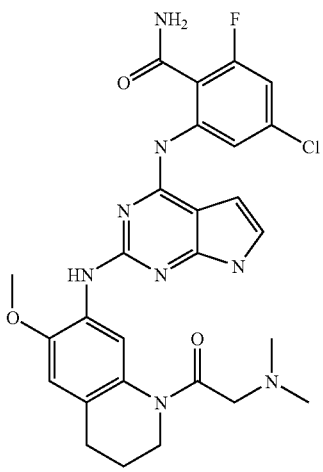

In a manner analogous to that described for Example 90, 4-chloro-2-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-6-fluorobenzamide (0.15, 94%) was prepared from 4-chioro-2-({2-chloro-7-[(4-methyl phenyl)sulfonyl]-7H-pyrrolo[2,3-d]pyrimidin-4-yl}amino)-6-fluorobenzamide (0.30 g, 0.60 mmol), 27% aqueous ammonium hydroxide, and 1-[(dimethylamino)acetyl]-6-(methyloxy)-1,2,3,4-tetrahydro-7-quinolinamine (0.2 g, 0.65 mmol). $^1$H NMR (400 MHz, DMSO-$d_6$) δ ppm 1.85 (br. s., 3 H), 1.88 (d, J=6.23 Hz, 1 H), 2.08 (br. s., 4 H), 2.69 (br. s., 2 H), 3.19 (s, 2 H), 3.70 (t, J=6.04 Hz, 2 H), 3.83 (s, 3 H), 6.27 (d, J=1.46 Hz, 1 H), 6.84 (br. s., 1 H), 7.04 (s, 1 H), 7.12 (dd, J=10.48, 1.69 Hz, 1 H), 7.64 (s, 1 H), 8.09 (br. s., 1 H), 8.20 (s, 1 H), 8.33 (s, 1 H), 8.59 (s, 1 H), 10.83 (s, 1 H), 11.45 (s, 1 H). ESIMS (M+H)$^+$=568.

Example 172

4-chloro-2-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-6-fluoro-N-methylbenzamide

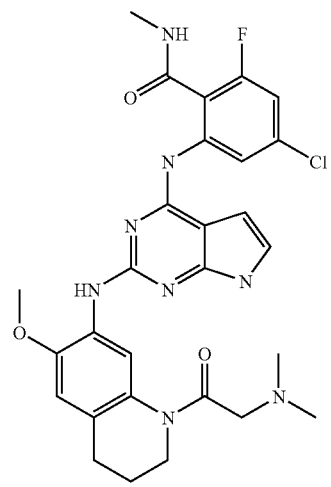

In a manner analogous to that described for Example 90, 4-chloro-2-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-6-fluoro-N-methylbenzamide (0.14, 84%) was prepared from 4-chloro-2-({2-chloro-7-[(4-methylphenyl)sulfonyl]-7H-pyrrolo[2,3-d]pyrimidin-4-yl}amino)-6-fluorobenzamide (0.30 g, 0.60 mmol), methylamine(2M in THF), and 1-[(dimethylamino)acetyl]-6-(methyloxy)-1,2,3,4-tetrahydro-7-quinolinamine (0.2 g, 0.65 mmol). $^1$HNMR (400 MHz, DMSO-$d_6$) δ ppm 1.84-1.89 (m, 2 H), 2.08 (br. s., 6H), 2.50 (s, 2 H), 2.68 (s, 2 H), 2.79 (d, J=4.30 Hz, 3 H), 3.19 (s, 2 H), 3.69 (t, J=5.86 Hz, 2 H), 3.83 (s, 3 H), 6.31 (s, 1 H), 6.84 (s, 1 H), 7.02 (s, 1 H), 7.14 (dd, J=10.30, 1.42 Hz, 1 H), 7.61 (s, 1 H), 8.34 (s, 1 H), 8.41 (s; 1 H), 8.63 (s, 1 H). ESIMS (M+H)$^+$=582.

Example 173

4-chloro-2-fluoro-6-[(2-{[6-(methyloxy)-1-(1-pyrrolidinylacetyl)-1,2,3,4-tetrahydro-7-quinolinyl]amino}-1H-pyrrolo[2,3-d]pyrimidin-4-yl)amino]benzamide

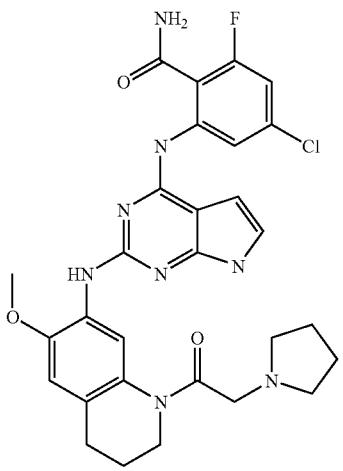

In a manner analogous to that described for Example 90, 4-chloro-2-fluoro-6-[(2-{[6-(methyloxy)-1-(1-pyrrolidinylacetyl)-1,2,3,4-tetrahydro-7-quinolinyl]amino}-1H-pyrrolo[2,3-d]pyrimidin-4-yl)amino]benzamide (0.12, 76%) was prepared from 4-chloro-2-({2-chloro-7-[(4-methylphenyl)sulfonyl]-7H-pyrrolo[2,3-d]pyrimidin-4-yl}amino)-6-fluorobenzamide (0.40 g, 0.80 mmol), 27% aqueous ammonium hydroxide, and 6-(methyloxy)-1-(1-pyrrolidinylacetyl)-1,2,3,4-tetrahydro-7-quinolinamine (0.25g, 0.85 mmol). $^1$H NMR (400 MHz, DMSO-$d_6$) δ ppm 1.63 (br. s., 4 H), 1.89 (br. s., 2 H), 2.71 (br. s., 6 H), 3.70 (br. s., 4 H), 3.84 (s, 3 H), 6.27 (s, 1 H), 6.88 (s, 1 H), 7.04 (s, 1 H), 7.13 (d, J=10.35 Hz, 1 H), 7.65 (s, 1 H), 8.10 (s, 1 H), 8.20 (s, 1 H), 8.36 (s, 1 H), 8.58 (s, 1 H), 10.82 (s, 1 H), 11.50 (s, 1 H), ESIMS (M+H)$^+$=594

Example 174

4-chloro-2-fluoro-N-methyl-6-[(2-{[6-(methyloxy)-1-(1-pyrrolidinylacetyl)-1,2,3,4-tetrahydro-7-quinolinyl]amino}-1H-pyrrolo[2,3-d]pyrimidin-4-yl)amino]benzamide

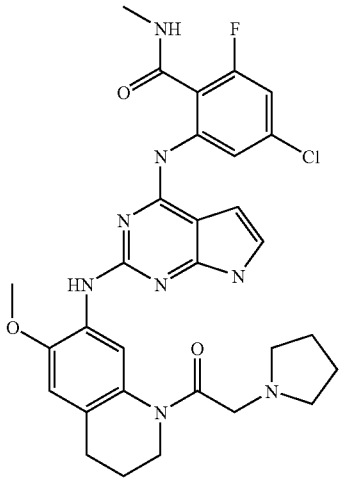

In a manner analogous to that described for Example 90, 4-chloro-2-fluoro-N-methyl-6-[(2-{[6-(methyloxy)-1-(1-pyrrolidinylacetyl)-1,2,3,4-tetrahydro-7-quinolinyl]amino}-1H-pyrrolo[2,3-d]pyrimidin-4-yl)amino]benzamide (0.22, 79%) was prepared from 4-chloro-2-({2-chloro-7-[(4-methylphenyl)sulfonyl]-7H-pyrrolo[2,3-d]pyrimidin-4-yl}amino)-6-fluorobenzamide (0.40 g, 0.80 mmol), methyl amine(2M in THF), and 6-(methyloxy)-1-(1-pyrrolidinylacetyl)-1,2,3,4-tetrahydro-7-quinolinamine (0.25 g, 0.85 mmol). $^1$H NMR (400 MHz, DMSO-$d_6$) δ ppm 1.48 (br. s., 4 H), 1.84 (d, J=5.86 Hz, 4 H), 2.37 (br. s., 4 H), 2.65 (br. s., 2 H), 2.77 (d, J=4.03 Hz, 3 H), 3.66 (t, J=5.72 Hz, 2 H), 3.80 (s, 3 H), 6.28 (s, 1 H), 6.81 (s, 1 H), 6.99 (s, 1 H), 7.11 (d, J=10.16 Hz, 1 H), 7.57 (s, 1 H), 8.38 (d, J=19.96 Hz, 2 H), 8.59 (s, 1 H), 10.43 (s, 1 H), 11.42 (s, 1 H). ESIMS (M+H)$^+$=608.

Example 175

4-chloro-2-fluoro-6-[(2-{[5-(methyloxy)-1-(1-pyrrolidinylacetyl)-2,3-dihydro-1H-indol-6-yl]amino}-1H-pyrrolo[2,3-d]pyrimidin-4-yl)amino]benzamide

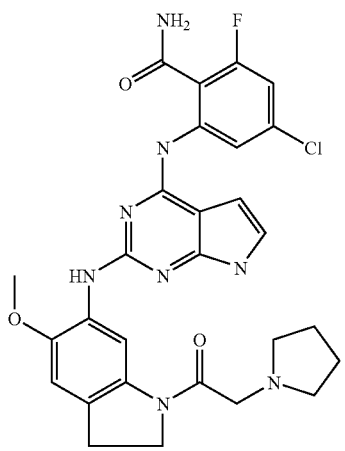

In a manner analogous to that described for Example 90, 4-chloro-2-fluoro-6-[(2-{[5-(methyloxy)-1-(1-pyrrolidinylacetyl)-2,3-dihydro-1H-indol-6-yl]amino}-1H-pyrrolo[2,3-d]pyrimidin-4-yl)amino]benzamide (0.15, 58%) was prepared from 4-chloro-2-({2-chloro-7-[(4-methylphenyl)sulfonyl]-7H-pyrrolo[2,3-d]pyrimidin-4-yl}amino)-6-fluorobenzamide (0.40 g, 0.80 mmol), 27% aqueous ammonium hydroxide, and 5-(methyloxy)-1-(1-pyrrolidinylacetyl)-2,3-dihydro-1H-indol-6-amine (0.25g, 0.90 mmol).

$^1$H NMR (400 MHz, DMSO-$d_6$) δ ppm 1.74 (br. s., 4 H), 2.71 (br. s., 4 H), 3.14 (t, J=8.10 Hz, 2 H), 3.59 (br. s., 2 H), 3.77 (s, 3 H), 4.12 (t, J=8.06 Hz, 2 H), 6.23 (s, 1H), 6.96-7.08 (m, 3 H), 7.74 (s, 1 H), 8.10 (s, 1 H), 8.24 (s, 1 H), 8.52 (s, 1 H), 8.68 (s, 1 H), 10.96 (s, 1 H), 11.36 (s, 1 H), ESIMS (M+H)$^+$=580.

Example 176

4-chloro-2-fluoro-N-methyl-6-[(2-{[5-(methyloxy)-1-(1-pyrrolidinylacetyl)-2,3-dihydro-1H-indol-6-yl]amino}-1H-pyrrolo[2,3-d]pyrimidin-4-yl)amino]benzamide

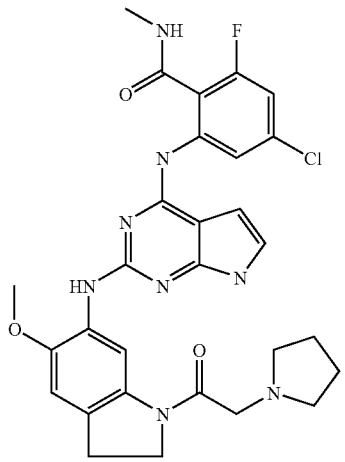

In a manner analogous to that described for Example 90, 4-chloro-2-fluoro-N-methyl-6-[(2-{[5-(methyloxy)-1-(1-pyrrolidinylacetyl)-2,3-dihydro-1H-indol-6-yl]amino}-1H-pyrrolo[2,3-d]pyrimidin-4-yl)amino]benzamide (0.19, 70%) was prepared from 4-chloro-2-({2-chloro-7-[(4-methylphenyl)sulfonyl]-7H-pyrrolo[2,3-d]pyrimidin-4-yl}amino)-6-fluorobenzamide (0.40 g, 0.80 mmol), methylamine (2M in THF), 5-(methyloxy)-1-(1-pyrrolidinylacetyl)-2,3-dihydro-1H-indol-6-amine (0.25g, 0.90 mmol). $^1$H NMR (400 MHz, DMSO-$d_6$) δ ppm 1.60-1.73 (m, 4 H), 2.44-2.52 (m, 6 H), 2.79 (d, J=4.39 Hz, 3 H), 3.08 (t, J=8.24 Hz, 2 H), 3.74 (s, 3 H), 4.11 (t, J=8.33 Hz, 2 H), 6.24 (d, J=1.47 Hz, 1 H), 6.90-6.98 (m, 2 H), 7.04 (dd, J=10.48, 1.51 Hz, 1 H), 7.66 (s, 1 H), 8.51 (d, J=5.95 Hz, 2 H), 8.59 (s, 1 H), 10.51 (s, 1 H), 11.30 (s, 1 H), ESIMS (M+H)$^+$=594.

Example 177

2-[(2-{[1-[N-ethyl-N-(2-hydroxyethyl)glycyl]-5-(methyloxy)-2,3-dihydro-1H-indol-6-yl]amino}-1H-pyrrolo[2,3-d]pyrimidin-4-yl)amino]-6-fluorobenzamide

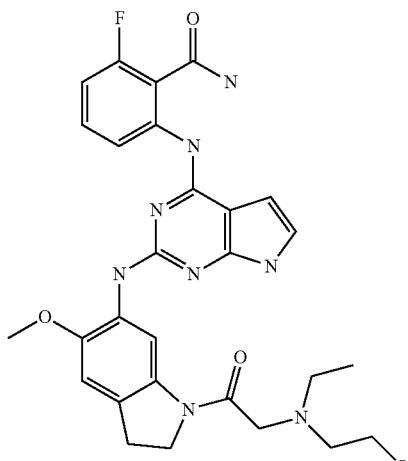

In a manner analogous to Example 165, 2-[(2-{[1-[N-ethyl-N-(2-hydroxyethyl)glycyl]-5-(methyloxy)-2,3-dihydro-1H-indol-6-yl]amino}-1H-pyrrolo[2,3-d]pyrimidin-4-yl)amino]-6-fluorobenzamide was prepared from 5-chloro-8-fluoro-3-[(4-methylphenyl)sulfonyl]pyrrolo[2',3':4,5]pyrimido[6,1-b]quinazolin-7(3H)-one hydrogen chloride (0.40 g, 0.90 mmol), 27% aqueous ammonium hydroxide, and 2-[{2-[6-amino-5-(methyloxy)-2,3-dihydro-1H-indol-1-yl]-2-oxoethyl}(ethyl)amino]ethanol (0.30 g, 1.1 mmol) and isolated as a yellow solid (0.05 g); $^1$H NMR (400 MHz, DMSO-$d_6$) δ ppm 1.04 (t, J=9.71 Hz, 3H), 2.72 (m,2H), 3.11 (q, J=8.70 Hz, 2H), 3.38 (s, 3H), 3.64-3.69 (m, 4H), 3.80 (s,2H), 3,96 (m 2H), 6.17(s., 1H), 6.41 (s,1H),6.75 (m,2H), 6.77(m, 2H), 7.40 (br.s, 2H), 8.92 (d, J=8.33 Hz, 1H), 9.61 (s, 1H), 10.38 (s, 1H), 11.64 (s, 1H).

Example 178

2-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-4,6-difluorobenzamide

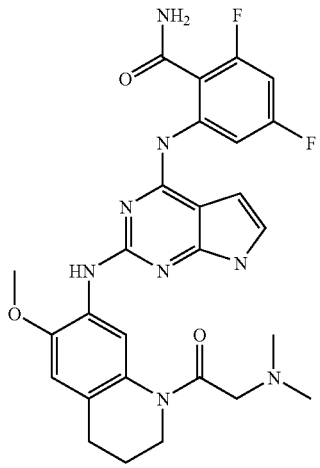

In a manner analogous to that described for Example 90, 2-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-4,6-difluorobenzamide (0.017 g, 32%) was prepared from 2-({2-chloro-7-[(4-methylphenyl)sulfonyl]-7H-pyrrolo[2,3-d]pyrimidin-4-yl}amino)-4,6-difluorobenzamide (0.350 g, 0.73 mmol), 27% aqueous ammonium hydroxide, and 1-[(dimethylamino)acetyl]-6-(methyloxy)-1,2,3,4-tetrahydro-7-quinolinamine (0.29 g, 1.1 mmol). $^1$H NMR (400 MHz, DMSO-$d_6$) δ ppm 1.96 (d, 2 H), 2.20 (br. s., 6 H), 2.77 (br. s., 2 H), 3.29-3.37 (m, 2 H), 3.77 (br. s., 2 H), 3.89 (s, 3 H), 6.31 (s, 1 H), 6.92 (br. s., 2 H), 7.10 (s, 1 H), 7.82 (s, 1 H), 8.10 (s, 1 H), 8.24 (s, 1 H), 8.37 (s, 1 H), 8.59 (br. s., 1 H), 11.21 (s, 1 H), 11.50 (s, 1 H), ESIMS (M+H)=551.

Example 179

2-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-4,6-difluoro-N-methylbenzamide

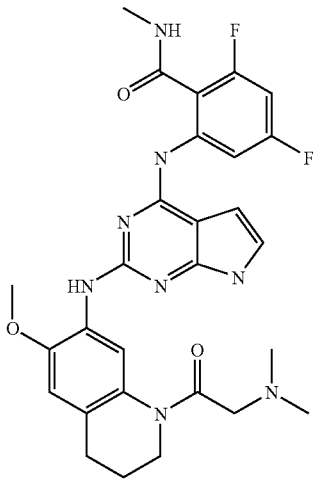

In a manner analogous to that described for Example 90, 2-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-4,6-difluoro-N-methyl benzamide (0.75 g, 78%) was prepared from 2-({2-chloro-7-[(4-methylphenyl)sulfonyl]-7H-pyrrolo[2,3-d]pyrimidin-4-yl}amino)-4,6-difluorobenzamide (3.0 g, 6.27 mmol), methylamine (2M in THF), and 1-[(dimethylamino)acetyl]-6-(methyloxy)-1,2,3,4-tetrahydro-7-quinolinamine (1.5g, 5.7 mmol). $^1$H NMR (400 MHz, DMSO-d$_6$) δ ppm 1.85 (br. s., 2 H), 1.98-2.18 (m, 6 H), 2.67 (br. s., 2 H), 2.79 (d, J=4.30 Hz, 3 H), 3.18 (s, 2 H), 3.67 (t, J=5.68 Hz, 2 H), 3.80 (s, 3 H), 6.26 (s, 1 H), 6.81 (s, 1 H), 6.92 (dd, J=19.96, 1.83 Hz, 1 H), 7.00 (s, 1 H), 7.69 (s, 1 H), 8.29 (s, 1 H), 8.35 (br. s., 1 H), 8.56 (s, 1 H), 10.70 (s, 1 H), 11.40 (s, 1 H).
ESIMS (M+H)=565.

Example 180

2-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-N-ethyl4,6-difluorobenzamide

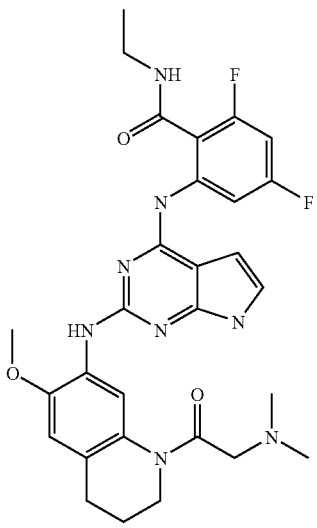

In a manner analogous to that described for Example 90, 2-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-N-ethyl-4,6-difluorobenzamide (0.020 g) was prepared from 2-({2-chloro-7-[(4-methylphenyl)sulfonyl]-7H-pyrrolo[2,3-d]pyrimidin-4-yl}amino)-4,6-difluorobenzamide (0.37, 0.73 mmol), ethylamine (2M in THF), and 1-[(dimethylamino)acetyl]-6-(methyloxy)-1,2,3,4-tetrahydro-7-quinolinamine (0.29, 1.1 mmol). $^1$H NMR (400 MHz, DMSO-d$_6$) δ ppm 1.15 (t, 3 H), 1.93 (br. s., 2 H), 2.16-2.30 (m, 6 H), 2.74 (br. s., 2 H), 3.34 (br. s., 2 H), 3.41-3.51 (m, 2 H), 3.70-3.79 (m, 2 H), 3.87 (s, 3 H), 6.32 (br. s., 1 H), 6.89 (s, 1 H), 6.93-7.04 (m, 1 H), 7.07 (br. s., 1 H), 7.76 (s, 1 H), 8.36 (s, 2 H), 8.68 (s, 1 H), 10.55 (s, 1 H), 11.46 (s, 1 H), ESIMS (M+H)=579.

Example 181

2-fluoro-6-[(2-{[1-[(3-hydroxy-1-pyrrolidinyl)acetyl]-5-(methyloxy)-2,3-dihydro-1H-indol-6-yl]amino}-1H-pyrrolo[2,3-d]pyrimidin-4-yl)amino]benzamide

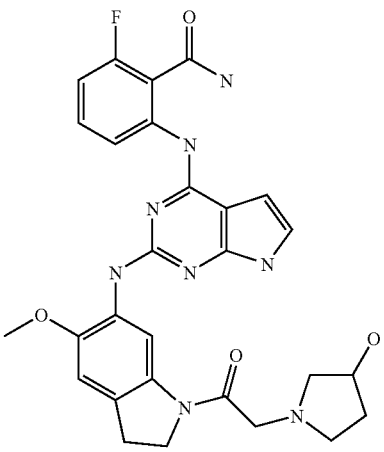

In a manner analogous to that described for Example 165, 2-fluoro-6-[(2-{[1-[(3-hydroxy-1-pyrrolidinyl)acetyl]-5-(methyloxy)-2,3-dihydro-1H-indol-6-yl]amino}-1H-pyrrolo[2,3-d]pyrimidin-4-yl)amino]benzamide was prepared from 5-chloro-8-fluoro-3-[(4-methylphenyl)sulfonyl]pyrrolo[2',3':4,5]pyrimido[6,1-b]quinazolin-7(3H)-one hydrogen chloride (0.40 g, 0.90 mmol), 27% aqueous ammonium hydroxide, and 1-{2-[6-amino-5-(methyloxy)-2,3-dihydro-1H-indol-1-yl]-2-oxoethyl}-3-pyrrolidinol (0.35 g, 1.1 mmol) and isolated as a yellow solid (0.23 g); $^1$H NMR (400 MHz, DMSO-d$_6$) δ ppm 1.55 (dd, 1 H), 1.97 (dd, J=12.96, 7.00 Hz, 1 H), 2.43 (dd, J=9.52, 3.39 Hz, 1 H), 2.53-2.61 (m, 1 H), 2.69 (q, J=7.60 Hz, 1 H), 2.83 (dd, J=9.48, 6.18 Hz, 1 H), 3.12 (t, J=8.24 Hz, 2 H), 3.35 (s, 2 H), 3.77 (s, 3 H), 4.17 (t, J=8.33 Hz, 3 H), 4.72 (d, J=4.49 Hz, 1 H), 6.23 (br. s., 1 H), 6.86 (d, J=8.79 Hz, 1 H), 6.96 (s, 2 H), 7.24-7.37 (m, 1 H), 7.61 (s, 1 H), 8.03 (s, 1 H), 8.11 (s, 1 H), 8.52 (d, J=8.42 Hz, 1 H), 8.61 (s, 1 H), 10.54 (s, 1 H), 11.30 (s, 1 H), ESIMS (M+H)=561.

Example 182

2-fluoro-6-[(2-{[1-[(3-hydroxy-1-pyrrolidinyl)acetyl]-5-(methyloxy)-2,3-dihydro-1H-indol-6-yl]amino}-1H-pyrrolo[2,3-d]pyrimidin-4-yl)amino]-N-methylbenzamide

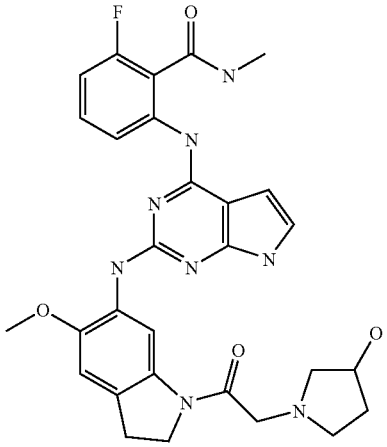

In a manner analogous to that described for Example 165, 2-fluoro-6-[(2-{[1-[(3-hydroxy-1-pyrrolidinyl)acetyl]-5-(methyloxy)-2,3-dihydro-1H-indol-6-yl]amino}-1H-pyrrolo[2,3-d]pyrimidin-4-yl)amino]-N-methylbenzamide was prepared from 5-chloro-8-fluoro-3-[(4-methylphenyl)sulfonyl]pyrrolo[2',3':4,5]pyrimido[6,1-b]quinazolin-7(3H)-one hydrogen chloride (0.40 g, 0.90 mmol), methylamine(2M in THF) and 1-{2-[6-amino-5-(methyloxy)-2,3-dihydro-1H-indol-1-yl]-2-oxoethyl}-3-pyrrolidinol (0.35 g, 1.1 mmol) and isolated as a yellow solid (0.23 g); $^1$H NMR (400 MHz, DMSO-$d_6$) δ ppm 1.49-1.63 (m, 1 H), 1.91-2.04 (m, 1 H), 2.38-2.46 (m, 1 H), 2.55 (d, J=5.86 Hz, 1H), 2.65-2.76 (m, 1 H), 2.80 (d, J=4.39 Hz, 4 H), 3.12 (br. s., 2 H), 3.33 (s, 2H), 3.37 (none, 1 H), 3.77 (s, 3 H), 4.16 (t, J=8.38 Hz, 3 H), 4.72 (d, J=4.49 Hz, 1 H), 6.28 (s, 1 H), 6.82-6.98 (m, 3 H), 7.33 (d, J=6.96 Hz, 1 H), 7.57 (s, 1 H), 8.35 (d, J=8.42 Hz, 1 H), 8.49-8.60 (m, 1 H), 8.62 (s, 1 H), 10.15 (s, 1 H), 11.28 (s, 1 H), ESIMS (M+H)=575.

Example 183

2-fluoro-6-[(2-{[1-[(3-hydroxy-1-piperidinyl)acetyl]-5-(methyloxy)-2,3-dihydro-1H-indol-6-yl]amino}-1H-pyrrolo[2,3-d]pyrimidin-4-yl)amino]benzamide

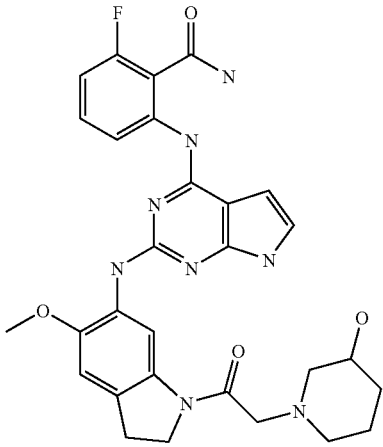

In a manner analogous to that described for Example 165, 2-fluoro-6-[(2-{[1-[(3-hydroxy-1-piperidinyl)acetyl]-5-(methyloxy)-2,3-dihydro-1H-indol-6-yl]amino}-1H-pyrrolo[2,3-d]pyrimidin-4-yl)amino]benzamide was prepared from 5-chloro-8-fluoro-3-[(4-methylphenyl)sulfonyl]pyrrolo[2',3':4,5]pyrimido[6,1-b]quinazolin-7(3H)-one hydrogen chloride (0.40 g, 0.90 mmol), 27% aqueous ammonium hydroxide, and 1-{2-[6-amino-5-(methyloxy)-2,3-dihydro-1H-indol-1-yl]-2-oxoethyl}-3-piperidinol (0.35 g, 1.1 mmol) and isolated as a yellow solid (0.12 g); $^1$H NMR (400 MHz, DMSO-$d_6$) δ ppm 1.08 (br. s., 1 H), 1.44 (br. s., 1 H), 1.61 (d, J=13.09 Hz, 1 H), 1.77 (br. s., 1H), 1.90 (t, J=9.70 Hz, 1 H), 1.97-2.07 (m, 1 H), 2.68 (br. s., 1 H), 2.88 (br. s., 1 H), 3.12 (t, J=8.24 Hz, 2 H), 3.17-3.28 (m, 2 H), 3.47 (dd, J=9.02, 4.53 Hz, 1 H), 3.78 (s, 3H), 4.14-4.27 (m, 2 H), 4.61 (d, J=4.76 Hz, 1 H), 6.23 (d, J=1.37 Hz, 1 H), 6.86 (d, J=8.79 Hz, 1 H), 6.96 (s, 2 H), 7.29-7.41 (m, 1 H), 7.60 (s, 1 H), 8.02 (s, 1 H), 8.11 (s, 1 H), 8.52 (d, J=8.42 Hz, 1 H), 8.62 (s, 1 H), 10.54 (s, 1 H), 11.30 (s, 1 H), ESIMS (M+H)=575.

Example 184

2-fluoro-6-[(2-{[1-[(3-hydroxy-1-piperidinyl)acetyl]-5-(methyloxy)-2,3-dihydro-1H-indol-6-yl]amino}-1H-pyrrolo[2,3-d]pyrimidin-4-yl)amino]-N-methylbenzamide

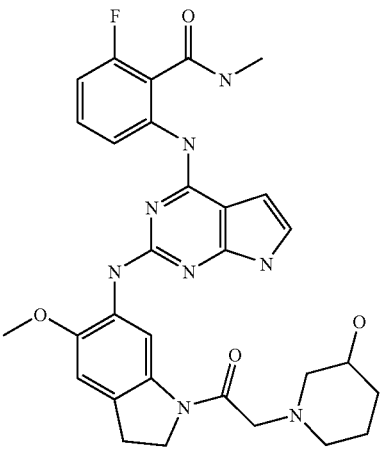

In a manner analogous to that described for Example 165, 2-fluoro-6-[(2-{[1-[(3-hydroxy-1-piperidinyl)acetyl]-5-(methyloxy)-2,3-dihydro-1H-indol-6-yl]amino}-1H-pyrrolo[2,3-d]pyrimidin-4-yl)amino]-N-methylbenzamide was prepared from 5-chloro-8-fluoro-3-[(4-methylphenyl)sulfonyl]pyrrolo[2',3':4,5]pyrimido[6,1-b]quinazolin-7(3H)-one hydrogen chloride (0.40 g, 0.90 mmol), methylamine and 1-{2-[6-amino-5-(methyloxy)-2,3-dihydro-1H-indol-1-yl]-2-oxoethyl}-3-piperidinol (0.35 g, 1.1 mmol and isolated as a yellow solid (0.15 g); $^1$H NMR (400 MHz, DMSO-$d_6$) δ ppm 1.04 (br. s., 1 H), 1.41 (br. s., 1 H), 1.56 (br. s., 1 H), 1.74 (br. s., 1 H), 1.83-1.91 (m, 1H), 1.99 (br. s., 1 H), 2.66 (br. s., 1 H), 2.77 (d, J=4.39 Hz, 3 H), 2.83-2.90 (m, 1 H), 3.09 (t, J=8.19 Hz, 2 H), 3.20 (d, J=9.71 Hz, 2 H), 3.75 (s, 3 H), 4.17 (br. s., 2 H), 4.60 (d, J=4.85 Hz, 2 H), 6.25 (s, 1 H), 6.83-6.95 (m, 3 H), 7.25-7.35 (m, 1 H), 7.55 (s, 1 H), 8.32 (d, J=8.33 Hz, 1 H), 8.47-8.54 (m, 1 H), 8.60 (s, 1 H), 10.13 (s, 1 H), 11.25(s, 1 H), ESIMS (M+H)=589.

Example 185

2-fluoro-6-[(2-{5-(methyloxy)-1-(4-morpholinylacetyl)-2,3-dihydro-1H-indol-6-yl]amino}-1H-pyrrolo[2,3-d]pyrimidin-4-yl)amino]benzamide

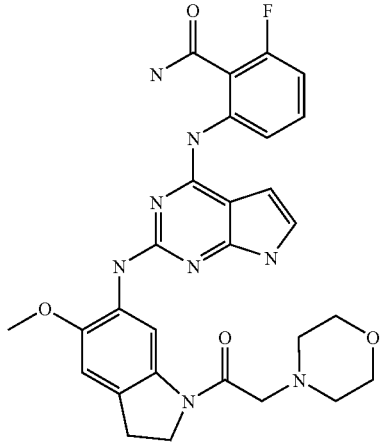

In a manner analogous to General Protocol III, 2-fluoro-6-[(2-{[5-(methyloxy)-1-(4-morpholinylacetyl)-2,3-dihydro-1H-indol-6-yl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-6-fluorobenzamide (0.3 g, 0.65 mmol), 27% aqueous ammonium hydroxide, and 5-(methyloxy)-1-(4-morpholinylacetyl)-2,3-dihydro-1H-indol-6-amine (0.29 g, 1.0 mmol) to afford the title compound (0.099 g, 30% over 3 steps) as a white solid. ESIMS (M+H)$^+$=561. 1H NMR (400 MHz, DMSO-d$_5$) δ ppm 2.39-2.49 (m, 4 H) 3.09 (t, J=8.15 Hz, 2 H) 3.21 (s, 2 H) 3.50-3.58 (m, 4 H) 3.73 (s, 3 H) 4.15 (t, J=8.33 Hz, 2 H) 6.18 (dd, J=3.39, 1.74 Hz, 1 H) 6.79-6.87 (m, 1 H) 6.89-6.99 (m, 2 H) 7.23-7.33 (m, 1 H) 7.55 (s, 1 H) 7.97 (s, 1 H) 8.06 (s, 1H) 8.47 (d, J=8.61 Hz, 1 H) 8.59 (s, 1 H) 10.51 (s, 1 H) 11.24 (s, 1 H).

Example 186

2-fluoro-6-[(2-{[1-{[4-(1-methylethyl)-1-piperazinyl]acetyl}-5-(methyloxy)-2,3-dihydro-1H-indol-6-yl]amino}-1H-pyrrolo[2,3-d]pyrimidin-4-yl)amino]benzamide

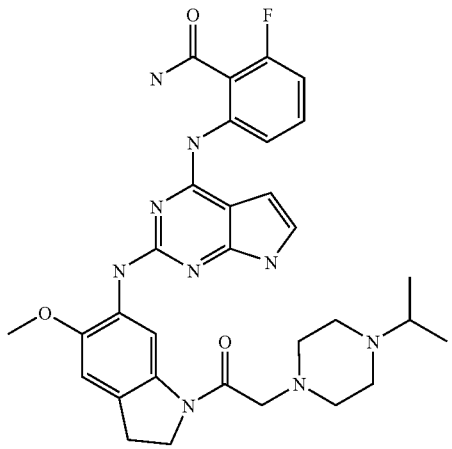

In a manner analogous to General Protocol III, 2-fluoro-6-[(2-{[1-{[4-(1-methylethyl)-1-piperazinyl]acetyl}-5-(methyloxy)-2,3-dihydro-1H-indol-6-yl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-6-fluorobenzamide (0.3 g, 0.65 mmol), 27% aqueous ammonium hydroxide, and 1-{[4-(1-methylethyl)-1-piperazinyl]acetyl}-5-(methyloxy)-2,3-dihydro-1H-indol-6-amine (0.32 g, 0.96 mmol) to afford the title compound (0.052 g, 13% over 3 steps) as a tan solid. ESIMS (M+H)$^+$=602. $^1$H NMR (400 MHz, DMSO-d$_5$) δ ppm 0.92 (s, 6 H) 2.37-2.47 (m, 8H) 2.51-2.59 (m, 1 H) 3.08 (t, J=8.15 Hz, 2 H) 3.17 (bs, 2 H) 3.73 (s, 3 H) 4.15 (t, J=8.15 Hz, 2 H) 6.18-6.19 (m, 1 H) 6.79-6.85 (m, 1 H) 6.89-6.94 (m, 2 H), 7.24-7.31 (m, 1 H) 7.55 (s, 1 H) 7.97 (s, 1 H) 8.06 (s, 1 H) 8.47 (d, J=8.24 Hz, 1 H), 8.58 (s, 1 H) 10.51 (s, 1 H) 11.24 (s, 1 H).

Example 187

2-fluoro-6-{[2-({5-(methyloxy)-1-[3-(4-morpholinyl)propanoyl]-2,3-dihydro-1H-indol-6-yl}amino)-1H-pyrrolo[2,3-d]pyrimidin-4-yl]amino}benzamide

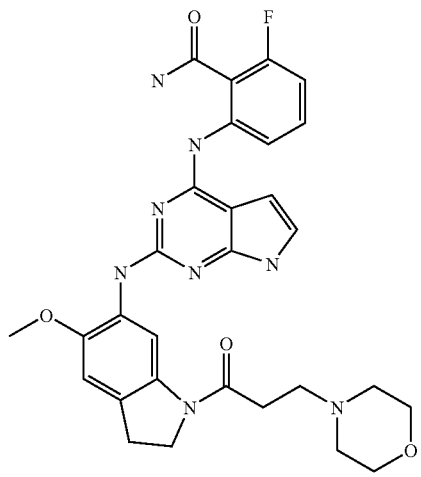

In a manner analogous to General Protocol III, 2-fluoro-6-{[2-({5-(methyloxy)-1-[3-(4-morpholinyl)propanoyl]-2,3-dihydro-1H-indol-6-yl}amino)-1H-pyrrolo[2,3-d]pyrimidin-4-yl]amino}benzamide was prepared from 2-({2-chloro-7-[(4-methylphenyl)sulfonyl]-7H-pyrrolo[2,3-d]pyrimidin-4-yl}amino)-6-fluorobenzamide (0.36 g, 0.78 mmol), 27% aqueous ammonium hydroxide, and 5-(methyloxy)-1-[3-(4-morpholinyl)propanoyl]-2,3-dihydro-1H-indol-6-amine (0.36 g, 1.18 mmol) to afford the title compound (0.168 g, 37% over 3 steps) as a yellow solid. ESIMS (M+H)$^+$=575. $^1$H NMR (400 MHz, DMSO-d$_6$) δ ppm 2.32-2.39 (m, 4 H) 2.52-2.59 (m, 4 H) 3.05-3.13 (m, 2 H) 3.50-3.55 (m, 4 H) 3.73 (s, 3 H) 4.07-4.11 (m, 2 H) 6.18 (d, J=2.93 Hz, 1 H) 6.79-6.88 (m, 1 H) 6.90 (s, 2 H) 7.23-7.33 (m, 1 H) 7.53 (s, 1 H) 7.97 (s, 1 H) 8.06 (s, 1 H) 8.47 (d, J=8.42 Hz, 1 H) 8.58 (s, 1 H) 10.50 (s, 1 H) 11.25 (s, 1 H).

Example 188

2-fluoro-6-[(2-{[1-{3-[4-(1-methylethyl)-1-piperazinyl]propanoyl}-5-(methyloxy)-2,3-dihydro-1H-indol-6-yl]amino}-1H-pyrrolo[2,3-d]pyrimidin-4-yl)amino]benzamide

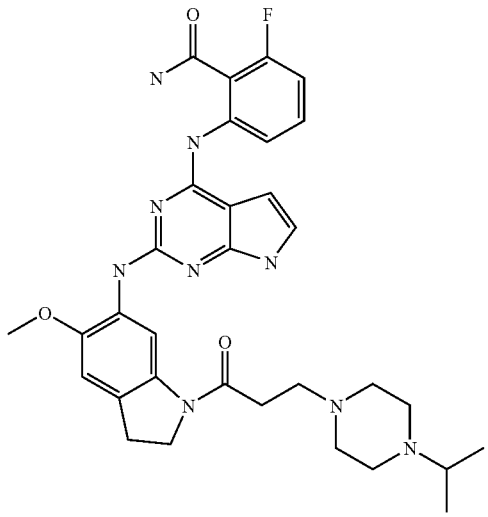

In a manner analogous to General Protocol III, 2-fluoro-6-[(2-{[1-{3-[4-(1-methylethyl)-1-piperazinyl]propanoyl}-5-(methyloxy)-2,3-dihydro-1H-indol-6-yl]amino}-1H-pyrrolo[2,3-d]pyrimidin-4-yl)amino]benzamide was prepared from 2-({2-chloro-7-[(4-methylphenyl)sulfonyl]-7H-pyrrolo[2,3-d]pyrimidin-4-yl}amino)-6-fluorobenzamide (0.41 g, 0.89 mmol), 27% ammonium hydroxide, and 1-{3-[4-(1-methylethyl)-1-piperazinyl]propanoyl}-5-(methyloxy)-2,3-dihydro-1H-indol-6-amine (0.46 g, 1.33 mmol) to afford the title compound (0.168 g, 37% over 3 steps) as a yellow solid. ESIMS (M+H)+=616. 1H NMR (400 MHz, DMSO-d6) δ ppm 0.91 (d, J=6.23 Hz, 6 H) 2.28-2.43 (m, 8 H) 2.50-2.59 (m, 5 H) 3.08 (t, J=8.15 Hz, 2 H) 3.73 (s, 3 H), 4.09 (t, J=8.24 Hz, 2 H) 6.16-6.20 (s, 1 H) 6.79-6.87 (m, 1 H) 6.88-6.92 (m, 2 H) 7.24-7.31 (m, 1 H) 7.52 (s, 1 H) 7.97 (s, 1 H) 8.05 (s, 1 H) 8.47 (d, J=8.42 Hz, 1 H) 8.58 (s, 1 H) 10.50 (s, 1 H) 11.24 (s, 1 H).

Example 189

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-4,6-difluorobenzamide

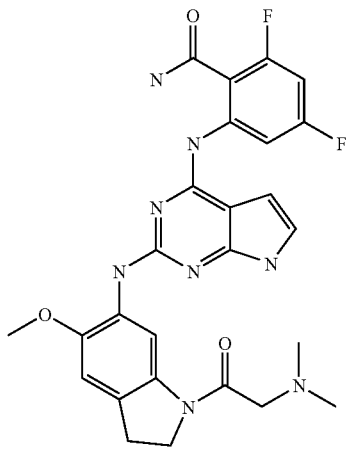

In a manner analogous to General Protocol III, 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-4,6-difluorobenzamide was prepared from 2-({2-chloro-7-[(4-methylphenyl)sulfonyl]-7H-pyrrolo[2,3-d]pyrimidin-4-yl}amino)-4,6-difluorobenzamide (0.3 g, 0.63 mmol), 27% aqueous ammonium hydroxide, and 1-[(dimethylamino)acetyl]-5-(methyloxy)-2,3-dihydro-1H-indol-6-amine (0.17 g, 0.75 mmol) to afford the title compound (0.083 g, 25% over 3 steps) as an off-white solid. ESIMS (M+H)+=537. 1H NMR (400 MHz, DMSO-d6) δ ppm 2.21 (s, 6 H) 3.11 (t, J=8.43 Hz, 2 H) 3.13 (s, 2 H) 3.75 (s, 3 H) 4.14 (t, J=8.43 Hz, 2 H) 6.19-6.21 (m, 1 H) 6.80-6.85 (m, 1 H) 6.95 (s, 1 H) 6.97-7.01 (m, 1 H) 7.80 (s, 1 H) 8.01 (s, 1 H) 8.17 (s, 1 H) 8.47 (s, 1 H) 8.53-8.59 (m, 1 H) 11.20 (s, 1 H) 11.33 (bs, 1 H).

Example 190

2-[(2-{[1(N,N-dimethylglycyl)-5-(methyloxy)-2,3-dihydro-1H-indol-6-yl]amino}-1H-pyrrolo[2,3-d]pyrimidin-4-yl)amino]-4,6-difluoro-N-methylbenzamide

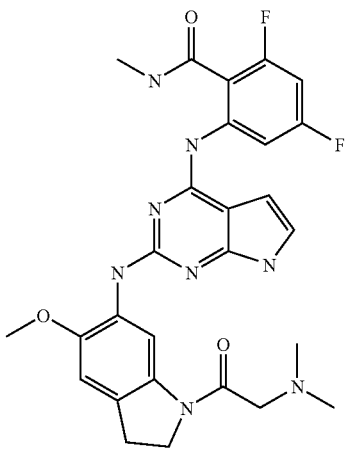

In a manner analogous to General Protocol III, 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-4,6-difluorobenzamide was prepared from 2-({2-chloro-7-[(4-methylphenyl)sulfonyl]-7H-pyrrolo[2,3-d]pyrimidin-4-yl}amino)-4,6-difluorobenzamide (0.3 g, 0.63 mmol), 2.0M methyl amine in tetrahydrofuran, and 1-[(dimethylamino)acetyl]-5-(methyloxy)-2,3-dihydro-1H-indol-6-amine (0.19 g, 0.75 mmol) to afford the title compound (0.043 g, 12% over 3 steps) as an off-white solid. ESIMS (M+H)+=551. 1H NMR (400 MHz, DMSO-d6) δ ppm 2.19 (s, 6 H) 2.79 (d, J=4.58 Hz, 3 H) 3.08 (t, J=8.24 Hz, 2 H) 3.10 (s, 2 H) 3.72 (s, 3 H) 4.11 (t, J=8.24 Hz, 2 H) 6.20-6.22 (m, 1 H) 6.78-6.87 (m, 1 H) 6.90-6.96 (m, 2 H) 7.74 (s, 1 H) 8.46 (s, 2 H) 8.51-8.55 (m, 1 H) 10.75 (s,1 H), 11.28 (bs, 1 H).

Example 190 (Alternative Preparation)

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-4,6-difluoro-N-methylbenzamide

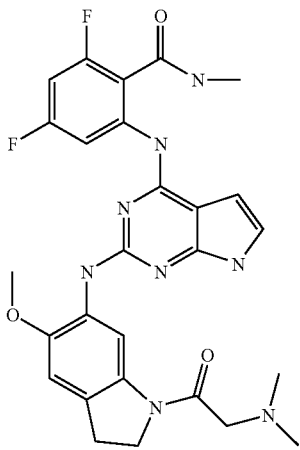

Step A/Intermediate D68: 2-({2-([1-(N,N-dimethylglycyl)-5-(methyloxy)-2,3-dihydro-1H-indol-6-yl]amino)-7-[(4-methylphenyl)sulfonyl]-7H-pyrrolo[2,3-d]pyrimidin-4-yl}amino)-4,6-difluoro-N-methylbenzamide

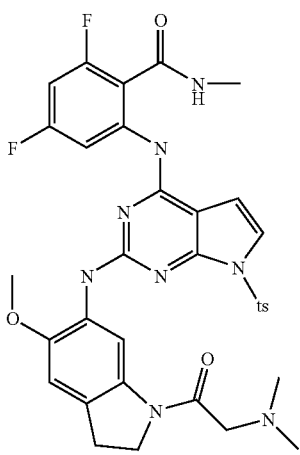

To a suspension of 2-({2-chloro-7-[(4-methylphenyl)sulfonyl]-7H-pyrrolo[2,3-d]pyrimidin-4-yl}amino)-4,6-difluorobenzamide (4 g, 8.37 mmol) in 2,2,2-trifluoroethanol (100 mL) was added 1-[(dimethylamino)acetyl]-5-(methyloxy)-2,3-dihydro-1H-indol-6-amine (3.13 g, 12.56 mmol), a solution of 4M HCl in dioxane (16.7 ml, 67 mmol) and a catalytic amount of KI. The resulting slurry was stirred in a pressure vessel at 80° C. for 48 h, with an additional 2 ml of 4M HCl in dioxane being added after 24 h.

The reaction mixture was diluted with dichloromethane and a saturated sodium bicarbonate solution (aq) as to adjust the aqueous layer to pH>10. The organic layer was washed with water and a saturated brine solution and dried over sodium sulfate. Solvents were removed under reduced pressure and the residue was purified via trituration from diethyl ether to afford a yellow solid (5.25 g, 7.77 mmol). A portion of the solid (3.1 g) was suspended in THF (100 ml) and 2M methylamine in THF (18.55 ml, 37.1 mmol) was added and the reaction let stir for 1 h. Additional 2M methylamine in THF (2 ml) was added and reaction let stir for an additional 1 h at which time the reaction mixture was diluted with ethyl acetate and washed with water and a saturated brine solution. The organic layer was dried over sodium sulfate and all volatiles were removed under reduced pressure to afford a yellow solid which was purified via chromatography on $SiO_2$ to afford 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-4,6-difluoro-N-methylbenzamide (1.6 g, 2.27 mmol) (ESIMS (M+H)$^+$=705) as a yellow solid. This method was repeated as necessary.

Step B: Example 190 (Alternative Preparation)

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-4,6-difluoro-N-methylbenzamide To a suspension of 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)-4,6-difluoro-N-methylbenzamide (0.950 g, 1.07 mmol) in 1,4 dioxane (10 mL) in a microwave vessel was added 6 N NaOH (10 ml) and water (3 mL). The resulting mixture was stirred in the microwave at 120° C. for 9 min. The reaction mixture was diluted with EtOAc and THF and the organic layer was washed with water and a saturated brine solution. Combined organic layers were dried over sodium sulfate and all solvents were removed under reduced pressure and purified via chromatography on $SiO_2$ to afford 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-4,6-difluoro-N-methylbenzamide (0.532 g, 0.966 mmol) as a beige solid. (ESIMS (M+H)$^+$=551). $^1$H NMR (400 MHz, DMSO-$d_6$) δ ppm 2.23 (s, 6 H) 2.83 (d, J=4.40 Hz, 3 H) 3.06-3.12 (m, 2 H) 3.33 (s, 2 H) 3.76 (s, 2 H) 4.05-4.23 (m, 2 H) 6.25 (dd, J=3.39, 1.74 Hz, 1 H) 6.80-6.94 (m, 1 H) 6.93-7.04 (m, 2 H) 7.80 (s, 1 H) 8.41-8.54 (m, 2 H) 8.54-8.64 (m, 1 H) 10.79 (s, 1 H) 11.33 (br. s., 1 H)

This reaction was repeated multiple times to afford a total amount of 1.8 g of 2-[(2-{[1-(N,N-dimethylglycyl)-5-(methyloxy)-2,3-dihydro-1H-indol-6-yl]amino}-1H-pyrrolo[2 3-d]pyrimidin-4-yl)amino]-4,6-difluoro-N-methylbenzamide

Example 191

2-[(2-{[1-(N,N-dipropyl-L-alanyl)-5-(methyloxy)-2,3-dihydro-1H-indol-6-yl]amino}-1H-pyrrolo[2,3-c]pyrimidin-4-yl)amino]-6-fluoro-N-methylbenzamide

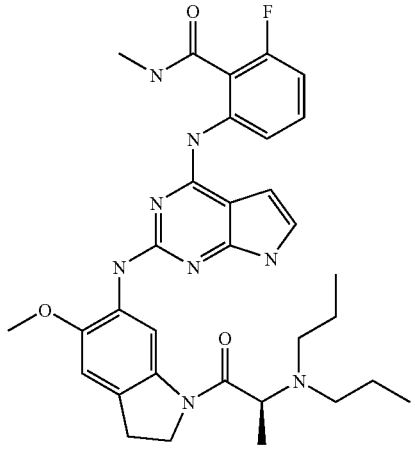

In a manner analogous to General Protocol III, 2-[(2-{[1-(N,N-dipropyl-L-alanyl)-5-(methyloxy)-2,3-dihydro-1H-indol-6-yl]amino}-1H-pyrrolo[2,3-d]pyrimidin-4-yl)amino]-6-fluoro-N-methylbenzamide was prepared from 2-({2-chloro-7-[(4-methylphenyl)sulfonyl]-7H-pyrrolo[2,3-d]pyrimidin-4-yl}amino)-6-fluorobenzamide (0.13 g, 0.28 mmol), 2.0M methyl amine in tetrahydrofuran, and 1-[(2S)-2-(dipropylamino)propanoyl]-5-(methyloxy)-2,3-dihydro-1H-indol-6-amine (0.10 g, 0.34 mmol) to afford the title compound (0.041 g, 25% over 3 steps) as a tan solid. ESIMS (M+H)$^+$=603. $^1$H NMR (400 MHz, DMSO-d$_6$) δ ppm 0.74 (t, J=6.78 Hz, 6 H) 0.96-1.04 (m, 3 H) 1.29-1.41 (m, 4 H) 2.25-2.35 (m, 2 H) 2.36-2.46 (m, 2 H) 2,73-2.80 (m, 3 H) 3.02-3.11 (m, 2 H) 3.69-3.82 (m, 4 H) 4.05-4.12 (m, 1 H) 4.54-4,65 (m, 1 H) 6.23 (s, 1 H) 6.81-6.88 (m, 1 H) 6.90 (s, 2 H) 7.21-7.32 (m, 1 H) 7.53 (s, 1 H) 8.31 (d, J=8.06 Hz, 1 H) 8.49 (s, 1 H) 8.58 (s, 1 H) 10.12 (s, 1 H) 11.21 (s, 1 H).

Example 192

2-[(2-{[1-(N,N-dipropyl-L-alanyl)-5-(methyloxy)-2,3-dihydro-1H-indol-6-yl]amino}-1H-pyrrolo[2,3-d]pyrimidin-4-yl)amino]-6-fluorobenzamide

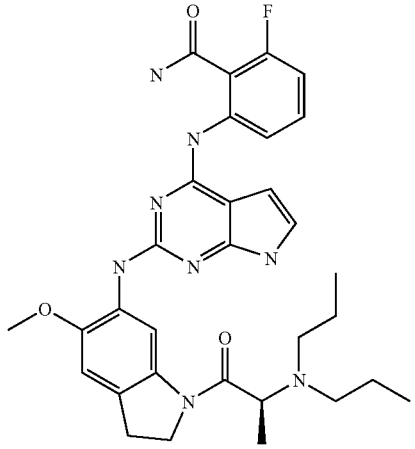

In a manner analogous to General Protocol III, 2-[(2-{[1-(N,N-dipropyl-L-alanyl)-5-(methyloxy)-2,3-dihydro-1H-indol-6-yl]amino}-1H-pyrrolo[2, 3-d]pyrimidin-4-yl)amino]-6-fluorobenzamide was prepared from 2-({2-chloro-7-[(4methylphenyl)sulfonyl]-7H-pyrrolo[2,3-d]pyrimidin-4-yl}amino)-6-fluorobenzamide (0.19 g, 0.41 mmol), 27% aqueous ammonium hydroxide, and 1-[(2S)-2-(dipropylamino)propanoyl]-5-(methyloxy)-2,3-dihydro-1H-indol-6-amine to afford the title compound (0.028 g, 12% over 3 steps) as a pale yellow solid. ESIMS (M+H)$^+$=589. $^1$H NMR (400 MHz, DMSO-d6) δ ppm 0.74 (t, J=7.33 Hz, 6 H) 1.00 (d, J=6.41 Hz, 3 H) 1.26-1.43 (m, 4 H) 2.26-2.33 (m, 2 H) 2.37-2.42 (m, 2 H) 2.42 (s, 1 H) 3.07 (t, J=8.42 Hz, 2 H) 3.74-3.81 (m, 1 H) 4.03-4.13 (m, 1 H) 4.55-4.65 (m, 1 H) 6.18-6.19 (m, 1 H) 6.78-6.87 (m, 1 H) 6.89-6.95 (m, 2 H) 7.22-7.30 (m, 1 H) 7.56 (s, 1 H) 7.97 (s, 1 H) 8.05 (s, 1 H) 8.47 (d, J=8.42 Hz, 1 H) 8.56 (s, 1 H) 10.51 (s, 1 H) 11.23 (s, 1 H)

Example 193

2-fluoro-6-[(2-{[1-(2-hydroxy-2-methylpropanoyl)-5-(methyloxy)-2,3-dihydro-1H-indol-6-yl]amino}-1H-pyrrolo[2,3-d]pyrimidin-4-yl)amino]-N-methyl-benzamide

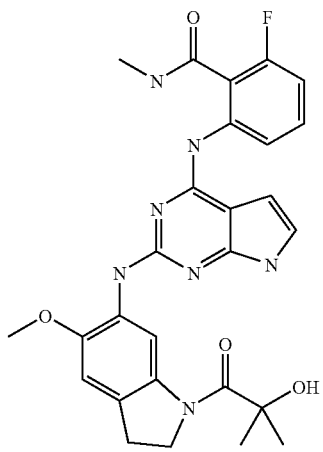

A suspension of 5-chloro-8-fluoro-3-[(4-methylphenyl)sulfonyl]pyrrolo[2',3':4,5]pyrimido[6,1-b]quinazolin-7(3H)-one hydrogen chloride (300 mg, 0.63 mmol) and 1-[6-amino-5-(methyloxy)-2,3-dihydro-1H-indol-1-yl]-2-methyl-1-oxo-2-propanol (157 mg, 0.63 mmol) in THF(250 ml) was heated at 65° C. for 4 hrs. The reaction was diluted with ethyl acetate (200 ml) and washed with saturated NaHCO$_3$ (300 ml). Organic layer was removed, concentrated by rotary evaporation, solids triturated from ethyl acetate/hexanes, and dried under house vacuum prior to next step. ESIMS (M+H)$^+$=657. The solids were then added to THF (200 ml) followed by a solution of methylamine (2M in THF, 11.42 ml, 22.84 mmol) and the resulting mixture was stirred at rt overnight. Next, the crude reaction was adsorbed onto silica gel and purified by silica gel chromatography (DCM to 10% MeOH/DCM over 30 min). ESIMS (M+H)$^+$=688. The isolated pure amide was redissolved in 1,4-dioxane (10 ml), and potassium hydroxide (8.72 ml, 8.72 mmol) was added and the reaction was heated in the microwave at 120° C. for 20 min. The resulting solution was adsorbed onto silica gel and purified by silica gel chromatography (DCM to 10% MeOH/DCM) to afford the title compound (0.130 g, 39% over three steps). ESIMS (M+H)$^+$=534. $^1$H NMR (400 MHz, DMSO-d$_6$) δ ppm 1.38 (s, 6 H) 2.80 (d, J=4.41 Hz, 3 H) 3.06 (t, J=8.03

Hz, 2 H) 3.78 (s, 3 H) 4.43 (t, J=8.23 Hz, 2 H) 5.42 (s, 1 H) 6.26-6.27 (m, 1 H) 6.85-6.93 (m, 1 H) 6.93 (m, 1 H) 6.96 (s, 1 H) 7.28-7.38 (m, 1 H) 7.55 (s, 1 H) 8.37 (d, J=8.43 Hz, 1 H) 8.51-8.58 (m, 1 H) 8.62 (s, 1 H) 10.17 (s, 1 H) 11.26 (s, 1 H).

Example 194

2-[(2-{[1-(N,N-dimethyl-L-alanyl)-5-(methyloxy)-2,3-dihydro-1H-indol-6-yl]amino}-1H-pyrrolo[2,3-d]pyrimidin-4-yl)amino]-6-fluoro-N-methylbenzamide

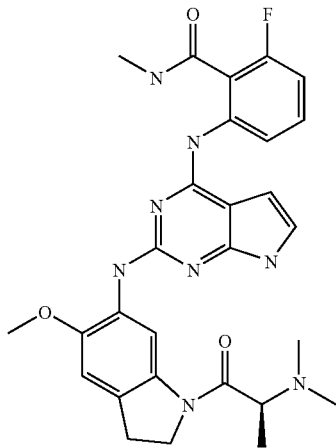

A suspension of 5-chloro-8-fluoro-3-[(4-methylphenyl)sulfonyl]pyrrolo[2',3':4,5]pyrimido[6,1-b]quinazolin-7(3H)-one hydrogen chloride (500 mg, 1.043 mmol) and 1-[(2S)-2-(dimethylamino)propanoyl]-5-(methyloxy)-2,3-dihydro-1H-indol-6-amine (302 mg, 1.147 mmol) in THF (50 ml) was heated at 65° C. for 4 hrs. The reaction was diluted with ethyl acetate (200 ml) and washed with saturated NaHCO₃ (300 ml). Organic layer was removed, concentrated by rotary evaporation, solids triturated from ethyl acetate/hexanes, and dried under house vacuum prior to next step. ESIMS (M+H)⁺=670. The solids were then added to THF (50 ml)mmol) followed by methylamine 2.0M/THF (16.80 ml, 33.6 mmol) and the resulting mixture was stirred at rt overnight. Next, the crude reaction was adsorbed onto silica gel and purified by silica gel chromatography (DCM to 10% MeOH/DCM over 30 min). ESIMS (M+H)⁺=701. The isolated pure amide was redissolved in 1,4-dioxane (10 ml), potassium hydroxide (2.497 ml, 12.49 mmol) added and the reaction was heated in the microwave at 120° C. for 20 min. The resulting solution was adsorbed onto silica gel and purified by silica gel chromatography (DCM to 10% MeOH/DCM) to afford the title compound (0.2 g, 35% over three steps). ESIMS (M+H)⁺=547. ¹H NMR (400 MHz, DMSO-d₆) δ ppm 1.04 (d, J=6.42 Hz, 3 H) 2.20 (s, 6 H) 2.80 (d, J=4.41 Hz, 3 H) 3.06-3.18 (m, 2 H) 3.55-3.66 (m, 1 H) 3.77 (s, 3 H) 4.11-4.21 (m, 1 H) 4.38-4.48 (m, 1 H) 6.25-6.31 (m, 1 H) 6.83-6.94 (m, 1 H) 6.94-7.02 (m, 2 H) 7.26-7.37 (m, 1 H) 7.57 (s, 1 H) 8.36 (d, J=8.43 Hz, 1 H) 8.54 (s, 1 H) 8.62 (s, 1 H) 10.16 (s, 1 H) 11.26 (s, 1 H).

Example 195

2-[(2-{[1-(N,N-dimethyl-D-alanyl)-5-(methyloxy)-2,3-dihydro-1H-indol-6-yl]amino}-1H-pyrrolo[2,3-d]pyrimidin-4-yl)amino]-6-fluoro-N-methylbenzamide

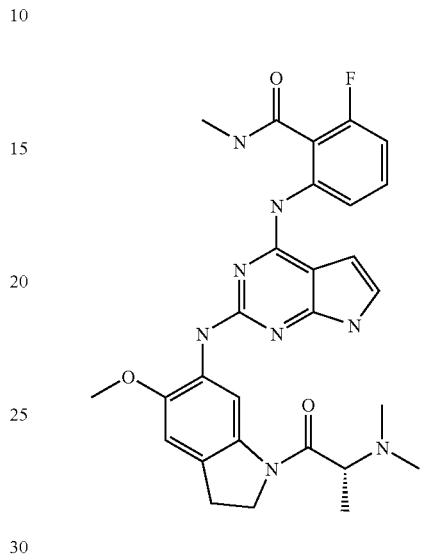

A suspension of 5-chloro-8-fluoro-3-[(4-methylphenyl)sulfonyl]pyrrolo[2',3':4,5]pyrimido[6,1-b]quinazolin-7(3H)-one hydrogen chloride (500 mg, 1.043 mmol) and 1-[(2R)-2-(dimethylamino)propanoyl]-5-(methyloxy)-2,3-dihydro-1H-indol-6-amine (302 mg, 1.147 mmol) in THF (50 ml) was heated at 65° C. for 4 hrs. The reaction was diluted with ethyl acetate (200 ml) and washed with saturated NaHCO₃ (300 ml). Organic layer was removed, concentrated by rotary evaporation, solids triturated from ethyl acetate/hexanes, and dried under house vacuum prior to next step. ESIMS (M+H)+=670. The solids were then added to THF (50 ml)mmol) followed by methylamine 2.0M/THF (26.1 ml, 52.3 mmol) and the resulting mixture was stirred at rt overnight. Next, the crude reaction was adsorbed onto silica gel and purified by silica gel chromatography (DCM to 10% MeOH/DCM over 30 min). ESIMS (M+H)⁺=701. The isolated pure amide was redissolved in 1,4-dioxane (10 ml), potassium hydroxide (2.497 ml, 12.49 mmol) added and the reaction was heated in the microwave at 120° C. for 20 min. The resulting solution was adsorbed onto silica gel and purified by silica gel chromatography (DCM to 10% MeOH/DCM) to afford the title compound (0.1 g, 17% over three steps). ESIMS (M+H)⁺=547. ¹H NMR (400 MHz, DMSO-d₆) δ ppm 1.04 (d, J=6.62 Hz, 3 H) 2.20 (s, 6 H) 2.80 (d, J=4.41 Hz, 3 H) 3.08-3.16 (m, 2 H) 3.56-3.64 (m, 1 H) 3.77 (s, 3 H) 4.12-4.23 (m, 1 H) 4.36-4.45 (m, 1 H) 6.26-6.28 (m, 1 H) 6.85-6.94 (m, 1 H) 6.94-7.00 (m, 2 H) 7.27-7.37 (m, 1 H) 7.57 (s, 1 H) 8.36 (d, J=8.43 Hz, 1 H) 8.52-8.60 (m, 1 H) 8.62 (s, 1 H) 10.16 (s, 1 H) 11.26 (s, 1 H)

Example 196

2-[(2-{[1-[2-(dimethylamino)-2-oxoethyl]-5-(methyloxy)-1H-indol-6-yl]amino}-1H-pyrrolo[2,3-d]pyrimidin-4-yl)amino]-6-fluorobenzamide

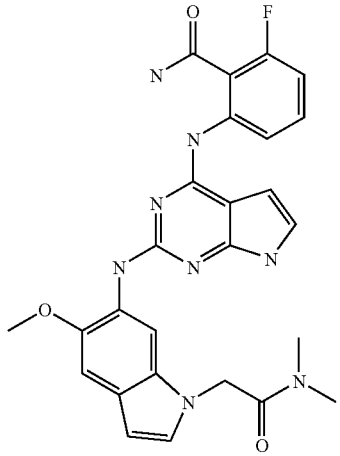

In a manner analogous to General Protocol III, 2-[(2-{[1-[2-(dimethylamino)-2-oxethyl]-5-(methyloxy)-1H-indol-6-yl]amino}-1H-pyrrolo[2,3-d]pyrimidin-4-yl)amino]-6-fluorobenzamide was prepared from 2-({2-chloro-7-[(4-methylphenyl)sulfonyl]-7H-pyrrolo[2,3-d]pyrimidin-4-yl}amino)-6-fluorobenzamide (0.25 g, 0.54 mmol) and 2-[6-amino-5-(methyloxy)-2,3-dihydro-1H-indol-1-yl]-N,N-dimethylacetamide (0.16 g, 0.64 mmol) to afford the title compound (0.016 g, 6% over 3 steps) as a grey solid. LCMS (ESI+) and $^1$H NMR indicate oxidation of the indoline to the indole. ESIMS (M+H)$^+$=517. $^1$H NMR (400 MHz, DMSO-d$_6$) δ ppm 2.78 (s, 3 H) 2.98 (s, 3 H) 3.80 (s, 3 H) 4.93 (s, 2 H) 6.19-6.20 (m, 1 H) 6.29-6.30 (m, 1 H) 6.82-6.91 (m, 1 H), 6.94-7.01 (m, 1 H) 7.04-7.11 (m, 2 H) 7.25-7.35 (m, 1 H) 7.60 (s, 1 H) 7.98 (s, 1 H) 8.04 (s, 1H) 8.09 (s, 1 H) 8.45 (d, J=8.42 Hz, 1 H) 10.48 (s, 1 H) 11.23 (s, 1 H).

Example 197

2-[(2-{[1-(N,N-dimethylglycyl)-6-(methyloxy)-2,3-dihydro-1H-indol-5-yl]amino}-1H-pyrrolo[2,3-cl]pyrimidin-4-yl)amino]-6-fluorobenzamide

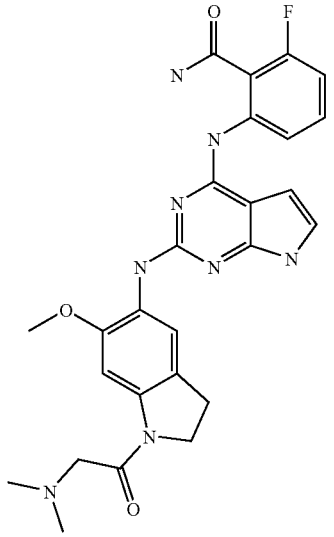

In a manner analogous to General Protocol III, 2-[(2-{[1-(N,N-dimethylglycyl)-6-(methyloxy)-2,3-dihydro-1H-indol-5-yl]amino}-1H-pyrrolo[2,3-d]pyrimidin-4-yl)amino]-6-fluorobenzamide was prepared from 2-({2-chloro-7-[(4-methylphenyl)sulfonyl]-7H-pyrrolo[2,3-d]pyrimidin-4-yl}amino)-6-fluorobenzamide (0.18 g, 0.39 mmol) and 1-[(dimethylamino)acetyl]-6-(methyloxy)-2,3-dihydro-1H-indol-5-amine (0.12 g, 0.47 mmol) to afford the title compound (0.050 g, 25% over 3 steps) as a pale yellow solid. ESIMS (M+H)$^+$=519. $^1$H NMR (400 MHz, DMSO-d$_6$) δ ppm 2.24 (s, 6 H) 3.02 (t, J=8.24 Hz, 2 H) 3.16 (s, 2 H) 3.79 (s, 3 H) 4.13 (t, J=8.15 Hz, 2 H) 6.22 (s, 1 H) 6.87-6.98 (m, 2 H) 7.38-7.45 (m, 2 H) 7.85 (s, 1 H) 7.97 (s, 1 H) 8.04 (s, 1 H) 8.15 (s, 1 H) 8.34 (d, J=8.42 Hz, 1 H) 10.35 (s, 1 H) 11.34 (s, 1 H)

Example 198

2-[(2-{[1-(N,N-dimethylglycyl)-6-(methyloxy)-2,3-dihydro-1H-indol-5-yl]amino}-1H-pyrrolo[2,3-d]pyrimidin-4-yl)amino]-6-fluoro-N-methylbenzamide

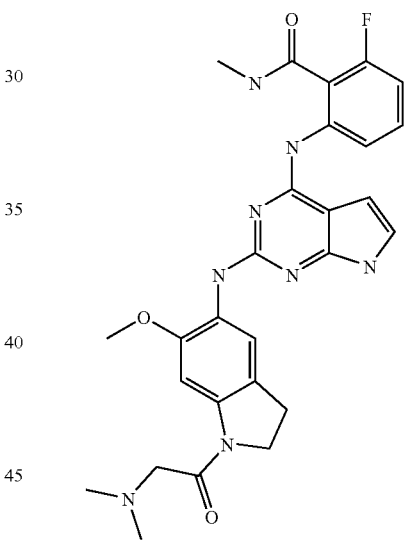

In a manner analogous to General Protocol III, 2-[(2-{[1-(N,N-dimethylglycyl)-6-(methyloxy)-2,3-dihydro-1H-indol-5-yl]amino}-1H-pyrrolo[2,3-d]pyrimidin-4-yl)amino]-6-fluoro-N-methylbenzamide was prepared from 2-({2-chloro-7-[(4-methylphenyl)sulfonyl]-7H-pyrrolo[2,3-d]pyrimidin-4-yl}amino)-6-fluorobenzamide (0.14 g, 0.31 mmol) and 1-[(dimethylamino)acetyl]-6-(methyloxy)-2,3-dihydro-1H-indol-5-amine (0.09 g, 0.37 mmol) to afford the title compound (0.050 g, 31% over 3 steps) as green scales. ESIMS (M+H)$^+$=533; $^1$H NMR (400 MHz, DMSO-d$_6$) δ ppm 2.24 (s, 6 H) 2.74 (d, J=4.58 Hz, 3 H) 3.02 (t, J=8.33 Hz, 2 H) 3.16 (s, 2 H) 3.79 (s, 3 H) 4.13 (t, J=8.24 Hz, 2 H) 6.26-6.27 (m, 1 H) 6.90-6.96 (m, 2 H) 7.38-7.45 (m, 2 H) 7.84 (s, 1 H) 8.16 (s, 1 H) 8.20 (d, J=8.24 Hz, 1 H) 8.48-8.51 (m, 1 H) 10.01 (s, 1 H) 11.32 (s, 1 H)

Example 199

7-[(2-{[4-[4-(1-methylethyl)-1-piperazinyl]-2-(methyloxy)phenyl]amino}-1H-pyrrolo[2,3-d]pyrimidin-4-yl)amino]-2,3-dihydro-1H-isoindol-1-one

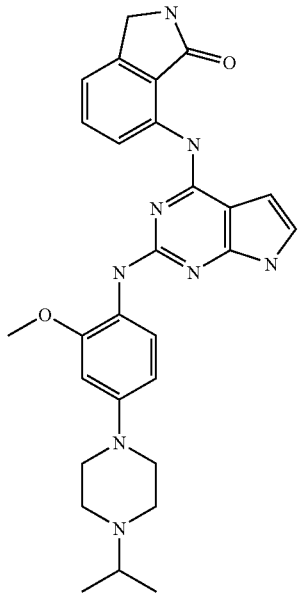

Step A/Intermediate D23: 2-bromo-6-({2-chloro-7-[(4-methylphenyl)sulfonyl]-7H-pyrrolo[2,3-d]pyrimidin-4-yl}amino)benzoic acid

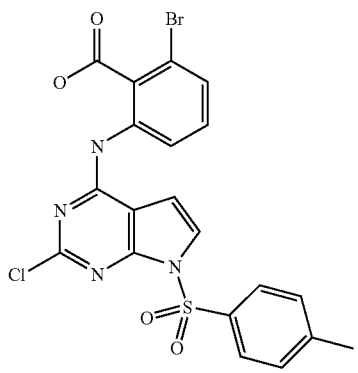

A suspension of 2,4-dichloro-7-[(4-methylphenyl)sulfonyl]-7H-pyrrolo[2,3-d]pyrimidine (2 g, 5.84 mmols), 2-amino-6-bromobenzoic acid (2.53 g, 11.69 mmols), and N-ethyl-N-(1-methylethyl)-2-propanamine (7.55 g, 58.4 mmols) in 2-propanol (150 ml) was heated at 90° C. for 5 days. The solvent was removed, residue redissolved in DCM (150 ml), washed with 1M HCl(100 ml), organic layer separated, adsorbed onto silica gel, and purified by silica gel chromatography (DCM to 10% MeOH/DCM). The crude product was then recrystallized from ethyl acetate/hexanes to obtain 2-bromo-6-({2-chloro-7-[(4-methylphenyl)sulfonyl]-7H-pyrrolo[2,3-d]pyrimidin-4-yl}amino)benzoic acid (1.5 g, 49%). ESIMS (M+H)$^+$=521.

Step B/Intermediate D24: 8-bromo-5-chloro-3-[(4-methylphenyl)sulfonyl]pyrrolo[2',3':4,5]pyrimido[6,1-b]quinazolin-7(3H)-one hydrogen chloride

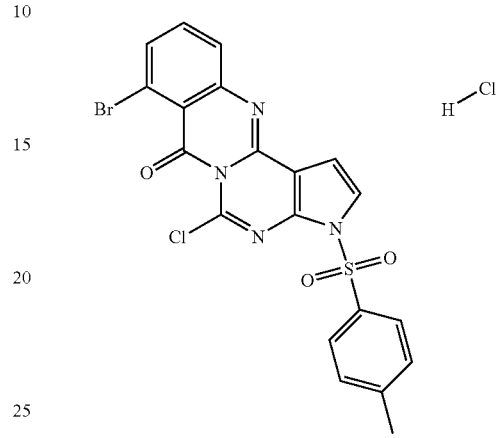

To a solution of 2-bromo-6-({2-chloro-7-[(4-methylphenyl)sulfonyl]-7H-pyrrolo[2,3-d]pyrimidin-4-yl}amino)benzoic acid (1.5 g, 2.87 mmol) in THF(200 ml) was added oxalyl chloride (4.31 ml, 8.62 mmol, 2.0M DCM) and the reaction was stirred at rt for 1 hr. The reaction was concentrated on rotovap, redissolved in THF, evaporated again, and high vacced prior to next step to yield 8-bromo-5-chloro-3-[(4-methylphenyl)sulfonyl]pyrrolo[2',3':4,5]pyrimido[6,1-b]quinazolin-7(3H)-one hydrogen chloride (1.3 g, 90%). ESIMS (M+H)$^+$=503.

Step C/Intermediate D25: 8-bromo-5-{[4-[4-(1-methylethyl)-1-piperazinyl]-2-(methyloxy)phenyl]amino}3-[(4-methylphenyl)sulfonyl]pyrrolo[2',3':4,5]pyrimido[6,1-b]quinazolin-7(3H)-one

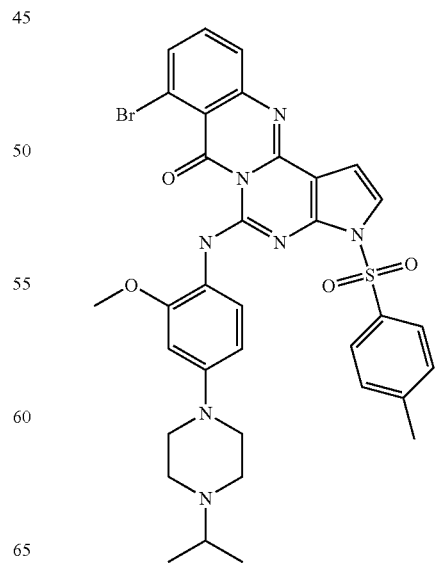

A suspension of 8-bromo-5-chloro-3-[(4-methylphenyl)sulfonyl]pyrrolo[2',3':4,5]pyrimido[6,1-b]quinazolin-7 (3H)-one hydrogen chloride (100 mg, 0.19 mmol), and [4-[4-(1-methylethyl)-1-piperazinyl]-2-(methyloxy)phenyl]amine 4-[4-(1-methylethyl)-1-piperazinyl]-2-(methyloxy)aniline (59.4 mg, 0.238 mmol) in THF(50 ml) was stirred overnight at rt. The reaction was diluted with ethyl acetate (25 ml) and washed with saturated NaHCO₃ (20 ml). Organic layer was filtered through a cotton plug, and concentrated by rotary evaporation to give 8-bromo-5-{[4-[4-(1-methylethyl)-1-piperazinyl]-2-(methyloxy)phenyl]amino}-3-[(4-methylphenyl)sulfonyl]pyrrolo[2',3':4,5]pyrimido[6,1-b]quinazolin-7 (3H)-one (0.120 g, 84%). ESIMS (M+H)⁺=716.

StepD/Intermediate D26: methyl 2-bromo-6-({2-{[4-[4-(1-methylethyl)-1-piperazinyl]-2-(methyloxy)phenyl]amino}-7-[(4-methylphenyl)sulfonyl]-7H-pyrrolo[2,3-d]pyrimidin-4-yl}amino)benzoate

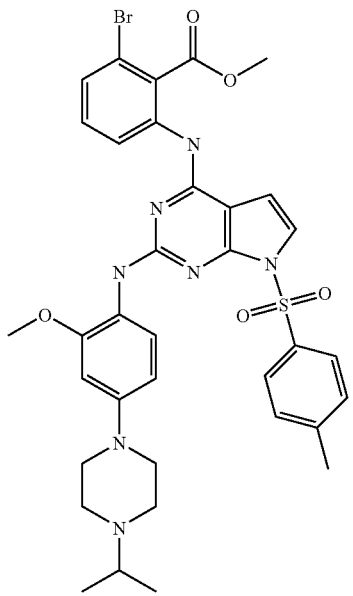

A solution of 8-bromo-5-{[4-[4-(1-methylethyl)-1-piperazinyl]-2-(methyloxy)phenyl]amino}-3-[(4-methylphenyl)sulfonyl]pyrrolo[2',3':4,5]pyrimido[6,1-b]quinazolin-7 (3H)-one (120 mg, 0.167 mmol), and potassium carbonate (69.4 mg, 0.502 mmol) in methanol (25 ml) was stirred at room temperature. The reaction was filtered to remove the base, organic layer was filtered through a cotton plug, concentrated by rotary evaporation, adsorbed onto silica gel, and purified by silica gel chromatography (DCM to 10% MeOH/DCM) to give methyl 2-bromo-6-({2-{[4-[4-(1-methylethyl)-1-piperazinyl]-2-(methyloxy)phenyl]amino}-7-[(4-methylphenyl)sulfonyl]-7H-pyrrolo[2,3-d]pyrimidin-4-yl}amino)benzoate (0.1 g, 80%). ESIMS (M+H)⁺=748.

Step E/Intermediate D27: methyl 2-cyano-6-({2-{[4-[4-(1-methylethyl)-1-piperazinyl]-2-(methyloxy)phenyl]amino}-7-[(4-methylphenyl)sulfonyl]-7H-pyrrolo[2,3-d]pyrimidin-4-yl}amino)benzoate

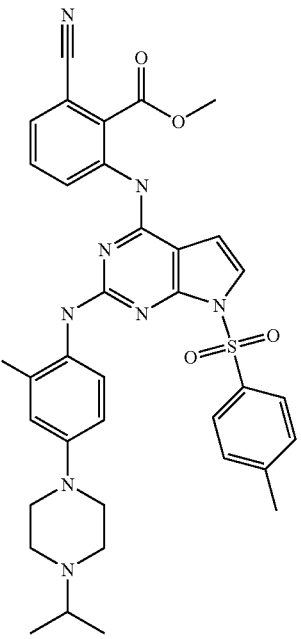

To a N₂ degassed solution of methyl 2-bromo-6-({2-{[4-[4-(1-methylethyl)-1-piperazinyl]-2-(methyloxy)phenyl]amino}-7-[(4-methylphenyl)sulfonyl]-7H-pyrrolo[2,3-d]pyrimidin-4-yl}amino)benzoate (500 mg, 0.668 mmol) in N,N-Dimethylformamide (DMF) (10 ml) was added tetrakis(triphenylphosphine)palladium(0) (154 mg, 0.134 mmol) and zinc cyanide (94 mg, 0.801 mmol). The reaction was heated in the microwave at 120° C. for 10 min. The solvent was then removed, the residue redissolved in DCM (50 ml), washed with water (50 ml), adsorbed onto silica gel, and purified by silica gel chromatography (DCM to 5% MeOH/DCM) to afford methyl 2-cyano-6-({2-{[4-[4-(1-methylethyl)-1-piperazinyl]-2-(methyloxy)phenyl]amino}-7-[(4-methylphenyl)sulfonyl]-7H-pyrrolo[2,3-d]pyrimidin-4-yl}amino)benzoate (0.4 g, 86%). ¹H NMR (400 MHz, DMSO-d₆) δ ppm 1.01 (d, J=6.62 Hz, 6 H) 2.33 (s, 3 H) 2.57-2.64 (m, 4 H) 2.65-2.72 (m, 1 H) 3.09-3.18 (m, 4 H) 3.63 (s, 3 H) 3.83 (s, 3 H) 6.53-55 (m, 1 H) 6.64-6.66 (m, 1 H) 6.81 (d, J=4.01 Hz, 1 H) 7.36 (d, J=8.03 Hz, 2 H) 7.38 (d, J=4.01 Hz, 1 H) 7.52-7.57 (m, 1 H) 7.58-7.65 (m, 1 H) 7.71-7.74 (m, 1 H) 7.91 (d, J=8.23 Hz, 2 H) 7.95 (s, 1 H) 7.99-8.04 (m, 1 H) 9.95 (s, 1 H).

429

Step F/Intermediate D28: 7-({2-{[4-[4-(1-methyl-ethyl)-1-piperazinyl]-2-(methyloxy)phenyl]amino}-7-[(4-methylphenyl)sulfonyl]-7H-pyrrolo[2,3-d]pyrimidin-4-yl}amino)-2,3-dihydro-1H-isoindol-1-one

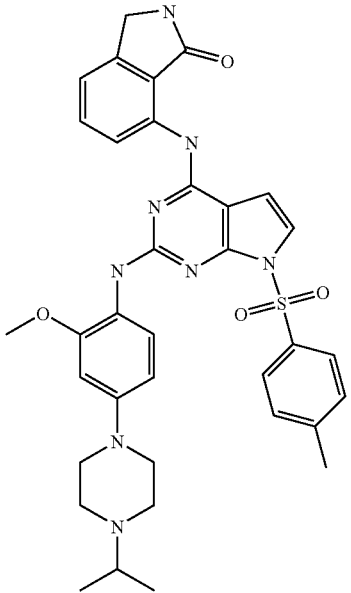

To a solution of methyl 2-cyano-6-({2-{[4-[4-(1-methylethyl)-1-piperazinyl]-2-(methyloxy)phenyl]amino}-7-[(4-methylphenyl)sulfonyl]-7H-pyrrolo[2,3-d]pyrimidin-4-yl}amino)benzoate (200 mg, 0.288 mmol) in methanol (50.0 ml) and THF (50 ml) was added cobalt (II) chloride hexahydrate (137 mg, 0.576 mmol). To this was added sodium borohydride (109 mg, 2.88 mmol) and reaction was stirred at rt for 1 hr. Water (25 ml) was added and the organic solvent was removed under reduced pressure. The aqueous layer was extracted with DCM (2×50 mL), organic layers combined, filtered through a cotton plug, adsorbed onto silica gel and purified by silica gel chromatography (DCM to 10% MeOH/DCM) to provide the lactam (165 mg, 86%). ESIMS (M+H)$^+$=667.

Step G/Example 199: 7-[(2-{[4-[4-(1-methylethyl)-1-piperazinyl]-2-(methyloxy)phenyl]amino}-1H-pyrrolo[2,3-d]pyrimidin-4-yl)amino]-2,3-dihydro-1H-isoindol-1-one To a solution of 7-({2-{[4-[4-(1-methylethyl)-1-piperazinyl]-2-(methyloxy)phenyl]amino}-7-[(4-methylphenyl)sulfonyl]-7H-pyrrolo[2,3-d]pyrimidin-4-yl}amino)-2,3-dihydro-1H-isoindol-1-one (140 mg, 0.210 mmol) in 1,4-dioxane (8 mL) was added 1.0M potassium hydroxide (6.30 mL, 6.30 mmol) and the resulting reaction was heated in a microwave reactor at 120° C. for 20 min. The reaction was washed with brine (5 ml), organic layer diluted with ethyl acetate (10 mL), adsorbed onto silica gel and purified by silica gel chromatography (DCM to 10% MeOH/DCM) to produce 7-[(2-{[4-[4-(1-methylethyl)-1-piperazinyl]-2-(methyloxy)phenyl]amino}-1H-pyrrolo[2,3-d]pyrimidin-4-yl)amino]-2,3-dihydro-1H-isoindol-1-one (0.070 g, 75%). ESIMS (M+H)$^+$=513. $^1$H NMR (400 MHz, DMSO-d$_6$) δ ppm 1.02 (d, J=6.42 Hz, 6 H) 2.61 (d, J=9.23 Hz, 4 H) 3.08-3.16 (m, 4 H) 3.81 (s, 3 H) 4.39 (s, 2 H) 6.27 (dd, J=3.41, 1.81 Hz, 1 H) 6.51 (dd, J=8.73, 2.51 Hz, 1 H) 6.64 (d, J=2.61 Hz, 1 H) 6.97 (dd, J=3.41, 2.21 Hz, 1 H) 7.10 (d, J=7.62 Hz, 1 H) 7.43-7.50 (m, 1 H) 7.53 (s, 1 H) 7.83 (d, J=8.83 Hz, 1 H) 8.69 (d, J=8.23 Hz, 2 H) 8.79 (s, 1 H) 10.45 (s, 1 H) 11.33 (s, 1 H).

Example 200

7-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-2,3-dihydro-1H-isoindol-1-one

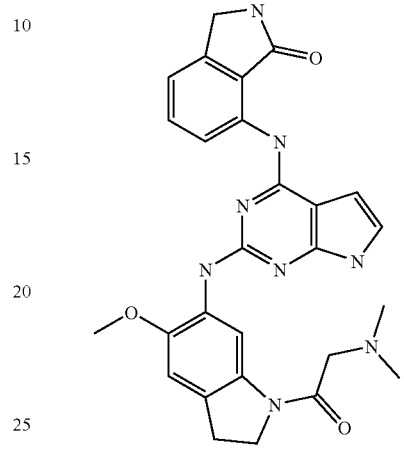

Utilizing a procedure similar to that of Example 199, 7-[(2-{[1-(N,N-dimethylglycyl)-5-(methyloxy)-2,3-dihydro-1H-indol-6-yl]amino}-pyrrolo[2,3-d]pyrimidin-4-yl)amino]-2,3-dihydro-1H-isoindol-1-one was obtained from 8-bromo-5-chloro-3-[(4-methylphenyl)sulfonyl]pyrrolo[2',3':4,5]pyrimido[6,1-b]quinazolin-7(3H)-one hydrogen chloride (0.5 g, 0.93 mmol) and 1-[(dimethylamino)acetyl]-5-(methyloxy)-2,3-dihydro-1H-indol-6-amine (0.27 g, 1.1 mmol) to afford the title compound (0.080 g, 17% over five steps). ESIMS (M+H)$^+$=513. $^1$H NMR (400 MHz, DMSO-d$_6$) δ ppm 2.23 (s, 6 H) 3.11-3.21 (m, 4 H) 3.77 (s, 3 H) 4.19 (t, J=8.43 Hz, 2 H) 4.37 (s, 2 H) 6.27 (s, 1 H) 6.98 (s, 2 H) 7.06 (d, J=7.42 Hz, 1 H) 7.37 (t, J=7.62 Hz, 1 H) 7.73 (s, 1 H) 8.58 (s, 1 H) 8.65 (d, J=8.23 Hz, 1 H) 8.78 (s, 1 H) 10.47 (s, 1 H) 11.31 (s, 1 H).

Example 201

7-[(2-{[6-(methyloxy)-1-(1-pyrrolidinylacetyl)-1,2,3,4-tetrahydro-7-quinolinyl]amino}-1H-pyrrolo[2,3-d]pyrimidin-4-yl)amino]-2,3-dihydro-1H-isoindol-1-one

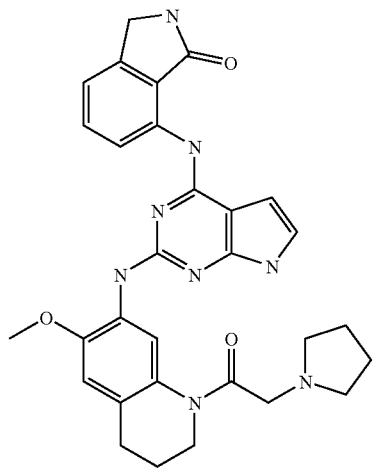

Utilizing a procedure similar to that of Example 199, 7-[(2-{[6-(methyloxy)-1-(1-pyrrolidinylacetyl)-1,2,3,4-tetrahydro-7-quinolinyl]amino}-1H-pyrrolo[2,3-d]pyrimidin-4-yl)amino]-2,3-dihydro-1H-isoindol-1-one was obtained from 8-bromo-5-chloro-3-[(4-methylphenyl)sulfonyl]pyrrolo[2',3':4,5]pyrimido[6,1-b]quinazolin-7(3H)-one hydrogen chloride (0.45 g, 0.83 mmol) and 6-(methyloxy)-1-(1-pyrrolidinylacetyl)-1,2,3,4-tetrahydro-7-quinolinamine (0.28 g, 0.98 mmol) to afford the title compound (0.050 g, 11% over five steps). ESIMS (M+H)$^+$=553. $^1$H NMR (400 MHz, DMSO-d$_6$) δ ppm 1.49-1.60 (m, 4 H) 1.84-1.95 (m, 2 H) 2.50-2.79 (m, 8 H) 3.74 (t, J=6.32 Hz, 2 H) 3.86 (s, 3 H) 4.40 (s, 2 H) 6.31 (s, 1 H) 6.88 (s, 1 H) 7.04 (s, 1 H) 7.09-7.12 (m, 1 H) 7.42-7.49 (m, 1 H) 7.66 (s, 1 H) 8.46 (s, 1 H) 8.67 (d, J=8.03 Hz, 1 H) 8.80 (s, 1 H) 10.52 (s, 1 H) 11.44 (bs, 1 H).

Example 202

2-fluoro-N-methyl-6-[(2-{[6-(methyloxy)-1-(1-methyl-L-prolyl)-1,2,3,4-tetrahydro-7-quinolinyl]amino}-1H-pyrrolo[2,3-d]pyrimidin-4-yl)amino]benzamide

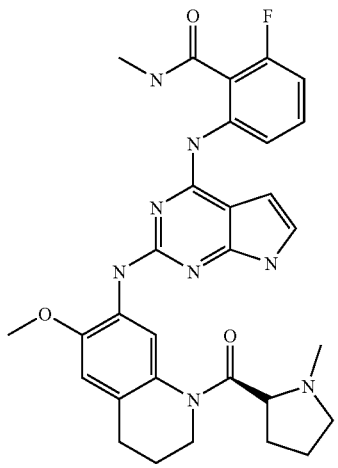

A suspension of 5-chloro-8-fluoro-3-[(4-methylphenyl)sulfonyl]pyrrolo[2',3':4,5]pyrimido[6,1-b]quinazolin-7(3H)-one hydrogen chloride (300 mg, 0.63 mmol) and 6-(methyloxy)-1-(1-methyl-L-prolyl)-1,2,3,4-tetrahydro-7-quinolinamine 217 mg, 0.75 mmol) in THF (50 ml) was heated at 65° C. for 4 hrs. The reaction was diluted with ethyl acetate (200 ml) and washed with saturated NaHCO$_3$ (300 ml). Organic layer was removed, concentrated by rotary evaporation, solids triturated from ethyl acetate/hexanes, and dried under house vacuum prior to next step. The solids were then added to THF (50 ml) followed by a solution of methylamine (2M in THF, 7.40 ml, 3.7 mmol) and the resulting mixture was stirred at rt overnight. Next, the crude reaction was adsorbed onto silica gel and purified by silica gel chromatography (DCM to 10% MeOH/DCM over 30 min). ESIMS (M+H)$^+$=727. The isolated pure amide was redissolved in 1,4-dioxane (10 ml), potassium hydroxide (2.497 ml, 12.49 mmol) added and the reaction was heated in the microwave at 120° C. for 20 min. The resulting solution was adsorbed onto silica gel and purified by silica gel chromatography (DCM to 10% MeOH/DCM) to afford 2-fluoro-N-methyl-6-[(2-{[6-(methyloxy)-1-(1-methyl-L-prolyl)-1,2,3,4-tetrahydro-7-quinolinyl]amino}-1H-pyrrolo[2,3-d]pyrimidin-4-yl)amino]benzamide (0.1 g, 28% over three steps). ESIMS (M+H)$^+$=573; $^1$H NMR (400 MHz, DMSO-d$_6$) δ ppm 1.72-1.98 (m, 6 H) 2.06 (s, 3 H) 2.11-2.20 (m, 1 H) 2.58-2.73 (m, 2 H) 2.78 (d, J=4.41 Hz, 3 H) 2.85-2.97 (m, 1 H) 3.41-3.52 (m, 2 H) 3.88 (s, 3 H).

Example 203

2-fluoro-6-({2-[(2-(methyloxy)-4-{[2-(4-methyl-1-piperazinyl)ethyl]oxy}phenyl)amino]-1H-pyrrolo[2,3-d]pyrimidin-4-yl}amino)benzamide

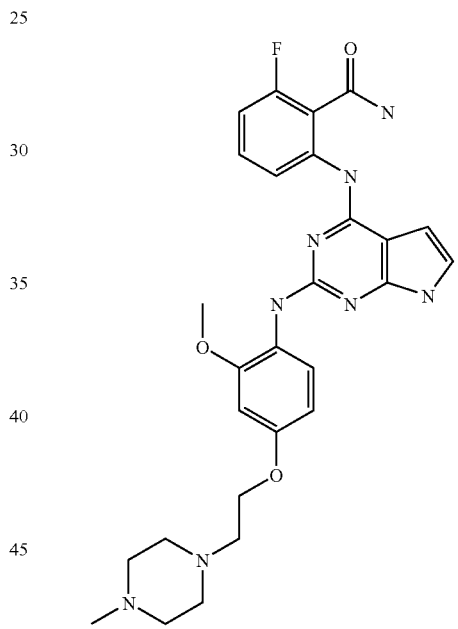

According to General Procedure III, 2-fluoro-6-({2-[(2-(methyloxy)-4-{[2-(4-methyl-1-piperazinyl)Ethyl]oxy}phenyl)amino]-1H-pyrrolo[2,3-d]pyrimidin-4-yl}amino)benzamide (0.182 g, 0.340 mmol, 51%) was prepared from 2-[(2-chloro-1H-pyrrolo[2,3-d]pyrimidin-4-yl)amino]-6-fluorobenzamide(0.400 g, 0.87 mmol), 27% ammonium hydroxide, and 2-(methyloxy)-4-{[2-(4-methyl-1-piperazinyl)Ethyl]oxy}aniline (0.346 g, 1.3 mmol) $^1$H NMR (400 MHz, DMSO-d$_6$) δ ppm 2.16 (s, 3 H) 2.24-2.48 (m, 8 H) 2.68 (t, J=5.87 Hz, 2 H) 3.82 (s, 3 H) 4.07 (t, J=5.87 Hz, 2 H) 6.22 (dd, J=3.39, 1.83 Hz, 1 H) 6.50 (dd, J=8.75, 2.61 Hz, 1 H) 6.64 (d, J=2.57 Hz, 1 H) 6.86-7.01 (m, 2 H) 7.35-7.50 (m, 2 H) 7.92-8.07 (m, 2 H) 8.10 (s, 1 H) 8.47 (d, J=8.34 Hz, 1 H) 10.45 (s, 1 H) 11.33 (s, 1 H) (ESIMS (M+H)$^+$=536)

Example 204

2-fluoro-6-{[2-({2-(methyloxy)-4-[4-(methylsulfonyl)-1-piperazinyl]phenyl}amino)-1H-pyrrolo[2,3-d]pyrimidin-4-yl]amino}benzamide

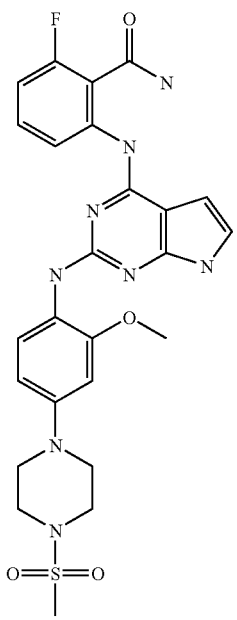

According to General Procedure III, 2-fluoro-6-{[2-({2-(methyloxy)-4-[4-(methylsulfonyl)-1-piperazinyl]phenyl}amino)-1H-pyrrolo[2,3-d]pyrimidin-4-yl]amino}benzamide (0.156 g, 0.28 mmol, 43%) was prepared from 2-[(2-chloro-1H-pyrrolo[2,3-d]pyrimidin-4-yl)amino]-6-fluorobenzamide(0.300 g, 0.65 mmol), 27% ammonium hydroxide and 2-(methyloxy)-4-[4-(methylsulfonyl)-1-piperazinyl]aniline (0.242 g, 0.85 mmol) $^1$H NMR (400 MHz, DMSO-d$_6$) δ ppm 2.94 (s, 3 H) 3.19-3.30 (m, 8 H) 3.83 (s, 3 H) 6.19-6.25 (m, 1 H) 6.49-6.56 (m, 1 H) 6.69 (d, J=2.29 Hz, 1 H) 6.87-7.00 (m, 2 H) 7.38-7.48 (m, 2 H) 7.94-8.04 (m, 2 H) 8.07-8.13 (m, 1 H) 8.48 (d, J=8.61 Hz, 1 H) 10.46 (s, 1 H) 11.30-11.36 (m, 1 H) (ESIMS (M+H)$^+$=555)

Example 205

2-fluoro-6-({2-[(2-(methyloxy)-4-{[3-(4-methyl-1-piperazinyl)propyl]oxy}phenyl)amino]-pyrrolo[2,3-d]pyrimidin-4-yl}amino)benzamide

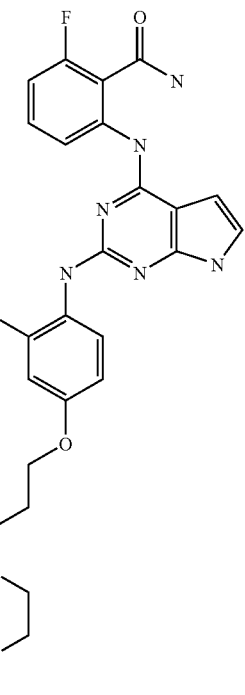

According to General Procedure III, 2-fluoro-6-({2-[(2-(methyloxy)-4-{[3-(4-methyl-1-piperazinyl)propyl]oxy}phenyl)amino]-1H-pyrrolo[2,3-d]pyrimidin-4-yl}amino)benzamide (0.206 g, 0.376 mmol, 56%) was prepared from 2-[(2-chloro-1H-pyrrolo[2,3-d]pyrimidin-4-yl)amino]-6-fluorobenzamide(0.400 g, 0.87 mmol), 27% aqueous ammonium hydroxide and 2-(methyloxy)-4-{[3-(4-methyl-1-piperazinyl)propyl]oxy}aniline (0.364 g, 1.3 mmol) $^1$H NMR (400 MHz, DMSO-d$_6$) δ ppm 1.77-1.92 (m, 2 H) 2.15 (s, 3 H) 2.21-2.46 (m, 10 H) 3.79 (s, 3 H) 3.94-4.01 (m, 2 H) 6.20 (dd, J=3.44, 1.88 Hz, 1 H) 6.47 (dd, J=8.75, 2.61 Hz, 1 H) 6.60 (d, J=2.66 Hz, 1 H) 6.84-6.98 (m, 2 H) 7.33-7.46 (m, 2 H) 7.87-8.14 (m, 3 H) 8.45 (d, J=8.34 Hz, 1 H) 10.44 (s, 1 H) 11.30 (s, 1 H) (ESIMS (M+H)$^+$=549)

Example 206

2-fluoro-6-({2-[(2-(methyloxy)-4-{[(1-propyl-4-piperidinyl)methyl]oxy}phenyl)amino]-1H-pyrrolo[2,3-d]pyrimidin-4-yl}amino)benzamide

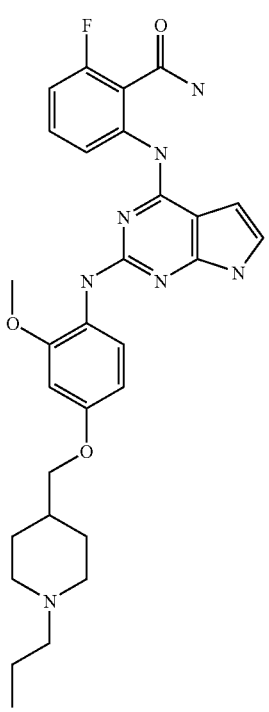

According to General Procedure III, 2-fluoro-6-({2-[(2-(methyloxy)-4-{[(1-propyl-4-piperidinyl)methyl]oxy}phenyl)amino]-1H-pyrrolo[2,3-d]pyrimidin-4-yl}amino)benzamide (0.200 g, 0.284 mmol, 63%) was prepared from 2-[(2-chloro-1H-pyrrolo[2,3-d]pyrimidin-4-yl)amino]-6-fluorobenzamide(0.300 g, 0.65 mmol), 27% ammonium hydroxide and 2-(methyloxy)-4-{[3-(4-methyl-1-piperazinyl)propyl]oxy}aniline (0.236 g, 0.848 mmol). $^1$H NMR (400 MHz, DMSO-$d_6$) δ ppm 0.85 (t, J=7.33 Hz, 3 H) 1.24-1.38 (m, 2 H) 1.38-1.50 (m, 2 H) 1.66-1.81 (m, 3 H) 1.81-1.94 (m, 2 H) 2.18-2.26 (m, 2 H) 2.83-2.93 (m, 2 H) 3.78-3.85 (m, 5 H) 6.22 (dd, J=3.44, 1.88 Hz, 1 H) 6.49 (dd, J=8.75, 2.61 Hz, 1 H) 6.62 (d, J=2.57 Hz, 1 H) 6.86-7.00 (m, 2 H) 7.37-7.48 (m, 2 H) 7.95 (d, J=8.80 Hz, 1 H) 8.02 (br. s., 1 H) 8.09 (s, 1 H) 8.47 (d, J=8.34 Hz, 1 H) 10.45 (s, 1 H) 11.32 (s, 1 H). (ESIMS (M+H)$^+$=549)

Example 207

2-fluoro-6-{[2-({2-(methyloxy)-4-[4-(methylsulfonyl)hexahydro-1H-1,4-diazepin-1-yl]phenyl}amino)-1H-pyrrolo[2,3-d]pyrimidin-4-yl]amino}benzamide

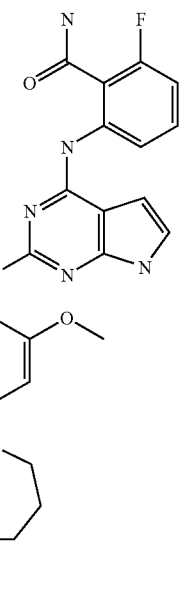

According to General Procedure III, 2-fluoro-6-{[2-({2-(methyloxy)-4-[4-(methylsulfonyl)hexahydro-1H-1,4-diazepin-1-yl]phenyl}amino)-1H-pyrrolo[2,3-d]pyrimidin-4-yl]amino}benzamide (158 mg, 0.278 mmol, 67%) was prepared from 2-[(2-chloro-1H-pyrrolo[2,3-d]pyrimidin-4-yl)amino]-6-fluorobenzamide (233 mg, 0.55 mmol), 27% aqueous ammonium hydroxide, and 2-(methyloxy)-4-[4-(methylsulfonyl)hexahydro-1H-1,4-diazepin-1-yl]aniline (216 mg, 0.72 mmol). $^1$H NMR (400 MHz, DMSO-$d_6$) δ ppm 1.87-1.97 (m, 2 H) 2.83 (s, 3 H) 3.20 (dd, J=6.14, 5.41 Hz, 2 H) 3.45 (t, J=5.04 Hz, 2 H) 3.57-3.69 (m, 4 H) 3.80 (s, 3 H) 6.19 (dd, J=3.48, 1.83 Hz, 1 H) 6.27-6.35 (m, 1 H) 6.40 (d, J=2.47 Hz, 1 H) 6.92 (t, J=2.84 Hz, 2 H) 7.33 (s, 1 H) 7.35-7.45 (m, 1 H) 7.73 (d, J=8.71 Hz, 1 H) 8.01 (br. s., 1 H) 8.09 (s, 1 H) 8.53 (d, J=8.43 Hz, 1 H) 10.47 (s, 1 H) 11.26 (s, 1 H) (ESIMS (M+H)$^+$=569)

Example 208

2-fluoro-6-[(2-{[4-[4-(1-methylethyl)hexahydro-1H-1,4-diazepin-1-yl]-2-(methyloxy)phenyl]amino}-1H-pyrrolo[2,3-d]pyrimidin-4-yl)amino]benzamide

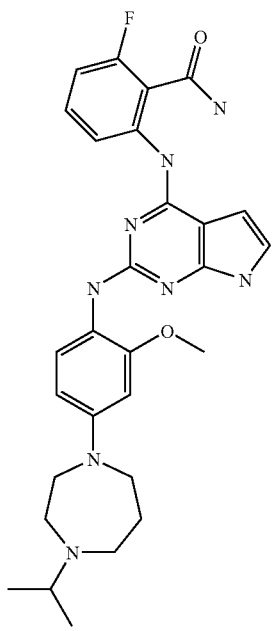

According to General Procedure III, 2-fluoro-6-[(2-{[4-[4-(1-methylethyl)hexahydro-1H-1,4-diazepin-1-yl]-2-(methyloxy)phenyl]amino}-1H-pyrrolo[2,3-d]pyrimidin-4-yl)amino]benzamide (70 mg, 0.132 mmol, 65%) was prepared from 2-[(2-chloro-1H-pyrrolo[2,3-d]pyrimidin-4-yl)amino]-6-fluorobenzamide (250 mg, 0.54 mmol), 27% aqueous ammonium hydroxide, and 4-[4-(1-methylethyl)hexahydro-1H-1,4-diazepin-1-yl]-2-(methyloxy)aniline (185 mg, 0.71 mmol). $^1$H NMR (400 MHz, DMSO-d$_6$) δ ppm 0.95 (d, J=5.49 Hz, 6 H) 1.82 (br. s., 2 H) 2.50 (br. s., 2 H)(under DMSO peak) 2.71 (br. s., 2 H) 2.81-2.96 (m, 1 H) 3.49 (d, J=5.13 Hz, 4 H) 3.77 (s, 3 H) 6.18 (d, J=1.65 Hz, 1 H) 6.25 (d, J=8.52 Hz, 1 H) 6.34 (br. s., 1 H) 6.82-6.96 (m, 2 H) 7.29-7.42 (m, 2 H) 7.62 (d, J=7.97 Hz, 1 H) 7.96-8.15 (m, 2 H) 8.55 (d, J=8.52 Hz, 1 H) 10.48 (s, 1 H) 11.23 (br. s., 1 H). (ESIMS (M+H)$^+$=533)

Example 209

2-fluoro-6-[(2-{[4-(4-methylhexahydro-1H-1,4-diazepin-1-yl-2-(methyloxy)phenyl]amino}-1H-pyrrolo[2,3-d]pyrimidin-4-yl)amino]benzamide

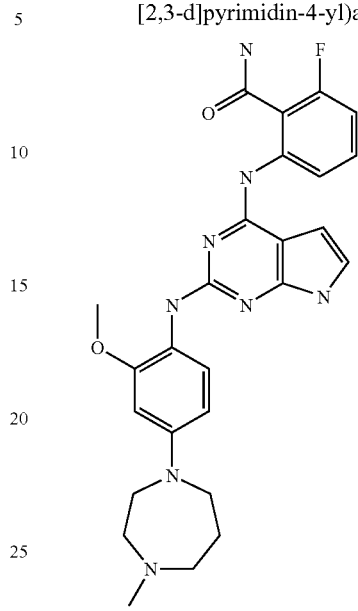

According to General Procedure III, 2-fluoro-6-[(2-{[4-(4-methylhexahydro-1H-1,4-diazepin-1-yl)-2-(methyloxy)phenyl]amino}-1H-pyrrolo[2,3-d]pyrimidin-4-yl)amino]benzamide (116 mg, 0.230 mmol, 57%) was prepared from 2-[(2-chloro-1H-pyrrolo[2,3-d]pyrimidin-4-yl)amino]-6-fluorobenzamide (300 mg, 0.85 mmol), 27% aqueous ammonium hydroxide, and 4-(4-methylhexahydro-1H-1,4-diazepin-1-yl)-2-(methyloxy)aniline (260 mg, 1.1 mmol). $^1$H NMR (400 MHz, DMSO-d$_6$) δ ppm 1.85-1.98 (m, 2 H) 2.31 (br. s., 3 H) 2.50 (br. s., 2 H) 2.67 (d, J=1.56 Hz, 2 H) 3.45 (t, J=6.13 Hz, 2 H) 3.49-3.59 (m, 2 H) 3.78 (s, 3 H) 6.19 (dd, J=3.16, 1.69 Hz, 1 H) 6.25 (dd, J=8.79, 2.29 Hz, 1 H) 6.34 (d, J=2.11 Hz, 1 H) 6.81-6.96 (m, 2 H) 7.27-7.47 (m, 2 H) 7.65 (d, J=8.70 Hz, 1 H) 7.96-8.17 (m, 2 H) 8.54 (d, J=8.42 H) 10.47 (s, 1 H) 11.23 (br. s., 1 H) (ESIMS (M+H)$^+$=505)

Example 210

2-[2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-6-fluorobenzamide

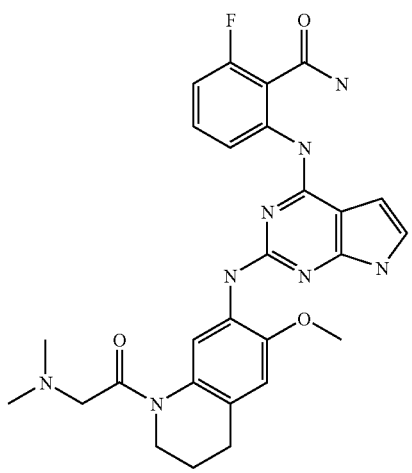

439

According to General Protocol III, 2-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-6-fluorobenzamide (0.036 g) was prepared from 2-({2-chloro-7-[(4-methylphenyl)sulfonyl]-7H-pyrrolo[2,3-d]pyrimidin-4-yl}amino)-6-fluorobenzamide (0.15 g, 0.33 mmol), 27% aqueous ammonium hydroxide, and 1-[(dimethylamino)acetyl]-6-(methyloxy)-1,2,3,4-tetrahydro-7-quinolinamine (0.090 g, 0.34 mmol). $^1$H NMR (400 MHz, DMSO-d$_6$) δ ppm 1.71-1.82 (m, 2 H), 2.01 (bs, 6 H), 2.52-2.62 (m, 2 H), 3.15 (s, 2 H), 3.57-3.64 (m, 2 H), 3.73 (s, 3 H), 6.14 (s, 1 H), 6.72 (s, 1 H), 6.78-6.86 (m, 1 H), 6.89 (m, 1 H), 7.25-7.33 (m, 1 H), 7.41 (s, 1 H), 7.90 (bs, 1 H), 7.97 (bs, 1 H), 8.23-8.35 (m, 2 H), 10.36 (bs, 1 H), 11.29 (bs, 1 H).

Example 211

2-fluoro-6-[(2-{[6-(methyloxy)-1,2,3,4-tetrahydro-7-quinolinyl]amino}-1H-pyrrolo[2,3-d]pyrimidin-4-yl)amino]benzamide

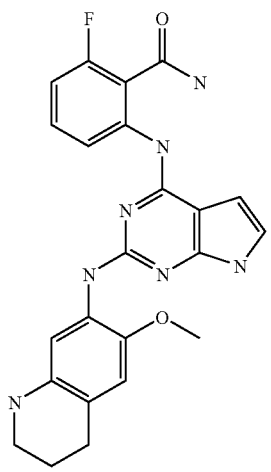

According to General Protocol III, 2-fluoro-6-[(2-{[6-(methyloxy)-1,2,3,4-tetrahydro-7-quinolinyl]amino}-1H-pyrrolo[2,3-d]pyrimidin-4-yl)amino]benzamide (0.015 g) was isolated as a byproduct during the hydrolysis of the tosyl group during the aforementioned preparation of 2-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-6-fluorobenzamide. $^1$H NMR (400 MHz, DMSO-d$_6$) δ ppm 1.76-1.85 (m, 2 H), 2.66 (t, J=6.2 Hz, 2 H), 3.14 (m, 2 H), 3.71 (s, 3 H), 4.91 (bs, 1 H), 6.22-6.24 (m, 1 H), 6.55 (s, 1 H), 6.90-6.99 (m, 2 H), 7.30 (s, 1 H), 7.36 (s, 1 H), 7.42-7.50 (m, 1 H), 8.02 (bs, 1 H), 8.10 (bs, 1 H), 8.52 (d, J=8.4 Hz, 1 H), 10.50 (s, 1 H), 11.31 (bs, 1 H); ESIMS (M+H)$^+$=448.

Example 212

2-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-6-fluoro-N-methylbenzamide

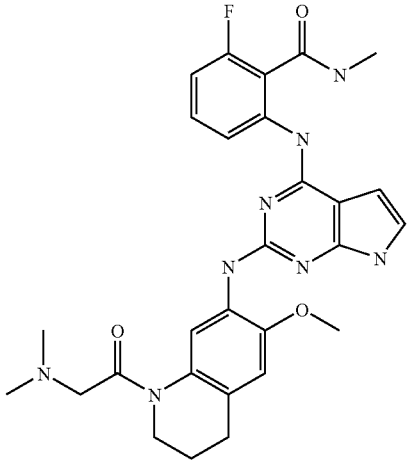

According to General Protocol III, 2-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-6-fluoro-N-methylbenzamide (0.041 g) was prepared from 2-({2-chloro-7-[(4-methylphenyl)sulfonyl]-7H-pyrrolo[2,3-d]pyrimidin-4-yl}amino)-6-fluorobenzamide (0.15 g, 0.33 mmol), methyl amine, and 1-[(dimethylamino)acetyl]-6-(methyloxy)-1,2,3,4-tetrahydro-7-quinolinamine (0.090 g, 0.34 mmol). $^1$H NMR (400 MHz, DMSO-d$_6$) δ ppm 1.82-1.93 (m, 2 H), 2.11 (bs, 6 H), 2.63-2.72 (m, 2 H), 2.78 (d, J=4.4 Hz, 3 H), 3.24 (s, 2 H), 3.70 (t, J=6.0 Hz, 2 H), 3.85 (s, 3 H), 6.31 (s, 1 H), 6.83 (bs, 1 H), 6.92-7.01 (m, 2 H), 7.35-7.44 (m, 1 H), 7.50 (s, 1 H), 8.21-8.28 (m, 1 H), 8.43 (m, 1 H), 8.51-8.58 (m, 1 H), 10.10 (bs, 1 H), 11.37 (bs, 1 H); ESIMS (M)$^+$=546.

Example 212 (Alternative Preparation)

2-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-6-fluoro-N-methylbenzamide

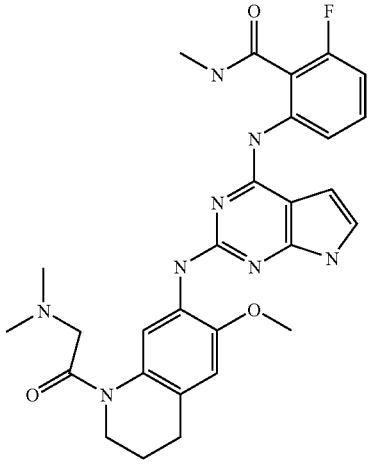

Step A/Intermediate D71: 5-{[1-(N,N-dimethylglycyl)-6-(methyloxy)-1,2,3,4-tetrahydro-7-quinolinyl]amino}-8-fluoro-3-[(4-methylphenyl)sulfonyl]pyrrolo[2',3':4,5]pyrimido[6,1-b]quinazolin-7(3H)-one

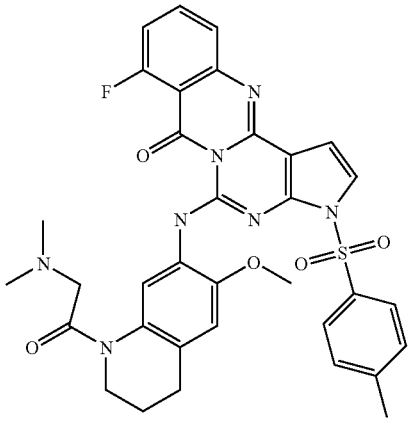

To a suspension of 2-({2-chloro-7-[(4-methylphenyl)sulfonyl]-7H-pyrrolo[2,3-d]pyrimidin-4-yl}amino)-6-fluorobenzamide (5.0 g, 10.87 mmol), 1-[(dimethylamino)acetyl]-6-(methyloxy)-1,2,3,4-tetrahydro-7-quinolinamine (3.44 g, 13.05 mmol), and potassium iodide (0.090 g, 0.544 mmol) in trifluroethanol (250 ml) was added 4M HCl/dioxane (10.87 ml, 43.5 mmol). The reaction was heated overnight in a pressure vessel equipped with a threaded teflon cap. The reaction was diluted with THF (300 ml) and washed with saturated NaHCO₃ (300 ml). The organic layer was removed, concentrated on rotovap, solids triturated from ethyl acetate/hexanes, and dried under house vacuum prior to next step to afford 5-{[1-(N,N-dimethylglycyl)-6-(methyloxy)-1,2,3,4-tetrahydro-7-quinolinyl]amino}-8-fluoro-3-[(4-methylphenyl)sulfonyl]pyrrolo[2',3':4,5]pyrimido[6,1-b]quinazolin-7(3H)-one (5.0 g, 68%). ESIMS (M+H)+=670.

Step B/Intermediate D72: 2-({2-{[1-(N,N-dimethylglycyl)-6-(methyloxy)-1,2,3,4-tetrahydro-7-quinolinyl]amino}-7-[(4-methylphenyl)sulfonyl]-7H-pyrrolo[2,3-d]pyrimidin-4-yl}amino)-6-fluoro-N-methylbenzamide

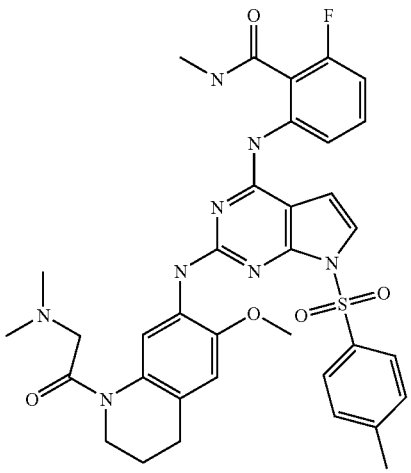

To a solution of 5-{[1-(N,N-dimethylglycyl)-6-(methyloxy)-1,2,3,4-tetrahydro-7-quinolinyl]amino}-8-fluoro-3-[(4-methylphenyl)sulfonyl]pyrrolo[2',3':4,5]pyrimido[6,1-b]quinazolin-7(3H)-one (5.0 g, 7.47 mmol) in THF (200 ml) was added 2.0 M methylamine in THF (74.7 ml, 149 mmol) and the resulting reaction was stirred overnight at rt. The crude reaction was adsorbed to silica gel and purified by LC (DCM to 5% MeOH/DCM) to give 2-({2-{[1-(N,N-dimethylglycyl)-6-(methyloxy)-1,2,3,4-tetrahydro-7-quinolinyl]amino}-7-[(4-methylphenyl)sulfonyl]-7H-pyrrolo[2,3-d]pyrimidin-4-yl}amino)-6-fluoro-N-methylbenzamide (3.2 g, 61%). ESIMS (M+H)+=701.

Step C/Example 212 (Alternative Preparation)

2-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-6-fluoro-N-methylbenzamide To a solution of 2-({2-{[1-(N,N-dimethylglycyl)-6-(methyloxy)-1,2,3,4-tetrahydro-7-quinolinyl]amino}-7-[(4-methylphenyl)sulfonyl]-7H-pyrrolo[2,3-d]pyrimidin-4-yl}amino)-6-fluoro-N-methylbenzamide (3.2 g, 4.57 mmol) in 1,4-dioxane (200 ml) was added 1.0M potassium hydroxide (91 ml, 91 mmol) and the resulting reaction was stirred at 80 C for 6 hrs. The reaction was diluted with ethyl acetate (200 ml), washed with brine (200 ml), adsorbed to silica gel and purified by LC (DCM to 5% MeOH/DCM) to provide 2-[(2-{[1-(N,N-dimethylglycyl)-6-(methyloxy)-1,2,3,4-tetrahydro-7-quinolinyl]amino}-1H-pyrrolo[2,3-d]pyrimidin-4-yl)amino]-6-fluoro-N-methylbenzamide (1.8 g, 72%). ESIMS (M+H)+=547. ¹H NMR (400 MHz, DMSO-d₆) δ ppm 1.79-1.88 (m, 2 H) 2.07 (br. s., 6 H) 2.59-2.68 (m, 2 H) 2.74 (d, J=4.58 Hz, 3 H) 3.20 ) (s, 2 H) 3.66 (t, J=6.13 Hz, 2 H) 3.80 (s, 3 H) 6.25-6.28 (m, 1 H) 6.78 (s, 1 H) 6.88-6.98 (m, 2 H) 7.32-7.39 (m, 1 H) 7.45 (s, 1 H) 8.20 (d, J=8.42 Hz, 1 H) 8.38 (s, 1H) 8.46-8.59 (m, 1 H) 10.06 (s, 1 H) 11.32 (br. s., 1 H).

Example 213

2-[(2-{[1-(N,N-dimethyl-β-alanyl)-6-(methyloxy)-1,2,3,4-tetrahydro-7-quinolinyl]amino}-1H-pyrrolo[2,3-d]pyrimidin-4-yl)amino]-6-fluoro-N-methylbenzamide

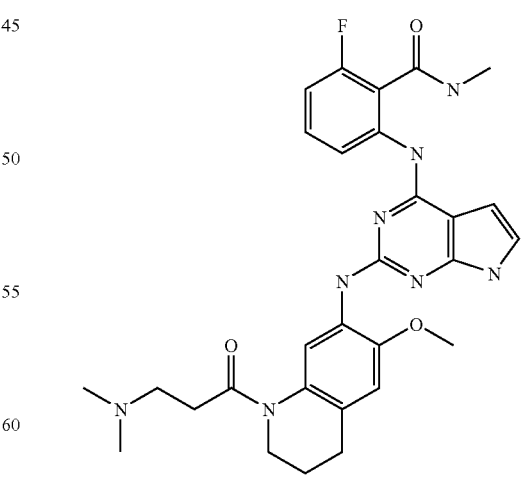

According to General Protocol III, 2-[(2-{[1-(N,N-dimethyl-β-alanyl)-6-(methyloxy)-1,2,3,4-tetrahydro-7-quinolinyl]amino}-1H-pyrrolo[2,3-d]pyrimidin-4-yl)amino]-6-fluoro-N-methylbenzamide (0.053 g) was prepared from

443

2-({2-chloro-7-[(4-methylphenyl)sulfonyl]-7H-pyrrolo[2,3-d]pyrimidin-4-yl}amino)-6-fluorobenzamide (0.15 g, 0.33 mmol), methyl amine, and 1-[3-(dimethylamino)propanoyl]-6-(methyloxy)-1,2,3,4-tetrahydro-7-quinolinamine (0.12 g, 0.42 mmol). $^1$H NMR (400 MHz, DMSO-d$_6$) δ ppm 1.80-1.90 (m, 2 H), 2.02 (s, 6 H), 2.51-2.55 (m, 2 H), 2.67 (t, J=6.2 Hz, 2 H), 2.74-2.83 (m, 5 H), 3.68 (t, J=6.1 Hz, 2 H), 3.86 (s, 3 H), 6.32 (s, 1 H), 6.85 (s, 1 H), 6.93-7.04 (m, 2 H), 7.39-7.49 (m, 1 H), 7.54 (s, 1 H), 8.25 (d, J=8.4 Hz, 1 H), 8.30 (s, 1 H), 8.53-8.60 (m, 1 H), 10.10 (bs, 1 H), 11.79 (bs, 1 H); ESIMS (M+H)$^+$=561.

Example 214

2-[(2-{[1-(N,N-dimethyl-β-alanyl)-6-(methyloxy)-1,2,3,4-tetrahydro-7-quinolinyl]amino}-1H-pyrrolo[2,3-d]pyrimidin-4-yl)amino]-6-fluorobenzamide

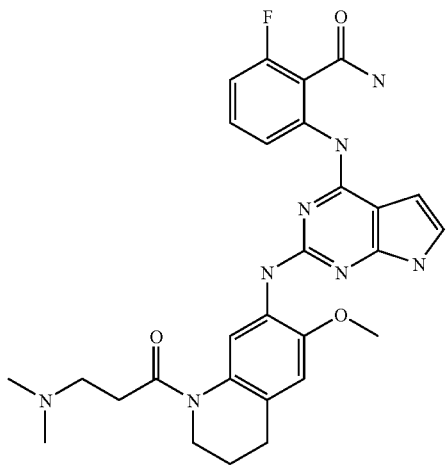

According to General Protocol III, 2-[(2-{[1-(N,N-dimethyl-β-alanyl)-6-(methyloxy)-1,2,3,4-tetrahydro-7-quinolinyl]amino}-1H-pyrrolo[2,3-d]pyrimidin-4-yl)amino]-6-fluoro-N-methylbenzamide (0.043 g) was prepared from 2-({2-chloro-7-[(4-methylphenyl)sulfonyl]-7H-pyrrolo[2,3-d]pyrimidin-4-yl}amino)-6-fluorobenzamide (0.15 g, 0.33 mmol), 27% aqueous ammonium hydroxide, and 1-[3-(dimethylamino)propanoyl]-6-(methyloxy)-1,2,3,4-tetrahydro-7-quinolinamine (0.12 g, 0.42 mmol). $^1$H NMR (400 MHz, DMSO-d$_6$) δ ppm 1.80-1.90 (m, 2 H), 1.97-2.08 (bs, 6 H), 2.53-2.59 (m, signal underneath DMSO, 2 H), 2.63-2.71 (m, 2 H), 2.73-2.83 (m, 2 H), 3.68 (m, 2 H), 3.86 (s, 3 H), 6.27 (s, 1 H), 6.83-6.88 (m, 1 H), 6.90-6.98 (m, 1 H), 7.00-7.05 (m, 1 H), 7.39-7.48 (m, 1 H), 7.56 (s, 1 H), 8.00-8.11 (m, 2 H), 8.31 (s, 1 H), 8.45 (d, J=7.7 Hz, 1 H), 10.47 (s, 1 H), 11.82 (bs, 1 H); ESIMS (M+H)$^+$=547.

444

Example 215

2-[(2-{[1-acetyl-6-(methyloxy)-1,2,3,4-tetrahydro-7-quinolinyl]amino}-1H-pyrrolo[2,3-d]pyrimidin-4-yl)amino]-6-fluoro-N-methylbenzamide

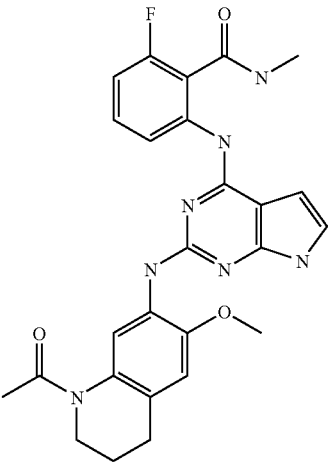

A mixture of 2-({2-chloro-7-[(4-methylphenyl)sulfonyl]-7H-pyrrolo[2,3-d]pyrimidin-4-yl}amino)-6-fluorobenzamide (0.2 g, 0.44 mmol), 1-acetyl-6-(methyloxy)-1,2,3,4-tetrahydro-7-quinolinamine (0.10 g mg, 0.43 mmol) was taken in 2,2,2-trifluoroethanol (10 mL) and hydrochloric acid (1.0 mL, 4.0 mmol, 4M in 1,4-dioxane) was added. The mixture was heated at 90° C. in a sealed tube for 24 h. The reaction was cooled; excess saturated aqueous sodium bicarbonate was added, and extracted with dichloromethane. The organic layer was separated, dried over magnesium sulfate, filtered, concentrated, diluted with tetrahydrofuran (10 mL) and treated with excess methyl amine (5.0 mL, 10 mmol, 2M in THF). The reaction was stirred for 16 h, diluted with water, and extracted with ethyl acetate. The organic layer was separated, dried over sodium sulfate, concentrated, and purified by flash silica gel column chromatography (0 to 20% methanol/dichloromethane spiked with aqueous ammonia). "Pure" fractions were isolated, concentrated, dissolved in 1,4-dioxane (7.0 mL), treated with 85% potassium hydroxide (750 mg, 11.4 mmol), water (1.0 mL), and stirred for 24 h at 80° C. The reaction was cooled; the organic layer was separated, dried over sodium sulfate, and purified by flash silica gel column chromatography. Further purification via reverse phase HPLC (5 to 90% acetonitrile/water, 0.05% trifluoroacetic acid) provided 2-[(2-{[1-acetyl-6-(methyloxy)-1,2,3,4-tetrahydro-7-quinolinyl]amino}-1H-pyrrolo[2,3-d]pyrimidin-4-yl)amino]-6-fluoro-N-methylbenzamide (0.03 g, 0.06 mmol, 14% over 3 steps). $^1$H NMR (400 MHz, DMSO-d$_6$) δ ppm 1.81-1.92 (m, 2 H), 2.16 (s, 3 H), 2.64-2.72 (m, 2 H), 2.78 (d, J=4.2 Hz, 3 H), 3.68 (t, J=6.2 Hz, 2 H), 3.87 (s, 3 H), 6.32 (bs, 1 H), 6.84 (m, 1 H), 6.94-7.03 (m, 2 H), 7.40-7.47 (m, 1 H), 7.50 (s, 1 H), 8.17-8.26 (m, 1 H), 8.46 (s, 1H), 8.52-8.59 (m, 1 H), 10.07 (s, 1 H), 11.42 (bs, 1 H); ESIMS (M+H)$^+$=504.

Example 216

2-[(2-{[1-acetyl-6-(methyloxy)-1,2,3,4-tetrahydro-7-quinolinyl]amino}-1H-pyrrolo[2,3-d]pyrimidin-4-yl)amino]-6-fluorobenzamide

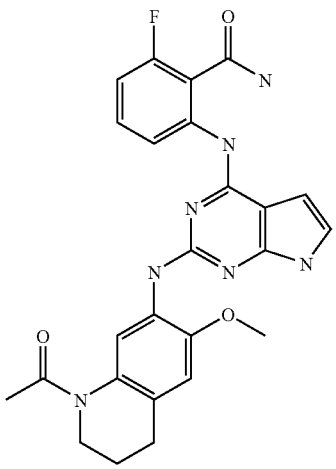

A mixture of 2-({2-chloro-7-[(4-methylphenyl)sulfonyl]-7H-pyrrolo[2,3-d]pyrimidin-4-yl}amino)-6-fluorobenzamide (0.20 g, 0.44 mmol), 1-acetyl-6-(methyloxy)-1,2,3,4-tetrahydro-7-quinolinamine (0.10 g mg, 0.43 mmol) was dissolved in 2,2,2-trifluoroethanol (10 mL) and hydrochloric acid (1.0 mL, 4.0 mmol, 4M in 1,4-dioxane) was added. The mixture was heated at 90° C. in a sealed tube for 24 h. The reaction was cooled, excess saturated aqueous sodium bicarbonate was added, and extracted with dichloromethane. The organic layer was separated, dried over magnesium sulfate, filtered, concentrated, diluted with tetrahydrofuran (35 mL) and treated with excess 27% aqueous ammonia (20 mL). The reaction was stirred in a sealed tube at 80° C. for 1 h, cooled, and the layers were separated. The organic layer was dried over sodium sulfate, concentrated, and purified by flash silica gel column chromatography (0 to 20% methanol/dichloromethane). "Pure" fractions were isolated, concentrated, dissolved in 1,4-dioxane (7.0 mL), treated with potassium hydroxide (4.0 mL, 20 mmol, 5M in water) and stirred for 24 h at 80° C. The reaction was cooled; the organic layer was separated, dried over sodium sulfate, and purified by flash silica gel column chromatography. Further purification via reverse phase HPLC (5 to 90% acetonitrile/water, 0.05% trifluoroacetic acid) provided 2-[(2-{[1-acetyl-6-(methyloxy)-1,2,3,4-tetrahydro-7-quinolinyl]amino}-1H-pyrrolo[2,3-d]pyrimidin-4-yl)amino]-6-fluorobenzamide (0.03 g, 91% pure, 0.054 mmol, 13% over 3 steps). $^1$H NMR (400 MHz, DMSO-$d_6$) δ ppm 1.81-1.91 (m, 2 H), 2.15 (s, 3 H), 2.68 (m, 2 H), 3.68 (t, J=6.1 Hz, 2 H), 3.86 (s, 3 H), 6.27 (s, 1 H), 6.85 (m, 1 H), 6.91-6.98 (m, 1 H), 7.02 (m, 1 H), 7.40-7.47 (m, 1 H), 7.52 (s, 1 H), 8.02 (bs, 1 H), 8.08 (bs, 1 H), 8.36-8.41 (m, 1 H), 8.46 (s, 1 H), 10.43 (s, 1 H), 11.44 (bs, 1H); ESIMS (M+H)$^+$=490.

Example 217

2-fluoro-N-methyl-6-[(2-{[6-(methyloxy)-1-(1-piperidinylacetyl)-1,2,3,4-tetrahydro-7-quinolinyl]amino}-1H-pyrrolo[2,3-d]pyrimidin-4-yl)amino]benzamide

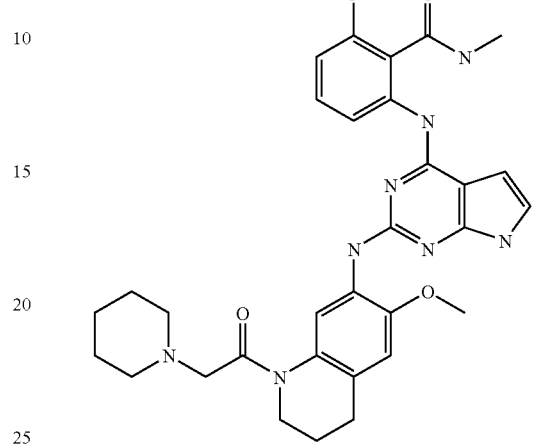

According to General Protocol III, 2-fluoro-N-methyl-6-[(2-{[6-(methyloxy)-1-(1-piperidinylacetyl)-1,2,3,4-tetrahydro-7-quinolinyl]amino}-1H-pyrrolo[2,3-d]pyrimidin-4-yl)amino]benzamide (0.085 g) was prepared from 2-({2-chloro-7-[(4-methylphenyl)sulfonyl]-7H-pyrrolo[2,3-d]pyrimidin-4-yl}amino)-6-fluorobenzamide (0.20 g, 0.44 mmol), methyl amine, and 6-(methyloxy)-1-(1-piperidinylacetyl)-1,2,3,4-tetrahydro-7-quinolinamine (0.20 g, 0.66 mmol). $^1$H NMR (400 MHz, DMSO-$d_6$) δ ppm 1.17-1.28 (m, 6 H), 1.84-1.93 (m, 2 H), 2.22-2.34 (m, 4 H), 2.64-2.69 (m, 2 H), 2.78 (d, J=4.4 Hz, 3 H), 3.21 (s, 2 H), 3.67-3.74 (m, 2 H), 3.84 (s, 3 H), 6.29-6.32 (m, 1 H), 6.80-6.86 (m, 1 H), 6.91-7.00 (m, 2 H), 7.36-7.43 (m, 1 H), 7.49 (s, 1 H), 8.23-8.29 (m, 1 H), 8.45 (s, 1 H), 8.54 (s, 1 H), 10.10 (s, 1 H), 11.39 (bs, 1 H); ESIMS (M+H)$^+$=587.

Example 218

2-fluoro-6-[(2-{[6-(methyloxy)-1-(1-piperidinylacetyl)-1,2,3,4-tetrahydro-7-quinolinyl]amino}-1H-pyrrolo[2,3-d]pyrimidin-4-yl)amino]benzamide

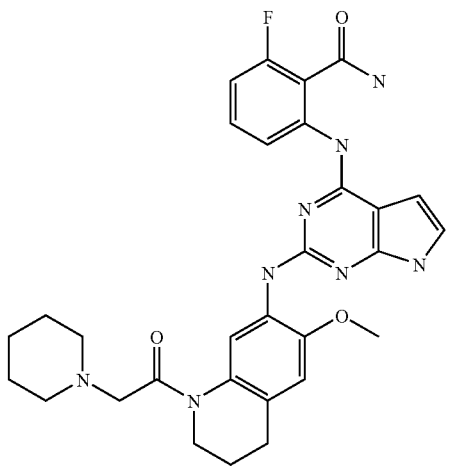

447

According to General Protocol III, 2-fluoro-6-[(2-{[6-(methyloxy)-1-(1-piperidinylacetyl)-1,2,3,4-tetrahydro-7-quinolinyl]amino}-1H-pyrrolo[2,3-d]pyrimidin-4-yl)amino]benzamide (0.095 g) was prepared from 2-({2-chloro-7-[(4-methylphenyl)sulfonyl]-7H-pyrrolo[2,3-d]pyrimidin-4-yl}amino)-6-fluorobenzamide (0.20 g, 0.44 mmol), 27% aqueous ammonia, and 6-(methyloxy)-1-(1-piperidinylacetyl)-1,2,3,4-tetrahydro-7-quinolinamine (0.20 g, 0.66 mmol). $^1$H NMR (400 MHz, DMSO-$d_6$) δ ppm 1.14-1.33 (m, 6 H), 1.83-1.94 (m, 2 H), 2.22-2.34 (m, 4 H), 2.62-2.72 (m, 2 H), 3.20 (s, 2 H), 3.65-3.74 (m, 2 H), 3.84 (s, 3 H), 6.26 (dd, J=3.5, 1.6 Hz, 1 H), 6.84 (m, 1 H), 6.93 (dd, J=10.3, 8.4 Hz, 1 H), 7.00 (m, 1 H), 7.34-7.42 (m, 1 H), 7.51 (s, 1 H), 8.01 (s, 1 H), 8.09 (s, 1 H), 8.39-8.47 (m, 2 H), 10.47 (s, 1 H), 11.41 (bs, 1 H); ESIMS (M+H)$^+$=573

Example 219

2,4-difluoro-6-[(2-{[6-(methyloxy)-1-(1-pyrrolidinylacetyl)-1,2,3,4-tetrahydro-7-quinolinyl]amino}-1H-pyrrolo[2,3-d]pyrimidin-4-yl)amino]benzamide

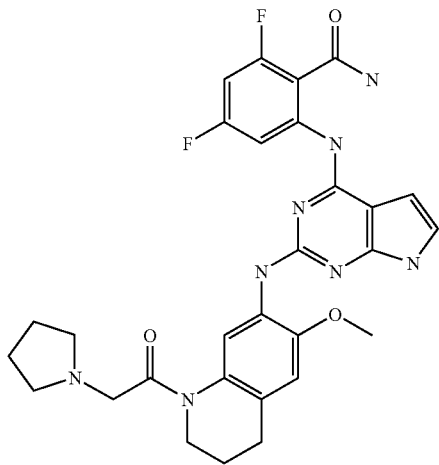

A mixture of 2-({2-chloro-7-[(4-methylphenyl)sulfonyl]-7H-pyrrolo[2,3-d]pyrimidin-4-yl}amino)-4,6-difluorobenzamide (0.20 g, 0.42 mmol) and 6-(methyloxy)-1-(1-pyrrolidinylacetyl)-1,2,3,4-tetrahydro-7-quinolinamine (0.20 g, 0.69 mmol) was taken in 2,2,2-trifluoroethanol (10 mL). Hydrochloric acid (1.5 mL, 6.0 mmol, 4M in 1,4-dioxane) was added and the mixture was heated at 90° C. in a sealed tube for 24 h. The reaction was cooled; excess saturated aqueous sodium bicarbonate was added, and extracted with dichloromethane. The organic layer was separated, dried over magnesium sulfate, filtered, concentrated, diluted with tetrahydrofuran (10 mL) and treated with excess 27% aqueous ammonia (5.0 mL). The reaction was stirred for 16 h. The organic layer was separated, dried over sodium sulfate, and concentrated. The crude material was dissolved in tetrahydrofuran (3.0 mL), diluted with 1,4-dioxane (10 mL), water (2.0 mL), treated with 85% potassium hydroxide (750 mg, 11.4 mmol) and stirred at 80° C. for 12 h. The reaction was cooled; the organic layer was separated, dried over sodium sulfate, and purified by flash silica gel column chromatography to provide 2,4-difluoro-6-[(2-{[6-(methyloxy)-1-(1-pyrrolidinylacetyl)-1,2,3,4-tetrahydro-7-quinolinyl]amino}-1H-pyrrolo[2,3-d]pyrimidin-4-yl)amino]benzamide (0.044 g, 0.073 mmol, 17% over 3 steps). $^1$H NMR (400 MHz, DMSO-$d_6$) δ ppm 1.41-1.57 (m, 4 H), 1.87 (m, 2 H), 2.30-2.45 (m, 4 H), 2.64-2.75 (m, 2 H), 3.24-3.33 (m, 2 H), 3.66-3.73 (m, 2 H), 3.83 (s, 3 H), 6.24 (m, 1 H), 6.82-6.96 (m, 2 H), 7.01-7.04 (m, 1 H), 7.73 (s, 1 H), 8.02-8.07 (m, 1 H), 8.19 (s, 1 H), 8.34-8.40 (m, 1 H), 8.50-8.56 (m, 1 H), 11.19 (s, 1 H), 11.46 (bs, 1 H); ESIMS (M+H)$^+$=577

Example 220

2,4-difluoro-6-[(2-{[6-(methyloxy)-1,2,3,4-tetrahydro-7-quinolinyl]amino}-1H-pyrrolo[2,3-d]pyrimidin-4-yl)amino]benzamide

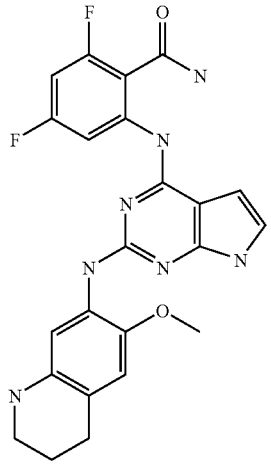

2,4-difluoro-6-[(2-{[6-(methyloxy)-1,2,3,4-tetrahydro-7-quinolinyl]amino}-1H-pyrrolo[2,3-d]pyrimidin-4-yl)amino]benzamide (0.023 g, 0.047 mmol, 11% over 3 steps) was isolated as a side product during the abovementioned preparation of 2,4-difluoro-6-[(2-{[6-(methyloxy)-1-(1-pyrrolidinylacetyl)-1,2,3,4-tetrahydro-7-quinolinyl]amino}-1H-pyrrolo[2,3-d]pyrimidin-4-yl)amino]benzamide. $^1$H NMR (400 MHz, DMSO-$d_6$) δ ppm 1.75-1.84 (m, 2 H), 2.65 (t, J=6.6 Hz, 2 H), 3.09-3.15 (m, 2 H), 3.68 (s, 3 H), 4.97 (m, 1 H), 6.21 (dd, J=3.5, 1.8 Hz, 1 H), 6.56 (s, 1 H), 6.89-6.95 (m, 1 H), 6.99 (dd, J=3.5, 2.4 Hz, 1 H), 7.09 (s, 1 H), 7.61 (s, 1 H), 8.04 (bs, 1 H), 8.19 (bs, 1 H), 8.58-8.63 (m, 1 H), 11.12 (s, 1 H), 11.36 (bs, 1 H); ESIMS (M+H)$^+$=466

Example 221

2,4-difluoro-N-methyl-6-[(2-{[6-(methyloxy)-1-(1-pyrrolidinylacetyl)-1,2,3,4-tetrahydro-7-quinolinyl]amino}-1H-pyrrolo[2,3-d]pyrimidin-4-yl)amino]benzamide

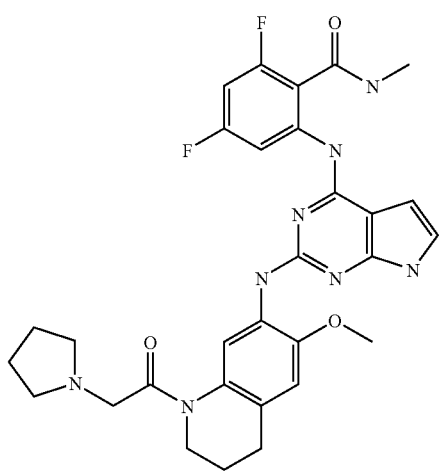

449

A mixture of 2-({2-chloro-7-[(4-methylphenyl)sulfonyl]-7H-pyrrolo[2,3-d]pyrimidin-4-yl}amino)-4,6-difluorobenzamide (0.20 g, 0.42 mmol) and 6-(methyloxy)-1-(1-pyrrolidinylacetyl)-1,2,3,4-tetrahydro-7-quinolinamine (0.20 g, 0.69 mmol) was dissolved in 2,2,2-trifluoroethanol (10 mL). Hydrochloric acid (1.5 mL, 6.0 mmol, 4M in 1,4-dioxane) was added and the mixture was heated at 90° C. in a sealed tube for 24 h. The reaction was cooled; excess saturated aqueous sodium bicarbonate was added, and extracted with dichloromethane. The organic layer was separated, dried over magnesium sulfate, filtered, concentrated, diluted with tetrahydrofuran (10 mL) and treated with excess methyl amine (3.0 mL, 6.0 mmol, 2M in THF). The reaction was stirred for 16 h, diluted with water and extracted with ethyl acetate. The organic layer was separated, dried over sodium sulfate, and concentrated. The crude material was dissolved in tetrahydrofuran (3.0 mL), diluted with 1,4-dioxane (10 mL), water (2.0 mL), treated with 85% potassium hydroxide (750 mg, 11.4 mmol) and stirred at 80° C. for 12 h. The reaction was cooled; the organic layer was separated, dried over sodium sulfate, and purified by flash silica gel column chromatography to provide 2,4-difluoro-N-methyl-6-[(2-{[6-(methyloxy)-1-(1-pyrrolidinylacetyl)-1,2,3,4-tetrahydro-7-quinolinyl]amino}-1H-pyrrolo[2,3-d]pyrimidin-4-yl)amino]benzamide (0.028 g, 0.047 mmol, 11% over 3 steps). $^1$H NMR (400 MHz, DMSO-$d_6$) δ ppm 1.41-1.58 (m, 4 H), 1.81-1.92 (m, 2 H), 2.31-2.46 (m, 4 H), 2.64-2.74 (m, 2 H), 2.82 (d, J=4.4 Hz, 3 H), 3.32 (signal underneath H$_2$O, 2 H), 3.69 (t, J=6.0 Hz, 2 H), 3.83 (s, 3 H), 6.28 (dd, J=3.3, 1.8 Hz, 1 H), 6.84 (s, 1 H), 6.91-6.98 (m, 1 H), 7.01-7.03 (m, 1 H), 7.70 (s, 1 H), 8.35-8.44 (m, 2 H), 8.55-8.61 (s, 1 H), 10.76 (s, 1 H), 11.44 (bs, 1 H); ESIMS (M+H)$^+$=591.

Example 222

2-fluoro-N-methyl-6-[(2-{[6-(methyloxy)-2-oxo-1,2,3,4-tetrahydro-7-quinolinyl]amino}-1H-pyrrolo[2,3-d]pyrimidin-4-yl)amino]benzamide

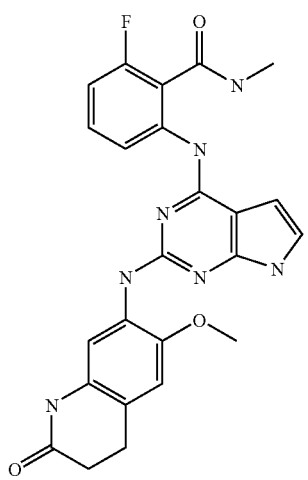

According to General Protocol III, 2-fluoro-N-methyl-6-[(2-{[6-(methyloxy)-2-oxo-1,2,3,4-tetrahydro-7-quinolinyl]amino}-1H-pyrrolo[2,3-d]pyrimidin-4-yl)amino]benzamide (0.026 g) was prepared from 2-({2-chloro-7-[(4-methylphenyl)sulfonyl]-7H-pyrrolo[2,3-d]pyrimidin-4-yl}amino)-6-fluorobenzamide (0.15 g, 0.33 mmol), methyl amine, and 7-amino-6-(methyloxy)-3,4-dihydro-2(1H)-quinolinone

450

(0.063 g, 0.33 mmol). $^1$H NMR (400 MHz, DMSO-$d_6$) δ ppm 2.43 (t, J=7.4 Hz, 2 H), 2.79 (d, J=4.6 Hz, 3 H), 2.84 (t, J=7.4 Hz, 2 H), 3.78 (s, 3 H), 6.27 (dd, J=3.5, 1.9 Hz, 1 H), 6.87 (s, 1 H), 6.91-6.99 (m, J=3.4, 2.2 Hz, 2 H), 7.34-7.41 (m, 1 H), 7.54 (s, 1 H), 7.55 (s, 1 H), 8.32 (d, J=8.4 Hz, 1 H), 8.52-8.57 (m, 1 H), 9.79 (s, 1 H), 10.14 (s, 1 H), 11.26 (s, 1 H); ESIMS (M+H)$^+$=476.

Example 223

2-[(2-{[4,4-dimethyl-6-(methyloxy)-1-(1-pyrrolidinylacetyl)-1,2,3,4-tetrahydro-7-quinolinyl]amino}-1H-pyrrolo[2,3-d]pyrimidin-4-yl)amino]-6-fluorobenzamide

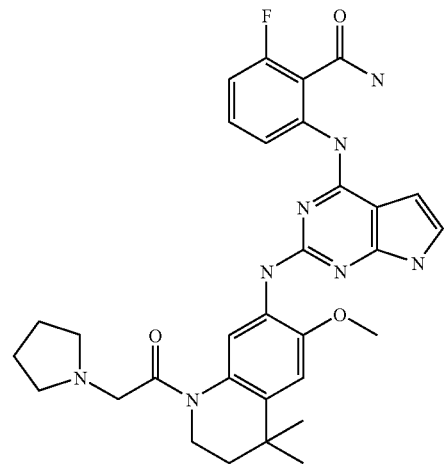

A mixture of 5-chloro-8-fluoro-3-[(4-methylphenyl)sulfonyl]pyrrolo[2',3':4,5]pyrimido[6,1-b]quinazolin-7(3H)-one hydrogen chloride (0.27 g, 0.54 mmol) and 4,4-dimethyl-6-(methyloxy)-1-(1-pyrrolidinylacetyl)-1,2,3,4-tetrahydro-7-quinolinamine (0.19 mg, 0.60 mmol) was taken in 2,2,2-trifluoroethanol (25 mL) and heated at 90° C. for 3 h. The reaction was cooled, diluted with saturated aqueous sodium bicarbonate and extracted with dichloromethane. The organic layer was separated, dried over magnesium sulfate, filtered, concentrated, diluted with tetrahydrofuran (15 mL) and treated with excess 27% aqueous ammonia (10 mL). The reaction was stirred for 16 h; the organic layer was separated, dried over sodium sulfate and concentrated. The crude material was dissolved in tetrahydrofuran (5.0 mL), diluted with methanol (5.0 mL) and treated with sodium methoxide (324 mg, 6.00 mmol) and stirred at 50° C. for 3 h. The reaction was cooled, diluted with water, and extracted with ethyl acetate. The organic layer was separated, dried over sodium sulfate, and purified by flash silica gel column chromatography (dichloromethane to 8:1:1 mixture of dichloromethane:methanol:2M ammonia in methanol) to provide 2-[(2-{[4,4-dimethyl-6-(methyloxy)-1-(1-pyrrolidinylacetyl)-1,2,3,4-tetrahydro-7-quinolinyl]amino}-1H-pyrrolo[2,3-d]pyrimidin-4-yl)amino]-6-fluorobenzamide (0.103 g, 0.22 mmol, 36% over 3 steps). $^1$H NMR (400 MHz, DMSO-$d_6$) δ ppm 1.27 (s, 6 H), 1.43-1.55 (m, 4 H), 1.65-1.76 (m, 2 H), 2.35-2.47 (m, 4 H), 3.36 (bs, 2 H), 3.76 (t, J=5.8 Hz, 2 H), 3.88 (s, 3 H), 6.25-6.28 (m, 1 H), 6.90-6.97 (m, 2 H), 7.01 (s, 1 H), 7.35-7.43 (m, 1 H), 7.51 (s, 1 H), 8.02 (s, 1 H), 8.09 (s, 1 H), 8.40-8.47 (m, 2 H), 10.49 (s, 1 H), 11.43 (s, 1 H); ESIMS (M+H)$^+$=587.

Example 224

2-[(2-{[4,4-dimethyl-6-(methyloxy)-1-(1-pyrrolidinylacetyl)-1,2,3,4-tetrahydro-7-quinolinyl]amino}-1H-pyrrolo[2,3-d]pyrimidin-4-yl)amino]-6-fluoro-N-methylbenzamide

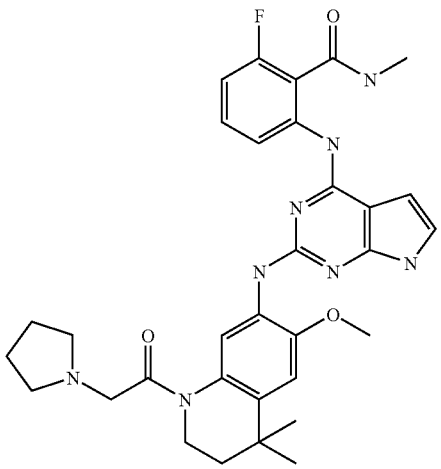

A mixture of 5-chloro-8-fluoro-3-[(4-methylphenyl)sulfonyl]pyrrolo[2',3':4,5]pyrimido[6,1-b]quinazolin-7(3H)-one hydrogen chloride (0.13 g, 0.27 mmol) and 4,4-dimethyl-6-(methyloxy)-1-(1-pyrrolidinylacetyl)-1,2,3,4-tetrahydro-7-quinolinamine (0.095 mg, 0.30 mmol) was taken in 2,2,2-trifluoroethanol (25 mL) and heated at 90° C. for 3 h. The reaction was cooled, diluted with saturated aqueous sodium bicarbonate and extracted with dichloromethane. The organic layer was separated, dried over magnesium sulfate, filtered, concentrated, diluted with tetrahydrofuran (10 mL) and treated with excess methyl amine (5.0 mL, 10 mmol, 2M in THF)). The reaction was stirred for 16 h, diluted with water, and extracted with ethyl acetate. The organic layer was separated, dried over sodium sulfate and concentrated. The crude material was dissolved in tetrahydrofuran (5.0 mL), diluted with methanol (5.0 mL) and treated with sodium methoxide (250 mg, 4.63 mmol) and stirred at 50° C. for 3 h. The reaction was cooled, diluted with water, and extracted with ethyl acetate. The organic layer was separated, dried over sodium sulfate, and purified by flash silica gel column chromatography (dichloromethane to 8:1:1 mixture of dichloromethane:methanol:2M ammonia in methanol) to provide 2-[(2-{[4,4-dimethyl-6-(methyloxy)-1-(1-pyrrolidinylacetyl)-1,2,3,4-tetrahydro-7-quinolinyl]amino}-1H-pyrrolo[2,3-d]pyrimidin-4-yl)amino]-6-fluoro-N-methylbenzamide (0.03 g, 0.05 mmol, 16% over 3 steps). $^1$H NMR (400 MHz, DMSO-d$_6$) δ ppm 1.27 (s, 6 H), 1.44-1.55 (m, 4 H), 1.68-1.75 (m, 2 H), 2.36-2.45 (m, 4 H), 2.78 (d, J=4.4 Hz, 3 H), 3.39 (s, 2 H, peak underneath H$_2$O), 3.72-3.79 (m, 2 H), 3.88 (s, 3 H), 6.30-6.33 (m, 1 H), 6.93-7.01 (m, 3 H), 7.36-7.43 (m, 1 H), 7.49 (s, 1 H), 8.25 (d, J=8.1 Hz, 1 H), 8.44 (bs, 1 H), 8.52-8.61 (m, 1 H), 10.11 (s, 1 H), 11.41 (bs, 1 H); ESIMS (M+H)$^+$=601.

Example 225

2-[(2-{[1-(N,N-dimethylglycyl)-4,4-dimethyl-6-(methyloxy)-1,2,3,4-tetrahydro-7-quinolinyl]amino}-1H-pyrrolo[2,3-d]pyrimidin-4-yl)amino]-6-fluorobenzamide

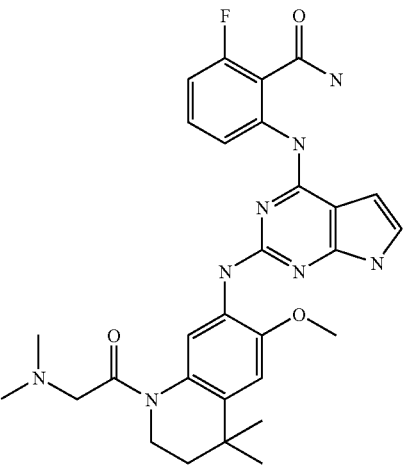

A mixture of 5-chloro-8-fluoro-3-[(4-methylphenyl)sulfonyl]pyrrolo[2',3':4,5]pyrimido[6,1-b]quinazolin-7(3H)-one hydrogen chloride (0.27 g, 0.54 mmol) and 1-[(dimethylamino)acetyl]-4,4-dimethyl-6-(methyloxy)-1,2,3,4-tetrahydro-7-quinolinamine (0.18 g, 0.60 mmol) was taken in 2,2,2-trifluoroethanol (20 mL) and heated at 90° C. for 3 h. The reaction was cooled, diluted with saturated aqueous sodium bicarbonate and extracted with dichloromethane. The organic layer was separated, dried over magnesium sulfate, filtered, concentrated, diluted with tetrahydrofuran (10 mL) and treated with excess 27% aqueous ammonia (10 mL). The reaction was stirred for 16 h at 50° C. in a sealed vial. The reaction was cooled; the organic layer was separated, dried over sodium sulfate, and concentrated. The crude material was dissolved in tetrahydrofuran (10 mL), diluted with methanol (10 mL) and treated with sodium methoxide (250 mg, 4.63 mmol) and stirred at 70° C. for 3 h. The reaction was cooled, diluted with water, and extracted with ethyl acetate. The organic layer was separated, dried over sodium sulfate, and purified by flash silica gel column chromatography (dichloromethane to 8:1:1 mixture of dichloromethane:methano1:2M ammonia in methanol) to provide 2-[(2-{[1-(N,N-dimethylglycyl)-4,4-dimethyl-6-(methyloxy)-1,2,3,4-tetrahydro-7-quinolinyl]amino}-1H-pyrrolo[2,3-d]pyrimidin-4-yl)amino]-6-fluorobenzamide (0.043 g, 0.077 mmol, 12% over 3 steps). $^1$H NMR (400 MHz, DMSO-d$_6$) δ ppm 1.27 (s, 6 H), 1.68-1.76 (m, 2 H), 2.12 (bs, 6 H), 3.28 (s, 2H), 3.75 (t, J=5.9 Hz, 2 H), 3.88 (s, 3 H), 6.25-6.28 (m, 1 H), 6.91-7.02 (mm 3 H), 7.38-7.45 (m, 1 H), 7.53 (s, 1 H), 8.02 (s, 1 H), 8.09 (s, 1 H), 8.35-8.43 (m, 2 H), 10.47 (s, 1 H), 11.42 (bs, 1 H); ESIMS (M+H)$^+$=561.

Example 226

2-[(2-{[1-(N,N-dimethylglycyl)-4,4-dimethyl-6-(methyloxy)-1,2,3,4-tetrahydro-7-quinolinyl]amino}-1H-pyrrolo[2,3-d]pyrimidin-4-yl)amino]-6-fluoro-N-methylbenzamide

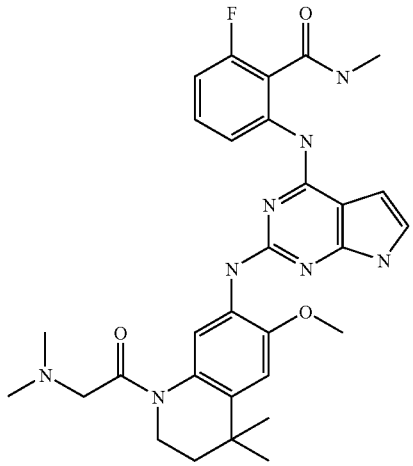

A mixture of 5-chloro-8-fluoro-3-[(4-methylphenyl)sulfonyl]pyrrolo[2',3':4,5]pyrimido[6,1-b]quinazolin-7(3H)-one hydrogen chloride (0.27 g, 0.54 mmol) and 1-[(dimethylamino)acetyl]-4,4-dimethyl-6-(methyloxy)-1,2,3,4-tetrahydro-7-quinolinamine (0.18 g, 0.60 mmol) was taken in 2,2,2-trifluoroethanol (20 mL) and heated at 90° C. for 3 h. The reaction was cooled, diluted with saturated aqueous sodium bicarbonate and extracted with dichloromethane. The organic layer was separated, dried over magnesium sulfate, filtered, concentrated, diluted with tetrahydrofuran (10 mL) and treated with excess methyl amine (10 mL, 20 mmol, 2M in THF). The reaction was stirred for 16 h at 50° C. in a sealed vial. The reaction was cooled and partitioned between water and ethyl acetate. Brine was added to assist in the separation of layers. The organic layer was separated, dried over sodium sulfate, and concentrated. The crude material was dissolved in tetrahydrofuran (10 mL), diluted with methanol (10 mL) and treated with sodium methoxide (250 mg, 4.63 mmol) and stirred at 70° C. for 3 h. The reaction was cooled, diluted with water, and extracted with ethyl acetate. The organic layer was separated, dried over sodium sulfate, and purified by flash silica gel column chromatography (dichloromethane to 8:1:1 mixture of dichloromethane:methanol:2M ammonia in methanol) to provide 2-[(2-{[1-(N,N-dimethylglycyl)-4,4-dimethyl-6-(methyloxy)-1,2,3,4-tetrahydro-7-quinolinyl]amino}-1H-pyrrolo[2,3-d]pyrimidin-4-yl)amino]-6-fluoro-N-methylbenzamide (0.128 g, 0.223 mmol, 36% over 3 steps). $^1$H NMR (400 MHz, DMSO-$d_6$) δ ppm 1.27 (s, 6 H), 1.67-1.77 (m, 2 H), 2.11 (bs, 6 H), 2.78 (d, J=4.4 Hz, 3 H), 3.27 (s, 2 H), 3.75 (t, J=6.0 Hz, 2 H), 3.88 (s, 3 H), 6.29-6.34 (m, 1 H), 6.92-7.02 (s, 3 H), 7.37-7.45 (m, 1 H), 7.51 (s, 1 H), 8.18-8.27 (m, 1 H), 8.38 (s, 1 H), 8.52-8.58 (m, 1 H), 10.10 (s, 1 H), 11.39 (bs, 1 H); ESIMS (M+H)$^+$=575.

Example 227

2-[(2-{[4,4-dimethyl-6-(methyloxy)-2-oxo-1,2,3,4-tetrahydro-7-quinolinyl]amino}-1H-pyrrolo[2,3-d]pyrimidin-4-yl)amino]-6-fluorobenzamide

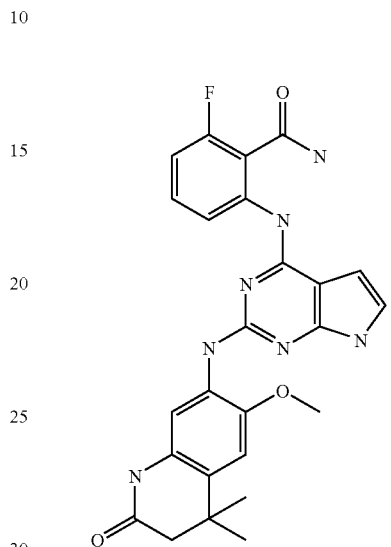

A mixture of 5-chloro-8-fluoro-3-[(4-methylphenyl)sulfonyl]pyrrolo[2',3':4,5]pyrimido[6,1-b]quinazolin-7(3H)-one hydrogen chloride (0.20 g, 0.41 mmol) and 7-amino-4,4-dimethyl-6-(methyloxy)-3,4-dihydro-2(1H)-quinolinone (0.10 g, 0.45 mmol) was taken in tetrahydrofuran (7.0 mL) and refluxed for 3 h. The reaction was cooled, diluted with saturated aqueous sodium bicarbonate and extracted with dichloromethane. The organic layer was separated, dried over magnesium sulfate, filtered, concentrated, diluted with tetrahydrofuran (10 mL) and treated with excess 27% aqueous ammonia (5.0 mL). The reaction was stirred for 16 h; the organic layer was separated, dried over sodium sulfate and concentrated. The crude material was dissolved in tetrahydrofuran (5.0 mL), diluted with methanol (5.0 mL) and treated with sodium methoxide (250 mg, 4.63 mmol) and stirred at 50° C. for 3 h. The reaction was cooled, diluted with water, and extracted with ethyl acetate. The organic layer was separated, dried over sodium sulfate, and purified by flash silica gel column chromatography (dichloromethane to 8:1:1 mixture of dichloromethane:methanol:2M ammonia in methanol) to provide 2-[(2-{[4,4-dimethyl-6-(methyloxy)-2-oxo-1,2,3,4-tetrahydro-7-quinolinyl]amino}-1H-pyrrolo[2,3-d]pyrimidin-4-yl)amino]-6-fluorobenzamide (0.020 g, 0.041 mmol, 9% over 3 steps). $^1$H NMR (400 MHz, DMSO-$d_6$) δ ppm 1.25 (s, 6 H), 2.33 (s, 2 H), 3.81 (s, 3 H), 6.21-6.25 (m, 1 H), 6.88-6.95 (m, 2 H), 6.96-7.00 (m, 1 H), 7.32-7.40 (m, 1 H), 7.54 (s, 1 H), 7.58 (s, 1 H), 8.03 (bs, 1 H), 8.11 (bs, 1 H), 8.49 (d, J=8.4 Hz, 1 H), 9.87 (s, 1 H), 10.52 (s, 1 H), 11.29 (bs, 1 H) ; ESIMS (M+H)$^+$=490.

Example 228

2-[(2-{[4,4-dimethyl-6-(methyloxy)-2-oxo-1,2,3,4-tetrahydro-7-quinolinyl]amino}-1H-pyrrolo[2,3-d]pyrimidin-4-yl)amino]-6-fluoro-N-methylbenzamide

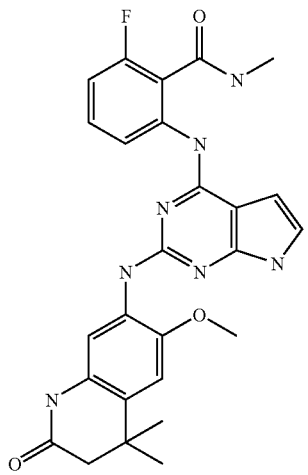

A mixture of 5-chloro-8-fluoro-3-[(4-methylphenyl)sulfonyl]pyrrolo[2',3':4,5]pyrimido[6,1-b]quinazolin-7(3H)-one hydrogen chloride (0.20 g, 0.41 mmol) and 7-amino-4,4-dimethyl-6-(methyloxy)-3,4-dihydro-2(1H)-quinolinone (0.10 g, 0.45 mmol) was taken in tetrahydrofuran (7.0 mL) and refluxed for 3 h. The reaction was cooled, diluted with saturated aqueous sodium bicarbonate and extracted with dichloromethane. The organic layer was separated, dried over magnesium sulfate, filtered, concentrated, diluted with tetrahydrofuran (10 mL) and treated with excess methyl amine (10 mL, 20 mmol, 2M in THF). The reaction was stirred for 16 h and then heated in a sealed tube at 50° C. for another 6 h. The reaction was cooled, diluted with water, and extracted with ethyl acetate. The organic layer was separated, dried over sodium sulfate and concentrated. The crude material was dissolved in tetrahydrofuran (5.0 mL), diluted with methanol (5.0 mL) and treated with sodium methoxide (700 mg, 28.5 mmol) and stirred at 50° C. for 3 h. The reaction was cooled, diluted with water, and extracted with ethyl acetate. The organic layer was separated, dried over sodium sulfate, and purified by flash silica gel column chromatography (dichloromethane to 8:1:1 mixture of dichloromethane:methanol:2M ammonia in methanol) to provide 2-[(2-{[4,4-dimethyl-6-(methyloxy)-2-oxo-1,2,3,4-tetrahydro-7-quinolinyl]amino}-1H-pyrrolo[2,3-d]pyrimidin-4-yl)amino]-6-fluoro-N-methylbenzamide (0.100 g, 0.195 mmol, 43% over 3 steps).

$^1$H NMR (400 MHz, DMSO-$d_6$) δppm 1.25 (s, 6 H), 2.32 (s, 2 H), 2.79 (d, J=4.6 Hz, 3 H), 3.81 (s, 3 H), 6.28 (dd, J=3.2, 1.7 Hz, 1 H), 6.89-6.98 (m, 3 H), 7.34-7.40 (m, 1 H), 7.54-7.57 (m, 2 H), 8.31 (d, J=8.2 Hz, 1 H), 8.52-8.58 (m, 1 H), 9.86 (s, 1 H), 10.13 (s, 1 H), 11.26 (bs, 1 H); ESIMS (M+H)$^+$=504.

Example 229

2-fluoro-6-[(2-{[2-{3-[4-(1-methylethyl)-1-piperazinyl]propanoyl}-6-(methyloxy)-1,2,3,4-tetrahydro-7-isoquinolinyl]amino}-1H-pyrrolo[2,3-d]pyrimidin-4-yl)amino]benzamide

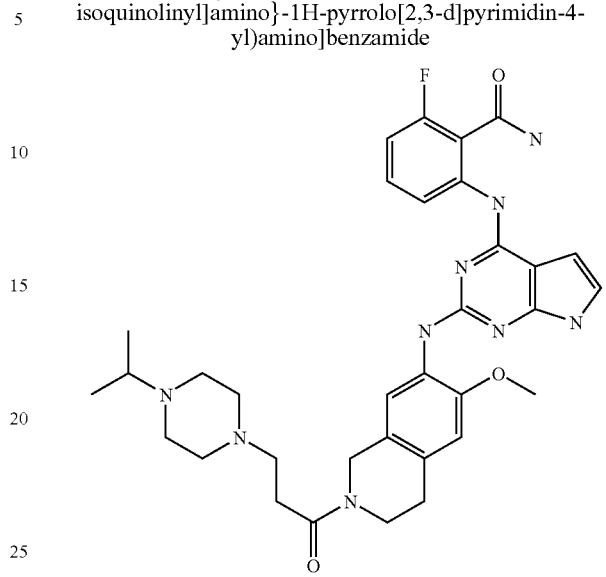

According to General Protocol III, 2-fluoro-6-[(2-{[2-{3-[4-(1-methylethyl)-1-piperazinyl]propanoyl}-6-(methyloxy)-1,2,3,4-tetrahydro-7-isoquinolinyl]amino}-1H-pyrrolo[2,3-d]pyrimidin-4-yl)amino]benzamide (0.099 g) was prepared from 2-({2-chloro-7-[(4-methylphenyl)sulfonyl]-7H-pyrrolo[2,3-d]pyrimidin-4-yl}amino)-6-fluorobenzamide (0.30 g, 0.65 mmol), 27% aqueous ammonium hydroxide, and 2-{3-[4-(1-methylethyl)-1-piperazinyl]propanoyl}-6-(methyloxy)-1,2,3,4-tetrahydro-7-isoquinolinamine (0.26 g, 0.73 mmol). $^1$H NMR (400 MHz, DMSO-$d_6$) is complicated by amide rotomers δ ppm 0.90-1.00 (m, 6 H), 2.31-2.85 (m, some signals underneath DMSO, 15 H), 3.64-3.73 (m, 2 H), 3.80-3.89 (m, 3 H), 4.49-4.57 (m, 2 H), 6.26-6.31 (m, 1 H), 6.80-6.86 (m, 1 H), 6.93-7.04 (m, 2 H), 7.47-7.57 (m, 2 H), 8.01-8.21 (m, 3 H), 8.34-8.44 (m, 1 H), 10.39-10.47 (m, 1 H), 11.35-11.47 (m, 1 H); ESIMS (M+H)$^+$=630.

Example 230

2-[(2-{[2-(N,N-dimethyl-β-alanyl)-6-(methyloxy)-1,2,3,4-tetrahydro-7-isoquinolinyl]amino}-1H-pyrrolo[2,3-d]pyrimidin-4-yl)amino]-6-fluorobenzamide

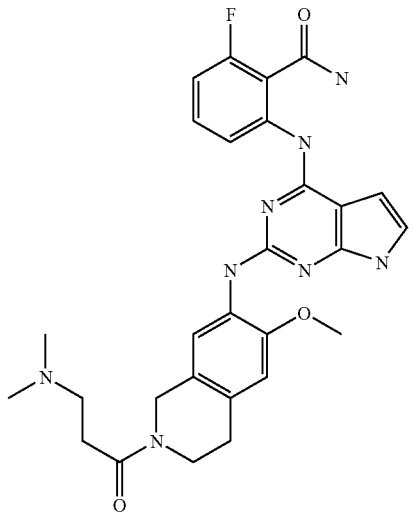

According to General Protocol III, 2-[(2-{[2-(N,N-dimethyl-β-alanyl)-6-(methyloxy)-1,2,3,4-tetrahydro-7-isoquinolinyl]amino}-1H-pyrrolo[2,3-d]pyrimidin-4-yl)amino]-6-fluorobenzamide (0.134 g) was prepared from 2-({2-chloro-7-[(4-methylphenyl)sulfonyl]-7H-pyrrolo[2,3-d]pyrimidin-4-yl}amino)-6-fluorobenzamide (0.30 g, 0.65 mmol), 27% aqueous ammonium hydroxide, and 2-[3-(dimethylamino)propanoyl]-6-(methyloxy)-1,2,3,4-tetrahydro-7-isoquinolinamine (0.26 g, 0.96 mmol). $^1$H NMR (400 MHz, DMSO-$d_6$) is complicated by amide rotomers δ ppm 2.15 (s, 6 H), 2.54 (m, signals underneath DMSO, 4 H), 2.67-2.85 (m, 2 H), 3.64-3.72 (m, 2 H), 3.81-3.89 (m, 3 H), 4.48-4.56 (m, 2 H), 6.25-6.31 (m, 1 H), 6.80-6.85 (m, 1 H), 6.92-6.99 (m, 1 H), 7.00-7.04 (m, 1 H), 7.45-7.55 (m, 2 H), 8.01-8.20 (m, 3 H), 8.36-8.43 (m, 1 H), 10.40-10.47 (m, 1 H), 11.42-11.48 (m, 1 H); ESIMS (M+H)$^+$=547.

Example 231

2-fluoro-6-{[2-({6-(methyloxy)-2-[3-(4-morpholinyl)propanoyl]-1,2,3,4-tetrahydro-7-isoquinolinyl}amino)-1H-pyrrolo[2,3-d]pyrimidin-4-yl]amino}benzamide

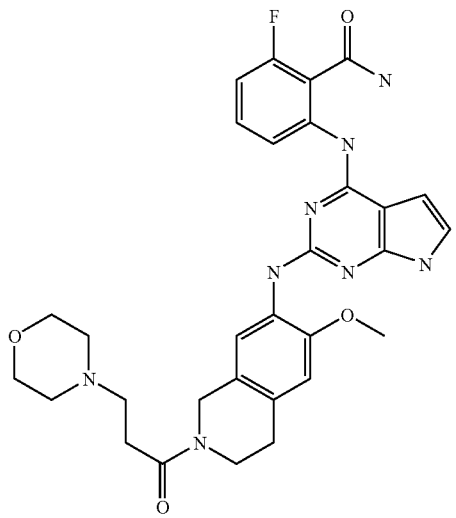

According to General Protocol III, 2-fluoro-6-{[2-({6-(methyloxy)-2-[3-(4-morpholinyl)propanoyl]-1,2,3,4-tetrahydro-7-isoquinolinyl}amino)-1H-pyrrolo[2,3-d]pyrimidin-4-yl]amino}benzamide (0.120 g) was prepared from 2-({2-chloro-7-[(4-methylphenyl)sulfonyl]-7H-pyrrolo[2,3-d]pyrimidin-4-yl}amino)-6-fluorobenzamide (0.30 g, 0.65 mmol), 27% aqueous ammonium hydroxide, and 6-(methyloxy)-2-[3-(4-morpholinyl)propanoyl]-1,2,3,4-tetrahydro-7-isoquinolinamine (0.35 g, 1.1 mmol). $^1$H NMR (400 MHz, DMSO-$d_6$) is complicated by amide rotomers δ ppm 2.34-2.44 (m, 4 H), 2.54-2.60 (m, 4 H), 2.66-2.84 (m, 2 H), 3.49-3.59 (m, 4 H), 3.63-3.72 (m, 2H), 3.85 (s, 3 H), 4.48-4.56 (m, 2 H), 6.24-6.33 (m, 1 H), 6.80-6.86 (m, 1 H), 6.93-7.00 (m, 1 H), 7.00-7.05 (m, 1 H), 7.47-7.57 (m, 2 H), 7.99-8.06 (m, 1 H), 8.08-8.22 (m, 2 H), 8.36-8.44 (m, 1 H), 10.40-10.45 (m, 1 H), 11.35-11.47 (m, 1 H); ESIMS (M+H)$^+$=589.

Example 232

2-[(2-{[2-[3-(dimethylamino)propyl]-6-(methyloxy)-1,2,3,4-tetrahydro-7-isoquinolinyl]amino}-1H-pyrrolo[2,3-d]pyrimidin-4-yl)amino]-6-fluorobenzamide

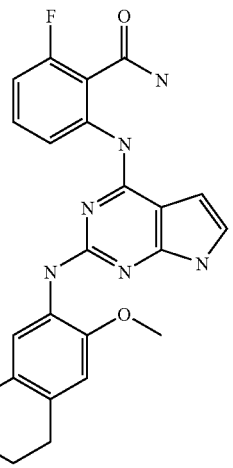

According to General Protocol III, 2-[(2-{[2-[3-(dimethylamino)propyl]-6-(methyloxy)-1,2,3,4-tetrahydro-7-isoquinolinyl]amino}-1H-pyrrolo[2,3-d]pyrimidin-4-yl)amino]-6-fluorobenzamide (0.130 g) was prepared from 2-({2-chloro-7-[(4-methylphenyl)sulfonyl]-7H-pyrrolo[2,3-d]pyrimidin-4-yl}amino)-6-fluorobenzamide (0.30 g, 0.65 mmol), 27% aqueous ammonium hydroxide, and 2-[3-(dimethylamino)propyl]-6-(methyloxy)-1,2,3,4-tetrahydro-7-isoquinolinamine (0.28 g, 1.1 mmol). $^1$H NMR (400 MHz, DMSO-$d_6$) δ ppm 1.62-1.72 (m, 2 H), 2.20 (s, 6 H), 2.30-2.38 (m, 2 H), 2.42-2.48 (m, 2 H), 2.59-2.67 (m, 2 H), 2.71-2.81 (m, 2 H), 3.43 (s, 2 H), 3.82 (s, 3 H), 6.25-6.29 (m, 1 H), 6.73 (s, 1 H), 6.92-7.03 (m, 2 H), 7.42-7.49 (m, 2 H), 7.95 (s, 1 H), 8.03 (bs, 1 H), 8.11 (bs, 1 H), 8.36-8.43 (m, 1 H), 10.41 (s, 1 H), 11.36 (bs, 1 H); ESIMS (M+N)$^+$=533.

Example 233

2-fluoro-6-[(2-{[2-(2-fluoroethyl)-6-(methyloxy)-1,2,3,4-tetrahydro-7-isoquinolinyl]amino}-1H-pyrrolo[2,3-d]pyrimidin-4-yl)amino]benzamide

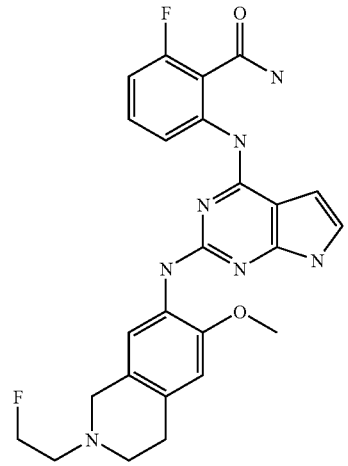

According to General Protocol III, 2-fluoro-6-[(2-{[2-(2-fluoroethyl)-6-(methyloxy)-1,2,3,4-tetrahydro-7-isoquinolinyl]amino}-1H-pyrrolo[2,3-d]pyrimidin-4-yl)amino]benzamide (0.060 g) was prepared from 2-({2-chloro-7-[(4-methylphenyl)sulfonyl]-7H-pyrrolo[2,3-d]pyrimidin-4-yl}amino)-6-fluorobenzamide (0.15 g, 0.33 mmol), 27% aqueous ammonium hydroxide, and 2-(2-fluoroethyl)-6-(methyloxy)-1,2,3,4-tetrahydro-7-isoquinolinamine (0.10 g, 0.45 mmol). $^1$H NMR (400 MHz, DMSO-$d_6$) δ ppm 2.71-2.85 (m, 6 H), 3.53 (s, 2 H), 3.82 (s, 3 H), 4.54-4.71 (dt, $J_{HF}$=47.5, J=4.8 Hz, 2 H), 6.25-6.28 (m, 1 H), 6.74 (s, 1 H), 6.91-7.02 (m, 2 H), 7.42-7.50 (m, 2 H), 7.93 (s, 1 H), 8.01 (bs, 1 H), 8.10 (bs, 1 H), 8.39 (d, J=8.2 Hz, 1 H), 10.41 (s, 1 H), 11.37 (bs, 1 H); ESIMS (M+H)$^+$=494.

Example 234

2-fluoro-6-[(2-{[2-(2-fluoroethyl)-6-(methyloxy)-1,2,3,4-tetrahydro-7-isoquinolinyl]amino}-1H-pyrrolo[2,3-d]pyrimidin-4-yl)amino]-N-methylbenzamide

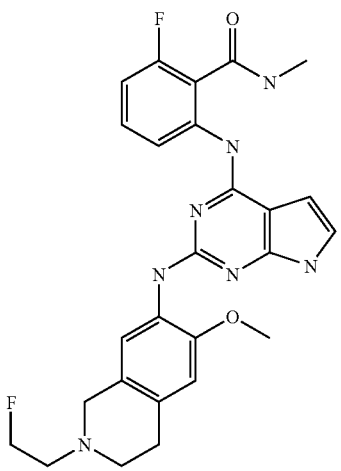

According to General Protocol III, 2-fluoro-6-[(2-{[2-(2-fluoroethyl)-6-(methyloxy)-1,2,3,4-tetrahydro-7-isoquinolinyl]amino}-1H-pyrrolo[2,3-d]pyrimidin-4-yl)amino]-N-methylbenzamide (0.023 g) was prepared from 2-({2-chloro-7-[(4-methylphenyl)sulfonyl]-7H-pyrrolo[2,3-d]pyrimidin-4-yl}amino)-6-fluorobenzamide (0.15 g, 0.33 mmol), methyl amine, and 2-(2-fluoroethyl)-6-(methyloxy)-1,2,3,4-tetrahydro-7-isoquinolinamine (0.10 g, 0.45 mmol). $^1$H NMR (400 MHz, DMSO-$d_6$) δ ppm 2.72-2.84 (m, 9 H), 3.53 (s, 2 H), 3.82 (s, 3 H), 4.55-4.71 (dt, $J_{HF}$=48.0, J=4.6 Hz, 2 H), 6.29-6.32 (m, 1 H), 6.73 (s, 1 H), 6.91-7.02 (m, 2 H), 7.40-7.49 (m, 2 H), 7.95 (s, 1 H), 8.25 (d, J=8.2 Hz, 1 H), 8.52-8.59 (m, 1 H), 10.07 (s, 1 H), 11.35 (bs, 1 H); ESIMS (M+H)$^+$=508.

Example 235

2-fluoro-N-methyl-6-[(2-{[2-(1-methylethyl)-6-(methyloxy)-1,2,3,4-tetrahydro-7-isoquinolinyl]amino}-1H-pyrrolo[2,3-d]pyrimidin-4-yl)amino]benzamide

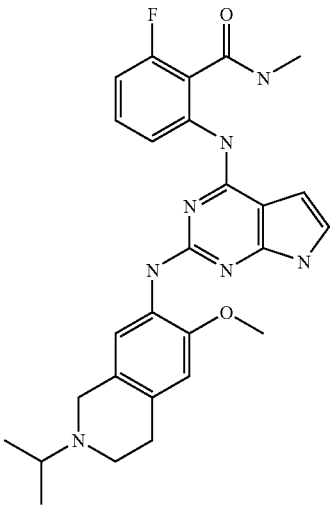

According to General Protocol III, 2-fluoro-N-methyl-6-[(2-{[2-(1-methylethyl)-6-(methyloxy)-1,2,3,4-tetrahydro-7-isoquinolinyl]amino}-1H-pyrrolo[2,3-d]pyrimidin-4-yl)amino]benzamide (0.060 g) was prepared from 2-({2-chloro-7-[(4-methylphenyl)sulfonyl]-7H-pyrrolo[2,3-d]pyrimidin-4-yl}amino)-6-fluorobenzamide (0.15 g, 0.33 mmol), methyl amine, and 2-(1-methylethyl)-6-(methyloxy)-1,2,3,4-tetrahydro-7-isoquinolinamine (0.105 g, 0.477 mmol). $^1$H NMR (400 MHz, DMSO-$d_6$) δ ppm 1.06 (d, J=6.4 Hz, 6 H), 2.65-2.86 (m, 8 H), 3.51 (s, 2 H), 3.82 (s, 3 H), 6.29-6.32 (m, 1 H), 6.71 (s, 1 H), 6.93-7.01 (m, 2 H), 7.41-7.48 (m, 2 H), 7.97 (s, 1 H), 8.26 (d, J=8.2 Hz, 1 H), 8.52-8.58 (m, 1 H), 10.07 (s, 1 H), 11.33 (bs, 1 H); ESIMS (M+H)$^+$=504.

Example 236

2-fluoro-6-[(2-{[2-(1-methylethyl)-6-(methyloxy)-1,2,3,4-tetrahydro-7-isoquinolinyl]amino}-1H-pyrrolo[2,3-d]pyrimidin-4-yl)amino]benzamide

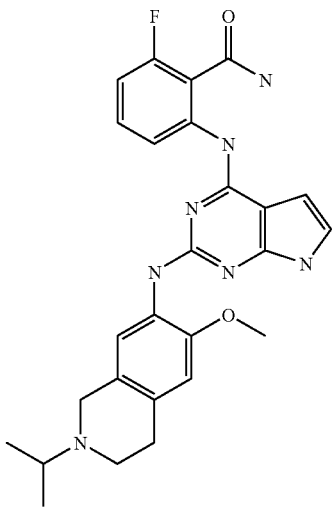

461

According to General Protocol III, 2-fluoro-6-[(2-{[2-(1-methylethyl)-6-(methyloxy)-1,2,3,4-tetrahydro-7-isoquinolinyl]amino}-1H-pyrrolo[2,3-d]pyrimidin-4-yl)amino]benzamide (0.059 g) was prepared from 2-({2-chloro-7-[(4-methylphenyl)sulfonyl]-7H-pyrrolo[2,3-d]pyrimidin-4-yl}amino)-6-fluorobenzamide (0.15 g, 0.33 mmol), 27% aqueous ammonia, and 2-(1-methylethyl)-6-(methyloxy)-1,2,3,4-tetrahydro-7-isoquinolinamine (0.105 g, 0.477 mmol). $^1$H NMR (400 MHz, DMSO-$d_6$) δ ppm 1.06 (d, J=6.4 Hz, 6 H), 2.65-2.77 (m, 4 H), 2.79-2.88 (m, 1 H), 3.52 (s, 2 H), 3.82 (s, 3 H), 6.27 (m, 1 H), 6.71 (s, 1 H), 6.92-7.02 (m, 2 H), 7.40-7.48 (m, 2 H), 7.95 (s, 1 H), 8.02 (bs, 1 H), 8.10 (bs, 1 H), 8.38 (d, J=8.2 Hz, 1 H), 10.40 (s, 1 H), 11.35 (bs, 1 H); ESIMS (M+H)$^+$=490.

Example 237

2-fluoro-6-[(2-{[6-(methyloxy)-2-(1-methylpropyl)-1,2,3,4-tetrahydro-7-isoquinolinyl]amino}-1H-pyrrolo[2,3-d]pyrimidin-4-yl)amino]benzamide

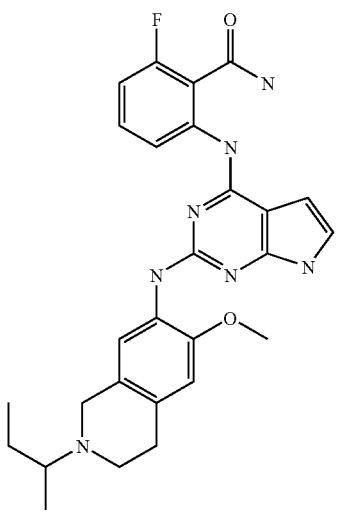

According to General Protocol III, 2-fluoro-6-[(2-{[6-(methyloxy)-2-(1-methylpropyl)-1,2,3,4-tetrahydro-7-isoquinolinyl]amino}-1H-pyrrolo[2,3-d]pyrimidin-4-yl)amino]benzamide (0.065 g) was prepared from 2-({2-chloro-7-[(4-methylphenyl)sulfonyl]-7H-pyrrolo[2,3-d]pyrimidin-4-yl}amino)-6-fluorobenzamide (0.15 g, 0.33 mmol), 27% aqueous ammonia, and 6-(methyloxy)-2-(1-methylpropyl)-1,2,3,4-tetrahydro-7-isoquinolinamine (0.098 g, 0.419 mmol). $^1$H NMR (400 MHz, DMSO-$d_6$) δ ppm 0.90 (t, J=7.3 Hz, 3 H), 1.00 (d, J=6.4 Hz, 3 H), 1.29-1.41 (m, 1 H), 1.52-1.63 (m, 1 H), 2.57-2.67 (m, 2 H), 2.67-2.77 (m, 3 H), 3.44-3.60 (m, 2 H), 3.81 (s, 3 H), 6.25-6.28 (m, 1 H), 6.71 (s, 1 H), 6.91-6.98 (m, 1 H), 6.99-7.03 (s, 1 H), 7.40-7.48 (s, 2 H), 7.94 (s, 1 H), 8.01 (bs, 1 H), 8.10 (bs, 1 H), 8.38 (d, J=8.4 Hz, 1 H), 10.40 (s, 1 H), 11.34 (bs, 1 H); ESIMS (M+H)$^+$=504.

462

Example 238

2-fluoro-N-methyl-6-[(2-{[6-(methyloxy)-2-(1-methylpropyl)-1,2,3,4-tetrahydro-7-isoquinolinyl]amino}-1H-pyrrolo[2,3-d]pyrimidin-4-yl)amino]benzamide

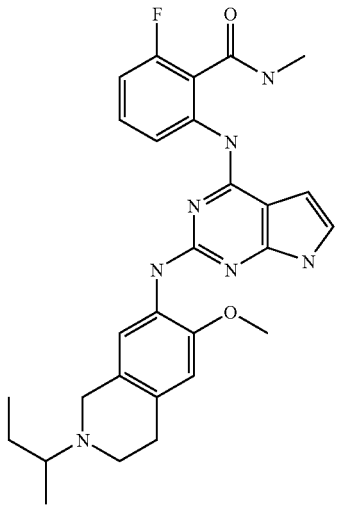

According to General Protocol III, 2-fluoro-N-methyl-6-[(2-{[6-(methyloxy)-2-(1-methylpropyl)-1,2,3,4-tetrahydro-7-isoquinolinyl]amino}-1H-pyrrolo[2,3-d]pyrimidin-4-yl)amino]benzamide (0.084 g) was prepared from 2-({2-chloro-7-[(4-methylphenyl)sulfonyl]-7H-pyrrolo[2,3-d]pyrimidin-4-yl}amino)-6-fluorobenzamide (0.15 g, 0.33 mmol), methyl amine, and 6-(methyloxy)-2-(1-methylpropyl)-1,2,3,4-tetrahydro-7-isoquinolinamine (0.098 g, 0.419 mmol). $^1$H NMR (400 MHz, DMSO-$d_6$) δ ppm 0.90 (t, J=7.2 Hz, 3 H), 1.00 (d, J=6.4 Hz, 3 H), 1.29-1.40 (m, 1 H), 1.52-1.63 (m, 1 H), 2.56-2.82 (m, 8 H), 3.44-3.59 (m, 2 H), 3.81 (s, 3 H), 6.27-6.36 (m, 1 H), 6.70 (s, 1 H), 6.92-7.03 (m, 2 H), 7.40-7.49 (m, 2 H), 7.96 (s, 1 H), 8.26 (d, J=8.2 Hz, 1 H), 8.51-8.62 (m, 1 H), 10.07 (s, 1 H), 11.32 (bs, 1 H); ESIMS (M+H)$^+$=518.

Example 239

2,4-difluoro-6-[(2-{[2-(2-fluoroethyl)-6-(methyloxy)-1,2,3,4-tetrahydro-7-isoqinolinyl]amino}-1H-pyrrolo[2.3-d]pyrimidin-4-yl)amino]benzamide

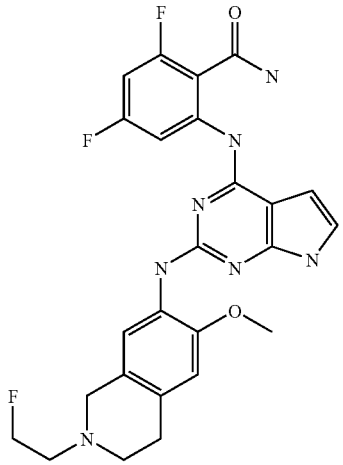

According to General Protocol III, 2,4-difluoro-6-[(2-{[2-(2-fluoroethyl)-6-(methyloxy)-1,2,3,4-tetrahydro-7-isoquinolinyl]amino}-1H-pyrrolo[2,3-d]pyrimidin-4-yl)amino]benzamide (0.031 g) was prepared from 2-({2-chloro-7-[(4-methylphenyl)sulfonyl]-7H-pyrrolo[2,3-d]pyrimidin-4-yl}amino)-4,6-difluorobenzamide (0.15 g, 0.31 mmol), 27% aqueous ammonium hydroxide, and 2-(2-fluoroethyl)-6-(methyloxy)-1,2,3,4-tetrahydro-7-isoquinolinamine (0.08 g, 0.36 mmol). $^1$H NMR (400 MHz, DMSO-d$_6$) δ ppm 2.71-2.83 (m, 6 H), 3.55 (s, 2 H), 3.81 (s, 3 H), 4.53-4.70 (dt, J$_{HF}$=47.4, J=4.7 Hz, 2 H), 6.22-6.27 (m, 1 H), 6.75 (s, 1 H), 6.95 (t, J=10.3 Hz, 1 H), 7.03 (s, 1 H), 7.66 (s, 1 H), 7.80 (s, 1 H), 8.05 (bs, 1 H), 8.19 (bs, 1 H), 8.49 (d, J=11.4 Hz, 1 H), 11.06 (s, 1 H), 11.42 (bs, 1 H); ESIMS (M+H)$^+$=512.

Example 240

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]benzamide

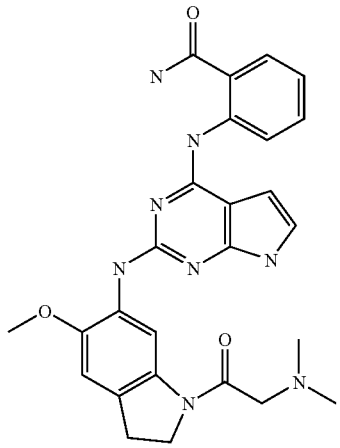

Step A/Intermediate D29: 2-({2-chloro-7-[(4-methylphenyl)sulfonyl]-7H-pyrrolo[2,3-d]pyrimidin-4-yl}amino)benzoic acid

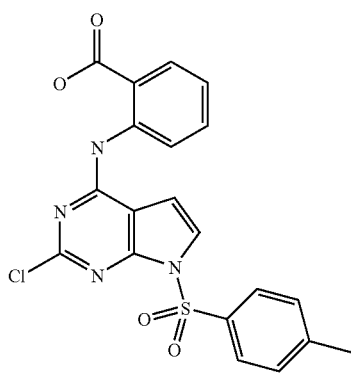

A mixture of 2,4-dichloro-7-[(4-methylphenyl)sulfonyl]-7H-pyrrolo[2,3-d]pyrimidine (25 g, 73.1 mmol), 2-aminobenzoic acid (10.02 g, 73.1 mmol) and DIPEA (63.8 mL, 365 mmol) in iPrOH (300 mL) was heated at 85° C. bath for 17 h. The resulting mixture was allowed to cool to rt and was concentrated to about half volume. EtOAc (400 mL) was added, followed by a 1N aqueous HCl solution (400 mL). The resulting slurry was filtered, the solids were washed with EtOAc and triturated using Et$_2$O to obtain 2-({2-chloro-7-[(4-methylphenyl)sulfonyl]-7H-pyrrolo[2,3-d]pyrimidin-4-yl}amino)benzoic acid as a yellow solid (28.44 g 88%). $^1$H NMR (400 MHz, DMSO-d$_6$) δ ppm 2.36 (s, 3H), 7.11-7.23 (m, 1H), 7.47 (d. J=8.61 Hz, 2H), 7.56-7.67 (m, 1H), 7.76 (d, J=3.85 Hz, 1H), 7.95 (dd, J=7.69 Hz, 1.46 Hz, 1H), 7.97-8.02 (m, 2H), 8.29-8.36 (m, 1H), 11.36 (s, 1H); ESIMS (M+H)$^+$= 443.06.

Step B/Intermediate D30: 5-chloro-3-[(4-methylphenyl)sulfonyl]pyrrolo[2',3':4,5]pyrimido[6,1-b]quinazolin-7(3H)-one hydrogen chloride

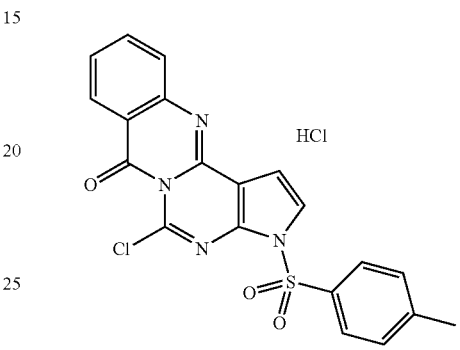

A mixture of 2-({2-chloro-7-[(4-methylphenyl)sulfonyl]-7H-pyrrolo[2,3-d]pyrimidin-4-yl}amino)benzoic acid (28 g, 63.2 mmol) in THF (500 mL) was treated with 2 drops of DMF and oxalyl chloride (8.30 mL, 95 mmol), and was stirred at rt for 3 h. The resulting slurry was filtered to obtain 5-chloro-3-[(4-methylphenyl)sulfonyl]pyrrolo[2',3':4,5]pyrimido[6,1-b]quinazolin-7(3H)-one hydrogen chloride as a yellow solid (27.67 g, 95%). $^1$H NMR (free base) (400 MHz, DMSO-d$_6$) δ ppm 2.37 (s, 3H), 7.07 (d, 4.21 Hz, 1H), 7.34 (d, J=4.21 Hz, 1H), 7.47 (d, 8.06 Hz, 2H), 7.53-7.63 (m, 1H), 7.78-7.90 (m, 1H), 8.00 (d, J=8.42 Hz, 2H), 8.18 (dd, J=7.78 Hz, 1.74 Hz, 1H), 9.28 (d, J=8.42 Hz, 1H); ESIMS (M+H)$^+$= 424.97.

Step C/Intermediate D31: 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)benzamide

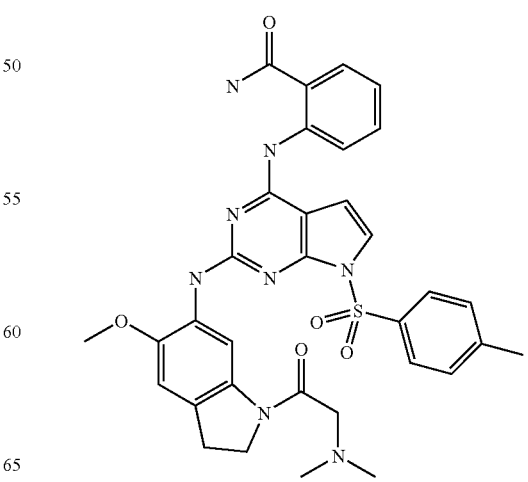

A mixture of 5-chloro-3-[(4-methylphenyl)sulfonyl]pyrrolo[2',3':4,5]pyrimido[6,1-b]quinazolin-7(3H)-one hydrogen chloride (500 mg, 1.084 mmol) and 1-[(dimethylamino)acetyl]-5-(methyloxy)-2,3-dihydro-1H-indol-6-amine (270 mg, 1.084 mmol) in THF (50 mL) was heated at 80° C. for 7.5 h. More 1-[(dimethylamino)acetyl]-5-(methyloxy)-2,3-dihydro-1H-indol-6-amine (270 mg, 1.084 mmol) was added and the reaction mixture was heated at 80° C. for 1 h. The resulting mixture was diluted to a total of 70 mL of which 40 mL was diluted with a 27% aqueous NH$_4$OH solution (100 mL), maintained at rt for 3 days, and diluted with EtOAc (200 mL) and washed with a saturated NaCl solution (4×125 mL). The organic layer was concentrated onto Celite and purified by silica gel chromatography using 1-10% MeOH (containing 0.2% NH$_3$)/CH$_2$Cl$_2$, followed by trituration using a mixture of CH$_2$Cl$_2$ and Et$_2$O to obtain 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)benzamide as a white solid (101 mg). $^1$H NMR (400 MHz, DMSO-d$_6$) δ ppm 2.24 (s, 6H), 2.35 (s, 3H), 3.14-3.28 (m, 4H), 3.74 (s, 3H), 4.24 (t, J=8.33 Hz, 2H), 6.47 (d, J=3.85 Hz, 1H), 6.91-7.03 (m, 1H), 7.08 (s, 1H), 7.24 (t, J=7.60 Hz, 1H), 7.29-7.42 (m, 3H), 7.70-7.87 (m, 2H), 7.98 (d, J=8.24 Hz, 2H), 8.23 (s, 1H), 8.31 (br s, 1H), 8.37 (s, 1H), 8.70 (d, J=8.42 Hz, 1H), 12.22 (s, 1H); ESIMS (M+H)+=655.37.

Step D/Example 240

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]benzamide A solution of 2-({2-{[1-(N,N-dimethylglycyl)-5-(methyloxy)-2,3-dihydro-1H-indol-6-yl]amino}-7-[(4-methylphenyl)sulfonyl]-7H-pyrrolo[2,3-d]pyrimidin-4-yl}amino)benzamide (100 mg, 0.153 mmol) in dioxane (13 mL) and a 1M aqueous KOH solution (0.764 mL, 0.764 mmol) was heated at 90° C. for 6 h. The resulting mixture was allowed to cool to rt, diluted with EtOAc (100 mL), washed with a saturated NaHCO$_3$ solution (50 mL) and a saturated NaCl solution (50 mL). The organic layer was concentrated onto Celite and purified by silica gel chromatography using 1-10% MeOH (containing 0.2% NH$_3$)/CH$_2$Cl$_2$ to obtain as a yellow solid (56 mg, 74%). $^1$H NMR (400 MHz, DMSO-d$_6$) δ ppm 2.40 (s, 6H), 3.07-3.20 (m, 2H), 3.50 (br s, 2H), 3.76 (s, 3H), 4.13 (d, J=8.24 Hz, 2H), 6.19-6.31 (m, 1H), 6.87-7.05 (m, 3H), 7.31 (t, J=7.87 Hz, 1H), 7.61 (s, 1H), 7.71 (br s, 1H), 7.78 (d, J=7.51 Hz, 1H), 8.26 (br s, 1H), 8.59 (s, 1H), 8.94 (d, J=8.61 Hz, 1H), 11.23 (s, 1H), 12.04 (s, 1H); ESIMS (M+H)+=501.25.

Example 241

2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-methylbenzamide

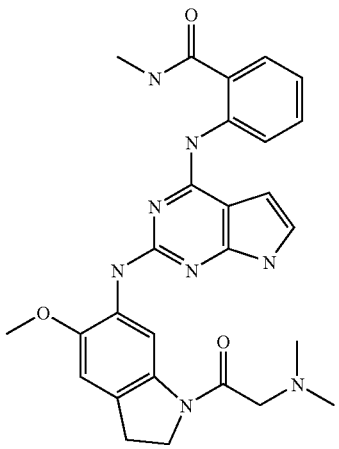

The remaining reaction mixture from the preparation of 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]benzamide was diluted with a solution of methylamine (2M in THF 15 mL, 30 mmol). The resulting mixture maintained at rt for 2 days and was diluted with EtOAc (200 mL), washed with a saturated NaHCO$_3$ solution (200 mL) and a saturated NaCl solution (125 mL). The organic layer was concentrated onto Celite and purified by silica gel chromatography using 1-10% MeOH (containing 0.2% NH$_3$)/CH$_2$Cl$_2$, followed by trituration using a mixture of CH$_2$Cl$_2$ and Et$_2$O. The crude product was dissolved in dioxane (13 mL) and was treated with a 1M aqueous KOH solution (1.121 mL, 1.121 mmol). The resulting mixture was heated at 90° C. for 6 h and was allowed to cool to rt and diluted with EtOAc (100 mL), washed with a saturated NaHCO$_3$ solution (50 mL) and a saturated NaCl solution (50 mL). The organic layer was concentrated onto Celite and purified by silica gel chromatography using 1-10% MeOH (containing 0.2% NH$_3$)/CH$_2$Cl$_2$ to obtain 2-[(2-{[1-(N,N-dimethylglycyl)-5-(methyloxy)-2,3-dihydro-1H-indol-6-yl]amino}-1H-pyrrolo[2,3-d]pyrimidin-4-yl)amino]-N-methylbenzamide as a beige solid (70 mg). $^1$H NMR (400 MHz, DMSO-d$_6$) δ ppm 2.26 (s, 6H), 2.83 (d, J=4.40 Hz, 3H), 3.04-3.28 (m, 4H), 3.78 (s, 3H), 4.18 (t, J=8.33 Hz, 2H), 6.23-6.38 (m, 1H), 6.87-7.07 (m, 3H), 7.60 Hz, 1H), 7.60 (s, 1H), 7.72 (d, 7.33 Hz, 1H), 8.64 (s, 1H), 8.67-8.81 (m, 1H), 8.90 (d, J=8.24 Hz, 1H), 11.26 (s, 1H), 11.73 (s, 1H); ESIMS (M+H)+=515.33.

Example 242

2-[(2-{5-[(N,N-dimethylglycyl)(methyl)amino]-2-(methyloxy)phenyl]amino}-1H-pyrrolo[2,3-d]pyrimidin-4-yl)amino]-6-fluoro-N-methylbenzamide

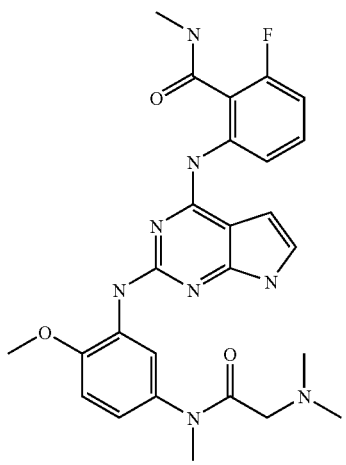

Step A/Intermediate D32: $N^1$-[3-({8-fluoro-3-[(4-methylphenyl)sulfonyl]-7-oxo-3,7-dihydropyrrolo[2',3':4,5]pyrimido[6,1-b]quinazolin-5-yl}amino)-4-(methyloxy)phenyl]-$N^1$,$N^2$,$N^2$-trimethylglycinamide

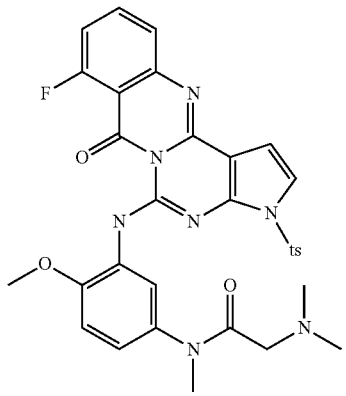

A suspension of 5-chloro-8-fluoro-3-[(4-methylphenyl)sulfonyl]pyrrolo[2',3':4,5]pyrimido[6,1-b]quinazolin-7(3H)-one (2.00 g, 4.17 mmol) and N1-[3-amino-4-(methyloxy)phenyl]-N1,N2,N2-trimethylglycinamide (1.040 g, 4.38 mmol) in tetrahydrofuran (75 ml) was maintained at 65° C. for 16 hours in a sealed pressure tube. The reaction was cooled, taken to a residue under reduced pressure, and partitioned between dichloromethane/saturated sodium bicarbonate with 2,2,2-trifluoroethanol added until all solids had dissolved. The organic layer was separated, taken to a residue under reduced pressure, and triturated with diethyl ether to afford analytically pure N1-[3-({8-fluoro-3-[(4-methylphenyl)sulfonyl]-7-oxo-3,7-dihydropyrrolo[2',3':4,5]pyrimido[6,1-b]quinazolin-5-yl}amino)-4-(methyloxy)phenyl]-N1,N2,N2-trimethylglycinamide (2.55 g, 3.96 mmol, 95% yield) as a pale yellow solid. ESIMS (M+H)$^+$=644.

Step B/Example 242

2-[(2-{5-[(N,N-dimethylglycyl)(methyl)amino]-2-(methyloxy)phenyl]amino}-1H-pyrrolo[2,3-d]pyrimidin-4-yl)amino]-6-fluoro-N-methylbenzamide A solution of N1-[3-({8-fluoro-3-[(4-methylphenyl)sulfonyl]-7-oxo-3,7-dihydropyrrolo[2',3':4,5]pyrimido[6,1-b]quinazolin-5-yl}amino)-4-(methyloxy)phenyl]-N1,N2,N2-trimethylglycinamide (0.800 g, 1.243 mmol) in tetrahydrofuran (75 ml) was treated with 2.0M methyl amine (3.11 ml, 6.21 mmol) and maintained at room temperature overnight. The reaction was taken to a residue under reduced pressure, dissolved in 1,4-dioxane (8 ml), and added to a microwave vial along with 2.0N NaOH (aq) (8 ml). The mixture was maintained under microwave heating at 120° C. for 12 minutes, cooled, and poured into saturated sodium bicarbonate and ethyl acetate. The organic layer was separated, dried over sodium sulfate, filtered, stripped onto celite, and purified by column chromatography to afford 2-[(2-{5-[(N,N-dimethylglycyl)(methyl)amino]-2-(methyloxy)phenyl]amino}-1H-pyrrolo[2,3-d]pyrimidin-4-yl)amino]-6-fluoro-N-methylbenzamide (0.140 g, 0.269 mmol, 21.64% yield) as a pale yellow solid. $^1$H NMR (400 MHz, DMSO-$d_6$) δ ppm 11.47 (br. s., 1 H), 10.05 (s, 1 H), 8.54 (d, J=3.8 Hz, 1 H), 8.44 (br. s., 1 H), 8.14 (d, J=8.2 Hz, 7.59 (s, 1 H), 7.36-7.50 (m, 1 H), 6.93-7.06 (m, 3 H), 6.84 (br. s., 1 H), 6.35 (br.s., 1 H), 3.91 (s, 3 H), 3.11 (s, 3 H), 2.86 (s, 2 H), 2.77 (d, J=4.4 Hz, 3 H), 2.11 (s, 6 H). ESIMS (M+H)$^+$=521.

Example 243

2-[(2-{5-(dimethylamino)-1-(N,N-dimethylglycyl)-2,3-dihydro-1H-indol-6-yl]amino}-1H-pyrrolo[2,3-d]pyrimidin-4-yl)amino]-6-fluorobenzamide

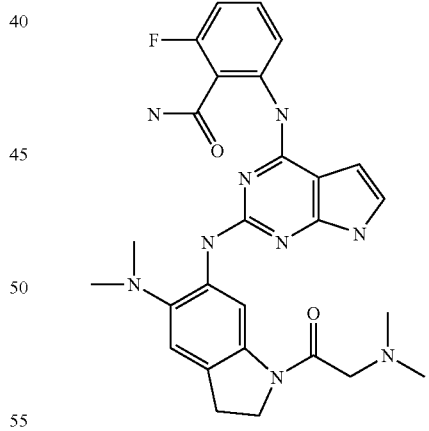

In a manner analogous to a procedure outlined previously, 2-[(2-{5-(dimethylamino)-1-(N,N-dimethylglycyl)-2,3-dihydro-1H-indol-6-yl]amino}-1H-pyrrolo[2,3-d]pyrimidin-4-yl)amino]-6-fluorobenzamide was prepared from 5-chloro-8-fluoro-3-[(4-methylphenyl)sulfonyl]pyrrolo[2',3':4,5]pyrimido[6,1-b]quinazolin-7(3H)-one hydrochloride, 1-[(dimethylamino)acetyl]-N5,N5-dimethyl-2,3-dihydro-1H-indole-5,6-diamine, and ammonium hydroxide to afford the title compound (0.20 g, 45% over 3 steps). ESIMS (M+H)+=532. 1H NMR (400 MHz, DMSO-$d_6$) δ ppm 2.21-2.28 (m, 6 H) 2.54-2.62 (m, 6 H) 3.03-3.12 (m, 2 H) 3.18 (s, 2 H) 4.17 (t, J=8.33 Hz, 2 H) 6.24-6.27 (m, 1 H) 6.85-6.90 (m, 1 H) 6.96-6.99 (m, 1 H) 7.06 (s, 1 H) 7.31-7.40 (m, 1 H) 7.67 (s, 1 H) 8.03 (br. s., 1 H) 8.11 (s, 1 H) 8.51 (d, J=8.23 Hz, 1 H) 8.77 (s, 1 H) 10.54 (s, 1 H) 11.32 (s, 1 H).

Example 244

2-[(2-{[5-[(N,N-dimethylglycyl)amino]-2-(methyloxy)phenyl]amino}-1H-pyrrolo[2,3-d]pyrimidin-4-yl)amino]-6-fluorobenzamide

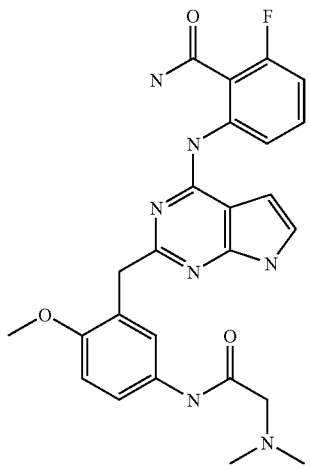

Step A/Intermediate D37: 2-({2-{[5-[(N,N-dimethylglycyl)amino]-2-(methyloxy)phenyl]amino}-7-[(4-methylphenyl)sulfonyl]-7H-pyrrolo[2,3-d]pyrimidin-4-yl}amino)-6-fluorobenzamide

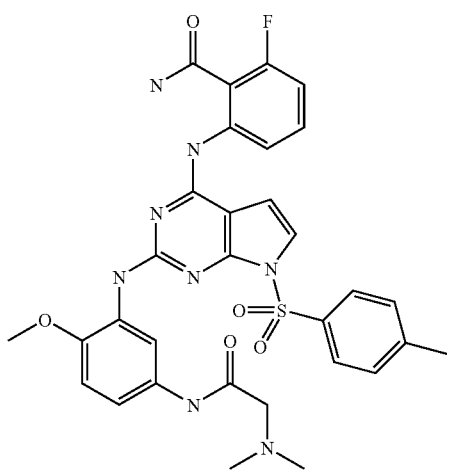

A slurry of 5-chloro-8-fluoro-3-[(4-methylphenyl)sulfonyl]pyrrolo[2',3':4,5]pyrimido[6,1-b]quinazolin-7(3H)-one hydrogen chloride (400 mg, 0.835 mmol) and N1-[3-amino-4-(methyloxy)phenyl]-N2,N2-dimethylglycinamide hydrogen chloride (217 mg, 0.835 mmol) in THF (15 mL) in 2,2,2-trifluoroethanol (40 mL) was stirred at rt for 3 days. LCMS indicated incomplete reaction, therefore more N1-[3-amino-4-(methyloxy)phenyl]-N2,N2-dimethylglycinamide hydrogen chloride (115 mg, 0.24 mmol) was added and the reaction mixture was heated at 80° C. for 4 h. After allowing to cool to rt the reaction mixture was diluted with THF (100 mL) and a 27% aqueous NH$_4$OH solution (100 mL) and stirred at rt. After 20 h CHCl$_3$ (200 mL) was added. The organic layer was washed with a saturated NaCl solution (100 mL), concentrated onto Celite and purified by silica gel chromatography using 1-10% MeOH (containing 0.2% NH$_3$)/CH$_2$Cl$_2$ to obtain 2-({2-{[5-[(N,N-dimethylglycyl)amino]-2-(methyloxy)phenyl]amino}-7-[(4-methylphenyl)sulfonyl]-7H-pyrrolo[2,3-d]pyrimidin-4-yl}amino)-6-fluorobenzamide as a white solid (364 mg, 67%). $^1$H NMR (400 MHz, DMSO-d$_6$) δ ppm 2.25 (s, 6H), 2.32 (s, 3H), 3.03 (s, 2H), 3.81 (s, 3H), 6.60 (d, J=4.03 Hz, 1H), 6.97-7.07 (m, 2H), 7.30-7.46 (m, 4H), 7.51 (dd, J=8.79, 2.56 Hz, 1H), 7.87-8.03 (m, 6H), 8.35 (br s, 1H), 9.50 (s, 1H), 10.38 (s, 1H); ESIMS (M+H)+=647.

Step B/Example 244

2-[(2-{[5-[(N,N-dimethylglycyl)amino]-2-(methyloxy)phenyl]amino}-1H-pyrrolo[2,3-d]pyrimidin-4-yl)amino]-6-fluorobenzamide A mixture of 2-({2-{[5-[(N,N-dimethylglycyl)amino]-2-(methyloxy)phenyl]amino}-7-[(4-methylphenyl)sulfonyl]-7H-pyrrolo[2,3-d]pyrimidin-4-yl}amino)-6-fluorobenzamide (362 mg, 0.560 mmol) and a 1M aqueous KOH solution (5.60 mL, 5.60 mmol) in dioxane (20 mL) was heated at 80° C. for 7 h. The resulting mixture was allowed to cool to rt. EtOAc (50 mL) was added, followed by a saturated NaHCO$_3$ solution (50 mL). The organic layer was washed with a saturated NaCl solution (50 mL), concentrated onto Celite and purified by silica gel chromatography using 1-10% MeOH (containing 0.2% NH$_3$)/CH$_2$Cl$_2$ to obtain 2-[(2-{[5-[(N,N-dimethylglycyl)amino]-2-(methyloxy)phenyl]amino}-1H-pyrrolo[2,3-d]pyrimidin-4-yl)amino]-6-fluorobenzamide as a yellow solid (131 mg, 48%). $^1$H NMR (400 MHz, DMSO-d$_6$) δ ppm 2.28 (s, 6H), 3.03 (s, 2H), 3.82 (s, 3H), 6.26 (dd, J=3.30, 1.83 Hz, 1H), 6.87-6.98 (m, 2H), 7.01 (dd, J=3.39, 2.29 Hz, 1H), 7.34 (dd, J=8.79, 2.56 Hz, 1H), 7.36-7.46 (m, 1H), 7.60 (s, 1H), 8.04 (s, 1H), 8.11 (s, 1H), 8.20 (d, J=2.56 Hz, 1H), 8.47 (d, J=8.42 Hz, 1H), 9.41 (s, 1H), 10.55 (s, 1H), 11.37 (s, 1H); ESIMS (M+H)+=493.

Example 245

2-[(2-{[5-[(N,N-dimethylglycyl)amino]-2-(methyloxy)phenyl]amino}-1H-pyrrolo[2,3-c]pyrimidin-4-yl)amino]-6-fluoro-N-methylbenzamide

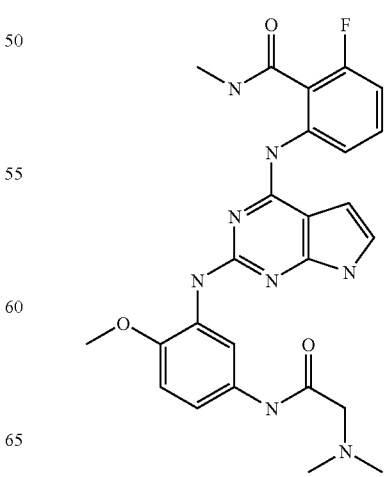

Step A/Intermediate D38: 2-({2-{[5-[(N,N-dimethylglycyl)amino]-2-(methyloxy)phenyl]amino}-7-[(4-methylphenyl)sulfonyl]-7H-pyrrolo[2,3-d]pyrimidin-4-yl}amino)-6-fluoro-N-methylbenzamide

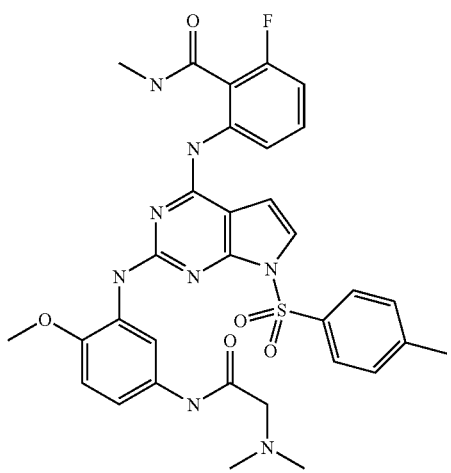

A slurry of 5-chloro-8-fluoro-3-[(4-methylphenyl)sulfonyl]pyrrolo[2',3':4,5]pyrimido[6,1-b]quinazolin-7(3H)-one hydrogen chloride (400 mg, 0.835 mmol) and N1-[3-amino-4-(methyloxy)phenyl]-N2,N2-dimethylglycinamide hydrogen chloride (217 mg, 0.835 mmol) in THF (15 mL) in 2,2,2-trifluoroethanol was stirred at rt. After 3 days LCMS indicated incomplete reaction, therefore more N1-[3-amino-4-(methyloxy)phenyl]-N2,N2-dimethylglycinamide hydrogen chloride (115 mg, 0.24 mmol) was added and the reaction mixture was heated at 80° C. for 4 h. After allowing to cool to rt the reaction mixture was treated with a MeNH$_2$ solution (2M in THF, 20 mL). The reaction mixture was stirred at it for 20 h, then concentrated onto Celite and purified by silica gel chromatography using 1-10% MeOH (containing 0.2% NH3)/CH2Cl2 to obtain 2-({2-{[5-[(N,N-dimethylglycyl)amino]-2-(methyloxy)phenyl]amino}-7-[(4-methylphenyl)sulfonyl]-7H-pyrrolo[2,3-d]pyrimidin-4-yl}amino)-6-fluoro-N-methylbenzamide as a yellow solid (487 mg, 88%). $^1$H NMR (400 MHz, DMSO-d$_6$) δ ppm 2.25 (s, 6H), 2.31 (s, 3H), 2.68 (d, J=4.58 Hz, 3H), 3.04 (s, 2H), 3.83 (s, 3H), 6.67 (d, J=4.03 Hz, 1H), 6.96-7.09 (m, 2H), 7.34 (d, J=8.42 Hz, 2H), 7.37-7.45 (m, 2H), 7.53 (dd, J=8.79, 2.56 Hz, 1H), 7.83 (d, J=8.24 Hz, 1H), 7.88-8.00 (m, 3H), 8.39 (br s, 1H), 8.44-8.54 (m, 1H), 9.50 (s, 1H), 10.09 (s, 1H); ESIMS (M+H)+= 661.

Step B/Example 245: 2-[(2-{[5-[(N,N-dimethylglycyl)amino]-2-(methyloxy)phenyl]amino}-1H-pyrrolo[2,3-d]pyrimidin-4-yl)amino]-6-fluoro-N-methylbenzamide A mixture of 2-({2-{[5-[(N,N-dimethylglycyl)amino]-2-(methyloxy)phenyl]amino}-7-[(4-methylphenyl)sulfonyl]-7H-pyrrolo[2,3-d]pyrimidin-4-yl}amino)-6-fluoro-N-methylbenzamide (485 mg, 0.734 mmol) and a 1M aqueous KOH solution (7.34 mL, 7.34 mmol) in dioxane (20 mL) was heated at 80° C. for 7 h. The resulting mixture was allowed to cool to rt. EtOAc (50 mL) was added, followed by a saturated NaHCO$_3$ solution (50 mL). The organic layer was washed with a saturated NaCl solution (50 mL), concentrated onto Celite and purified by silica gel chromatography using 1-10% MeOH (containing 0.2% NH$_3$)/CH$_2$Cl$_2$ to obtain 2-[(2-{[5-[(N,N-dimethylglycyl)amino]-2-(methyloxy)phenyl]amino}-1H-pyrrolo[2,3-d]pyrimidin-4-yl)amino]-6-fluoro-N-methylbenzamide as a white solid (220 mg, 59%). $^1$H NMR (400 MHz, DMSO-d$_6$) δ ppm 2.28 (s, 6H), 2.80 (d, J=4.58 Hz, 3H), 3.03 (s, 2H), 3.82 (s, 3H), 6.31 (dd, J=3.48, 1.83 Hz, 1H), 6.89-7.03 (m, 3H), 7.33 (dd, J=8.79, 2.56 Hz, 1H), 7.36-7.45 (m, 1H), 7.57 (s, 1H), 8.21 (d, J=2.38 Hz, 1H), 8.31 (d, J=8.24 Hz, 1H), 8.51-8.61 (m, 1H), 9.40 (s, 1H), 10.17 (s, 1H), 11.35 (s, 1H); ESIMS (M+H)+=507.

Example 246

2-[(2-{[1-(N,N-dimethylglycyl)-6-methyl-1,2,3,4-tetrahydro-7-quinolinyl]amino}-1H-pyrrolo[2,3-d]pyrimidin-4-yl)amino]-6-fluorobenzamide

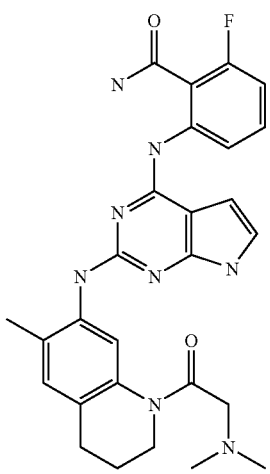

Step A/Intermediate D39: 2-({2-{[1-(N,N-dimethylglycyl)-6-methyl-1,2,3,4-tetrahydro-7-quinolinyl]amino}-7-[(4-methylphenyl)sulfonyl]-7H-pyrrolo[2,3-d]pyrimidin-4-yl}amino)-6-fluorobenzamide

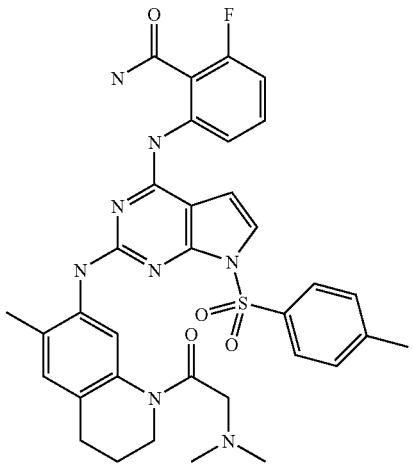

A slurry of 5-chloro-8-fluoro-3-[(4-methylphenyl)sulfonyl]pyrrolo[2',3':4,5]pyrimido[6,1-b]quinazolin-7(3H)-one hydrogen chloride (400 mg, 0.835 mmol) and 1-[(dimethylamino)acetyl]-6-methyl-1,2,3,4-tetrahydro-7-quinolinamine (206 mg, 0.835 mmol) in 2,2,2-trifluoroethanol (50 mL) was stirred at rt for 4 days. The resulting green solution was diluted with THF (50 mL) and a 27% aqueous NH$_4$OH solution (100 mL). The clear orange reaction mixture was stirred at rt for 5 h. EtOAc (200 mL) was added and the mixture was washed with a saturated NaCl solution (3×100 mL). The organic layer was dried (Na$_2$SO$_4$), concentrated onto Celite and purified by silica gel chromatography using 1-10% MeOH (containing 0.2% NH$_3$)/CH$_2$Cl$_2$ to obtain 2-({2-{[1-(N,N-dimethylglycyl)-6-methyl-1,2,3,4-tetrahydro-7-quinolinyl]amino}-7-[(4-methylphenyl)sulfonyl]-7H-pyrrolo[2,3-d]pyrimidin-4-yl}amino)-6-fluorobenzamide as a white solid (416 mg, 74%). $^1$H NMR (400 MHz, DMSO-d$_6$) δ ppm 1.85-2.01 (m, 2H), 2.13 (br s, 6H), 2.16 (s, 3H), 2.32 (s, 3H), 2.76 (t, J=6.41 Hz, 2H), 3.18 (br s, 2H), 3.77 (t, J=5.77 Hz, 2H), 6.49 (d, J=4.03 Hz, 1H), 6.68 (br s, 1H), 6.88-7.01 (m, 1H), 7.11 (s, 1H), 7.15-7.38 (m, 3H), 7.70 (br s, 1H), 7.80 (d, J=7.51 Hz, 2H), 7.92 (br s, 1H), 8.02 (br s, 1H), 8.10 (d, J=8.06 Hz, 1k), 8.58 (s, 1H), 10.49 (s, 1H); ESIMS (M+H)+= 671.23.

Step B/Example 246

2-[(2-{[1-(N,N-dimethylglycyl)-6-methyl-1,2,3,4-tetrahydro-7-quinolinyl]amino}-1H-pyrrolo[2,3-d]pyrimidin-4-yl)amino]-6-fluorobenzamide A mixture of 2-({2-{[1-(N,N-dimethylglycyl)-6-methyl-1,2,3,4-tetrahydro-7-quinolinyl]amino}-7-[(4-methylphenyl)sulfonyl]-7H-pyrrolo[2,3-d]pyrimidin-4-yl}amino)-6-fluorobenzamide (414 mg, 0.617 mmol) and a 1N aqueous KOH solution (6.17 mL, 6.17 mmol) in dioxane (20 mL) was heated at 80° C. for 17 h. EtOAc (50 mL) and a saturated NaHCO$_3$ solution (50 mL) were added. The organic layer was washed with a saturated NaCl solution (50 mL), concentrated onto Celite and purified by silica gel chromatography using 1-10% MeOH (containing 0.2% NH$_3$)/CH$_2$Cl$_2$ to afford 2-[(2-{[1-(N,N-dimethylglycyl)-6-methyl-1,2,3,4-tetrahydro-7-quinolinyl]amino}-1H-pyrrolo[2,3-d]pyrimidin-4-yl)amino]-6-fluorobenzamide as a white solid (237 mg, 74%). $^1$H NMR (400 MHz, DMSO-d$_6$) δ ppm 1.82-1.96 (m, 2H), 2.12 (s, 6H), 2.17 (s, 3H), 2.70 (t, J=6.50 Hz, 2H), 3.17 (s, 2H), 3.72 (t, J=6.04 Hz, 2H), 6.19 (dd, H=3.39, 1.92 Hz, 1H), 6.82-6.91 (m, 1H), 6.93 (dd, J=3.39, 2.29 Hz, 1H), 7.00 (s, 1H), 7.19-7.30 (m, 1H), 7.78 (br s, 1H), 8.00 (s, 1H), 8.09 (s, 1H), 8.11 (s, 1H), 8.47 (d, J=8.61 Hz, 1H), 10.54 (s, 1H), 11.24 (s, 1H); ESIMS (M+H)+=517.26.

Example 247

2-[(2-{[1-(N,N-dimethylglycyl)-6-methyl-1,2,3,4-tetrahydro-7-quinolinyl]amino}-1H-pyrrolo[2,3-d]pyrimidin-4-yl)amino]-6-fluoro-N-methylbenzamide

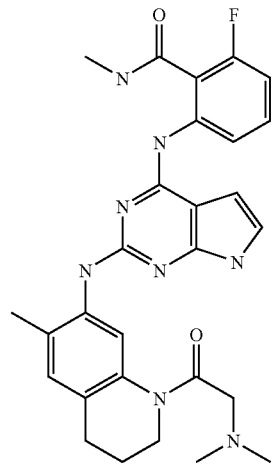

Step A/Intermediate D40: 2-({2-{[1-(N,N-dimethylglycyl)-6-methyl-1,2,3,4-tetrahydro-7-quinolinyl]amino}-7-[(4-methylphenyl)sulfonyl]-7H-pyrrolo[2,3-d]pyrimidin-4-yl}amino)-6-fluoro-N-methylbenzamide

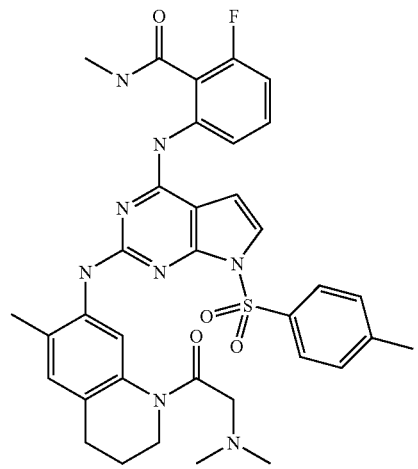

A slurry of 5-chloro-8-fluoro-3-[(4-methylphenyl)sulfonyl]pyrrolo[2',3':4,5]pyrimido[6,1-b]quinazolin-7(3H)-one hydrogen chloride (300 mg, 0.626 mmol) and 1-[(dimethylamino)acetyl]-6-methyl-1,2,3,4-tetrahydro-7-quinolinamine (155 mg, 0.626 mmol) in THF (50 mL) was heated at 70° C. for 20 h. The resulting mixture was allowed to cool to rt and was treated with a 2M MeNH$_2$ solution in THF (10 mL). The reaction mixture was stirred at rt for 3 days, then concentrated onto Celite and purified by silica gel chromatography using 1-20% MeOH (containing 0.2% NH$_3$)/CH$_2$Cl$_2$ to afford 2-({2-{[1-(N,N-dimethylglycyl)-6-methyl-1,2,3,4-tetrahydro-7-quinolinyl]amino}-7-[(4- methylphenyl)sulfonyl]-7H-pyrrolo[2,3-d]pyrimidin-4-yl}amino)-6-fluoro-N-methylbenzamide (87 mg, 20%). ESIMS (M+H)+=685.18.

Step B/Example 247

2-[(2-{[1-(N,N-dimethylglycyl)-6-methyl-1,2,3,4-tetrahydro-7-quinolinyl]amino}-1H-pyrrolo[2,3-d]pyrimidin-4-yl)amino]-6-fluoro-N-methylbenzamide A mixture of 2-({2-{[1-(N,N-dimethylglycyl)-6-methyl-1,2,3,4-tetrahydro-7-quinolinyl]amino}-7-[(4-methylphenyl)sulfonyl]-7H-pyrrolo[2,3-d]pyrimidin-4-yl}amino)-6-fluoro-N-methylbenzamide (87 mg, 0.127 mmol) and a 1M aqueous KOH solution (1.270 mL, 1.270 mmol) in dioxane (50 mL) was heated at 80° C. for 10 h. The resulting mixture was allowed to cool to rt, diluted with EtOAc (100 mL) and a saturated NaHCO$_3$ solution. The organic layer was washed with a saturated NaCl solution (100 mL), concentrated onto Celite and purified by silica gel chromatography (ISCO 12 g) using 1-10% MeOH (containing 0.2% NH$_3$)/CH$_2$Cl$_2$. The product was taken up into a mixture of CH$_2$Cl$_2$ and Et$_2$O and concentrated again to afford 2-[(2-{[1-(N,N-dimethylglycyl)-6-methyl-1,2,3,4-tetrahydro-7-quinolinyl]amino}-1H-pyrrolo[2,3-d]pyrimidin-4-yl)amino]-6-fluoro-N-methylbenzamide as a pale yellow solid (41 mg, 61%). $^1$H NMR (400 MHz, DMSO-d$_6$) δ ppm 1.79-1.96 (m, 2H), 2.12 (s, 6H), 2.16 (s, 3H), 2.69 (t, J=6.41 Hz, 2H), 2.81 (d, J=4.58 Hz, 3H), 3.18 (br s, 2H), 3.71 (t, J=5.86 Hz, 2H), 6.23 (d, J=1.47 Hz, 1H), 6.82-6.96 (m, 2H), 7.00 (s, 1H), 7.16-7.34 (m, 1H), 7.79 (br s, 1H), 8.04 (s, 1H), 8.34 (d, J=8.42 Hz, 1H), 8.44-8.61 Hz, 1H), 10.16 (s, 1H), 11.22 (br s, 1H); ESIMS (M+H)+=531.17.

Example 248

2-[(2-{[2R]-1-(N,N-dimethylglycyl)-2-methyl-5-(methyloxy)-2,3-dihydro-1H-indol-6-yl]amino}-1H-pyrrolo[2,3-d]pyrimidin-4-yl)amino]-6-fluorobenzamide

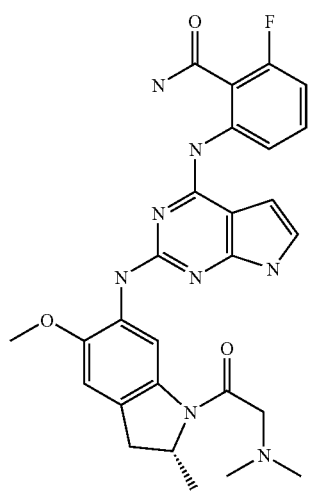

Step A/Intermediate D41: 2-({2-{[(2R)-1-(N,N-dimethylglycyl)-2-methyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluorobenzamide

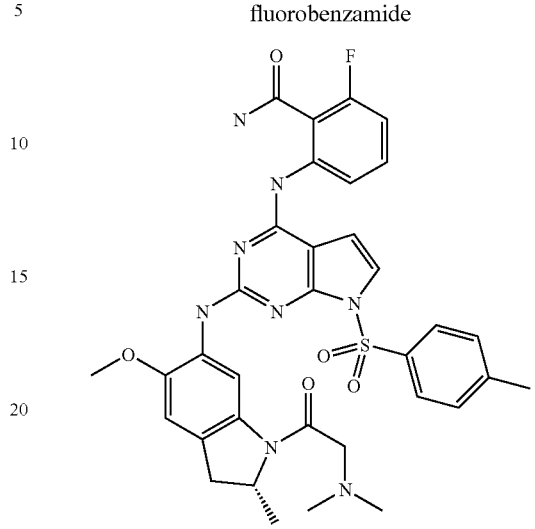

A slurry of 5-chloro-8-fluoro-3-[(4-methylphenyl)sulfonyl]pyrrolo[2',3':4,5]pyrimido[6,1-b]quinazolin-7(3H)-one hydrogen chloride (600 mg, 1.252 mmol) and (2R)-1-[(dimethylamino)acetyl]-2-methyl-5-(methyloxy)-2,3-dihydro-1H-indol-6-amine (330 mg, 1.252 mmol) in 2,2,2-trifluoroethanol (10 mL) was stirred at rt for 18 h. The resulting bright green slurry was divided into two equal batches. One of the batches was treated with a 27% aqueous NH$_4$OH solution (10 mL). The resulting orange slurry was stirred at rt for 2 days, then was diluted with EtOAc (50 mL) and a saturated NaHCO$_3$ solution (50 mL). The organic layer was washed with a saturated NaCl solution (50 mL), concentrated onto Celite and purified by silica gel chromatography using 1-10% MeOH (containing 0.2% NH$_3$)/CH$_2$Cl$_2$ to afford 2-({2-{[(2R)-1-(N,N-dimethylglycyl)-2-methyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluorobenzamide as a yellow solid (249 mg, 58%). $^1$H NMR (400 MHz, DMSO-d$_5$) δ ppm 1.18-1.32 (m, 3H), 2.27 (br s, 6H), 2.33 (s, 3H), 2.63 (d, J=16.12 Hz, 1H), 3.14 (d, J=14.65 Hz, 1H), 3.27-3.51 (m, 2H), 3.76 (s, 3H), 4.75-4.87 (m, 1H), 6.53 (d, J=4.03 Hz, 1H), 6.94 (t, J=9.34 Hz, 1H), 7.06 (s, 1H), 7.14-7.42 (m, 4H), 7.72-8.04 (m, 4H), 8.07 (d, J=8.24 Hz, 1H), 8.18 (s, 1H), 8.25 (s, 1H), 10.46 (s, 1H). ESIMS (M+H)+=687.26.

Step B/Example 248

2-[(2-{[(2R)-1-(N,N-dimethylglycyl)-2-methyl-5-(methyloxy)-2,3-dihydro-1H-indol-6-yl]amino}-1H-pyrrolo[2,3-d]pyrimidin-4-yl)amino]-6-fluorobenzamide A solution of 2-({2-{[(2R)-1-(N,N-dimethylglycyl)-2-methyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluorobenzamide (246 mg, 0.358 mmol) in dioxane (10 mL) and a 2M aqueous NaOH solution (2 mL) was heated at 80° C. for 5 h. The resulting mixture was allowed to cool to rt, diluted with EtOAc (50 mL) and a saturated NaCl solution (10 mL). The organic layer was concentrated onto Celite and purified by silica gel chromatography using 1-10% MeOH (containing 0.2% NH₃)/CH₂Cl₂ to afford 2-[(2-{[(2R)-1-(N,N-dimethylglycyl)-2-methyl-5-(methyloxy)-2,3-dihydro-1H-indol-6-yl]amino}-1H-pyrrolo[2,3-d]pyrimidin-4-yl)amino]-6-fluorobenzamide as a yellow solid (143 mg, 75%). ¹H NMR (400 MHz, DMSO-d₆) δ ppm 1.26 (d, J=5.49 Hz, 3H), 2.27 (s, 6H), 2.60 (d, J=15.57 Hz, 1H), 3.08 (d, J=14.28 Hz, 1H), 3.26-3.48 (m, 2H), 3.80 (s, 3H), 4.71-4.86 (m, 1H), 6.24 (dd, J=3.11, 1.65 Hz, 1H), 6.89 (t, J=9.25 Hz, 1H), 6.98 (s, 2H), 7.23-7.43 (m, 1H), 7.56 (s, 1H), 8.03 (s, 1H), 8.11 (s, 1H), 8.49 (d, J=8.24 Hz, 1H), 8.63 (s, 1H), 10.53 (s, 1H), 11.33 (s, 1H); ESIMS (M+H)+= 533.36; Optical rotation +14.4 (1 mg/mL MeOH, rt).

Example 249

2-[(2-{[(2S)-1-(N,N-dimethylglycyl)-2-methyl-5-(methyloxy)-2,3-dihydro-1H-indol-6-yl]amino}-1H-pyrrolo[2,3-d]pyrimidin-4-yl)amino]-6-fluorobenzamide

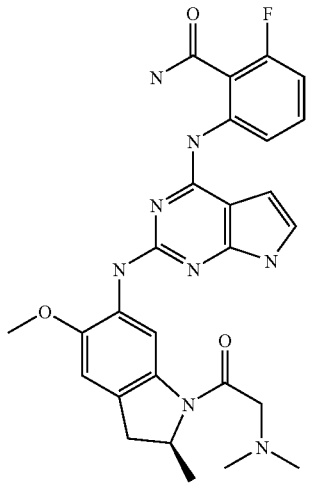

Step A/Intermediate D42: 2-({2-{[(2S)-1-(N,N-dimethylglycyl)-2-methyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluorobenzamide

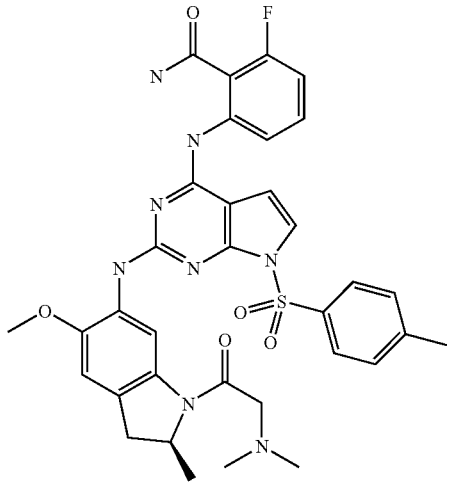

A slurry of 5-chloro-8-fluoro-3-[(4-methylphenyl)sulfonyl]pyrrolo[2',3':4,5]pyrimido[6,1-b]quinazolin-7(3H)-one hydrogen chloride (600 mg, 1.252 mmol) and (2S)-1-[(dimethylamino)acetyl]-2-methyl-5-(methyloxy)-2,3-dihydro-1H-indol-6-amine (330 mg, 1.252 mmol) in 2,2,2-trifluoroethanol (10 mL) was stirred at rt for 18 h The resulting bright green slurry was split into two equal batches. One of the batches was treated with a 27% aqueous NH₄OH solution (10 mL). The orange slurry was stirred at rt for 2 days. The resulting mixture was diluted with EtOAc (50 mL) and a saturated NaHCO₃ solution (50 mL). The organic layer was washed with a saturated NaCl solution (50 mL), concentrated onto Celite and purified by silica gel chromatography using 1-10% MeOH (containing 0.2% NH₃)/CH₂Cl₂ to afford 2-({2-{[(2S)-1-(N,N-dimethylglycyl)-2-methyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluorobenzamide as a yellow solid (220 mg, 51%). ¹H NMR (400 MHz, DMSO-d₆) δ ppm 1.18-1.32 (m, 3H), 2.27 (br s, 6H), 2.33 (s, 3H), 2.65 (d, J=15.57 Hz, 1H), 3.14 (d, J=14.47 Hz, 1H), 3.27-3.51 (m, 2H), 3.76 (s, 3H), 4.75-4.87 (m, 1H), 6.53 (d, J=4.03 Hz, 1H), 6.94 (t, J=9.06 Hz, 1H), 7.06 (s, 1H), 7.14-7.42 (m, 4H), 7.72-8.04 (m, 4H), 8.08 (d, J=8.42 Hz, 1H), 8.18 (s, 1H), 8.25 (s, 1H), 10.47 (s, 1H); ESIMS (M+H)+ =687.23

Step B/Example 249

2-[(2-{[(2S)-1-(N,N-dimethylglycyl)-2-methyl-5-(methyloxy)-2,3-dihydro-1H-indol-6-yl]amino}-1H-pyrrolo[2,3-d]pyrimidin-4-yl)amino]-6-fluorobenzamide A solution of 2-({2-{[(2S)-1-(N,N-dimethylglycyl)-2-methyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluorobenzamide (216 mg, 0.315 mmol) in dioxane (5 mL) and a 2M aqueous NaOH solution (10 mL) was heated at 80° C. for 5 h. The resulting mixture was allowed to cool to rt, diluted with EtOAc (50 mL) and a saturated NaCl solution (10 mL). The organic layer was concentrated onto Celite and purified by silica gel chromatography using 1-10% MeOH (containing 0.2% NH₃)/CH₂Cl₂ to afford 2-[(2-{[(2S)-1-(N,N-dimethylglycyl)-2-methyl-5-(methyloxy)-2,3-dihydro-1H-indol-6-yl]amino}-1H-pyrrolo[2,3-d]pyrimidin-4-yl)amino]-6-fluorobenzamide as a yellow solid (106 mg, 63%). ¹H NMR (400 MHz, DMSO-d₆) δ ppm 1.26 (d, J=5.49 Hz, 3H), 2.27 (s, 6H), 2.60 (d, J=15.57 Hz, 1H), 3.09 (d, J=14.28 Hz, 1H), 3.25-3.50 (m, 2H), 3.80 (s, 3H), 4.71-4.86 (m, 1H), 6.24 (dd, J=3.11, 1.65 Hz, 1H), 6.89 (t, J=9.25 Hz, 1H), 6.98 (s, 2H), 7.25-7.43 (m, 1H), 7.57 (s, 1H), 8.03 (s, 1H), 8.10 (s, 1H), 8.49 (d, J=8.24 Hz, 1H), 8.63 (s, 1H), 10.53 (s, 1H), 11.33 (s, 1H); ESIMS (M+H)+= 533.36; Optical rotation −13.1 (1 mg/mL MeOH, rt).

Example 250

2-[(2-{[(2R)-1-(N,N-dimethylglycyl)-2-methyl-5-(methyloxy)-2,3-dihydro-1H-indol-6-yl]amino}-1H-pyrrolo[2,3-d]pyrimidin-4-yl)amino]-6-fluoro-N-methylbenzamide

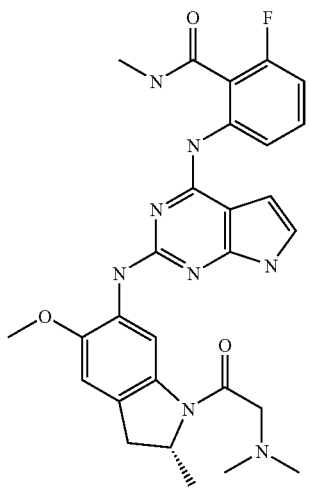

Step A/Intermediate D43: 2-({2-{[(2R)-1-(N,N-dimethylglycyl)-2-methyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-methylbenzamide

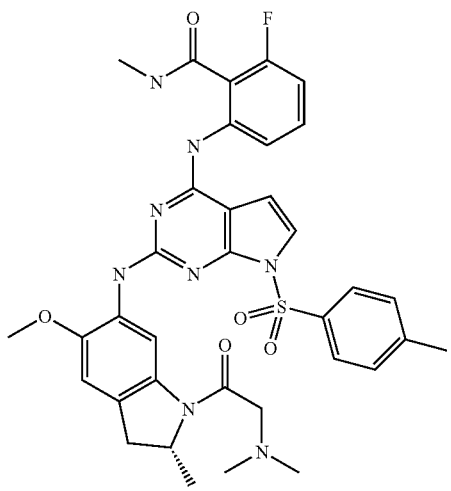

A slurry of 5-chloro-8-fluoro-3-[(4-methylphenyl)sulfonyl]pyrrolido[2',3':4,5]pyrimido[6,1-b]quinazolin-7(3H)-one hydrogen chloride (600 mg, 1.252 mmol) and (2R)-1-[(dimethylamino)acetyl]-2-methyl-5-(methyloxy)-2,3-dihydro-1H-indol-6-amine (330 mg, 1.252 mmol) in 2,2,2-trifluoroethanol (10 mL) was stirred at rt for 18 h. The resulting bright green slurry was split into two equal batches. One of the batches was treated with a 2M MeNH$_2$ solution in THF (10 mL). The orange slurry was stirred at rt for 2 days. The resulting mixture was diluted with EtOAc (50 mL) and a saturated NaCl solution (50 mL). The organic layer was washed with a saturated NaCl solution (50 mL), concentrated onto Celite and purified by silica gel chromatography using 1-10% MeOH (containing 0.2% NH$_3$)/CH$_2$Cl$_2$ to afford 2-({2-{[(2R)-1-(N,N-dimethylglycyl)-2-methyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-methylbenzamide as a light brown solid (281 mg, 64%). $^1$H NMR (400 MHz, DMSO-d$_6$) δ ppm 1.26 (s, 3H), 2.27 (s, 6H), 2.32 (s, 3H), 2.57-2.82 (m, 4H), 3.14 (d, J=14.47 Hz, 1H), 3.27-3.52 (m, 2H), 3.76 (s, 3H), 4.73-4.88 (m, 1H), 6.59 (d, J=4.03 Hz, 1H), 6.88-7.03 (m, 1H), 7.06 (s, 1H), 7.14-7.47 (m, 4H), 7.71-8.03 (m, 3H), 8.13 (s, 1H), 8.26 (s, 1H), 8.45 (d, J=3.48 Hz, 1H), 10.13 (s, 1H); ESIMS (M+H)+=701.31

Step B/Example 250

2-[(2-{[(2R)-1-(N,N-dimethylglycyl)-2-methyl-5-(methyloxy)-2,3-dihydro-1H-indol-6-yl]amino}-1H-pyrrolo[2,3-d]pyrimidin-4:yl)amino]-6-fluoro-N-methylbenzamide A solution of 2-({2-{[(2R)-1-(N,N-dimethylglycyl)-2-methyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-methylbenzamide (278 mg, 0.397 mmol) in dioxane (10 mL) and a 2M aqueous NaOH solution (2 mL) was heated at 80° C. for 6 h. The resulting mixture was allowed to cool to rt, diluted with EtOAc (50 mL) and a saturated NaCl solution (10 mL). The organic layer was concentrated onto Celite and purified by silica gel chromatography using 1-10% MeOH (containing 0.2% NH$_3$)/CH$_2$Cl$_2$ to afford 2-[(2-{[(2R)-1-(N,N-dimethylglycyl)-2-methyl-5-(methyloxy)-2,3-dihydro-1H-indol-6-yl]amino}-1H-pyrrolo[2,3-d]pyrimidin-4-yl)amino]-6-fluoro-N-methylbenzamide as a pink solid (172 mg, 79%). $^1$H NMR (400 MHz, DMSO-d$_6$) δ ppm 1.25 (d, J=5.68 Hz, 3H), 2.27 (s, 6H), 2.59 (d, J=15.57 Hz, 1H), 2.80 (d, J=4.58 Hz, 3H), 3.07 (d, J=14.28 Hz, 1H), 3.24-3.46 (m, 2H), 3.80 (s, 3H), 4.71-4.85 (m, 1H), 6.29 (dd, J=3.02, 1.74 Hz, 1H), 6.85-7.07 (m, 3H), 7.26-7.43 (m, 1H), 7.54 (s, 1H), 8.32 (d, J=8.24 Hz, 1H), 8.55 (dd, J=4.40, 1.65 Hz, 1H), 8.64 (s, 1H), 10.15 (s, 1H), 11.30 (s, 1H). ESIMS (M+H)+=547.43; Optical rotation +11.0 (1 mg/mL MeOH, rt).

Example 251

2-[(2-{[(2S)-1-(N,N-dimethylglycyl)-2-methyl-5-(methyloxy)-2,3-dihydro-1H-indol-6-yl]amino}-1H-pyrrolo[2,3-d]pyrimidin-4-yl)amino]-6-fluoro-N-methylbenzamide

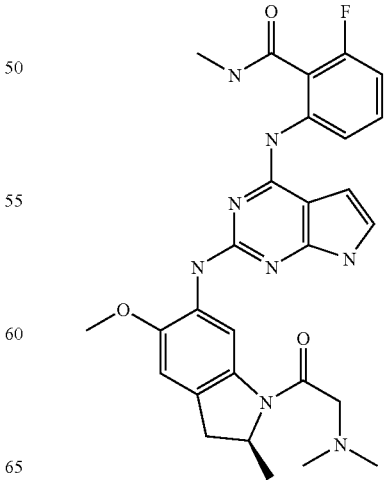

481

Step A/Intermediate D44: 2-({2-{[(2S)-1-(N,N-dimethylglycyl)-2-methyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-methylbenzamide

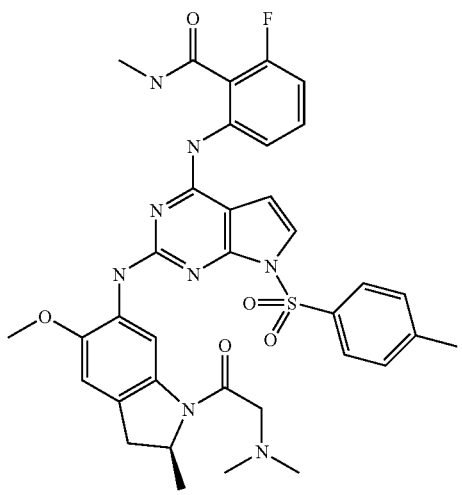

A slurry of 5-chloro-8-fluoro-3-[(4-methylphenyl)sulfonyl]pyrrolo[2',3':4,5]pyrimido[6,1-b]quinazolin-7(3H)-one hydrogen chloride (600 mg, 1.252 mmol) and (2S)-1-[(dimethylamino)acetyl]-2-methyl-5-(methyloxy)-2,3-dihydro-1H-indol-6-amine (330 mg, 1.252 mmol) in 2,2,2-trifluoroethanol (10 mL) was stirred at rt for 18 h The resulting bright green slurry was split into two equal batches. One of the batches was treated with a 2M MeNH$_2$ solution in THF (10 mL). The orange slurry was stirred at rt for 2 days. The resulting mixture was diluted with EtOAc (50 mL) and a saturated NaCl solution (50 mL). The organic layer was washed with a saturated NaCl solution (50 mL), concentrated onto Celite and purified by silica gel chromatography using 1-10% MeOH (containing 0.2% NH$_3$)/CH$_2$Cl$_2$ to afford 2-({2-{[(2S)-1-(N,N-dimethylglycyl)-2-methyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-methylbenzamide as a light brown solid (258 mg, 59%). $^1$H NMR (400 MHz, DMSO-d$_6$) δ ppm 1.27 (s, 3H), 2.27 (s, 6H), 2.32 (s, 3H), 2.57-2.87 (m, 4H), 3.15 (d, J=14.28 Hz, 1H), 3.28-3.54 (m, 2H), 3.76 (s, 3H), 4.73-4.87 (m, 1H), 6.59 (d, J=3.85 Hz, 1H), 6.89-7.03 (m, 1H), 7.06 (s, 1H), 7.15-7.41 (m, 4H), 7.71-8.02 (m, 3H), 8.13 (s, 1H), 8.26 (s, 1H), 8.45 (d, J=4.39 Hz, 1H), 10.12 (s, 1H); ESIMS (M+H)+= 701.28.

Step B/Example 251

2-[(2-{[(2S)-1-(N,N-dimethylglycyl)-2-methyl-5-(methyloxy)-2,3-dihydro-1H-indol-6-yl]amino}-1H-pyrrolo[2,3-d]pyrimidin-4-yl)amino]-6-fluoro-N-methylbenzamide A solution of 2-({2-{[(2S)-1-(N,N-dimethylglycyl)-2-methyl-5-(methyloxy)-2,3-dihydro-1H-indol-6-yl]amino}-7-[(4-methylphenyl)sulfonyl]-7H-pyrrolo[2,3-d]pyrimidin-4-yl}amino)-6-fluoro-N-methylbenzamide (254 mg, 0.362 mmol) in dioxane (10 mL) and a 2M aqueous NaOH solution (2 mL) was heated at 80° C. for 6 h. The resulting mixture was allowed to cool to rt, diluted with EtOAc (50 mL) and a saturated NaCl solution (10 mL). The organic layer was concentrated onto Celite and purified by silica gel chromatography using 1-10% MeOH (containing 0.2% NH$_3$)/CH$_2$Cl$_2$ to afford 2-[(2-{[(2S)-1-(N,N-dimethylglycyl)-2-methyl-5-(methyloxy)-2,3-dihydro-1H-indol-6-yl]amino}-1H-pyrrolo[2,3-d]pyrimidin-4-yl)amino]-6-fluoro-N-methylbenzamide as a pink solid (144 mg, 73%). $^1$H NMR (400 MHz, DMSO-d$_6$) δ ppm 1.25 (d, J=5.49 Hz, 3H), 2.27 (s, 6H), 2.59 (d, J=15.57 Hz, 1H), 2.80 (d, J=4.40 Hz, 3H), 3.08 (d, J=14.28 Hz, 1H), 3.21-3.46 (m, 2H), 3.80 (s, 3H), 4.71-4.85 (m, 1H), 6.27-6.34 (m, 1H), 6.83-7.08 (m, 3H), 7.26-7.44 (m, 1H), 7.54 (s, 1H), 8.33 (d, J=8.06 Hz, 1H), 547.40; Optical rotation −11.4 (1 mg/mL MeOH, rt).

Example 252

2-[(2-{[1-(N,N-dimethylglycyl)-5-(methyloxy)-2,3-dihydro-1H-indol-6-yl]amino}-5-fluoro-1H-pyrrolo[2,3-d]pyrimidin-4-yl) amino]-6-fluorobenzamide

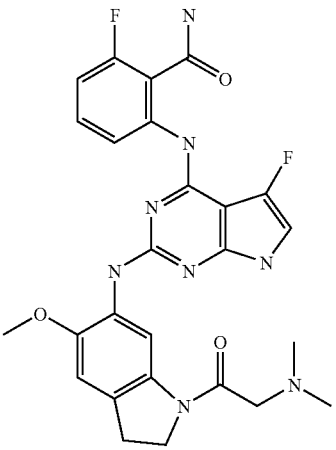

Step A/Intermediate D45:
2,4-dichloro-5-fluoro-7H-pyrrolo[2,3-d]pyrimidine

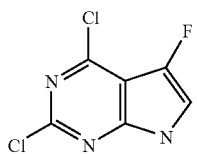

A solution of 2,4-dichloro-1H-pyrrolo[2,3-d]pyrimidine (7 g, 37.2 mmol) and Selectofluor (16.49 g, 46.5 mmol) in acetonitrile (150 ml)/acetic acid (30 ml) was warmed to 80° C. with stirring for 3 hours. The reaction was poured into cold water (800 mL),left to crystalize for 45 minutes, filtered, and solids analyzed (NMR: N2869-100-1, crop 1). A second crop of crystals was collected after additional cooling to 0° C. for 4 hours. Combined solids afford 2,4-dichloro-5-fluoro-1H-pyrrolo[2,3-d]pyrimidine (1.56 g, 7.57 mmol, 20.34% yield) with roughly 80% purity as a brown solid.

Step B/Intermediate D46: 2,4-dichloro-5-fluoro-7-[(4-methylphenyl)sulfonyl]-7H-pyrrolo[2,3-d]pyrimidine

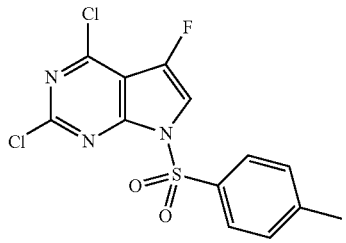

A solution of 2,4-dichloro-5-fluoro-1H-pyrrolo[2,3-d]pyrimidine (1.65 g, 8.01 mmol, crude material from abovefl) in dichloromethane (100 ml) was treated with DIPEA (2.80 ml, 16.02 mmol) and p-toluenesulfonylchloride (1.756 g, 9.21 mmol) and stirred for 24 hours. The mixture was poured into saturated sodium bicarbonate/DCM and the organic layer was dried over sodium sulfate, filtered, stripped onto celite, and purified by column chromatography (10% EtOAc/Hex). The chromatographic residue (still containing multiple impurities) was further purified with a 65% isocratic MeCN mobile phase on a Luna C18 5 um, 21×150mm column, 20 mL/min, UV @275 nm. The final purity of 2,4-dichloro-5-fluoro-7-[(4-methylphenyl)sulfonyl]-7H-pyrrolo[2,3-d]pyrimidine was estimated at 99.5% at 254 nm using the same method (1.128 g). $^1$H NMR (400 MHz, DMSO-$d_6$) δ ppm 8.23 (d, J=2.20 Hz, 1H), 7.96 (d, J=8.24 Hz, 2H), 7.47 (d, J=8.79 Hz, 2H), 2.34 (s, 3H).

Step C/Intermediate D47: 2-({2-chloro-5-fluoro-7-[(4-methylphenyl)sulfonyl]-7H-pyrrolo[2,3-d]pyrimidin-4-yl}amino)-6-fluorobenzoic acid

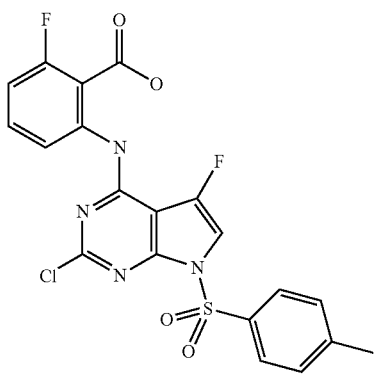

A slurry of 2,4-dichloro-5-fluoro-7-[(4-methylphenyl)sulfonyl]-7H-pyrrolo[2,3-d]pyrimidine (1.250 g, 3.47 mmol) DIPEA (3.03 mL, 17.35 mmol) and 2-amino-6-fluorobenzoic acid (0.646 g, 4.16 mmol) in iPrOH (30 mL) was heated at 90° C. for 3 h. The resulting mixture was allowed to cool to rt and diluted with EtOAc (100 mL) and a 1N HCl solution (100 mL). The organic layer was washed with a saturated NaHCO$_3$ solution (100 mL) and a saturated NaCl solution (100 mL). The organic layer was diluted with Et$_2$O and the resulting slurry filtered. The solids were washed with Et$_2$O and dried in vacuum to afford 2-({2-chloro-5-fluoro-7-[(4-methylphenyl) sulfonyl]-7H-pyrrolo[2,3-d]pyrimidin-4-yl}amino)-6-fluorobenzoic acid (0.69 g, 41%). $^1$H NMR (400 MHz, DMSO-$d_6$) δ ppm 2.38 (s, 3H), 6.71-6.87 (m, 1H), 7.21-7.36 (m, 1H), 7.48 (d, J=8.06 Hz, 2H), 7.76 (s, 1H), 7.96 (d, J=8.42 Hz, 2H), 8.26 (d, J=8.61 Hz, 1H).

Step D/Intermediate D48: 5-chloro-1,8-difluoro-3-[(4-methylphenyl)sulfonyl]pyrrolo[2',3':4,5]pyrimido[6,1-b]quinazolin-7(3H)-one hydrogen chloride

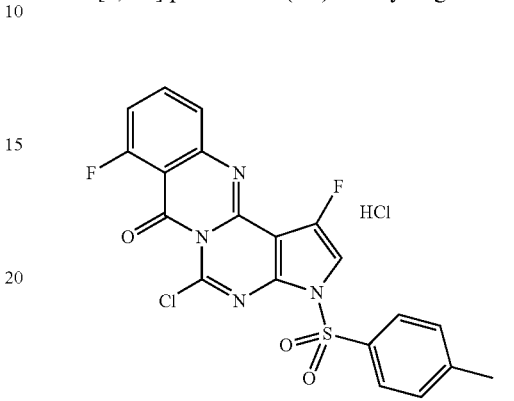

A slurry of 2-({2-chloro-5-fluoro-7-[(4-methylphenyl)sulfonyl]-7H-pyrrolo[2,3-d]pyrimidin-4-yl}amino)-6-fluorobenzoic acid (0.68 g, 1.420 mmol) in THF (100 mL) was treated with a drop of DMF, followed by a solution of oxalyl chloride (2M in CH$_2$Cl$_2$, 2.84 mL, 5.48 mmol). After 30 min Et$_2$O (50 mL) was added. The resulting slurry was filtered and the solids were washed with Et$_2$O, then dried in vacuum to obtain 5-chloro-1,8-difluoro-3-[(4-methylphenyl)sulfonyl]pyrrolo[2',3':4,5]pyrimido[6,1-b]quinazolin-7(3H)-one hydrogen chloride as a pale yellow solid (580 mg, 82%). $^1$H NMR (400 MHz, THF-$d_8$) δ ppm 2.41 (s, 3H), 7.14 (dd, J=10.07, 8.61 Hz, 1H), 7.45 (d, 8.06 Hz, 3H), 7.56 (d, J=2.56 Hz, 1H), 7.69-7.83 (m, 1H), 8.09 (d, J=8.42 Hz, 2H), 10.84 (br s, 1H); ESIMS (M+H)$^+$=460.98.

Step E/Example 252

2-[(2-{[1-(N,N-dimethylglycyl)-5-(methyloxy)-2,3-dihydro-1H-indol-6-yl]amino}-5-fluoro-1H-pyrrolo[2,3-d]pyrimidin-4-yl)amino]-6-fluorobenzamide A yellow slurry of 5-chloro-1,8-difluoro-3-[(4-methylphenyl)sulfonyl]pyrrolo[2',3':4,5]pyrimido[6,1-b]quinazolin-7(3H)-one hydrogen chloride (578 mg, 1.162 mmol) and 1-[(dimethylamino)acetyl]-5-(methyloxy)-2,3-dihydro-1H-indol-6-amine (290 mg, 1.162 mmol) in THF (110 mL) was stirred at rt for 18 h. 80 mL of the resulting mixture was treated with a 27% aqueous NH$_4$OH solution (100 mL). The reaction mixture was stirred at rt for 4 h. EtOAc (200 mL) and a saturated NaCl solution (50 mL) were added. The organic layer was washed with a saturated NaCl solution (2×100 mL), dried (Na$_2$SO$_4$) and concentrated. The residue was triturated with CH$_2$Cl$_2$ and Et$_2$O. The crude intermediate was taken up into dioxane (10 mL) and treated with a 1N aqueous KOH solution (3 mL, 3.00 mmol). The reaction mixture was heated at 80° C. for 1 h. EtOAc (100 mL) and a saturated NaHCO$_3$ solution (50 mL) were added. The organic layer was washed with a saturated NaCl solution (50 mL), concentrated onto Celite and purified by silica gel chromatography using 1-10% MeOH (containing 0.2% NH$_3$)/CH$_2$Cl$_2$ to obtain 2-[(2-{[1-(N,N-dimethylglycyl)-5-(methyloxy)-2,3-dihydro-1H-indol-6-yl]amino}-5-fluoro-1H-pyrrolo[2,3-d]pyrimidin-4-yl) amino]-6-fluorobenzamide as a pale yellow solid (80 mg). $^1$H NMR (400 MHz, DMSO-$d_6$) δ ppm 2.25 (s, 6H), 3.06-3.25 (m, 4H), 3.75 (s, 3H), 4.18 (t, J=8.33 Hz, 2H), 6.75-6.94 (m, 2H), 6.98 (s, 1H), 7.18-7.34 (m, 1H), 7.84 (s, 1H), 8.05 (s, 1H), 8.14 (s, 1H), 8.45 (s, 1H), 8.60 (d, J=8.42 Hz, 1H), 10.26 (s, 1H), 11.02 (s, 1H); ESIMS (M+H)$^+$=537.27.

Example 253

2-[(2-{[1-(N,N-dimethylglycyl)-5-(methyloxy)-2,3-dihydro-1H-indol-6-yl]amino}-5-fluoro-1H-pyrrolo[2,3-d]pyrimidin-4-yl)amino]-6-fluoro-N-methylbenzamide

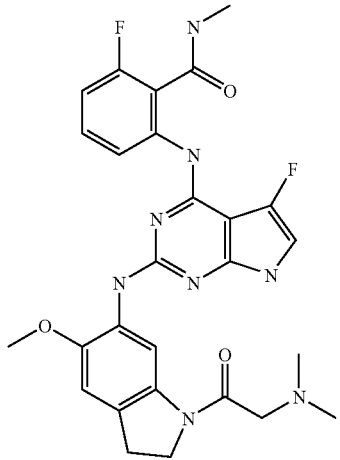

Step A/Intermediate D49: 2-({2-{[1-(N,N-dimethylglycyl)-5-(methyloxy)-2,3-dihydro-1H-indol-6-yl]amino}-5-fluoro-7-[(4-methylphenyl)sulfonyl]-7H-pyrrolo[2,3-d]pyrimidin-4-yl}amino)-6-fluoro-N-methylbenzamide

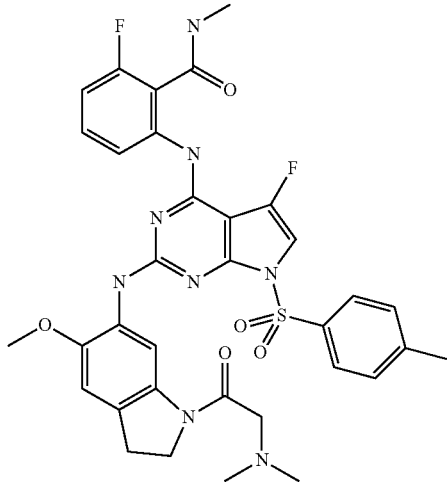

The remaining 30 mL solution left over from the synthesis of 2-[(2-{[1-(N,N-dimethylglycyl)-5-(methyloxy)-2,3-dihydro-1H-indol-6-yl]amino}-5-fluoro-1H-pyrrolo[2,3-d]pyrimidin-4-yl)amino]-6-fluorobenzamide was treated with a solution of MeNH$_2$ (2M in THF, 3.16 mL, 6.32 mmol). The reaction mixture was stirred at rt for 4 h and diluted with EtOAc (100 mL). The organic layer was washed with a saturated NaCl solution (2×50 mL), dried (Na$_2$SO$_4$) and concentrated. The residue was triturated using CH$_2$Cl$_2$ and Et$_2$O to obtain 2-({2-{[1-(N,N-dimethylglycyl)-5-(methyloxy)-2,3-dihydro-1H-indol-6-yl]amino}-5-fluoro-7-[(4-methylphenyl)sulfonyl]-7H-pyrrolo[2,3-d]pyrimidin-4-yl}amino)-6-fluoro-N-methylbenzamide as a beige solid (112 mg, 50%). $^1$H NMR (400 MHz, DMSO-$d_6$) δ ppm 2.25 (s, 6H), 2.35 (s, 3H), 2.77 (d, J=4.4 Hz, 3H), 3.12-3.28 (m, 4H), 3.72 (s, 3H), 4.22 (d, J=8.42 Hz, 2H), 6.91 (t, J=9.43 Hz, 1H), 7.08 (s, 1H), 7.14-7.26 (m, 1H), 7.27-7.43 (m, 3H), 7.92 (d, J=6.78 Hz, 2H), 8.11 (s, 1H), 8.27 (d, J=7.51 Hz, 1H), 8.57 (d, J=3.11 Hz, 1H), 8.65 (s, 1H), 10.08 (s, 1H); ESIMS (M+H)$^+$=705.30.

Step B/Example 253

2-[(2-{[1-(N,N-dimethylglycyl)-5-(methyloxy)-2,3-dihydro-1H-indol-6-yl]amino}-5-fluoro-1H-pyrrolo[2,3-d]pyrimidin-4-yl)amino]-6-fluoro-N-methylbenzamide A solution of 2-({2-{[1-(N,N-dimethylglycyl)-5-(methyloxy)-2,3-dihydro-1H-indol-6-yl]amino}-5-fluoro-7-[(4-methylphenyl)sulfonyl]-7H-pyrrolo[2,3-d]pyrimidin-4-yl}amino)-6-fluoro-N-methylbenzamide (102 mg, 0.15 mmol) in dioxane (10 mL) and a 1N aqueous KOH solution (2 mL, 2.0 mmol) was heated at 80° C. for 6 h. The resulting mixture was allowed to cool to rt and diluted with EtOAc (50 mL) and a saturated NaHCO$_3$ solution (50 mL). The organic layer was washed with a saturated NaCl solution (50 mL), concentrated onto Celite and purified by silica gel chromatography using 1-10% MeOH (containing 0.2% NH$_3$)/CH$_2$Cl$_2$ to obtain 2-[(2-{[1-(N,N-dimethylglycyl)-5-(methyloxy)-2,3-dihydro-1H-indol-6-yl]amino}-5-fluoro-1H-pyrrolo[2,3-d]pyrimidin-4-yl)amino]-6-fluoro-N-methylbenzamide as a brown solid (44 mg, 55%). $^1$H NMR (400 MHz, THF-$d_8$) δ ppm 2.31 (s, 6H), 2.93 (d, J=4.58 Hz, 3H), 3.06 (t, J=8.24 Hz, 2H), 3.14 (s, 2H), 3.84 (s, 3H), 4.18 (t, J=8.33 Hz, 2H), 6.64 (s, 1H), 6.67-6.85 (m, 2H), 7.22-7.49 (m, 2H), 7.77 (br s, 1H), 8.75 (d, J=8.61 Hz, 1H), 9.35 (s, 1H), 10.50 (s, 1H), 10.76 (s, 1H); ESIMS (M+H)$^+$=551.24.

Example 254

2-[(2-{[5-[(N,N-dimethylglycyl)(methyl)amino]-4-methyl-2-(methyloxy)phenyl]amino}-1H-pyrrolo[2,3-d]pyrimidin-4-yl)amino]-6-fluoro-N-methylbenzamide

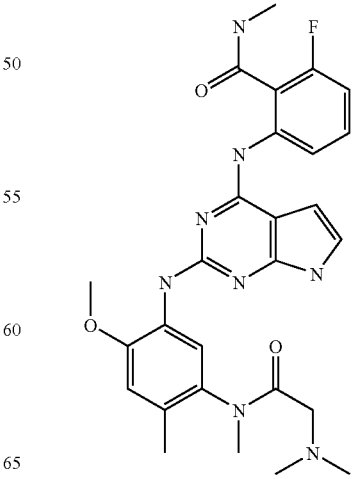

To a suspension of 5-chloro-8-fluoro-3-[(4-methylphenyl)sulfonyl]pyrrolo[2',3':4,5]pyrimido[6,1-b]quinazolin-7(3H)-one HCl salt (0.5 g, 1.04 mmol) in 2,2,2-trifluoroethanol (10 mL) was added N1-[5-amino-2-methyl-4-(methyloxy)phenyl]-N1,N2,N2-trimethylglycinamide (0.275 g, 1.10 mmol). The resulting mixture was let stir at 50° C. for 90 min. Solvents were then removed under reduced pressure to afford a brown residue. Half of this material was dissolved in THF (10 mL) and a 2M solution of methyl amine in THF (2.5 mL, 4.90 mmol) was added. After stirring at rt for 30 min, the reaction was diluted with EtOAc and the organic layer was washed with water and a saturated brine solution and dried over sodium sulfate. Solvents were removed under reduced pressure and the residue purified by chromatography on $SiO_2$. This material was dissolved in dioxane (6 mL) and 2N NaOH (4 mL) was added in a microwave safe vessel. The reaction was heated in a microwave at 120° C. for 15 min. The reaction was diluted with EtOAc and the organic layer was washed with water and a saturated brine solution and dried over sodium sulfate. Solvents were removed under reduced pressure and the residue purified by chromatography on $SiO_2$ to afford 2-[(2-{[5-[(N,N-dimethylglycyl)(methyl)amino]-4-methyl-2-(methyloxy)phenyl]amino}-1H-pyrrolo[2,3-d]pyrimidin-4-yl)amino]-6-fluoro-N-methylbenzamide (119 mg, 0.223 mmol) as a beige solid. $^1$H NMR (400 MHz, DMSO-$d_6$) δ ppm 2.10 (s, 6 H) 2.12 (s, 3 H) 2.61 (d, J=15.75 Hz, 1 H) 2.77 (d, J=4.58 Hz, 3 H) 2.83 (d, J=15.75 Hz, 1 H) 3.03 (s, 3 H) 3.91 (s, 3 H) 6.34 (dd, J=3.11, 1.83 Hz, 1 H) 6.93-7.05 (m, 3 H) 7.44 (d, J=6.59 Hz, 1 H) 7.52 (s, 1 H) 8.16 (d, J=8.42 Hz, 1 H) 8.27 (s, 1 H) 8.54 (d, J=3.85 Hz, 1 H) 10.06 (s, 1H) 11.44 (br. s., 1H). ESIMS (M+H)$^+$=535.

Example 255

2-[(2-{[5-[(N,N-dimethylglycyl)(methyl)amino]-4-methyl-2-(methyloxy)phenyl]amino}-1H-pyrrolo[2,3-d]pyrimidin-4-yl)amino]-6-fluorobenzamide

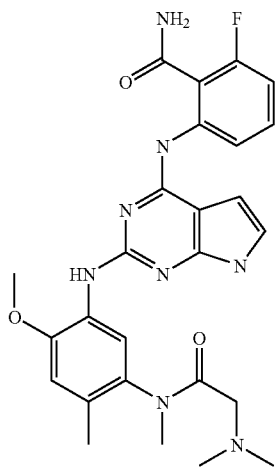

To a suspension of 5-chloro-8-fluoro-3-[(4-methylphenyl)sulfonyl]pyrrolo[2',3':4,5]pyrimido[6,1-b]quinazolin-7(3H)-one HCl salt (0.5 g, 1.04 mmol) in 2,2,2-trifluoroethanol (10 mL) was added N1-[5-amino-2-methyl-4-(methyloxy)phenyl]-N1,N2,N2-trimethylglycinamide (0.275 g, 1.10 mmol). The resulting mixture was let stir at 50° C. for 90 min. Solvents were then removed under reduced pressure to afford a brown residue. Half of this material was then dissolved in THF (10 mL) and aqueous ammonium hydroxide (27%) (30 mL, excess) was added. After stirring at 30° C. for 24 h and rt for 18 h, the reaction was diluted with ethyl acetate and the organic layer was washed with water and a saturated brine solution and dried over sodium sulfate. Solvents were removed under reduced pressure and the residue purified by chromatography on $SiO_2$. This material was dissolved in dioxane (6 mL) and 2N NaOH (4 mL) was added in a microwave safe vessel. The reaction was then heated in a microwave at 120° C. for 15 min. The reaction was diluted with EtOAc and the organic layer was washed with water and saturated brine solution and dried over sodium sulfate. Solvents were removed under reduced pressure and the residue purified by chromatography on $SiO_2$ to afford 2-[(2-{[5-[(N,N-dimethylglycyl)(methyl)amino]-4-methyl-2-(methyloxy)phenyl]amino}-1H-pyrrolo[2,3-d]pyrimidin-4-yl)amino]-6-fluorobenzamide (95 mg, 0.182 mmol) as a light green solid. $^1$H NMR (400 MHz, DMSO-$d_6$) δ ppm 2.10 (s, 6 H) 2.13 (s, 3 H) 2.62 (d, J=15.57 Hz, 1 H) 2.83 (d, J=15.57 Hz, 1 H) 3.04 (s, 3 H) 3.91 (s, 3 H) 6.29 (dd, J=3.20, 1.74 Hz, 1 H) 6.91-7.00 (m, 2H) 7.00-7.07 (m, 1 H) 7.45 (d, J=6.78 Hz, 1 H) 7.54 (s, 1 H) 7.96-8.11 (m, 2 H) 8.23-8.34 (m, 2H) 10.38 (s, 1 H) 11.47 (br. s., 1 H). ESIMS (M+H)$^+$=521.

Example 256

2-[(2-{[5-[(N,N-dimethylglycyl)amino]-4-methyl-2-(methyloxy)phenyl]amino}-1H-pyrrolo[2,3-d]pyrimidin-4-yl)amino]-6-fluoro-N-methylbenzamide

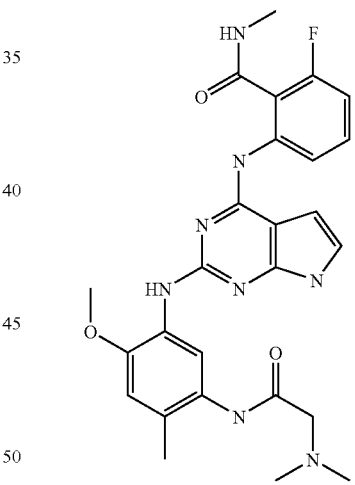

To a suspension of 5-chloro-8-fluoro-3-[(4-methylphenyl)sulfonyl]pyrrolo[2',3':4,5]pyrimido[6,1-b]quinazolin-7(3H)-one HCl salt (375 mg, 0.782 mmol) in 2,2,2-trifluoroethanol (10 mL) was added N1-[5-amino-2-methyl-4-(methyloxy)phenyl]-N2,N2-dimethylglycinamide (204 mg, 0.861 mmol). The resulting mixture was let stir at 60° C. for 45 min. Solvents were removed under reduced pressure to afford a green residue. Half of this material was dissolved in THF (10 mL) and a 2M solution of methylamine in THF (3.88 ml, 7.77 mmol) was added. After stirring at rt for 18 h, the reaction was diluted with EtOAc and the organic layer was washed with water and a saturated brine solution and dried over sodium sulfate. Solvents were removed under reduced pressure. The residue was dissolved in dioxane (6 mL) in a microwave safe vessel and 2N NaOH (3 mL) was added. The reaction was then heated in a microwave at 120° C. for 25 min. The reaction was diluted with EtOAc and the organic layer was washed with water and saturated brine solution and dried over sodium sulfate. Solvents were removed under reduced pressure and the residue purified by chromatography on SiO$_2$ to afford 2-[(2-{[5-[(N,N-dimethylglycyl)amino]-4-methyl-2-(methyloxy)phenyl]amino}-1H-pyrrolo[2,3-d]pyrimidin-4-yl)amino]-6-fluoro-N-methylbenzamide (124 mg, 0.238 mmol) as a tan solid. 1H NMR (400 MHz, DMSO-d$_6$) δ ppm 2.16 (s, 3 H) 2.31 (s, 6H) 2.79 (d, J=4.58 Hz, 3 H) 3.01 (s, 2 H) 3.83 (s, 3 H) 6.29 (dd, J=3.11, 1.83 Hz, 1 H) 6.83-7.02 (m, 3 H) 7.38-7.53 (m, 2 H) 8.16 (s, 1 H) 8.31 (d, J=8.24 Hz, 1 H) 8.55 (d, J=2.75 Hz, 1 H) 9.17 (s, 1 H) 10.16 (s, 1 H) 11.34 (s, 1 H). ESIMS (M+H)$^+$=521.

Example 257

2-[(2-{[5-[(N,N-dimethylglycyl)amino]-4-methyl-2-(methyloxy)phenyl]amino}-1H-pyrrolo[2,3-d]pyrimidin-4-yl)amino]-6-fluorobenzamide

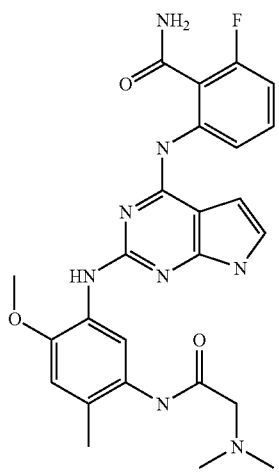

To a suspension of 5-chloro-8-fluoro-3-[(4-methylphenyl) sulfonyl]pyrrolo[2',3':4,5]pyrimido[6,1-b]quinazolin-7(3H)-one HCl salt (375 mg, 0.782 mmol) in 2,2,2-trifluoroethanol (10 mL) was added N1-[5-amino-2-methyl-4-(methyloxy)phenyl]-N2,N2-dimethylglycinamide (204 mg, 0.861 mmol). The resulting mixture was let stir at 60° C. for 45 min. Solvents were removed under reduced pressure to afford a green residue. Half of this material was dissolved in THF (10 mL) and aqueous ammonium hydroxide (27%) (30 mL, excess) was added. After stirring at rt for ~36 h, the reaction was diluted with EtOAc and the organic layer was washed with water and a saturated brine solution and dried over sodium sulfate. Solvents were removed under reduced pressure. The residue was dissolved in dioxane (6 mL) in a microwave safe vessel and 2N NaOH (4 mL) was added. The reaction was then heated in a microwave at 120° C. for 15 min and then diluted with EtOAc. The organic layer was washed with water and a saturated brine solution and dried over sodium sulfate. Solvents were removed under reduced pressure and the residue purified by chromatography on SiO$_2$ to afford 2-[(2-{[5-[(N,N-dimethylglycyl)amino]-4-methyl-2-(methyloxy)phenyl]amino}-1H-pyrrolo[2,3-d]pyrimidin-4-yl)amino]-6-fluorobenzamide (52 mg, 0.103 mmol) as a beige solid. 1H NMR (400 MHz, DMSO-d$_6$) δ ppm 2.17 (s, 3 H) 2.32 (s, 6 H) 3.03 (s, 2 H) 3.84 (s, 3H) 6.25 (dd, J=3.30, 1.65 Hz, 1 H) 6.86-6.97 (m, 2 H) 6.97-7.03 (m, 1 H) 7.40-7.49 (m, 1 H) 7.52 (s, 1 H) 8.04 (br. s., 1 H) 8.11 (s, 1 H) 8.16 (s, 1 H) 8.47 (d, J=8.42 Hz, 1 H) 9.19 (s, 1 H) 10.53 (s, 1 H) 11.37 (br. s., 1 H). ESIMS (M+H)$^+$=507.

Example 258

2-[(2-{[1-(N,N-dimethylglycyl)-5-(methyloxy)-2,3-dihydro-1H-indol-6-yl]amino}-5-methyl-1H-pyrrolo[2,3-d]pyrimidin-4-yl)amino]-6-fluoro-N-methylbenzamide

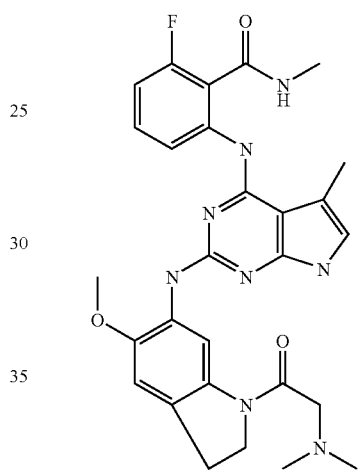

Step A\Intermediate D50:
2,4-dichloro-5-iodo-1H-pyrrolo[2,3-d]pyrimidine

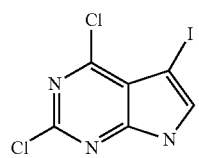

2,4-dichloro-1H-pyrrolo[2,3-d]pyrimidine (0.5 g, 2.66 mmol) was dissolved in anhydrous DMF (20 mL) and N-iodo succinimide (718 mg, 3.19 mmol) was added. After stirring for 45 minutes at rt, reaction mixture was poured into water (400 mL) and extracted with EtOAc (2×500 mL) Organics were combined and washed with brine (500 mL) and dried over sodium sulfate. Solvents were removed under reduced pressure and purified via column chromatography to afford 2,4-dichloro-5-iodo-1H-pyrrolo[2,3-d]pyrimidine (660 mg, 2.103 mmol) as a yellow solid. ESIMS (M+H)$^+$=315

Step B/Intermediate D51: 2,4-dichloro-5-iodo-7-[(4-methylphenyl)sulfonyl]-7H-pyrrolo[2,3-d]pyrimidine

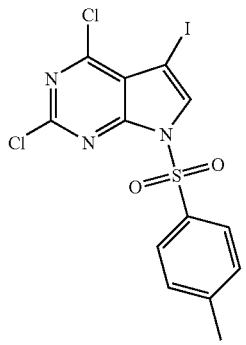

2,4-dichloro-5-iodo-1H-pyrrolo[2,3-d]pyrimidine (660 mg, 2.103 mmol) and tosyl-chloride (441 mg, 2.31 mmol) were combined in dry dichloromethane (20 ml). Diisopropylethylamine (0.734 mL, 4.21 mmol) was added and the reaction mixture was let stir at rt for 18 h. The reaction was then diluted with dichloromethane and the organic layer was washed with a saturated solution of sodium bicarbonate, water and a saturated solution of brine, then dried over sodium sulfate. Solvents were removed under reduced pressure and the residue purified by chromatography on $SiO_2$ to afford 2,4-dichloro-5-iodo-7-[(4-methylphenyl)sulfonyl]-7H-pyrrolo[2,3-d]pyrimidine (901 mg, 1.94 mmol) as a yellow solid. ESIMS $(M+H)^+=469$.

Step C/Intermediate D52: 2,4-dichloro-5-methyl-7-[(4-methylphenyl)sulfonyl]-7H-pyrrolo[2,3-d]pyrimidine

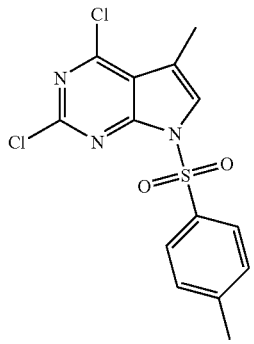

2,4-dichloro-5-iodo-7-[(4-methylphenyl)sulfonyl]-7H-pyrrolo[2,3-d]pyrimidine (800 mg, 1.71 mmol) and $Pd(PPh_3)_4$ (40 mg, 0.034 mmol) were combined in dry THF (20 ml) and a 2M solution of methylzinc chloride in THF (1.28 ml, 2.56 mmol) was added under $N_2$. The reaction mixture was let stir at 60° C. for 18 h at which time the reaction was diluted with ethyl acetate and the organic layer was washed with a saturated solution of sodium bicarbonate, water and a saturated brine solution, then dried over sodium sulfate. Solvents were removed under reduced pressure and the residue purified by chromatography on $SiO_2$ to afford 2,4-dichloro-5-methyl-7-[(4-methylphenyl)sulfonyl]-7H-pyrrolo[2,3-d]pyrimidine (487 mg, 1.37 mmol) as a tan solid. This reaction was repeated to synthesize sufficient material as needed for subsequent reactions. ESIMS $(M+H)^+=357$.

Step D/Intermediate D53: 5-chloro-8-fluoro-1-methyl-3-[(4-methylphenyl)sulfonyl]pyrrolo[2',3':4,5]pyrimido[6,1-b]quinazolin-7(3H)-one HCl salt

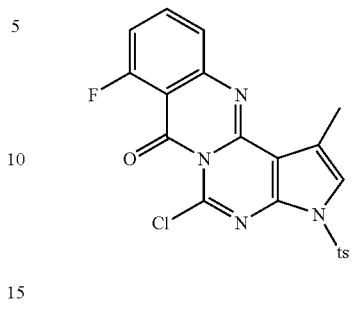

To a suspension of 2,4-dichloro-5-methyl-7-[(4-methylphenyl)sulfonyl]-7H-pyrrolo[2,3-d]pyrimidine (535 mg, 1.50 mmol) and 2-amino-6-fluorobenzoic acid (233 mg, 1.50 mmol) in isopropanol (5 mL) was added diisopropylethylamine (971 mg, 7.51 mmol) and the mixture was heated at 85° C. for ~48 h. At this time the reaction was diluted with ethyl acetate (100 ml) and washed with a solution of 1N HCl, a saturated solution of sodium bicarbonate and a saturated solution of NaCl, then dried over sodium sulfate. Solvents were removed under reduced pressure to afford a solid containing about 60% 2-({2-chloro-6-methyl-7-[(4-methylphenyl)sulfonyl]-7H-pyrrolo[2,3-d]pyrimidin-4-yl}amino)-6-fluorobenzoic acid (726 mg, 1.52 mmol). This material was dissolved in THF (10 mL) and DMF (few drops) and a solution of 2M oxalyl chloride in dichloromethane (0.90 mL, 1.80 mmol) was added dropwise. LCMS analysis indicated a small amount of starting material remained so an additional 0.1 eq of oxalyl chloride was added. The reaction mixture was cooled in an ice bath and filtered via a buchner funnel and the solid washed with THF. The solid was dried under reduced pressure to afford 5-chloro-8-fluoro-2-methyl-3-[(4-methylphenyl)sulfonyl]pyrrolo[2',3':4,5]pyrimido[6,1-b]quinazolin-7(3H)-one HCl salt (280 mg, 0.0.57 mmol). ESIMS $(M+H)^+=457$

Step E/Intermediate D54: 2-({2-{[1-(N,N-dimethylglycyl)-5-(methyloxy)-2,3-dihydro-1H-indol-6-yl]amino}-5-methyl-7-[(4-methylphenyl)sulfonyl]-7H-pyrrolo[2,3-d]pyrimidin-4-yl}amino)-6-fluoro-N-methylbenzamide

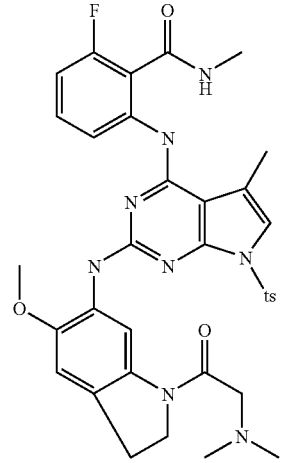

To a flask containing 5-chloro-8-fluoro-2-methyl-3-[(4-methylphenyl)sulfonyl]pyrrolo[2',3':4,5]pyrimido[6,1-b]quinazolin-7(3H)-one HCl salt (260 mg, 0.53 mmol) in 2,2,2-trifluoroethanol (5 mL) was added 1-[(dimethylamino)acetyl]-5-(methyloxy)-2,3-dihydro-1H-indol-6-amine (145 mg, 0.580 mmol). The resulting slurry was stirred at 80° C. for 16 h. Solvents were removed under reduced pressure to afford a green residue that was dissolved in THF (5 mL). A solution of 2M methyl amine in THF (2.64 mL, 5.27 mmol) was added and the reaction was let stir at rt for 1 h. The reaction mixture was then diluted with ethyl acetate and washed with a saturated solution of sodium bicarbonate, water and saturated brine solution. Organics were dried over sodium sulfate and solvents removed under reduced pressure to afford a solid that was purified via chromatography on SiO$_2$ to afford 2-({2-{[1-(N,N-dimethylglycyl)-5-(methyloxy)-2,3-dihydro-1H-indol-6-yl]amino}-5-methyl-7-[(4-methylphenyl)sulfonyl]-7H-pyrrolo[2,3-d]pyrimidin-4-yl}amino)-6-fluoro-N-methylbenzamide (225 mg, 0.321 mmol). ESIMS (M+H)$^+$=701.

Step F/Example 258: 2-[(2-{[1-(N,N-dimethylglycyl)-5-(methyloxy)-2,3-dihydro-1H-indol-6-yl]amino}-5-methyl-1H-pyrrolo[2,3-d]pyrimidin-4-yl)amino]-6-fluoro-N-methylbenzamide 2-({2-{[1-(N,N-dimethylglycyl)-5-(methyloxy)-2,3-dihydro-1H-indol-6-yl]amino}-5-methyl-7-[(4-methylphenyl)sulfonyl]-7H-pyrrolo[2,3-d]pyrimidin-4-yl}amino)-6-fluoro-N-methylbenzamide (225 mg, 0.321 mmol) was dissolved in dioxane (6 mL), 6N NaOH (2 mL) and water (2 mL) was added in a microwave safe vessel. The reaction was then heated in a microwave at 120° C. for 23 min. Reaction was diluted with EtOAc and the organic layer was washed with water and a saturated brine solution and dried over sodium sulfate. Solvents were removed under reduced pressure and the residue purified by chromatography on SiO$_2$ to afford 2-[(2-{[1-(N,N-dimethylglycyl)-5-(methyloxy)-2,3-dihydro-1H-indol-6-yl]amino}-5-methyl-1H-pyrrolo[2,3-d]pyrimidin-4-yl)amino]-6-fluoro-N-methylbenzamide (124 mg, 0.227 mmol) as an off white solid. $^1$H NMR (400 MHz, DMSO-d$_6$) δ ppm 2.25 (s, 6 H) 2.41 (s, 3 H) 2.81 (d, J=4.39 Hz, 3 H) 3.12 (t, J=8.24 Hz, 2 H) 3.17 (s, 2 H) 3.76 (s, 3 H) 4.18 (t, J=8.33 Hz, 2 H) 6.68 (s, 1 H) 6.86 (t, J=9.25 Hz, 1 H) 6.95 (s, 1 H) 7.25 (d, J=7.14 Hz, 1 H) 7.52 (s, 1 H) 8.45 (d, J=8.42 Hz, 1 H) 8.57 (s, 1 H) 8.66 (d, J=4.39 Hz, 1 H) 9.44 (s, 1 H) 10.92 (s, 1 H). ESIMS (M+H)$^+$=547.

Example 259

2-[(2-{[1-(N,N-dimethylglycyl)-5-(methyloxy)-2,3-dihydro-1H-indol-6-yl]amino}-5-methyl-1H-pyrrolo[2,3-d]pyrimidin-4-yl)amino]-6-fluorobenzamide

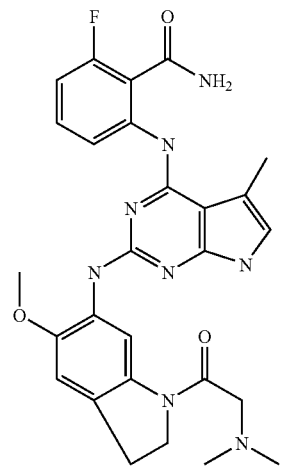

Step A/Intermediate D55: 2-({2-{[1-(N,N-dimethylglycyl)-5-(methyloxy)-2,3-dihydro-1H-indol-6-yl]amino}-5-methyl-7-[(4-methylphenyl)sulfonyl]-7H-pyrrolo[2,3-d]pyrimidin-4-yl}amino)-6-fluorobenzamide

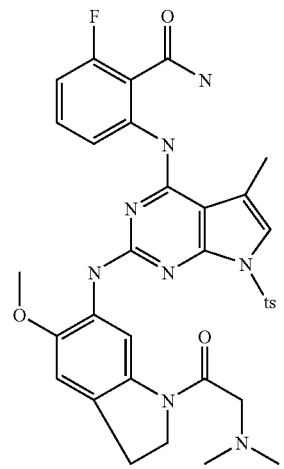

To a flask containing 5-chloro-8-fluoro-2-methyl-3-[(4-methylphenyl)sulfonyl]pyrrolo[2',3':4,5]pyrimido[6,1-b]quinazolin-7(3H)-one HCl salt (200 mg, 0.405 mmol) in 2,2,2-trifluoroethanol (5 mL) was added 1-[(dimethylamino)acetyl]-5-(methyloxy)-2,3-dihydro-1H-indol-6-amine (111 mg, 0.446 mmol). The resulting slurry was stirred at 80° C. for 6 h. Solvents were removed under reduced pressure to afford a green residue that was dissolved in THF (5 mL). An excess of aqueous ammonium hydroxide (5 ml) was added and the reaction was let stir at rt overnight. The reaction was not complete in the morning so it was transferred to a larger flask and 20 ml of ammonium hydroxide was added and let stir for an additional 24 h. At this time the reaction mixture was diluted with ethyl acetate and washed with a saturated solution of sodium bicarbonate, water and saturated brine solution. Organics were dried over sodium sulfate and solvents removed under reduced pressure to afford a solid that was purified via chromatography on SiO$_2$ to afford 2-({2-{[1-(N,N-dimethylglycyl)-5-(methyloxy)-2,3-dihydro-1H-indol-6-yl]amino}-5-methyl-7-[(4-methylphenyl)sulfonyl]-7H-pyrrolo[2,3-d]pyrimidin-4-yl}amino)-6-fluorobenzamide (194 mg, 0.282 mmol) as a yellow foam. ESIMS (M+H)$^+$=687.

Step B/Example 259

2-[(2-{[1-(N,N-dimethylglycyl)-5-(methyloxy)-2,3-dihydro-1H-indol-6-yl]amino}-5-methyl-1H-pyrrolo[2,3-d]pyrimidin-4-yl)amino]-6-fluorobenzamide 2-({2-{[1-(N,N-dimethylglycyl)-5-(methyloxy)-2,3-dihydro-1H-indol-6-yl]amino}-5-methyl-7-[(4-methylphenyl)sulfonyl]-7H-pyrrolo[2,3-d]pyrimidin-4-yl}amino)-6-fluorobenzamide (194 mg, 0.282 mmol) was dissolved in dioxane (6 mL), 6N NaOH (2 mL) and water (2 mL) was added in a microwave safe vessel. The reaction was then heated in a microwave at 120° C. for 17 min. The reaction was diluted with EtOAc and the organic layer was washed with water and saturated brine solution and dried over sodium sulfate. Solvents were removed under reduced pressure and the residue purified by chromatography on SiO$_2$ to afford 2-[(2-{[1-(N,N-dimethylglycyl)-5-(methyloxy)-2,3-dihydro-1H-indol-6-yl]amino}-5-methyl-1H-pyrrolo[2,3-d]pyrimidin-4-yl)amino]-6-fluorobenzamide (104 mg, 0.195 mmol) as a pale yellow solid. 1H NMR (400 MHz, DMSO-d$_6$) δ ppm 2.25 (s, 6 H) 2.41 (s, 3 H) 3.08-3.17 (m, 4 H) 3.76 (s, 3 H) 4.18 (t, J=8.42 Hz, 2 H) 6.68 (s, 1 H) 6.85 (t, J=9.25 Hz, 1 H) 6.95 (s, 1H) 7.19-7.30 (m, 1 H) 7.52 (s, 1 H) 8.10 (d, J=15.93 Hz, 2 H) 8.48 (d, J=8.42 Hz, 1H) 8.57 (s, 1 H) 9.81 (s, 1 H) 10.92 (s, 1 H). ESIMS (M+H)$^+$=533.

Example 260

2-[(2-{[1-(N,N-dimethylglycyl)-6-(methyloxy)-1,2,3,4-tetrahydro-7-quinolinyl]amino}-5-methyl-1H-pyrrolo[2,3-d]pyrimidin-4-yl)amino]-6-fluoro-N-methylbenzamide

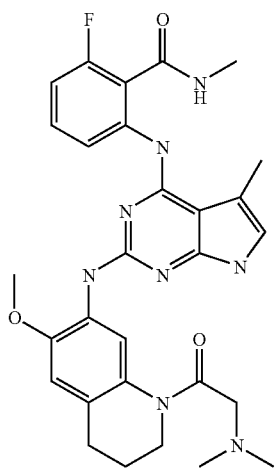

Step A/Intermediate D56: 2-({2-{[1-(N,N-dimethylglycyl)-6-(methyloxy)-1,2,3,4-tetrahydro-7-quinolinyl]amino}-5-methyl-7-[(4-methylphenyl)sulfonyl]-7H-pyrrolo[2,3-d]pyrimidin-4-yl}amino)-6-fluoro-N-methylbenzamide

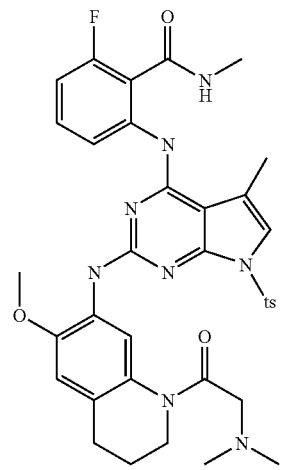

To a flask containing 5-chloro-8-fluoro-2-methyl-3-[(4-methylphenyl)sulfonyl]pyrrolo[2',3':4,5]pyrimido[6,1-b]quinazolin-7(3H)-one HCl salt (414 mg, 0.839 mmol) in 2,2,2-trifluoroethanol (5 mL) was added 1-[(dimethylamino)acetyl]-6-(methyloxy)-1,2,3,4-tetrahydro-7-quinolinamine (243 mg, 0.923 mmol). The resulting slurry was stirred at 80° C. for 16 h. Solvents were removed under reduced pressure to afford a green residue. Half of this material was dissolved in THF (5 mL) and a 2M solution of MeNH$_2$ in THF 2M (2.01 ml, 4.02 mmol) was added. The reaction was let stir at rt for 1 h and was then diluted with ethyl acetate and washed with a saturated solution of sodium bicarbonate, water and saturated brine solution. Organics were dried over sodium sulfate and solvents removed under reduced pressure to afford a solid that was purified via chromatography on SiO$_2$ to afford 2-({2-{[1-(N,N-dimethylglycyl)-6-(methyloxy)-1,2,3,4-tetrahydro-7-quinolinyl]amino}-5-methyl-7-[(4-methylphenyl)sulfonyl]-7H-pyrrolo[2,3-d]pyrimidin-4-yl}amino)-6-fluoro-N-methylbenzamide (249 mg, 0.348 mmol) as a yellow solid. ESIMS (M+H)$^+$=715.

Step B/Example 260: 2-[(2-{[1-(N,N-dimethylglycyl)-6-(methyloxy)-1,2,3,4-tetrahydro-7-quinolinyl]amino}-5-methyl-1H-pyrrolo[2,3-d]pyrimidin-4-yl)amino]-6-fluoro-N-methylbenzamide 2-({2-{[1-(N,N-dimethylglycyl)-6-(methyloxy)-1,2,3,4-tetrahydro-7-quinolinyl]amino}-5-methyl-7-[(4-methylphenyl)sulfonyl]-7H-pyrrolo[2,3-d]pyrimidin-4-yl}amino)-6-fluoro-N-methylbenzamide (249 mg, 0.348 mmol) was dissolved in dioxane (3 mL) and 2N NaOH (2 mL) was added in a microwave safe vessel. The reaction was then heated in a microwave at 120° C. for 17 min. Reaction was diluted with EtOAc and the organic layer was washed with water and a saturated brine solution and dried over sodium sulfate. Solvents were removed under reduced pressure and the residue purified by chromatography on SiO$_2$ to afford 2-[(2-{[1-(N,N-dimethylglycyl)-6-(methyloxy)-1,2,3,4-tetrahydro-7-quinolinyl]amino}-5-methyl-1H-pyrrolo[2,3-d]pyrimidin-4-yl)amino]-6-fluoro-N-methylbenzamide (132 mg, 0.235 mmol) as a pale yellow solid. $^1$H NMR (400 MHz, DMSO-$d_6$) δ ppm 1.83-1.93 (m, 2 H) 2.11 (br. s., 6 H) 2.42 (s, 3H) 2.68 (br. s., 2 H) 2.81 (d, J=4.49 Hz, 3 H) 3.21 (s, 2 H) 3.66-3.74 (m, 2 H) 3.84 (s, 3 H) 6.70-6.78 (m, 1 H) 6.79-6.88 (m, 1 H) 6.88-6.98 (m, 1 H) 7.31-7.41 (m, 1H) 7.43 (s, 1 H) 8.34-8.42 (m, 2 H) 8.63-8.72 (m, 1 H) 9.49-9.59 (m, 1 H) 11.00-11.12 (m, 1 H). ESIMS (M+H)$^+$=561

Example 261

2-[(2-{[1-(N,N-dimethylglycyl)-6-(methyloxy)-1,2,3,4-tetrahydro-7-quinolinyl]amino}-5-methyl-1H-pyrrolo[2,3-d]pyrimidin-4-yl)amino]-6-fluorobenzamide

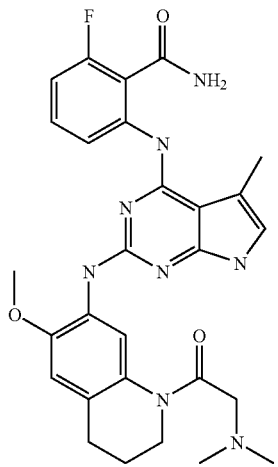

Step A/Intermediate D57: 2-({2-{[1-(N,N-dimethylglycyl)-6-(methyloxy)-1,2,3,4-tetrahydro-7-quinolinyl]amino}-5-methyl-7-[(4-methylphenyl)sulfonyl]-7H-pyrrolo[2,3-d]pyrimidin-4-yl}amino)-6-fluorobenzamide

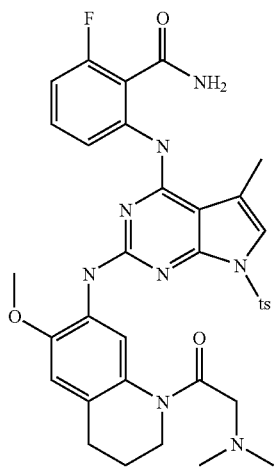

To a flask containing 5-chloro-8-fluoro-2-methyl-3-[(4-methylphenyl)sulfonyl]pyrrolo[2',3':4,5]pyrimido[6,1-b]quinazolin-7(3H)-one HCl salt (414 mg, 0.839 mmol) in 2,2,2-trifluoroethanol (5 mL) was added 1-[(dimethylamino)acetyl]-6-(methyloxy)-1,2,3,4-tetrahydro-7-quinolinamine (243 mg, 0.923 mmol). The resulting slurry was stirred at 80° C. for 16 h. Solvents were removed under reduced pressure to afford a green residue. Half of this material was dissolved in THF (5 mL) and an excess of aqueous ammonium hydroxide (27%) (~100 ml) was added. The reaction was let stir at rt for 16 h and then heated at 40° C. for 3 h. At this time the reaction was then diluted with ethyl acetate and washed with a saturated solution of sodium bicarbonate, water and saturated brine solution. Organics were dried over sodium sulfate and solvents removed under reduced pressure to afford a solid that was purified via chromatography on SiO$_2$ to afford 2-({2-{[1-(N,N-dimethylglycyl)-6-(methyloxy)-1,2,3,4-tetrahydro-7-quinolinyl]amino}-5-methyl-7-[(4-methylphenyl)sulfonyl]-7H-pyrrolo[2,3-d]pyrimidin-4-yl}amino)-6-fluorobenzamide (146 mg, 0.208 mmol). ESIMS (M+H)$^+$=701.

Step B/Example 261

2-[(2-{[1-(N,N-dimethylglycyl)-6-(methyloxy)-1,2,3,4-tetrahydro-7-quinolinyl]amino}-5-methyl-1H-pyrrolo[2,3-d]pyrimidin-4-yl)amino]-6-fluorobenzamide 2-({2-{[1-(N,N-dimethylglycyl)-6-(methyloxy)-1,2,3,4-tetrahydro-7-quinolinyl]amino}-5-methyl-7-[(4-methylphenyl)sulfonyl]-7H-pyrrolo[2,3-d]pyrimidin-4-yl}amino)-6-fluorobenzamide (146 mg, 0.208 mmol) was dissolved in dioxane (3 mL) and 2N NaOH (2 mL) was added in a microwave safe vessel. The reaction was then heated in a microwave at 120° C. for 10 min. Reaction was diluted with EtOAc and the organic layer was washed with water and a saturated brine solution and dried over sodium sulfate. Solvents were removed under reduced pressure and the residue purified by chromatography on SiO$_2$ to afford 2-[(2-{[1-(N,N-dimethylglycyl)-6-(methyloxy)-1,2,3,4-tetrahydro-7-quinolinyl]amino}-5-methyl-1H-pyrrolo[2,3-d]pyrimidin-4-yl)amino]-6-fluorobenzamide (89 mg, 0.163 mmol) as a pink solid. $^1$H NMR (400 MHz, DMSO-$d_6$) δ ppm 1.81-1.92 (m, 2 H) 2.10 (br. s., 6 H) 2.42 (s, 3 H) 2.67 (br. s., 2 H) 3.20 (s, 2 H) 3.66-3.74 (m, 2 H) 3.84 (s, 3 H) 6.74 (s, 1 H) 6.79-6.86 (m, 1 H) 6.86-6.96 (m, 1 H) 7.31-7.40 (m, 1 H) 7.42 (s, 1 H) 8.12 (d, J=14.92 Hz, 2 H) 8.40 (d, J=8.61 Hz, 2 H) 9.88 (s, 1 H) 10.99-11.11 (m, 1 H). ESIMS (M+H)$^+$=547

Example 262

2-[(2-{[1-(N,N-dimethylglycyl)-5-(methyloxy)-2,3-dihydro-1H-indol-6-yl]amino}-6-methyl-1H-pyrrolo[2,3-d]pyrimidin-4-yl)amino]-6-fluorobenzamide

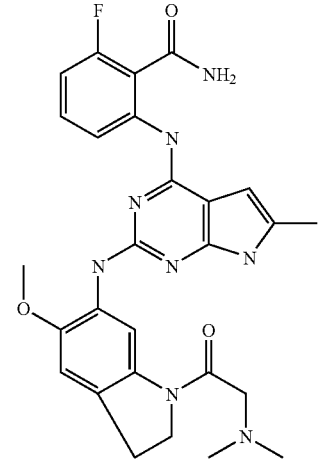

Step A/Intermediate D58: 2,4-dichloro-6-methyl-7-[(4-methylphenyl)sulfonyl]-7H-pyrrolo[2,3-d]pyrimidine

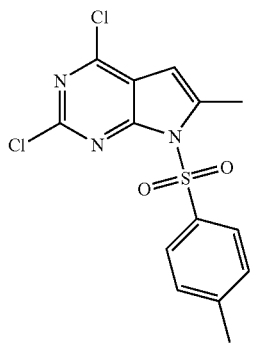

To a solution of diisopropylamine(2.2 g, 21.9 mmol, 1.5 eq) in THF (50 mL) was added nBuLi (2.5 mol/L, 6.4 mL, 16.07 mmol, 1.1 eq) dropwise under N₂ at −78° C., then the mixture was stirred for 30 min at −78° C. And followed by 2,4-dichloro-7-[(4-methylphenyl)sulfonyl]-7H-pyrrolo[2,3-d]pyrimidine (5 g, 14.6 mmol, 1 eq) in THF (50 mL) was added to the mixture, then the mixture was stirred for another 30 min at −78° C. MeI (2.28 g, 16 mmol, 1.1 eq) was added to the mixture for 30min at −78° C. The mixture was stirred at room temperature overnight and quenched with sat NH₄Cl, then extracted with EtOAc. The organic layer was dried over Na₂SO₄, and the solvent was removed under reduced pressure to give the crude product which was purified by reverse phase preparative HPLC to afford 2.5 g of 2,4-dichloro-6-methyl-7-[(4-methylphenyl)sulfonyl]-7H-pyrrolo[2,3-d]pyrimidine as a white solid. ESIMS (M+H)⁺=358.

Step B/Intermediate D59: 2-({2-chloro-6-methyl-7-[(4-methylphenyl)sulfonyl]-7H-pyrrolo[2,3-d]pyrimidin-4-yl}amino)-6-fluorobenzoic acid

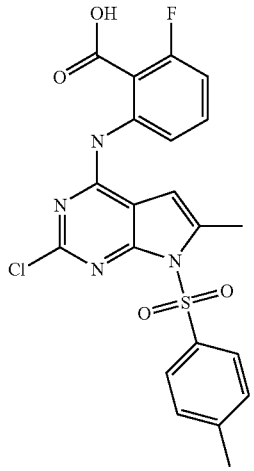

To a suspension of 2,4-dichloro-6-methyl-7-[(4-methylphenyl)sulfonyl]-7H-pyrrolo[2,3-d]pyrimidine (500 mg, 1.40 mmol) and 2-amino-6-fluorobenzoic acid (218 mg, 1.40 mmol) in isopropanol (15 mL) was added diisopropylethylamine (907 mg, 7.02 mmol) and the mixture was heated at 85° C. for ~72 h. The reaction was diluted with EtOAc (100 ml) and washed with a solution of 1N HCl, a saturated solution of sodium bicarbonate and a saturated solution of NaCl. Solid began to crash out on addition of brine. Ether was added to force everything out of solution and also water was added to ensure NaCl was all in solution. The solids were filtered and dried under reduced pressure to afford 2-({2-chloro-6-methyl-7-[(4-methylphenyl)sulfonyl]-7H-pyrrolo[2,3-d]pyrimidin-4-yl}amino)-6-fluorobenzoic acid (439 mg, 0.924 mmol) as a pale yellow solid. ESIMS (M+H)⁺=475.

Step C/Intermediate D60: 5-chloro-8-fluoro-2-methyl-3-[(4-methylphenyl)sulfonyl]pyrrolo[2',3':4,5]pyrimido[6,1-b]quinazolin-7(3H)-one HCl salt

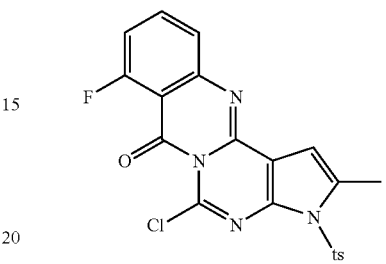

To a solution of 2-({2-chloro-6-methyl-7-[(4-methylphenyl)sulfonyl]-7H-pyrrolo[2,3-d]pyrimidin-4-yl}amino)-6-fluorobenzoic acid (439 mg, 0.924 mmol) in THF (15 mL) and DMF (few drops) was added 2M oxalyl chloride solution in dichloromethane (0.56 mL, 1.13 mmol) dropwise. After ~15 min, LCMS analysis shows reaction complete so reaction mixture was cooled in an ice bath and filtered via a buchner funnell and thet solid was washed with THF and dried under reduced pressure to afford 5-chloro-8-fluoro-2-methyl-3-[(4-methylphenyl)sulfonyl]pyrrolo[2',3':4,5]pyrimido[6,1-b]quinazolin-7(3H)-one HCl salt (423 mg, 0.86 mmol) as a yellow solid. ESIMS (M+H)⁺=457.

Step D/Intermediate D61: 2-({2-{[1-(N,N-dimethylglycyl)-5-(methyloxy)-2,3-dihydro-1H-indol-6-yl]amino}-6-methyl-7-[(4-methylphenyl)sulfonyl]-7H-pyrrolo[2,3-d]pyrimidin-4-yl}amino)-6-fluorobenzamide

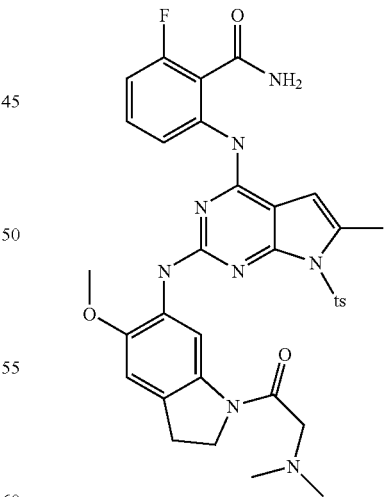

To a flask containing 5-chloro-8-fluoro,2-methyl-3-[(4-methylphenyl)sulfonyl]pyrrolo[2',3':4,5]pyrimido[6,1-b]quinazolin-7(3H)-one HCl salt (423 mg, 0.86 mmol) in 2,2,2-trifluoroethanol (10 mL) was added 1-[(dimethylamino)acetyl]-5-(methyloxy)-2,3-dihydro-1H-indol-6-amine (254 mg, 1.02 mmol). The resulting slurry was stirred at 80° C. for 6 h. Solvents were removed under reduced pressure to afford a yellow solid. One third of this material (~200 mg) was suspended in THF (5 mL) and excess aqueous ammonium hydroxide (27%) (~12 mL) was added. The reaction was let stir at rt for 5 h, at which time the reaction mixture was diluted with ethyl acetate and washed with water and saturated brine solution. Organics were dried over sodium sulfate and solvents removed under reduced pressure to afford a yellow solid that was purified via chromatography on SiO$_2$ to afford 2-({2-{[1-(N,N-dimethylglycyl)-5-(methyloxy)-2,3-dihydro-1H-indol-6-yl]amino}-6-methyl-7-[(4-methylphenyl)sulfonyl]-7H-pyrrolo[2,3-d]pyrimidin-4-yl}amino)-6-fluorobenzamide (117 mg, 0.17 mmol) as a yellow solid. ESIMS (M+H)$^+$=688.

Step E/Example 262

2-[(2-{[1-(N,N-dimethylglycyl)-5-(methyloxy)-2,3-dihydro-1H-indol-6-yl]amino}-6-methyl-1H-pyrrolo[2,3-d]pyrimidin-4-yl)amino]-6-fluorobenzamide 2-({2-{[1-(N,N-dimethylglycyl)-5-(methyloxy)-2,3-dihydro-1H-indol-6-yl]amino}-6-methyl-7-[(4-methylphenyl)sulfonyl]-7H-pyrrolo[2,3-d]pyrimidin-4-yl}amino)-6-fluorobenzamide (117 mg, 0.17 mmol) was dissolved in dioxane (3 mL) and 2N NaOH (2 mL) was added in a microwave safe vessel. The reaction was then heated in a microwave at 120° C. for 35 min. Reaction was diluted with EtOAc and the organic layer was washed with water and saturated brine solution and dried over sodium sulfate. Solvents were removed under reduced pressure and the residue purified by chromatography on SiO$_2$ to afford 2-[(2-{[1-(N,N-dimethylglycyl)-5-(methyloxy)-2,3-dihydro-1H-indol-6-y]amino}-6-methyl-1H-pyrrolo[2,3-d]pyrimidin-4-yl)amino]-6-fluorobenzamide (35 mg, 0.066 mmol) as an off white solid. 1H NMR (400 MHz, DMSO-d$_6$) δ ppm 2.25 (s, 6 H) 2.28 (s, 3 H) 3.12 (t, J=8.24 Hz, 2 H) 3.17 (s, 2 H) 3.78 (s, 3 H) 4.18 (t, J=8.33 Hz, 2 H) 5.90 (s, 1 H) 6.76-6.91 (m, 1 H) 6.95 (s, 1H) 7.30 (d, J=6.96 Hz, 1 H) 7.50 (s, 1 H) 7.95-8.14 (m, 2 H) 8.53 (d, J=8.61 Hz, 1 H) 8.65 (s, 1 H) 10.42 (s, 1 H) 11.17 (s, 1 H). ESIMS (M+H)$^+$=533.

Example 263

2-[(2-{[5-(dimethylamino)-1-(N,N-dimethylglycyl)-2,3-dihydro-1H-indol-6-yl]amino}-1H-pyrrolo[2,3-d]pyrimidin-4-yl)amino]-6-fluoro-N-methylbenzamide

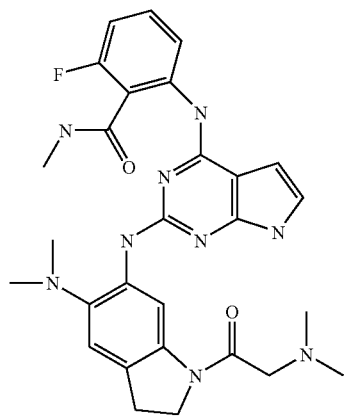

In a manner analogous to a procedure outlined previously, 2-[(2-{[5-(dimethylamino)-1-(N,N-dimethylglycyl)-2,3-dihydro-1H-indol-6-yl]amino}-1H-pyrrolo[2,3-d]pyrimidin-4-yl)amino]-6-fluoro-N-methylbenzamide was prepared from 5-chloro-8-fluoro-3-[(4-methylphenyl)sulfonyl]pyrrolo[2',3':4,5]pyrimido[6,1-b]quinazolin-7(3H)-one hydrochloride, 1-[(dimethylamino)acetyl]-N5,N5-dimethyl-2,3-dihydro-1H-indole-5,6-diamine, and methyl amine to afford the title compound (0.20 g, 44% over 3 steps). ESIMS (M+H)+=546. 1H NMR (400 MHz, DMSO-d$_6$) δ ppm 2.25 (s, 6 H) 2.58 (s, 6H) 2.81 (d, J=3.61 Hz, 3 H) 3.02-3.14 (m, 2 H) 3.18 (s, 211) 4.16 (t, J=8.23 Hz, 2 H) 6.27 (br. s., 1 H) 6.87-6.99 (m, 2 H) 7.06 (s, 1 H) 7.32-7.45 (m, 1 H) 7.66 (s, 1 H) 8.38 (d, J=8.23 Hz, 1 H) 8.56 (br. s., 1 H) 8.77 (s, 1H) 10.17 (s, 1 H) 11.30 (br. s., 1H).

ASSAYS

Time Resolved Fluorescence Resonance Energy Transfer (TR-FRET) assays were carried out on the exemplified compounds as follows:
The Source of Substrate Peptide
The biotinylated substrate peptide, (sequence—Biotin-aminohexyl-AEEEEY*MMMMAKKKK-NH$_2$) is purchased from QCB, Inc. (Hopkinton, Mass.). Purity is determined by HPLC. The calculated molecular mass of the peptide is 2216 dalton. Tyrosine phosphorylation by human IGF1R (hIGF1R) or human IR (hIR) occurs as indicated (Y*) in the peptide sequence described. Solid peptide sample is dissolved to approximately 1 mM in DMSO, aliquoted, and stored at –20° C. until use. True peptide concentration is determined by amino acid analysis.
The Source of Enzyme:
hIGF1R: GST-rTEV-IGF-1R(957-1367) containing amino acid residues 957-1367 of human IGF1R (as annotated by National Center for Biotechnology Information (NCBI) accession number NP_000866) is purified from a baculovirus expression system in Sf9 cells using Glutathione Sepharose 4FF column chromatography followed by Sephadex-200 size exclusion column chromatography. Enzyme purity of approximately 95% is achieved. Samples, in 25 mM Tris-HCl, 250 mM NaCl, 5% glycerol, 1 mM DTT, pH 7.5, are stored at –80° C. until use.
hIR: GST-rTEV-IR(979-1382) containing amino acid residues 979-1382 of human IR (as annotated by NCBI accession number NP_000199) is expressed and purified by the same process as hIGF1R. Enzyme purity of approximately 92% is achieved. Samples, in 25 mM Tris-HCl, 250 mM NaCl, 5% glycerol, 1 mM DTT, pH 7.5, are stored at –80° C. until use.
Activation of hIGF1 R and hIR by Autophosphorylation:
hIGF1R: Activation of GST-rTEV-IGF-1R(957-1367) is achieved by a 4 minute incubation of hIGF1R (2.7 μM final) with 2 mM ATP in 50 mM HEPES, 20 mM MgCL$_2$, 0.1 mg/ml BSA, at room temperature. Autophosphorylation is stopped by addition of EDTA (to 100 mM final). Aliquoted samples are flash frozen in liquid nitrogen and stored at –80° C. until use.
hIR: Activation of GST-rTEV-IGF-1R(957-1367) is achieved by a 5 minute incubation of hIR (2.7 μM final) with 2 mM ATP in 100 mM HEPES, 10 mM MgCL$_2$, 0.1 mg/ml BSA, at room temperature. Autophosphorylation is stopped by addition of EDTA (to 100 mM final). Aliquoted samples are flash frozen in liquid nitrogen and stored at –80° C. until use.
Kinase Assay of Purified hIGF1R or hIR:
Assays are performed in 384-well (Greiner, Catalog No. 784076) microtiter plates. Reaction buffer (50 mM HEPES buffer, pH 7.5; 10 mM MgCL$_2$; 3 mM DTT; 1 mM CHAPS; 0.1 mg/ml BSA) for peptide phosphorylation (10 µl volume) contained, in final concentrations, 500 nM biotinylated peptide substrate; 10 µM ATP; and purified, activated hIGF1R or hIR (0.5 nM). Compounds, titrated in DMSO, are evaluated at eleven concentrations ranging from 50 µM to 0.2 nM. Final assay concentrations of DMSO do not exceed 10%. No effect on activity relative to controls without DMSO is observed for hIGF1R or IR at these DMSO amounts. Reactions are incubated for 1 hour at room temperature and are stopped by a 5 µl addition of EDTA (to 33 mM). A further addition of 5 µl detection reagents (for final 7 nM Streptavidin-APC (Perkin Elmer #CR$^{13}$0-150), 1 nM Europium-labeled anti-phosphotyrosine monoclonal antibody (PerkinElmer #AD0067), added in reaction buffer (without DTT), is required for signal generation. After 30 minutes, signal is read on PerkinElmer Viewlux microplate imager or Wallac Victor fluorometer.

The data for compound concentration responses were plotted as % Inhibition, calculated with the data reduction formula 100*(1-[(U1-C2)/(C1-C2)]), versus concentration of compound, where U is the unknown value,
C1 is the average control value obtained for DMSO only, and
C2 is the average control value obtained for reactions stopped with EDTA at
t=0.
Data were fitted to the curve described by:

$y=((V\max *x)/(K+x))$ where

Vmax is the upper asymptote and
K is the IC$_{50}$.
The results for each compound were recorded as pIC$_{50}$ calculated as follows:

pIC$_{50}$=−Log10(K).

pIC50 values for the compounds of the examples (if available) were categorized by relative inhibition of IGF-1R and IR. The results are summarized in the tables below.

| IGF-1R pIC$_{50}$ | Example no. |
|---|---|
| 9.0-9.6 | 2-7, 15-18, 28, 42, 53, 54, 58, 50, 63, 70-76, 78, 79, 84, 86, 89, 91, 92, 95-105, 107, 108, 124, 125, 119, 120, 143, 151, 152, 168, 170, 175, 176, 178, 179, 180, 189, 190, 200, 201, 210, 218, 219, 221, 223, 224, 225, 226, 244, 249, 252, 256, 257, 258, 259, 260, and 261 |
| 8.4-8.9 | 8-14, 19, 21-25, 29, 30, 32, 33, 36, 38, 40-41, 43-49, 51, 52, 59, 61, 62, 64, 65, 67-69, 77, 80-83, 85, 87, 88, 90, 93, 94, 106, 109-115, 116, 123, 126, 127, 131, 133, 136, 138, 139, 141, 142, 148, 153, 154, 155, 156, 157, 158, 159, 160, 162, 163, 166, 167, 169, 174, 177, 194, 195, 197, 198, 199, 206, 209, 212, 217, 227, 228, 233, 236, 237, 239, 245, 246, 251, and 253 |
| 6.7-8.3 | 1, 20, 26, 27, 31, 34, 35, 37, 39, 50, 66, 117, 118, 121, 122, 128, 129, 130, 132, 134, 135, 137, 140, 144, 145, 146, 147, 149, 150, 161, 164, 165, 185-188, 191-193, 196, 202, 203, 204, 205, 207, 208, 211, 213-216, 220, 222, 229, 230, 231, 232, 234, 235, 238, 242, 247, 248, 250, 255, 262, and 265 |

| IR pIC$_{50}$ | Example No. |
|---|---|
| 9.0-9.6 | 2-8, 12-18, 21-23, 28, 30, 42, 54-63, 68, 70-77, 79, 80, 84-86, 89, 92, 95-109, 113, 124, 125, 119, 120, 138, 143, 151, 162, 168, 170, 175, 176, 178, 179, 189, 190, 197, 200, 201, 210, 218, 219, 221, 223, 224, 225, 226, 227, 244, 245, 246, 249, 252, 256, 257, 258, 259, 260, and 261 |
| 8.4-8.9 | 9-11, 19, 25-27, 29, 32-34, 36, 38, 39, 41, 43-45, 49, 51-5364-67, 69, 78, 81-83, 87, 88, 90, 91, 93, 94, 110-112, 114, 115, 116, 121, 122, 123, 126, 127, 131, 132, 133, 134, 136, 139, 141, 142, 147, 148, 152, 153, 154, 155, 156, 157, 158, 159, 160, 163, 166, 167, 169, 174, 177, 180, 192, 194, 195, 198, 199, 203, 204, 205, 206, 209, 212, 217, 228, 232, 233, 234, 235, 236, 237, 238, 239, 245, 246, 251, and 253 |
| 6.8-8.3 | 1, 20, 31, 35, 117, 118, 128, 129, 130, 135, 137, 140, 144, 145, 146, 149, 150, 161, 164, 165, 185, 186, 187, 188, 191, 193, 202, 207, 208, 211, 213, 214, 215, 216, 229, 230, 231, 242, 248, 250, 254, 255, 262, and 265 |

ALK Enzyme Assay:

The method measures the ability of the isolated enzyme to catalyse the transfer of the gamma-phosphate from ATP onto the tyrosine residue of a biotinylated synthetic peptide. The extent of tyrosine phosphorylation was measured using an anti-phosphotyrosine antibody, and quantified by homogenous time-resolved fluorescence (HTRF) assay purchased from CisBio (62TK0PEJ).

Reactions were performed in black 384-well polystyrene low volume plates in a final volume of 5 µl. Assays were performed by adding 2.5 µl of each of the following solutions, enzyme mix and substrate: The enzyme mix, final concentration in plate, contained 50 mM MOPS (pH 7.0); 10 nM supplement enzymatic buffer; 0.03% NaN3; 0.01% BSA, 0.1 mM orthovanadate, 5 mM MgCl2, 1 mM CHAPS, 1 mM dithiothreitol and 0.25 nM ALK. The Substrate mix, final concentration in plate, contained 50 mM MOPS (pH 7.0); 10 nM supplement enzymatic buffer; 0.03% NaN3; 0.01% BSA, 0.1 mM orthovanadate, 5 mM MgCl2, 1 mM CHAPS, 1 mM dithiothreitol, 15.0 µM ATP, and 0.25 uM TK substrate-biotin.

To quantify compound potencies, the enzyme mix was added to the compound plates and the plates were incubated at 20° C. for 30 minutes. The reactions were then started by adding the substrate mix. The reactions were allowed to proceed for 120 minutes at 20° C. The reactions were then terminated by the addition of 5 µl HTRF detection mix to each well. The final concentrations of the detection reagents were: 50 mM HEPES (pH7.0); 0.1% BSA; 0.8 M KF; 20 mM EDTA; 1 mM CHAPS; TK-antibody Europium Cryptate; and 41 nM streptavidin-XL665. Assay plates were left unsealed, stacked and incubated at 20° for 60 minutes. Quantification of activity was achieved by counting in an Envision Counter (PerkinElmer).

Compounds under analysis were dissolved in Me$_2$SO to 1.0 mM and serially diluted 1 to 3 with Me$_2$SO through twelve dilutions. 0.05 µl of each concentration was transferred to the corresponding well of an assay plate. This creates a final compound concentration range from 0.00017 to 10 µM.

The data for dose responses were plotted as % Inhibition calculated with the data reduction formula 100*(1-(U1-C2)/

(C1-C2)) versus concentration of compound where U is the unknown value, C1 is the average control value obtained for 1% DMSO, and C2 is the average control value obtained for 0.1 M EDTA. Data were fitted with a curve described by:

$$y = A + \frac{B-A}{\left[1+\frac{10x}{10c}\right]D}$$

where A is the minimum y, B is the maximum y concentration [M], D is the slope factor, and x is the $\log_{10}$ of the compound. The results for each compound were recorded as pIC50s, calculated as follows:

pIC50=−Log10(K)

pIC50 values for the compounds of the examples (if available) were categorized by relative inhibition of IGF-1R and IR. The results are summarized in the tables below.

| ALK pIC$_{50}$ | Example no. |
| --- | --- |
| 9.0-9.6 | 1-7, 12, 15-17, 21-25, 28, 33, 38, 41, 46, 48, 53-60, 68, 70-73, 78, 80, 81, 86, 87, 89, 91-102, 108, 110, 112, 113, 115, 116, 120, 126, 127, 139, 151-153, 156, 158, 171, 173, 167, 178-180, 182, 183, 190, 194, 199, 201, 203, 204, 208-210, 218, 219, 223, 225, 224, 234, 240, 244, 245, 251, 253, and 256-258 |
| 8.4-8.9 | 9-11, 13, 14, 18, 19, 29, 32, 36, 37, 39, 40, 43, 44, 47, 49-52, 61, 63-67, 74-77, 82, 84, 88, 103-105, 107, 114, 119, 121, 123, 124, 131, 133-136, 138, 141-143, 154, 157, 159-170, 172, 174, 175, 177, 181, 184, 187, 189, 195, 197, 198, 200, 205-207, 212, 221, 224, 227, 228, 232, 233, 235-239, and 249 |
| 6.7-8.3 | 20, 26, 27, 30, 31, 34, 35, 62, 83, 85, 106, 109, 111, 117, 118, 122, 125, 128-130, 132, 137, 140, 144-150, 155, 169, 185, 186, 188, 191, 192, 193, 196, 202, 211, 213, 214, 217, 220, 222, 229-231, 241, 242, 246, 248, 250, 254, 255, 262, 265 |

Cell Proliferation Data

A. Inhibition of Cell Proliferation by IGF-1R Inhibitors

Cell proliferation was measured by either CellTiter-Glo (measures cellular ATP level as a surrogate for total cell number) or by InCell analyzer (counts number of nuclei as a measure of cell number).

For CellTiter-Glo assay, exponentially growing cell lines of different tumor origins, cultured in appropriate media containing 10% fetal bovine serum at 37° C. in a 5% CO$_2$ incubator, were plated at low density (less than 2000cells/well) in 96-well plates. Twenty four hours post-plating, cells were treated with different concentrations of test compounds ranging from 30 uM to 1.5 nM. Several wells were left untreated as a control. Seventy two hours post-treatment, cell numbers were determined using 50-100 ul per well of CellTiter-Glo (Promega #G7573). Plates were incubated at 37° C. for 30 minutes and the chemiluminescent signal was read on the Victor V or Envison 2100 reader. Percent inhibition of cell growth was expressed as percent proliferation relative to 100% proliferation (control). Concentration of test compound that inhibited 50% of cell growth (IC$_{50}$) was determined by 4 parameter fit of data using XLfit, (value of no cell control was substracted from all samples for background).

For InCell Analyser assay, various cell lines of different tumor origins were grown to 70-80% confluency in appropriate culture media containing 10% fetal bovine serum at 37° C. in a 5% CO$_2$ incubator. On day −1, cells were seeded at 2 densities in 384-well plates and incubated at 37° C. overnight. Stock compound plates were prepared in advance which contained dimethyl sulfoxide (DMSO) alone and a 9-point half-log decreasing dose range of the compound in DMSO. The compound plates were stored at −80° C. and each plate was only thawed once and used. On day 0, the main assay plates received compound or DMSO via a sonic delivery system (ECHO). The highest final concentration of compound of the dose range in the culture plates was 10 uM. These plates were cultured at 37° C. for 3 days. A parallel set of cell line plates, which did not receive compound, were processed and read on day 0 to provide a T=0 (time zero). On day 3, the compound treated plates were stained and fixed to measure proliferation, apoptosis, and mitotic index using an InCellL$_1$000 analyser. A nuclear stain was used to identify cells in the wells. By counting the number of nuclei, the proliferation index of compound treated groups were calculated as a percentage relative to the DMSO control, which was set to 100%. The IC50 values were calculated using model 205 in ExcelFit.

IC50 (nM) values for compounds of select examples were categorized by relative inhibition of cell proliferation. The results are summarized in the tables below.

| IC50 for Colo205 | Example No. |
| --- | --- |
| <250 nM | 2, 3, 7, 9, 10, 15, 17, 18, 42, 46, 47, 49, 53, 54, 57, 58, 59, 60, 61, 66, 68, 70, 71, 73, 74, 75, 81, 82, 84, 86, 91, 92, 94, 97, 98, 100, 103, 105, 112-115, 124, 132, 159, 162, 168, 171, 178, 179, 189, 194, 197, 198, 199, 200, 204, 205, 209, 210, 218, 219, 223, 225, 244, and 252 |
| 250 nM to 1000 nM | 16, 39, 43, 44, 45, 48, 51, 64, 65, 67, 69, 72, 76, 77, 78, 87, 88, 89, 90, 93, 99, 101, 107, 116, 118, 119, 121, 123, 125-127, 134, 136-143, 147, 148, 151, 152, 158, 160, 163, 166, 167, 172-176, 180, 188, 190, 192, 195, 202, 203, 206-208, 212, 214, 217, 221, 224, 226, 227, 233, 236, 237, 245, 246, 253, 258, and 259 |
| >1000 nM | 50, 52, 83, 104, 117, 122, 135, 144-146, 149, 150, 153-157, 161, 164, 165, 177, 185-187, 191, 193, 211, 213, 215, 216, 220, 222, 228-232, 235, 238, 239, 242, 247, 262, and 265 |

| IC50 for NCI-H929 | Example No. |
| --- | --- |
| <250 nM | 2, 7, 42, 44, 45, 46, 48, 53, 57, 58, 60, 70, 71, 73, 81, 89, 91, 92, 93, 94, 97, 98, 112-115, 116, 118, 119, 121-127, 132, 134, 136-139, 143, 147, 159, 160, 162, 163, 166-168, 171-173, 175, 178, 179, 185, 187, 189, 190, 192, 194, 197, 199, 200, 202-206, 208-210, 212, 214, 217-219, 221, 223-226, 232, 233, 235-237, 244, 245, 246, 252, and 259 |
| 250 nM to 1000 nM | 50, 51, 52, 83, 117, 135, 141, 142, 144, 146, 148-152, 154, 156-158, 161, 164, 165, 174, 176, 177, 180, 186, 188, 195, 198, 207, 213, 215, 216, 222, 227-231, 238, 239, 247, 253, and 258 |
| >1000 nM | 140, 145, 153, 155, 191, 193, 196, 211, 220, 242, 262, and 265 |

B. IGF-1R and IR Cellular Autophosphorylation

NIH-3T3 cells overexpressing human IGF-1R or IR were plated in 96-well plates (10,000 cells/well) in culture media containing 10% fetal bovine serum and incubated at 37° C. in a 5% $CO_2$ incubator. Twenty four hours post-plating, cells were treated with different concentrations of test compounds ranging from 30 uM to 1.5 nM. Two hours after compound addition, cells were stimulated with either human IGF-1 (30 ng/ml) or insulin (3 ug/ml) for 15 minutes. Cell lysates are analyzed for phosphorylated receptors using dissociation enhanced lanthanide fluor-immuno assay (DELFIA) with anti-IGF-1R (MAB391, R&D Systems, Minneapolis, Minn.) or anti-IRβ (sc-711, Santa Cruz Biotechnology, Santa Cruz, Calif.) capture antibody and europium-labeled anti-pTyr antibody (Eu-N1 PT66, Perkin Elmer, Waltham, Mass.) for detection. The fluorescence signal for cells treated with compounds was expressed as percent relative to 100% stimulation (IGF-1 or insulin stimulated signal). Concentration of test compound that inhibited 50% of ligand-induced receptor phosphorylation ($IC_{50}$) was determined by 4 parameter fit of data using XLfit, (value of no cell control was substracted from all samples for background).

IC50 values for the compounds of the examples (if available) were categorized by relative inhibition of IGF-1R and IR. The results are summarized in the tables below.

| IGF-1R $IC_{50}$ | Example no. |
|---|---|
| <100 nM | 3-8, 15, 17, 18, 47, 52, 53, 56-61, 64, 70-73, 75, 76, 78, 80-84, 89-92, 96-105, 113, 114, 116, 119, 124, 127, 132, 136, 138, 139, 142, 162, 163, 166, 168, 173, 175, 178, 179, 180, 185, 189, 190, 192, 199, 200, 210, 217, 218, 219, 221, 244, 249, 251, 252, 256, 257, 260, and 261 |
| 100 nM-500 nM | 2, 9-12, 14, 16, 21-25, 29, 36, 38-43, 45, 46, 48, 49, 54, 55, 62, 63, 65, 67-69, 74, 77, 79, 86, 93-95, 107, 108, 110, 112, 115, 118, 120, 121, 122, 123, 125, 126, 134, 137, 143, 147, 149, 151, 152, 153, 154, 155, 156-158, 161, 165, 167, 174, 176, 177, 186, 187, 191, 197, 202, 203, 205, 206, 208, 209, 212, 214, 220, 231, 233, 236, 237, 242, 246, 248, 253, 258, 259, and 262 |
| >500 nM | 26, 27, 28, 31, 33, 44, 50, 51, 66, 85, 87, 88, 106, 111, 117, 135, 140, 141, 144-146, 150, 188, 193, 196, 198, 204, 207, 211, 213, 215, 216, 222, 229, 230, 232, 235, 238, 239, 245, 250, 254, 255, and 265 |

| IR $IC_{50}$ | Example No. |
|---|---|
| <100 nM | 3, 48, 53, 57, 58, 61, 70, 73, 75, 77, 79, 83, 84, 89-92, 97, 98, 105, 114, 116, 119, 122, 127, 132, 134, 136, 138, 162, 163, 166, 168, 175, 178, 179, 180, 189, 190, 192, 199, 200, 203, 210, 217, 218, 219, 221, 233, 237, 242, 244, 249, 251, 252, 257, 260, and 261 |
| 100 nM-500 nM | 2, 7, 10, 12, 14, 16, 23, 24, 28, 29, 36, 41-43, 45, 46, 49, 54, 55, 60, 62, 65, 69, 71, 72, 74, 76, 78, 80, 81, 82, 93, 94, 103, 108, 112, 113, 115, 120, 121, 123-126, 137, 139, 142, 143, 147, 149, 151, 152, 155, 156, 157, 165, 167, 173, 174, 176, 177, 187, 202, 205, 206, 208, 209, 212, 214, 230, 236, 238, 246, 248, 253, 256, 258, 259, and 262 |
| >500 nM | 27, 28, 30, 44, 50-52, 66, 86, 87, 88, 101, 107, 110, 112, 117, 118, 135, 140, 141, 144-146, 150, 153, 154, 158, 161, 185, 186, 188, 191, 193, 196, 197, 198, 204, 207, 211, 213, 215, 216, 220, 222, 229, 231, 232, 235, 239, 245, 254, 255, and 265 |

We claim:

1. A compound of formula (I):

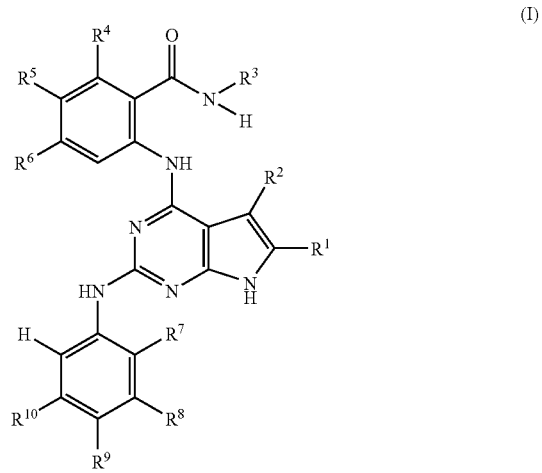

or a pharmaceutically acceptable salt thereof wherein:

$R^1$ is selected from H and alkyl$_{C1-C3}$;

$R^2$ is selected from H, alkyl$_{C1-C3}$, and halo;

$R^3$ is selected from H, OH, alkyl$_{C1-C6}$, -alkylene$_{C1-C6}$-OH, -alkylene$_{C1-C6}$-phenyl (optionally substituted with a halo), and -alkylene$_{C1-C6}$-C(O)NH$_2$;

$R^4$ is selected from H, halo, alkyl$_{C1-C6}$, and —O-alkyl$_{C1-C6}$; or, $R^3$ and $R^4$, together with the atoms to which they are bound, form a five or six membered lactam;

$R^5$ and $R^6$ are each independently selected from H, halo, alkyl$_{C1-C6}$, and —O-alkyl$_{C1-C6}$, or $R^5$ and $R^6$ together with the aryl to which they are attached form a napthalene;

$R^7$ is selected from alkyl$_{C1-C6}$, —O-alkyl$_{C1-C6}$, halo, —N—R$^{19}$R$^{19}$, and —O-alkylene$_{C1-C6}$-halo$_{1-3}$;

$R^8$ is selected from H, halo, and alkyl$_{C1-C6}$;

one of $R^9$ and $R^{10}$ is selected from -alkylene$_{C1-C6}$-SO$_2$-alkyl$_{C1-C6}$, —NR$^{19}$-alkylene$_{C0-C6}$-C(O)-alkylene$_{C0-C6}$-NR$^{22}$R$^{23}$, —O-alkylene$_{C0-C6}$(optionally substituted with —OH)—NR$^{22}$R$^{23}$,

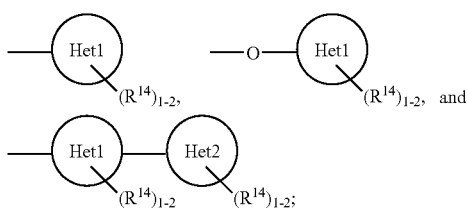

and the other of $R^9$ and $R^{10}$ is selected from H, alkyl$_{C1-C6}$, —O-alkyl$_{C1-C6}$, and halo;

wherein Het1 and Het2 are each independently a five or six membered heterocyclic ring having an N atom and optionally one or two additional heteroatoms selected from N and O, and each $R^{14}$ is independently selected from H, OH, halo, alkyl$_{C1-C6}$, —O-alkyl$_{C1-C6}$, -cyclopropyl, —C(O)-alkyl$_{C1-C6}$, SO$_2$-alkyl$_{C1-C6}$, —(CH$_2$)$_{1-4}$-halo, and —(CH$_2$)$_{1-4}$—SO$_2$-alkyl$_{C1-C6}$;

or $R^9$ and $R^{10}$, together with the atoms to which they are attached form a five, six, or seven-membered heterocyclic ring containing one or two N atom and the remainder C atoms, wherein at least one N atom is substituted with $R^{15}$, and the C atoms of the heterocyclic ring are optionally substituted with one or more groups selected from $R^{16}$ and $(R^{19})_{1-2}$;

wherein $R^{15}$ is selected from H, -alkyl$_{C1-C4}$, -alkylene$_{C1-C4}$-halo, —C(O)-alkylene$_{C0-C6}$-NR$^{22}$R$^{23}$, —C(O)-alkyl$_{C1-C6}$, -alkylene$_{C1-C4}$-NR$^{22}$R$^{23}$, -alkylene$_{C1-C4}$-C(O)—NR$^{23}$R$^{23}$, —C(O)-alkylene$_{C1-C4}$-O-alkyl$_{C1-C6}$, —C(O)-pyrrolidine, and —C(O)-pyrrolidine-alkyl$_{C1-C6}$;

$R^{16}$ is selected from H and =O; and, each $R^{19}$ is independently selected from H and alkyl$_{C1-C6}$;

$R^{22}$ is selected from H, alkyl$_{C1-C6}$, —O-alkyl$_{C1-C6}$, -alkylene$_{C1-C6}$-O-alkyl$_{C1-C6}$, —(CH$_2$)$_{2-4}$-halo, and —(CH$_2$)$_{2-4}$—SO$_2$-alkyl$_{C1-C6}$; and, $R^{23}$ is selected from H, alkyl$_{C1-C6}$, —(CH$_2$)$_{2-4}$-halo, and —(CH$_2$)$_{2-4}$-SO$_2$alkyl$_{C1-C6}$; or $R^{22}$ and $R^{23}$ combine to form a four, five, or six membered, heterocyclic ring containing the N atom to which they are attached and optionally an additional heteroatom selected from N and O, wherein the ring is optionally substituted with —OH or -alkyl$_{C1-C6}$.

2. The compound of claim 1, wherein $R^4$, $R^5$, and $R^6$ are each independently selected from H and halo.

3. The compound of claim 1, wherein $R^3$ is H.

4. The compound of claim 1, wherein $R^3$ is methyl.

5. The compound of claim 1, wherein $R^7$ is —O-alkyl$_{C1-C6}$.

6. The compound of claim 1, wherein $R^7$ is —O-methyl.

7. The compound of claim 1, wherein $R^8$ is H.

8. The compound of claim 1, wherein $R^{10}$ is H and $R^9$ is selected from -alkylene$_{C1-C6}$-SO$_2$-alkyl$_{C1-C6}$, —NR$^{19}$-alkylene$_{C0-C6}$-C(O)-alkylene$_{C0-C6}$-NR$^{22}$R$^{23}$, —O-alkylene$_{C0-C6}$ (optionally substituted with —OH)—NR$^{22}$R$^{23}$,

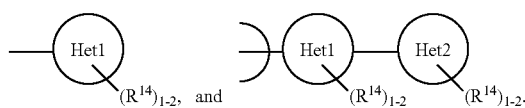

9. The compound of claim 1, wherein $R^{10}$ is H and $R^9$ is selected from

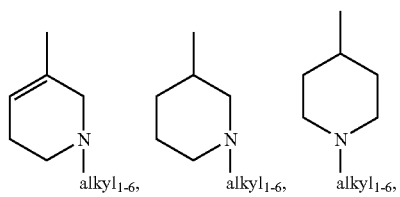

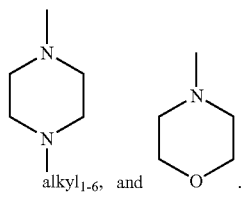

10. The compound of claim 1, wherein $R^9$ and $R^{10}$, together with the atoms to which they are attached form a five or six-membered heterocyclic ring selected from

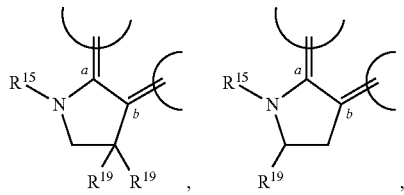

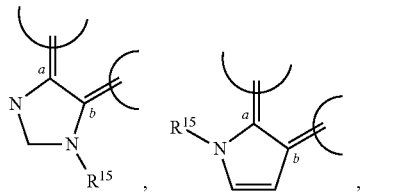

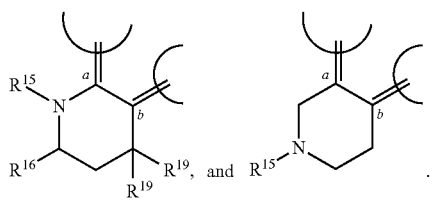

11. The compound of claim 1, having formula (Ia):
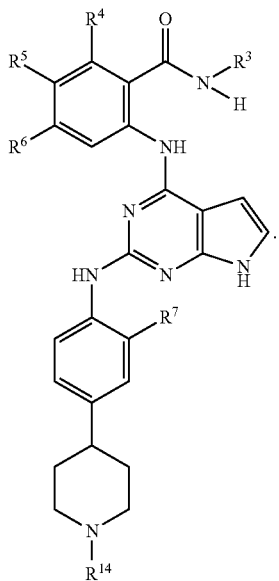
(Ia)
12. The compound of claim 1, having formula (Ib):
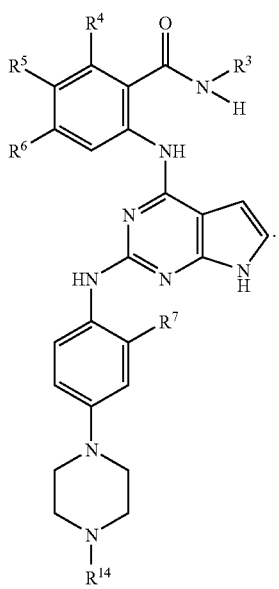
(Ib)
13. The compound of claim 1, having formula (Ic):
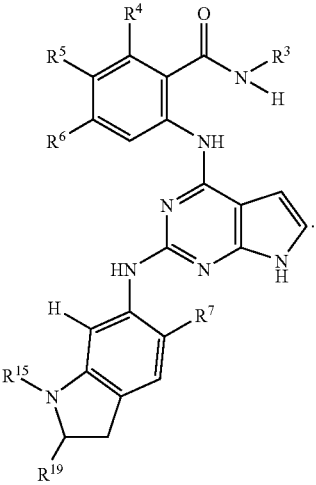
(Ic)
14. The compound of claim 1, having formula (Id):
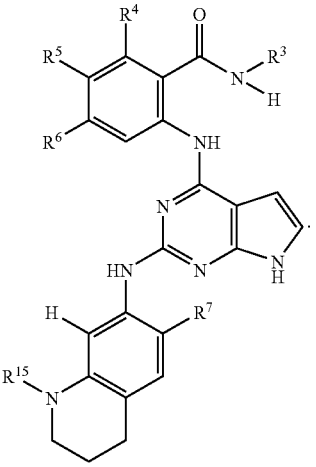
(Id)

15. The compound of claim 1, having formula (Ie):
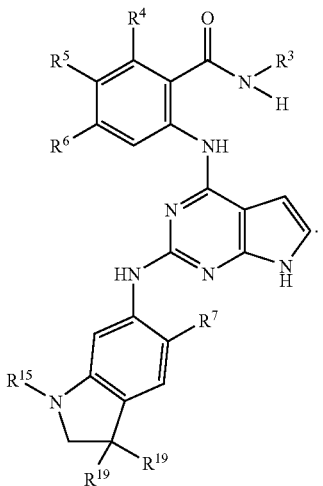
16. A pharmaceutical composition comprising a compound according to claim 1 and a pharmaceutically acceptable carrier, diluent or excipient.
17. A compound selected from the following:
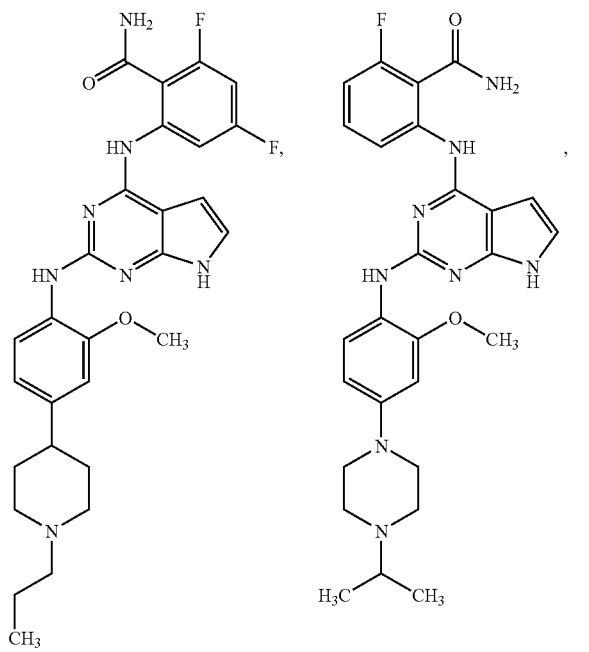
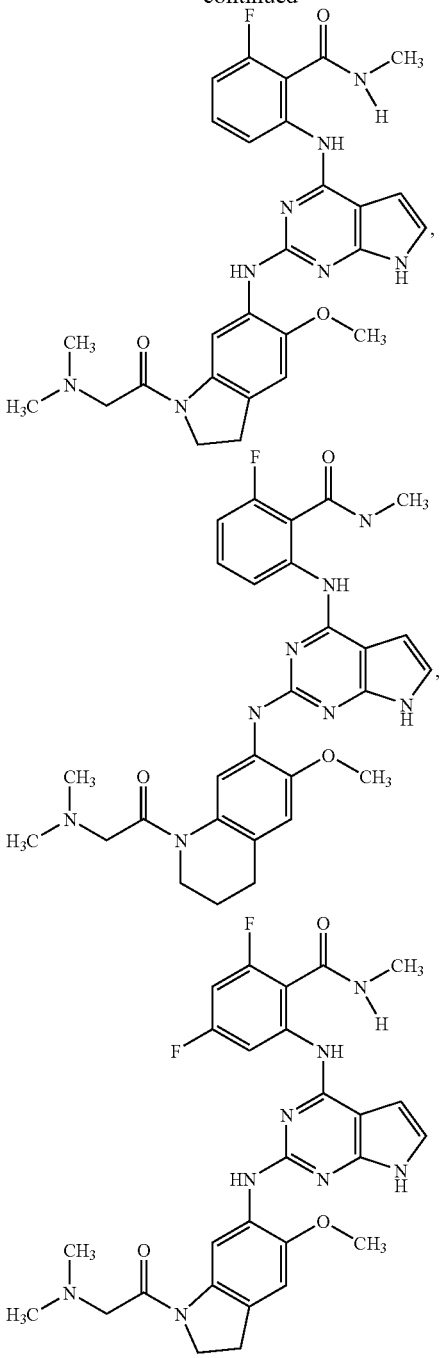
or a pharmaceutically acceptable salt thereof.
* * * * *